US011779653B2

(12) United States Patent
Meng et al.

(10) Patent No.: US 11,779,653 B2
(45) Date of Patent: Oct. 10, 2023

(54) MULTI-ARMED POLYROTAXANE PLATFORM FOR PROTECTED NUCLEIC ACID DELIVERY

(71) Applicant: The Regents of the University of California, Oakland, CA (US)

(72) Inventors: Huan Meng, Los Angeles, CA (US); Melissa J. Spencer, Los Angeles, CA (US); April D. Pyle, Los Angeles, CA (US); Courtney S. Young, Los Angeles, CA (US); Xiangsheng Liu, Los Angeles, CA (US); Ying Ji, Los Angeles, CA (US); Michael Reza Emami, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 479 days.

(21) Appl. No.: 16/648,204

(22) PCT Filed: Sep. 27, 2018

(86) PCT No.: PCT/US2018/053221
§ 371 (c)(1),
(2) Date: Mar. 17, 2020

(87) PCT Pub. No.: WO2019/067786
PCT Pub. Date: Apr. 4, 2019

(65) Prior Publication Data
US 2020/0376139 A1 Dec. 3, 2020

Related U.S. Application Data

(60) Provisional application No. 62/687,713, filed on Jun. 20, 2018, provisional application No. 62/566,100, filed on Sep. 29, 2017.

(51) Int. Cl.
*A61K 47/69* (2017.01)
*A61K 47/60* (2017.01)
*A61P 35/00* (2006.01)
*A61K 48/00* (2006.01)
*C08B 37/16* (2006.01)
*C08G 83/00* (2006.01)

(52) U.S. Cl.
CPC .......... *A61K 47/6951* (2017.08); *A61K 47/60* (2017.08); *A61K 48/0008* (2013.01); *A61P 35/00* (2018.01); *C08B 37/0015* (2013.01); *C08G 83/007* (2013.01)

(58) Field of Classification Search
None
See application file for complete search history.

(56) References Cited

U.S. PATENT DOCUMENTS

| | | | |
|---|---|---|---|
| 7,976,834 B2 | 7/2011 | Zhao et al. |
| 2003/0138398 A1 | 7/2003 | Okumura et al. |
| 2005/0042753 A1 | 2/2005 | Yang et al. |
| 2006/0211643 A1 | 9/2006 | Li et al. |
| 2007/0205395 A1 | 9/2007 | Nakajima et al. |
| 2008/0097039 A1 | 4/2008 | Ito et al. |
| 2009/0011933 A1 | 1/2009 | Ito et al. |
| 2009/0088546 A1 | 4/2009 | Ito et al. |
| 2009/0131588 A1 | 5/2009 | Ito et al. |
| 2009/0149579 A1 | 6/2009 | Ito et al. |
| 2009/0202461 A1 | 8/2009 | Rodriguez et al. |
| 2009/0215919 A1 | 8/2009 | Ito et al. |
| 2009/0234049 A1 | 9/2009 | Ito et al. |
| 2009/0281213 A1 | 11/2009 | Ito et al. |
| 2009/0297464 A1 | 12/2009 | Jegou |
| 2009/0312490 A1 | 12/2009 | Ruslim et al. |
| 2009/0312491 A1 | 12/2009 | Ruslim et al. |
| 2009/0312492 A1 | 12/2009 | Ruslim et al. |
| 2010/0047200 A1 | 2/2010 | Luukas et al. |
| 2010/0184934 A1 | 7/2010 | Ito et al. |
| 2011/0105688 A1 | 5/2011 | Ruslim et al. |
| 2011/0118376 A1 | 5/2011 | Hayashi et al. |
| 2011/0124823 A1 | 5/2011 | Hayashi et al. |
| 2012/0083582 A1 | 4/2012 | Ikeda et al. |
| 2012/0316278 A1 | 12/2012 | Inoue et al. |
| 2013/0224881 A1 | 8/2013 | Thompson et al. |
| 2013/0331562 A1 | 12/2013 | Yamasaki et al. |

(Continued)

FOREIGN PATENT DOCUMENTS

WO WO 2017/139505 A2 8/2017

OTHER PUBLICATIONS

Cha, Human Vaccines & Immunotherapeutics 8:11, 1734-1738, 2012. (Year: 2012).*
PCT International Search Report and Written Opinion dated Jan. 30, 2019 issued in PCT/US2018/053221.
PCT International Preliminary Report on Patentability dated Mar. 31, 2020 issued in PCT/US2018/053221.
Dandekar, et al. (2015) "Enhanced uptake and siRNA-mediated knockdown of a biologically relevant gene using cyclodextrin polyrotaxane." *Journal of Materials Chemistry B*, 3: 2590-2598.

(Continued)

*Primary Examiner* — Layla D Berry
(74) *Attorney, Agent, or Firm* — Tom Hunter; Weaver Austin Villeneuve & Sampson LLP

(57) ABSTRACT

In various embodiments a polyrotaxane carrier for in vivo delivery of a nucleic acid is provided. In certain embodiments the carrier comprises: a multi-arm polyethylene glycol (PEG) backbone comprising at least three arms; at least one cyclic compound having a cavity, where an arm of said multi-arm PEG backbone is threaded into the cavity of said cyclic compound forming an inclusion complex; a bulky moiety capping the terminal of the arm(s) threaded into said cyclic compound where said moiety inhibits dethreading of the cyclodextrin from the arm(s) of said backbone; and where at least one arm of said PEG backbone is free of cyclic compounds; and where said carrier has a net positive charge.

21 Claims, 66 Drawing Sheets

Specification includes a Sequence Listing.

(56) References Cited

U.S. PATENT DOCUMENTS

| | | |
|---|---|---|
| 2014/0058078 A1 | 2/2014 | Yamasaki et al. |
| 2014/0066403 A1 | 3/2014 | Yamasaki et al. |
| 2014/0066615 A1 | 3/2014 | Yamasaki et al. |
| 2014/0066616 A1 | 3/2014 | Yamasaki et al. |
| 2014/0296450 A1 | 10/2014 | Hayashi et al. |
| 2015/0051390 A1 | 2/2015 | Yokota et al. |
| 2015/0094463 A1 | 4/2015 | Oomori et al. |
| 2015/0240036 A1 | 8/2015 | Yamasaki et al. |
| 2016/0122605 A1 | 5/2016 | Hayashi |
| 2016/0199512 A1 | 7/2016 | Tamura et al. |
| 2016/0229963 A1 | 8/2016 | Masuhara et al. |
| 2017/0096559 A1 | 4/2017 | Nakai et al. |
| 2018/0312643 A1 | 11/2018 | Shimizu et al. |
| 2018/0362691 A1 | 12/2018 | Eisenbarth et al. |
| 2018/0371199 A1 | 12/2018 | Hayashi et al. |
| 2019/0119408 A1 | 4/2019 | Harada et al. |
| 2019/0161585 A1 | 5/2019 | Izumi et al. |
| 2019/0263961 A1 | 8/2019 | Shimizu et al. |
| 2019/0322814 A1 | 10/2019 | Ali et al. |
| 2019/0345294 A1 | 11/2019 | Hayashi et al. |
| 2020/0071467 A1 | 3/2020 | Shimizu et al. |
| 2020/0087418 A1 | 3/2020 | Inoue et al. |
| 2020/0172681 A1 | 6/2020 | Takenaka et al. |

OTHER PUBLICATIONS

Li Jiajing (2012) "Supramolecular Self-Assembled Nanostructures Based On Star Polymers For Drug And Gene Delivery," *Thesis, Department of Bioengineering, National University of Singapore*, pp. 1-274. Retrieved from the Internet: URL: <https://core.ac.uk/download/pdf/48678191.pdf> on Dec. 5, 2018.

Long, et al. (2016) "Postnatal genome editing partially restores dystrophin expression in a mouse model of muscular dystrophy." *Science,* 351(6271): 400-403.

Neal, et al. (2014) "Enhanced uptake and siRNA-mediated knockdown of a biologically relevant gene using cyclodextrin polyrotaxane." *Chem. Commun.,* 50: 5128-5142.

Nelson, et al. (2016) "In vivo genome editing improves muscle function in a mouse model of Duchenne muscular dystrophy," *Science,* 351: 403-407.

Reardon, S. (2016) "First CRISPR clinical trial gets green light from US panel." *Nature,* Retrieved from the Internet: URL: doi:10.1038/nature.2016.20137 [3 pages].

Sun, et al. (2015) "Self-Assembled DNA Nanoclews for the Efficient Delivery of CRISPR-Cas9 for Genome Editing." *Angew Chem Int Ed Engl.,* 54: 12029-12033.

Tabebordbar, et al. (2016) "In vivo gene editing in dystrophic mouse muscle and muscle stem cells." *Science,* 351: 407-411.

Wang, et al. (2013) "Biomimetic pseudopolyrotaxane prodrug micelles with high drug content for intracellular drug delivery." *Chem. Commun.,* 49: 7123-7125.

Wang, et al. (2016) "Efficient delivery of genome-editing proteins using bioreducible lipid nanoparticles." *Proceedings of the National Academy of Sciences,* 113: 2868-2873.

Yin, et al. (2016) "Therapeutic genome editing by combined viral and non-viral delivery of CRISPR system components in vivo." *Nat Biotech,* 34: 328-333 [Advance Online Publication—published online Feb. 1, 2016; doi:10.1038/nbt.3471; 26 pages].

Zuris, et al. (2015) "Cationic lipid-mediated delivery of proteins enables efficient protein-based genome editing in vitro and in vivo." *Nat Biotech,* 33: 73-80.

EP Extended European Search Report dated Apr. 29, 2021 issued in EP18861241.0.

Ji et al. (2019) "Development of self-assembled multi-arm polyrotaxanes nanocarries for systemic plasmid delivery in vivo" Biomaterials 192: 416-428.

\* cited by examiner

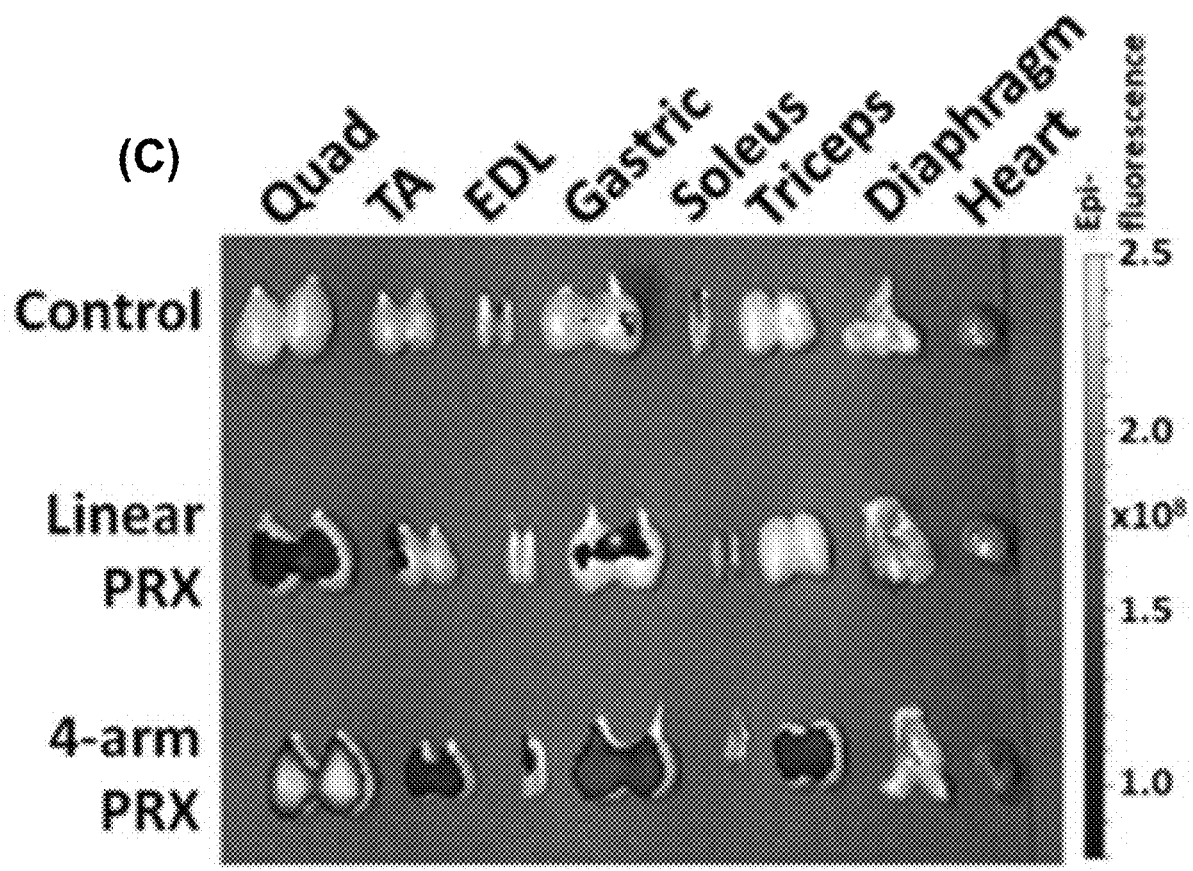
*FIG. 6, cont'd.*

Mechanism of DTT reaction

Size 147.7±1.6 nm
PDI 0.151

Size 1048.1±14.3 nm
PDI 0.301

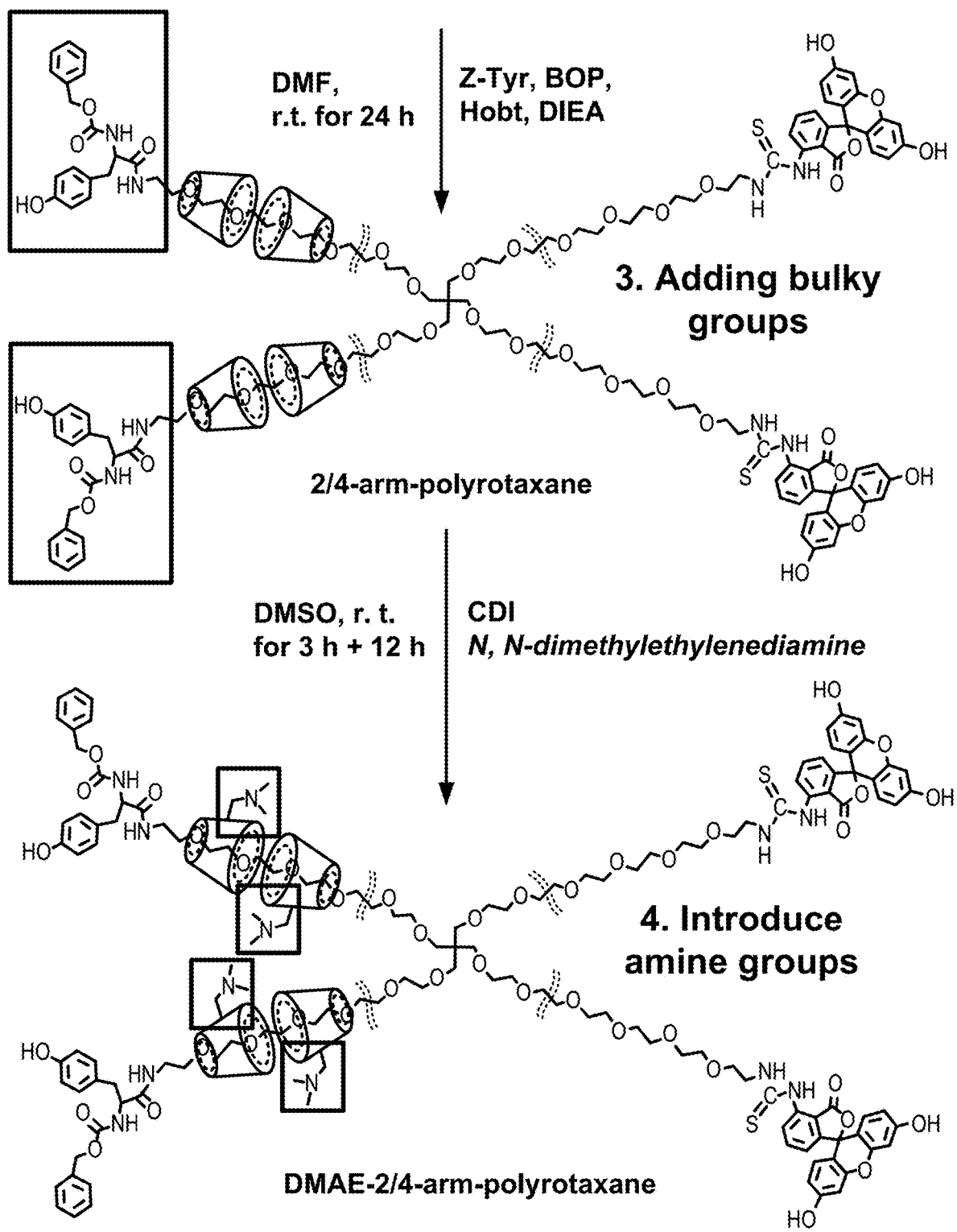
FIG. 11, cont'd.

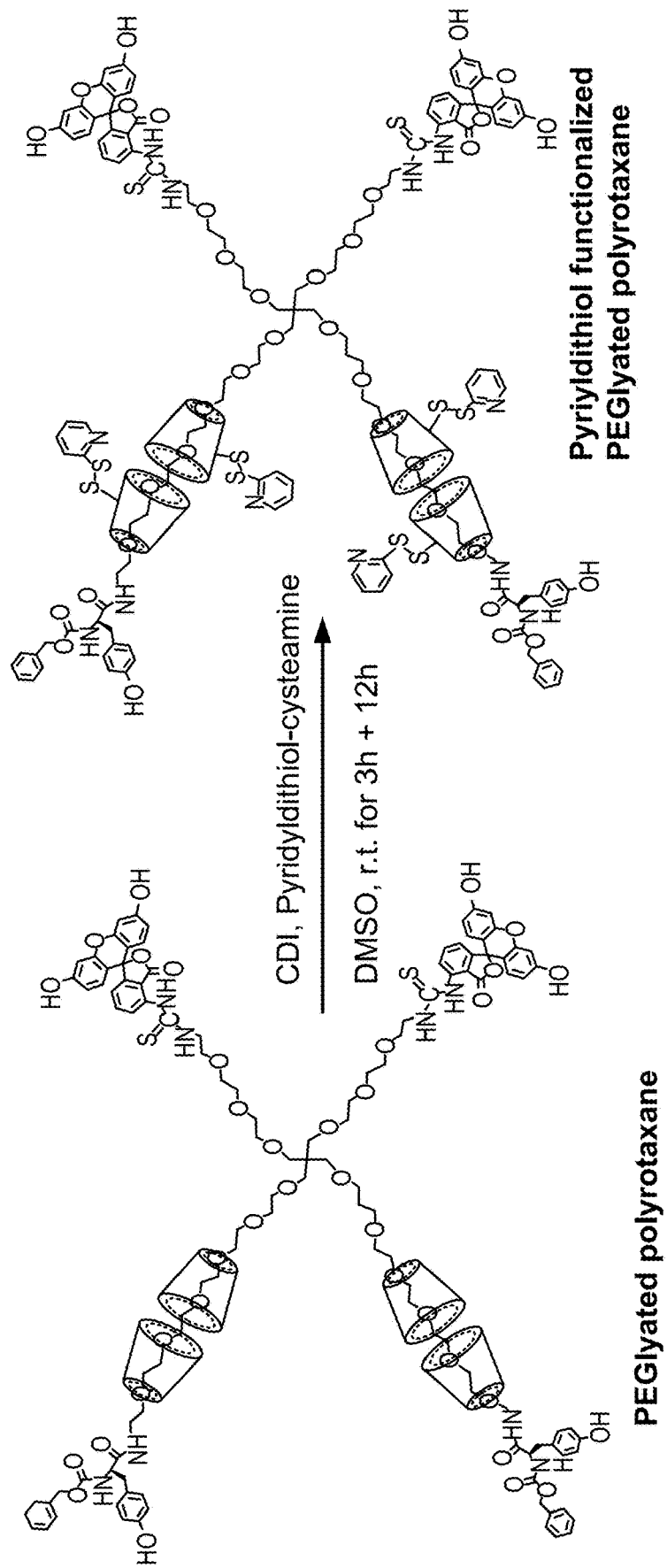
FIG. 12, cont'd.

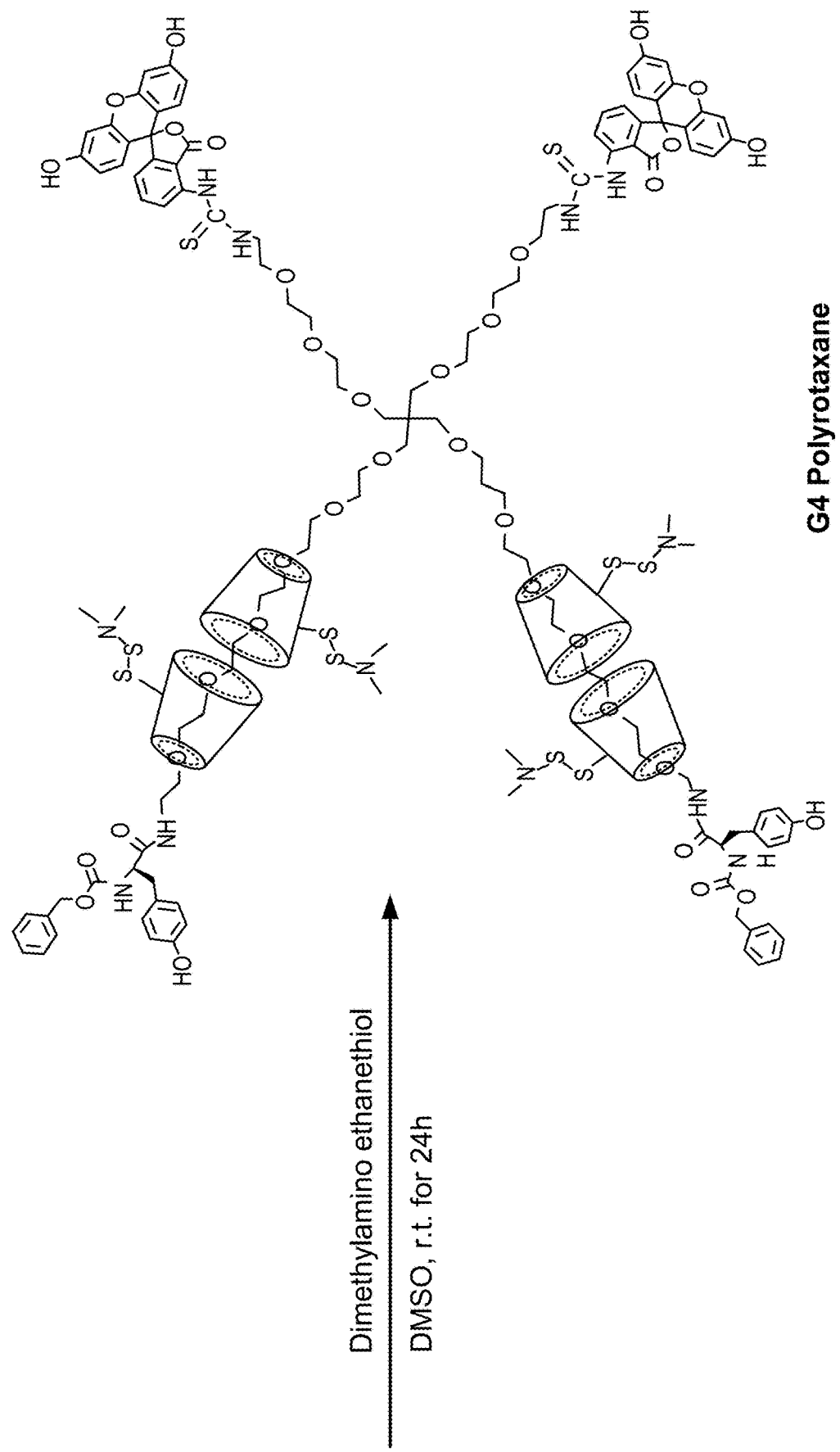
FIG. 12, cont'd.

CRISPR plasmid (MW= 9.3 kbp)

CFP plasmid (MW= 3.4 kbp)

B16 melanoma cells transfected with G3 PRX/GFP plasmid

Panc-1 cells (KRAS mutated)

HCT116 cells (KRAS mutated)

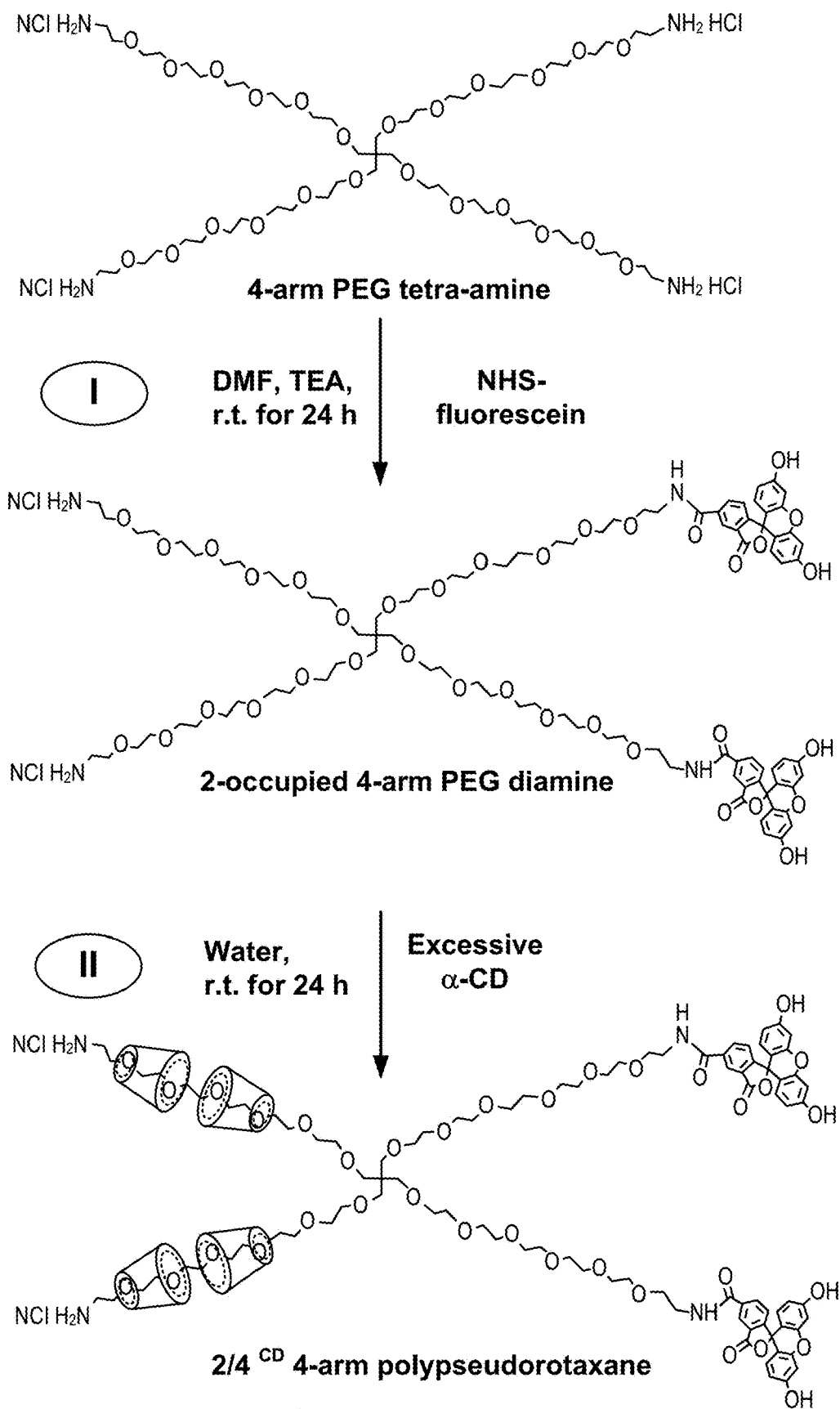
FIG. 18, cont'd.

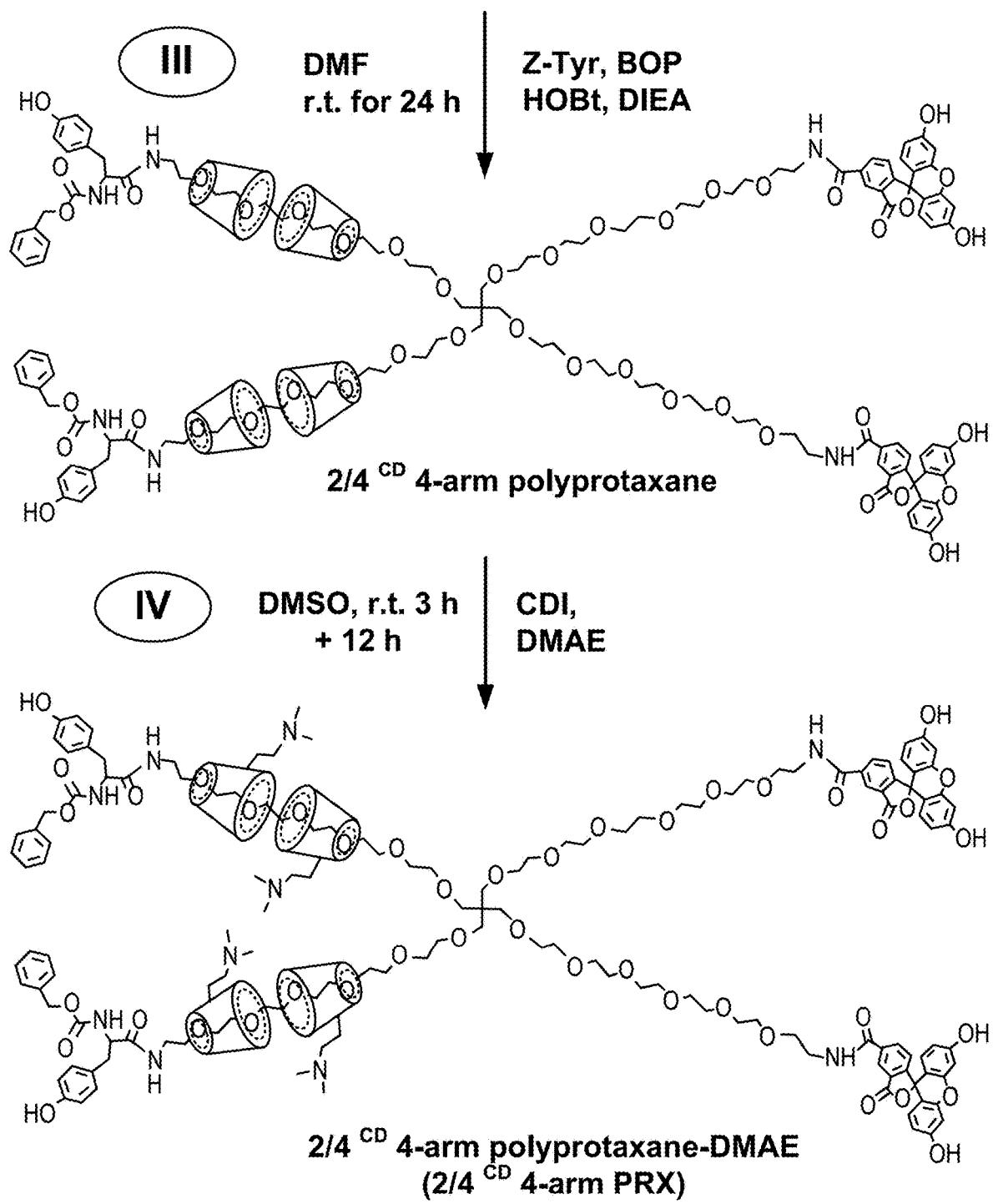
FIG. 18, cont'd.

(C) Cationic charge density (per CD) = $\frac{(\delta a)/6}{(\delta a)/6}$
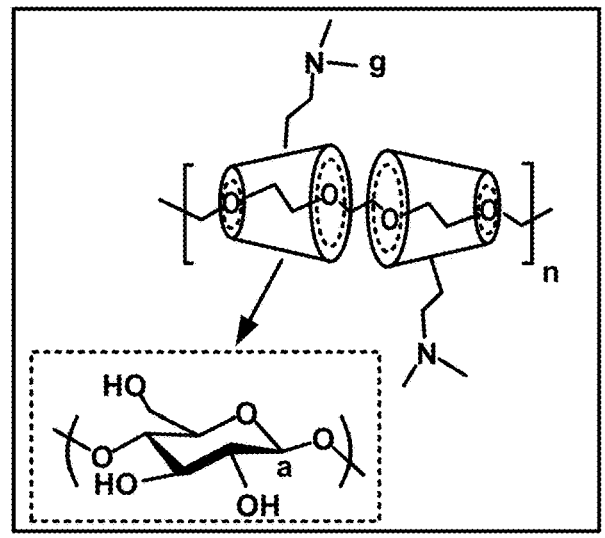
4-arm PRX:
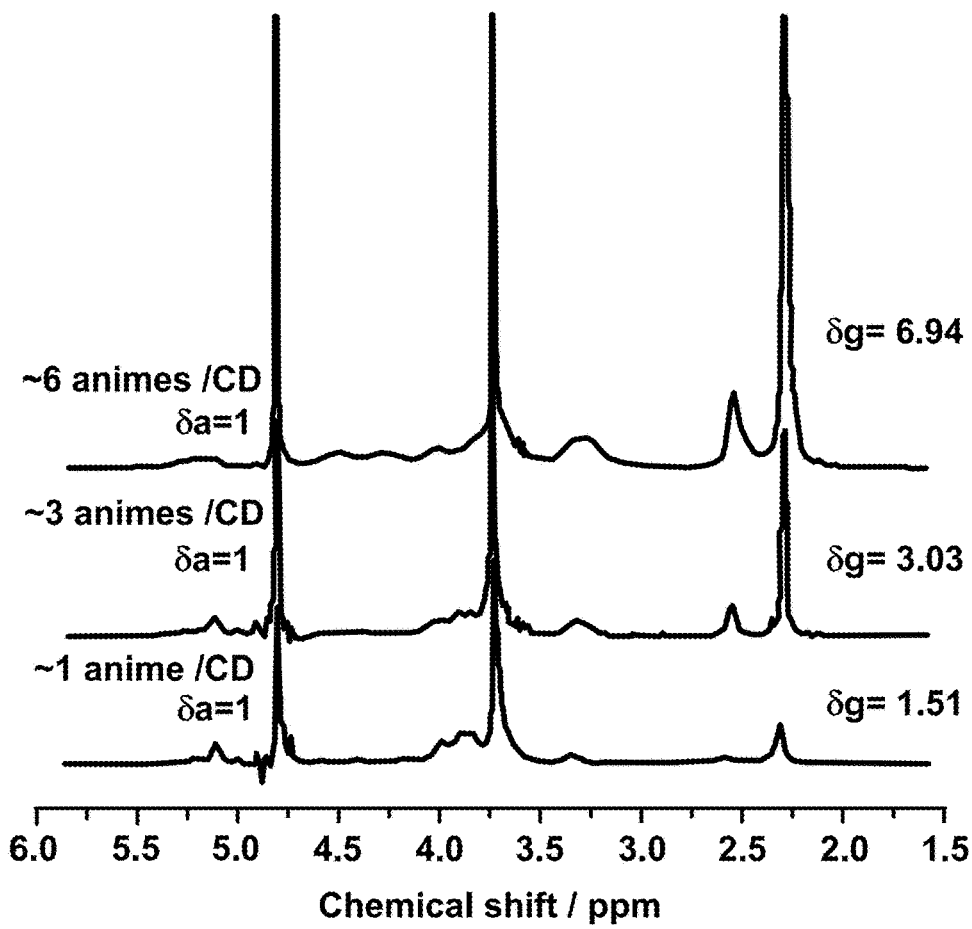
FIG. 18, cont'd.

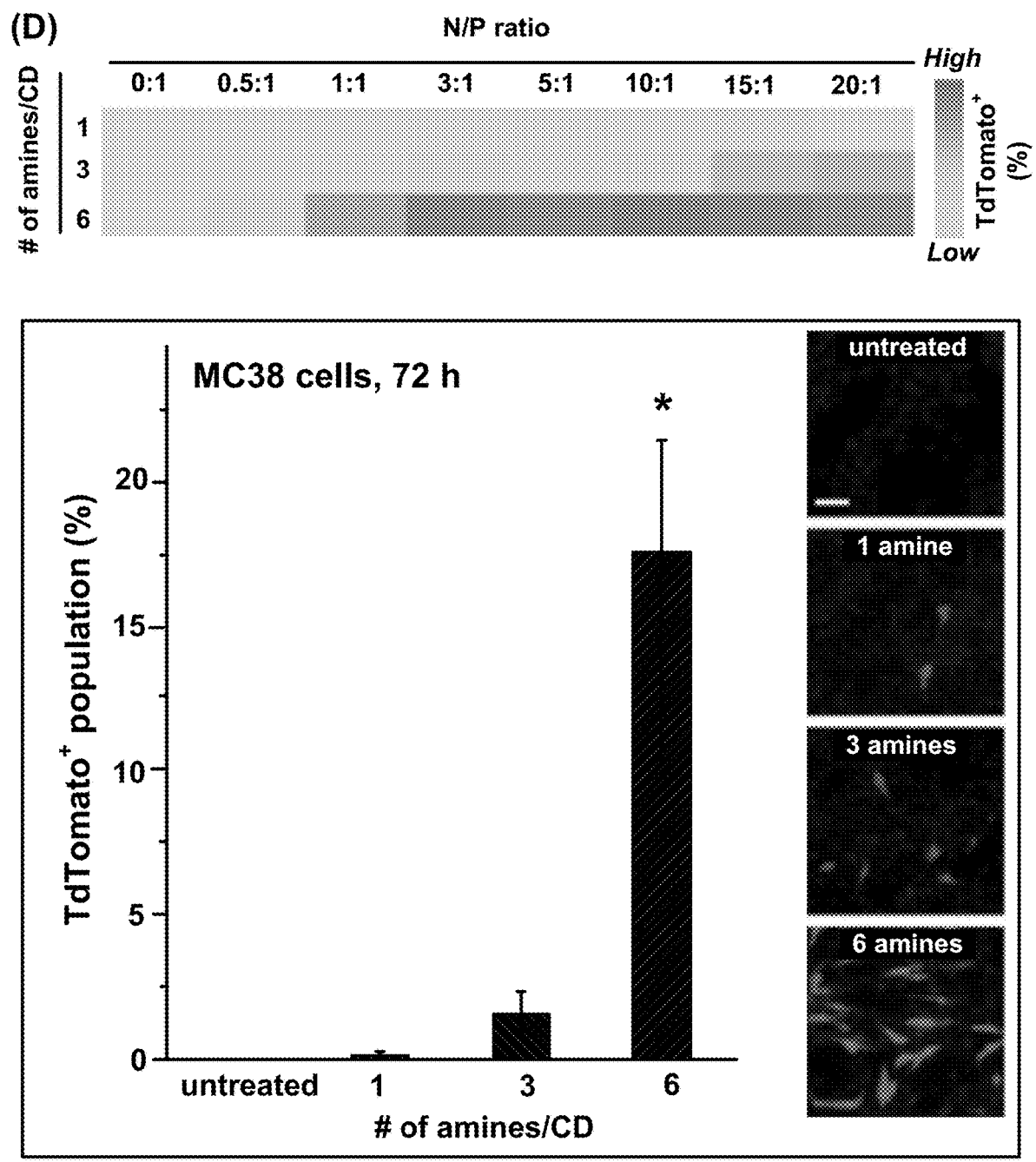
*FIG. 18, cont'd.*

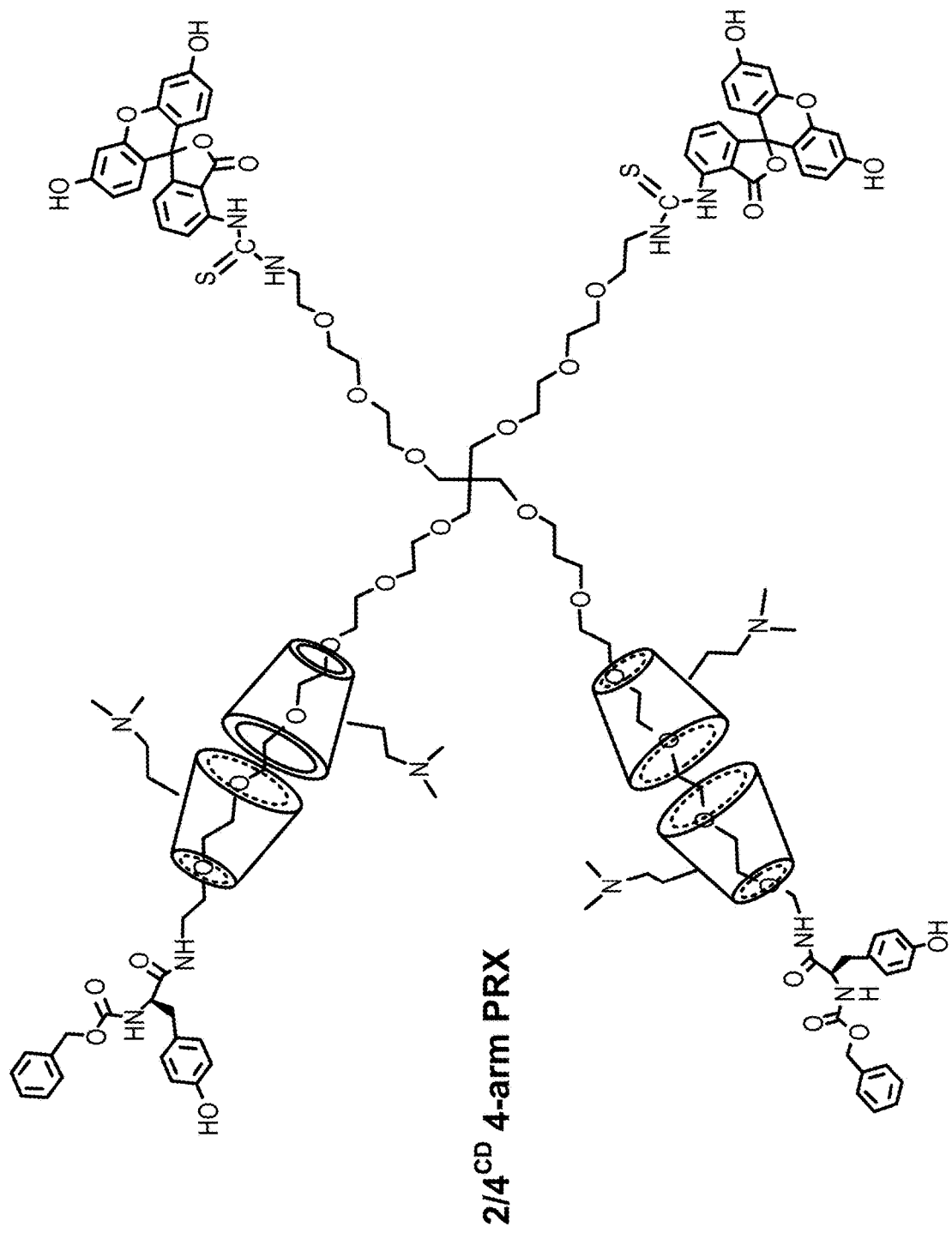
FIG. 19, cont'd.

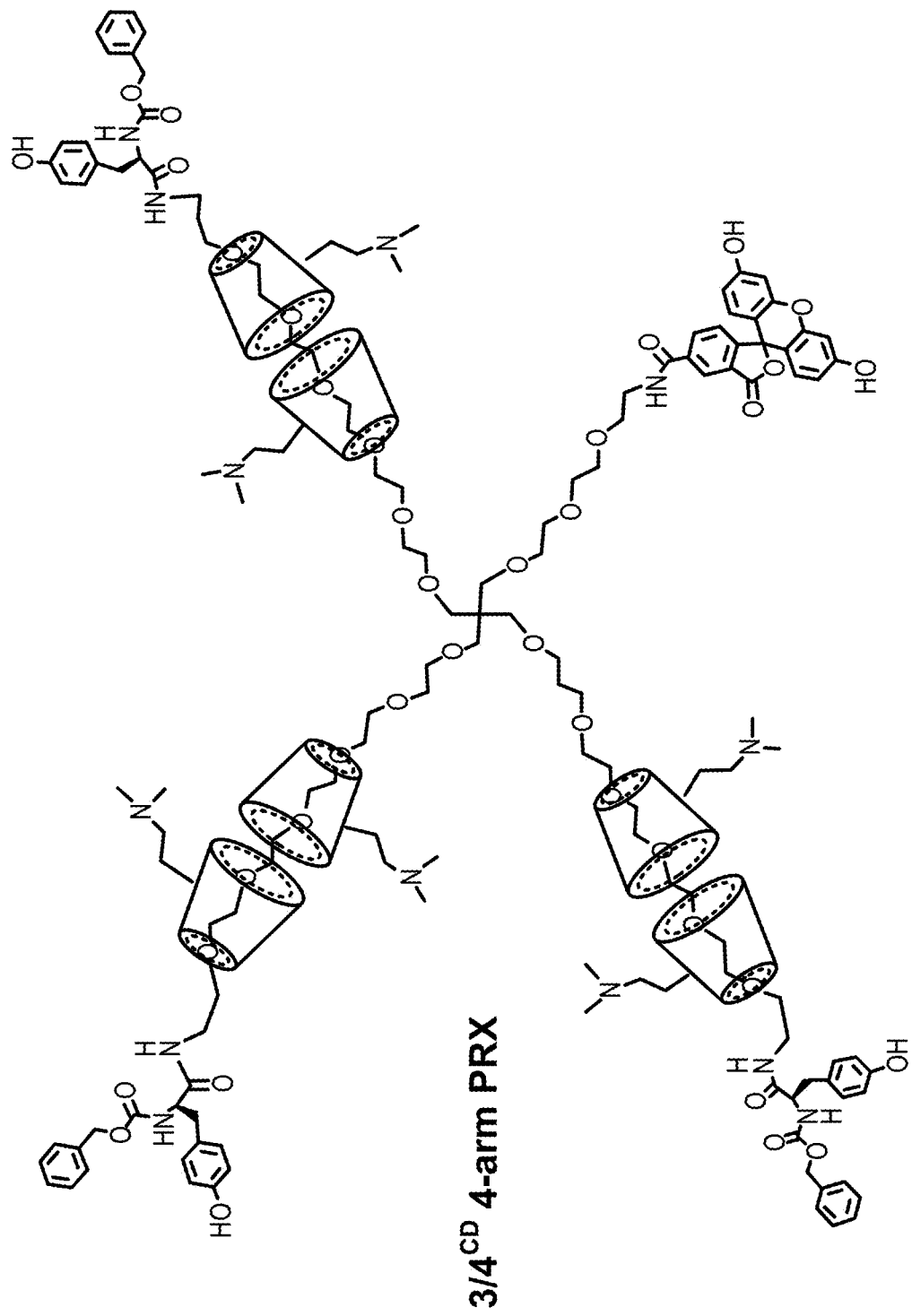
FIG. 19, cont'd.

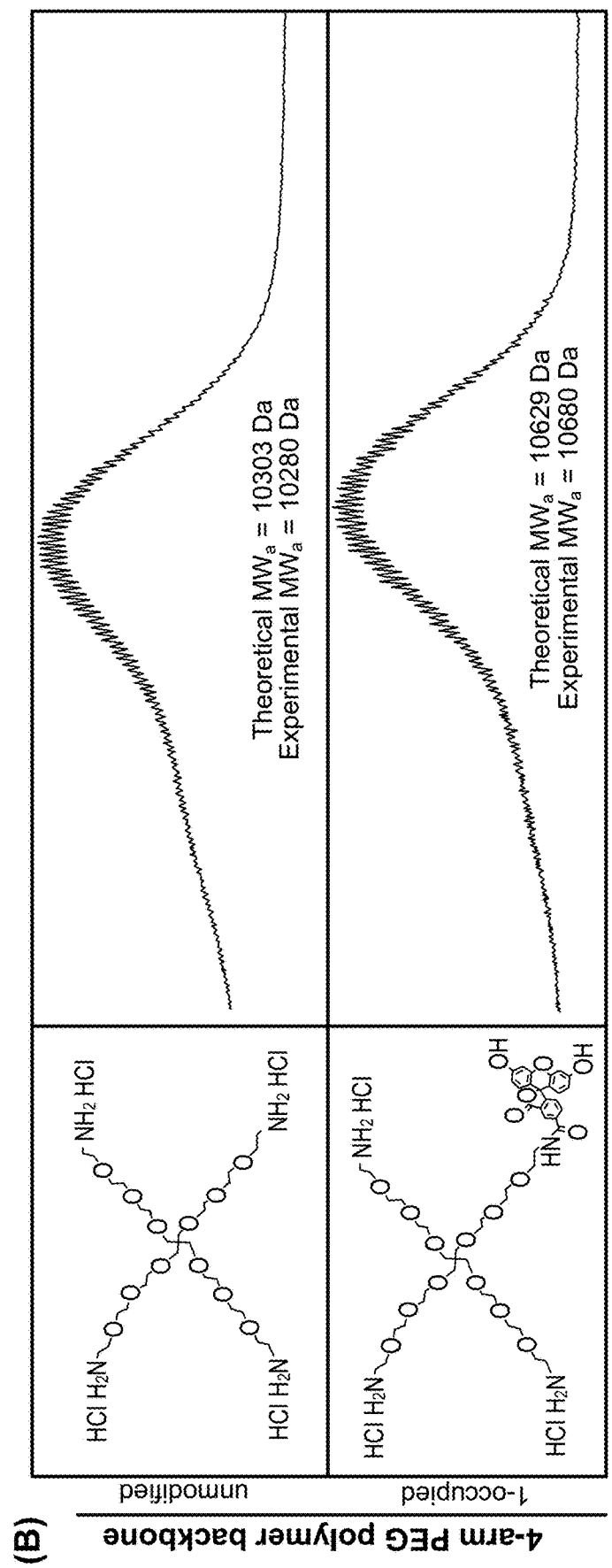
FIG. 19, cont'd.

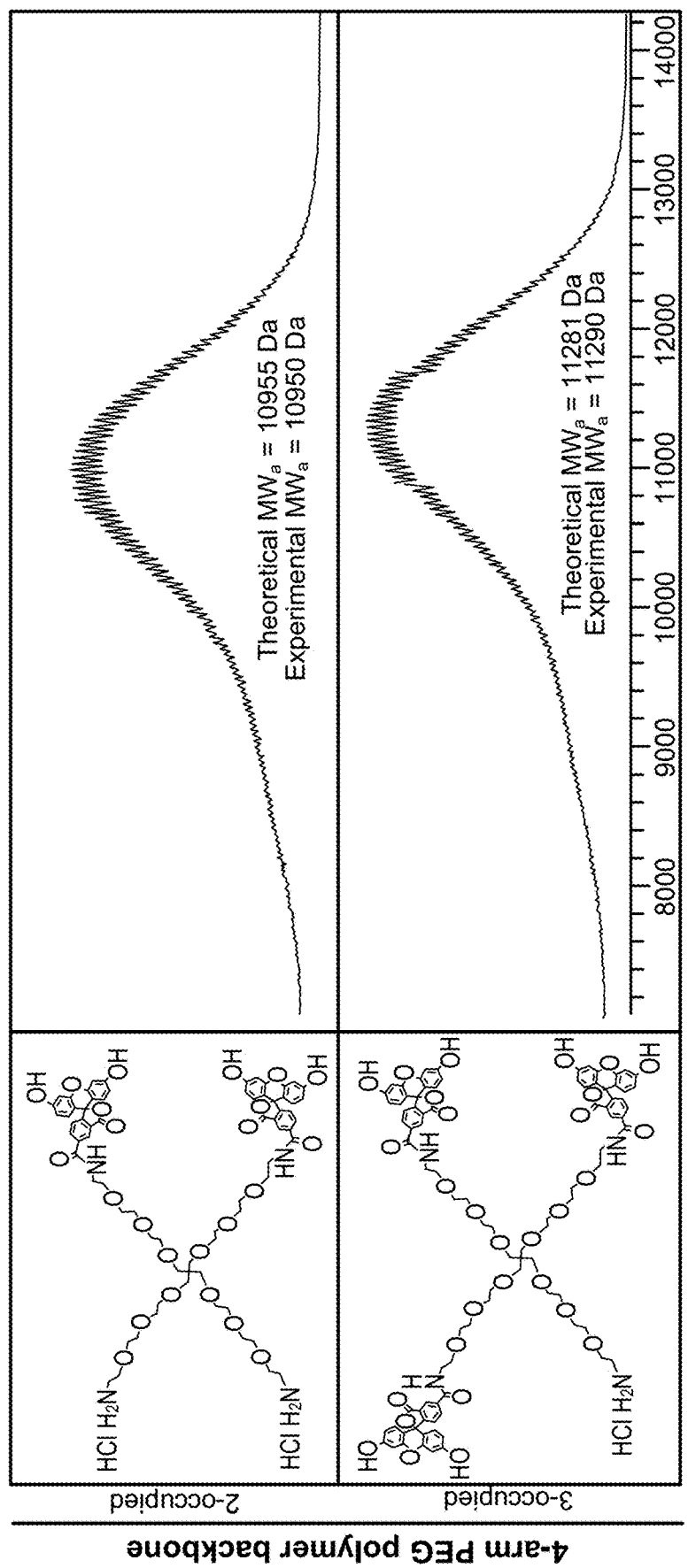
FIG. 19, cont'd.

(C)
$$\text{Total CD per PRX} = \frac{\delta(a)/6}{[\delta(b\text{-}f) - 4\delta(a)]/4} \times \frac{MW_{(4\text{-arm PEG})}}{MW_{(EO)}}$$
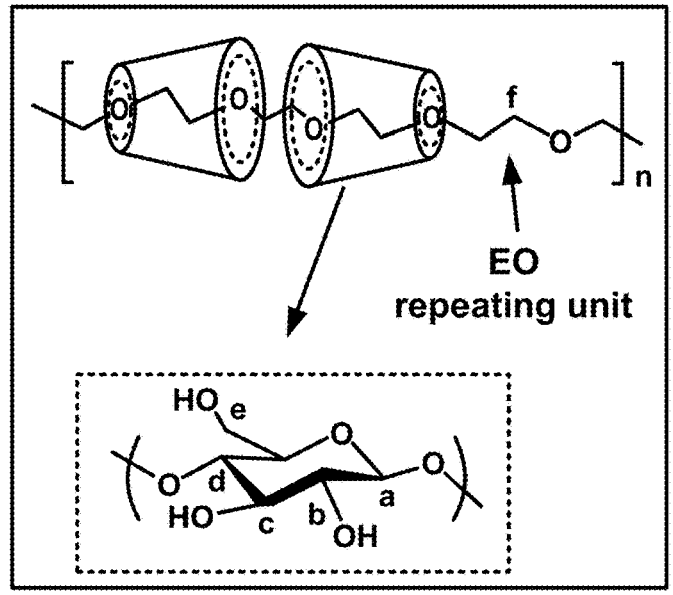
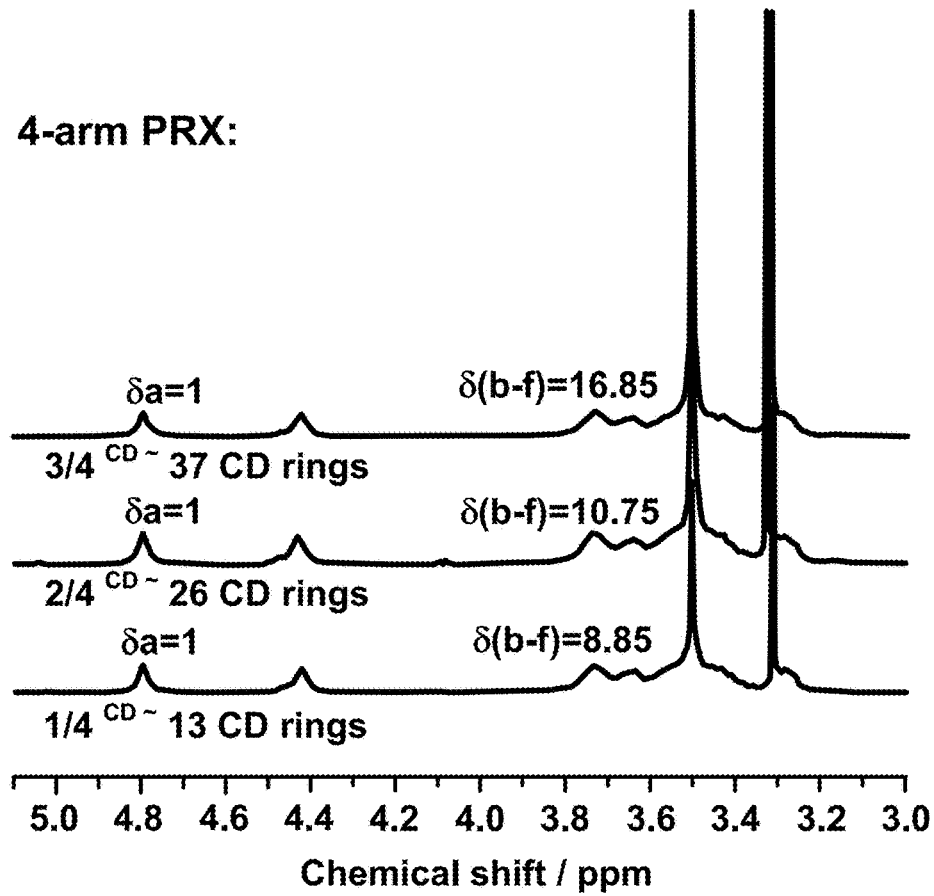
FIG. 19, cont'd.

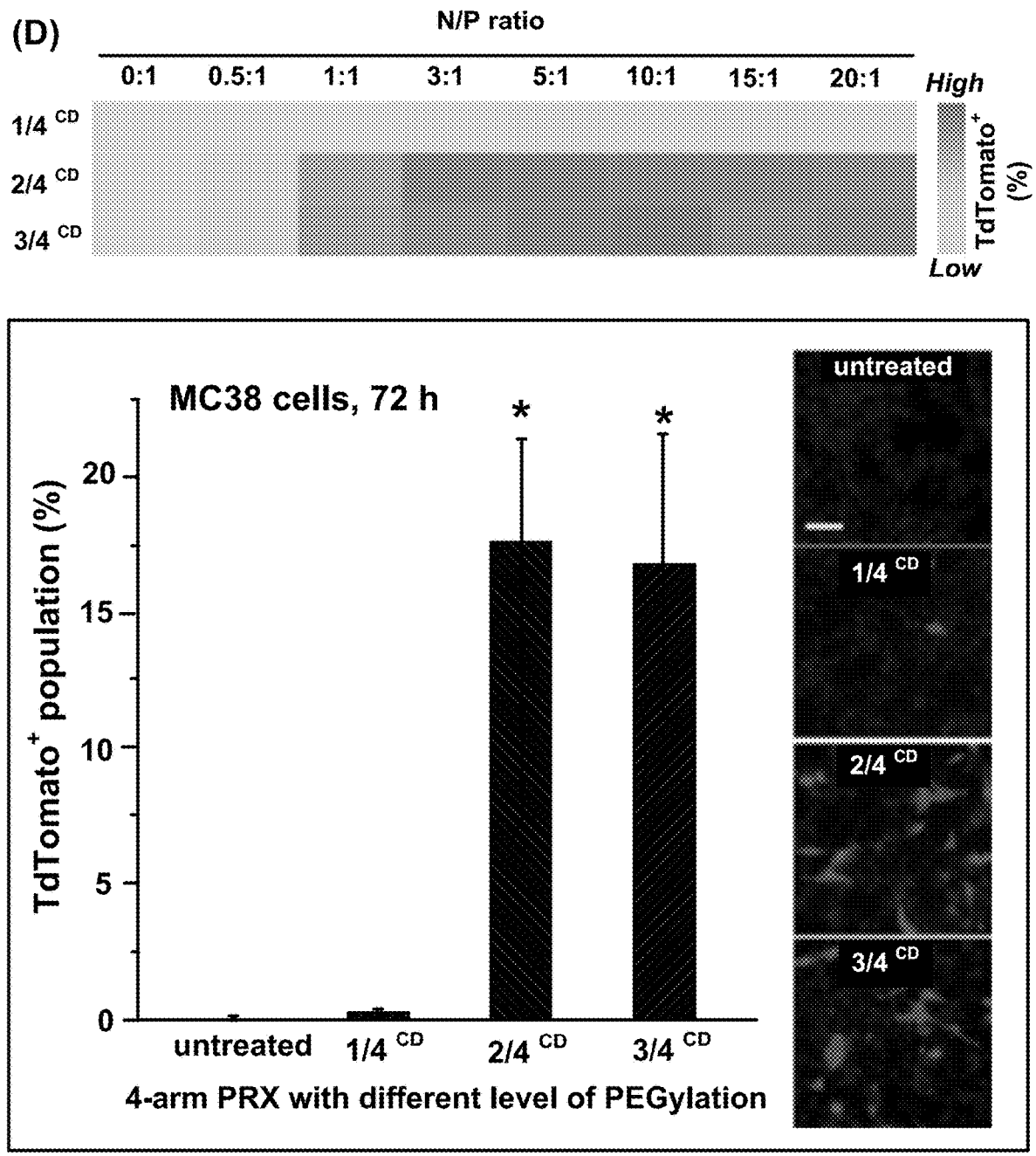
FIG. 19, cont'd.

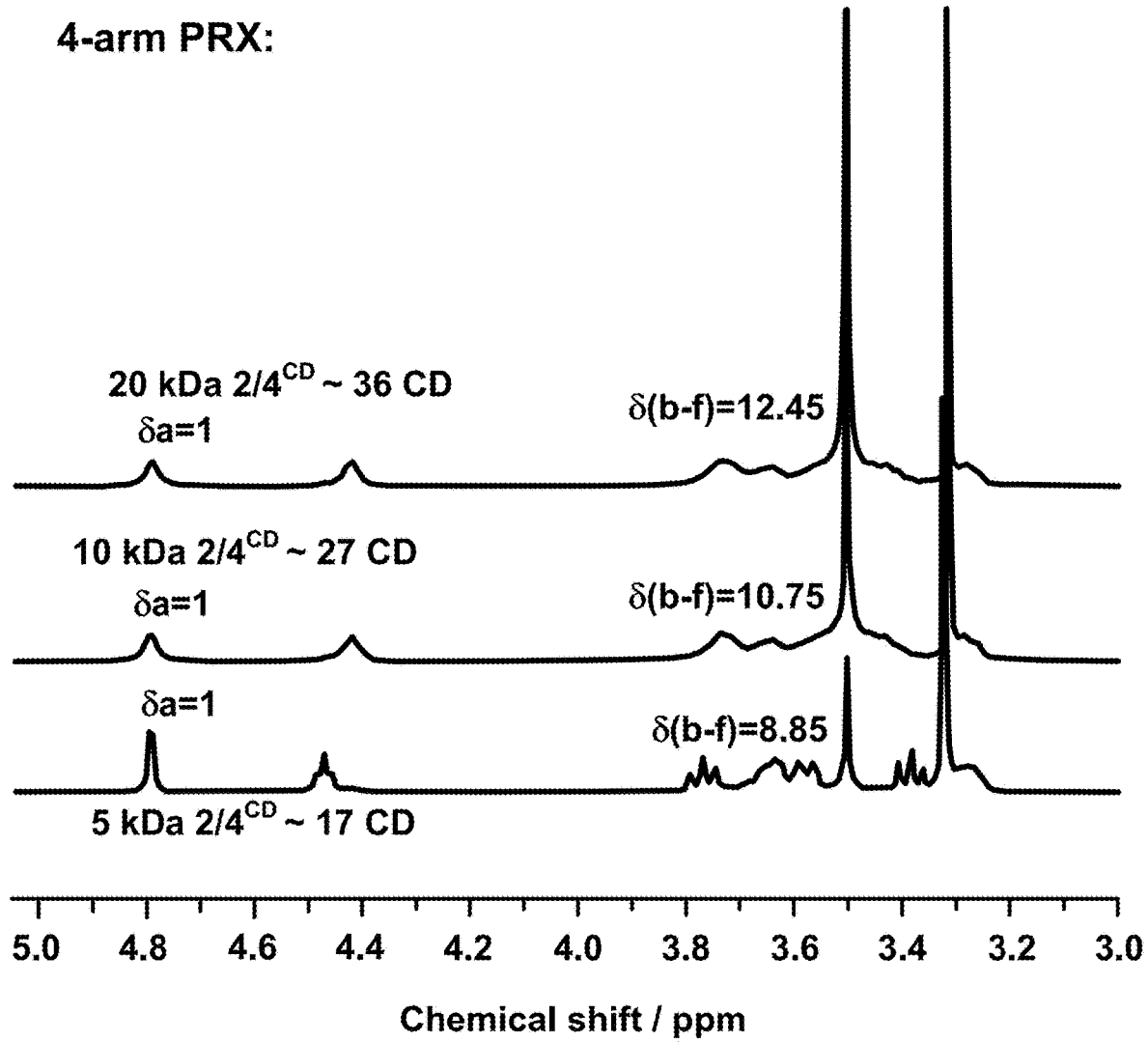
FIG. 19, cont'd.

(C)
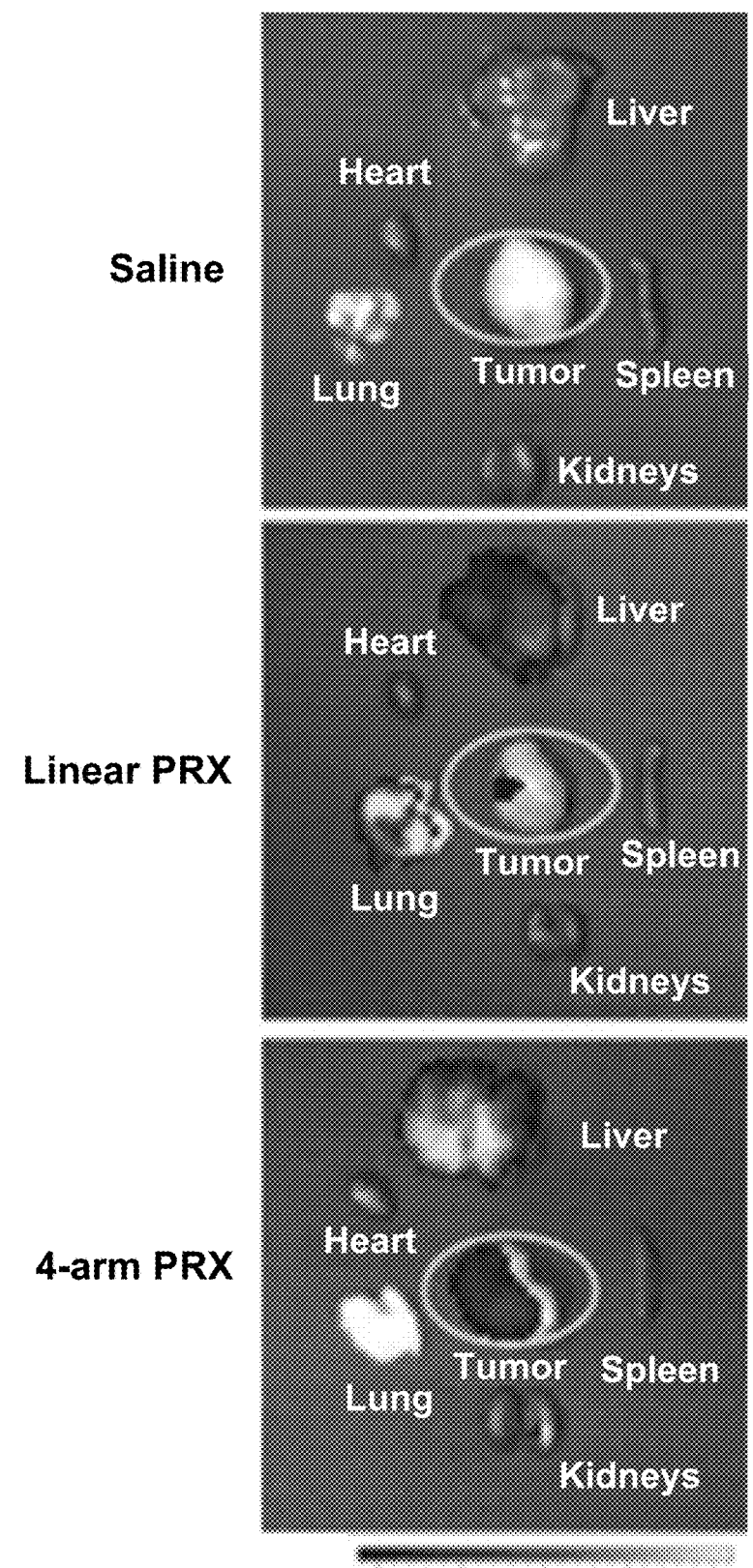
FIG. 20, cont'd.

(C) Continued
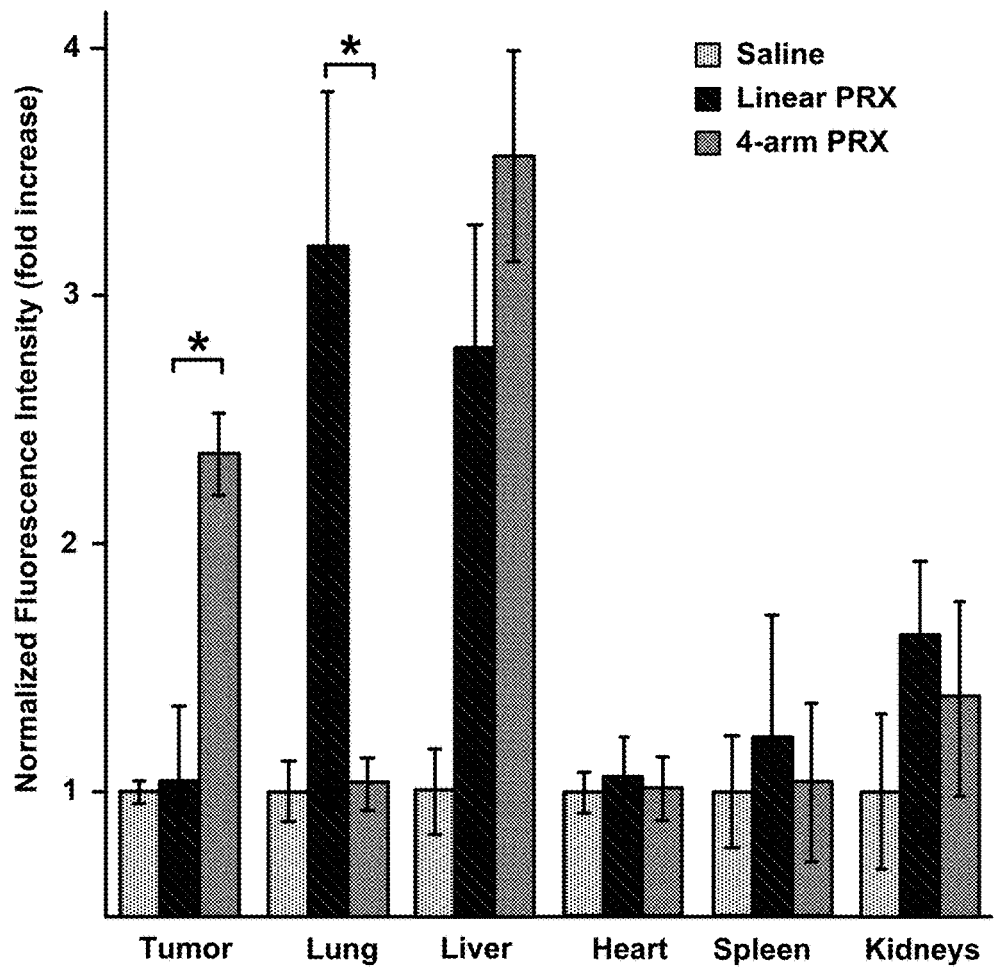
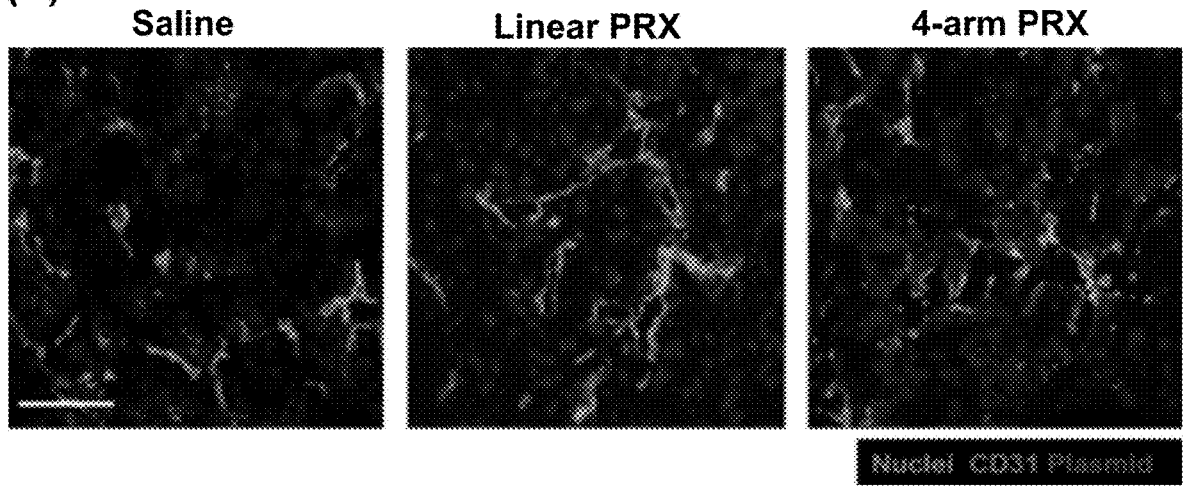
*FIG. 20, cont'd.*

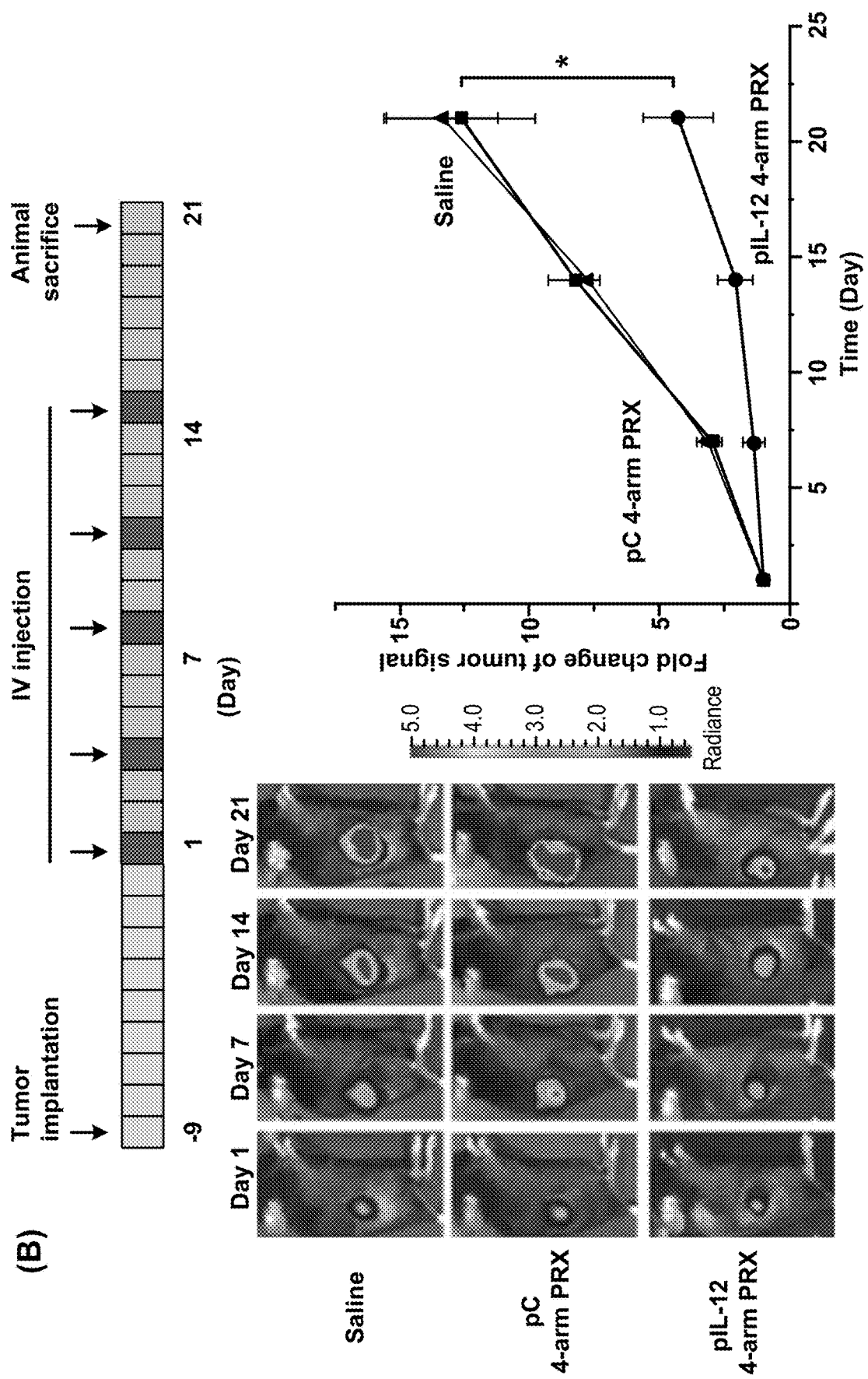
FIG. 21, cont'd.

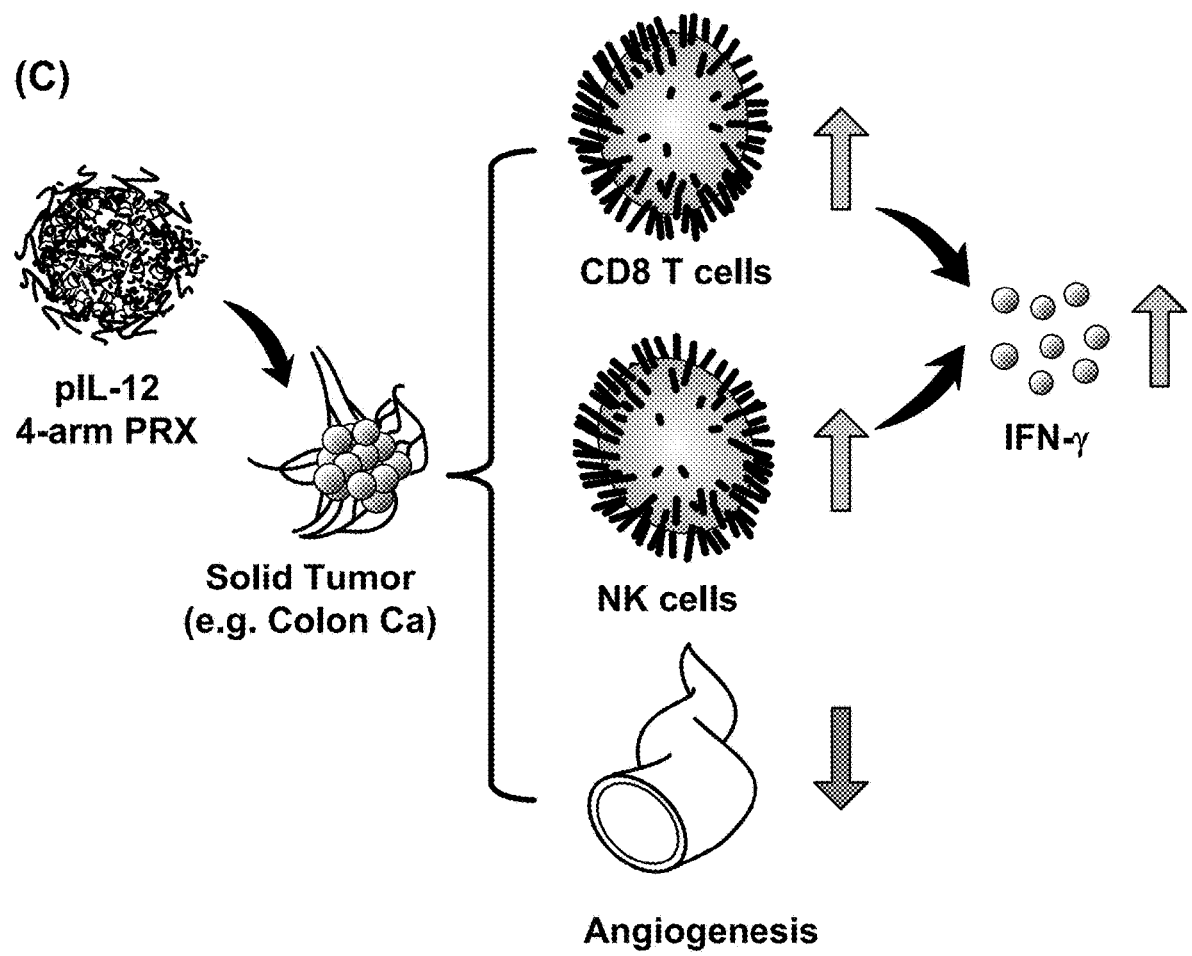
FIG. 21, cont'd.

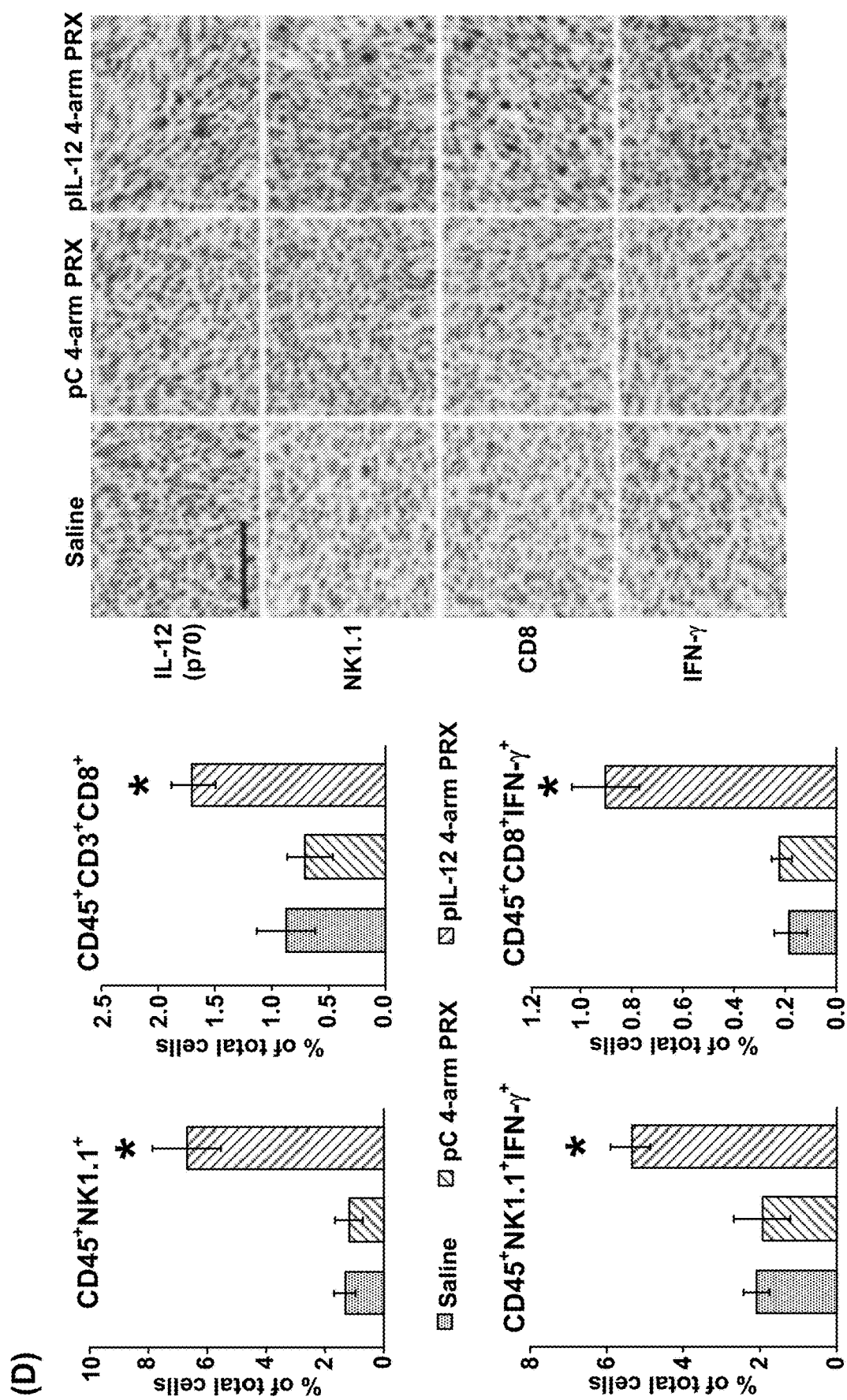
FIG. 21, cont'd.

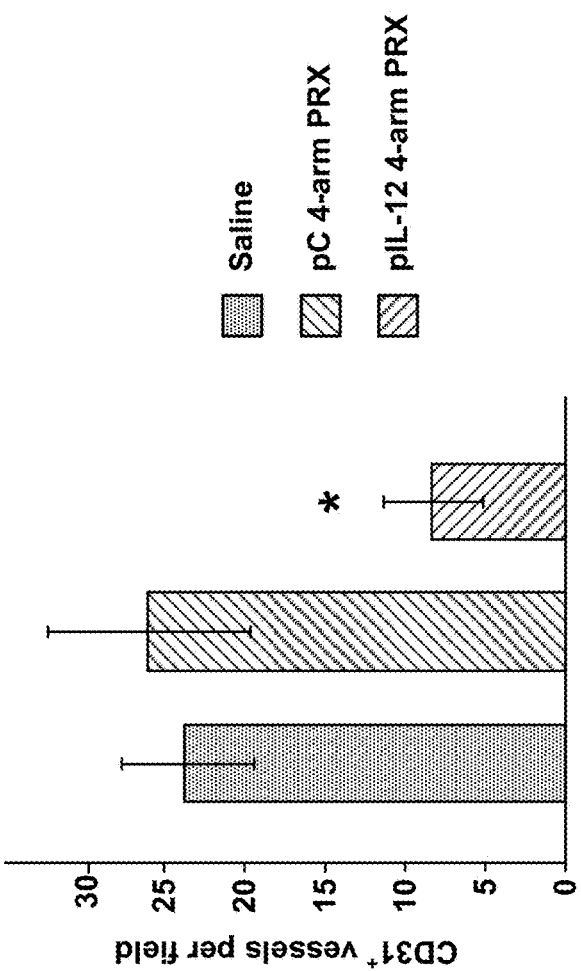
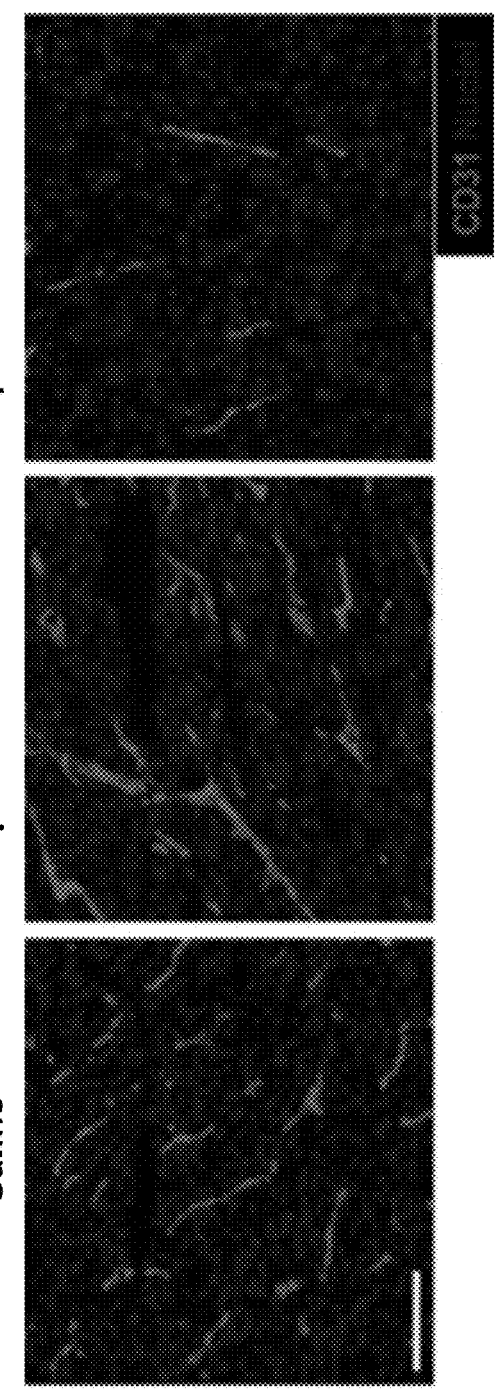
FIG. 21, cont'd.

(A)

| | 7 Day | | | 21 Day | | | 7 Day | 21 Day |
|---|---|---|---|---|---|---|---|---|
| | Saline | pC 4-arm PRX | pIL-12 4-arm PRX | Saline | pC 4-arm PRX | pIL-12 4-arm PRX | rIL-12 | rIL-12 |
| ALT (U/L) | 12.5 ± 2.3 | 16 ± 1.7 | 23.3 ± 2.4 | 20.4 ± 3.1 | 19.2 ± 2.8 | 21.7 ± 3.5 | 48.0 ± 3.8* | 30.8 ± 6.3* |
| AST (U/L) | 76.2 ± 13.5 | 83.0 ± 21.2 | 85.7 ± 14.5 | 87.7 ± 17.1 | 98.3 ± 16.0 | 90.8 ± 18.7 | 102.5 ± 7.9* | 204.1 ± 30.8* |
| ALP (U/L) | 72.9 ± 7.6 | 80.3 ± 11.6 | 84.3 ± 10.1 | 67.5 ± 9.2 | 79.5 ± 6.0 | 83.5 ± 9.1 | 129.3 ± 15.2* | 112.4 ± 9.2* |
| BUN (mg/dL) | 18.3 ± 1.9 | 19.6 ± 1.4 | 17.7 ± 2.1 | 21.7 ± 2.5 | 24.2 ± 3.3 | 19.0 ± 1.6 | 39.4 ± 5.3* | 28.4 ± 4.3* |
| CREAT (mg/dL) | 0.27 ± 0.02 | 0.33 ± 0.03 | 0.32 ± 0.05 | 0.30 ± 0.04 | 0.32 ± 0.05 | 0.34 ± 0.03 | 0.47 ± 0.03* | 0.40 ± 0.02 |
| RBC ($10^7/\mu L$) | 9.14 ± 0.61 | 8.82 ± 0.38 | 8.98 ± 0.57 | 8.21 ± 0.44 | 9.02 ± 0.72 | 8.61 ± 0.41 | 7.73 ± 0.87* | 7.92 ± 0.77* |
| PLT ($10^7/\mu L$) | 819.8 ± 90.4 | 764.0 ± 134.9 | 776.1 ± 115.9 | 843.6 ± 167.5 | 813.4 ± 75.8 | 811.2 ± 93.1 | 735.0 ± 69.2 | 604.0 ± 59.1* |
| WBC ($10^7/\mu L$) | 4.14 ± 0.36 | 3.82 ± 0.28 | 1.98 ± 0.17* | 3.91 ± 0.24 | 3.74 ± 0.12 | 3.67 ± 0.41 | 1.03 ± 0.05* | 4.07 ± 0.55 |
| NE ($10^7/\mu L$) | 1.20 ± 0.21 | 1.37 ± 0.08 | 0.73 ± 0.17* | 0.91 ± 0.15 | 1.02 ± 0.09 | 1.23 ± 0.21 | 0.56 ± 0.13* | 1.15 ± 0.17 |
| LY ($10^7/\mu L$) | 2.72 ± 0.61 | 3.3 ± 0.58 | 0.98 ± 0.27* | 3.2 ± 0.45 | 3.02 ± 0.49 | 2.61 ± 0.41 | 1.63 ± 0.32* | 1.82 ± 0.11* |
| MO ($10^7/\mu L$) | 0.34 ± 0.12 | 0.43 ± 0.08 | 0.26 ± 0.07 | 0.32 ± 0.05 | 0.37 ± 0.09 | 0.44 ± 0.14 | 0.27 ± 0.03 | 0.23 ± 0.04 |

*FIG. 22*

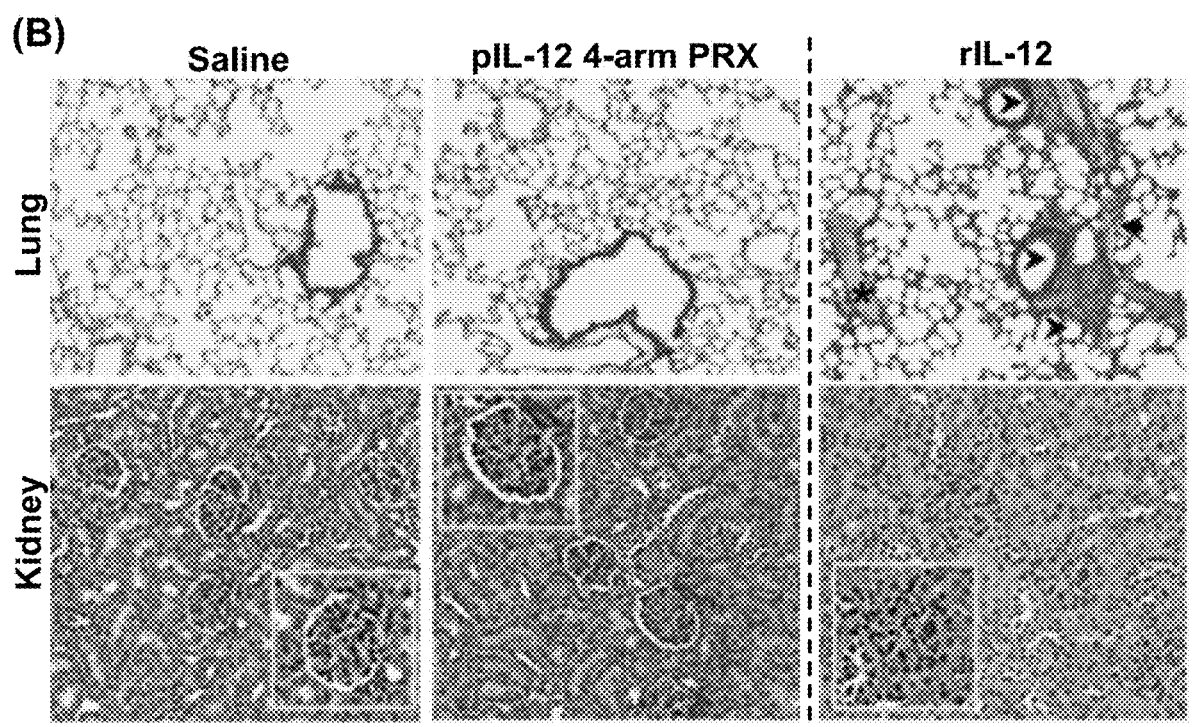
FIG. 22, cont'd.

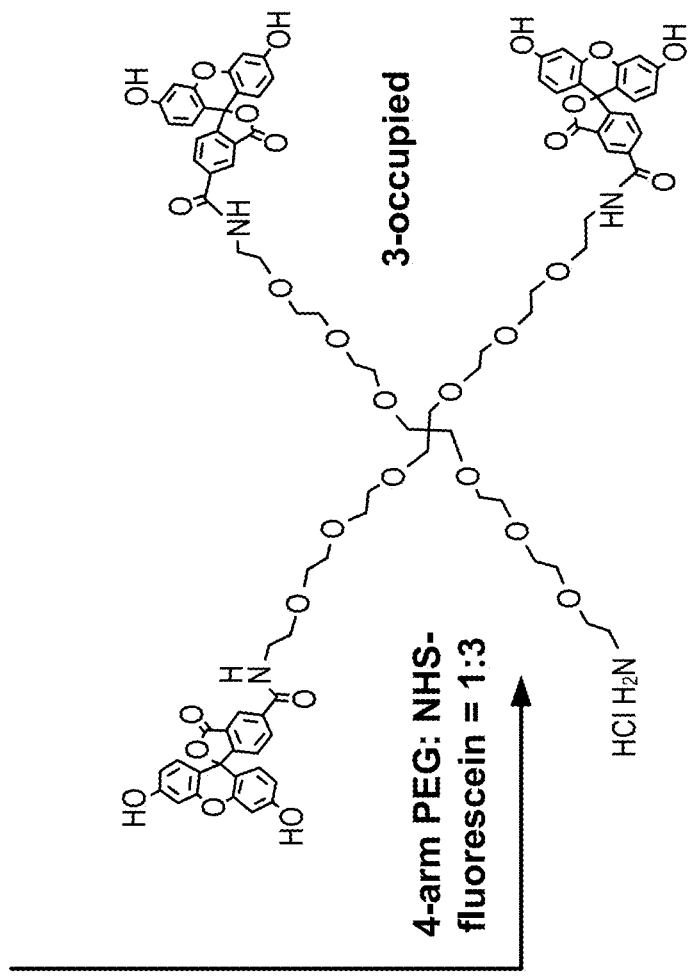
FIG. 25, cont'd.

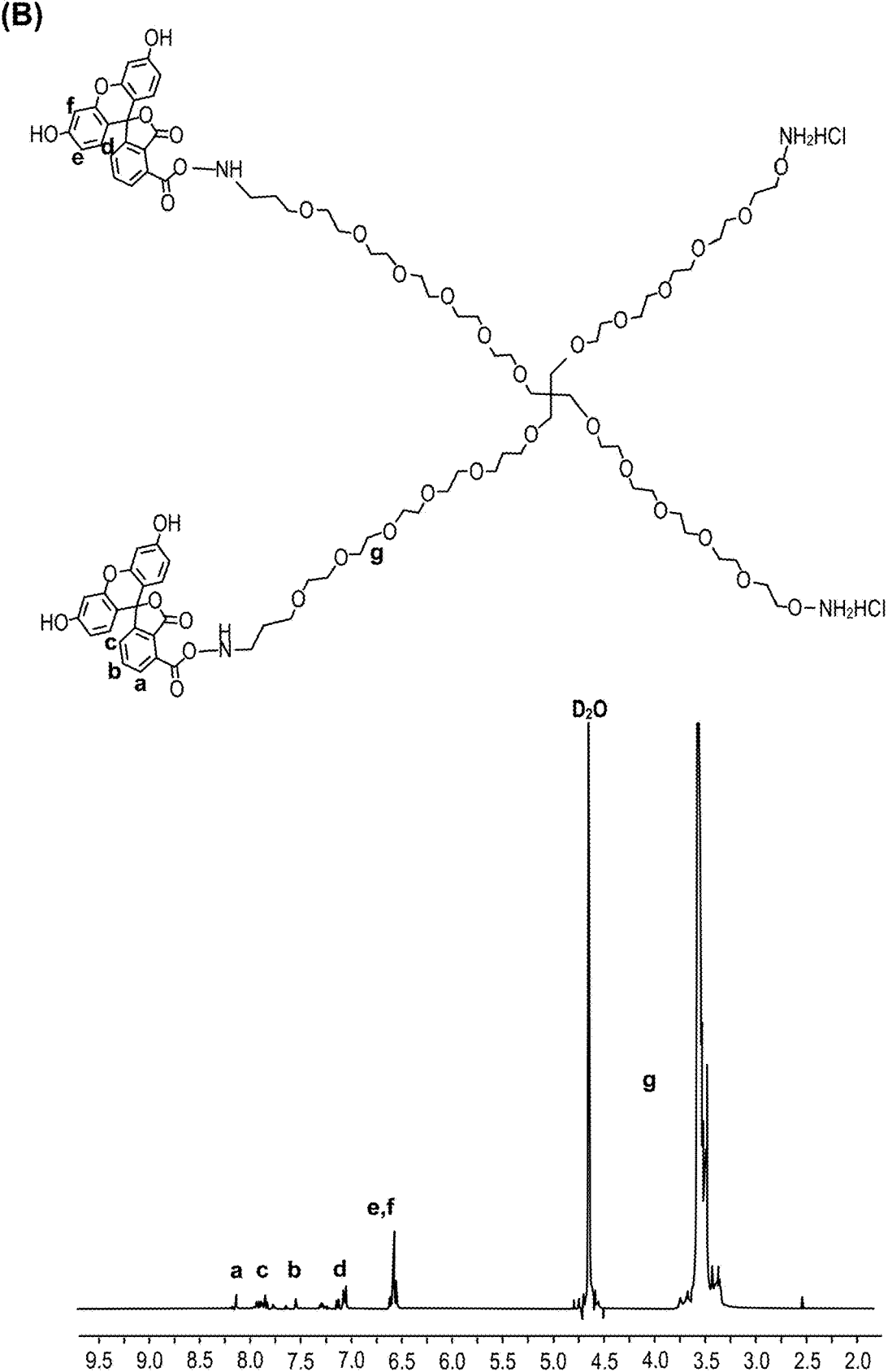
FIG. 25, cont'd.

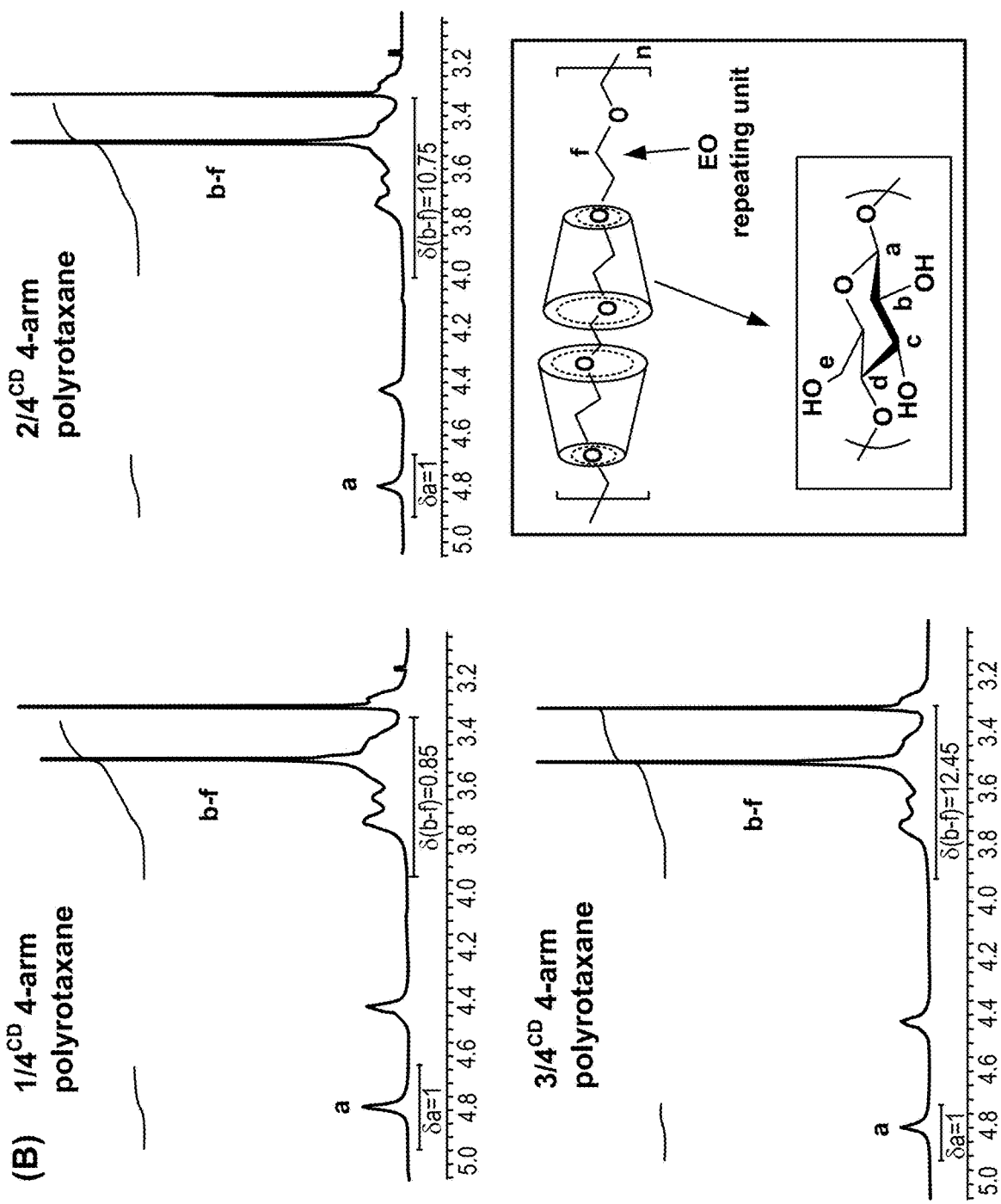
FIG. 26, cont'd.

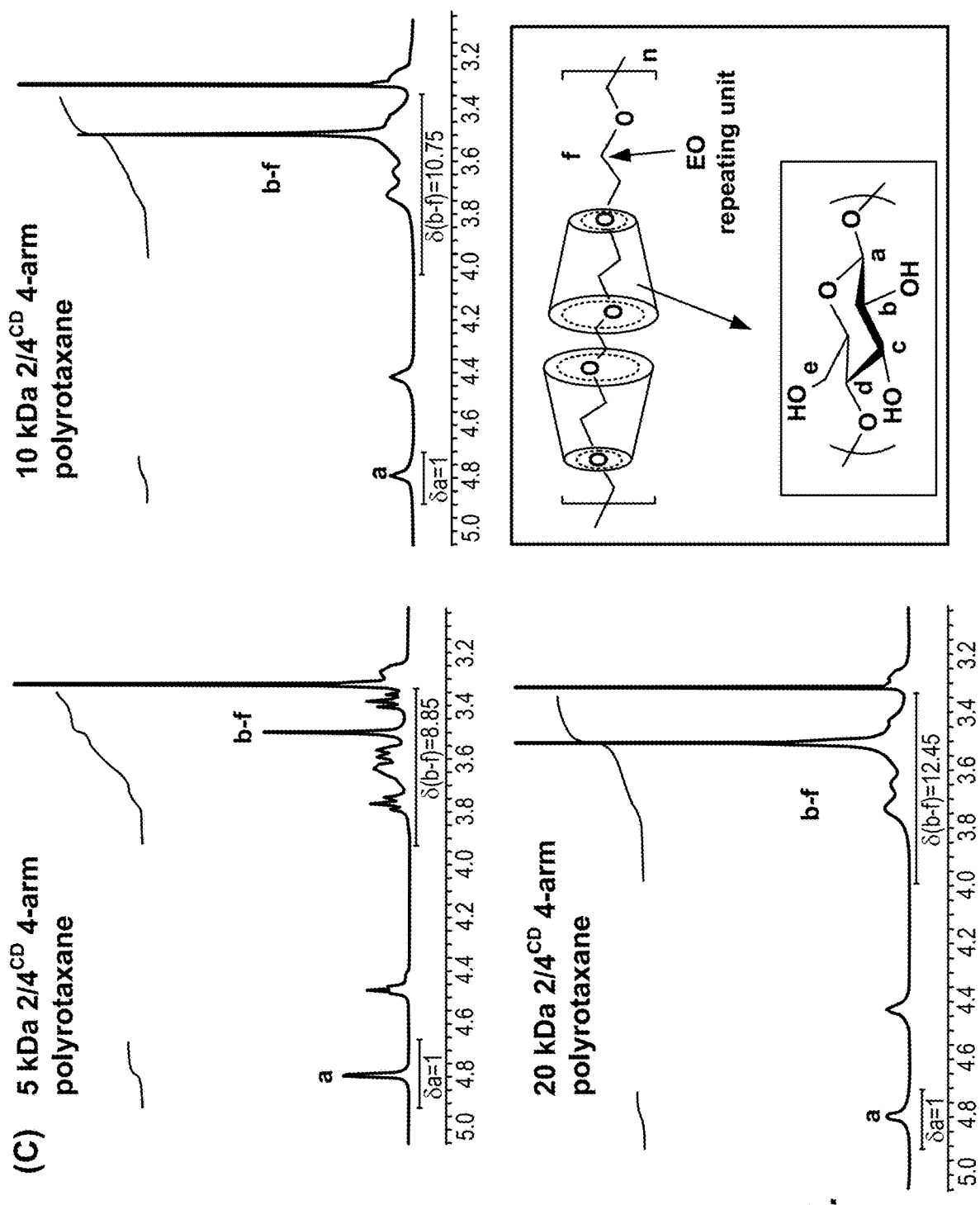
FIG. 26, cont'd.

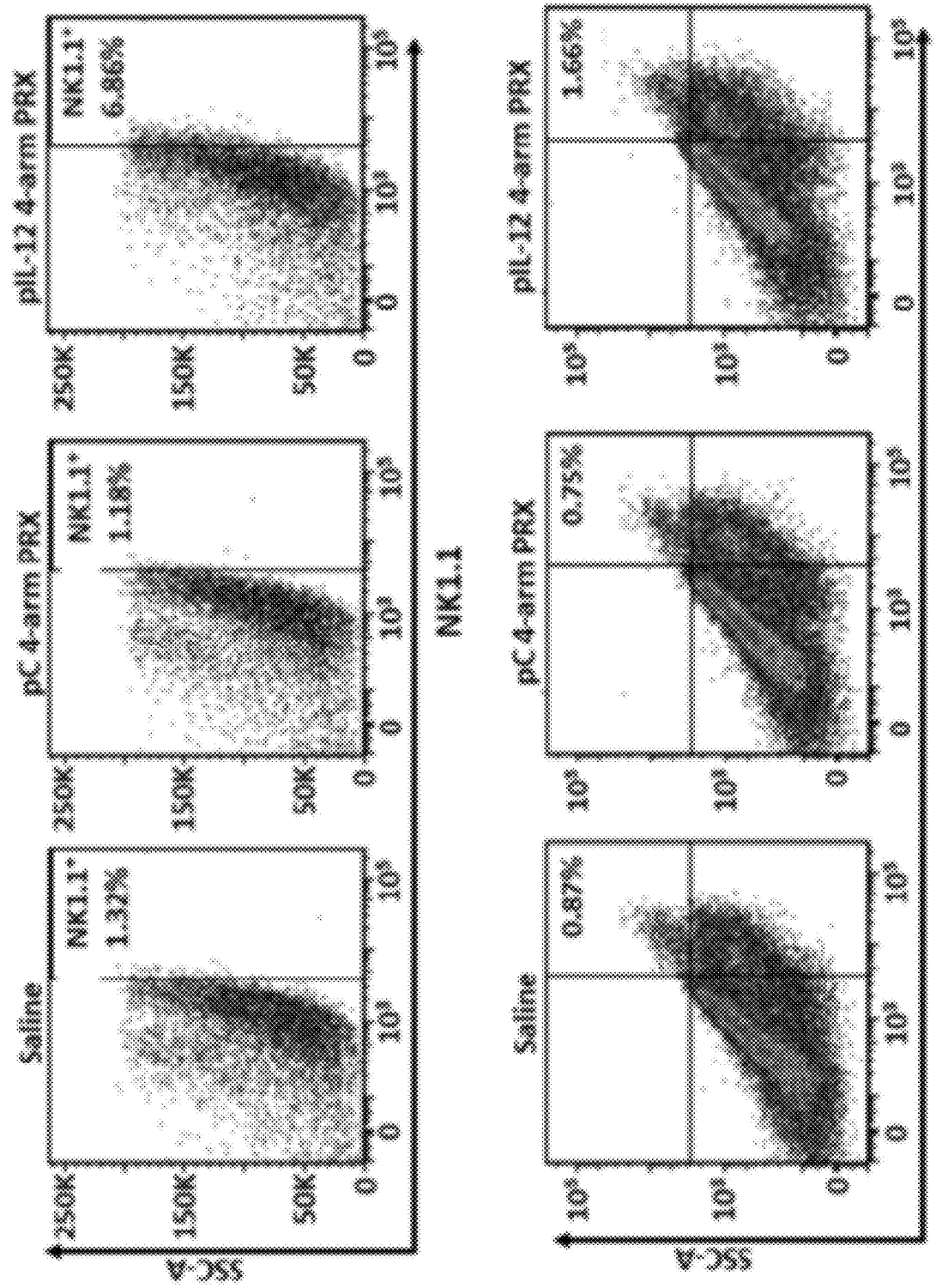
FIG. 35, cont'd.

SEQUENCE LISTING

```
<160> NUMBER OF SEQ ID NOS: 343

<210> SEQ ID NO 1
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 1
ctgaattagc tgtatcgtca                                              20

<210> SEQ ID NO 2
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 2
gaatataaac ttgtggtagt                                              20

<210> SEQ ID NO 3
<211> LENGTH: 12
<212> TYPE: PRT
<213> ORGANISM: Artificial
<220> FEATURE:
<223> OTHER INFORMATION: Cell penetrating peptide

<400> SEQUENCE: 3

Gly Arg Lys Lys Arg Arg Gln Arg Arg Arg Pro Gln
1               5                   10

<210> SEQ ID NO 4
<211> LENGTH: 8
<212> TYPE: PRT
<213> ORGANISM: Artificial
<220> FEATURE:
<223> OTHER INFORMATION: Cell penetrating peptide
```

```
<400> SEQUENCE: 4

Arg Arg Arg Arg Arg Arg Arg Arg
1               5

<210> SEQ ID NO 5
<211> LENGTH: 27
<212> TYPE: PRT
<213> ORGANISM: Artificial
<220> FEATURE:
<223> OTHER INFORMATION: Cell penetrating peptide

<400> SEQUENCE: 5

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 6
<211> LENGTH: 21
<212> TYPE: PRT
<213> ORGANISM: Artificial
<220> FEATURE:
<223> OTHER INFORMATION: Cell penetrating peptide

<400> SEQUENCE: 6

Lys Glu Thr Trp Trp Glu Thr Trp Trp Thr Glu Trp Ser Gln Pro Lys
1               5                   10                  15

Lys Lys Arg Lys Cys
            20

<210> SEQ ID NO 7
<211> LENGTH: 23
<212> TYPE: PRT
<213> ORGANISM: Artificial
<220> FEATURE:
<223> OTHER INFORMATION: Cell penetrating peptide

<400> SEQUENCE: 7

Leu Ile Lys Leu Trp Ser His Leu Ile His Ile Trp Phe Gln Asn Arg
1               5                   10                  15

Arg Leu Lys Trp Lys Lys Lys
            20

<210> SEQ ID NO 8
<211> LENGTH: 27
<212> TYPE: PRT
<213> ORGANISM: Artificial
<220> FEATURE:
<223> OTHER INFORMATION: Cell penetrating peptide

<400> SEQUENCE: 8

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 9
<211> LENGTH: 16
<212> TYPE: PRT
<213> ORGANISM: Artificial
<220> FEATURE:
<223> OTHER INFORMATION: Cell penetrating peptide
```

```
<400> SEQUENCE: 9

Arg Gln Ile Lys Ile Trp Phe Gln Asn Arg Arg Met Lys Trp Lys Lys
1               5                   10                  15

<210> SEQ ID NO 10
<211> LENGTH: 15
<212> TYPE: PRT
<213> ORGANISM: Artificial
<220> FEATURE:
<223> OTHER INFORMATION: Cell penetrating peptide

<400> SEQUENCE: 10

Lys Phe His Thr Phe Pro Gln Thr Ala Ile Gly Val Gly Ala Pro
1               5                   10                  15

<210> SEQ ID NO 11
<211> LENGTH: 18
<212> TYPE: PRT
<213> ORGANISM: Artificial
<220> FEATURE:
<223> OTHER INFORMATION: Cell penetrating peptide

<400> SEQUENCE: 11

Lys Leu Ala Leu Lys Leu Ala Leu Lys Ala Leu Lys Ala Ala Leu Lys
1               5                   10                  15

Leu Ala

<210> SEQ ID NO 12
<211> LENGTH: 15
<212> TYPE: PRT
<213> ORGANISM: Artificial
<220> FEATURE:
<223> OTHER INFORMATION: CAS9 motif

<400> SEQUENCE: 12

Ile Gly Leu Asp Ile Gly Thr Asn Ser Val Gly Trp Ala Val Ile
1               5                   10                  15

<210> SEQ ID NO 13
<211> LENGTH: 8
<212> TYPE: PRT
<213> ORGANISM: Artificial
<220> FEATURE:
<223> OTHER INFORMATION: CAS9 motif

<400> SEQUENCE: 13

Ile Val Ile Glu Met Ala Arg Glu
1               5

<210> SEQ ID NO 14
<211> LENGTH: 27
<212> TYPE: PRT
<213> ORGANISM: Artificial
<220> FEATURE:
<223> OTHER INFORMATION: CAS9 motif

<400> SEQUENCE: 14

Asp Val Asp His Ile Val Pro Gln Ser Phe Leu Lys Asp Ser Ile
1               5                   10                  15

Asp Asn Lys Val Leu Thr Arg Ser Asp Lys Asn
            20                  25

<210> SEQ ID NO 15
<211> LENGTH: 8
```

```
<212> TYPE: PRT
<213> ORGANISM: Artificial
<220> FEATURE:
<223> OTHER INFORMATION: CAS9 motif

<400> SEQUENCE: 15

His His Ala His Asp Ala Tyr Leu
1               5

<210> SEQ ID NO 16
<211> LENGTH: 82
<212> TYPE: DNA
<213> ORGANISM: Artificial
<220> FEATURE:
<223> OTHER INFORMATION: Nucleic acid encoding CRISPR guide RNA

<400> SEQUENCE: 16
gttttagagc tagaaatagc aagttaaaat aaggctagtc cgttatcaac ttgaaaaagt     60
ggcaccgagt cggtgctttt tt                                              82

<210> SEQ ID NO 17
<211> LENGTH: 82
<212> TYPE: RNA
<213> ORGANISM: Artificial
<220> FEATURE:
<223> OTHER INFORMATION: Nucleic acid encoding CRISPR guide RNA

<400> SEQUENCE: 17
guuuuagagc uagaaauagc aaguuaaaau aaggcuaguc cguuaucaac uugaaaaagu     60
ggcaccgagu cggugcuuuu uu                                              82

<210> SEQ ID NO 18
<211> LENGTH: 19
<212> TYPE: RNA
<213> ORGANISM: Artificial
<220> FEATURE:
<223> OTHER INFORMATION: Nucleic acid encoding CRISPR guide RNA

<400> SEQUENCE: 18
aauuucuacu guguagau                                                   19

<210> SEQ ID NO 19
<211> LENGTH: 19
<212> TYPE: RNA
<213> ORGANISM: Artificial
<220> FEATURE:
<223> OTHER INFORMATION: Nucleic acid encoding CRISPR guide RNA

<400> SEQUENCE: 19
aauuucugcu guugcagau                                                  19

<210> SEQ ID NO 20
<211> LENGTH: 19
<212> TYPE: RNA
<213> ORGANISM: Artificial
<220> FEATURE:
<223> OTHER INFORMATION: Nucleic acid encoding CRISPR guide RNA

<400> SEQUENCE: 20
aauuuccacu guguggau                                                   19

<210> SEQ ID NO 21
<211> LENGTH: 19
<212> TYPE: RNA
<213> ORGANISM: Artificial
```

```
<220> FEATURE:
<223> OTHER INFORMATION: Nucleic acid encoding CRISPR guide RNA

<400> SEQUENCE: 21
aauuccuacu guuguaggu                                                19

<210> SEQ ID NO 22
<211> LENGTH: 19
<212> TYPE: RNA
<213> ORGANISM: Artificial
<220> FEATURE:
<223> OTHER INFORMATION: Nucleic acid encoding CRISPR guide RNA

<400> SEQUENCE: 22
aauuucuacu auuguagau                                                19

<210> SEQ ID NO 23
<211> LENGTH: 19
<212> TYPE: RNA
<213> ORGANISM: Artificial
<220> FEATURE:
<223> OTHER INFORMATION: Nucleic acid encoding CRISPR guide RNA

<400> SEQUENCE: 23
aauuucuacu gcuguagau                                                19

<210> SEQ ID NO 24
<211> LENGTH: 18
<212> TYPE: RNA
<213> ORGANISM: Artificial
<220> FEATURE:
<223> OTHER INFORMATION: Nucleic acid encoding CRISPR guide RNA

<400> SEQUENCE: 24
aauuucuacu uuguagau                                                 18

<210> SEQ ID NO 25
<211> LENGTH: 17
<212> TYPE: RNA
<213> ORGANISM: Artificial
<220> FEATURE:
<223> OTHER INFORMATION: Nucleic acid encoding CRISPR guide RNA

<400> SEQUENCE: 25
aauuucuacu uguagau                                                  17

<210> SEQ ID NO 26
<211> LENGTH: 67
<212> TYPE: RNA
<213> ORGANISM: Artificial
<220> FEATURE:
<223> OTHER INFORMATION: Nucleic acid encoding CRISPR guide RNA

<400> SEQUENCE: 26
gaauuuuuca acgggugugc caauggccac uuuccaggug gcaaagcccg uugagcuucu    60
caaaaag                                                             67

<210> SEQ ID NO 27
<211> LENGTH: 79
<212> TYPE: RNA
<213> ORGANISM: Artificial
<220> FEATURE:
<223> OTHER INFORMATION: Nucleic acid encoding CRISPR guide RNA
```

```
<400> SEQUENCE: 27
gucuagagga cagaauuuuu caacggguguu gccaauggcc acuuccagg uggcaaagcc      60 cguugagcuu cucaaaaag                                                  79

<210> SEQ ID NO 28
<211> LENGTH: 78
<212> TYPE: RNA
<213> ORGANISM: Artificial
<220> FEATURE:
<223> OTHER INFORMATION: Nucleic acid encoding CRISPR guide RNA

<400> SEQUENCE: 28
ucuagaggac agaauuuuuc aacggguguug ccaauggcca cuuccaggu ggcaaagccc      60 guugagcuuc ucaaaaag                                                   78

<210> SEQ ID NO 29
<211> LENGTH: 36
<212> TYPE: RNA
<213> ORGANISM: Artificial
<220> FEATURE:
<223> OTHER INFORMATION: Nucleic acid encoding CRISPR guide RNA

<400> SEQUENCE: 29 acuuccagg caaagcccgu ugagcuucuc aaaaag                                36

<210> SEQ ID NO 30
<211> LENGTH: 9
<212> TYPE: RNA
<213> ORGANISM: Artificial
<220> FEATURE:
<223> OTHER INFORMATION: Nucleic acid encoding CRISPR guide RNA

<400> SEQUENCE: 30 agcuucuca                                                             9

<210> SEQ ID NO 31
<211> LENGTH: 8
<212> TYPE: RNA
<213> ORGANISM: Artificial
<220> FEATURE:
<223> OTHER INFORMATION: Nucleic acid encoding CRISPR guide RNA

<400> SEQUENCE: 31 gcuucuca                                                              8

<210> SEQ ID NO 32
<211> LENGTH: 34
<212> TYPE: RNA
<213> ORGANISM: Artificial
<220> FEATURE:
<223> OTHER INFORMATION: Nucleic acid encoding CRISPR guide RNA
<220> FEATURE:
<221> NAME/KEY: misc_feature
<222> LOCATION: (15)..(34)
<223> OTHER INFORMATION: n is a, c, g, or u

<400> SEQUENCE: 32
cugagaagug gcacnnnnn nnnnnnnnnn nnnn                                  34

<210> SEQ ID NO 33
<211> LENGTH: 14
<212> TYPE: RNA
<213> ORGANISM: Artificial
<220> FEATURE:
```

<223> OTHER INFORMATION: Nucleic acid encoding CRISPR guide RNA

<400> SEQUENCE: 33
cugagaagug gcac                                                        14

<210> SEQ ID NO 34
<211> LENGTH: 9
<212> TYPE: RNA
<213> ORGANISM: Artificial
<220> FEATURE:
<223> OTHER INFORMATION: Nucleic acid encoding CRISPR guide RNA

<400> SEQUENCE: 34 cugagaagu                                                               9

<210> SEQ ID NO 35
<211> LENGTH: 13
<212> TYPE: RNA
<213> ORGANISM: Artificial
<220> FEATURE:
<223> OTHER INFORMATION: Nucleic acid encoding CRISPR guide RNA

<400> SEQUENCE: 35
ugagaagugg cac                                                         13

<210> SEQ ID NO 36
<211> LENGTH: 8
<212> TYPE: RNA
<213> ORGANISM: Artificial
<220> FEATURE:
<223> OTHER INFORMATION: Nucleic acid encoding CRISPR guide RNA

<400> SEQUENCE: 36 ugagaagu                                                                8

<210> SEQ ID NO 37
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 37
gtggtgtcct ttgaatatgc                                                  20

<210> SEQ ID NO 38
<211> LENGTH: 17
<212> TYPE: DNA
<213> ORGANISM: Artificial
<220> FEATURE:
<223> OTHER INFORMATION: Nucleic acid encoding CRISPR guide RNA

<400> SEQUENCE: 38
gtgtcctttg aatatgc                                                     17

<210> SEQ ID NO 39
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 39
gugguguccu uugaauaugc                                                  20

```
<210> SEQ ID NO 40
<211> LENGTH: 17
<212> TYPE: RNA
<213> ORGANISM: Artificial
<220> FEATURE:
<223> OTHER INFORMATION: Nucleic acid encoding CRISPR guide RNA

<400> SEQUENCE: 40
guguccuuug aauaugc                                                    17

<210> SEQ ID NO 41
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 41
agattgtcca ggatataatt                                                 20

<210> SEQ ID NO 42
<211> LENGTH: 17
<212> TYPE: DNA
<213> ORGANISM: Artificial
<220> FEATURE:
<223> OTHER INFORMATION: Nucleic acid encoding CRISPR guide RNA

<400> SEQUENCE: 42
ttgtccagga tataatt                                                    17

<210> SEQ ID NO 43
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 43
agauugucca ggauauaauu                                                 20

<210> SEQ ID NO 44
<211> LENGTH: 17
<212> TYPE: RNA
<213> ORGANISM: Artificial
<220> FEATURE:
<223> OTHER INFORMATION: Nucleic acid encoding CRISPR guide RNA

<400> SEQUENCE: 44
uuguccagga uauaauu                                                    17

<210> SEQ ID NO 45
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 45
ttagcaacca aattatatcc                                                 20

<210> SEQ ID NO 46
<211> LENGTH: 17
<212> TYPE: DNA
<213> ORGANISM: Artificial
<220> FEATURE:
<223> OTHER INFORMATION: Nucleic acid encoding CRISPR guide RNA
```

```
<400> SEQUENCE: 46
gcaaccaaat tatatcc                                                   17

<210> SEQ ID NO 47
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 47
uuagcaacca aauuauaucc                                                20

<210> SEQ ID NO 48
<211> LENGTH: 17
<212> TYPE: RNA
<213> ORGANISM: Artificial
<220> FEATURE:
<223> OTHER INFORMATION: Nucleic acid encoding CRISPR guide RNA

<400> SEQUENCE: 48
gcaaccaaau uauaucc                                                   17

<210> SEQ ID NO 49
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 49
gttgaaatta aactacacac                                                20

<210> SEQ ID NO 50
<211> LENGTH: 17
<212> TYPE: DNA
<213> ORGANISM: Artificial
<220> FEATURE:
<223> OTHER INFORMATION: Nucleic acid encoding CRISPR guide RNA

<400> SEQUENCE: 50
gaaattaaac tacacac                                                   17

<210> SEQ ID NO 51
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 51
guugaaauua aacuacacac                                                20

<210> SEQ ID NO 52
<211> LENGTH: 17
<212> TYPE: RNA
<213> ORGANISM: Artificial
<220> FEATURE:
<223> OTHER INFORMATION: Nucleic acid encoding CRISPR guide RNA

<400> SEQUENCE: 52
gaaauuaaac uacacac                                                   17

<210> SEQ ID NO 53
<211> LENGTH: 20
```

```
<212> TYPE: DNA
<213> ORGANISM: Artificial
<220> FEATURE:
<223> OTHER INFORMATION: Nucleic acid encoding CRISPR guide RNA

<400> SEQUENCE: 53
atctttacct gcatattcaa                                              20

<210> SEQ ID NO 54
<211> LENGTH: 17
<212> TYPE: DNA
<213> ORGANISM: Artificial
<220> FEATURE:
<223> OTHER INFORMATION: Nucleic acid encoding CRISPR guide RNA

<400> SEQUENCE: 54
tttacctgca tattcaa                                                 17

<210> SEQ ID NO 55
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 55
aucuuuaccu gcauauucaa                                              20

<210> SEQ ID NO 56
<211> LENGTH: 17
<212> TYPE: RNA
<213> ORGANISM: Artificial
<220> FEATURE:
<223> OTHER INFORMATION: Nucleic acid encoding CRISPR guide RNA

<400> SEQUENCE: 56
uuuaccugca uauucaa                                                 17

<210> SEQ ID NO 57
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 57
tacacatttt taggcttgac                                              20

<210> SEQ ID NO 58
<211> LENGTH: 17
<212> TYPE: DNA
<213> ORGANISM: Artificial
<220> FEATURE:
<223> OTHER INFORMATION: Nucleic acid encoding CRISPR guide RNA

<400> SEQUENCE: 58
acatttttag gcttgac                                                 17

<210> SEQ ID NO 59
<211> LENGTH: 20
<212> TYPE: RNA
<213> ORGANISM: Artificial
<220> FEATURE:
<223> OTHER INFORMATION: Nucleic acid encoding CRISPR guide RNA
```

<400> SEQUENCE: 59
uacacauuuu uaggcuugac                                              20

<210> SEQ ID NO 60
<211> LENGTH: 17
<212> TYPE: RNA
<213> ORGANISM: Artificial
<220> FEATURE:
<223> OTHER INFORMATION: Nucleic acid encoding CRISPR guide RNA

<400> SEQUENCE: 60
acauuuuuag gcuugac                                                 17

<210> SEQ ID NO 61
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 61
cattcctggg agtctgtcat                                              20

<210> SEQ ID NO 62
<211> LENGTH: 17
<212> TYPE: DNA
<213> ORGANISM: Artificial
<220> FEATURE:
<223> OTHER INFORMATION: Nucleic acid encoding CRISPR guide RNA

<400> SEQUENCE: 62
tcctgggagt ctgtcat                                                 17

<210> SEQ ID NO 63
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 63
cauuccuggg agucugucau                                              20

<210> SEQ ID NO 64
<211> LENGTH: 17
<212> TYPE: RNA
<213> ORGANISM: Artificial
<220> FEATURE:
<223> OTHER INFORMATION: Nucleic acid encoding CRISPR guide RNA

<400> SEQUENCE: 64
uccugggagu cugucau                                                 17

<210> SEQ ID NO 65
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 65
tgtatgatgc tataatacca                                              20

<210> SEQ ID NO 66

```
<211> LENGTH: 17
<212> TYPE: DNA
<213> ORGANISM: Artificial
<220> FEATURE:
<223> OTHER INFORMATION: Nucleic acid encoding CRISPR guide RNA

<400> SEQUENCE: 66
atgatgctat aatacca                                                      17

<210> SEQ ID NO 67
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 67
uguaugaugc uauaauacca                                                   20

<210> SEQ ID NO 68
<211> LENGTH: 17
<212> TYPE: RNA
<213> ORGANISM: Artificial
<220> FEATURE:
<223> OTHER INFORMATION: Nucleic acid encoding CRISPR guide RNA

<400> SEQUENCE: 68
augaugcuau aauacca                                                      17

<210> SEQ ID NO 69
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 69
gtggaaagta cataggacct                                                   20

<210> SEQ ID NO 70
<211> LENGTH: 17
<212> TYPE: DNA
<213> ORGANISM: Artificial
<220> FEATURE:
<223> OTHER INFORMATION: Nucleic acid encoding CRISPR guide RNA

<400> SEQUENCE: 70
gaaagtacat aggacct                                                      17

<210> SEQ ID NO 71
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 71
guggaaagua cauaggaccu                                                   20

<210> SEQ ID NO 72
<211> LENGTH: 17
<212> TYPE: RNA
<213> ORGANISM: Artificial
<220> FEATURE:
<223> OTHER INFORMATION: Nucleic acid encoding CRISPR guide RNA
```

```
<400> SEQUENCE: 72
gaaaguacau aggaccu                                                    17

<210> SEQ ID NO 73
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 73
tcttatcata actcttacca                                                 20

<210> SEQ ID NO 74
<211> LENGTH: 17
<212> TYPE: DNA
<213> ORGANISM: Artificial
<220> FEATURE:
<223> OTHER INFORMATION: Nucleic acid encoding CRISPR guide RNA

<400> SEQUENCE: 74
tatcataact cttacca                                                    17

<210> SEQ ID NO 75
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 75
ucuuaucaua acucuuacca                                                 20

<210> SEQ ID NO 76
<211> LENGTH: 17
<212> TYPE: RNA
<213> ORGANISM: Artificial
<220> FEATURE:
<223> OTHER INFORMATION: Nucleic acid encoding CRISPR guide RNA

<400> SEQUENCE: 76
uaucauaacu cuuacca                                                    17

<210> SEQ ID NO 77
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 77
gtggtgtcct ttgaatatgc                                                 20

<210> SEQ ID NO 78
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 78
gugguguccu uugaauaugc                                                 20

<210> SEQ ID NO 79
```

```
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 79
agattgtcca ggatataatt                                              20

<210> SEQ ID NO 80
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 80
agauugucca ggauauaauu                                              20

<210> SEQ ID NO 81
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 81
ttagcaacca aattatatcc                                              20

<210> SEQ ID NO 82
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 82
uuagcaacca aauuauaucc                                              20

<210> SEQ ID NO 83
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 83
gttgaaatta aactacacac                                              20

<210> SEQ ID NO 84
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 84
guugaaauua aacuacacac                                              20

<210> SEQ ID NO 85
<211> LENGTH: 20
<212> TYPE: DNA
<213> ORGANISM: Artificial
<220> FEATURE:
<223> OTHER INFORMATION: Nucleic acid encoding CRISPR guide RNA
```

```
<400> SEQUENCE: 85
atctttacct gcatattcaa                                              20

<210> SEQ ID NO 86
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 86
aucuuuaccu gcauauucaa                                              20

<210> SEQ ID NO 87
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 87
ctctgcattg ttttggcctc                                              20

<210> SEQ ID NO 88
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 88
cucugcauug uuuuggccuc                                              20

<210> SEQ ID NO 89
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 89
tcctccaaag agtagaatgg                                              20

<210> SEQ ID NO 90
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 90
uccuccaaag aguagaaugg                                              20

<210> SEQ ID NO 91
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 91
gccctaaact tacactgttc                                              20

<210> SEQ ID NO 92
```

```
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 92
gcccuaaacu uacacuguuc                                              20

<210> SEQ ID NO 93
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 93
aaagatagat tagattgtcc                                              20

<210> SEQ ID NO 94
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 94
aaagauagau uagauugucc                                              20

<210> SEQ ID NO 95
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 95
gttgctaaat tacatagttt                                              20

<210> SEQ ID NO 96
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 96
guugcuaaau uacauaguuu                                              20

<210> SEQ ID NO 97
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 97
tgttgcaata gtcaatcaag                                              20

<210> SEQ ID NO 98
<211> LENGTH: 20
<212> TYPE: RNA
<213> ORGANISM: Artificial
<220> FEATURE:
<223> OTHER INFORMATION: Nucleic acid encoding CRISPR guide RNA
```

<400> SEQUENCE: 98
uguugcaaua gucaaucaag                                            20

<210> SEQ ID NO 99
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 99
atactgatta agacagatga                                            20

<210> SEQ ID NO 100
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 100
auacugauua agacagauga                                            20

<210> SEQ ID NO 101
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 101
aatactgatt aagacagatg                                            20

<210> SEQ ID NO 102
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 102
aauacugauu aagacagaug                                            20

<210> SEQ ID NO 103
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 103
ctctatacaa atgccaacgc                                            20

<210> SEQ ID NO 104
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 104
cucuauacaa augccaacgc                                            20

<210> SEQ ID NO 105

```
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 105
acttgcatgc acaccagcgt                                               20

<210> SEQ ID NO 106
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 106
acuugcaugc acaccagcgu                                               20

<210> SEQ ID NO 107
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 107
ttgggctaat gtagcataat                                               20

<210> SEQ ID NO 108
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 108
uugggcuaau guagcauaau                                               20

<210> SEQ ID NO 109
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 109
gcgttggcat ttgtatagag                                               20

<210> SEQ ID NO 110
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 110
gcguuggcau uuguauagag                                               20

<210> SEQ ID NO 111
<211> LENGTH: 20
<212> TYPE: DNA
<213> ORGANISM: Artificial
<220> FEATURE:
<223> OTHER INFORMATION: Nucleic acid encoding CRISPR guide RNA
```

<400> SEQUENCE: 111
tgggctaatg tagcataatg                                                    20

<210> SEQ ID NO 112
<211> LENGTH: 19
<212> TYPE: RNA
<213> ORGANISM: Artificial
<220> FEATURE:
<223> OTHER INFORMATION: Nucleic acid encoding CRISPR guide RNA

<400> SEQUENCE: 112
ugggcuaagu agcauaaug                                                     19

<210> SEQ ID NO 113
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 113
tttgggctaa tgtagcataa                                                    20

<210> SEQ ID NO 114
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 114
uuugggcuaa uguagcauaa                                                    20

<210> SEQ ID NO 115
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 115
gcttaactcc ttaatattaa                                                    20

<210> SEQ ID NO 116
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 116
gcuuaacucc uuaauauuaa                                                    20

<210> SEQ ID NO 117
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 117
tcttctatat taaagcagat                                                    20

<210> SEQ ID NO 118

```
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 118
ucuucuauau uaaagcagau                                                   20

<210> SEQ ID NO 119
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 119
cttctatatt aaagcagatt                                                   20

<210> SEQ ID NO 120
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 120
cuucuauauu aaagcagauu                                                   20

<210> SEQ ID NO 121
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 121
aatatataac taccttgggt                                                   20

<210> SEQ ID NO 122
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 122
aauauauaac uaccuugggu                                                   20

<210> SEQ ID NO 123
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 123
acctccattc tactctttgg                                                   20

<210> SEQ ID NO 124
<211> LENGTH: 20
<212> TYPE: RNA
<213> ORGANISM: Artificial
<220> FEATURE:
<223> OTHER INFORMATION: Nucleic acid encoding CRISPR guide RNA
```

```
<400> SEQUENCE: 124
accuccauuc uacucuuugg                                         20

<210> SEQ ID NO 125
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 125
tttcaatgat atccaaccca                                         20

<210> SEQ ID NO 126
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 126
uuucaaugau auccaaccca                                         20

<210> SEQ ID NO 127
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 127
agtacctcca ttctactctt                                         20

<210> SEQ ID NO 128
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 128
aguaccucca uucuacucuu                                         20

<210> SEQ ID NO 129
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 129
ctatcctcca aagagtagaa                                         20

<210> SEQ ID NO 130
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 130
cuauccucca aagaguagaa                                         20

<210> SEQ ID NO 131
```

```
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 131
ttttgctaca tatttcaggc                                              20

<210> SEQ ID NO 132
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 132
uuuugcuaca uauuucaggc                                              20

<210> SEQ ID NO 133
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 133
tttgctacat atttcaggct                                              20

<210> SEQ ID NO 134
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 134
uuugcuacau auuucaggcu                                              20

<210> SEQ ID NO 135
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 135
gggttggata tcattgaaaa                                              20

<210> SEQ ID NO 136
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 136
ggguuggaua ucauugaaaa                                              20

<210> SEQ ID NO 137
<211> LENGTH: 20
<212> TYPE: DNA
<213> ORGANISM: Artificial
<220> FEATURE:
<223> OTHER INFORMATION: Nucleic acid encoding CRISPR guide RNA
```

```
<400> SEQUENCE: 137
atatttcagg ctgggtttct                                              20

<210> SEQ ID NO 138
<211> LENGTH: 19
<212> TYPE: RNA
<213> ORGANISM: Artificial
<220> FEATURE:
<223> OTHER INFORMATION: Nucleic acid encoding CRISPR guide RNA

<400> SEQUENCE: 138
auauuucagg cugdguucu                                               19

<210> SEQ ID NO 139
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 139
ttgaaatata taactaccct                                              20

<210> SEQ ID NO 140
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 140
uugaaauaua uaacuaccuu                                              20

<210> SEQ ID NO 141
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 141
attgaaatat ataactacct                                              20

<210> SEQ ID NO 142
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 142
auugaaauau auaacuaccu                                              20

<210> SEQ ID NO 143
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 143
gtgagtagtg gggcacttta                                              20

<210> SEQ ID NO 144
```

<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 144
gugaguagug gggcacuuua                                              20

<210> SEQ ID NO 145
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 145
tgtatgtaga aggttaacta                                              20

<210> SEQ ID NO 146
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 146
uguauguaga agguuaacua                                              20

<210> SEQ ID NO 147
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 147
gagcctaata aatgtacaat                                              20

<210> SEQ ID NO 148
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 148
gagccuaaua aauguacaau                                              20

<210> SEQ ID NO 149
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 149
ttgtatgtag aaggttaact                                              20

<210> SEQ ID NO 150
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 150
uuguauguag aagguuaacu          20

<210> SEQ ID NO 151
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 151
caatttgttt tgatgtaact          20

<210> SEQ ID NO 152
<211> LENGTH: 19
<212> TYPE: RNA
<213> ORGANISM: Artificial
<220> FEATURE:
<223> OTHER INFORMATION: Nucleic acid encoding CRISPR guide RNA

<400> SEQUENCE: 152
caauuuguuu ugaguaacu          19

<210> SEQ ID NO 153
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 153
tgccttctga aatagtccag          20

<210> SEQ ID NO 154
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 154
ugccuucuga aauaguccag          20

<210> SEQ ID NO 155
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 155
gttaataggg aaacagcata          20

<210> SEQ ID NO 156
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 156
guuaauaggg aaacagcaua          20

<210> SEQ ID NO 157

```
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 157
aacaatgcag agttaattgt                                              20

<210> SEQ ID NO 158
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 158
aacaaugcag aguuaauugu                                              20

<210> SEQ ID NO 159
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 159
gaacatgttg agtagacaca                                              20

<210> SEQ ID NO 160
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 160
gaacauguug aguagacaca                                              20

<210> SEQ ID NO 161
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 161
tttatcatct gtgtctattc                                              20

<210> SEQ ID NO 162
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 162
uuuaucaucu gugucuauuc                                              20

<210> SEQ ID NO 163
<211> LENGTH: 20
<212> TYPE: DNA
<213> ORGANISM: Artificial
<220> FEATURE:
<223> OTHER INFORMATION: Nucleic acid encoding CRISPR guide RNA
```

```
<400> SEQUENCE: 163
tctttacttt cttgactata                                               20

<210> SEQ ID NO 164
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 164
ucuuuacuuu cuugacuaua                                               20

<210> SEQ ID NO 165
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 165
aatattctca aacctcgttc                                               20

<210> SEQ ID NO 166
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 166
aauauucuca aaccucguuc                                               20

<210> SEQ ID NO 167
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 167
attaactgtg ttccagaacg                                               20

<210> SEQ ID NO 168
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 168
auuaacugug uuccagaacg                                               20

<210> SEQ ID NO 169
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 169
taactgcttc tttggatgac                                               20

<210> SEQ ID NO 170
```

```
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 170
uaacugcuuc uuuggaugac                                               20

<210> SEQ ID NO 171
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 171
gaccagaaca gtgtaagttt                                               20

<210> SEQ ID NO 172
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 172
gaccagaaca guguaaguuu                                               20

<210> SEQ ID NO 173
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 173
accagaacag tgtaagttta                                               20

<210> SEQ ID NO 174
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 174
accagaacag uguaaguuua                                               20

<210> SEQ ID NO 175
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 175 ctacttttc cccactactg                                                20

<210> SEQ ID NO 176
<211> LENGTH: 20
<212> TYPE: RNA
<213> ORGANISM: Artificial
<220> FEATURE:
<223> OTHER INFORMATION: Nucleic acid encoding CRISPR guide RNA
```

```
<400> SEQUENCE: 176
cuacuuuuuc cccacuacug                                          20

<210> SEQ ID NO 177
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 177
tggaacacag ttaattcact                                          20

<210> SEQ ID NO 178
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 178
uggaacacag uuaauucacu                                          20

<210> SEQ ID NO 179
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 179
gtgttgttta actgcttctt                                          20

<210> SEQ ID NO 180
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 180
guguuguuua acugcuucuu                                          20

<210> SEQ ID NO 181
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 181
tacacatttt taggcttgac                                          20

<210> SEQ ID NO 182
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 182
uacacauuuu uaggcuugac                                          20

<210> SEQ ID NO 183
```

```
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 183
cattcctggg agtctgtcat                                              20

<210> SEQ ID NO 184
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 184
cauuccuggg agucugucau                                              20

<210> SEQ ID NO 185
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 185
tgtatgatgc tataatacca                                              20

<210> SEQ ID NO 186
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 186
uguaugaugc uauaauacca                                              20

<210> SEQ ID NO 187
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 187
gtggaaagta cataggacct                                              20

<210> SEQ ID NO 188
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 188
guggaaagua cauaggaccu                                              20

<210> SEQ ID NO 189
<211> LENGTH: 20
<212> TYPE: DNA
<213> ORGANISM: Artificial
<220> FEATURE:
<223> OTHER INFORMATION: Nucleic acid encoding CRISPR guide RNA
```

```
<400> SEQUENCE: 189
tcttatcata actcttacca                                          20

<210> SEQ ID NO 190
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 190
ucuuaucaua acucuuacca                                          20

<210> SEQ ID NO 191
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 191
aactgtcagt tgcatattcc                                          20

<210> SEQ ID NO 192
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 192
aacugucagu ugcauauucc                                          20

<210> SEQ ID NO 193
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 193
cagaaaggaa tgctggtacc                                          20

<210> SEQ ID NO 194
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 194
cagaaaggaa ugcugguacc                                          20

<210> SEQ ID NO 195
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 195
tctgcctaca caatgaatgg                                          20

<210> SEQ ID NO 196
```

<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 196
ucugccuaca caaugaaugg        20

<210> SEQ ID NO 197
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 197
cacagatcaa tccaattgtt        20

<210> SEQ ID NO 198
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 198
cacagaucaa uccaauuguu        20

<210> SEQ ID NO 199
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 199
ttgacaggtg gaaagtacat        20

<210> SEQ ID NO 200
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 200
uugacaggug gaaaguacau        20

<210> SEQ ID NO 201
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 201
acatttttag gcttgacagg        20

<210> SEQ ID NO 202
<211> LENGTH: 20
<212> TYPE: RNA
<213> ORGANISM: Artificial
<220> FEATURE:
<223> OTHER INFORMATION: Nucleic acid encoding CRISPR guide RNA

```
<400> SEQUENCE: 202
acauuuuuag gcuugacagg                                               20

<210> SEQ ID NO 203
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 203
ctctcccatg acagactccc                                               20

<210> SEQ ID NO 204
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 204
cucucccaug acagacuccc                                               20

<210> SEQ ID NO 205
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 205
ttggtaagag ttatgataag                                               20

<210> SEQ ID NO 206
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 206
uugguaagag uuaugauaag                                               20

<210> SEQ ID NO 207
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 207
aacacaaatt aagttcacct                                               20

<210> SEQ ID NO 208
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 208
aacacaaauu aaguucaccu                                               20

<210> SEQ ID NO 209
```

```
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 209
aggatcagtg ctgtagtgcc                                              20

<210> SEQ ID NO 210
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 210
aggaucagug cuguagugcc                                              20

<210> SEQ ID NO 211
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 211
ggccgtttat tattattgac                                              20

<210> SEQ ID NO 212
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 212
ggccguuuau uauuauugac                                              20

<210> SEQ ID NO 213
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 213
tctcaggatt gctatgcaac                                              20

<210> SEQ ID NO 214
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 214
ucucaggauu gcuaugcaac                                              20

<210> SEQ ID NO 215
<211> LENGTH: 20
<212> TYPE: DNA
<213> ORGANISM: Artificial
<220> FEATURE:
<223> OTHER INFORMATION: Nucleic acid encoding CRISPR guide RNA
```

```
<400> SEQUENCE: 215
caggaagaca taccatgtaa                                          20

<210> SEQ ID NO 216
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 216
caggaagaca uaccauguaa                                          20

<210> SEQ ID NO 217
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 217
agcagggctc tttcagtttc                                          20

<210> SEQ ID NO 218
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 218
agcagggcuc uuucaguuuc                                          20

<210> SEQ ID NO 219
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 219
taacattttc agcttgaacc                                          20

<210> SEQ ID NO 220
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 220
uaacauuuuc agcuugaacc                                          20

<210> SEQ ID NO 221
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 221
tcaagctgaa aatgttacac                                          20

<210> SEQ ID NO 222
```

```
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 222
ucaagcugaa aauguuacac                                              20

<210> SEQ ID NO 223
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 223
gtaacatttt cagcttgaac                                              20

<210> SEQ ID NO 224
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 224
guaacauuuu cagcuugaac                                              20

<210> SEQ ID NO 225
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 225
cagaatgaat tttggagcac                                              20

<210> SEQ ID NO 226
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 226
cagaaugaau uuuggagcac                                              20

<210> SEQ ID NO 227
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 227
tttattatta ttgactggtg                                              20

<210> SEQ ID NO 228
<211> LENGTH: 20
<212> TYPE: RNA
<213> ORGANISM: Artificial
<220> FEATURE:
<223> OTHER INFORMATION: Nucleic acid encoding CRISPR guide RNA
```

```
<400> SEQUENCE: 228
uuuauuauua uugacugguq                                            20

<210> SEQ ID NO 229
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 229
agaagaatct gacctttaca                                            20

<210> SEQ ID NO 230
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 230
agaagaaucu gaccuuuaca                                            20

<210> SEQ ID NO 231
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 231
gcagggctct ttcagtttct                                            20

<210> SEQ ID NO 232
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 232
gcagggcucu uucaguuucu                                            20

<210> SEQ ID NO 233
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 233
ctaaacagta gccaggcgtg                                            20

<210> SEQ ID NO 234
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 234
cuaaacagua gccaggcgug                                            20

<210> SEQ ID NO 235
```

```
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 235
cgcctggcta ctgtttagtg                                              20

<210> SEQ ID NO 236
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 236
cgccuggcua cuguuuagug                                              20

<210> SEQ ID NO 237
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 237
ctccgcacta aacagtagcc                                              20

<210> SEQ ID NO 238
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 238
cuccgcacua aacaguagcc                                              20

<210> SEQ ID NO 239
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 239
gtagccaggc gtgtggatgt                                              20

<210> SEQ ID NO 240
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 240
guagccaggc guguggaugu                                              20

<210> SEQ ID NO 241
<211> LENGTH: 20
<212> TYPE: DNA
<213> ORGANISM: Artificial
<220> FEATURE:
<223> OTHER INFORMATION: Nucleic acid encoding CRISPR guide RNA
```

```
<400> SEQUENCE: 241
cttggctttg actattctgc                                              20

<210> SEQ ID NO 242
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 242
cuuggcuuug acuauucugc                                              20

<210> SEQ ID NO 243
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 243
agtagccagg cgtgtggatg                                              20

<210> SEQ ID NO 244
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 244
aguagccagg cguguggaug                                              20

<210> SEQ ID NO 245
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 245
tcctcccaca tccacacgcc                                              20

<210> SEQ ID NO 246
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 246
uccucccaca uccacacgcc                                              20

<210> SEQ ID NO 247
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 247
ttggctttga ctattctgct                                              20

<210> SEQ ID NO 248
```

```
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 248
uuggcuuuga cuauucugcu                                                   20

<210> SEQ ID NO 249
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 249
ataatgtctc tggcttgtaa                                                   20

<210> SEQ ID NO 250
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 250
auaaugucuc uggcuuguaa                                                   20

<210> SEQ ID NO 251
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 251
tggtacccgg cagctctctg                                                   20

<210> SEQ ID NO 252
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 252
ugguacccgg cagcucucug                                                   20

<210> SEQ ID NO 253
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 253
gtgggaggaa cctcaaagag                                                   20

<210> SEQ ID NO 254
<211> LENGTH: 20
<212> TYPE: RNA
<213> ORGANISM: Artificial
<220> FEATURE:
<223> OTHER INFORMATION: Nucleic acid encoding CRISPR guide RNA
```

```
<400> SEQUENCE: 254
gugggaggaa ccucaaagag                                              20

<210> SEQ ID NO 255
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 255
tgactattct gctgggaaca                                              20

<210> SEQ ID NO 256
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 256
ugacuauucu gcugggaaca                                              20

<210> SEQ ID NO 257
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 257
ctctctgagg aatgttccct                                              20

<210> SEQ ID NO 258
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 258
cucucugagg aauguucccu                                              20

<210> SEQ ID NO 259
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 259
aacattcctc agagagctgc                                              20

<210> SEQ ID NO 260
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 260
aacauuccuc agagagcugc                                              20

<210> SEQ ID NO 261
```

```
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 261
attctgaagc tccaaacaat                                              20

<210> SEQ ID NO 262
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 262
auucugaagc uccaaacaau                                              20

<210> SEQ ID NO 263
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 263
taaattactc tgctaaagta                                              20

<210> SEQ ID NO 264
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 264
uaaauuacuc ugcuaaagua                                              20

<210> SEQ ID NO 265
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 265
agtacaaacc aggtttgtac                                              20

<210> SEQ ID NO 266
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 266
aguacaaacc agguuuguac                                              20

<210> SEQ ID NO 267
<211> LENGTH: 20
<212> TYPE: DNA
<213> ORGANISM: Artificial
<220> FEATURE:
<223> OTHER INFORMATION: Nucleic acid encoding CRISPR guide RNA
```

```
<400> SEQUENCE: 267
atatccttcc agtacaaacc                                              20

<210> SEQ ID NO 268
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 268
auauccuucc aguacaaacc                                              20

<210> SEQ ID NO 269
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 269
caaaccaggt ttgtactgga                                              20

<210> SEQ ID NO 270
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 270
caaaccaggu uuguacugga                                              20

<210> SEQ ID NO 271
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 271
ggcagctaaa gcatcactga                                              20

<210> SEQ ID NO 272
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 272
ggcagcuaaa gcaucacuga                                              20

<210> SEQ ID NO 273
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 273
atctctgagt agtacaaacc                                              20

<210> SEQ ID NO 274
```

```
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 274
aucucugagu aguacaaacc                                                 20

<210> SEQ ID NO 275
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 275
gtgtcccatt ctctttgact                                                 20

<210> SEQ ID NO 276
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 276
gugucccauu cucuuugacu                                                 20

<210> SEQ ID NO 277
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 277
tgtgtcccat tctctttgac                                                 20

<210> SEQ ID NO 278
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 278
ugugucccau ucucuuugac                                                 20

<210> SEQ ID NO 279
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 279
ttctgaatgt tgaacaagta                                                 20

<210> SEQ ID NO 280
<211> LENGTH: 20
<212> TYPE: RNA
<213> ORGANISM: Artificial
<220> FEATURE:
<223> OTHER INFORMATION: Nucleic acid encoding CRISPR guide RNA
```

```
<400> SEQUENCE: 280
uucugaaugu ugaacaagua                                              20

<210> SEQ ID NO 281
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 281
gtctcccagt caaagagaat                                              20

<210> SEQ ID NO 282
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 282
gucucccagu caaagagaau                                              20

<210> SEQ ID NO 283
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 283
attctctttg actgggagac                                              20

<210> SEQ ID NO 284
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 284
auucucuuug acugggagac                                              20

<210> SEQ ID NO 285
<211> LENGTH: 20
<212> TYPE: DNA
<213> ORGANISM: Artificial
<220> FEATURE:
<223> OTHER INFORMATION: Nucleic acid encoding CRISPR guide RNA

<400> SEQUENCE: 285
tctttgactg ggagacaggc                                              20

<210> SEQ ID NO 286
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 286
ucuuugacug ggagacaggc                                              20

<210> SEQ ID NO 287
```

<211> LENGTH: 82
<212> TYPE: DNA
<213> ORGANISM: Artificial
<220> FEATURE:
<223> OTHER INFORMATION: Nucleic acid encoding CRISPR guide RNA

<400> SEQUENCE: 287
gttttagagc tagaaatagc aagttaaaat aaggctagtc cgttatcaac ttgaaaaagt    60
ggcaccgagt cggtgctttt tt                                              82

<210> SEQ ID NO 288
<211> LENGTH: 11
<212> TYPE: PRT
<213> ORGANISM: Artificial
<220> FEATURE:
<223> OTHER INFORMATION: Nucleic acid encoding CRISPR guide RNA

<400> SEQUENCE: 288

Tyr Gly Arg Lys Lys Arg Arg Gln Arg Arg Arg
1               5                   10

<210> SEQ ID NO 289
<211> LENGTH: 12
<212> TYPE: PRT
<213> ORGANISM: Artificial
<220> FEATURE:
<223> OTHER INFORMATION: Protein transduction domain

<400> SEQUENCE: 289

Arg Arg Gln Arg Arg Thr Ser Lys Leu Met Lys Arg
1               5                   10

<210> SEQ ID NO 290
<211> LENGTH: 27
<212> TYPE: PRT
<213> ORGANISM: Artificial
<220> FEATURE:
<223> OTHER INFORMATION: Protein transduction domain

<400> SEQUENCE: 290

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 291
<211> LENGTH: 33
<212> TYPE: PRT
<213> ORGANISM: Artificial
<220> FEATURE:
<223> OTHER INFORMATION: Protein transduction domain

<400> SEQUENCE: 291

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 292
<211> LENGTH: 16
<212> TYPE: PRT
<213> ORGANISM: Artificial
<220> FEATURE:
<223> OTHER INFORMATION: Protein transduction domain

```
<400> SEQUENCE: 292

Arg Gln Ile Lys Ile Trp Phe Gln Asn Arg Arg Met Lys Trp Lys Lys
1               5                   10                  15

<210> SEQ ID NO 293
<211> LENGTH: 11
<212> TYPE: PRT
<213> ORGANISM: Artificial
<220> FEATURE:
<223> OTHER INFORMATION: Protein transduction domain

<400> SEQUENCE: 293

Tyr Gly Arg Lys Lys Arg Arg Gln Arg Arg Arg
1               5                   10

<210> SEQ ID NO 294
<211> LENGTH: 9
<212> TYPE: PRT
<213> ORGANISM: Artificial
<220> FEATURE:
<223> OTHER INFORMATION: Protein transduction domain

<400> SEQUENCE: 294

Arg Lys Lys Arg Arg Gln Arg Arg Arg
1               5

<210> SEQ ID NO 295
<211> LENGTH: 11
<212> TYPE: PRT
<213> ORGANISM: Artificial
<220> FEATURE:
<223> OTHER INFORMATION: Protein transduction domain

<400> SEQUENCE: 295

Tyr Gly Arg Lys Lys Arg Arg Gln Arg Arg Arg
1               5                   10

<210> SEQ ID NO 296
<211> LENGTH: 8
<212> TYPE: PRT
<213> ORGANISM: Artificial
<220> FEATURE:
<223> OTHER INFORMATION: Protein transduction domain

<400> SEQUENCE: 296

Arg Lys Lys Arg Arg Gln Arg Arg
1               5

<210> SEQ ID NO 297
<211> LENGTH: 11
<212> TYPE: PRT
<213> ORGANISM: Artificial
<220> FEATURE:
<223> OTHER INFORMATION: Protein transduction domain

<400> SEQUENCE: 297

Tyr Ala Arg Ala Ala Ala Arg Gln Ala Arg Ala
1               5                   10

<210> SEQ ID NO 298
<211> LENGTH: 11
<212> TYPE: PRT
<213> ORGANISM: Artificial
<220> FEATURE:
<223> OTHER INFORMATION: Protein transduction domain
```

```
<400> SEQUENCE: 298

Thr His Arg Leu Pro Arg Arg Arg Arg Arg
1               5                   10

<210> SEQ ID NO 299
<211> LENGTH: 11
<212> TYPE: PRT
<213> ORGANISM: Artificial
<220> FEATURE:
<223> OTHER INFORMATION: Protein transduction domain

<400> SEQUENCE: 299

Gly Gly Arg Arg Ala Arg Arg Arg Arg Arg
1               5                   10

<210> SEQ ID NO 300
<211> LENGTH: 82
<212> TYPE: RNA
<213> ORGANISM: Artificial
<220> FEATURE:
<223> OTHER INFORMATION: Nucleic acid encoding CRISPR guide RNA

<400> SEQUENCE: 300
guuuuagagc uagaaauagc aaguuaaaau aaggcuaguc cguuaucaac uugaaaaagu      60
ggcaccgagu cggugcuuuu uu                                              82

<210> SEQ ID NO 301
<211> LENGTH: 19
<212> TYPE: DNA
<213> ORGANISM: Artificial
<220> FEATURE:
<223> OTHER INFORMATION: PCR primer

<400> SEQUENCE: 301
aacctcacct gtacacgcc                                                  19

<210> SEQ ID NO 302
<211> LENGTH: 22
<212> TYPE: DNA
<213> ORGANISM: Artificial
<220> FEATURE:
<223> OTHER INFORMATION: PCR primer

<400> SEQUENCE: 302
caagtccatg tttctttgca cg                                              22

<210> SEQ ID NO 303
<211> LENGTH: 20
<212> TYPE: DNA
<213> ORGANISM: Artificial
<220> FEATURE:
<223> OTHER INFORMATION: PCR primer

<400> SEQUENCE: 303
agagctacga gctgcctgac                                                 20

<210> SEQ ID NO 304
<211> LENGTH: 20
<212> TYPE: DNA
<213> ORGANISM: Artificial
<220> FEATURE:
<223> OTHER INFORMATION: PCR primer

<400> SEQUENCE: 304
agcactgtgt tggcgtacag                                                 20
```

<210> SEQ ID NO 305
<211> LENGTH: 17
<212> TYPE: RNA
<213> ORGANISM: Artificial
<220> FEATURE:
<223> OTHER INFORMATION: Nucleic acid encoding CRISPR guide RNA

<400> SEQUENCE: 305
gaaauuaaac uacacac                                                17

<210> SEQ ID NO 306
<211> LENGTH: 17
<212> TYPE: RNA
<213> ORGANISM: Artificial
<220> FEATURE:
<223> OTHER INFORMATION: Nucleic acid encoding CRISPR guide RNA

<400> SEQUENCE: 306
augaugcuau aauacca                                                17

<210> SEQ ID NO 307
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 307
guugaaauua aacuacacac                                             20

<210> SEQ ID NO 308
<211> LENGTH: 20
<212> TYPE: RNA
<213> ORGANISM: Artificial
<220> FEATURE:
<223> OTHER INFORMATION: Nucleic acid encoding CRISPR guide RNA

<400> SEQUENCE: 308
uguaugaugc uauaauacca                                             20

<210> SEQ ID NO 309
<211> LENGTH: 1368
<212> TYPE: PRT
<213> ORGANISM: S. pyrogenes

<400> SEQUENCE: 309

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Ser
                85                  90                  95

Phe Phe His Arg Leu Glu Glu Ser Phe Leu Val Glu Glu Asp Lys Lys
                100                 105                 110

```
His Glu Arg His Pro Ile Phe Gly Asn Ile Val Asp Glu Val Ala Tyr
            115                 120                 125
His Glu Lys Tyr Pro Thr Ile Tyr His Leu Arg Lys Lys Leu Val Asp
        130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
            180                 185                 190
Asn Gln Leu Phe Glu Glu Asn Pro Ile Asn Ala Ser Gly Val Asp Ala
        195                 200                 205
Lys Ala Ile Leu Ser Ala Arg Leu Ser Lys Ser Arg Arg Leu Glu Asn
    210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
            260                 265                 270
Asp Asp Leu Asp Asn Leu Leu Ala Gln Ile Gly Asp Gln Tyr Ala Asp
        275                 280                 285
Leu Phe Leu Ala Ala Lys Asn Leu Ser Asp Ala Ile Leu Leu Ser Asp
    290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
        515                 520                 525
```

-continued

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
930                 935                 940

```
Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260

His Tyr Leu Asp Glu Ile Ile Glu Gln Ile Ser Glu Phe Ser Lys
        1265                1270                1275

Arg Val Ile Leu Ala Asp Ala Asn Leu Asp Lys Val Leu Ser Ala
        1280                1285                1290

Tyr Asn Lys His Arg Asp Lys Pro Ile Arg Glu Gln Ala Glu Asn
        1295                1300                1305

Ile Ile His Leu Phe Thr Leu Thr Asn Leu Gly Ala Pro Ala Ala
        1310                1315                1320

Phe Lys Tyr Phe Asp Thr Thr Ile Asp Arg Lys Arg Tyr Thr Ser
        1325                1330                1335
```

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
1355                1360                1365

<210> SEQ ID NO 310
<211> LENGTH: 1300
<212> TYPE: PRT
<213> ORGANISM: Francisella tularensis

<400> SEQUENCE: 310

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
                20                  25                  30

Ala Arg Gly Leu Ile Leu Asp Asp Glu Lys Arg Ala Lys Asp Tyr Lys
            35                  40                  45

Lys Ala Lys Gln Ile Ile Asp Lys Tyr His Gln Phe Phe Ile Glu Glu
        50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

-continued

```
Gln Ser Phe Tyr Glu Gln Ile Ala Ala Phe Lys Thr Val Glu Glu Lys
        355                 360                 365
Ser Ile Lys Glu Thr Leu Ser Leu Leu Phe Asp Asp Leu Lys Ala Gln
        370                 375                 380
Lys Leu Asp Leu Ser Lys Ile Tyr Phe Lys Asn Asp Lys Ser Leu Thr
385                 390                 395                 400
Asp Leu Ser Gln Gln Val Phe Asp Asp Tyr Ser Val Ile Gly Thr Ala
                405                 410                 415
Val Leu Glu Tyr Ile Thr Gln Gln Ile Ala Pro Lys Asn Leu Asp Asn
                420                 425                 430
Pro Ser Lys Lys Glu Gln Glu Leu Ile Ala Lys Lys Thr Glu Lys Ala
                435                 440                 445
Lys Tyr Leu Ser Leu Glu Thr Ile Lys Leu Ala Leu Glu Glu Phe Asn
        450                 455                 460
Lys His Arg Asp Ile Asp Lys Gln Cys Arg Phe Glu Glu Ile Leu Ala
465                 470                 475                 480
Asn Phe Ala Ala Ile Pro Met Ile Phe Asp Glu Ile Ala Gln Asn Lys
                485                 490                 495
Asp Asn Leu Ala Gln Ile Ser Ile Lys Tyr Gln Asn Gln Gly Lys Lys
                500                 505                 510
Asp Leu Leu Gln Ala Ser Ala Glu Asp Val Lys Ala Ile Lys Asp
                515                 520                 525
Leu Leu Asp Gln Thr Asn Asn Leu Leu His Lys Leu Lys Ile Phe His
        530                 535                 540
Ile Ser Gln Ser Glu Asp Lys Ala Asn Ile Leu Asp Lys Asp Glu His
545                 550                 555                 560
Phe Tyr Leu Val Phe Glu Glu Cys Tyr Phe Glu Leu Ala Asn Ile Val
                565                 570                 575
Pro Leu Tyr Asn Lys Ile Arg Asn Tyr Ile Thr Gln Lys Pro Tyr Ser
                580                 585                 590
Asp Glu Lys Phe Lys Leu Asn Phe Glu Asn Ser Thr Leu Ala Asn Gly
        595                 600                 605
Trp Asp Lys Asn Lys Glu Pro Asp Asn Thr Ala Ile Leu Phe Ile Lys
        610                 615                 620
Asp Asp Lys Tyr Tyr Leu Gly Val Met Asn Lys Lys Asn Asn Lys Ile
625                 630                 635                 640
Phe Asp Asp Lys Ala Ile Lys Glu Asn Lys Gly Glu Gly Tyr Lys Lys
                645                 650                 655
Ile Val Tyr Lys Leu Leu Pro Gly Ala Asn Lys Met Leu Pro Lys Val
                660                 665                 670
Phe Phe Ser Ala Lys Ser Ile Lys Phe Tyr Asn Pro Ser Glu Asp Ile
        675                 680                 685
Leu Arg Ile Arg Asn His Ser Thr His Thr Lys Asn Gly Ser Pro Gln
        690                 695                 700
Lys Gly Tyr Glu Lys Phe Glu Phe Asn Ile Glu Asp Cys Arg Lys Phe
705                 710                 715                 720
Ile Asp Phe Tyr Lys Gln Ser Ile Ser Lys His Pro Glu Trp Lys Asp
                725                 730                 735
Phe Gly Phe Arg Phe Ser Asp Thr Gln Arg Tyr Asn Ser Ile Asp Glu
                740                 745                 750
Phe Tyr Arg Glu Val Glu Asn Gln Gly Tyr Lys Leu Thr Phe Glu Asn
        755                 760                 765
```

```
Ile Ser Glu Ser Tyr Ile Asp Ser Val Val Asn Gln Gly Lys Leu Tyr
770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
                820                 825                 830

Arg Lys Gln Ser Ile Pro Lys Lys Ile Thr His Pro Ala Lys Glu Ala
                835                 840                 845

Ile Ala Asn Lys Asn Lys Asp Asn Pro Lys Lys Glu Ser Val Phe Glu
850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
                900                 905                 910

Ile Leu Ser Ile Asp Arg Gly Glu Arg His Leu Ala Tyr Tyr Thr Leu
                915                 920                 925

Val Asp Gly Lys Gly Asn Ile Ile Lys Gln Asp Thr Phe Asn Ile Ile
930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
                980                 985                 990

Ala Lys Leu Val Ile Glu Tyr Asn Ala Ile Val Val Phe Glu Asp Leu
                995                 1000                1005

Asn Phe Gly Phe Lys Arg Gly Arg Phe Lys Val Glu Lys Gln Val
    1010                1015                1020

Tyr Gln Lys Leu Glu Lys Met Leu Ile Glu Lys Leu Asn Tyr Leu
    1025                1030                1035

Val Phe Lys Asp Asn Glu Phe Asp Lys Thr Gly Gly Val Leu Arg
    1040                1045                1050

Ala Tyr Gln Leu Thr Ala Pro Phe Glu Thr Phe Lys Lys Met Gly
    1055                1060                1065

Lys Gln Thr Gly Ile Ile Tyr Tyr Val Pro Ala Gly Phe Thr Ser
    1070                1075                1080

Lys Ile Cys Pro Val Thr Gly Phe Val Asn Gln Leu Tyr Pro Lys
    1085                1090                1095

Tyr Glu Ser Val Ser Lys Ser Gln Glu Phe Phe Ser Lys Phe Asp
    1100                1105                1110

Lys Ile Cys Tyr Asn Leu Asp Lys Gly Tyr Phe Glu Phe Ser Phe
    1115                1120                1125

Asp Tyr Lys Asn Phe Gly Asp Lys Ala Ala Lys Gly Lys Trp Thr
    1130                1135                1140

Ile Ala Ser Phe Gly Ser Arg Leu Ile Asn Phe Arg Asn Ser Asp
    1145                1150                1155

Lys Asn His Asn Trp Asp Thr Arg Glu Val Tyr Pro Thr Lys Glu
    1160                1165                1170
```

Leu Glu Lys Leu Leu Lys Asp Tyr Ser Ile Glu Tyr Gly His Gly
1175                1180                1185

Glu Cys Ile Lys Ala Ala Ile Cys Gly Glu Ser Asp Lys Lys Phe
1190                1195                1200

Phe Ala Lys Leu Thr Ser Val Leu Asn Thr Ile Leu Gln Met Arg
1205                1210                1215

Asn Ser Lys Thr Gly Thr Glu Leu Asp Tyr Leu Ile Ser Pro Val
1220                1225                1230

Ala Asp Val Asn Gly Asn Phe Phe Asp Ser Arg Gln Ala Pro Lys
1235                1240                1245

Asn Met Pro Gln Asp Ala Asp Ala Asn Gly Ala Tyr His Ile Gly
1250                1255                1260

Leu Lys Gly Leu Met Leu Leu Gly Arg Ile Lys Asn Asn Gln Glu
1265                1270                1275

Gly Lys Lys Leu Asn Leu Val Ile Lys Asn Glu Glu Tyr Phe Glu
1280                1285                1290

Phe Val Gln Asn Arg Asn Asn
1295                1300

<210> SEQ ID NO 311
<211> LENGTH: 1307
<212> TYPE: PRT
<213> ORGANISM: S. pyogenes

<400> SEQUENCE: 311

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
                20                  25                  30

Glu Gln Gly Phe Ile Glu Glu Asp Lys Ala Arg Asn Asp His Tyr Lys
            35                  40                  45

Glu Leu Lys Pro Ile Ile Asp Arg Ile Tyr Lys Thr Tyr Ala Asp Gln
        50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

```
Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
            275                 280                 285

Asp Glu Thr Ala His Ile Ile Ala Ser Leu Pro His Arg Phe Ile Pro
            290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
            355                 360                 365

Lys Lys Leu Glu Thr Ile Ser Ser Ala Leu Cys Asp His Trp Asp Thr
370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
                435                 440                 445

Ala Leu Asp Gln Pro Leu Pro Thr Thr Leu Lys Lys Gln Glu Glu Lys
            450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
            515                 520                 525

Glu Lys Phe Lys Leu Asn Phe Gln Met Pro Thr Leu Ala Ser Gly Trp
            530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Thr Ser Glu Gly Phe Asp Lys
            580                 585                 590

Met Tyr Tyr Asp Tyr Phe Pro Asp Ala Ala Lys Met Ile Pro Lys Cys
            595                 600                 605

Ser Thr Gln Leu Lys Ala Val Thr Ala His Phe Gln Thr His Thr Thr
            610                 615                 620

Pro Ile Leu Leu Ser Asn Asn Phe Ile Glu Pro Leu Glu Ile Thr Lys
625                 630                 635                 640
```

-continued

Glu Ile Tyr Asp Leu Asn Asn Pro Glu Lys Glu Pro Lys Lys Phe Gln
            645                 650                 655

Thr Ala Tyr Ala Lys Lys Thr Gly Asp Gln Lys Gly Tyr Arg Glu Ala
660                 665                 670

Leu Cys Lys Trp Ile Asp Phe Thr Arg Asp Phe Leu Ser Lys Tyr Thr
            675                 680                 685

Lys Thr Thr Ser Ile Asp Leu Ser Ser Leu Arg Pro Ser Ser Gln Tyr
690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
            725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
            755                 760                 765

Phe Ser Pro Glu Asn Leu Ala Lys Thr Ser Ile Lys Leu Asn Gly Gln
            770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
            805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
            835                 840                 845

Val Ile Thr Lys Glu Val Ser His Glu Ile Ile Lys Asp Arg Arg Phe
850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
            885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
            915                 920                 925

Gln Arg Ser Leu Asn Thr Ile Gln Gln Phe Asp Tyr Gln Lys Lys Leu
            930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
            965                 970                 975

His Glu Ile Val Asp Leu Met Ile His Tyr Gln Ala Val Val Val Leu
            980                 985                 990

Glu Asn Leu Asn Phe Gly Phe Lys Ser Lys Arg Thr Gly Ile Ala Glu
            995                 1000                1005

Lys Ala Val Tyr Gln Gln Phe Glu Lys Met Leu Ile Asp Lys Leu
            1010                1015                1020

Asn Cys Leu Val Leu Lys Asp Tyr Pro Ala Glu Lys Val Gly Gly
            1025                1030                1035

Val Leu Asn Pro Tyr Gln Leu Thr Asp Gln Phe Thr Ser Phe Ala
            1040                1045                1050

-continued

Lys Met Gly Thr Gln Ser Gly Phe Leu Phe Tyr Val Pro Ala Pro
    1055            1060                1065

Tyr Thr Ser Lys Ile Asp Pro Leu Thr Gly Phe Val Asp Pro Phe
    1070            1075                1080

Val Trp Lys Thr Ile Lys Asn His Glu Ser Arg Lys His Phe Leu
    1085            1090                1095

Glu Gly Phe Asp Phe Leu His Tyr Asp Val Lys Thr Gly Asp Phe
    1100            1105                1110

Ile Leu His Phe Lys Met Asn Arg Asn Leu Ser Phe Gln Arg Gly
    1115            1120                1125

Leu Pro Gly Phe Met Pro Ala Trp Asp Ile Val Phe Glu Lys Asn
    1130            1135                1140

Glu Thr Gln Phe Asp Ala Lys Gly Thr Pro Phe Ile Ala Gly Lys
    1145            1150                1155

Arg Ile Val Pro Val Ile Glu Asn His Arg Phe Thr Gly Arg Tyr
    1160            1165                1170

Arg Asp Leu Tyr Pro Ala Asn Glu Leu Ile Ala Leu Leu Glu Glu
    1175            1180                1185

Lys Gly Ile Val Phe Arg Asp Gly Ser Asn Ile Leu Pro Lys Leu
    1190            1195                1200

Leu Glu Asn Asp Asp Ser His Ala Ile Asp Thr Met Val Ala Leu
    1205            1210                1215

Ile Arg Ser Val Leu Gln Met Arg Asn Ser Asn Ala Ala Thr Gly
    1220            1225                1230

Glu Asp Tyr Ile Asn Ser Pro Val Arg Asp Leu Asn Gly Val Cys
    1235            1240                1245

Phe Asp Ser Arg Phe Gln Asn Pro Glu Trp Pro Met Asp Ala Asp
    1250            1255                1260

Ala Asn Gly Ala Tyr His Ile Ala Leu Lys Gly Gln Leu Leu Leu
    1265            1270                1275

Asn His Leu Lys Glu Ser Lys Asp Leu Lys Leu Gln Asn Gly Ile
    1280            1285                1290

Ser Asn Gln Asp Trp Leu Ala Tyr Ile Gln Glu Leu Arg Asn
    1295            1300                1305

<210> SEQ ID NO 312
<211> LENGTH: 1246
<212> TYPE: PRT
<213> ORGANISM: S. pyrogenes

<400> SEQUENCE: 312

Met Leu Lys Asn Val Gly Ile Asp Arg Leu Asp Val Glu Lys Gly Arg
1               5                   10                  15

Lys Asn Met Ser Lys Leu Glu Lys Phe Thr Asn Cys Tyr Ser Leu Ser
            20                  25                  30

Lys Thr Leu Arg Phe Lys Ala Ile Pro Val Gly Lys Thr Gln Glu Asn
        35                  40                  45

Ile Asp Asn Lys Arg Leu Leu Val Glu Asp Glu Lys Arg Ala Glu Asp
    50                  55                  60

Tyr Lys Gly Val Lys Lys Leu Leu Asp Arg Tyr Tyr Leu Ser Phe Ile
65                  70                  75                  80

Asn Asp Val Leu His Ser Ile Lys Leu Lys Asn Leu Asn Asn Tyr Ile
                85                  90                  95

```
Ser Leu Phe Arg Lys Lys Thr Arg Thr Glu Lys Glu Asn Lys Glu Leu
            100                 105                 110

Glu Asn Leu Glu Ile Asn Leu Arg Lys Glu Ile Ala Lys Ala Phe Lys
            115                 120                 125

Gly Asn Glu Gly Tyr Lys Ser Leu Phe Lys Lys Asp Ile Ile Glu Thr
        130                 135                 140

Ile Leu Pro Glu Phe Leu Asp Asp Lys Asp Glu Ile Ala Leu Val Asn
145                 150                 155                 160

Ser Phe Asn Gly Phe Thr Thr Ala Phe Thr Gly Phe Phe Asp Asn Arg
                165                 170                 175

Glu Asn Met Phe Ser Glu Glu Ala Lys Ser Thr Ser Ile Ala Phe Arg
            180                 185                 190

Cys Ile Asn Glu Asn Leu Thr Arg Tyr Ile Ser Asn Met Asp Ile Phe
        195                 200                 205

Glu Lys Val Asp Ala Ile Phe Asp Lys His Glu Val Gln Glu Ile Lys
    210                 215                 220

Glu Lys Ile Leu Asn Ser Asp Tyr Asp Val Glu Asp Phe Phe Glu Gly
225                 230                 235                 240

Glu Phe Phe Asn Phe Val Leu Thr Gln Glu Gly Ile Asp Val Tyr Asn
                245                 250                 255

Ala Ile Ile Gly Gly Phe Val Thr Glu Ser Gly Glu Lys Ile Lys Gly
            260                 265                 270

Leu Asn Glu Tyr Ile Asn Leu Tyr Asn Gln Lys Thr Lys Gln Lys Leu
        275                 280                 285

Pro Lys Phe Lys Pro Leu Tyr Lys Gln Val Leu Ser Asp Arg Glu Ser
    290                 295                 300

Leu Ser Phe Tyr Gly Glu Gly Tyr Thr Ser Asp Glu Glu Val Leu Glu
305                 310                 315                 320

Val Phe Arg Asn Thr Leu Asn Lys Asn Ser Glu Ile Phe Ser Ser Ile
                325                 330                 335

Lys Lys Leu Glu Lys Leu Phe Lys Asn Phe Asp Glu Tyr Ser Ser Ala
            340                 345                 350

Gly Ile Phe Val Lys Asn Gly Pro Ala Ile Ser Thr Ile Ser Lys Asp
        355                 360                 365

Ile Phe Gly Glu Trp Asn Val Ile Arg Asp Lys Trp Asn Ala Glu Tyr
    370                 375                 380

Asp Asp Ile His Leu Lys Lys Ala Val Val Thr Glu Lys Tyr Glu
385                 390                 395                 400

Asp Asp Arg Arg Lys Ser Phe Lys Lys Ile Gly Ser Phe Ser Leu Glu
                405                 410                 415

Gln Leu Gln Glu Tyr Ala Asp Ala Asp Leu Ser Val Val Glu Lys Leu
            420                 425                 430

Lys Glu Ile Ile Ile Gln Lys Val Asp Glu Ile Tyr Lys Val Tyr Gly
        435                 440                 445

Ser Ser Glu Lys Leu Phe Asp Ala Asp Phe Val Leu Glu Lys Ser Leu
    450                 455                 460

Lys Lys Asn Asp Ala Val Val Ala Ile Met Lys Asp Leu Leu Asp Ser
465                 470                 475                 480

Val Lys Ser Phe Glu Asn Tyr Ile Lys Ala Phe Phe Gly Glu Gly Lys
                485                 490                 495

Glu Thr Asn Arg Asp Glu Ser Phe Tyr Gly Asp Phe Val Leu Ala Tyr
            500                 505                 510
```

```
Asp Ile Leu Leu Lys Val Asp His Ile Tyr Asp Ala Ile Arg Asn Tyr
            515                 520                 525
Val Thr Gln Lys Pro Tyr Ser Lys Asp Lys Phe Lys Leu Tyr Phe Gln
530                 535                 540
Asn Pro Gln Phe Met Gly Gly Trp Asp Lys Asp Lys Glu Thr Asp Tyr
545                 550                 555                 560
Arg Ala Thr Ile Leu Arg Tyr Gly Ser Lys Tyr Tyr Leu Ala Ile Met
                565                 570                 575
Asp Lys Lys Tyr Ala Lys Cys Leu Gln Lys Ile Asp Lys Asp Asp Val
            580                 585                 590
Asn Gly Asn Tyr Glu Lys Ile Asn Tyr Lys Leu Leu Pro Gly Pro Asn
            595                 600                 605
Lys Met Leu Pro Lys Val Phe Phe Ser Lys Lys Trp Met Ala Tyr Tyr
610                 615                 620
Asn Pro Ser Glu Asp Ile Gln Lys Ile Tyr Lys Asn Gly Thr Phe Lys
625                 630                 635                 640
Lys Gly Asp Met Phe Asn Leu Asn Asp Cys His Lys Leu Ile Asp Phe
                645                 650                 655
Phe Lys Asp Ser Ile Ser Arg Tyr Pro Lys Trp Ser Asn Ala Tyr Asp
            660                 665                 670
Phe Asn Phe Ser Glu Thr Glu Lys Tyr Lys Asp Ile Ala Gly Phe Tyr
            675                 680                 685
Arg Glu Val Glu Glu Gln Gly Tyr Lys Val Ser Phe Glu Ser Ala Ser
690                 695                 700
Lys Lys Glu Val Asp Lys Leu Val Glu Glu Gly Lys Leu Tyr Met Phe
705                 710                 715                 720
Gln Ile Tyr Asn Lys Asp Phe Ser Asp Lys Ser His Gly Thr Pro Asn
                725                 730                 735
Leu His Thr Met Tyr Phe Lys Leu Leu Phe Asp Glu Asn Asn His Gly
            740                 745                 750
Gln Ile Arg Leu Ser Gly Gly Ala Glu Leu Phe Met Arg Arg Ala Ser
            755                 760                 765
Leu Lys Lys Glu Glu Leu Val Val His Pro Ala Asn Ser Pro Ile Ala
770                 775                 780
Asn Lys Asn Pro Asp Asn Pro Lys Lys Thr Thr Thr Leu Ser Tyr Asp
785                 790                 795                 800
Val Tyr Lys Asp Lys Arg Phe Ser Glu Asp Gln Tyr Glu Leu His Ile
                805                 810                 815
Pro Ile Ala Ile Asn Lys Cys Pro Lys Asn Ile Phe Lys Ile Asn Thr
            820                 825                 830
Glu Val Arg Val Leu Leu Lys His Asp Asp Asn Pro Tyr Val Ile Gly
            835                 840                 845
Ile Asp Arg Gly Glu Arg Asn Leu Leu Tyr Ile Val Val Val Asp Gly
850                 855                 860
Lys Gly Asn Ile Val Glu Gln Tyr Ser Leu Asn Glu Ile Ile Asn Asn
865                 870                 875                 880
Phe Asn Gly Ile Arg Ile Lys Thr Asp Tyr His Ser Leu Leu Asp Lys
                885                 890                 895
Lys Glu Lys Glu Arg Phe Glu Ala Arg Gln Asn Trp Thr Ser Ile Glu
            900                 905                 910
Asn Ile Lys Glu Leu Lys Ala Gly Tyr Ile Ser Gln Val Val His Lys
            915                 920                 925
```

Ile Cys Glu Leu Val Glu Lys Tyr Asp Ala Val Ile Ala Leu Glu Asp
   930                 935                 940

Leu Asn Ser Gly Phe Lys Asn Ser Arg Val Lys Val Glu Lys Gln Val
945                 950                 955                 960

Tyr Gln Lys Phe Glu Lys Met Leu Ile Asp Lys Leu Asn Tyr Met Val
                965                 970                 975

Asp Lys Lys Ser Asn Pro Cys Ala Thr Gly Gly Ala Leu Lys Gly Tyr
            980                 985                 990

Gln Ile Thr Asn Lys Phe Glu Ser Phe Lys Ser Met Ser Thr Gln Asn
        995                 1000                1005

Gly Phe Ile Phe Tyr Ile Pro Ala Trp Leu Thr Ser Lys Ile Asp
    1010                1015                1020

Pro Ser Thr Gly Phe Val Asn Leu Leu Lys Thr Lys Tyr Thr Ser
    1025                1030                1035

Ile Ala Asp Ser Lys Lys Phe Ile Ser Ser Phe Asp Arg Ile Met
    1040                1045                1050

Tyr Val Pro Glu Glu Asp Leu Phe Glu Phe Ala Leu Asp Tyr Lys
    1055                1060                1065

Asn Phe Ser Arg Thr Asp Ala Asp Tyr Ile Lys Lys Trp Lys Leu
    1070                1075                1080

Tyr Ser Tyr Gly Asn Arg Ile Arg Ile Phe Arg Asn Pro Lys Lys
    1085                1090                1095

Asn Asn Val Phe Asp Trp Glu Glu Val Cys Leu Thr Ser Ala Tyr
    1100                1105                1110

Lys Glu Leu Phe Asn Lys Tyr Gly Ile Asn Tyr Gln Gln Gly Asp
    1115                1120                1125

Ile Arg Ala Leu Leu Cys Glu Gln Ser Asp Lys Ala Phe Tyr Ser
    1130                1135                1140

Ser Phe Met Ala Leu Met Ser Leu Met Leu Gln Met Arg Asn Ser
    1145                1150                1155

Ile Thr Gly Arg Thr Asp Val Asp Phe Leu Ile Ser Pro Val Lys
    1160                1165                1170

Asn Ser Asp Gly Ile Phe Tyr Asp Ser Arg Asn Tyr Glu Ala Gln
    1175                1180                1185

Glu Asn Ala Ile Leu Pro Lys Asn Ala Asp Ala Asn Gly Ala Tyr
    1190                1195                1200

Asn Ile Ala Arg Lys Val Leu Trp Ala Ile Gly Gln Phe Lys Lys
    1205                1210                1215

Ala Glu Asp Glu Lys Leu Asp Lys Val Lys Ile Ala Ile Ser Asn
    1220                1225                1230

Lys Glu Trp Leu Glu Tyr Ala Gln Thr Ser Val Lys His
    1235                1240                1245

<210> SEQ ID NO 313
<211> LENGTH: 1246
<212> TYPE: PRT
<213> ORGANISM: Porphyromonas macacae

<400> SEQUENCE: 313

Met Lys Thr Gln His Phe Phe Glu Asp Phe Thr Ser Leu Tyr Ser Leu
1               5                   10                  15

Ser Lys Thr Ile Arg Phe Glu Leu Lys Pro Ile Gly Lys Thr Leu Glu
            20                  25                  30

```
Asn Ile Lys Lys Asn Gly Leu Ile Arg Arg Asp Glu Gln Arg Leu Asp
         35                  40                  45

Asp Tyr Glu Lys Leu Lys Lys Val Ile Asp Glu Tyr His Glu Asp Phe
     50                  55                  60

Ile Ala Asn Ile Leu Ser Ser Phe Ser Phe Ser Glu Glu Ile Leu Gln
65                  70                  75                  80

Ser Tyr Ile Gln Asn Leu Ser Glu Ser Glu Ala Arg Ala Lys Ile Glu
                 85                  90                  95

Lys Thr Met Arg Asp Thr Leu Ala Lys Ala Phe Ser Glu Asp Glu Arg
                100                 105                 110

Tyr Lys Ser Ile Phe Lys Lys Glu Leu Val Lys Lys Asp Ile Pro Val
            115                 120                 125

Trp Cys Pro Ala Tyr Lys Ser Leu Cys Lys Lys Phe Asp Asn Phe Thr
        130                 135                 140

Thr Ser Leu Val Pro Phe His Glu Asn Arg Lys Asn Leu Tyr Thr Ser
145                 150                 155                 160

Asn Glu Ile Thr Ala Ser Ile Pro Tyr Arg Ile Val His Val Asn Leu
                165                 170                 175

Pro Lys Phe Ile Gln Asn Ile Glu Ala Leu Cys Glu Leu Gln Lys Lys
            180                 185                 190

Met Gly Ala Asp Leu Tyr Leu Glu Met Met Glu Asn Leu Arg Asn Val
        195                 200                 205

Trp Pro Ser Phe Val Lys Thr Pro Asp Asp Leu Cys Asn Leu Lys Thr
    210                 215                 220

Tyr Asn His Leu Met Val Gln Ser Ser Ile Ser Glu Tyr Asn Arg Phe
225                 230                 235                 240

Val Gly Gly Tyr Ser Thr Glu Asp Gly Thr Lys His Gln Gly Ile Asn
                245                 250                 255

Glu Trp Ile Asn Ile Tyr Arg Gln Arg Asn Lys Glu Met Arg Leu Pro
            260                 265                 270

Gly Leu Val Phe Leu His Lys Gln Ile Leu Ala Lys Val Asp Ser Ser
        275                 280                 285

Ser Phe Ile Ser Asp Thr Leu Glu Asn Asp Asp Gln Val Phe Cys Val
    290                 295                 300

Leu Arg Gln Phe Arg Lys Leu Phe Trp Asn Thr Val Ser Ser Lys Glu
305                 310                 315                 320

Asp Asp Ala Ala Ser Leu Lys Asp Leu Phe Cys Gly Leu Ser Gly Tyr
                325                 330                 335

Asp Pro Glu Ala Ile Tyr Val Ser Asp Ala His Leu Ala Thr Ile Ser
            340                 345                 350

Lys Asn Ile Phe Asp Arg Trp Asn Tyr Ile Ser Asp Ala Ile Arg Arg
        355                 360                 365

Lys Thr Glu Val Leu Met Pro Arg Lys Lys Glu Ser Val Glu Arg Tyr
    370                 375                 380

Ala Glu Lys Ile Ser Lys Gln Ile Lys Arg Gln Ser Tyr Ser Leu
385                 390                 395                 400

Ala Glu Leu Asp Asp Leu Leu Ala His Tyr Ser Glu Glu Ser Leu Pro
                405                 410                 415

Ala Gly Phe Ser Leu Leu Ser Tyr Phe Thr Ser Leu Gly Gly Gln Lys
            420                 425                 430

Tyr Leu Val Ser Asp Gly Glu Val Ile Leu Tyr Glu Glu Gly Ser Asn
        435                 440                 445
```

```
Ile Trp Asp Glu Val Leu Ile Ala Phe Arg Asp Leu Gln Val Ile Leu
450                 455                 460

Asp Lys Asp Phe Thr Glu Lys Lys Leu Gly Lys Asp Glu Glu Ala Val
465                 470                 475                 480

Ser Val Ile Lys Lys Ala Leu Asp Ser Ala Leu Arg Leu Arg Lys Phe
            485                 490                 495

Phe Asp Leu Leu Ser Gly Thr Gly Ala Glu Ile Arg Arg Asp Ser Ser
            500                 505                 510

Phe Tyr Ala Leu Tyr Thr Asp Arg Met Asp Lys Leu Lys Gly Leu Leu
            515                 520                 525

Lys Met Tyr Asp Lys Val Arg Asn Tyr Leu Thr Lys Lys Pro Tyr Ser
530                 535                 540

Ile Glu Lys Phe Lys Leu His Phe Asp Asn Pro Ser Leu Leu Ser Gly
545                 550                 555                 560

Trp Asp Lys Asn Lys Glu Leu Asn Asn Leu Ser Val Ile Phe Arg Gln
                565                 570                 575

Asn Gly Tyr Tyr Tyr Leu Gly Ile Met Thr Pro Lys Gly Lys Asn Leu
            580                 585                 590

Phe Lys Thr Leu Pro Lys Leu Gly Ala Glu Glu Met Phe Tyr Glu Lys
            595                 600                 605

Met Glu Tyr Lys Gln Ile Ala Glu Pro Met Leu Met Leu Pro Lys Val
610                 615                 620

Phe Phe Pro Lys Lys Thr Lys Pro Ala Phe Ala Pro Asp Gln Ser Val
625                 630                 635                 640

Val Asp Ile Tyr Asn Lys Lys Thr Phe Lys Thr Gly Gln Lys Gly Phe
                645                 650                 655

Asn Lys Lys Asp Leu Tyr Arg Leu Ile Asp Phe Tyr Lys Glu Ala Leu
            660                 665                 670

Thr Val His Glu Trp Lys Leu Phe Asn Phe Ser Phe Ser Pro Thr Glu
            675                 680                 685

Gln Tyr Arg Asn Ile Gly Glu Phe Phe Asp Glu Val Arg Glu Gln Ala
    690                 695                 700

Tyr Lys Val Ser Met Val Asn Val Pro Ala Ser Tyr Ile Asp Glu Ala
705                 710                 715                 720

Val Glu Asn Gly Lys Leu Tyr Leu Phe Gln Ile Tyr Asn Lys Asp Phe
                725                 730                 735

Ser Pro Tyr Ser Lys Gly Ile Pro Asn Leu His Thr Leu Tyr Trp Lys
            740                 745                 750

Ala Leu Phe Ser Glu Gln Asn Gln Ser Arg Val Tyr Lys Leu Cys Gly
            755                 760                 765

Gly Gly Glu Leu Phe Tyr Arg Lys Ala Ser Leu His Met Gln Asp Thr
770                 775                 780

Thr Val His Pro Lys Gly Ile Ser Ile His Lys Lys Asn Leu Asn Lys
785                 790                 795                 800

Lys Gly Glu Thr Ser Leu Phe Asn Tyr Asp Leu Val Lys Asp Lys Arg
                805                 810                 815

Phe Thr Glu Asp Lys Phe Phe Phe His Val Pro Ile Ser Ile Asn Tyr
            820                 825                 830

Lys Asn Lys Lys Ile Thr Asn Val Asn Gln Met Val Arg Asp Tyr Ile
            835                 840                 845

Ala Gln Asn Asp Asp Leu Gln Ile Ile Gly Ile Asp Arg Gly Glu Arg
850                 855                 860
```

```
Asn Leu Leu Tyr Ile Ser Arg Ile Asp Thr Arg Gly Asn Leu Leu Glu
865                 870                 875                 880

Gln Phe Ser Leu Asn Val Ile Glu Ser Asp Lys Gly Asp Leu Arg Thr
            885                 890                 895

Asp Tyr Gln Lys Ile Leu Gly Asp Arg Glu Gln Glu Arg Leu Arg Arg
        900                 905                 910

Arg Gln Glu Trp Lys Ser Ile Glu Ser Ile Lys Asp Leu Lys Asp Gly
    915                 920                 925

Tyr Met Ser Gln Val Val His Lys Ile Cys Asn Met Val Glu His
930                 935                 940

Lys Ala Ile Val Val Leu Glu Asn Leu Asn Leu Ser Phe Met Lys Gly
945                 950                 955                 960

Arg Lys Lys Val Glu Lys Ser Val Tyr Glu Lys Phe Glu Arg Met Leu
                965                 970                 975

Val Asp Lys Leu Asn Tyr Leu Val Val Asp Lys Lys Asn Leu Ser Asn
            980                 985                 990

Glu Pro Gly Gly Leu Tyr Ala Ala Tyr Gln Leu Thr Asn Pro Leu Phe
        995                 1000                1005

Ser Phe Glu Glu Leu His Arg Tyr Pro Gln Ser Gly Ile Leu Phe
    1010                1015                1020

Phe Val Asp Pro Trp Asn Thr Ser Leu Thr Asp Pro Ser Thr Gly
    1025                1030                1035

Phe Val Asn Leu Leu Gly Arg Ile Asn Tyr Thr Asn Val Gly Asp
    1040                1045                1050

Ala Arg Lys Phe Phe Asp Arg Phe Asn Ala Ile Arg Tyr Asp Gly
    1055                1060                1065

Lys Gly Asn Ile Leu Phe Asp Leu Asp Leu Ser Arg Phe Asp Val
    1070                1075                1080

Arg Val Glu Thr Gln Arg Lys Leu Trp Thr Leu Thr Thr Phe Gly
    1085                1090                1095

Ser Arg Ile Ala Lys Ser Lys Lys Ser Gly Lys Trp Met Val Glu
    1100                1105                1110

Arg Ile Glu Asn Leu Ser Leu Cys Phe Leu Glu Leu Phe Glu Gln
    1115                1120                1125

Phe Asn Ile Gly Tyr Arg Val Glu Lys Asp Leu Lys Lys Ala Ile
    1130                1135                1140

Leu Ser Gln Asp Arg Lys Glu Phe Tyr Val Arg Leu Ile Tyr Leu
    1145                1150                1155

Phe Asn Leu Met Met Gln Ile Arg Asn Ser Asp Gly Glu Glu Asp
    1160                1165                1170

Tyr Ile Leu Ser Pro Ala Leu Asn Glu Lys Asn Leu Gln Phe Asp
    1175                1180                1185

Ser Arg Leu Ile Glu Ala Lys Asp Leu Pro Val Asp Ala Asp Ala
    1190                1195                1200

Asn Gly Ala Tyr Asn Val Ala Arg Lys Gly Leu Met Val Val Gln
    1205                1210                1215

Arg Ile Lys Arg Gly Asp His Glu Ser Ile His Arg Ile Gly Arg
    1220                1225                1230

Ala Gln Trp Leu Arg Tyr Val Gln Glu Gly Ile Val Glu
    1235                1240                1245

<210> SEQ ID NO 314
<211> LENGTH: 1326
```

<212> TYPE: PRT
<213> ORGANISM: Prevotella disiens

<400> SEQUENCE: 314

```
Met Lys Val Met Glu Asn Tyr Gln Glu Phe Thr Asn Leu Phe Gln Leu
1               5                   10                  15

Asn Lys Thr Leu Arg Phe Glu Leu Lys Pro Ile Gly Lys Thr Cys Glu
            20                  25                  30

Leu Leu Glu Glu Gly Lys Ile Phe Ala Ser Gly Ser Phe Leu Glu Lys
        35                  40                  45

Asp Lys Val Arg Ala Asp Asn Val Ser Tyr Val Lys Lys Glu Ile Asp
    50                  55                  60

Lys Lys His Lys Ile Phe Ile Glu Glu Thr Leu Ser Ser Phe Ser Ile
65                  70                  75                  80

Ser Asn Asp Leu Leu Lys Gln Tyr Phe Asp Cys Tyr Asn Glu Leu Lys
                85                  90                  95

Ala Phe Lys Lys Asp Cys Lys Ser Asp Glu Glu Val Lys Lys Thr
            100                 105                 110

Ala Leu Arg Asn Lys Cys Thr Ser Ile Gln Arg Ala Met Arg Glu Ala
        115                 120                 125

Ile Ser Gln Ala Phe Leu Lys Ser Pro Gln Lys Lys Leu Leu Ala Ile
    130                 135                 140

Lys Asn Leu Ile Glu Asn Val Phe Lys Ala Asp Glu Asn Val Gln His
145                 150                 155                 160

Phe Ser Glu Phe Thr Ser Tyr Phe Ser Gly Phe Glu Thr Asn Arg Glu
                165                 170                 175

Asn Phe Tyr Ser Asp Glu Glu Lys Ser Thr Ser Ile Ala Tyr Arg Leu
            180                 185                 190

Val His Asp Asn Leu Pro Ile Phe Ile Lys Asn Ile Tyr Ile Phe Glu
        195                 200                 205

Lys Leu Lys Glu Gln Phe Asp Ala Lys Thr Leu Ser Glu Ile Phe Glu
    210                 215                 220

Asn Tyr Lys Leu Tyr Val Ala Gly Ser Ser Leu Asp Glu Val Phe Ser
225                 230                 235                 240

Leu Glu Tyr Phe Asn Asn Thr Leu Thr Gln Lys Gly Ile Asp Asn Tyr
                245                 250                 255

Asn Ala Val Ile Gly Lys Ile Val Lys Glu Asp Lys Gln Glu Ile Gln
            260                 265                 270

Gly Leu Asn Glu His Ile Asn Leu Tyr Asn Gln Lys His Lys Asp Arg
        275                 280                 285

Arg Leu Pro Phe Phe Ile Ser Leu Lys Lys Gln Ile Leu Ser Asp Arg
    290                 295                 300

Glu Ala Leu Ser Trp Leu Pro Asp Met Phe Lys Asn Asp Ser Glu Val
305                 310                 315                 320

Ile Lys Ala Leu Lys Gly Phe Tyr Ile Glu Asp Gly Phe Glu Asn Asn
                325                 330                 335

Val Leu Thr Pro Leu Ala Thr Leu Leu Ser Leu Asp Lys Tyr Asn
            340                 345                 350

Leu Asn Gly Ile Phe Ile Arg Asn Asn Glu Ala Leu Ser Ser Leu Ser
        355                 360                 365

Gln Asn Val Tyr Arg Asn Phe Ser Ile Asp Glu Ala Ile Asp Ala Asn
    370                 375                 380

Ala Glu Leu Gln Thr Phe Asn Asn Tyr Glu Leu Ile Ala Asn Ala Leu
385                 390                 395                 400
```

```
Arg Ala Lys Ile Lys Lys Glu Thr Lys Gln Gly Arg Lys Ser Phe Glu
            405                 410                 415
Lys Tyr Glu Glu Tyr Ile Asp Lys Lys Val Lys Ala Ile Asp Ser Leu
            420                 425                 430
Ser Ile Gln Glu Ile Asn Glu Leu Val Glu Asn Tyr Val Ser Glu Phe
            435                 440                 445
Asn Ser Asn Ser Gly Asn Met Pro Arg Lys Val Glu Asp Tyr Phe Ser
            450                 455                 460
Leu Met Arg Lys Gly Asp Phe Gly Ser Asn Asp Leu Ile Glu Asn Ile
465                 470                 475                 480
Lys Thr Lys Leu Ser Ala Ala Glu Lys Leu Leu Gly Thr Lys Tyr Gln
            485                 490                 495
Glu Thr Ala Lys Asp Ile Phe Lys Lys Asp Glu Asn Ser Lys Leu Ile
            500                 505                 510
Lys Glu Leu Leu Asp Ala Thr Lys Gln Phe Gln His Phe Ile Lys Pro
            515                 520                 525
Leu Leu Gly Thr Gly Glu Glu Ala Asp Arg Asp Leu Val Phe Tyr Gly
            530                 535                 540
Asp Phe Leu Pro Leu Tyr Glu Lys Phe Glu Glu Leu Thr Leu Leu Tyr
545                 550                 555                 560
Asn Lys Val Arg Asn Arg Leu Thr Gln Lys Pro Tyr Ser Lys Asp Lys
            565                 570                 575
Ile Arg Leu Cys Phe Asn Lys Pro Lys Leu Met Thr Gly Trp Val Asp
            580                 585                 590
Ser Lys Thr Glu Lys Ser Asp Asn Gly Thr Gln Tyr Gly Gly Tyr Leu
            595                 600                 605
Phe Arg Lys Lys Asn Glu Ile Gly Glu Tyr Asp Tyr Phe Leu Gly Ile
            610                 615                 620
Ser Ser Lys Ala Gln Leu Phe Arg Lys Asn Glu Ala Val Ile Gly Asp
625                 630                 635                 640
Tyr Glu Arg Leu Asp Tyr Tyr Gln Pro Lys Ala Asn Thr Ile Tyr Gly
            645                 650                 655
Ser Ala Tyr Glu Gly Glu Asn Ser Tyr Lys Glu Asp Lys Lys Arg Leu
            660                 665                 670
Asn Lys Val Ile Ile Ala Tyr Ile Glu Gln Ile Lys Gln Thr Asn Ile
            675                 680                 685
Lys Lys Ser Ile Ile Glu Ser Ile Ser Lys Tyr Pro Asn Ile Ser Asp
            690                 695                 700
Asp Asp Lys Val Thr Pro Ser Ser Leu Leu Glu Lys Ile Lys Lys Val
705                 710                 715                 720
Ser Ile Asp Ser Tyr Asn Gly Ile Leu Ser Phe Lys Ser Phe Gln Ser
            725                 730                 735
Val Asn Lys Glu Val Ile Asp Asn Leu Leu Lys Thr Ile Ser Pro Leu
            740                 745                 750
Lys Asn Lys Ala Glu Phe Leu Asp Leu Ile Asn Lys Asp Tyr Gln Ile
            755                 760                 765
Phe Thr Glu Val Gln Ala Val Ile Asp Glu Ile Cys Lys Gln Lys Thr
            770                 775                 780
Phe Ile Tyr Phe Pro Ile Ser Asn Val Glu Leu Glu Lys Glu Met Gly
785                 790                 795                 800
Asp Lys Asp Lys Pro Leu Cys Leu Phe Gln Ile Ser Asn Lys Asp Leu
            805                 810                 815
```

```
Ser Phe Ala Lys Thr Phe Ser Ala Asn Leu Arg Lys Lys Arg Gly Ala
                820                 825                 830

Glu Asn Leu His Thr Met Leu Phe Lys Ala Leu Met Glu Gly Asn Gln
                835                 840                 845

Asp Asn Leu Asp Leu Gly Ser Gly Ala Ile Phe Tyr Arg Ala Lys Ser
                850                 855                 860

Leu Asp Gly Asn Lys Pro Thr His Pro Ala Asn Glu Ala Ile Lys Cys
865                 870                 875                 880

Arg Asn Val Ala Asn Lys Asp Lys Val Ser Leu Phe Thr Tyr Asp Ile
                885                 890                 895

Tyr Lys Asn Arg Arg Tyr Met Glu Asn Lys Phe Leu Phe His Leu Ser
                900                 905                 910

Ile Val Gln Asn Tyr Lys Ala Ala Asn Asp Ser Ala Gln Leu Asn Ser
                915                 920                 925

Ser Ala Thr Glu Tyr Ile Arg Lys Ala Asp Asp Leu His Ile Ile Gly
                930                 935                 940

Ile Asp Arg Gly Glu Arg Asn Leu Leu Tyr Tyr Ser Val Ile Asp Met
945                 950                 955                 960

Lys Gly Asn Ile Val Glu Gln Asp Ser Leu Asn Ile Ile Arg Asn Asn
                965                 970                 975

Asp Leu Glu Thr Asp Tyr His Asp Leu Leu Asp Lys Arg Glu Lys Glu
                980                 985                 990

Arg Lys Ala Asn Arg Gln Asn Trp Glu Ala Val Glu Gly Ile Lys Asp
                995                 1000                1005

Leu Lys Lys Gly Tyr Leu Ser Gln Ala Val His Gln Ile Ala Gln
                1010                1015                1020

Leu Met Leu Lys Tyr Asn Ala Ile Ile Ala Leu Glu Asp Leu Gly
                1025                1030                1035

Gln Met Phe Val Thr Arg Gly Gln Lys Ile Glu Lys Ala Val Tyr
                1040                1045                1050

Gln Gln Phe Glu Lys Ser Leu Val Asp Lys Leu Ser Tyr Leu Val
                1055                1060                1065

Asp Lys Lys Arg Pro Tyr Asn Glu Leu Gly Gly Ile Leu Lys Ala
                1070                1075                1080

Tyr Gln Leu Ala Ser Ser Ile Thr Lys Asn Asn Ser Asp Lys Gln
                1085                1090                1095

Asn Gly Phe Leu Phe Tyr Val Pro Ala Trp Asn Thr Ser Lys Ile
                1100                1105                1110

Asp Pro Val Thr Gly Phe Thr Asp Leu Leu Arg Pro Lys Ala Met
                1115                1120                1125

Thr Ile Lys Glu Ala Gln Asp Phe Phe Gly Ala Phe Asp Asn Ile
                1130                1135                1140

Ser Tyr Asn Asp Lys Gly Tyr Phe Glu Phe Glu Thr Asn Tyr Asp
                1145                1150                1155

Lys Phe Lys Ile Arg Met Lys Ser Ala Gln Thr Arg Trp Thr Ile
                1160                1165                1170

Cys Thr Phe Gly Asn Arg Ile Lys Arg Lys Lys Asp Lys Asn Tyr
                1175                1180                1185

Trp Asn Tyr Glu Glu Val Glu Leu Thr Glu Glu Phe Lys Lys Leu
                1190                1195                1200

Phe Lys Asp Ser Asn Ile Asp Tyr Glu Asn Cys Asn Leu Lys Glu
                1205                1210                1215
```

-continued

Glu Ile Gln Asn Lys Asp Asn Arg Lys Phe Phe Asp Asp Leu Ile
1220                1225                1230

Lys Leu Leu Gln Leu Thr Leu Gln Met Arg Asn Ser Asp Asp Lys
    1235                1240                1245

Gly Asn Asp Tyr Ile Ile Ser Pro Val Ala Asn Ala Glu Gly Gln
    1250                1255                1260

Phe Phe Asp Ser Arg Asn Gly Asp Lys Lys Leu Pro Leu Asp Ala
    1265                1270                1275

Asp Ala Asn Gly Ala Tyr Asn Ile Ala Arg Lys Gly Leu Trp Asn
    1280                1285                1290

Ile Arg Gln Ile Lys Gln Thr Lys Asn Asp Lys Lys Leu Asn Leu
    1295                1300                1305

Ser Ile Ser Ser Thr Glu Trp Leu Asp Phe Val Arg Glu Lys Pro
    1310                1315                1320

Tyr Leu Lys
    1325

<210> SEQ ID NO 315
<211> LENGTH: 1129
<212> TYPE: PRT
<213> ORGANISM: Alicyclobacillus acidoterrestris

<400> SEQUENCE: 315

Met Ala Val Lys Ser Ile Lys Val Lys Leu Arg Leu Asp Asp Met Pro
1               5                   10                  15

Glu Ile Arg Ala Gly Leu Trp Lys Leu His Lys Glu Val Asn Ala Gly
            20                  25                  30

Val Arg Tyr Tyr Thr Glu Trp Leu Ser Leu Leu Arg Gln Glu Asn Leu
        35                  40                  45

Tyr Arg Arg Ser Pro Asn Gly Asp Gly Glu Gln Glu Cys Asp Lys Thr
    50                  55                  60

Ala Glu Glu Cys Lys Ala Glu Leu Leu Glu Arg Leu Arg Ala Arg Gln
65                  70                  75                  80

Val Glu Asn Gly His Arg Gly Pro Ala Gly Ser Asp Asp Glu Leu Leu
                85                  90                  95

Gln Leu Ala Arg Gln Leu Tyr Glu Leu Leu Val Pro Gln Ala Ile Gly
            100                 105                 110

Ala Lys Gly Asp Ala Gln Gln Ile Ala Arg Lys Phe Leu Ser Pro Leu
        115                 120                 125

Ala Asp Lys Asp Ala Val Gly Gly Leu Gly Ile Ala Lys Ala Gly Asn
    130                 135                 140

Lys Pro Arg Trp Val Arg Met Arg Glu Ala Gly Glu Pro Gly Trp Glu
145                 150                 155                 160

Glu Glu Lys Glu Lys Ala Glu Thr Arg Lys Ser Ala Asp Arg Thr Ala
                165                 170                 175

Asp Val Leu Arg Ala Leu Ala Asp Phe Gly Leu Lys Pro Leu Met Arg
            180                 185                 190

Val Tyr Thr Asp Ser Glu Met Ser Ser Val Glu Trp Lys Pro Leu Arg
        195                 200                 205

Lys Gly Gln Ala Val Arg Thr Trp Asp Arg Asp Met Phe Gln Gln Ala
    210                 215                 220

Ile Glu Arg Met Met Ser Trp Glu Ser Trp Asn Gln Arg Val Gly Gln
225                 230                 235                 240

```
Glu Tyr Ala Lys Leu Val Gln Lys Asn Arg Phe Glu Gln Lys Asn
                245                 250                 255
Phe Val Gly Gln Glu His Leu Val His Leu Val Asn Gln Leu Gln Gln
            260                 265                 270
Asp Met Lys Glu Ala Ser Pro Gly Leu Glu Ser Lys Glu Gln Thr Ala
            275                 280                 285
His Tyr Val Thr Gly Arg Ala Leu Arg Gly Ser Asp Lys Val Phe Glu
            290                 295                 300
Lys Trp Gly Lys Leu Ala Pro Asp Ala Pro Phe Asp Leu Tyr Asp Ala
305                 310                 315                 320
Glu Ile Lys Asn Val Gln Arg Arg Asn Thr Arg Arg Phe Gly Ser His
                325                 330                 335
Asp Leu Phe Ala Lys Leu Ala Glu Pro Glu Tyr Gln Ala Leu Trp Arg
            340                 345                 350
Glu Asp Ala Ser Phe Leu Thr Arg Tyr Ala Val Tyr Asn Ser Ile Leu
            355                 360                 365
Arg Lys Leu Asn His Ala Lys Met Phe Ala Thr Phe Thr Leu Pro Asp
            370                 375                 380
Ala Thr Ala His Pro Ile Trp Thr Arg Phe Asp Lys Leu Gly Gly Asn
385                 390                 395                 400
Leu His Gln Tyr Thr Phe Leu Phe Asn Glu Phe Gly Glu Arg Arg His
            405                 410                 415
Ala Ile Arg Phe His Lys Leu Leu Lys Val Glu Asn Gly Val Ala Arg
            420                 425                 430
Glu Val Asp Asp Val Thr Val Pro Ile Ser Met Ser Glu Gln Leu Asp
            435                 440                 445
Asn Leu Leu Pro Arg Asp Pro Asn Glu Pro Ile Ala Leu Tyr Phe Arg
            450                 455                 460
Asp Tyr Gly Ala Glu Gln His Phe Thr Gly Glu Phe Gly Gly Ala Lys
465                 470                 475                 480
Ile Gln Cys Arg Arg Asp Gln Leu Ala His Met His Arg Arg Arg Gly
                485                 490                 495
Ala Arg Asp Val Tyr Leu Asn Val Ser Val Arg Val Gln Ser Gln Ser
            500                 505                 510
Glu Ala Arg Gly Glu Arg Arg Pro Tyr Ala Ala Val Phe Arg Leu
            515                 520                 525
Val Gly Asp Asn His Arg Ala Phe Val His Phe Asp Lys Leu Ser Asp
530                 535                 540
Tyr Leu Ala Glu His Pro Asp Asp Gly Lys Leu Gly Ser Glu Gly Leu
545                 550                 555                 560
Leu Ser Gly Leu Arg Val Met Ser Val Asp Leu Gly Leu Arg Thr Ser
                565                 570                 575
Ala Ser Ile Ser Val Phe Arg Val Ala Arg Lys Asp Glu Leu Lys Pro
            580                 585                 590
Asn Ser Lys Gly Arg Val Pro Phe Phe Pro Ile Lys Gly Asn Asp
            595                 600                 605
Asn Leu Val Ala Val His Glu Arg Ser Gln Leu Leu Lys Leu Pro Gly
            610                 615                 620
Glu Thr Glu Ser Lys Asp Leu Arg Ala Ile Arg Glu Glu Arg Gln Arg
625                 630                 635                 640
Thr Leu Arg Gln Leu Arg Thr Gln Leu Ala Tyr Leu Arg Leu Leu Val
                645                 650                 655
```

-continued

Arg Cys Gly Ser Glu Asp Val Gly Arg Arg Glu Ser Trp Ala Lys
            660                 665                 670

Leu Ile Glu Gln Pro Val Asp Ala Ala Asn His Met Thr Pro Asp Trp
        675                 680                 685

Arg Glu Ala Phe Glu Asn Glu Leu Gln Lys Leu Lys Ser Leu His Gly
    690                 695                 700

Ile Cys Ser Asp Lys Glu Trp Met Asp Ala Val Tyr Glu Ser Val Arg
705                 710                 715                 720

Arg Val Trp Arg His Met Gly Lys Gln Val Arg Asp Trp Arg Lys Asp
                725                 730                 735

Val Arg Ser Gly Glu Arg Pro Lys Ile Arg Gly Tyr Ala Lys Asp Val
            740                 745                 750

Val Gly Gly Asn Ser Ile Glu Gln Ile Glu Tyr Leu Glu Arg Gln Tyr
        755                 760                 765

Lys Phe Leu Lys Ser Trp Ser Phe Phe Gly Lys Val Ser Gly Gln Val
    770                 775                 780

Ile Arg Ala Glu Lys Gly Ser Arg Phe Ala Ile Thr Leu Arg Glu His
785                 790                 795                 800

Ile Asp His Ala Lys Glu Asp Arg Leu Lys Lys Leu Ala Asp Arg Ile
                805                 810                 815

Ile Met Glu Ala Leu Gly Tyr Val Tyr Ala Leu Asp Glu Arg Gly Lys
            820                 825                 830

Gly Lys Trp Val Ala Lys Tyr Pro Pro Cys Gln Leu Ile Leu Leu Glu
        835                 840                 845

Glu Leu Ser Glu Tyr Gln Phe Asn Asn Asp Arg Pro Pro Ser Glu Asn
    850                 855                 860

Asn Gln Leu Met Gln Trp Ser His Arg Gly Val Phe Gln Glu Leu Ile
865                 870                 875                 880

Asn Gln Ala Gln Val His Asp Leu Leu Val Gly Thr Met Tyr Ala Ala
                885                 890                 895

Phe Ser Ser Arg Phe Asp Ala Arg Thr Gly Ala Pro Gly Ile Arg Cys
            900                 905                 910

Arg Arg Val Pro Ala Arg Cys Thr Gln Glu His Asn Pro Glu Pro Phe
        915                 920                 925

Pro Trp Trp Leu Asn Lys Phe Val Val Glu His Thr Leu Asp Ala Cys
    930                 935                 940

Pro Leu Arg Ala Asp Asp Leu Ile Pro Thr Gly Glu Gly Glu Ile Phe
945                 950                 955                 960

Val Ser Pro Phe Ser Ala Glu Glu Gly Asp Phe His Gln Ile His Ala
                965                 970                 975

Asp Leu Asn Ala Ala Gln Asn Leu Gln Gln Arg Leu Trp Ser Asp Phe
            980                 985                 990

Asp Ile Ser Gln Ile Arg Leu Arg Cys Asp Trp Gly Glu Val Asp Gly
        995                 1000                1005

Glu Leu Val Leu Ile Pro Arg Leu Thr Gly Lys Arg Thr Ala Asp
    1010                1015                1020

Ser Tyr Ser Asn Lys Val Phe Tyr Thr Asn Thr Gly Val Thr Tyr
    1025                1030                1035

Tyr Glu Arg Glu Arg Gly Lys Lys Arg Arg Lys Val Phe Ala Gln
    1040                1045                1050

Glu Lys Leu Ser Glu Glu Glu Ala Glu Leu Leu Val Glu Ala Asp
    1055                1060                1065

```
Glu Ala Arg Glu Lys Ser Val Val Leu Met Arg Asp Pro Ser Gly
    1070            1075                1080

Ile Ile Asn Arg Gly Asn Trp Thr Arg Gln Lys Glu Phe Trp Ser
    1085            1090                1095

Met Val Asn Gln Arg Ile Glu Gly Tyr Leu Val Lys Gln Ile Arg
    1100            1105                1110

Ser Arg Val Pro Leu Gln Asp Ser Ala Cys Glu Asn Thr Gly Asp
    1115            1120                1125

Ile

<210> SEQ ID NO 316
<211> LENGTH: 872
<212> TYPE: PRT
<213> ORGANISM: Alicyclobacillus contaminans

<400> SEQUENCE: 316

Met Gly Phe Asn Thr Ala Glu Leu Leu Arg Lys Val Glu Glu Met
1               5                   10                  15

Arg Lys Thr Ser Val Gly Phe Asp Thr Asp Asn Pro Phe Ala His Arg
            20                  25                  30

Ile Thr Arg Arg Ala Ile Arg Gly Trp Asp Arg Ile Ala Glu Ala Trp
        35                  40                  45

Arg Arg Leu Pro Pro Asp Ala Pro Glu Ser Gly Tyr Ile Glu Ala Phe
    50                  55                  60

Lys Asp Ile Gln Arg Lys Asn Pro Arg Lys Ile Gly Ser Glu Pro Leu
65                  70                  75                  80

Phe Lys Asn Leu Ala Ala Pro Gly Val Arg Ser Glu Leu Leu Asn Asn
                85                  90                  95

Pro Gln Val Leu Ile Thr Phe Ala Lys Tyr Asn Glu Leu Gln Arg Gln
            100                 105                 110

Leu Ala Lys Ala Lys Gln Phe Ala Gln Lys Thr Leu Pro His Pro Val
        115                 120                 125

Phe His Pro Val Trp Val Arg Tyr Asp Lys Leu Gly Gly Asn Leu His
    130                 135                 140

His Tyr Gln Ile Glu Pro Ala Val His Ala Asn Asp Thr His Lys Val
145                 150                 155                 160

Lys Phe Ser Ser Leu Leu Leu Pro Gln Glu Asp Gly Ser Tyr Ala Glu
                165                 170                 175

Val Lys Asp Val Thr Val Ser Leu Ala Pro Ser Leu Gln Phe Pro Thr
            180                 185                 190

Gly Leu Val His Pro Lys Val Thr Thr Pro Pro Arg Thr Gly Leu Val
        195                 200                 205

Thr Val Met Asp Glu Glu Ala Gly Lys Pro Val Val Cys Tyr Arg Asp
    210                 215                 220

Arg Gly His Asp Ala Leu Val Pro Val Ala Phe Gly Gly Ala Lys Leu
225                 230                 235                 240

Gln Phe Asn Arg Ala His Leu Ser Ala Gly Tyr Arg Lys Gly Val Leu
                245                 250                 255

Ser Ala Gly Gly Gly Ser Ile Tyr Phe Asn Val Thr Leu Asp Val
            260                 265                 270

Gln Val Pro Asn Glu Arg Asp Val Ser Lys Thr Phe Ser Phe Ser Arg
        275                 280                 285

Asp Arg Asp Leu Val Ser Leu Lys Ala Glu Glu Leu Lys Arg Tyr Met
    290                 295                 300
```

-continued

```
Glu Thr Lys Pro Leu Gly Met Pro Gly Val Arg Val Met Ser Val Asp
305                 310                 315                 320

Leu Gly Val Arg Tyr Gly Ala Ala Ile Ser Val Phe Glu Val Lys Pro
                325                 330                 335

Phe Ala Glu Val Arg Lys Asp Lys Leu His Tyr Pro Ile Thr Gly Cys
            340                 345                 350

Glu Gly Phe Val Ala Glu His Glu Arg Ser Val Ile Leu Lys Leu Pro
        355                 360                 365

Gly Glu Gly Val Arg Thr Ala Gly Lys Gln Ser Glu Arg Lys Gln Ala
    370                 375                 380

Leu Ala Ala Ile Arg Ala Glu Met Ser Ile Leu Arg Lys Trp Leu Arg
385                 390                 395                 400

Val Ser Gln Val Thr Glu Glu Asp Arg Ala Lys Ala Val Arg Gly Leu
                405                 410                 415

Leu Glu Asp Glu Arg Gly Gly Gly Trp Thr Met Asp Pro Gly Glu Asp
            420                 425                 430

Ser Asp His Gln Pro Leu Gln Gln Phe Leu His Glu Ala Arg Leu Ala
        435                 440                 445

Val Gly Glu Leu Val Asn Leu Val His Leu Ser Pro Ala Glu Trp Glu
    450                 455                 460

Arg Ala Val Ile Glu Arg His Arg Arg Leu Glu Arg Ile Thr Ala Ser
465                 470                 475                 480

His Ile Arg Val Phe Gln Thr Met Arg Lys Val Trp Gly Lys Arg Arg
                485                 490                 495

Asn Glu Asp Ala Ala His Thr Gly Gly Ile Ser Leu Ala His Ile Glu
            500                 505                 510

His Leu Ile Gln Gln Arg Lys Leu Phe Ile Arg Trp Ser Thr His Ala
        515                 520                 525

Arg Thr Tyr Gly Glu Val Arg Arg Leu Pro Lys His Glu Gly Phe Ala
    530                 535                 540

Lys Arg Leu Gln Lys His Thr Asn His Val Lys Glu Asp Arg Ile Lys
545                 550                 555                 560

Lys Leu Ala Asp Met Ile Val Met Ala Ala Arg Gly Tyr Arg Phe Leu
                565                 570                 575

Asp Lys Arg Ala Arg Trp Val Lys Thr Arg His Ala Pro Cys Asp Leu
            580                 585                 590

Ile Leu Phe Glu Asp Leu Ser Arg Tyr Arg Phe Thr Met Asp Arg Pro
        595                 600                 605

Pro Thr Glu Asn Ser Gln Leu Met Asn Trp Ser His Arg Glu Leu Leu
    610                 615                 620

Lys Thr Val Lys Met Gln Ala Ala Leu Phe Gly Ile Gly Val Gly Thr
625                 630                 635                 640

Val Pro Ala Ala Phe Thr Ser Arg Phe Asp Ala Gln Thr Gly Ala Pro
                645                 650                 655

Gly Leu Arg Cys Lys Arg Val Thr Lys Gln Asp Lys Glu Lys Thr Pro
            660                 665                 670

Phe Trp Leu Ile Gln Phe Ala Glu Ile Thr Gly Val Asn Val Thr Asn
        675                 680                 685

Val Glu Pro Gly Gln Leu Ile Pro Val Asp Gly Glu Trp Phe Val
    690                 695                 700

Ser Pro Lys Gly Pro Arg Ala Ala Asp Gly Leu Lys Cys Val His Ala
705                 710                 715                 720
```

Asp Ile Asn Ala Ala His Asn Leu Gln Arg Arg Phe Trp Ile Pro Arg
            725                 730                 735

Leu Pro Ser Val Lys Cys Arg Arg Tyr Val Glu Ala Glu Gly Phe Ala
        740                 745                 750

Ala Val Pro Ser Ser Thr Ala Phe Met Lys Val His Gly Lys Gly Ala
        755                 760                 765

Phe Val Ser Val Asp Gly Glu Phe Tyr Glu Tyr Gln Lys Gly Arg Arg
        770                 775                 780

Val Ala Val Asn Arg Ala Asp Arg Thr Ser Thr Leu Asp Glu Asp
785                 790                 795                 800

Glu Gly Asp Ile Gly Glu Glu Met Leu Val Ser Ser Asn Gly Ala Gly
                805                 810                 815

Glu Phe Val Arg Met Phe Tyr Asp Glu Ser Gly Tyr Val Gly Tyr Gly
                820                 825                 830

Arg Trp Met Asp Ser Lys Val Phe Trp Gly Lys Val Arg Gln Ile Val
                835                 840                 845

His Arg Ala Ile Gln Asp Gln Val Glu Lys Arg Ala Ala Arg Gly
            850                 855                 860

Glu Asn Gly Ala Thr Ser Ser Arg
865                 870

<210> SEQ ID NO 317
<211> LENGTH: 1149
<212> TYPE: PRT
<213> ORGANISM: Desulfovibrio inopinatus

<400> SEQUENCE: 317

Met Pro Thr Arg Thr Ile Asn Leu Lys Leu Val Leu Gly Lys Asn Pro
1               5                   10                  15

Glu Asn Ala Thr Leu Arg Arg Ala Leu Phe Ser Thr His Arg Leu Val
            20                  25                  30

Asn Gln Ala Thr Lys Arg Ile Glu Glu Phe Leu Leu Leu Cys Arg Gly
        35                  40                  45

Glu Ala Tyr Arg Thr Val Asp Asn Glu Gly Lys Glu Ala Glu Ile Pro
    50                  55                  60

Arg His Ala Val Gln Glu Glu Ala Leu Ala Phe Ala Lys Ala Ala Gln
65                  70                  75                  80

Arg His Asn Gly Cys Ile Ser Thr Tyr Glu Asp Gln Glu Ile Leu Asp
                85                  90                  95

Val Leu Arg Gln Leu Tyr Glu Arg Leu Val Pro Ser Val Asn Glu Asn
            100                 105                 110

Asn Glu Ala Gly Asp Ala Gln Ala Ala Asn Ala Trp Val Ser Pro Leu
        115                 120                 125

Met Ser Ala Glu Ser Glu Gly Gly Leu Ser Val Tyr Asp Lys Val Leu
    130                 135                 140

Asp Pro Pro Val Trp Met Lys Leu Lys Glu Glu Lys Ala Pro Gly
145                 150                 155                 160

Trp Glu Ala Ala Ser Gln Ile Trp Ile Gln Ser Asp Glu Gly Gln Ser
                165                 170                 175

Leu Leu Asn Lys Pro Gly Ser Pro Arg Trp Ile Arg Lys Leu Arg
            180                 185                 190

Ser Gly Gln Pro Trp Gln Asp Asp Phe Val Ser Asp Gln Lys Lys Lys
        195                 200                 205

Gln Asp Glu Leu Thr Lys Gly Asn Ala Pro Leu Ile Lys Gln Leu Lys
    210                 215                 220

```
Glu Met Gly Leu Leu Pro Leu Val Asn Pro Phe Phe Arg His Leu Leu
225                 230                 235                 240

Asp Pro Glu Gly Lys Gly Val Ser Pro Trp Asp Arg Leu Ala Val Arg
            245                 250                 255

Ala Ala Val Ala His Phe Ile Ser Trp Glu Ser Trp Asn His Arg Thr
                260                 265                 270

Arg Ala Glu Tyr Asn Ser Leu Lys Leu Arg Arg Asp Glu Phe Glu Ala
            275                 280                 285

Ala Ser Asp Glu Phe Lys Asp Asp Phe Thr Leu Leu Arg Gln Tyr Glu
            290                 295                 300

Ala Lys Arg His Ser Thr Leu Lys Ser Ile Ala Leu Ala Asp Asp Ser
305                 310                 315                 320

Asn Pro Tyr Arg Ile Gly Val Arg Ser Leu Arg Ala Trp Asn Arg Val
                325                 330                 335

Arg Glu Glu Trp Ile Asp Lys Gly Ala Thr Glu Glu Gln Arg Val Thr
            340                 345                 350

Ile Leu Ser Lys Leu Gln Thr Gln Leu Arg Gly Lys Phe Gly Asp Pro
            355                 360                 365

Asp Leu Phe Asn Trp Leu Ala Gln Asp Arg His Val His Leu Trp Ser
370                 375                 380

Pro Arg Asp Ser Val Thr Pro Leu Val Arg Ile Asn Ala Val Asp Lys
385                 390                 395                 400

Val Leu Arg Arg Arg Lys Pro Tyr Ala Leu Met Thr Phe Ala His Pro
                405                 410                 415

Arg Phe His Pro Arg Trp Ile Leu Tyr Glu Ala Pro Gly Gly Ser Asn
                420                 425                 430

Leu Arg Gln Tyr Ala Leu Asp Cys Thr Glu Asn Ala Leu His Ile Thr
            435                 440                 445

Leu Pro Leu Leu Val Asp Asp Ala His Gly Thr Trp Ile Glu Lys Lys
            450                 455                 460

Ile Arg Val Pro Leu Ala Pro Ser Gly Gln Ile Gln Asp Leu Thr Leu
465                 470                 475                 480

Glu Lys Leu Glu Lys Lys Asn Arg Leu Tyr Tyr Arg Ser Gly Phe
                485                 490                 495

Gln Gln Phe Ala Gly Leu Ala Gly Ala Glu Val Leu Phe His Arg
            500                 505                 510

Pro Tyr Met Glu His Asp Glu Arg Ser Glu Glu Ser Leu Leu Glu Arg
            515                 520                 525

Pro Gly Ala Val Trp Phe Lys Leu Thr Leu Asp Val Ala Thr Gln Ala
            530                 535                 540

Pro Pro Asn Trp Leu Asp Gly Lys Gly Arg Val Arg Thr Pro Pro Glu
545                 550                 555                 560

Val His His Phe Lys Thr Ala Leu Ser Asn Lys Ser Lys His Thr Arg
                565                 570                 575

Thr Leu Gln Pro Gly Leu Arg Val Leu Ser Val Asp Leu Gly Met Arg
            580                 585                 590

Thr Phe Ala Ser Cys Ser Val Phe Glu Leu Ile Glu Gly Lys Pro Glu
            595                 600                 605

Thr Gly Arg Ala Phe Pro Val Ala Asp Glu Arg Ser Met Asp Ser Pro
            610                 615                 620

Asn Lys Leu Trp Ala Lys His Glu Arg Ser Phe Lys Leu Thr Leu Pro
625                 630                 635                 640
```

Gly Glu Thr Pro Ser Arg Lys Glu Glu Glu Arg Ser Ile Ala Arg
              645                 650                 655

Ala Glu Ile Tyr Ala Leu Lys Arg Asp Ile Gln Arg Leu Lys Ser Leu
        660                 665                 670

Leu Arg Leu Gly Glu Glu Asp Asn Asp Asn Arg Arg Asp Ala Leu Leu
            675                 680                 685

Glu Gln Phe Phe Lys Gly Trp Gly Glu Glu Asp Val Val Pro Gly Gln
690                 695                 700

Ala Phe Pro Arg Ser Leu Phe Gln Gly Leu Ala Ala Pro Phe Arg
705                 710                 715                 720

Ser Thr Pro Glu Leu Trp Arg Gln His Cys Gln Thr Tyr Tyr Asp Lys
                725                 730                 735

Ala Glu Ala Cys Leu Ala Lys His Ile Ser Asp Trp Arg Lys Arg Thr
                740                 745                 750

Arg Pro Arg Pro Thr Ser Arg Glu Met Trp Tyr Lys Thr Arg Ser Tyr
            755                 760                 765

His Gly Gly Lys Ser Ile Trp Met Leu Glu Tyr Leu Asp Ala Val Arg
            770                 775                 780

Lys Leu Leu Leu Ser Trp Ser Leu Arg Gly Arg Thr Tyr Gly Ala Ile
785                 790                 795                 800

Asn Arg Gln Asp Thr Ala Arg Phe Gly Ser Leu Ala Ser Arg Leu Leu
                805                 810                 815

His His Ile Asn Ser Leu Lys Glu Asp Arg Ile Lys Thr Gly Ala Asp
            820                 825                 830

Ser Ile Val Gln Ala Ala Arg Gly Tyr Ile Pro Leu Pro His Gly Lys
            835                 840                 845

Gly Trp Glu Gln Arg Tyr Glu Pro Cys Gln Leu Ile Leu Phe Glu Asp
            850                 855                 860

Leu Ala Arg Tyr Arg Phe Arg Val Asp Arg Pro Arg Arg Glu Asn Ser
865                 870                 875                 880

Gln Leu Met Gln Trp Asn His Arg Ala Ile Val Ala Glu Thr Thr Met
                885                 890                 895

Gln Ala Glu Leu Tyr Gly Gln Ile Val Glu Asn Thr Ala Gly Phe
            900                 905                 910

Ser Ser Arg Phe His Ala Ala Thr Gly Ala Pro Gly Val Arg Cys Arg
            915                 920                 925

Phe Leu Leu Glu Arg Asp Phe Asp Asn Asp Leu Pro Lys Pro Tyr Leu
            930                 935                 940

Leu Arg Glu Leu Ser Trp Met Leu Gly Asn Thr Lys Val Glu Ser Glu
945                 950                 955                 960

Glu Glu Lys Leu Arg Leu Leu Ser Glu Lys Ile Arg Pro Gly Ser Leu
                965                 970                 975

Val Pro Trp Asp Gly Glu Gln Phe Ala Thr Leu His Pro Lys Arg
            980                 985                 990

Gln Thr Leu Cys Val Ile His Ala Asp Met Asn Ala Ala Gln Asn Leu
            995                 1000                1005

Gln Arg Arg Phe Phe Gly Arg Cys Gly Glu Ala Phe Arg Leu Val
        1010                1015                1020

Cys Gln Pro His Gly Asp Asp Val Leu Arg Leu Ala Ser Thr Pro
        1025                1030                1035

Gly Ala Arg Leu Leu Gly Ala Leu Gln Gln Leu Glu Asn Gly Gln
        1040                1045                1050

```
Gly Ala Phe Glu Leu Val Arg Asp Met Gly Ser Thr Ser Gln Met
    1055                1060                1065

Asn Arg Phe Val Met Lys Ser Leu Gly Lys Lys Lys Ile Lys Pro
    1070                1075                1080

Leu Gln Asp Asn Asn Gly Asp Asp Glu Leu Glu Asp Val Leu Ser
    1085                1090                1095

Val Leu Pro Glu Glu Asp Asp Thr Gly Arg Ile Thr Val Phe Arg
    1100                1105                1110

Asp Ser Ser Gly Ile Phe Phe Pro Cys Asn Val Trp Ile Pro Ala
    1115                1120                1125

Lys Gln Phe Trp Pro Ala Val Arg Ala Met Ile Trp Lys Val Met
    1130                1135                1140

Ala Ser His Ser Leu Gly
    1145

<210> SEQ ID NO 318
<211> LENGTH: 1194
<212> TYPE: PRT
<213> ORGANISM: Desulfonatronum thiodismutans

<400> SEQUENCE: 318

Met Val Leu Gly Arg Lys Asp Asp Thr Ala Glu Leu Arg Arg Ala Leu
1               5                   10                  15

Trp Thr Thr His Glu His Val Asn Leu Ala Val Ala Glu Val Glu Arg
                20                  25                  30

Val Leu Leu Arg Cys Arg Gly Arg Ser Tyr Trp Thr Leu Asp Arg Arg
            35                  40                  45

Gly Asp Pro Val His Val Pro Glu Ser Gln Val Ala Glu Asp Ala Leu
        50                  55                  60

Ala Met Ala Arg Glu Ala Gln Arg Arg Asn Gly Trp Pro Val Val Gly
65                  70                  75                  80

Glu Asp Glu Glu Ile Leu Leu Ala Leu Arg Tyr Leu Tyr Glu Gln Ile
                85                  90                  95

Val Pro Ser Cys Leu Leu Asp Asp Leu Gly Lys Pro Leu Lys Gly Asp
            100                 105                 110

Ala Gln Lys Ile Gly Thr Asn Tyr Ala Gly Pro Leu Phe Asp Ser Asp
        115                 120                 125

Thr Cys Arg Arg Asp Glu Gly Lys Asp Val Ala Cys Cys Gly Pro Phe
    130                 135                 140

His Glu Val Ala Gly Lys Tyr Leu Gly Ala Leu Pro Glu Trp Ala Thr
145                 150                 155                 160

Pro Ile Ser Lys Gln Glu Phe Asp Gly Lys Asp Ala Ser His Leu Arg
                165                 170                 175

Phe Lys Ala Thr Gly Gly Asp Asp Ala Phe Phe Arg Val Ser Ile Glu
            180                 185                 190

Lys Ala Asn Ala Trp Tyr Glu Asp Pro Ala Asn Gln Asp Ala Leu Lys
        195                 200                 205

Asn Lys Ala Tyr Asn Lys Asp Trp Lys Lys Glu Lys Asp Lys Gly
    210                 215                 220

Ile Ser Ser Trp Ala Val Lys Tyr Ile Gln Lys Gln Leu Gln Leu Gly
225                 230                 235                 240

Gln Asp Pro Arg Thr Glu Val Arg Arg Lys Leu Trp Leu Glu Leu Gly
                245                 250                 255
```

```
Leu Leu Pro Leu Phe Ile Pro Val Phe Asp Lys Thr Met Val Gly Asn
            260                 265                 270

Leu Trp Asn Arg Leu Ala Val Arg Leu Ala Leu Ala His Leu Leu Ser
            275                 280                 285

Trp Glu Ser Trp Asn His Arg Ala Val Gln Asp Gln Ala Leu Ala Arg
        290                 295                 300

Ala Lys Arg Asp Glu Leu Ala Ala Leu Phe Leu Gly Met Glu Asp Gly
305                 310                 315                 320

Phe Ala Gly Leu Arg Glu Tyr Glu Leu Arg Arg Asn Glu Ser Ile Lys
                325                 330                 335

Gln His Ala Phe Glu Pro Val Asp Arg Pro Tyr Val Val Ser Gly Arg
            340                 345                 350

Ala Leu Arg Ser Trp Thr Arg Val Arg Glu Glu Trp Leu Arg His Gly
            355                 360                 365

Asp Thr Gln Glu Ser Arg Lys Asn Ile Cys Asn Arg Leu Gln Asp Arg
        370                 375                 380

Leu Arg Gly Lys Phe Gly Asp Pro Asp Val Phe His Trp Leu Ala Glu
385                 390                 395                 400

Asp Gly Gln Glu Ala Leu Trp Lys Glu Arg Asp Cys Val Thr Ser Phe
                405                 410                 415

Ser Leu Leu Asn Asp Ala Asp Gly Leu Leu Glu Lys Arg Lys Gly Tyr
            420                 425                 430

Ala Leu Met Thr Phe Ala Asp Ala Arg Leu His Pro Arg Trp Ala Met
            435                 440                 445

Tyr Glu Ala Pro Gly Gly Ser Asn Leu Arg Thr Tyr Gln Ile Arg Lys
        450                 455                 460

Thr Glu Asn Gly Leu Trp Ala Asp Val Val Leu Leu Ser Pro Arg Asn
465                 470                 475                 480

Glu Ser Ala Ala Val Glu Glu Lys Thr Phe Asn Val Arg Leu Ala Pro
                485                 490                 495

Ser Gly Gln Leu Ser Asn Val Ser Phe Asp Gln Ile Gln Lys Gly Ser
            500                 505                 510

Lys Met Val Gly Arg Cys Arg Tyr Gln Ser Ala Asn Gln Gln Phe Glu
            515                 520                 525

Gly Leu Leu Gly Gly Ala Glu Ile Leu Phe Asp Arg Lys Arg Ile Ala
        530                 535                 540

Asn Glu Gln His Gly Ala Thr Asp Leu Ala Ser Lys Pro Gly His Val
545                 550                 555                 560

Trp Phe Lys Leu Thr Leu Asp Val Arg Pro Gln Ala Pro Gln Gly Trp
                565                 570                 575

Leu Asp Gly Lys Gly Arg Pro Ala Leu Pro Pro Glu Ala Lys His Phe
            580                 585                 590

Lys Thr Ala Leu Ser Asn Lys Ser Lys Phe Ala Asp Gln Val Arg Pro
            595                 600                 605

Gly Leu Arg Val Leu Ser Val Asp Leu Gly Val Arg Ser Phe Ala Ala
        610                 615                 620

Cys Ser Val Phe Glu Leu Val Arg Gly Gly Pro Asp Gln Gly Thr Tyr
625                 630                 635                 640

Phe Pro Ala Ala Asp Gly Arg Thr Val Asp Asp Pro Glu Lys Leu Trp
                645                 650                 655

Ala Lys His Glu Arg Ser Phe Lys Ile Thr Leu Pro Gly Glu Asn Pro
            660                 665                 670
```

```
Ser Arg Lys Glu Glu Ile Ala Arg Arg Ala Ala Met Glu Leu Arg
            675                 680                 685

Ser Leu Asn Gly Asp Ile Arg Arg Leu Lys Ala Ile Leu Arg Leu Ser
    690                 695                 700

Val Leu Gln Glu Asp Asp Pro Arg Thr Glu His Leu Arg Leu Phe Met
705                 710                 715                 720

Glu Ala Ile Val Asp Asp Pro Ala Lys Ser Ala Leu Asn Ala Glu Leu
                725                 730                 735

Phe Lys Gly Phe Gly Asp Arg Phe Arg Ser Thr Pro Asp Leu Trp
            740                 745                 750

Lys Gln His Cys His Phe Phe His Asp Lys Ala Glu Lys Val Val Ala
        755                 760                 765

Glu Arg Phe Ser Arg Trp Arg Thr Glu Thr Arg Pro Lys Ser Ser Ser
770                 775                 780

Trp Gln Asp Trp Arg Glu Arg Arg Gly Tyr Ala Gly Gly Lys Ser Tyr
785                 790                 795                 800

Trp Ala Val Thr Tyr Leu Glu Ala Val Arg Gly Leu Ile Leu Arg Trp
                805                 810                 815

Asn Met Arg Gly Arg Thr Tyr Gly Glu Val Asn Arg Gln Asp Lys Lys
            820                 825                 830

Gln Phe Gly Thr Val Ala Ser Ala Leu Leu His His Ile Asn Gln Leu
        835                 840                 845

Lys Glu Asp Arg Ile Lys Thr Gly Ala Asp Met Ile Ile Gln Ala Ala
    850                 855                 860

Arg Gly Phe Val Pro Arg Lys Asn Gly Ala Gly Trp Val Gln Val His
865                 870                 875                 880

Glu Pro Cys Arg Leu Ile Leu Phe Glu Asp Leu Ala Arg Tyr Arg Phe
                885                 890                 895

Arg Thr Asp Arg Ser Arg Arg Glu Asn Ser Arg Leu Met Arg Trp Ser
            900                 905                 910

His Arg Glu Ile Val Asn Glu Val Gly Met Gln Gly Glu Leu Tyr Gly
        915                 920                 925

Leu His Val Asp Thr Thr Glu Ala Gly Phe Ser Ser Arg Tyr Leu Ala
    930                 935                 940

Ser Ser Gly Ala Pro Gly Val Arg Cys Arg His Leu Val Glu Glu Asp
945                 950                 955                 960

Phe His Asp Gly Leu Pro Gly Met His Leu Val Gly Glu Leu Asp Trp
                965                 970                 975

Leu Leu Pro Lys Asp Lys Asp Arg Thr Ala Asn Glu Ala Arg Arg Leu
            980                 985                 990

Leu Gly Gly Met Val Arg Pro Gly Met Leu Val Pro Trp Asp Gly Gly
        995                 1000                1005

Glu Leu Phe Ala Thr Leu Asn Ala Ala Ser Gln Leu His Val Ile
    1010                1015                1020

His Ala Asp Ile Asn Ala Ala Gln Asn Leu Gln Arg Arg Phe Trp
    1025                1030                1035

Gly Arg Cys Gly Glu Ala Ile Arg Ile Val Cys Asn Gln Leu Ser
    1040                1045                1050

Val Asp Gly Ser Thr Arg Tyr Glu Met Ala Lys Ala Pro Lys Ala
    1055                1060                1065

Arg Leu Leu Gly Ala Leu Gln Gln Leu Lys Asn Gly Asp Ala Pro
    1070                1075                1080
```

```
Phe His Leu Thr Ser Ile Pro Asn Ser Gln Lys Pro Glu Asn Ser
    1085                1090                1095

Tyr Val Met Thr Pro Thr Asn Ala Gly Lys Lys Tyr Arg Ala Gly
    1100                1105                1110

Pro Gly Glu Lys Ser Ser Gly Glu Glu Asp Glu Leu Ala Leu Asp
    1115                1120                1125

Ile Val Glu Gln Ala Glu Glu Leu Ala Gln Gly Arg Lys Thr Phe
    1130                1135                1140

Phe Arg Asp Pro Ser Gly Val Phe Phe Ala Pro Asp Arg Trp Leu
    1145                1150                1155

Pro Ser Glu Ile Tyr Trp Ser Arg Ile Arg Arg Ile Trp Gln
    1160                1165                1170

Val Thr Leu Glu Arg Asn Ser Ser Gly Arg Gln Glu Arg Ala Glu
    1175                1180                1185

Met Asp Glu Met Pro Tyr
    1190

<210> SEQ ID NO 319
<211> LENGTH: 1132
<212> TYPE: PRT
<213> ORGANISM: Tuberibacillus calidus

<400> SEQUENCE: 319

Met Ala Thr Lys Ser Phe Ile Leu Lys Met Lys Thr Lys Asn Asn Pro
1               5                   10                  15

Gln Leu Arg Leu Ser Leu Trp Lys Thr His Glu Leu Phe Asn Phe Gly
                20                  25                  30

Val Ala Tyr Tyr Met Asp Leu Leu Ser Leu Phe Arg Gln Lys Asp Leu
            35                  40                  45

Tyr Met His Asn Asp Glu Asp Pro Asp His Pro Val Val Leu Lys Lys
        50                  55                  60

Glu Glu Ile Gln Glu Arg Leu Trp Met Lys Val Arg Glu Thr Gln Gln
65                  70                  75                  80

Lys Asn Gly Phe His Gly Glu Val Ser Lys Asp Glu Val Leu Glu Thr
                85                  90                  95

Leu Arg Ala Leu Tyr Glu Glu Leu Val Pro Ser Ala Val Gly Lys Ser
            100                 105                 110

Gly Glu Ala Asn Gln Ile Ser Asn Lys Tyr Leu Tyr Pro Leu Thr Asp
        115                 120                 125

Pro Ala Ser Gln Ser Gly Lys Gly Thr Ala Asn Ser Gly Arg Lys Pro
    130                 135                 140

Arg Trp Lys Lys Leu Lys Glu Ala Gly Asp Pro Ser Trp Lys Asp Ala
145                 150                 155                 160

Tyr Glu Lys Trp Glu Lys Glu Arg Gln Glu Asp Pro Lys Leu Lys Ile
                165                 170                 175

Leu Ala Ala Leu Gln Ser Phe Gly Leu Ile Pro Leu Phe Arg Pro Phe
            180                 185                 190

Thr Glu Asn Asp His Lys Ala Val Ile Ser Val Lys Trp Met Pro Lys
        195                 200                 205

Ser Lys Asn Gln Ser Val Arg Lys Phe Asp Lys Asp Met Phe Asn Gln
    210                 215                 220

Ala Ile Glu Arg Phe Leu Ser Trp Glu Ser Trp Asn Glu Lys Val Ala
225                 230                 235                 240
```

```
Glu Asp Tyr Glu Lys Thr Val Ser Ile Tyr Glu Ser Leu Gln Lys Glu
                245                 250                 255

Leu Lys Gly Ile Ser Thr Lys Ala Phe Glu Ile Met Glu Arg Val Glu
            260                 265                 270

Lys Ala Tyr Glu Ala His Leu Arg Glu Ile Thr Phe Ser Asn Ser Thr
        275                 280                 285

Tyr Arg Ile Gly Asn Arg Ala Ile Arg Gly Trp Thr Glu Ile Val Lys
    290                 295                 300

Lys Trp Met Lys Leu Asp Pro Ser Ala Pro Gln Gly Asn Tyr Leu Asp
305                 310                 315                 320

Val Val Lys Asp Tyr Gln Arg His Pro Arg Glu Ser Gly Asp Phe
                325                 330                 335

Lys Leu Phe Glu Leu Leu Ser Arg Pro Glu Asn Gln Ala Ala Trp Arg
            340                 345                 350

Glu Tyr Pro Glu Phe Leu Pro Leu Tyr Val Lys Tyr Arg His Ala Glu
            355                 360                 365

Gln Arg Met Lys Thr Ala Lys Lys Gln Ala Thr Phe Thr Leu Cys Asp
        370                 375                 380

Pro Ile Arg His Pro Leu Trp Val Arg Tyr Glu Glu Arg Ser Gly Thr
385                 390                 395                 400

Asn Leu Asn Lys Tyr Arg Leu Ile Met Asn Glu Lys Glu Lys Val Val
            405                 410                 415

Gln Phe Asp Arg Leu Ile Cys Leu Asn Ala Asp Gly His Tyr Glu Glu
        420                 425                 430

Gln Glu Asp Val Thr Val Pro Leu Ala Pro Ser Gln Phe Asp Asp
            435                 440                 445

Gln Ile Lys Phe Ser Ser Glu Asp Thr Gly Lys Gly Lys His Asn Phe
    450                 455                 460

Ser Tyr Tyr His Lys Gly Ile Asn Tyr Glu Leu Lys Gly Thr Leu Gly
465                 470                 475                 480

Gly Ala Arg Ile Gln Phe Asp Arg Glu His Leu Leu Arg Arg Gln Gly
            485                 490                 495

Val Lys Ala Gly Asn Val Gly Arg Ile Phe Leu Asn Val Thr Leu Asn
            500                 505                 510

Ile Glu Pro Met Gln Pro Phe Ser Arg Ser Gly Asn Leu Gln Thr Ser
        515                 520                 525

Val Gly Lys Ala Leu Lys Val Tyr Val Asp Gly Tyr Pro Lys Val Val
    530                 535                 540

Asn Phe Lys Pro Lys Glu Leu Thr Glu His Ile Lys Glu Ser Glu Lys
545                 550                 555                 560

Asn Thr Leu Thr Leu Gly Val Glu Ser Leu Pro Thr Gly Leu Arg Val
            565                 570                 575

Met Ser Val Asp Leu Gly Gln Arg Gln Ala Ala Ala Ile Ser Ile Phe
            580                 585                 590

Glu Val Val Ser Glu Lys Pro Asp Asp Asn Lys Leu Phe Tyr Pro Val
        595                 600                 605

Lys Asp Thr Asp Leu Phe Ala Val His Arg Thr Ser Phe Asn Ile Lys
    610                 615                 620

Leu Pro Gly Glu Lys Arg Thr Glu Arg Arg Met Leu Glu Gln Gln Lys
625                 630                 635                 640

Arg Asp Gln Ala Ile Arg Asp Leu Ser Arg Lys Leu Lys Phe Leu Lys
            645                 650                 655
```

```
Asn Val Leu Asn Met Gln Lys Leu Glu Lys Thr Asp Glu Arg Glu Lys
            660                 665                 670

Arg Val Asn Arg Trp Ile Lys Asp Arg Glu Arg Glu Glu Asn Pro
        675                 680                 685

Val Tyr Val Gln Glu Phe Glu Met Ile Ser Lys Val Leu Tyr Ser Pro
    690                 695                 700

His Ser Val Trp Val Asp Gln Leu Lys Ser Ile His Arg Lys Leu Glu
705                 710                 715                 720

Glu Gln Leu Gly Lys Glu Ile Ser Lys Trp Arg Gln Ser Ile Ser Gln
                725                 730                 735

Gly Arg Gln Gly Val Tyr Gly Ile Ser Leu Lys Asn Ile Glu Asp Ile
            740                 745                 750

Glu Lys Thr Arg Arg Leu Leu Phe Arg Trp Ser Met Arg Pro Glu Asn
        755                 760                 765

Pro Gly Glu Val Lys Gln Leu Gln Pro Gly Glu Arg Phe Ala Ile Asp
    770                 775                 780

Gln Gln Asn His Leu Asn His Leu Lys Asp Asp Arg Ile Lys Lys Leu
785                 790                 795                 800

Ala Asn Gln Ile Val Met Thr Ala Leu Gly Tyr Arg Tyr Asp Gly Lys
                805                 810                 815

Arg Lys Lys Trp Ile Ala Lys His Pro Ala Cys Gln Leu Val Leu Phe
            820                 825                 830

Glu Asp Leu Ser Arg Tyr Ala Phe Tyr Asp Glu Arg Ser Arg Leu Glu
        835                 840                 845

Asn Arg Asn Leu Met Arg Trp Ser Arg Arg Glu Ile Pro Lys Gln Val
    850                 855                 860

Ala Gln Ile Gly Gly Leu Tyr Gly Leu Leu Val Gly Glu Val Gly Ala
865                 870                 875                 880

Gln Tyr Ser Ser Arg Phe His Ala Lys Ser Gly Ala Pro Gly Ile Arg
                885                 890                 895

Cys Arg Val Val Lys Glu His Glu Leu Tyr Ile Thr Glu Gly Gly Gln
            900                 905                 910

Lys Val Arg Asn Gln Lys Phe Leu Asp Ser Leu Val Glu Asn Asn Ile
        915                 920                 925

Ile Glu Pro Asp Asp Ala Arg Arg Leu Glu Pro Gly Asp Leu Ile Arg
    930                 935                 940

Asp Gln Gly Gly Asp Lys Phe Ala Thr Leu Asp Glu Arg Gly Glu Leu
945                 950                 955                 960

Val Ile Thr His Ala Asp Ile Asn Ala Ala Gln Asn Leu Gln Lys Arg
                965                 970                 975

Phe Trp Thr Arg Thr His Gly Leu Tyr Arg Ile Arg Cys Glu Ser Arg
            980                 985                 990

Glu Ile Lys Asp Ala Val Val Leu  Val Pro Ser Asp Lys  Asp Gln Lys
        995                 1000                1005

Glu Lys  Met Glu Asn Leu Phe  Gly Ile Gly Tyr Leu  Gln Pro Phe
    1010                1015                1020

Lys Gln  Glu Asn Asp Val Tyr  Lys Trp Val Lys Gly  Glu Lys Ile
    1025                1030                1035

Lys Gly  Lys Lys Thr Ser Ser  Gln Ser Asp Asp Lys  Glu Leu Val
    1040                1045                1050

Ser Glu  Ile Leu Gln Glu Ala  Ser Val Met Ala Asp  Glu Leu Lys
    1055                1060                1065
```

```
Gly Asn Arg Lys Thr Leu Phe Arg Asp Pro Ser Gly Tyr Val Phe
        1070                1075                1080

Pro Lys Asp Arg Trp Tyr Thr Gly Gly Arg Tyr Phe Gly Thr Leu
    1085                1090                1095

Glu His Leu Leu Lys Arg Lys Leu Ala Glu Arg Arg Leu Phe Asp
    1100                1105                1110

Gly Gly Ser Ser Arg Arg Gly Leu Phe Asn Gly Thr Asp Ser Asn
    1115                1120                1125

Thr Asn Val Glu
    1130

<210> SEQ ID NO 320
<211> LENGTH: 1108
<212> TYPE: PRT
<213> ORGANISM: Bacillus thermoamylovorans

<400> SEQUENCE: 320

Met Ala Thr Arg Ser Phe Ile Leu Lys Ile Glu Pro Asn Glu Glu Val
1               5                   10                  15

Lys Lys Gly Leu Trp Lys Thr His Glu Val Leu Asn His Gly Ile Ala
            20                  25                  30

Tyr Tyr Met Asn Ile Leu Lys Leu Ile Arg Gln Glu Ala Ile Tyr Glu
        35                  40                  45

His His Glu Gln Asp Pro Lys Asn Pro Lys Lys Val Ser Lys Ala Glu
    50                  55                  60

Ile Gln Ala Glu Leu Trp Asp Phe Val Leu Lys Met Gln Lys Cys Asn
65                  70                  75                  80

Ser Phe Thr His Glu Val Asp Lys Asp Val Phe Asn Ile Leu Arg
                85                  90                  95

Glu Leu Tyr Glu Glu Leu Val Pro Ser Ser Val Glu Lys Lys Gly Glu
            100                 105                 110

Ala Asn Gln Leu Ser Asn Lys Phe Leu Tyr Pro Leu Val Asp Pro Asn
        115                 120                 125

Ser Gln Ser Gly Lys Gly Thr Ala Ser Ser Gly Arg Lys Pro Arg Trp
    130                 135                 140

Tyr Asn Leu Lys Ile Ala Gly Asp Pro Ser Trp Glu Glu Lys Lys
145                 150                 155                 160

Lys Trp Glu Glu Asp Lys Lys Asp Pro Leu Ala Lys Ile Leu Gly
                165                 170                 175

Lys Leu Ala Glu Tyr Gly Leu Ile Pro Leu Phe Ile Pro Phe Thr Asp
            180                 185                 190

Ser Asn Glu Pro Ile Val Lys Glu Ile Lys Trp Met Glu Lys Ser Arg
        195                 200                 205

Asn Gln Ser Val Arg Arg Leu Asp Lys Asp Met Phe Ile Gln Ala Leu
    210                 215                 220

Glu Arg Phe Leu Ser Trp Glu Ser Trp Asn Leu Lys Val Lys Glu Glu
225                 230                 235                 240

Tyr Glu Lys Val Glu Lys Glu His Lys Thr Leu Glu Glu Arg Ile Lys
                245                 250                 255

Glu Asp Ile Gln Ala Phe Lys Ser Leu Glu Gln Tyr Glu Lys Glu Arg
            260                 265                 270

Gln Glu Gln Leu Leu Arg Asp Thr Leu Asn Thr Asn Gly Tyr Arg Leu
        275                 280                 285
```

```
Ser Lys Arg Gly Leu Arg Gly Trp Arg Glu Ile Ile Gln Lys Trp Leu
    290                 295                 300

Lys Met Asp Glu Asn Glu Pro Ser Glu Lys Tyr Leu Glu Val Phe Lys
305                 310                 315                 320

Asp Tyr Gln Arg Lys His Pro Arg Glu Ala Gly Asp Tyr Ser Val Tyr
                325                 330                 335

Glu Phe Leu Ser Lys Lys Glu Asn His Phe Ile Trp Arg Asn His Pro
                340                 345                 350

Glu Tyr Pro Tyr Leu Tyr Ala Thr Phe Cys Glu Ile Asp Lys Lys Lys
                355                 360                 365

Lys Asp Ala Lys Gln Gln Ala Thr Phe Thr Leu Ala Asp Pro Ile Asn
370                 375                 380

His Pro Leu Trp Val Arg Phe Glu Glu Arg Ser Gly Ser Asn Leu Asn
385                 390                 395                 400

Lys Tyr Arg Ile Leu Thr Glu Gln Leu His Thr Glu Lys Leu Lys Lys
                405                 410                 415

Lys Leu Thr Val Gln Leu Asp Arg Leu Ile Tyr Pro Thr Glu Ser Gly
                420                 425                 430

Gly Trp Glu Glu Lys Gly Lys Val Asp Ile Val Leu Leu Pro Ser Arg
        435                 440                 445

Gln Phe Tyr Asn Gln Ile Phe Leu Asp Ile Glu Glu Lys Gly Lys His
    450                 455                 460

Ala Phe Thr Tyr Lys Asp Glu Ser Ile Lys Phe Pro Leu Lys Gly Thr
465                 470                 475                 480

Leu Gly Gly Ala Arg Val Gln Phe Asp Arg Asp His Leu Arg Arg Tyr
                485                 490                 495

Pro His Lys Val Glu Ser Gly Asn Val Gly Arg Ile Tyr Phe Asn Met
            500                 505                 510

Thr Val Asn Ile Glu Pro Thr Glu Ser Pro Val Ser Lys Ser Leu Lys
            515                 520                 525

Ile His Arg Asp Asp Phe Pro Lys Phe Val Asn Phe Lys Pro Lys Glu
    530                 535                 540

Leu Thr Glu Trp Ile Lys Asp Ser Lys Gly Lys Lys Leu Lys Ser Gly
545                 550                 555                 560

Ile Glu Ser Leu Glu Ile Gly Leu Arg Val Met Ser Ile Asp Leu Gly
                565                 570                 575

Gln Arg Gln Ala Ala Ala Ala Ser Ile Phe Glu Val Val Asp Gln Lys
            580                 585                 590

Pro Asp Ile Glu Gly Lys Leu Phe Phe Pro Ile Lys Gly Thr Glu Leu
        595                 600                 605

Tyr Ala Val His Arg Ala Ser Phe Asn Ile Lys Leu Pro Gly Glu Thr
610                 615                 620

Leu Val Lys Ser Arg Glu Val Leu Arg Lys Ala Arg Glu Asp Asn Leu
625                 630                 635                 640

Lys Leu Met Asn Gln Lys Leu Asn Phe Leu Arg Asn Val Leu His Phe
                645                 650                 655

Gln Gln Phe Glu Asp Ile Thr Glu Arg Glu Lys Arg Val Thr Lys Trp
            660                 665                 670

Ile Ser Arg Gln Glu Asn Ser Asp Val Pro Leu Val Tyr Gln Asp Glu
        675                 680                 685

Leu Ile Gln Ile Arg Glu Leu Met Tyr Lys Pro Tyr Lys Asp Trp Val
690                 695                 700
```

```
Ala Phe Leu Lys Gln Leu His Lys Arg Leu Glu Val Glu Ile Gly Lys
705                 710                 715                 720

Glu Val Lys His Trp Arg Lys Ser Leu Ser Asp Gly Arg Lys Gly Leu
            725                 730                 735

Tyr Gly Ile Ser Leu Lys Asn Ile Asp Glu Ile Asp Arg Thr Arg Lys
            740                 745                 750

Phe Leu Leu Arg Trp Ser Leu Arg Pro Thr Glu Pro Gly Glu Val Arg
            755                 760                 765

Arg Leu Glu Pro Gly Gln Arg Phe Ala Ile Asp Gln Leu Asn His Leu
            770                 775                 780

Asn Ala Leu Lys Glu Asp Arg Leu Lys Lys Met Ala Asn Thr Ile Ile
785                 790                 795                 800

Met His Ala Leu Gly Tyr Cys Tyr Asp Val Arg Lys Lys Lys Trp Gln
                805                 810                 815

Ala Lys Asn Pro Ala Cys Gln Ile Ile Leu Phe Glu Asp Leu Ser Asn
                820                 825                 830

Tyr Asn Pro Tyr Glu Glu Arg Ser Arg Phe Glu Asn Ser Lys Leu Met
                835                 840                 845

Lys Trp Ser Arg Arg Glu Ile Pro Arg Gln Val Ala Leu Gln Gly Glu
                850                 855                 860

Ile Tyr Gly Leu Gln Val Gly Glu Val Gly Ala Gln Phe Ser Ser Arg
865                 870                 875                 880

Phe His Ala Lys Thr Gly Ser Pro Gly Ile Arg Cys Ser Val Val Thr
                885                 890                 895

Lys Glu Lys Leu Gln Asp Asn Arg Phe Phe Lys Asn Leu Gln Arg Glu
                900                 905                 910

Gly Arg Leu Thr Leu Asp Lys Ile Ala Val Leu Lys Glu Gly Asp Leu
                915                 920                 925

Tyr Pro Asp Lys Gly Gly Glu Lys Phe Ile Ser Leu Ser Lys Asp Arg
                930                 935                 940

Lys Leu Val Thr Thr His Ala Asp Ile Asn Ala Ala Gln Asn Leu Gln
945                 950                 955                 960

Lys Arg Phe Trp Thr Arg Thr His Gly Phe Tyr Lys Val Tyr Cys Lys
                965                 970                 975

Ala Tyr Gln Val Asp Gly Gln Thr Val Tyr Ile Pro Glu Ser Lys Asp
                980                 985                 990

Gln Lys Gln Lys Ile Ile Glu Glu Phe Gly Glu Gly Tyr Phe Ile Leu
                995                 1000                1005

Lys Asp Gly Val Tyr Glu Trp Gly Asn Ala Gly Lys Leu Lys Ile
        1010                1015                1020

Lys Lys Gly Ser Ser Lys Gln Ser Ser Ser Glu Leu Val Asp Ser
        1025                1030                1035

Asp Ile Leu Lys Asp Ser Phe Asp Leu Ala Ser Glu Leu Lys Gly
        1040                1045                1050

Glu Lys Leu Met Leu Tyr Arg Asp Pro Ser Gly Asn Val Phe Pro
        1055                1060                1065

Ser Asp Lys Trp Met Ala Ala Gly Val Phe Phe Gly Lys Leu Glu
        1070                1075                1080

Arg Ile Leu Ile Ser Lys Leu Thr Asn Gln Tyr Ser Ile Ser Thr
        1085                1090                1095

Ile Glu Asp Asp Ser Ser Lys Gln Ser Met
        1100                1105
```

<210> SEQ ID NO 321
<211> LENGTH: 1108
<212> TYPE: PRT
<213> ORGANISM: S. pyrogenes

<400> SEQUENCE: 321

```
Met Ala Ile Arg Ser Ile Lys Leu Lys Leu Lys Thr His Thr Gly Pro
1               5                   10                  15

Glu Ala Gln Asn Leu Arg Lys Gly Ile Trp Arg Thr His Arg Leu Leu
            20                  25                  30

Asn Glu Gly Val Ala Tyr Tyr Met Lys Met Leu Leu Leu Phe Arg Gln
        35                  40                  45

Glu Ser Thr Gly Glu Arg Pro Lys Glu Glu Leu Gln Glu Glu Leu Ile
    50                  55                  60

Cys His Ile Arg Glu Gln Gln Arg Asn Gln Ala Asp Lys Asn Thr
65                  70                  75                  80

Gln Ala Leu Pro Leu Asp Lys Ala Leu Glu Ala Leu Arg Gln Leu Tyr
                85                  90                  95

Glu Leu Leu Val Pro Ser Ser Val Gly Gln Ser Gly Asp Ala Gln Ile
            100                 105                 110

Ile Ser Arg Lys Phe Leu Ser Pro Leu Val Asp Pro Asn Ser Glu Gly
        115                 120                 125

Gly Lys Gly Thr Ser Lys Ala Gly Ala Lys Pro Thr Trp Gln Lys Lys
    130                 135                 140

Lys Glu Ala Asn Asp Pro Thr Trp Glu Gln Asp Tyr Glu Lys Trp Lys
145                 150                 155                 160

Lys Arg Arg Glu Glu Asp Pro Thr Ala Ser Val Ile Thr Thr Leu Glu
                165                 170                 175

Glu Tyr Gly Ile Arg Pro Ile Phe Pro Leu Tyr Thr Asn Thr Val Thr
            180                 185                 190

Asp Ile Ala Trp Leu Pro Leu Gln Ser Asn Gln Phe Val Arg Thr Trp
        195                 200                 205

Asp Arg Asp Met Leu Gln Gln Ala Ile Glu Arg Leu Leu Ser Trp Glu
    210                 215                 220

Ser Trp Asn Lys Arg Val Gln Glu Glu Tyr Ala Lys Leu Lys Glu Lys
225                 230                 235                 240

Met Ala Gln Leu Asn Glu Gln Leu Glu Gly Gly Gln Glu Trp Ile Ser
                245                 250                 255

Leu Leu Glu Gln Tyr Glu Glu Asn Arg Glu Arg Glu Leu Arg Glu Asn
            260                 265                 270

Met Thr Ala Ala Asn Asp Lys Tyr Arg Ile Thr Lys Arg Gln Met Lys
        275                 280                 285

Gly Trp Asn Glu Leu Tyr Glu Leu Trp Ser Thr Phe Pro Ala Ser Ala
    290                 295                 300

Ser His Glu Gln Tyr Lys Glu Ala Leu Lys Arg Val Gln Gln Arg Leu
305                 310                 315                 320

Arg Gly Arg Phe Gly Asp Ala His Phe Phe Gln Tyr Leu Met Glu Glu
                325                 330                 335

Lys Asn Arg Leu Ile Trp Lys Gly Asn Pro Gln Arg Ile His Tyr Phe
            340                 345                 350

Val Ala Arg Asn Glu Leu Thr Lys Arg Leu Glu Glu Ala Lys Gln Ser
        355                 360                 365

Ala Thr Met Thr Leu Pro Asn Ala Arg Lys His Pro Leu Trp Val Arg
    370                 375                 380
```

```
Phe Asp Ala Arg Gly Gly Asn Leu Gln Asp Tyr Tyr Leu Thr Ala Glu
385                 390                 395                 400

Ala Asp Lys Pro Arg Ser Arg Arg Phe Val Thr Phe Ser Gln Leu Ile
            405                 410                 415

Trp Pro Ser Glu Ser Gly Trp Met Glu Lys Lys Asp Val Glu Val Glu
        420                 425                 430

Leu Ala Leu Ser Arg Gln Phe Tyr Gln Gln Val Lys Leu Leu Lys Asn
        435                 440                 445

Asp Lys Gly Lys Gln Lys Ile Glu Phe Lys Asp Lys Gly Ser Gly Ser
    450                 455                 460

Thr Phe Asn Gly His Leu Gly Gly Ala Lys Leu Gln Leu Glu Arg Gly
465                 470                 475                 480

Asp Leu Glu Lys Glu Glu Lys Asn Phe Glu Asp Gly Glu Ile Gly Ser
            485                 490                 495

Val Tyr Leu Asn Val Val Ile Asp Phe Glu Pro Leu Gln Glu Val Lys
                500                 505                 510

Asn Gly Arg Val Gln Ala Pro Tyr Gly Gln Val Leu Gln Leu Ile Arg
            515                 520                 525

Arg Pro Asn Glu Phe Pro Lys Val Thr Thr Tyr Lys Ser Gln Leu
530                 535                 540

Val Glu Trp Ile Lys Ala Ser Pro Gln His Ser Ala Gly Val Glu Ser
545                 550                 555                 560

Leu Ala Ser Gly Phe Arg Val Met Ser Ile Asp Leu Gly Leu Arg Ala
                565                 570                 575

Ala Ala Ala Thr Ser Ile Phe Ser Val Glu Ser Ser Asp Lys Asn
            580                 585                 590

Ala Ala Asp Phe Ser Tyr Trp Ile Glu Gly Thr Pro Leu Val Ala Val
            595                 600                 605

His Gln Arg Ser Tyr Met Leu Arg Leu Pro Gly Glu Gln Val Glu Lys
610                 615                 620

Gln Val Met Glu Lys Arg Asp Glu Arg Phe Gln Leu His Gln Arg Val
625                 630                 635                 640

Lys Phe Gln Ile Arg Val Leu Ala Gln Ile Met Arg Met Ala Asn Lys
                645                 650                 655

Gln Tyr Gly Asp Arg Trp Asp Glu Leu Asp Ser Leu Lys Gln Ala Val
            660                 665                 670

Glu Gln Lys Lys Ser Pro Leu Asp Gln Thr Asp Arg Thr Phe Trp Glu
            675                 680                 685

Gly Ile Val Cys Asp Leu Thr Lys Val Leu Pro Arg Asn Glu Ala Asp
690                 695                 700

Trp Glu Gln Ala Val Val Gln Ile His Arg Lys Ala Glu Glu Tyr Val
705                 710                 715                 720

Gly Lys Ala Val Gln Ala Trp Arg Lys Arg Phe Ala Ala Asp Glu Arg
            725                 730                 735

Lys Gly Ile Ala Gly Leu Ser Met Trp Asn Ile Glu Glu Leu Glu Gly
            740                 745                 750

Leu Arg Lys Leu Leu Ile Ser Trp Ser Arg Arg Thr Arg Asn Pro Gln
            755                 760                 765

Glu Val Asn Arg Phe Glu Arg Gly His Thr Ser His Gln Arg Leu Leu
770                 775                 780

Thr His Ile Gln Asn Val Lys Glu Asp Arg Leu Lys Gln Leu Ser His
785                 790                 795                 800
```

```
Ala Ile Val Met Thr Ala Leu Gly Tyr Val Tyr Asp Glu Arg Lys Gln
                805                 810                 815

Glu Trp Cys Ala Glu Tyr Pro Ala Cys Gln Val Ile Leu Phe Glu Asn
            820                 825                 830

Leu Ser Gln Tyr Arg Ser Asn Leu Asp Arg Ser Thr Lys Glu Asn Ser
            835                 840                 845

Thr Leu Met Lys Trp Ala His Arg Ser Ile Pro Lys Tyr Val His Met
850                 855                 860

Gln Ala Glu Pro Tyr Gly Ile Gln Ile Gly Asp Val Arg Ala Glu Tyr
865                 870                 875                 880

Ser Ser Arg Phe Tyr Ala Lys Thr Gly Thr Pro Gly Ile Arg Cys Lys
                885                 890                 895

Lys Val Arg Gly Gln Asp Leu Gln Gly Arg Phe Glu Asn Leu Gln
                900                 905             910

Lys Arg Leu Val Asn Glu Gln Phe Leu Thr Glu Gln Val Lys Gln
915                 920                 925

Leu Arg Pro Gly Asp Ile Val Pro Asp Asp Ser Gly Glu Leu Phe Met
        930                 935                 940

Thr Leu Thr Asp Gly Ser Gly Ser Lys Glu Val Val Phe Leu Gln Ala
945                 950                 955                 960

Asp Ile Asn Ala Ala His Asn Leu Gln Lys Arg Phe Trp Gln Arg Tyr
                965                 970                 975

Asn Glu Leu Phe Lys Val Ser Cys Arg Val Ile Val Arg Asp Glu Glu
            980                 985                 990

Glu Tyr Leu Val Pro Lys Thr Lys  Ser Val Gln Ala Lys  Leu Gly Lys
            995                 1000                1005

Gly Leu  Phe Val Lys Lys Ser  Asp Thr Ala Trp Lys  Asp Val Tyr
1010                1015                1020

Val Trp  Asp Ser Gln Ala Lys  Leu Lys Gly Lys Thr  Thr Phe Thr
1025                1030                1035

Glu Glu  Ser Glu Ser Pro Glu  Gln Leu Glu Asp Phe  Gln Glu Ile
1040                1045                1050

Ile Glu  Glu Ala Glu Glu Ala  Lys Gly Thr Tyr Arg  Thr Leu Phe
1055                1060                1065

Arg Asp  Pro Ser Gly Val Phe  Phe Pro Glu Ser Val  Trp Tyr Pro
1070                1075                1080

Gln Lys  Asp Phe Trp Gly Glu  Val Lys Arg Lys Leu  Tyr Gly Lys
1085                1090                1095

Leu Arg  Glu Arg Phe Leu Thr  Lys Ala Arg
1100                1105

<210> SEQ ID NO 322
<211> LENGTH: 658
<212> TYPE: PRT
<213> ORGANISM: Methylobacterium nodulans

<400> SEQUENCE: 322

Met Leu Thr Lys Gln Asp Lys Gln Lys Ile Thr Tyr Cys Thr Asn
1               5                   10                  15

Met Asn Glu Val Phe Glu Ala Lys Leu Gly Ser Ala Asp Leu Leu Leu
            20                  25                  30

Asn Trp Asp His Leu Arg Gly Arg Ile Arg Asp Arg Val Asp Ala Gly
        35                  40                  45
```

-continued

```
Asp Ile Gly Ser Ala Phe Leu Lys Leu Ala Leu Asp Val Ala His Val
 50                  55                  60

Leu Pro Asp Gly Val Asp Gln Leu Ala Arg Ala Ala Phe His Phe
 65                  70                  75                  80

Gln Ser Ala Lys Gly Ala Lys Ser Lys His Ala Asp Ser Val Gln Ala
                 85                  90                  95

Gly Leu Arg Val Leu Ser Ile Asp Leu Gly Val Arg Ser Phe Ala Thr
                100                 105                 110

Cys Ser Val Phe Glu Leu Lys Asp Thr Ala Pro Thr Thr Gly Val Ala
                115                 120                 125

Phe Pro Leu Ala Glu Phe Arg Leu Trp Ala Val His Glu Arg Ser Phe
130                 135                 140

Thr Leu Glu Leu Pro Gly Glu Asn Val Gly Ala Ala Gly Gln Gln Trp
145                 150                 155                 160

Arg Ala Gln Ala Asp Ala Glu Leu Arg Gln Leu Arg Gly Gly Leu Asn
                165                 170                 175

Arg His Arg Gln Leu Leu Arg Ala Ala Thr Val Gln Lys Gly Glu Arg
                180                 185                 190

Asp Ala Tyr Leu Thr Asp Leu Arg Glu Ala Trp Ser Ala Lys Glu Leu
                195                 200                 205

Trp Pro Phe Glu Ala Ser Leu Leu Ser Glu Leu Glu Arg Cys Ser Thr
210                 215                 220

Val Ala Asp Pro Leu Trp Gln Asp Thr Cys Lys Arg Ala Ala Arg Leu
225                 230                 235                 240

Tyr Arg Thr Glu Phe Gly Ala Val Val Ser Glu Trp Arg Ser Arg Thr
                245                 250                 255

Arg Ser Arg Glu Asp Arg Lys Tyr Ala Gly Lys Ser Met Trp Ser Val
                260                 265                 270

Gln His Leu Thr Asp Val Arg Arg Phe Leu Gln Ser Trp Ser Leu Ala
                275                 280                 285

Gly Arg Ala Ser Gly Asp Ile Arg Arg Leu Asp Arg Glu Arg Gly Gly
                290                 295                 300

Val Phe Ala Lys Asp Leu Leu Asp His Ile Asp Ala Leu Lys Asp Asp
305                 310                 315                 320

Arg Leu Lys Thr Gly Ala Asp Leu Ile Val Gln Ala Ala Arg Gly Phe
                325                 330                 335

Gln Arg Asn Glu Phe Gly Tyr Trp Val Gln Lys His Ala Pro Cys His
                340                 345                 350

Val Ile Leu Phe Glu Asp Leu Ser Arg Tyr Arg Met Arg Thr Asp Arg
                355                 360                 365

Pro Arg Arg Glu Asn Ser Gln Leu Met Gln Trp Ala His Arg Gly Val
370                 375                 380

Pro Asp Met Val Gly Met Gln Gly Glu Ile Tyr Gly Ile Gln Asp Arg
385                 390                 395                 400

Arg Asp Pro Asp Ser Ala Arg Lys His Ala Arg Gln Pro Leu Ala Ala
                405                 410                 415

Phe Cys Leu Asp Thr Pro Ala Ala Phe Ser Ser Arg Tyr His Ala Ser
                420                 425                 430

Thr Met Thr Pro Gly Ile Arg Cys His Pro Leu Arg Lys Arg Glu Phe
                435                 440                 445

Glu Asp Gln Gly Phe Leu Glu Leu Leu Lys Arg Glu Asn Glu Gly Leu
450                 455                 460
```

```
Asp Leu Asn Gly Tyr Lys Pro Gly Asp Leu Val Pro Leu Pro Gly Gly
465                 470                 475                 480

Glu Val Phe Val Cys Leu Asn Ala Asn Gly Leu Ser Arg Ile His Ala
                485                 490                 495

Asp Ile Asn Ala Ala Gln Asn Leu Gln Arg Arg Phe Trp Thr Gln His
            500                 505                 510

Gly Asp Ala Phe Arg Leu Pro Cys Gly Lys Ser Ala Val Gln Gly Gln
        515                 520                 525

Ile Arg Trp Ala Pro Leu Ser Met Gly Lys Arg Gln Ala Gly Ala Leu
    530                 535                 540

Gly Gly Phe Gly Tyr Leu Glu Pro Thr Gly His Asp Ser Gly Ser Cys
545                 550                 555                 560

Gln Trp Arg Lys Thr Thr Glu Ala Glu Trp Arg Arg Leu Ser Gly Ala
                565                 570                 575

Gln Lys Asp Arg Asp Glu Ala Ala Ala Glu Asp Glu Glu Leu Gln
            580                 585                 590

Gly Leu Glu Glu Glu Leu Leu Glu Arg Ser Gly Glu Arg Val Val Phe
        595                 600                 605

Phe Arg Asp Pro Ser Gly Val Val Leu Pro Thr Asp Leu Trp Phe Pro
    610                 615                 620

Ser Ala Ala Phe Trp Ser Ile Val Arg Ala Lys Thr Val Gly Arg Leu
625                 630                 635                 640

Arg Ser His Leu Asp Ala Gln Ala Glu Ala Ser Tyr Ala Val Ala Ala
                645                 650                 655

Gly Leu

<210> SEQ ID NO 323
<211> LENGTH: 1302
<212> TYPE: PRT
<213> ORGANISM: S. pyrogenes

<400> SEQUENCE: 323

Met Lys Lys Phe Glu Leu Lys Gln Asn Phe Arg Asn Asn Tyr Ser Gly
1               5                   10                  15

Lys Thr Leu Arg Asn Phe Arg Gln Thr Leu Ala Gln Ile Ala Asn Lys
                20                  25                  30

Lys Ser Ser Asp Ser Ile Leu Thr Ile Lys Phe Lys Leu Asp Cys Ser
            35                  40                  45

Lys Thr Gly Lys Leu Pro Lys Tyr Glu Asn Leu Ile Ser Leu Tyr Asp
        50                  55                  60

Thr Ile Glu Asp Ile Lys Lys Gly Thr Leu Ser Tyr Tyr Leu Phe Thr
65                  70                  75                  80

Leu Ile Val Ser Gly Phe Lys Phe Phe Gly Ser Ala Ser Gln Ala Lys
                85                  90                  95

Ala Phe Ser Thr Lys Asp Ile Phe Lys Asp Asn Asp Phe Tyr Asn Gln
            100                 105                 110

Phe Lys Ile Gln Ser His Leu Asp Leu Pro Asp Phe Val Pro Ser Lys
        115                 120                 125

Ile Tyr Gln Arg Leu Lys Lys Asn Val Arg Ser Thr Asn Gly Lys Asp
    130                 135                 140

Asn Ala Phe Lys Ala Ser Val Ile Val Ala Glu Tyr Arg Lys Glu Ile
145                 150                 155                 160

Gly Lys Leu Lys Asn Lys Asp Glu Ser Ser Glu His Gln Cys Glu Glu
                165                 170                 175
```

```
Leu Phe Lys Lys Ile Gly Thr Ala Leu Glu Thr Arg Phe Ser Ser Trp
            180                 185                 190

Gln Asp Leu Ile Asn Asn Cys Ser Thr Gly Cys Glu Ile Ile Asp Glu
            195                 200                 205

Ile Leu Asn Asp Ser Phe Gly Thr Leu Pro Ser Ile Lys Lys Met Val
            210                 215                 220

Leu Ala Ser Thr Thr Gln Ser Ser Asp Gly Glu Gln Asp Gly Ile Ala
225                 230                 235                 240

Ile Ala Tyr Asp Pro Asp Ser Thr Phe Ile Lys Ser Asp Glu Leu Leu
            245                 250                 255

Asn Pro Tyr Phe Ala Val Ala Thr Ile Leu Lys Ser Met Pro Pro Glu
            260                 265                 270

Ile Gln Gln Asp Lys Lys Ser Ala Tyr Val Lys Ala Asn Leu Thr Thr
            275                 280                 285

Pro Thr His Asn Ala Leu Ser Trp Ile Phe Gly Lys Gly Leu Thr Leu
            290                 295                 300

Phe Gln Thr Glu Ser Thr Glu Lys Leu Cys Ala Met Phe Asn Val Ser
305                 310                 315                 320

Asp Lys Arg Val Ile Glu Gln Val Gln Asp Ala Ala Lys Ala Val Lys
            325                 330                 335

Leu Pro Ala Glu Leu Asp Leu Asn His Cys Thr Leu Lys Phe Gln Asp
            340                 345                 350

Phe Arg Ser Ser Leu Gly Gly His Leu Asp Ser Trp Thr Thr Asn Tyr
            355                 360                 365

Leu Lys Arg Leu Asp Glu Leu Asn Asp Leu Leu Leu Asn Leu Pro Lys
            370                 375                 380

Asn Leu Ser Leu Pro Asp Ile Phe Met Ile Asp Gly Lys Asp Phe Ile
385                 390                 395                 400

Glu Tyr Ser Gly Cys Asn Arg Asp Glu Ile Gln Gln Met Ile Asp Phe
            405                 410                 415

Val Val Asn Glu Gln Asn Arg Ile Lys Leu Gln Glu Ser Leu Asn Ala
            420                 425                 430

Leu Leu Gly Lys Gly Asn Asn Gln Ile Cys Ser Asp Asp Ile Ser Thr
            435                 440                 445

Val Lys Asp Phe Ser Glu Ile Val Asn Ser Leu His Ser Phe Val Gln
450                 455                 460

Gln Ile Asp Asn Ser Leu Glu Gln Ser Ser Asn Glu Ala Asn Ser Ile
465                 470                 475                 480

Phe Ser Glu Leu Lys Lys Lys Ile Glu Lys Asn Glu Lys Trp Asp Ile
            485                 490                 495

Trp Lys Asn Asn Leu Lys Lys Ile Pro Lys Leu Asn Lys Leu Ser Gly
            500                 505                 510

Gly Val Pro Asp Ala Trp Lys Glu Ile Arg Glu Ile Glu Gln Lys Phe
            515                 520                 525

His Glu Ile Ser Glu Asn Gln Lys Lys His Phe Thr Glu Val Met Glu
            530                 535                 540

Trp Ile Asp Ala Gly Asn Gly Thr Ile Asp Ile Phe Gly Ser Arg Phe
545                 550                 555                 560

Lys Tyr Asp Glu Leu Leu Lys Lys Ser Lys Asn Asn Leu Gln Ser
            565                 570                 575

Ala Asp Glu Leu Ala Phe Arg Ser Val Leu Asn Lys Leu Gly Arg Phe
            580                 585                 590
```

-continued

Ala Arg Gln Gly Asn Asp Leu Val Cys Glu Lys Ile Lys Asn Trp Phe
            595                 600                 605

Lys Glu Gln Asn Ile Phe Asp Ser Ser Lys Asp Phe Asn Arg Tyr Phe
    610                 615                 620

Ile Asn Gln Lys Gly Phe Ile Phe Lys His Pro Ser Ser Lys Lys Asp
625                 630                 635                 640

Asn Ser Pro Tyr Asn Leu Ser Ala Asn Leu Leu Glu Lys Arg Tyr Glu
                645                 650                 655

Val Thr Asn Thr Val Gly Ala Leu Leu Glu Gln Cys Glu Ser Asp Pro
            660                 665                 670

Ala Ile Val Asn Asp Pro Phe Ser Met Arg Ser Leu Val Glu Phe Arg
        675                 680                 685

Ala Leu Trp Phe Ser Ile Asn Ile Ser Gly Ile Ser Lys Glu Gln His
    690                 695                 700

Ile Pro Thr Lys Ile Ala Gln Pro Lys Leu Asp Asp Ser Thr Tyr Gln
705                 710                 715                 720

Glu Ser Val Ser Pro Thr Leu Lys Tyr Arg Leu Glu Lys Gly Gln Ile
                725                 730                 735

Thr Ser Ser Glu Leu Asn Ser Ile Phe Thr Val Tyr Lys Ser Leu Leu
            740                 745                 750

Ser Gly Leu Ser Ile Arg Leu Ser Arg Asn Ser Phe Tyr Leu Arg Thr
        755                 760                 765

Lys Phe Ser Trp Ile Gly Asn Asn Ser Leu Ile Tyr Cys Pro Lys Glu
    770                 775                 780

Thr Thr Trp Lys Ile Pro Ala Ala Tyr Phe Lys Ser Asp Leu Trp Asn
785                 790                 795                 800

Glu Tyr Lys Asp Lys Gln Ile Leu Ile Val Asn Glu Glu Tyr Asp Val
                805                 810                 815

Asp Val Val Lys Thr Phe Glu Ser Val Tyr Lys Ile Val Lys Ser Lys
            820                 825                 830

Asp Asn Asn Glu Lys Asn Arg Ile Leu Pro Leu Leu Lys Gln Leu Pro
        835                 840                 845

His Asp Trp Met Phe Lys Leu Pro Phe Gly Ala Ser Asn Ala Glu Lys
    850                 855                 860

Cys Lys Val Leu Lys Leu Glu Lys Asn Asn Lys Lys Phe Lys Pro Leu
865                 870                 875                 880

Ser Val Ser Lys Asp Ser Leu Ala Arg Leu Ser Gly Pro Ser Thr Tyr
                885                 890                 895

Phe Asn Gln Ile Asp Glu Ile Met Met Asn Asp Glu Ser Glu Leu Ser
            900                 905                 910

Glu Met Thr Leu Leu Ala Asp Glu Pro Val Arg Gln Gln Met Ser Asn
        915                 920                 925

Gly Lys Ile Glu Ile Pro Asp Asp Tyr Val Met Ser Leu Ala Ile
    930                 935                 940

Pro Ile Thr Arg Ser Leu Lys Lys Gly Asn Thr Glu Ser Phe Pro Phe
945                 950                 955                 960

Lys Asn Ile Val Ser Ile Asp Gln Gly Glu Ala Gly Phe Ala Tyr Ala
                965                 970                 975

Val Phe Lys Leu Ser Asp Cys Gly Asn Glu Arg Ala Glu Pro Ile Ala
            980                 985                 990

Thr Gly Leu Ile Pro Ile Pro Ser Ile Arg Arg Leu Ile His Ser Val
        995                 1000                1005

-continued

```
Lys Lys Tyr Arg Gly Lys Lys Gln Arg Ile Gln Asn Phe Asn Gln
1010                1015                1020

Lys Phe Asp Ser Thr Met Phe Thr Leu Arg Glu Asn Val Thr Gly
    1025                1030                1035

Asp Ile Cys Gly Leu Ile Val Ala Leu Met Lys Lys Tyr Asn Ala
    1040                1045                1050

Phe Pro Ile Leu Glu Lys Gln Val Gly Asn Leu Glu Ser Gly Ser
    1055                1060                1065

Lys Gln Leu Met Leu Val Tyr Lys Ala Val Asn Ser Lys Phe Leu
    1070                1075                1080

Ala Ala Lys Val Asp Met Gln Asn Asp Gln Arg Arg Ser Trp Trp
    1085                1090                1095

Tyr Gln Gly Asn Ser Trp Asn Thr Pro Ile Leu Arg Ile Ser Asn
    1100                1105                1110

Pro Asn Gln Ser Asn Asn Lys Asn Ile Val Lys Asn Ile Asn Gly
    1115                1120                1125

Lys Lys Tyr Glu Glu Leu Lys Ile Tyr Pro Gly Tyr Ser Val Ser
    1130                1135                1140

Ala Tyr Met Thr Ser Cys Ile Cys His Val Cys Gly Arg Asn Ala
    1145                1150                1155

Leu Glu Leu Leu Lys Asn Asp Asp Ser Thr Gly Lys Val Lys Lys
    1160                1165                1170

Tyr Gln Ile Asn Gln Asp Gly Glu Val Thr Ile Gly Gly Glu Val
    1175                1180                1185

Ile Lys Leu Tyr Arg Lys Pro Asp Arg Leu Thr Pro Val Lys Asn
    1190                1195                1200

Leu Ala Lys Lys Gly Asn Arg Glu Arg Thr Tyr Ala Ser Ile Asn
    1205                1210                1215

Glu Arg Ala Pro Thr Val Ser Val Gln Lys Ala Glu Leu Ser Ala
    1220                1225                1230

Asp Glu Leu Gln Lys Ile Ile Lys Lys Asn Met Arg Arg Ala Pro
    1235                1240                1245

Arg Ser Leu Met Ser Lys Asp Thr Thr Gln Ser Arg Tyr Phe Cys
    1250                1255                1260

Val Phe Lys Asn Cys Pro Cys His Asn Lys Glu Gln His Ala Asp
    1265                1270                1275

Val Asn Ala Ala Ile Asn Ile Gly Arg Arg Phe Leu Lys Asp Cys
    1280                1285                1290

Ile Leu Asp Asp Asn Lys Glu Lys Asp
    1295                1300

<210> SEQ ID NO 324
<211> LENGTH: 1255
<212> TYPE: PRT
<213> ORGANISM: S. pyrogenes

<400> SEQUENCE: 324

Met Arg Ser Asn Tyr His Gly Gly Arg Asn Ala Arg Gln Trp Arg Lys
1               5                   10                  15

Gln Ile Ser Gly Leu Ala Arg Arg Thr Lys Glu Thr Val Phe Thr Tyr
                20                  25                  30

Lys Phe Pro Leu Glu Thr Asp Ala Ala Glu Ile Asp Phe Asp Lys Ala
            35                  40                  45

Val Gln Thr Tyr Gly Ile Ala Glu Gly Val Gly His Gly Ser Leu Ile
        50                  55                  60
```

-continued

```
Gly Leu Val Cys Ala Phe His Leu Ser Gly Phe Arg Leu Phe Ser Lys
 65                  70                  75                  80

Ala Gly Glu Ala Met Ala Phe Arg Asn Arg Ser Arg Tyr Pro Thr Asp
                 85                  90                  95

Ala Phe Ala Glu Lys Leu Ser Ala Ile Met Gly Ile Gln Leu Pro Thr
            100                 105                 110

Leu Ser Pro Glu Gly Leu Asp Leu Ile Phe Gln Ser Pro Pro Arg Ser
        115                 120                 125

Arg Asp Gly Ile Ala Pro Val Trp Ser Glu Asn Glu Val Arg Asn Arg
    130                 135                 140

Leu Tyr Thr Asn Trp Thr Gly Arg Gly Pro Ala Asn Lys Pro Asp Glu
145                 150                 155                 160

His Leu Leu Glu Ile Ala Gly Glu Ile Ala Lys Gln Val Phe Pro Lys
                165                 170                 175

Phe Gly Gly Trp Asp Asp Leu Ala Ser Asp Pro Asp Lys Ala Leu Ala
            180                 185                 190

Ala Ala Asp Lys Tyr Phe Gln Ser Gln Gly Asp Phe Pro Ser Ile Ala
        195                 200                 205

Ser Leu Pro Ala Ala Ile Met Leu Ser Pro Ala Asn Ser Thr Val Asp
210                 215                 220

Phe Glu Gly Asp Tyr Ile Ala Ile Asp Pro Ala Ala Glu Thr Leu Leu
225                 230                 235                 240

His Gln Ala Val Ser Arg Cys Ala Ala Arg Leu Gly Arg Glu Arg Pro
                245                 250                 255

Asp Leu Asp Gln Asn Lys Gly Pro Phe Val Ser Ser Leu Gln Asp Ala
            260                 265                 270

Leu Val Ser Ser Gln Asn Asn Gly Leu Ser Trp Leu Phe Gly Val Gly
        275                 280                 285

Phe Gln His Trp Lys Glu Lys Ser Pro Lys Glu Leu Ile Asp Glu Tyr
    290                 295                 300

Lys Val Pro Ala Asp Gln His Gly Ala Val Thr Gln Val Lys Ser Phe
305                 310                 315                 320

Val Asp Ala Ile Pro Leu Asn Pro Leu Phe Asp Thr Thr His Tyr Gly
                325                 330                 335

Glu Phe Arg Ala Ser Val Ala Gly Lys Val Arg Ser Trp Val Ala Asn
            340                 345                 350

Tyr Trp Lys Arg Leu Leu Asp Leu Lys Ser Leu Leu Ala Thr Thr Glu
        355                 360                 365

Phe Thr Leu Pro Glu Ser Ile Ser Asp Pro Lys Ala Val Ser Leu Phe
    370                 375                 380

Ser Gly Leu Leu Val Asp Pro Gln Gly Leu Lys Lys Val Ala Asp Ser
385                 390                 395                 400

Leu Pro Ala Arg Leu Val Ser Ala Glu Ala Ile Asp Arg Leu Met
                405                 410                 415

Gly Val Gly Ile Pro Thr Ala Ala Asp Ile Ala Gln Val Glu Arg Val
            420                 425                 430

Ala Asp Glu Ile Gly Ala Phe Ile Gly Gln Val Gln Gln Phe Asn Asn
        435                 440                 445

Gln Val Lys Gln Lys Leu Glu Asn Leu Gln Asp Ala Asp Asp Glu Glu
    450                 455                 460

Phe Leu Lys Gly Leu Lys Ile Glu Leu Pro Ser Gly Asp Lys Glu Pro
465                 470                 475                 480
```

```
Pro Ala Ile Asn Arg Ile Ser Gly Gly Ala Pro Asp Ala Ala Ala Glu
                485                 490                 495

Ile Ser Glu Leu Glu Glu Lys Leu Gln Arg Leu Leu Asp Ala Arg Ser
            500                 505                 510

Glu His Phe Gln Thr Ile Ser Glu Trp Ala Glu Glu Asn Ala Val Thr
            515                 520                 525

Leu Asp Pro Ile Ala Ala Met Val Glu Leu Glu Arg Leu Arg Leu Ala
        530                 535                 540

Glu Arg Gly Ala Thr Gly Asp Pro Glu Glu Tyr Ala Leu Arg Leu Leu
545                 550                 555                 560

Leu Gln Arg Ile Gly Arg Leu Ala Asn Arg Val Ser Pro Val Ser Ala
                565                 570                 575

Gly Ser Ile Arg Glu Leu Leu Lys Pro Val Phe Met Glu Glu Arg Glu
            580                 585                 590

Phe Asn Leu Phe Phe His Asn Arg Leu Gly Ser Leu Tyr Arg Ser Pro
        595                 600                 605

Tyr Ser Thr Ser Arg His Gln Pro Phe Ser Ile Asp Val Gly Lys Ala
        610                 615                 620

Lys Ala Ile Asp Trp Ile Ala Gly Leu Asp Gln Ile Ser Ser Asp Ile
625                 630                 635                 640

Glu Lys Ala Leu Ser Gly Ala Gly Glu Ala Leu Gly Asp Gln Leu Arg
                645                 650                 655

Asp Trp Ile Asn Leu Ala Gly Phe Ala Ile Ser Gln Arg Leu Arg Gly
            660                 665                 670

Leu Pro Asp Thr Val Pro Asn Ala Leu Ala Gln Val Arg Cys Pro Asp
        675                 680                 685

Asp Val Arg Ile Pro Pro Leu Leu Ala Met Leu Leu Glu Glu Asp Asp
        690                 695                 700

Ile Ala Arg Asp Val Cys Leu Lys Ala Phe Asn Leu Tyr Val Ser Ala
705                 710                 715                 720

Ile Asn Gly Cys Leu Phe Gly Ala Leu Arg Glu Gly Phe Ile Val Arg
                725                 730                 735

Thr Arg Phe Gln Arg Ile Gly Thr Asp Gln Ile His Tyr Val Pro Lys
            740                 745                 750

Asp Lys Ala Trp Glu Tyr Pro Asp Arg Leu Asn Thr Ala Lys Gly Pro
        755                 760                 765

Ile Asn Ala Ala Val Ser Ser Asp Trp Ile Glu Lys Asp Gly Ala Val
        770                 775                 780

Ile Lys Pro Val Glu Thr Val Arg Asn Leu Ser Ser Thr Gly Phe Ala
785                 790                 795                 800

Gly Ala Gly Val Ser Glu Tyr Leu Val Gln Ala Pro His Asp Trp Tyr
                805                 810                 815

Thr Pro Leu Asp Leu Arg Asp Val Ala His Leu Val Thr Gly Leu Pro
            820                 825                 830

Val Glu Lys Asn Ile Thr Lys Leu Lys Arg Leu Thr Asn Arg Thr Ala
        835                 840                 845

Phe Arg Met Val Gly Ala Ser Ser Phe Lys Thr His Leu Asp Ser Val
        850                 855                 860

Leu Leu Ser Asp Lys Ile Lys Leu Gly Asp Phe Thr Ile Ile Ile Asp
865                 870                 875                 880

Gln His Tyr Arg Gln Ser Val Thr Tyr Gly Gly Lys Val Lys Ile Ser
                885                 890                 895
```

Tyr Glu Pro Glu Arg Leu Gln Val Glu Ala Ala Val Pro Val Val Asp
                900                 905                 910

Thr Arg Asp Arg Thr Val Pro Glu Pro Asp Thr Leu Phe Asp His Ile
            915                 920                 925

Val Ala Ile Asp Leu Gly Glu Arg Ser Val Gly Phe Ala Val Phe Asp
    930                 935                 940

Ile Lys Ser Cys Leu Arg Thr Gly Glu Val Lys Pro Ile His Asp Asn
945                 950                 955                 960

Asn Gly Asn Pro Val Val Gly Thr Val Ala Val Pro Ser Ile Arg Arg
                965                 970                 975

Leu Met Lys Ala Val Arg Ser His Arg Arg Arg Gln Pro Asn Gln
            980                 985                 990

Lys Val Asn Gln Thr Tyr Ser Thr Ala Leu Gln Asn Tyr Arg Glu Asn
        995                 1000                1005

Val Ile Gly Asp Val Cys Asn Arg Ile Asp Thr Leu Met Glu Arg
    1010                1015                1020

Tyr Asn Ala Phe Pro Val Leu Glu Phe Gln Ile Lys Asn Phe Gln
    1025                1030                1035

Ala Gly Ala Lys Gln Leu Glu Ile Val Tyr Gly Ser Val Leu His
    1040                1045                1050

Arg Tyr Thr Phe Ser Gly Val Asp Ala His Lys Ala Lys Arg Arg
    1055                1060                1065

Glu Tyr Trp Tyr Asn Gly Glu Leu Trp Glu His Pro Tyr Leu Met
    1070                1075                1080

Ala Lys Lys Trp Asn Glu Glu Thr Asn Ser Met Ser Gly Ala Pro
    1085                1090                1095

Lys Pro Val Ser Leu Phe Pro Gly Val Thr Val Asn Ala Ala Arg
    1100                1105                1110

Thr Ser Gln Ile Cys His Gln Cys Gln Arg Asn Pro Met Ser His
    1115                1120                1125

Leu Arg Gly Leu Thr Gly Thr Ile Glu Ile Ser Ser Asp Gly Leu
    1130                1135                1140

Leu Glu Leu Asp Asp Gly Thr Ile Arg Leu Phe Glu Thr Ser Asp
    1145                1150                1155

Tyr Asp Glu Asp Lys Phe Lys Gln Ser Arg Arg Glu Lys Arg Arg
    1160                1165                1170

Leu Asp Ala Asn Val Leu Leu Ser Gly Arg His Arg Ala Glu Tyr
    1175                1180                1185

Ile Tyr Thr Val Ala Lys Arg Asn Leu Arg Arg Pro Pro Lys Asn
    1190                1195                1200

Val Met Thr Lys Asp Thr Thr Gln Ser Arg Tyr Thr Cys Leu Tyr
    1205                1210                1215

Lys Asn Cys Ser Trp Thr Gly His Ala Asp Glu Asn Ala Ala Ile
    1220                1225                1230

Asn Ile Gly Arg Arg Tyr Leu Ala Glu Arg Ile Asp Met Pro Ala
    1235                1240                1245

Ser Lys Thr Lys Ala Ala Val
    1250                1255

<210> SEQ ID NO 325
<211> LENGTH: 1266
<212> TYPE: PRT
<213> ORGANISM: S. pyrogenes

<400> SEQUENCE: 325

```
Met Arg Pro Arg Phe His Gly Met Asn Ala Arg Asp Trp Arg Lys
1               5                   10                  15

His Val Gly Val Leu Ala Gln Gln His Lys Glu Thr Thr Arg Thr Tyr
            20                  25                  30

Thr Phe Pro Leu Asp Thr Thr Gly Ser Ala Ile Asp Phe Asp Ala Ala
        35                  40                  45

Leu Gln Ala Tyr Asn Ala Val Glu Gly Val Tyr Gly Ser Leu Leu
    50                  55                  60

Gly Leu Ala Cys Ala Val His Leu Ser Gly Phe Arg Leu Phe Ser Thr
65                  70                  75                  80

Gly Lys Glu Ala Ala Thr Phe Arg Asn Arg Ala Arg Tyr Pro Asn Ala
                85                  90                  95

Ala Phe Gln Ala Ala Leu Arg Lys Glu Leu Gly Thr Thr Ile Thr Thr
                100                 105                 110

Leu Thr Pro Glu Thr Leu Asp Arg Leu Phe Ser Ser Arg Pro Lys Arg
            115                 120                 125

Arg Asn Gly Val Pro Leu Pro Trp Asn Gln Asp Ser Ile Arg Asp Arg
130                 135                 140

Leu Tyr Thr Asn Trp Val Lys Pro Arg Pro Gly Asp Thr Pro Asp Ala
145                 150                 155                 160

Val Leu Phe Gln Ile Ala Thr Gly Ile Ala Gln Glu Ile Thr Glu Asp
                165                 170                 175

Val Ser Ser Trp Thr Asp Leu Ala Lys Asn Ser Asp Arg Gly Leu Lys
            180                 185                 190

Ala Ala His Arg Tyr Phe Ala Arg Val Gly Gly Phe Pro Ala Phe Asp
        195                 200                 205

Asn Leu Thr Pro Pro Ala Thr Val Gln Pro Thr Asp Thr Ile Asp
    210                 215                 220

Tyr Asp Pro Asn Ala Pro Phe His Leu Val Ser His Ala Asp Gln Thr
225                 230                 235                 240

Leu Ile His Gln Ser Ile Ser Leu Cys Ala His Arg Ile Arg Gln Glu
                245                 250                 255

Asp Pro Ala Leu Asp Pro Asn Lys Ser Gly Phe Ile Lys Gln Leu Gln
            260                 265                 270

Asn Asn Phe Leu Ser Gln Thr Phe Tyr Gly Leu Ser Trp Leu Phe Gly
        275                 280                 285

Ala Gly Tyr Val His Phe Arg Glu Cys Thr Ala Asn Asp Leu Ala Ile
    290                 295                 300

Gln Tyr Gly Ile Pro Asn Asn Cys Arg Asp Gly Ile His Gln Ile Lys
305                 310                 315                 320

Ser Phe Ala Asp Ala Ile Leu Pro Asn Thr Phe Phe Glu Lys Lys His
                325                 330                 335

Tyr Arg Lys Asp Ser Arg Ser Val Gly Lys Lys Ala Lys Ser Trp Ile
            340                 345                 350

Ser Asn Tyr Trp Gln Arg Leu Leu Gln Leu Gln Thr Trp Val Asp Asp
        355                 360                 365

His Thr Trp Val Thr Leu Pro Gln Glu Leu Thr Glu Ala Gln Phe Lys
    370                 375                 380

Pro Leu Phe Arg Gly Leu Leu Val Asp Ala Val Glu Leu Met Ala Ile
385                 390                 395                 400

Ala Glu Arg Leu Pro Gln Arg Leu Ala Asp Cys Arg Asp Ser Leu Asp
                405                 410                 415
```

```
Cys Leu Met Gly Lys Gly Pro Gln Ala Ala Thr Lys Asn Asp Val Glu
            420                 425                 430

Ile Val Glu Lys Val Arg Glu Ile Glu Ser Phe Val Gly Gln Ile
            435                 440                 445

Glu Gln Leu Gly Asn Gln Leu Arg His Gln Leu Glu Asn Glu Asn Asn
    450                 455                 460

Asp Gln Val His Arg Asp Asn Leu His Gln Leu Lys Asn Arg Leu Pro
465                 470                 475                 480

Leu Asp Leu Arg Arg Pro Gln Ala Leu Asn Lys Ile Ser Gly Val
                485                 490                 495

Pro Asp Val Ala Lys Ser Ile Arg Gly Leu Glu Thr Gln Leu Asp Gln
                500                 505                 510

Val Leu Lys Glu Arg Arg Ser His Phe Gly Arg Leu Thr Lys Trp Ala
            515                 520                 525

Lys Glu Cys Gly Ile Thr Leu Asp Pro Leu Gln Pro Leu Ile Glu Ser
            530                 535                 540

Glu Lys Gln Arg Val Ala Glu Arg Gly Ser Ala His Asp Ala Lys Glu
545                 550                 555                 560

Leu Ala Ile Arg Leu Leu Leu Gln Arg Ile Gly Arg Leu Gly His Arg
                565                 570                 575

Leu Ser Pro Thr Asn Ala Thr Ala Ile Gln Glu Leu Leu Arg Pro Val
                580                 585                 590

Phe Ala Val Lys Arg Glu Phe Asn Leu Phe Phe His Asn His Met Gly
            595                 600                 605

Ala Leu Tyr Arg Ser Pro Tyr Ser Thr Ser Arg His Gln Pro Phe Gln
            610                 615                 620

Ile Asn Val Asp Val Ala His Gly Thr Asp Trp Ile Gly Thr Ile Glu
625                 630                 635                 640

Thr Leu Ile Gln Asn Leu Phe Thr Gln Ile Gln Asp Asp Ala Leu Leu
                645                 650                 655

Arg Asp Leu Val Gln Leu Glu Gly Phe Val Phe Ser His Lys Leu Arg
                660                 665                 670

Ala Leu Pro Gly Val Ile Pro Ser Glu Leu Ala Arg Pro Asn Asn Leu
            675                 680                 685

Gln Gln Met Gly Leu Pro Ala Leu Leu Leu Val Leu Leu Gln Ala Asp
    690                 695                 700

Gln Val His Arg Glu Thr Val Leu Arg Val Phe Asn Leu Tyr Gly Ser
705                 710                 715                 720

Ala Ile Asn Gly Tyr Leu Phe Gln Ala Leu Arg Pro Gly Phe Ile Val
                725                 730                 735

Arg Ala Gly Phe Gln Arg Leu Glu Thr Lys Lys Leu Arg Tyr Val Pro
            740                 745                 750

Lys Ala Gln Ser Trp Gln Tyr Pro Asp Arg Leu His His Ala Lys Ser
            755                 760                 765

Ala Ile Lys Asn Ser Leu Ser Ala Gly Trp Ile Lys Lys Asn His Gln
            770                 775                 780

Gly Ala Ile Leu Pro Gln Lys Thr Leu Thr Ala Leu Val Lys Gln Lys
785                 790                 795                 800

Ser Leu Lys Asp Thr Gly Val Pro Glu Tyr Leu Val Gln Ala Pro His
                805                 810                 815

Asp Trp Tyr Val Pro Ile Asp Leu Arg Gly Pro Ala Ile Pro Ile Glu
                820                 825                 830
```

```
Gly Leu Thr Val Gly Thr Glu Gly Pro Glu Leu Thr Gln Leu Gly Pro
        835                 840                 845

Met Lys Asp Asp Cys Ala Phe Arg Ala Ile Gly Pro Ser Ser Phe Lys
850                 855                 860

Ser Lys Ile Asp Ala Gly Leu Leu Pro Gln Asp Val Lys Tyr Gly Asp
865                 870                 875                 880

Met Thr Leu Ile Phe Asp Gln His Tyr Gln Gln Ser Ile Ser Phe Ala
                885                 890                 895

Asn Gly Thr Phe Ser Ile Gln Tyr Gln Pro Thr Ser Leu Gln Val Lys
            900                 905                 910

Ala Ala Ile Pro Val Val Asp Lys Arg Pro Arg Asp Thr Arg Asn Asn
        915                 920                 925

Ser His Leu Tyr Asp Arg Ile Val Ala Ile Asp Leu Gly Glu Arg Lys
    930                 935                 940

Ile Gly Tyr Ala Ile Phe Asp Leu Lys Gln Val Leu Lys Ser Glu Gln
945                 950                 955                 960

Leu Glu Pro Met Arg Glu Asp Gly Lys Pro Leu Ile Gly Ser Ile Ser
                965                 970                 975

Ile Arg Ser Ile Arg Gly Leu Met Lys Ala Val Gln Thr His Arg Asn
            980                 985                 990

Arg Arg Gln Pro Asn Tyr Arg Ile Asp Gln Thr Tyr Ser Lys Ala Leu
        995                 1000                1005

Met His Tyr Arg Glu Ser Val Ile Gly Asp Val Cys Asn Ala Ile
        1010                1015                1020

Asp Thr Leu Cys Ala Arg Tyr Gly Gly Phe Pro Val Leu Glu Ser
        1025                1030                1035

Ser Val Arg Asn Phe Glu Val Gly Ser Ala Gln Leu Lys Thr Val
        1040                1045                1050

Tyr Gly Ser Val Ser Arg Arg Tyr Thr Trp Ser Ala Val Asp Ala
        1055                1060                1065

His Lys Asn Gln Arg Gln Gln Tyr Trp Leu Gly Gly Thr Lys Asp
        1070                1075                1080

Lys Ile Pro Ile Trp Thr His Pro Tyr Leu Met Thr Arg Glu Trp
        1085                1090                1095

Asp Glu Lys Asn Ser Lys Trp Ser Asn Arg Ser Lys Pro Leu Lys
        1100                1105                1110

Met His Pro Gly Val Glu Val His Pro Ala Gly Thr Ser Gln Ile
        1115                1120                1125

Cys His Gln Cys Lys Arg Asn Pro Ile Gly Ala Leu Trp Asn Val
        1130                1135                1140

Ala Asp Thr Val Val Leu Asp Gln Gly Gln Leu Asp Leu Asp
        1145                1150                1155

Asp Gly Thr Ile Arg Leu Asn Ser Gly Tyr Ile Asp Thr Thr Glu
        1160                1165                1170

Ile Lys Arg Ala Arg Arg Lys Lys Ile Arg Leu Pro Glu Asn Lys
        1175                1180                1185

Pro Leu Thr Gly Ser His Lys Thr Ser His Val Arg Ala Val Ala
        1190                1195                1200

Arg Arg Asn Leu Arg Gln Pro Pro Lys Ser Thr Arg Ala Lys Asp
        1205                1210                1215

Thr Thr Gln Ser Arg Tyr Thr Cys Leu Tyr Val Asp Cys Gly His
        1220                1225                1230
```

-continued

```
Glu Cys His Ala Asp Glu Asn Ala Ala Ile Asn Ile Gly Arg Lys
    1235                1240                1245

Tyr Leu Gln Glu Arg Ile His Ile Glu Ala Ser Arg Gln Ala Leu
    1250                1255                1260

Ser Thr Arg
    1265

<210> SEQ ID NO 326
<211> LENGTH: 1269
<212> TYPE: PRT
<213> ORGANISM: S. pyrogenes

<400> SEQUENCE: 326

Met Val Ala Gly Leu Lys Lys Ile Lys Arg Asp Gly Val Thr Met Lys
1               5                   10                  15

Ser Asn Tyr His Gly Gly Val Lys Ala Arg Ala Trp Arg Lys Arg Ile
                20                  25                  30

Gly Gly Leu Ala Arg Arg Gln Lys Glu Thr Val Phe Thr Tyr Lys Phe
            35                  40                  45

Pro Leu Glu Thr Glu Glu Ala Gly Ile Asp Phe Asp Lys Ala Val Gln
50                  55                  60

Thr Tyr Gly Ile Ala Glu Gly Ile Ser Gln Gly Ser Leu Ile Gly Leu
65                  70                  75                  80

Val Cys Ala Phe His Leu Ser Gly Phe Arg Leu Phe Ser Lys Ala Asp
                85                  90                  95

Glu Thr Lys Ala Phe Cys Asn Gln Gly Arg Tyr Pro Asn Gln Ala Phe
            100                 105                 110

Ala Glu Lys Leu Arg Asn Glu Leu Ser Val Thr Leu Pro Lys Leu Ser
            115                 120                 125

Pro Gln Ser Leu Asp Val Leu Phe Gln Ser Ser Pro Lys Ser Lys Asn
130                 135                 140

Gly Val Ala Pro Glu Trp Ser Lys Asn Ala Ile Arg Asn Arg Leu Tyr
145                 150                 155                 160

Thr Asn Trp Thr Gly Lys Gly Ala Gly Thr Asn Pro Asp Glu His Leu
                165                 170                 175

Leu Glu Ile Ala Glu Asp Ile Ala Ala Glu Ile Asp Ser Asp Leu Asp
            180                 185                 190

Gly Trp Lys Asp Leu Glu Glu His Pro Glu Lys Gly Leu Ser Ala Ala
            195                 200                 205

Asp Arg Tyr Phe Gln Ala Gln Gly Asp Phe Pro Ser Leu Thr Gly Leu
210                 215                 220

Pro Pro Ser Val Pro Leu Thr Pro Gln Asn Ser Thr Val Ala Phe Glu
225                 230                 235                 240

Gly Asp Pro Val Cys Leu Asn Pro Ser Asp Asn Thr Leu Leu His Gln
                245                 250                 255

Ala Val Ala Arg Cys Ala Gly Arg Ile Leu Gln Glu Gln Pro Asn Leu
            260                 265                 270

Ser Pro Asp Lys Asn Arg Phe Ile Asn Gln Leu Gln Asp Glu Leu Val
            275                 280                 285

Ser Ser Gln Asn Asn Gly Leu Ser Trp Leu Phe Gly Val Gly Phe Lys
290                 295                 300

Tyr Trp Lys Glu Met Ser Val Asp Gln Leu Ala Asp Asp Tyr Lys Val
305                 310                 315                 320
```

```
Lys Ser Thr Asp Leu Asp Ala Leu Lys Gln Val Lys Ser Phe Ile Asp
                325                 330                 335

Ala Ile Pro Leu Asn Pro Leu Phe Asp Thr Pro His Tyr Gly Glu Phe
            340                 345                 350

Arg Ala Ser Val Ala Gly Lys Met Arg Ser Trp Val Lys Asn Tyr Trp
        355                 360                 365

Lys Arg Leu Leu Asp Leu Lys Ser Gln Leu Gly Thr Ala Asn Ile Asn
    370                 375                 380

Leu Pro Glu Gly Leu Asp Glu Gln Arg Ala Glu Asn Leu Phe Ser Gly
385                 390                 395                 400

Leu Leu Ile Asp Ser Lys Gly Leu Arg Gln Val Thr Asp Lys Leu Pro
                405                 410                 415

Ser Arg Leu Lys Lys Ala Glu Asp Thr Ile Asp Arg Leu Met Gly Asp
            420                 425                 430

Gly Asn Pro Thr Ser Asp Asp Ile Glu Gln Val Glu Thr Val Ala Ala
        435                 440                 445

Glu Ile Ser Ala Phe Ile Gly Gln Val Glu Gln Phe Asn Asn Gln Leu
    450                 455                 460

Glu Gln Arg Leu Glu Asn Pro Leu Glu Gly Asp Asp Glu Thr Phe Leu
465                 470                 475                 480

Lys Gln Leu Lys Ile Asp Leu Pro Ala Glu Phe Lys Lys Pro Pro Ala
                485                 490                 495

Ile Asn Arg Ile Ser Gly Gly Ser Pro Asp Pro Thr Ala Glu Ile Ala
            500                 505                 510

Glu Leu Glu Glu Lys Leu Asp Arg Leu Met Ser Ala Arg Lys Glu His
        515                 520                 525

Tyr Glu Thr Ile Ala Glu Trp Ala Ser Ala Asn Lys Val Thr Leu Asp
    530                 535                 540

Pro Met Glu Ala Met Thr Thr Leu Glu Ala Gln Arg Leu Thr Glu Arg
545                 550                 555                 560

Gly Ala Glu Gly Asp Gln Glu Glu Phe Ala Leu Arg Leu Leu Leu Gln
                565                 570                 575

Arg Ile Gly Arg Leu Ala Asn Arg Leu Ser Pro Gln Gly Ala Thr Ala
            580                 585                 590

Ile Arg Asp Leu Leu Arg Pro Val Phe Thr Glu Lys Arg Glu Phe Asn
        595                 600                 605

Leu Phe Phe His Asn Arg Met Gly Ser Leu Tyr Arg Ser Pro Tyr Ser
    610                 615                 620

Thr Ser Arg His Gln Pro Phe Thr Ile Asp Val Ala Val Ala Lys Asn
625                 630                 635                 640

Thr Asp Trp Met Asp Ala Leu Asp Gly Ile Ala Glu Thr Ile Met Lys
                645                 650                 655

Gly Leu Ser Gln Ala Gly Asp Glu Leu Ser Leu Arg Leu Arg Asp Trp
            660                 665                 670

Ile Asn Ile Ser Gly Phe Ser Leu Ser Gln Arg Leu Arg Gly Leu Pro
        675                 680                 685

Asp Thr Val Pro Gly Glu Leu Ala Leu Val Arg Ser Ala Asp Asp Val
    690                 695                 700

Arg Ile Pro Pro Met Leu Ala Leu Gln Leu Glu Glu Asp Glu Val Ser
705                 710                 715                 720

Arg Glu Val Cys Leu Lys Ala Phe Asn Leu Tyr Val Ser Ala Ile Asn
                725                 730                 735
```

```
Gly Cys Leu Phe Arg Ala Leu Arg Glu Gly Phe Ile Val Arg Thr Lys
            740                 745                 750

Phe Gln Arg Leu Glu Arg Asp Val Leu Ser Tyr Val Pro Lys Thr Lys
            755                 760                 765

Leu Trp Asn Tyr Pro Gln Arg Leu Asp Thr Ala Arg Gly Pro Ile His
            770                 775                 780

Ser Ala Leu Ala Ala Ala Trp Ile Asn Lys Glu Gly Ser Val Ile Asp
785                 790                 795                 800

Pro Val Glu Thr Val Thr Ala Leu Ser Asp Thr Gly Phe Ser Asp Asp
                    805                 810                 815

Gly Ile Pro Glu Tyr Leu Val Gln Ala Pro His Asp Trp Tyr Thr Pro
                    820                 825                 830

Ile Asp Leu Arg Asp Ile Ser Lys Pro Val Ser Gly Leu Pro Val Lys
                    835                 840                 845

Lys Asn Ile Thr Gly Leu Lys Arg Gln Lys Lys Gln Thr Ala Phe Arg
            850                 855                 860

Met Val Gly Pro Ser Ser Phe Lys Ser His Leu Asp Ser Thr Leu Leu
865                 870                 875                 880

Ser Glu Glu Val Lys Leu Gly Asp Phe Thr Leu Ile Phe Asp Gln Tyr
                    885                 890                 895

Tyr Lys Gln Arg Val Ser Tyr Asn Gly Arg Val Lys Ile Thr Phe Glu
                    900                 905                 910

Pro Asp Arg Leu His Val Glu Ala Ala Val Pro Val Ile Asp Lys Arg
                    915                 920                 925

Val Arg Pro Ser Thr Glu Glu Asp Ala Leu Phe Asp His Leu Leu Ala
            930                 935                 940

Ile Asp Leu Gly Glu Lys Arg Val Gly Tyr Ala Val Tyr Asp Ile Lys
945                 950                 955                 960

Ala Cys Leu Arg Thr Gly Asp Ile Lys Pro Leu Glu Asp Gly Asp Gly
                    965                 970                 975

Lys Pro Ile Val Gly Ser Val Ala Val Pro Ser Ile Arg Arg Leu Met
                    980                 985                 990

Lys Ala Val Arg Ser His Arg Gln Gln Arg Gln Pro Asn Gln Lys Val
            995                 1000                1005

Asn Gln Thr Tyr Ser Thr Ala Leu Met Asn Tyr Arg Glu Asn Val
        1010                1015                1020

Ile Gly Asp Val Cys Asn Arg Ile Asp Thr Leu Met Glu Lys Tyr
        1025                1030                1035

Asn Ala Phe Pro Val Leu Glu Ser Ser Val Met Asn Phe Glu Ala
        1040                1045                1050

Gly Ser Arg Gln Leu Glu Met Val Tyr Gly Ser Val Leu His Arg
        1055                1060                1065

Tyr Thr Tyr Ser Lys Ile Asp Ala His Thr Ala Lys Arg Lys Glu
        1070                1075                1080

Tyr Trp Tyr Thr Gly Glu Tyr Trp Asp His Pro Tyr Leu Met Ala
        1085                1090                1095

His Lys Trp Asn Glu Arg Thr Arg Ser Tyr Ser Gly Ser Leu Ser
        1100                1105                1110

Ala Leu Thr Leu Tyr Pro Gly Val Met Val His Pro Ala Gly Thr
        1115                1120                1125

Ser Gln Arg Cys His Gln Cys Lys Arg Asn Pro Met Val Glu Ile
        1130                1135                1140
```

-continued

```
Lys Gln Leu Thr Gly Gln Val Glu Ile Asn Ala Asp Gly Ser Leu
    1145                1150                1155

Glu Leu Asp Asp Gly Thr Ile Cys Leu Tyr Glu Gly Tyr Asp Tyr
    1160                1165                1170

Ser Pro Glu Glu Tyr Lys Lys Ala Lys Arg Glu Lys Arg Arg Leu
    1175                1180                1185

Asp Pro Asn Val Pro Leu Ser Gly Arg His Gln Ala Lys His Val
    1190                1195                1200

Ser Ala Val Ala Lys Arg Asn Leu Arg Arg Pro Thr Val Ser Met
    1205                1210                1215

Met Ser Gly Asp Thr Thr Gln Ala Arg Tyr Val Cys Leu Tyr Thr
    1220                1225                1230

Asp Cys Asp Phe Thr Gly His Ala Asp Glu Asn Ala Ala Ile Asn
    1235                1240                1245

Ile Gly Trp Lys Tyr Leu Thr Glu Arg Ile Ala Leu Ser Glu Ser
    1250                1255                1260

Lys Asp Lys Ala Gly Val
    1265

<210> SEQ ID NO 327
<211> LENGTH: 1340
<212> TYPE: PRT
<213> ORGANISM: S. pyrogenes

<400> SEQUENCE: 327

Met Gln Ile Ser Lys Val Asn His Lys His Val Ala Val Gly Gln Lys
1               5                   10                  15

Asp Arg Glu Arg Ile Thr Gly Phe Ile Tyr Asn Asp Pro Val Gly Asp
                20                  25                  30

Glu Lys Ser Leu Glu Asp Val Val Ala Lys Arg Ala Asn Asp Thr Lys
            35                  40                  45

Val Leu Phe Asn Val Phe Asn Thr Lys Asp Leu Tyr Asp Ser Gln Glu
        50                  55                  60

Ser Asp Lys Ser Glu Lys Asp Lys Glu Ile Ile Ser Lys Gly Ala Lys
    65                  70                  75                  80

Phe Val Ala Lys Ser Phe Asn Ser Ala Ile Thr Ile Leu Lys Lys Gln
                85                  90                  95

Asn Lys Ile Tyr Ser Thr Leu Thr Ser Gln Gln Val Ile Lys Glu Leu
                100                 105                 110

Lys Asp Lys Phe Gly Gly Ala Arg Ile Tyr Asp Asp Ile Glu Glu
            115                 120                 125

Ala Leu Thr Glu Thr Leu Lys Lys Ser Phe Arg Lys Glu Asn Val Arg
    130                 135                 140

Asn Ser Ile Lys Val Leu Ile Glu Asn Ala Ala Gly Ile Arg Ser Ser
145                 150                 155                 160

Leu Ser Lys Asp Glu Glu Leu Ile Gln Glu Tyr Phe Val Lys Gln
                165                 170                 175

Leu Val Glu Glu Tyr Thr Lys Thr Lys Leu Gln Lys Asn Val Val Lys
                180                 185                 190

Ser Ile Lys Asn Gln Asn Met Val Ile Gln Pro Asp Ser Asp Ser Gln
            195                 200                 205

Val Leu Ser Leu Ser Glu Ser Arg Arg Glu Lys Gln Ser Ser Ala Val
        210                 215                 220
```

-continued

```
Ser Ser Asp Thr Leu Val Asn Cys Lys Glu Lys Asp Val Leu Lys Ala
225                 230                 235                 240

Phe Leu Thr Asp Tyr Ala Val Leu Asp Glu Asp Arg Asn Ser Leu
            245                 250                 255

Leu Trp Lys Leu Arg Asn Leu Val Asn Leu Tyr Phe Tyr Gly Ser Glu
            260                 265                 270

Ser Ile Arg Asp Tyr Ser Tyr Thr Lys Glu Lys Ser Val Trp Lys Glu
            275                 280                 285

His Asp Glu Gln Lys Ala Asn Lys Thr Leu Phe Ile Asp Glu Ile Cys
            290                 295                 300

His Ile Thr Lys Ile Gly Lys Asn Gly Lys Glu Gln Lys Val Leu Asp
305                 310                 315                 320

Tyr Glu Glu Asn Arg Ser Arg Cys Arg Lys Gln Asn Ile Asn Tyr Tyr
            325                 330                 335

Arg Ser Ala Leu Asn Tyr Ala Lys Asn Asn Thr Ser Gly Ile Phe Glu
            340                 345                 350

Asn Glu Asp Ser Asn His Phe Trp Ile His Leu Ile Glu Asn Glu Val
            355                 360                 365

Glu Arg Leu Tyr Asn Gly Ile Glu Asn Gly Glu Phe Lys Phe Glu
370                 375                 380

Thr Gly Tyr Ile Ser Glu Lys Val Trp Lys Ala Val Ile Asn His Leu
385                 390                 395                 400

Ser Ile Lys Tyr Ile Ala Leu Gly Lys Ala Val Tyr Asn Tyr Ala Met
            405                 410                 415

Lys Glu Leu Ser Ser Pro Gly Asp Ile Glu Pro Gly Lys Ile Asp Asp
            420                 425                 430

Ser Tyr Ile Asn Gly Ile Thr Ser Phe Asp Tyr Glu Ile Ile Lys Ala
            435                 440                 445

Glu Glu Ser Leu Gln Arg Asp Ile Ser Met Asn Val Val Phe Ala Thr
450                 455                 460

Asn Tyr Leu Ala Cys Ala Thr Val Asp Thr Asp Lys Asp Phe Leu Leu
465                 470                 475                 480

Phe Ser Lys Glu Asp Ile Arg Ser Cys Thr Lys Lys Asp Gly Asn Leu
            485                 490                 495

Cys Lys Asn Ile Met Gln Phe Trp Gly Gly Tyr Ser Thr Trp Lys Asn
            500                 505                 510

Phe Cys Glu Glu Tyr Leu Lys Asp Asp Lys Asp Ala Leu Glu Leu Leu
            515                 520                 525

Tyr Ser Leu Lys Ser Met Leu Tyr Ser Met Arg Asn Ser Ser Phe His
            530                 535                 540

Phe Ser Thr Glu Asn Val Asp Asn Gly Ser Trp Asp Thr Glu Leu Ile
545                 550                 555                 560

Gly Lys Leu Phe Glu Glu Asp Cys Asn Arg Ala Ala Arg Ile Glu Lys
            565                 570                 575

Glu Lys Phe Tyr Asn Asn Asn Leu His Met Phe Tyr Ser Ser Ser Leu
            580                 585                 590

Leu Glu Lys Val Leu Glu Arg Leu Tyr Ser Ser His His Glu Arg Ala
            595                 600                 605

Ser Gln Val Pro Ser Phe Asn Arg Val Phe Val Arg Lys Asn Phe Pro
            610                 615                 620

Ser Ser Leu Ser Glu Gln Arg Ile Thr Pro Lys Phe Thr Asp Ser Lys
625                 630                 635                 640
```

-continued

```
Asp Glu Gln Ile Trp Gln Ser Ala Val Tyr Tyr Leu Cys Lys Glu Ile
                645                 650                 655

Tyr Tyr Asn Asp Phe Leu Gln Ser Lys Glu Ala Tyr Lys Leu Phe Arg
        660                 665                 670

Glu Gly Val Lys Asn Leu Asp Lys Asn Asp Ile Asn Asn Gln Lys Ala
        675                 680                 685

Ala Asp Ser Phe Lys Gln Ala Val Val Tyr Gly Lys Ala Ile Gly
    690                 695                 700

Asn Ala Thr Leu Ser Gln Val Cys Gln Ala Ile Met Thr Glu Tyr Asn
705                 710                 715                 720

Arg Gln Asn Asn Asp Gly Leu Lys Lys Lys Ser Ala Tyr Ala Glu Lys
                725                 730                 735

Gln Asn Ser Asn Lys Tyr Lys His Tyr Pro Leu Phe Leu Lys Gln Val
            740                 745                 750

Leu Gln Ser Ala Phe Trp Glu Tyr Leu Asp Glu Asn Lys Glu Ile Tyr
        755                 760                 765

Gly Phe Ile Ser Ala Gln Ile His Lys Ser Asn Val Glu Ile Lys Ala
    770                 775                 780

Glu Asp Phe Ile Ala Asn Tyr Ser Ser Gln Gln Tyr Lys Lys Leu Val
785                 790                 795                 800

Asp Lys Val Lys Lys Thr Pro Glu Leu Gln Lys Trp Tyr Thr Leu Gly
                805                 810                 815

Arg Leu Ile Asn Pro Arg Gln Ala Asn Gln Phe Leu Gly Ser Ile Arg
            820                 825                 830

Asn Tyr Val Gln Phe Val Lys Asp Ile Gln Arg Arg Ala Lys Glu Asn
        835                 840                 845

Gly Asn Pro Ile Arg Asn Tyr Tyr Glu Val Leu Glu Ser Asp Ser Ile
    850                 855                 860

Ile Lys Ile Leu Glu Met Cys Thr Lys Leu Asn Gly Thr Thr Ser Asn
865                 870                 875                 880

Asp Ile His Asp Tyr Phe Arg Asp Glu Asp Tyr Ala Glu Tyr Ile
                885                 890                 895

Ser Gln Phe Val Asn Phe Gly Asp Val His Ser Gly Ala Ala Leu Asn
        900                 905                 910

Ala Phe Cys Asn Ser Glu Ser Glu Gly Lys Lys Asn Gly Ile Tyr Tyr
    915                 920                 925

Asp Gly Ile Asn Pro Ile Val Asn Arg Asn Trp Val Leu Cys Lys Leu
    930                 935                 940

Tyr Gly Ser Pro Asp Leu Ile Ser Lys Ile Ile Ser Arg Val Asn Glu
945                 950                 955                 960

Asn Met Ile His Asp Phe His Lys Gln Glu Asp Leu Ile Arg Glu Tyr
                965                 970                 975

Gln Ile Lys Gly Ile Cys Ser Asn Lys Lys Glu Gln Gln Asp Leu Arg
            980                 985                 990

Thr Phe Gln Val Leu Lys Asn Arg Val Glu Leu Arg Asp Ile Val Glu
        995                 1000                1005

Tyr Ser Glu Ile Ile Asn Glu Leu Tyr Gly Gln Leu Ile Lys Trp
        1010                1015                1020

Cys Tyr Leu Arg Glu Arg Asp Leu Met Tyr Phe Gln Leu Gly Phe
        1025                1030                1035

His Tyr Leu Cys Leu Asn Asn Ala Ser Ser Lys Glu Ala Asp Tyr
        1040                1045                1050
```

```
Ile Lys Ile Asn Val Asp Asp Arg Asn Ile Ser Gly Ala Ile Leu
    1055                1060                1065

Tyr Gln Ile Ala Ala Met Tyr Ile Asn Gly Leu Pro Val Tyr Tyr
    1070                1075                1080

Lys Lys Asp Asp Met Tyr Val Ala Leu Lys Ser Gly Lys Lys Ala
    1085                1090                1095

Ser Asp Glu Leu Asn Ser Asn Glu Gln Thr Ser Lys Lys Ile Asn
    1100                1105                1110

Tyr Phe Leu Lys Tyr Gly Asn Asn Ile Leu Gly Asp Lys Lys Asp
    1115                1120                1125

Gln Leu Tyr Leu Ala Gly Leu Glu Leu Phe Glu Asn Val Ala Glu
    1130                1135                1140

His Glu Asn Ile Ile Ile Phe Arg Asn Glu Ile Asp His Phe His
    1145                1150                1155

Tyr Phe Tyr Asp Arg Asp Arg Ser Met Leu Asp Leu Tyr Ser Glu
    1160                1165                1170

Val Phe Asp Arg Phe Phe Thr Tyr Asp Met Lys Leu Arg Lys Asn
    1175                1180                1185

Val Val Asn Met Leu Tyr Asn Ile Leu Leu Asp His Asn Ile Val
    1190                1195                1200

Ser Ser Phe Val Phe Glu Thr Gly Glu Lys Lys Val Gly Arg Gly
    1205                1210                1215

Asp Ser Glu Val Ile Lys Pro Ser Ala Lys Ile Arg Leu Arg Ala
    1220                1225                1230

Asn Asn Gly Val Ser Ser Asp Val Phe Thr Tyr Lys Val Gly Ser
    1235                1240                1245

Lys Asp Glu Leu Lys Ile Ala Thr Leu Pro Ala Lys Asn Glu Glu
    1250                1255                1260

Phe Leu Leu Asn Val Ala Arg Leu Ile Tyr Tyr Pro Asp Met Glu
    1265                1270                1275

Ala Val Ser Glu Asn Met Val Arg Glu Gly Val Val Lys Val Glu
    1280                1285                1290

Lys Ser Asn Asp Lys Lys Gly Lys Ile Ser Arg Gly Ser Asn Thr
    1295                1300                1305

Arg Ser Ser Asn Gln Ser Lys Tyr Asn Asn Lys Ser Lys Asn Arg
    1310                1315                1320

Met Asn Tyr Ser Met Gly Ser Ile Phe Glu Lys Met Asp Leu Lys
    1325                1330                1335

Phe Asp
    1340

<210> SEQ ID NO 328
<211> LENGTH: 1437
<212> TYPE: PRT
<213> ORGANISM: S. pyrogenes

<400> SEQUENCE: 328

Met Lys Ile Ser Lys Val Arg Glu Glu Asn Arg Gly Ala Lys Leu Thr
1               5                   10                  15

Val Asn Ala Lys Thr Ala Val Val Ser Glu Asn Arg Ser Gln Glu Gly
                20                  25                  30

Ile Leu Tyr Asn Asp Pro Ser Arg Tyr Gly Lys Ser Arg Lys Asn Asp
            35                  40                  45
```

-continued

```
Glu Asp Arg Asp Arg Tyr Ile Glu Ser Arg Leu Lys Ser Ser Gly Lys
 50                   55                  60

Leu Tyr Arg Ile Phe Asn Glu Asp Lys Asn Lys Arg Glu Thr Asp Glu
 65              70                  75                  80

Leu Gln Trp Phe Leu Ser Glu Ile Val Lys Lys Ile Asn Arg Arg Asn
                 85                  90                  95

Gly Leu Val Leu Ser Asp Met Leu Ser Val Asp Asp Arg Ala Phe Glu
            100                 105                 110

Lys Ala Phe Glu Lys Tyr Ala Glu Leu Ser Tyr Thr Asn Arg Arg Asn
            115                 120                 125

Lys Val Ser Gly Ser Pro Ala Phe Glu Thr Cys Gly Val Asp Ala Ala
            130                 135                 140

Thr Ala Glu Arg Leu Lys Gly Ile Ile Ser Glu Thr Asn Phe Ile Asn
145                 150                 155                 160

Arg Ile Lys Asn Asn Ile Asp Asn Lys Val Ser Glu Asp Ile Ile Asp
                165                 170                 175

Arg Ile Ile Ala Lys Tyr Leu Lys Lys Ser Leu Cys Arg Glu Arg Val
                180                 185                 190

Lys Arg Gly Leu Lys Lys Leu Leu Met Asn Ala Phe Asp Leu Pro Tyr
            195                 200                 205

Ser Asp Pro Asp Ile Asp Val Gln Arg Asp Phe Ile Asp Tyr Val Leu
210                 215                 220

Glu Asp Phe Tyr His Val Arg Ala Lys Ser Gln Val Ser Arg Ser Ile
225                 230                 235                 240

Lys Asn Met Asn Met Pro Val Gln Pro Glu Gly Asp Gly Lys Phe Ala
                245                 250                 255

Ile Thr Val Ser Lys Gly Gly Thr Glu Ser Gly Asn Lys Arg Ser Ala
            260                 265                 270

Glu Lys Glu Ala Phe Lys Lys Phe Leu Ser Asp Tyr Ala Ser Leu Asp
            275                 280                 285

Glu Arg Val Arg Asp Asp Met Leu Arg Arg Met Arg Arg Leu Val Val
290                 295                 300

Leu Tyr Phe Tyr Gly Ser Asp Ser Lys Leu Ser Asp Val Asn Glu
305                 310                 315                 320

Lys Phe Asp Val Trp Glu Asp His Ala Ala Arg Arg Val Asp Asn Arg
                325                 330                 335

Glu Phe Ile Lys Leu Pro Leu Glu Asn Lys Leu Ala Asn Gly Lys Thr
            340                 345                 350

Asp Lys Asp Ala Glu Arg Ile Arg Lys Asn Thr Val Lys Glu Leu Tyr
            355                 360                 365

Arg Asn Gln Asn Ile Gly Cys Tyr Arg Gln Ala Val Lys Ala Val Glu
370                 375                 380

Glu Asp Asn Asn Gly Arg Tyr Phe Asp Asp Lys Met Leu Asn Met Phe
385                 390                 395                 400

Phe Ile His Arg Ile Glu Tyr Gly Val Glu Lys Ile Tyr Ala Asn Leu
                405                 410                 415

Lys Gln Val Thr Glu Phe Lys Ala Arg Thr Gly Tyr Leu Ser Glu Lys
            420                 425                 430

Ile Trp Lys Asp Leu Ile Asn Tyr Ile Ser Ile Lys Tyr Ile Ala Met
            435                 440                 445

Gly Lys Ala Val Tyr Asn Tyr Ala Met Asp Glu Leu Asn Ala Ser Asp
450                 455                 460
```

```
Lys Lys Glu Ile Glu Leu Gly Lys Ile Ser Glu Tyr Leu Ser Gly
465                 470                 475                 480

Ile Ser Ser Phe Asp Tyr Glu Leu Ile Lys Ala Glu Glu Met Leu Gln
                485                 490                 495

Arg Glu Thr Ala Val Tyr Val Ala Phe Ala Ala Arg His Leu Ser Ser
            500                 505                 510

Gln Thr Val Glu Leu Asp Ser Glu Asn Ser Asp Phe Leu Leu Leu Lys
        515                 520                 525

Pro Lys Gly Thr Met Asp Lys Asn Asp Lys Asn Lys Leu Ala Ser Asn
    530                 535                 540

Asn Ile Leu Asn Phe Leu Lys Asp Lys Glu Thr Leu Arg Asp Thr Ile
545                 550                 555                 560

Leu Gln Tyr Phe Gly Gly His Ser Leu Trp Thr Asp Phe Pro Phe Asp
                565                 570                 575

Lys Tyr Leu Ala Gly Gly Lys Asp Asp Val Asp Phe Leu Thr Asp Leu
            580                 585                 590

Lys Asp Val Ile Tyr Ser Met Arg Asn Asp Ser Phe His Tyr Ala Thr
        595                 600                 605

Glu Asn His Asn Gly Lys Trp Asn Lys Glu Leu Ile Ser Ala Met
    610                 615                 620

Phe Glu His Glu Thr Glu Arg Met Thr Val Val Met Lys Asp Lys Phe
625                 630                 635                 640

Tyr Ser Asn Asn Leu Pro Met Phe Tyr Lys Asn Asp Asp Leu Lys Lys
                645                 650                 655

Leu Leu Ile Asp Leu Tyr Lys Asp Asn Val Glu Arg Ala Ser Gln Val
            660                 665                 670

Pro Ser Phe Asn Lys Val Phe Val Arg Lys Asn Phe Pro Ala Leu Val
        675                 680                 685

Arg Asp Lys Asp Asn Leu Gly Ile Glu Leu Asp Leu Lys Ala Asp Ala
690                 695                 700

Asp Lys Gly Glu Asn Glu Leu Lys Phe Tyr Asn Ala Leu Tyr Tyr Met
705                 710                 715                 720

Phe Lys Glu Ile Tyr Tyr Asn Ala Phe Leu Asn Asp Lys Asn Val Arg
                725                 730                 735

Glu Arg Phe Ile Thr Lys Ala Thr Lys Val Ala Asp Asn Tyr Asp Arg
            740                 745                 750

Asn Lys Glu Arg Asn Leu Lys Asp Arg Ile Lys Ser Ala Gly Ser Asp
        755                 760                 765

Glu Lys Lys Lys Leu Arg Glu Gln Leu Gln Asn Tyr Ile Ala Glu Asn
770                 775                 780

Asp Phe Gly Gln Arg Ile Lys Asn Ile Val Gln Val Asn Pro Asp Tyr
785                 790                 795                 800

Thr Leu Ala Gln Ile Cys Gln Leu Ile Met Thr Glu Tyr Asn Gln Gln
                805                 810                 815

Asn Asn Gly Cys Met Gln Lys Lys Ser Ala Ala Arg Lys Asp Ile Asn
            820                 825                 830

Lys Asp Ser Tyr Gln His Tyr Lys Met Leu Leu Leu Val Asn Leu Arg
        835                 840                 845

Lys Ala Phe Leu Glu Phe Ile Lys Glu Asn Tyr Ala Phe Val Leu Lys
850                 855                 860

Pro Tyr Lys His Asp Leu Cys Asp Lys Ala Asp Phe Val Pro Asp Phe
865                 870                 875                 880
```

-continued

Ala Lys Tyr Val Lys Pro Tyr Ala Gly Leu Ile Ser Arg Val Ala Gly
            885                 890                 895

Ser Ser Glu Leu Gln Lys Trp Tyr Ile Val Ser Arg Phe Leu Ser Pro
        900                 905                 910

Ala Gln Ala Asn His Met Leu Gly Phe Leu His Ser Tyr Lys Gln Tyr
        915                 920                 925

Val Trp Asp Ile Tyr Arg Arg Ala Ser Glu Thr Gly Thr Glu Ile Asn
    930                 935                 940

His Ser Ile Ala Glu Asp Lys Ile Ala Gly Val Asp Ile Thr Asp Val
945                 950                 955                 960

Asp Ala Val Ile Asp Leu Ser Val Lys Leu Cys Gly Thr Ile Ser Ser
                965                 970                 975

Glu Ile Ser Asp Tyr Phe Lys Asp Asp Glu Val Tyr Ala Glu Tyr Ile
            980                 985                 990

Ser Ser Tyr Leu Asp Phe Glu Tyr Asp Gly Gly Asn Tyr Lys Asp Ser
        995                 1000                1005

Leu Asn Arg Phe Cys Asn Ser Asp Ala Val Asn Asp Gln Lys Val
    1010                1015                1020

Ala Leu Tyr Tyr Asp Gly Glu His Pro Lys Leu Asn Arg Asn Ile
    1025                1030                1035

Ile Leu Ser Lys Leu Tyr Gly Glu Arg Arg Phe Leu Glu Lys Ile
    1040                1045                1050

Thr Asp Arg Val Ser Arg Ser Asp Ile Val Glu Tyr Tyr Lys Leu
    1055                1060                1065

Lys Lys Glu Thr Ser Gln Tyr Gln Thr Lys Gly Ile Phe Asp Ser
    1070                1075                1080

Glu Asp Glu Gln Lys Asn Ile Lys Lys Phe Gln Glu Met Lys Asn
    1085                1090                1095

Ile Val Glu Phe Arg Asp Leu Met Asp Tyr Ser Glu Ile Ala Asp
    1100                1105                1110

Glu Leu Gln Gly Gln Leu Ile Asn Trp Ile Tyr Leu Arg Glu Arg
    1115                1120                1125

Asp Leu Met Asn Phe Gln Leu Gly Tyr His Tyr Ala Cys Leu Asn
    1130                1135                1140

Asn Asp Ser Asn Lys Gln Ala Thr Tyr Val Thr Leu Asp Tyr Gln
    1145                1150                1155

Gly Lys Lys Asn Arg Lys Ile Asn Gly Ala Ile Leu Tyr Gln Ile
    1160                1165                1170

Cys Ala Met Tyr Ile Asn Gly Leu Pro Leu Tyr Tyr Val Asp Lys
    1175                1180                1185

Asp Ser Ser Glu Trp Thr Val Ser Asp Gly Lys Glu Ser Thr Gly
    1190                1195                1200

Ala Lys Ile Gly Glu Phe Tyr Arg Tyr Ala Lys Ser Phe Glu Asn
    1205                1210                1215

Thr Ser Asp Cys Tyr Ala Ser Gly Leu Glu Ile Phe Glu Asn Ile
    1220                1225                1230

Ser Glu His Asp Asn Ile Thr Glu Leu Arg Asn Tyr Ile Glu His
    1235                1240                1245

Phe Arg Tyr Tyr Ser Ser Phe Asp Arg Ser Phe Leu Gly Ile Tyr
    1250                1255                1260

Ser Glu Val Phe Asp Arg Phe Phe Thr Tyr Asp Leu Lys Tyr Arg
    1265                1270                1275

-continued

```
Lys Asn Val Pro Thr Ile Leu Tyr Asn Ile Leu Leu Gln His Phe
    1280            1285                1290

Val Asn Val Arg Phe Glu Phe Val Ser Gly Lys Lys Met Ile Gly
    1295            1300                1305

Ile Asp Lys Lys Asp Arg Lys Ile Ala Lys Glu Lys Glu Cys Ala
    1310            1315                1320

Arg Ile Thr Ile Arg Glu Lys Asn Gly Val Tyr Ser Glu Gln Phe
    1325            1330                1335

Thr Tyr Lys Leu Lys Asn Gly Thr Val Tyr Val Asp Ala Arg Asp
    1340            1345                1350

Lys Arg Tyr Leu Gln Ser Ile Ile Arg Leu Leu Phe Tyr Pro Glu
    1355            1360                1365

Lys Val Asn Met Asp Glu Met Ile Glu Val Lys Glu Lys Lys Lys
    1370            1375                1380

Pro Ser Asp Asn Asn Thr Gly Lys Gly Tyr Ser Lys Arg Asp Arg
    1385            1390                1395

Gln Gln Asp Arg Lys Glu Tyr Asp Lys Tyr Lys Glu Lys Lys Lys
    1400            1405                1410

Lys Glu Gly Asn Phe Leu Ser Gly Met Gly Gly Asn Ile Asn Trp
    1415            1420                1425

Asp Glu Ile Asn Ala Gln Leu Lys Asn
    1430            1435

<210> SEQ ID NO 329
<211> LENGTH: 1385
<212> TYPE: PRT
<213> ORGANISM: Clostridium aminophilum

<400> SEQUENCE: 329

Met Lys Phe Ser Lys Val Asp His Thr Arg Ser Ala Val Gly Ile Gln
1               5                   10                  15

Lys Ala Thr Asp Ser Val His Gly Met Leu Tyr Thr Asp Pro Lys Lys
            20                  25                  30

Gln Glu Val Asn Asp Leu Asp Lys Arg Phe Asp Gln Leu Asn Val Lys
        35                  40                  45

Ala Lys Arg Leu Tyr Asn Val Phe Asn Gln Ser Lys Ala Glu Glu Asp
    50                  55                  60

Asp Asp Glu Lys Arg Phe Gly Lys Val Val Lys Lys Leu Asn Arg Glu
65                  70                  75                  80

Leu Lys Asp Leu Leu Phe His Arg Glu Val Ser Arg Tyr Asn Ser Ile
                85                  90                  95

Gly Asn Ala Lys Tyr Asn Tyr Tyr Gly Ile Lys Ser Asn Pro Glu Glu
            100                 105                 110

Ile Val Ser Asn Leu Gly Met Val Glu Ser Leu Lys Gly Glu Arg Asp
        115                 120                 125

Pro Gln Lys Val Ile Ser Lys Leu Leu Leu Tyr Tyr Leu Arg Lys Gly
    130                 135                 140

Leu Lys Pro Gly Thr Asp Gly Leu Arg Met Ile Leu Glu Ala Ser Cys
145                 150                 155                 160

Gly Leu Arg Lys Leu Ser Gly Asp Glu Lys Glu Leu Lys Val Phe Leu
                165                 170                 175

Gln Thr Leu Asp Glu Asp Phe Glu Lys Lys Thr Phe Lys Lys Asn Leu
            180                 185                 190

Ile Arg Ser Ile Glu Asn Gln Asn Met Ala Val Gln Pro Ser Asn Glu
        195                 200                 205
```

-continued

Gly Asp Pro Ile Ile Gly Ile Thr Gln Gly Arg Phe Asn Ser Gln Lys
210                 215                 220

Asn Glu Glu Lys Ser Ala Ile Glu Arg Met Met Ser Met Tyr Ala Asp
225                 230                 235                 240

Leu Asn Glu Asp His Arg Glu Asp Val Leu Arg Lys Leu Arg Arg Leu
                245                 250                 255

Asn Val Leu Tyr Phe Asn Val Asp Thr Glu Lys Thr Glu Pro Thr
                260                 265                 270

Leu Pro Gly Glu Val Asp Thr Asn Pro Val Phe Glu Val Trp His Asp
            275                 280                 285

His Glu Lys Gly Lys Glu Asn Asp Arg Gln Phe Ala Thr Phe Ala Lys
290                 295                 300

Ile Leu Thr Glu Asp Arg Glu Thr Arg Lys Lys Glu Lys Leu Ala Val
305                 310                 315                 320

Lys Glu Ala Leu Asn Asp Leu Lys Ser Ala Ile Arg Asp His Asn Ile
                325                 330                 335

Met Ala Tyr Arg Cys Ser Ile Lys Val Thr Glu Gln Asp Lys Asp Gly
                340                 345                 350

Leu Phe Phe Glu Asp Gln Arg Ile Asn Arg Phe Trp Ile His His Ile
            355                 360                 365

Glu Ser Ala Val Glu Arg Ile Leu Ala Ser Ile Asn Pro Glu Lys Leu
370                 375                 380

Tyr Lys Leu Arg Ile Gly Tyr Leu Gly Glu Lys Val Trp Lys Asp Leu
385                 390                 395                 400

Leu Asn Tyr Leu Ser Ile Lys Tyr Ile Ala Val Gly Lys Ala Val Phe
                405                 410                 415

His Phe Ala Met Glu Asp Leu Gly Lys Thr Gly Gln Asp Ile Glu Leu
            420                 425                 430

Gly Lys Leu Ser Asn Ser Val Ser Gly Gly Leu Thr Ser Phe Asp Tyr
            435                 440                 445

Glu Gln Ile Arg Ala Asp Glu Thr Leu Gln Arg Gln Leu Ser Val Glu
450                 455                 460

Val Ala Phe Ala Ala Asn Asn Leu Phe Arg Ala Val Val Gly Gln Thr
465                 470                 475                 480

Gly Lys Lys Ile Glu Gln Ser Lys Ser Glu Glu Asn Glu Glu Asp Phe
                485                 490                 495

Leu Leu Trp Lys Ala Glu Lys Ile Ala Glu Ser Ile Lys Lys Glu Gly
            500                 505                 510

Glu Gly Asn Thr Leu Lys Ser Ile Leu Gln Phe Gly Gly Ala Ser
            515                 520                 525

Ser Trp Asp Leu Asn His Phe Cys Ala Ala Tyr Gly Asn Glu Ser Ser
530                 535                 540

Ala Leu Gly Tyr Glu Thr Lys Phe Ala Asp Asp Leu Arg Lys Ala Ile
545                 550                 555                 560

Tyr Ser Leu Arg Asn Glu Thr Phe His Phe Thr Thr Leu Asn Lys Gly
                565                 570                 575

Ser Phe Asp Trp Asn Ala Lys Leu Ile Gly Asp Met Phe Ser His Glu
            580                 585                 590

Ala Ala Thr Gly Ile Ala Val Glu Arg Thr Arg Phe Tyr Ser Asn Asn
            595                 600                 605

Leu Pro Met Phe Tyr Arg Glu Ser Asp Leu Lys Arg Ile Met Asp His
610                 615                 620

```
Leu Tyr Asn Thr Tyr His Pro Arg Ala Ser Gln Val Pro Ser Phe Asn
625                 630                 635                 640

Ser Val Phe Val Arg Lys Asn Phe Arg Leu Phe Leu Ser Asn Thr Leu
                645                 650                 655

Asn Thr Asn Thr Ser Phe Asp Thr Glu Val Tyr Gln Lys Trp Glu Ser
            660                 665                 670

Gly Val Tyr Tyr Leu Phe Lys Glu Ile Tyr Tyr Asn Ser Phe Leu Pro
        675                 680                 685

Ser Gly Asp Ala His His Leu Phe Phe Glu Gly Leu Arg Arg Ile Arg
    690                 695                 700

Lys Glu Ala Asp Asn Leu Pro Ile Val Gly Lys Glu Ala Lys Lys Arg
705                 710                 715                 720

Asn Ala Val Gln Asp Phe Gly Arg Arg Cys Asp Glu Leu Lys Asn Leu
                725                 730                 735

Ser Leu Ser Ala Ile Cys Gln Met Ile Met Thr Glu Tyr Asn Glu Gln
            740                 745                 750

Asn Asn Gly Asn Arg Lys Val Lys Ser Thr Arg Glu Asp Lys Arg Lys
        755                 760                 765

Pro Asp Ile Phe Gln His Tyr Lys Met Leu Leu Leu Arg Thr Leu Gln
770                 775                 780

Glu Ala Phe Ala Ile Tyr Ile Arg Arg Glu Glu Phe Lys Phe Ile Phe
785                 790                 795                 800

Asp Leu Pro Lys Thr Leu Tyr Val Met Lys Pro Val Glu Glu Phe Leu
                805                 810                 815

Pro Asn Trp Lys Ser Gly Met Phe Asp Ser Leu Val Glu Arg Val Lys
            820                 825                 830

Gln Ser Pro Asp Leu Gln Arg Trp Tyr Val Leu Cys Lys Phe Leu Asn
        835                 840                 845

Gly Arg Leu Leu Asn Gln Leu Ser Gly Val Ile Arg Ser Tyr Ile Gln
850                 855                 860

Phe Ala Gly Asp Ile Gln Arg Arg Ala Lys Ala Asn His Asn Arg Leu
865                 870                 875                 880

Tyr Met Asp Asn Thr Gln Arg Val Glu Tyr Tyr Ser Asn Val Leu Glu
                885                 890                 895

Val Val Asp Phe Cys Ile Lys Gly Thr Ser Arg Phe Ser Asn Val Phe
            900                 905                 910

Ser Asp Tyr Phe Arg Asp Glu Asp Ala Tyr Ala Asp Tyr Leu Asp Asn
        915                 920                 925

Tyr Leu Gln Phe Lys Asp Glu Lys Ile Ala Glu Val Ser Ser Phe Ala
930                 935                 940

Ala Leu Lys Thr Phe Cys Asn Glu Glu Glu Val Lys Ala Gly Ile Tyr
945                 950                 955                 960

Met Asp Gly Glu Asn Pro Val Met Gln Arg Asn Ile Val Met Ala Lys
                965                 970                 975

Leu Phe Gly Pro Asp Glu Val Leu Lys Asn Val Val Pro Lys Val Thr
            980                 985                 990

Arg Glu Glu Ile Glu Glu Tyr Tyr  Gln Leu Glu Lys Gln  Ile Ala Pro
        995                 1000                 1005

Tyr Arg  Gln Asn Gly Tyr Cys  Lys Ser Glu Glu Asp  Gln Lys Lys
    1010                 1015                 1020

Leu Leu  Arg Phe Gln Arg Ile  Lys Asn Arg Val Glu  Phe Gln Thr
    1025                 1030                 1035
```

```
Ile Thr Glu Phe Ser Glu Ile Ile Asn Glu Leu Leu Gly Gln Leu
    1040                1045                1050

Ile Ser Trp Ser Phe Leu Arg Glu Arg Asp Leu Leu Tyr Phe Gln
    1055                1060                1065

Leu Gly Phe His Tyr Leu Cys Leu His Asn Asp Thr Glu Lys Pro
    1070                1075                1080

Ala Glu Tyr Lys Glu Ile Ser Arg Glu Asp Gly Thr Val Ile Arg
    1085                1090                1095

Asn Ala Ile Leu His Gln Val Ala Ala Met Tyr Val Gly Gly Leu
    1100                1105                1110

Pro Val Tyr Thr Leu Ala Asp Lys Lys Leu Ala Ala Phe Glu Lys
    1115                1120                1125

Gly Glu Ala Asp Cys Lys Leu Ser Ile Ser Lys Asp Thr Ala Gly
    1130                1135                1140

Ala Gly Lys Lys Ile Lys Asp Phe Phe Arg Tyr Ser Lys Tyr Val
    1145                1150                1155

Leu Ile Lys Asp Arg Met Leu Thr Asp Gln Asn Gln Lys Tyr Thr
    1160                1165                1170

Ile Tyr Leu Ala Gly Leu Glu Leu Phe Glu Asn Thr Asp Glu His
    1175                1180                1185

Asp Asn Ile Thr Asp Val Arg Lys Tyr Val Asp His Phe Lys Tyr
    1190                1195                1200

Tyr Ala Thr Ser Asp Glu Asn Ala Met Ser Ile Leu Asp Leu Tyr
    1205                1210                1215

Ser Glu Ile His Asp Arg Phe Phe Thr Tyr Asp Met Lys Tyr Gln
    1220                1225                1230

Lys Asn Val Ala Asn Met Leu Glu Asn Ile Leu Leu Arg His Phe
    1235                1240                1245

Val Leu Ile Arg Pro Glu Phe Phe Thr Gly Ser Lys Lys Val Gly
    1250                1255                1260

Glu Gly Lys Lys Ile Thr Cys Lys Ala Arg Ala Gln Ile Glu Ile
    1265                1270                1275

Ala Glu Asn Gly Met Arg Ser Glu Asp Phe Thr Tyr Lys Leu Ser
    1280                1285                1290

Asp Gly Lys Lys Asn Ile Ser Thr Cys Met Ile Ala Ala Arg Asp
    1295                1300                1305

Gln Lys Tyr Leu Asn Thr Val Ala Arg Leu Leu Tyr Tyr Pro His
    1310                1315                1320

Glu Ala Lys Lys Ser Ile Val Asp Thr Arg Glu Lys Lys Asn Asn
    1325                1330                1335

Lys Lys Thr Asn Arg Gly Asp Gly Thr Phe Asn Lys Gln Lys Gly
    1340                1345                1350

Thr Ala Arg Lys Glu Lys Asp Asn Gly Pro Arg Glu Phe Asn Asp
    1355                1360                1365

Thr Gly Phe Ser Asn Thr Pro Phe Ala Gly Phe Asp Pro Phe Arg
    1370                1375                1380

Asn Ser
    1385

<210> SEQ ID NO 330
<211> LENGTH: 1334
<212> TYPE: PRT
<213> ORGANISM: S. pyrogenes
```

```
<400> SEQUENCE: 330

Met Lys Ile Ser Lys Val Asp His Thr Arg Met Ala Val Ala Lys Gly
1               5                   10                  15

Asn Gln His Arg Arg Asp Glu Ile Ser Gly Ile Leu Tyr Lys Asp Pro
            20                  25                  30

Thr Lys Thr Gly Ser Ile Asp Phe Asp Glu Arg Phe Lys Lys Leu Asn
        35                  40                  45

Cys Ser Ala Lys Ile Leu Tyr His Val Phe Asn Gly Ile Ala Glu Gly
    50                  55                  60

Ser Asn Lys Tyr Lys Asn Ile Val Asp Lys Val Asn Asn Leu Asp
65                  70                  75                  80

Arg Val Leu Phe Thr Gly Lys Ser Tyr Asp Arg Lys Ser Ile Ile Asp
                85                  90                  95

Ile Asp Thr Val Leu Arg Asn Val Glu Lys Ile Asn Ala Phe Asp Arg
            100                 105                 110

Ile Ser Thr Glu Glu Arg Glu Gln Ile Ile Asp Asp Leu Leu Glu Ile
        115                 120                 125

Gln Leu Arg Lys Gly Leu Arg Lys Gly Lys Ala Gly Leu Arg Glu Val
    130                 135                 140

Leu Leu Ile Gly Ala Gly Val Ile Val Arg Thr Asp Lys Lys Gln Glu
145                 150                 155                 160

Ile Ala Asp Phe Leu Glu Ile Leu Asp Glu Asp Phe Asn Lys Thr Asn
                165                 170                 175

Gln Ala Lys Asn Ile Lys Leu Ser Ile Glu Asn Gln Gly Leu Val Val
            180                 185                 190

Ser Pro Val Ser Arg Gly Glu Glu Arg Ile Phe Asp Val Ser Gly Ala
        195                 200                 205

Gln Lys Gly Lys Ser Ser Lys Ala Gln Glu Lys Glu Ala Leu Ser
    210                 215                 220

Ala Phe Leu Leu Asp Tyr Ala Asp Leu Asp Lys Asn Val Arg Phe Glu
225                 230                 235                 240

Tyr Leu Arg Lys Ile Arg Arg Leu Ile Asn Leu Tyr Phe Tyr Val Lys
                245                 250                 255

Asn Asp Asp Val Met Ser Leu Thr Glu Ile Pro Ala Glu Val Asn Leu
            260                 265                 270

Glu Lys Asp Phe Asp Ile Trp Arg Asp His Glu Gln Arg Lys Glu Glu
        275                 280                 285

Asn Gly Asp Phe Val Gly Cys Pro Asp Ile Leu Leu Ala Asp Arg Asp
    290                 295                 300

Val Lys Lys Ser Asn Ser Lys Gln Val Lys Ile Ala Glu Arg Gln Leu
305                 310                 315                 320

Arg Glu Ser Ile Arg Glu Lys Asn Ile Lys Arg Tyr Arg Phe Ser Ile
                325                 330                 335

Lys Thr Ile Glu Lys Asp Asp Gly Thr Tyr Phe Phe Ala Asn Lys Gln
            340                 345                 350

Ile Ser Val Phe Trp Ile His Arg Ile Glu Asn Ala Val Glu Arg Ile
        355                 360                 365

Leu Gly Ser Ile Asn Asp Lys Lys Leu Tyr Arg Leu Arg Leu Gly Tyr
    370                 375                 380

Leu Gly Glu Lys Val Trp Lys Asp Ile Leu Asn Phe Leu Ser Ile Lys
385                 390                 395                 400

Tyr Ile Ala Val Gly Lys Ala Val Phe Asn Phe Ala Met Asp Asp Leu
                405                 410                 415
```

```
Gln Glu Lys Asp Arg Asp Ile Glu Pro Gly Lys Ile Ser Glu Asn Ala
            420                 425                 430

Val Asn Gly Leu Thr Ser Phe Asp Tyr Glu Gln Ile Lys Ala Asp Glu
            435                 440                 445

Met Leu Gln Arg Glu Val Ala Val Asn Val Ala Phe Ala Ala Asn Asn
450                 455                 460

Leu Ala Arg Val Thr Val Asp Ile Pro Gln Asn Gly Glu Lys Glu Asp
465                 470                 475                 480

Ile Leu Leu Trp Asn Lys Ser Asp Ile Lys Lys Tyr Lys Lys Asn Ser
                485                 490                 495

Lys Lys Gly Ile Leu Lys Ser Ile Leu Gln Phe Phe Gly Gly Ala Ser
                500                 505                 510

Thr Trp Asn Met Lys Met Phe Glu Ile Ala Tyr His Asp Gln Pro Gly
                515                 520                 525

Asp Tyr Glu Glu Asn Tyr Leu Tyr Asp Ile Gln Ile Ile Tyr Ser
            530                 535                 540

Leu Arg Asn Lys Ser Phe His Phe Lys Thr Tyr Asp His Gly Asp Lys
545                 550                 555                 560

Asn Trp Asn Arg Glu Leu Ile Gly Lys Met Ile Glu His Asp Ala Glu
                565                 570                 575

Arg Val Ile Ser Val Glu Arg Glu Lys Phe His Ser Asn Asn Leu Pro
            580                 585                 590

Met Phe Tyr Lys Asp Ala Asp Leu Lys Lys Ile Leu Asp Leu Leu Tyr
            595                 600                 605

Ser Asp Tyr Ala Gly Arg Ala Ser Gln Val Pro Ala Phe Asn Thr Val
            610                 615                 620

Leu Val Arg Lys Asn Phe Pro Glu Phe Leu Arg Lys Asp Met Gly Tyr
625                 630                 635                 640

Lys Val His Phe Asn Asn Pro Glu Val Glu Asn Gln Trp His Ser Ala
                645                 650                 655

Val Tyr Tyr Leu Tyr Lys Glu Ile Tyr Tyr Asn Leu Phe Leu Arg Asp
                660                 665                 670

Lys Glu Val Lys Asn Leu Phe Tyr Thr Ser Leu Lys Asn Ile Arg Ser
                675                 680                 685

Glu Val Ser Asp Lys Lys Gln Lys Leu Ala Ser Asp Asp Phe Ala Ser
            690                 695                 700

Arg Cys Glu Glu Ile Glu Asp Arg Ser Leu Pro Glu Ile Cys Gln Ile
705                 710                 715                 720

Ile Met Thr Glu Tyr Asn Ala Gln Asn Phe Gly Asn Arg Lys Val Lys
                725                 730                 735

Ser Gln Arg Val Ile Glu Lys Asn Lys Asp Ile Phe Arg His Tyr Lys
            740                 745                 750

Met Leu Leu Ile Lys Thr Leu Ala Gly Ala Phe Ser Leu Tyr Leu Lys
            755                 760                 765

Gln Glu Arg Phe Ala Phe Ile Gly Lys Ala Thr Pro Ile Pro Tyr Glu
            770                 775                 780

Thr Thr Asp Val Lys Asn Phe Leu Pro Glu Trp Lys Ser Gly Met Tyr
785                 790                 795                 800

Ala Ser Phe Val Glu Glu Ile Lys Asn Asn Leu Asp Leu Gln Glu Trp
                805                 810                 815

Tyr Ile Val Gly Arg Phe Leu Asn Gly Arg Met Leu Asn Gln Leu Ala
                820                 825                 830
```

Gly Ser Leu Arg Ser Tyr Ile Gln Tyr Ala Glu Asp Ile Glu Arg Arg
835                 840                 845

Ala Ala Glu Asn Arg Asn Lys Leu Phe Ser Lys Pro Asp Glu Lys Ile
850                 855                 860

Glu Ala Cys Lys Lys Ala Val Arg Val Leu Asp Leu Cys Ile Lys Ile
865                 870                 875                 880

Ser Thr Arg Ile Ser Ala Glu Phe Thr Asp Tyr Phe Asp Ser Glu Asp
            885                 890                 895

Asp Tyr Ala Asp Tyr Leu Glu Lys Tyr Leu Lys Tyr Gln Asp Asp Ala
            900                 905                 910

Ile Lys Glu Leu Ser Gly Ser Ser Tyr Ala Ala Leu Asp His Phe Cys
            915                 920                 925

Asn Lys Asp Asp Leu Lys Phe Asp Ile Tyr Val Asn Ala Gly Gln Lys
930                 935                 940

Pro Ile Leu Gln Arg Asn Ile Val Met Ala Lys Leu Phe Gly Pro Asp
945                 950                 955                 960

Asn Ile Leu Ser Glu Val Met Glu Lys Val Thr Glu Ser Ala Ile Arg
            965                 970                 975

Glu Tyr Tyr Asp Tyr Leu Lys Lys Val Ser Gly Tyr Arg Val Arg Gly
            980                 985                 990

Lys Cys Ser Thr Glu Lys Glu Gln Glu Asp Leu Leu Lys Phe Gln Arg
            995                 1000                1005

Leu Lys Asn Ala Val Glu Phe Arg Asp Val Thr Glu Tyr Ala Glu
    1010                1015                1020

Val Ile Asn Glu Leu Leu Gly Gln Leu Ile Ser Trp Ser Tyr Leu
    1025                1030                1035

Arg Glu Arg Asp Leu Leu Tyr Phe Gln Leu Gly Phe His Tyr Met
    1040                1045                1050

Cys Leu Lys Asn Lys Ser Phe Lys Pro Ala Glu Tyr Val Asp Ile
    1055                1060                1065

Arg Arg Asn Asn Gly Thr Ile Ile His Asn Ala Ile Leu Tyr Gln
    1070                1075                1080

Ile Val Ser Met Tyr Ile Asn Gly Leu Asp Phe Tyr Ser Cys Asp
    1085                1090                1095

Lys Glu Gly Lys Thr Leu Lys Pro Ile Glu Thr Gly Lys Gly Val
    1100                1105                1110

Gly Ser Lys Ile Gly Gln Phe Ile Lys Tyr Ser Gln Tyr Leu Tyr
    1115                1120                1125

Asn Asp Pro Ser Tyr Lys Leu Glu Ile Tyr Asn Ala Gly Leu Glu
    1130                1135                1140

Val Phe Glu Asn Ile Asp Glu His Asp Asn Ile Thr Asp Leu Arg
    1145                1150                1155

Lys Tyr Val Asp His Phe Lys Tyr Tyr Ala Tyr Gly Asn Lys Met
    1160                1165                1170

Ser Leu Leu Asp Leu Tyr Ser Glu Phe Phe Asp Arg Phe Phe Thr
    1175                1180                1185

Tyr Asp Met Lys Tyr Gln Lys Asn Val Val Asn Val Leu Glu Asn
    1190                1195                1200

Ile Leu Leu Arg His Phe Val Ile Phe Tyr Pro Lys Phe Gly Ser
    1205                1210                1215

Gly Lys Lys Asp Val Gly Ile Arg Asp Cys Lys Lys Glu Arg Ala
    1220                1225                1230

Gln Ile Glu Ile Ser Glu Gln Ser Leu Thr Ser Glu Asp Phe Met
    1235                1240                1245

Phe Lys Leu Asp Asp Lys Ala Gly Glu Glu Ala Lys Lys Phe Pro
    1250                1255                1260

Ala Arg Asp Glu Arg Tyr Leu Gln Thr Ile Ala Lys Leu Leu Tyr
    1265                1270                1275

Tyr Pro Asn Glu Ile Glu Asp Met Asn Arg Phe Met Lys Lys Gly
    1280                1285                1290

Glu Thr Ile Asn Lys Lys Val Gln Phe Asn Arg Lys Lys Lys Ile
    1295                1300                1305

Thr Arg Lys Gln Lys Asn Asn Ser Ser Asn Glu Val Leu Ser Ser
    1310                1315                1320

Thr Met Gly Tyr Leu Phe Lys Asn Ile Lys Leu
    1325                1330

<210> SEQ ID NO 331
<211> LENGTH: 1175
<212> TYPE: PRT
<213> ORGANISM: Carnobacterium gallinarum

<400> SEQUENCE: 331

Met Arg Ile Thr Lys Val Lys Ile Lys Leu Asp Asn Lys Leu Tyr Gln
1               5                   10                  15

Val Thr Met Gln Lys Glu Glu Lys Tyr Gly Thr Leu Lys Leu Asn Glu
                20                  25                  30

Glu Ser Arg Lys Ser Thr Ala Glu Ile Leu Arg Leu Lys Lys Ala Ser
            35                  40                  45

Phe Asn Lys Ser Phe His Ser Lys Thr Ile Asn Ser Gln Lys Glu Asn
    50                  55                  60

Lys Asn Ala Thr Ile Lys Lys Asn Gly Asp Tyr Ile Ser Gln Ile Phe
65                  70                  75                  80

Glu Lys Leu Val Gly Val Asp Thr Asn Lys Asn Ile Arg Lys Pro Lys
                85                  90                  95

Met Ser Leu Thr Asp Leu Lys Asp Leu Pro Lys Lys Asp Leu Ala Leu
            100                 105                 110

Phe Ile Lys Arg Lys Phe Lys Asn Asp Asp Ile Val Glu Ile Lys Asn
    115                 120                 125

Leu Asp Leu Ile Ser Leu Phe Tyr Asn Ala Leu Gln Lys Val Pro Gly
    130                 135                 140

Glu His Phe Thr Asp Glu Ser Trp Ala Asp Phe Cys Gln Glu Met Met
145                 150                 155                 160

Pro Tyr Arg Glu Tyr Lys Asn Lys Phe Ile Glu Arg Lys Ile Ile Leu
                165                 170                 175

Leu Ala Asn Ser Ile Glu Gln Asn Lys Gly Phe Ser Ile Asn Pro Glu
            180                 185                 190

Thr Phe Ser Lys Arg Lys Arg Val Leu His Gln Trp Ala Ile Glu Val
    195                 200                 205

Gln Glu Arg Gly Asp Phe Ser Ile Leu Asp Glu Lys Leu Ser Lys Leu
    210                 215                 220

Ala Glu Ile Tyr Asn Phe Lys Lys Met Cys Lys Arg Val Gln Asp Glu
225                 230                 235                 240

Leu Asn Asp Leu Glu Lys Ser Met Lys Lys Gly Lys Asn Pro Glu Lys
                245                 250                 255

-continued

Glu Lys Glu Ala Tyr Lys Lys Gln Lys Asn Phe Lys Ile Lys Thr Ile
            260                 265                 270

Trp Lys Asp Tyr Pro Tyr Lys Thr His Ile Gly Leu Ile Glu Lys Ile
            275                 280                 285

Lys Glu Asn Glu Glu Leu Asn Gln Phe Asn Ile Glu Ile Gly Lys Tyr
            290                 295                 300

Phe Glu His Tyr Phe Pro Ile Lys Lys Glu Arg Cys Thr Glu Asp Glu
305                 310                 315                 320

Pro Tyr Tyr Leu Asn Ser Glu Thr Ile Ala Thr Thr Val Asn Tyr Gln
            325                 330                 335

Leu Lys Asn Ala Leu Ile Ser Tyr Leu Met Gln Ile Gly Lys Tyr Lys
            340                 345                 350

Gln Phe Gly Leu Glu Asn Gln Val Leu Asp Ser Lys Lys Leu Gln Glu
            355                 360                 365

Ile Gly Ile Tyr Glu Gly Phe Gln Thr Lys Phe Met Asp Ala Cys Val
            370                 375                 380

Phe Ala Thr Ser Ser Leu Lys Asn Ile Ile Glu Pro Met Arg Ser Gly
385                 390                 395                 400

Asp Ile Leu Gly Lys Arg Glu Phe Lys Glu Ala Ile Ala Thr Ser Ser
            405                 410                 415

Phe Val Asn Tyr His His Phe Phe Pro Tyr Phe Pro Phe Glu Leu Lys
            420                 425                 430

Gly Met Lys Asp Arg Glu Ser Glu Leu Ile Pro Phe Gly Glu Gln Thr
            435                 440                 445

Glu Ala Lys Gln Met Gln Asn Ile Trp Ala Leu Arg Gly Ser Val Gln
            450                 455                 460

Gln Ile Arg Asn Glu Ile Phe His Ser Phe Asp Lys Asn Gln Lys Phe
465                 470                 475                 480

Asn Leu Pro Gln Leu Asp Lys Ser Asn Phe Glu Phe Asp Ala Ser Glu
            485                 490                 495

Asn Ser Thr Gly Lys Ser Gln Ser Tyr Ile Glu Thr Asp Tyr Lys Phe
            500                 505                 510

Leu Phe Glu Ala Glu Lys Asn Gln Leu Glu Gln Phe Phe Ile Glu Arg
            515                 520                 525

Ile Lys Ser Ser Gly Ala Leu Glu Tyr Tyr Pro Leu Lys Ser Leu Glu
530                 535                 540

Lys Leu Phe Ala Lys Lys Glu Met Lys Phe Ser Leu Gly Ser Gln Val
545                 550                 555                 560

Val Ala Phe Ala Pro Ser Tyr Lys Lys Leu Val Lys Lys Gly His Ser
            565                 570                 575

Tyr Gln Thr Ala Thr Glu Gly Thr Ala Asn Tyr Leu Gly Leu Ser Tyr
            580                 585                 590

Tyr Asn Arg Tyr Glu Leu Lys Glu Glu Ser Phe Gln Ala Gln Tyr Tyr
            595                 600                 605

Leu Leu Lys Leu Ile Tyr Gln Tyr Val Phe Leu Pro Asn Phe Ser Gln
            610                 615                 620

Gly Asn Ser Pro Ala Phe Arg Glu Thr Val Lys Ala Ile Leu Arg Ile
625                 630                 635                 640

Asn Lys Asp Glu Ala Arg Lys Lys Met Lys Lys Asn Lys Lys Phe Leu
            645                 650                 655

Arg Lys Tyr Ala Phe Glu Gln Val Arg Glu Met Glu Phe Lys Glu Thr
            660                 665                 670

```
Pro Asp Gln Tyr Met Ser Tyr Leu Gln Ser Glu Met Arg Glu Glu Lys
        675                 680                 685

Val Arg Lys Ala Glu Lys Asn Asp Lys Gly Phe Glu Lys Asn Ile Thr
690                 695                 700

Met Asn Phe Glu Lys Leu Leu Met Gln Ile Phe Val Lys Gly Phe Asp
705                 710                 715                 720

Val Phe Leu Thr Thr Phe Ala Gly Lys Glu Leu Leu Ser Ser Glu
            725                 730                 735

Glu Lys Val Ile Lys Glu Thr Glu Ile Ser Leu Ser Lys Lys Ile Asn
        740                 745                 750

Glu Arg Glu Lys Thr Leu Lys Ala Ser Ile Gln Val Glu His Gln Leu
        755                 760                 765

Val Ala Thr Asn Ser Ala Ile Ser Tyr Trp Leu Phe Cys Lys Leu Leu
770                 775                 780

Asp Ser Arg His Leu Asn Glu Leu Arg Asn Glu Met Ile Lys Phe Lys
785                 790                 795                 800

Gln Ser Arg Ile Lys Phe Asn His Thr Gln His Ala Glu Leu Ile Gln
            805                 810                 815

Asn Leu Leu Pro Ile Val Glu Leu Thr Ile Leu Ser Asn Asp Tyr Asp
            820                 825                 830

Glu Lys Asn Asp Ser Gln Asn Val Asp Val Ser Ala Tyr Phe Glu Asp
            835                 840                 845

Lys Ser Leu Tyr Glu Thr Ala Pro Tyr Val Gln Thr Asp Asp Arg Thr
850                 855                 860

Arg Val Ser Phe Arg Pro Ile Leu Lys Leu Glu Lys Tyr His Thr Lys
865                 870                 875                 880

Ser Leu Ile Glu Ala Leu Leu Lys Asp Asn Pro Gln Phe Arg Val Ala
            885                 890                 895

Ala Thr Asp Ile Gln Glu Trp Met His Lys Arg Glu Glu Ile Gly Glu
            900                 905                 910

Leu Val Glu Lys Arg Lys Asn Leu His Thr Glu Trp Ala Glu Gly Gln
        915                 920                 925

Gln Thr Leu Gly Ala Glu Lys Arg Glu Glu Tyr Arg Asp Tyr Cys Lys
        930                 935                 940

Lys Ile Asp Arg Phe Asn Trp Lys Ala Asn Lys Val Thr Leu Thr Tyr
945                 950                 955                 960

Leu Ser Gln Leu His Tyr Leu Ile Thr Asp Leu Leu Gly Arg Met Val
            965                 970                 975

Gly Phe Ser Ala Leu Phe Glu Arg Asp Leu Val Tyr Phe Ser Arg Ser
            980                 985                 990

Phe Ser Glu Leu Gly Gly Glu Thr Tyr His Ile Ser Asp Tyr Lys Asn
        995                 1000                1005

Leu Ser Gly Val Leu Arg Leu Asn Ala Glu Val Lys Pro Ile Lys
        1010                1015                1020

Ile Lys Asn Ile Lys Val Ile Asp Asn Glu Glu Asn Pro Tyr Lys
        1025                1030                1035

Gly Asn Glu Pro Glu Val Lys Pro Phe Leu Asp Arg Leu His Ala
        1040                1045                1050

Tyr Leu Glu Asn Val Ile Gly Ile Lys Ala Val His Gly Lys Ile
        1055                1060                1065

Arg Asn Gln Thr Ala His Leu Ser Val Leu Gln Leu Glu Leu Ser
        1070                1075                1080
```

```
Met Ile Glu Ser Met Asn Asn Leu Arg Asp Leu Met Ala Tyr Asp
    1085                1090                1095

Arg Lys Leu Lys Asn Ala Val Thr Lys Ser Met Ile Lys Ile Leu
    1100                1105                1110

Asp Lys His Gly Met Ile Leu Lys Leu Lys Ile Asp Glu Asn His
    1115                1120                1125

Lys Asn Phe Glu Ile Glu Ser Leu Ile Pro Lys Glu Ile Ile His
    1130                1135                1140

Leu Lys Asp Lys Ala Ile Lys Thr Asn Gln Val Ser Glu Glu Tyr
    1145                1150                1155

Cys Gln Leu Val Leu Ala Leu Leu Thr Thr Asn Pro Gly Asn Gln
    1160                1165                1170

Leu Asn
    1175

<210> SEQ ID NO 332
<211> LENGTH: 1154
<212> TYPE: PRT
<213> ORGANISM: Paludibacter propionicigenes

<400> SEQUENCE: 332

Met Arg Val Ser Lys Val Lys Val Lys Asp Gly Gly Lys Asp Lys Met
1               5                   10                  15

Val Leu Val His Arg Lys Thr Thr Gly Ala Gln Leu Val Tyr Ser Gly
                20                  25                  30

Gln Pro Val Ser Asn Glu Thr Ser Asn Ile Leu Pro Glu Lys Lys Arg
            35                  40                  45

Gln Ser Phe Asp Leu Ser Thr Leu Asn Lys Thr Ile Ile Lys Phe Asp
        50                  55                  60

Thr Ala Lys Lys Gln Lys Leu Asn Val Asp Gln Tyr Lys Ile Val Glu
65                  70                  75                  80

Lys Ile Phe Lys Tyr Pro Lys Gln Glu Leu Pro Lys Gln Ile Lys Ala
                85                  90                  95

Glu Glu Ile Leu Pro Phe Leu Asn His Lys Phe Gln Glu Pro Val Lys
            100                 105                 110

Tyr Trp Lys Asn Gly Lys Glu Glu Ser Phe Asn Leu Thr Leu Leu Ile
        115                 120                 125

Val Glu Ala Val Gln Ala Gln Asp Lys Arg Lys Leu Gln Pro Tyr Tyr
    130                 135                 140

Asp Trp Lys Thr Trp Tyr Ile Gln Thr Lys Ser Asp Leu Leu Lys Lys
145                 150                 155                 160

Ser Ile Glu Asn Asn Arg Ile Asp Leu Thr Glu Asn Leu Ser Lys Arg
                165                 170                 175

Lys Lys Ala Leu Leu Ala Trp Glu Thr Glu Phe Thr Ala Ser Gly Ser
            180                 185                 190

Ile Asp Leu Thr His Tyr His Lys Val Tyr Met Thr Asp Val Leu Cys
        195                 200                 205

Lys Met Leu Gln Asp Val Lys Pro Leu Thr Asp Lys Gly Lys Ile
    210                 215                 220

Asn Thr Asn Ala Tyr His Arg Gly Leu Lys Lys Ala Leu Gln Asn His
225                 230                 235                 240

Gln Pro Ala Ile Phe Gly Thr Arg Glu Val Pro Asn Glu Ala Asn Arg
                245                 250                 255
```

```
Ala Asp Asn Gln Leu Ser Ile Tyr His Leu Glu Val Val Lys Tyr Leu
            260                 265                 270

Glu His Tyr Phe Pro Ile Lys Thr Ser Lys Arg Arg Asn Thr Ala Asp
            275                 280                 285

Asp Ile Ala His Tyr Leu Lys Ala Gln Thr Leu Lys Thr Thr Ile Glu
            290                 295                 300

Lys Gln Leu Val Asn Ala Ile Arg Ala Asn Ile Ile Gln Gln Gly Lys
305                 310                 315                 320

Thr Asn His His Glu Leu Lys Ala Asp Thr Thr Ser Asn Asp Leu Ile
            325                 330                 335

Arg Ile Lys Thr Asn Glu Ala Phe Val Leu Asn Leu Thr Gly Thr Cys
            340                 345                 350

Ala Phe Ala Ala Asn Asn Ile Arg Asn Met Val Asp Asn Glu Gln Thr
            355                 360                 365

Asn Asp Ile Leu Gly Lys Gly Asp Phe Ile Lys Ser Leu Leu Lys Asp
            370                 375                 380

Asn Thr Asn Ser Gln Leu Tyr Ser Phe Phe Gly Glu Gly Leu Ser
385                 390                 395                 400

Thr Asn Lys Ala Glu Lys Glu Thr Gln Leu Trp Gly Ile Arg Gly Ala
            405                 410                 415

Val Gln Gln Ile Arg Asn Asn Val Asn His Tyr Lys Lys Asp Ala Leu
            420                 425                 430

Lys Thr Val Phe Asn Ile Ser Asn Phe Glu Asn Pro Thr Ile Thr Asp
            435                 440                 445

Pro Lys Gln Gln Thr Asn Tyr Ala Asp Thr Ile Tyr Lys Ala Arg Phe
            450                 455                 460

Ile Asn Glu Leu Glu Lys Ile Pro Glu Ala Phe Ala Gln Gln Leu Lys
465                 470                 475                 480

Thr Gly Gly Ala Val Ser Tyr Tyr Thr Ile Glu Asn Leu Lys Ser Leu
            485                 490                 495

Leu Thr Thr Phe Gln Phe Ser Leu Cys Arg Ser Thr Ile Pro Phe Ala
            500                 505                 510

Pro Gly Phe Lys Lys Val Phe Asn Gly Gly Ile Asn Tyr Gln Asn Ala
            515                 520                 525

Lys Gln Asp Glu Ser Phe Tyr Glu Leu Met Leu Glu Gln Tyr Leu Arg
530                 535                 540

Lys Glu Asn Phe Ala Glu Glu Ser Tyr Asn Ala Arg Tyr Phe Met Leu
545                 550                 555                 560

Lys Leu Ile Tyr Asn Asn Leu Phe Leu Pro Gly Phe Thr Thr Asp Arg
            565                 570                 575

Lys Ala Phe Ala Asp Ser Val Gly Phe Val Gln Met Gln Asn Lys Lys
            580                 585                 590

Gln Ala Glu Lys Val Asn Pro Arg Lys Lys Glu Ala Tyr Ala Phe Glu
            595                 600                 605

Ala Val Arg Pro Met Thr Ala Ala Asp Ser Ile Ala Asp Tyr Met Ala
            610                 615                 620

Tyr Val Gln Ser Glu Leu Met Gln Glu Gln Asn Lys Lys Glu Glu Lys
625                 630                 635                 640

Val Ala Glu Glu Thr Arg Ile Asn Phe Glu Lys Phe Val Leu Gln Val
            645                 650                 655

Phe Ile Lys Gly Phe Asp Ser Phe Leu Arg Ala Lys Glu Phe Asp Phe
            660                 665                 670
```

-continued

Val Gln Met Pro Gln Pro Gln Leu Thr Ala Thr Ala Ser Asn Gln Gln
        675                 680                 685

Lys Ala Asp Lys Leu Asn Gln Leu Glu Ala Ser Ile Thr Ala Asp Cys
690                 695                 700

Lys Leu Thr Pro Gln Tyr Ala Lys Ala Asp Asp Ala Thr His Ile Ala
705                 710                 715                 720

Phe Tyr Val Phe Cys Lys Leu Leu Asp Ala Ala His Leu Ser Asn Leu
        725                 730                 735

Arg Asn Glu Leu Ile Lys Phe Arg Glu Ser Val Asn Glu Phe Lys Phe
        740                 745                 750

His His Leu Leu Glu Ile Ile Glu Ile Cys Leu Leu Ser Ala Asp Val
        755                 760                 765

Val Pro Thr Asp Tyr Arg Asp Leu Tyr Ser Ser Glu Ala Asp Cys Leu
770                 775                 780

Ala Arg Leu Arg Pro Phe Ile Glu Gln Gly Ala Asp Ile Thr Asn Trp
785                 790                 795                 800

Ser Asp Leu Phe Val Gln Ser Asp Lys His Ser Pro Val Ile His Ala
        805                 810                 815

Asn Ile Glu Leu Ser Val Lys Tyr Gly Thr Thr Lys Leu Leu Glu Gln
        820                 825                 830

Ile Ile Asn Lys Asp Thr Gln Phe Lys Thr Thr Glu Ala Asn Phe Thr
835                 840                 845

Ala Trp Asn Thr Ala Gln Lys Ser Ile Glu Gln Leu Ile Lys Gln Arg
        850                 855                 860

Glu Asp His His Glu Gln Trp Val Lys Ala Lys Asn Ala Asp Asp Lys
865                 870                 875                 880

Glu Lys Gln Glu Arg Lys Arg Glu Lys Ser Asn Phe Ala Gln Lys Phe
        885                 890                 895

Ile Glu Lys His Gly Asp Asp Tyr Leu Asp Ile Cys Asp Tyr Ile Asn
        900                 905                 910

Thr Tyr Asn Trp Leu Asp Asn Lys Met His Phe Val His Leu Asn Arg
        915                 920                 925

Leu His Gly Leu Thr Ile Glu Leu Leu Gly Arg Met Ala Gly Phe Val
        930                 935                 940

Ala Leu Phe Asp Arg Asp Phe Gln Phe Phe Asp Glu Gln Gln Ile Ala
945                 950                 955                 960

Asp Glu Phe Lys Leu His Gly Phe Val Asn Leu His Ser Ile Asp Lys
        965                 970                 975

Lys Leu Asn Glu Val Pro Thr Lys Lys Ile Lys Glu Ile Tyr Asp Ile
        980                 985                 990

Arg Asn Lys Ile Ile Gln Ile Asn Gly Asn Lys Ile Asn Glu Ser Val
        995                 1000                1005

Arg Ala Asn Leu Ile Gln Phe Ile Ser Ser Lys Arg Asn Tyr Tyr
   1010                1015                1020

Asn Asn Ala Phe Leu His Val Ser Asn Asp Glu Ile Lys Glu Lys
   1025                1030                1035

Gln Met Tyr Asp Ile Arg Asn His Ile Ala His Phe Asn Tyr Leu
   1040                1045                1050

Thr Lys Asp Ala Ala Asp Phe Ser Leu Ile Asp Leu Ile Asn Glu
   1055                1060                1065

Leu Arg Glu Leu Leu His Tyr Asp Arg Lys Leu Lys Asn Ala Val
   1070                1075                1080

```
Ser Lys Ala Phe Ile Asp Leu Phe Asp Lys His Gly Met Ile Leu
    1085                1090                1095

Lys Leu Lys Leu Asn Ala Asp His Lys Leu Lys Val Glu Ser Leu
    1100                1105                1110

Glu Pro Lys Lys Ile Tyr His Leu Gly Ser Ser Ala Lys Asp Lys
    1115                1120                1125

Pro Glu Tyr Gln Tyr Cys Thr Asn Gln Val Met Met Ala Tyr Cys
    1130                1135                1140

Asn Met Cys Arg Ser Leu Leu Glu Met Lys Lys
    1145                1150
```

<210> SEQ ID NO 333
<211> LENGTH: 1120
<212> TYPE: PRT
<213> ORGANISM: Listeria seeligeri

<400> SEQUENCE: 333

```
Met Trp Ile Ser Ile Lys Thr Leu Ile His His Leu Gly Val Leu Phe
1               5                   10                  15

Phe Cys Asp Tyr Met Tyr Asn Arg Arg Glu Lys Lys Ile Ile Glu Val
                20                  25                  30

Lys Thr Met Arg Ile Thr Lys Val Glu Val Asp Arg Lys Lys Val Leu
        35                  40                  45

Ile Ser Arg Asp Lys Asn Gly Gly Lys Leu Val Tyr Glu Asn Glu Met
    50                  55                  60

Gln Asp Asn Thr Glu Gln Ile Met His His Lys Lys Ser Ser Phe Tyr
65                  70                  75                  80

Lys Ser Val Val Asn Lys Thr Ile Cys Arg Pro Glu Gln Lys Gln Met
                85                  90                  95

Lys Lys Leu Val His Gly Leu Leu Gln Glu Asn Ser Gln Glu Lys Ile
            100                 105                 110

Lys Val Ser Asp Val Thr Lys Leu Asn Ile Ser Asn Phe Leu Asn His
        115                 120                 125

Arg Phe Lys Lys Ser Leu Tyr Tyr Phe Pro Glu Asn Ser Pro Asp Lys
    130                 135                 140

Ser Glu Glu Tyr Arg Ile Glu Ile Asn Leu Ser Gln Leu Leu Glu Asp
145                 150                 155                 160

Ser Leu Lys Lys Gln Gln Gly Thr Phe Ile Cys Trp Glu Ser Phe Ser
                165                 170                 175

Lys Asp Met Glu Leu Tyr Ile Asn Trp Ala Glu Asn Tyr Ile Ser Ser
            180                 185                 190

Lys Thr Lys Leu Ile Lys Lys Ser Ile Arg Asn Asn Arg Ile Gln Ser
        195                 200                 205

Thr Glu Ser Arg Ser Gly Gln Leu Met Asp Arg Tyr Met Lys Asp Ile
    210                 215                 220

Leu Asn Lys Asn Lys Pro Phe Asp Ile Gln Ser Val Ser Glu Lys Tyr
225                 230                 235                 240

Gln Leu Glu Lys Leu Thr Ser Ala Leu Lys Ala Thr Phe Lys Glu Ala
                245                 250                 255

Lys Lys Asn Asp Lys Glu Ile Asn Tyr Lys Leu Lys Ser Thr Leu Gln
            260                 265                 270

Asn His Glu Arg Gln Ile Ile Glu Glu Leu Lys Glu Asn Ser Glu Leu
        275                 280                 285
```

-continued

```
Asn Gln Phe Asn Ile Glu Ile Arg Lys His Leu Glu Thr Tyr Phe Pro
    290                 295                 300
Ile Lys Lys Thr Asn Arg Lys Val Gly Asp Ile Arg Asn Leu Glu Ile
305                 310                 315                 320
Gly Glu Ile Gln Lys Ile Val Asn His Arg Leu Lys Asn Lys Ile Val
                325                 330                 335
Gln Arg Ile Leu Gln Glu Gly Lys Leu Ala Ser Tyr Glu Ile Glu Ser
            340                 345                 350
Thr Val Asn Ser Asn Ser Leu Gln Lys Ile Lys Ile Glu Glu Ala Phe
        355                 360                 365
Ala Leu Lys Phe Ile Asn Ala Cys Leu Phe Ala Ser Asn Asn Leu Arg
370                 375                 380
Asn Met Val Tyr Pro Val Cys Lys Lys Asp Ile Leu Met Ile Gly Glu
385                 390                 395                 400
Phe Lys Asn Ser Phe Lys Glu Ile Lys His Lys Lys Phe Ile Arg Gln
                405                 410                 415
Trp Ser Gln Phe Phe Ser Gln Glu Ile Thr Val Asp Asp Ile Glu Leu
            420                 425                 430
Ala Ser Trp Gly Leu Arg Gly Ala Ile Ala Pro Ile Arg Asn Glu Ile
        435                 440                 445
Ile His Leu Lys Lys His Ser Trp Lys Lys Phe Phe Asn Asn Pro Thr
450                 455                 460
Phe Lys Val Lys Lys Ser Lys Ile Ile Asn Gly Lys Thr Lys Asp Val
465                 470                 475                 480
Thr Ser Glu Phe Leu Tyr Lys Glu Thr Leu Phe Lys Asp Tyr Phe Tyr
                485                 490                 495
Ser Glu Leu Asp Ser Val Pro Glu Leu Ile Ile Asn Lys Met Glu Ser
            500                 505                 510
Ser Lys Ile Leu Asp Tyr Tyr Ser Ser Asp Gln Leu Asn Gln Val Phe
        515                 520                 525
Thr Ile Pro Asn Phe Glu Leu Ser Leu Leu Thr Ser Ala Val Pro Phe
530                 535                 540
Ala Pro Ser Phe Lys Arg Val Tyr Leu Lys Gly Phe Asp Tyr Gln Asn
545                 550                 555                 560
Gln Asp Glu Ala Gln Pro Asp Tyr Asn Leu Lys Leu Asn Ile Tyr Asn
                565                 570                 575
Glu Lys Ala Phe Asn Ser Glu Ala Phe Gln Ala Gln Tyr Ser Leu Phe
            580                 585                 590
Lys Met Val Tyr Tyr Gln Val Phe Leu Pro Gln Phe Thr Thr Asn Asn
        595                 600                 605
Asp Leu Phe Lys Ser Ser Val Asp Phe Ile Leu Thr Leu Asn Lys Glu
610                 615                 620
Arg Lys Gly Tyr Ala Lys Ala Phe Gln Asp Ile Arg Lys Met Asn Lys
625                 630                 635                 640
Asp Glu Lys Pro Ser Glu Tyr Met Ser Tyr Ile Gln Ser Gln Leu Met
                645                 650                 655
Leu Tyr Gln Lys Lys Gln Glu Glu Lys Glu Lys Ile Asn His Phe Glu
            660                 665                 670
Lys Phe Ile Asn Gln Val Phe Ile Lys Gly Phe Asn Ser Phe Ile Glu
        675                 680                 685
Lys Asn Arg Leu Thr Tyr Ile Cys His Pro Thr Lys Asn Thr Val Pro
690                 695                 700
```

-continued

Glu Asn Asp Asn Ile Glu Ile Pro Phe His Thr Asp Met Asp Asp Ser
705                 710                 715                 720

Asn Ile Ala Phe Trp Leu Met Cys Lys Leu Leu Asp Ala Lys Gln Leu
            725                 730                 735

Ser Glu Leu Arg Asn Glu Met Ile Lys Phe Ser Cys Ser Leu Gln Ser
            740                 745                 750

Thr Glu Glu Ile Ser Thr Phe Thr Lys Ala Arg Glu Val Ile Gly Leu
            755                 760                 765

Ala Leu Leu Asn Gly Glu Lys Gly Cys Asn Asp Trp Lys Glu Leu Phe
770                 775                 780

Asp Asp Lys Glu Ala Trp Lys Lys Asn Met Ser Leu Tyr Val Ser Glu
785                 790                 795                 800

Glu Leu Leu Gln Ser Leu Pro Tyr Thr Gln Glu Asp Gly Gln Thr Pro
            805                 810                 815

Val Ile Asn Arg Ser Ile Asp Leu Val Lys Lys Tyr Gly Thr Glu Thr
            820                 825                 830

Ile Leu Glu Lys Leu Phe Ser Ser Asp Asp Tyr Lys Val Ser Ala
            835                 840                 845

Lys Asp Ile Ala Lys Leu His Glu Tyr Asp Val Thr Glu Lys Ile Ala
850                 855                 860

Gln Gln Glu Ser Leu His Lys Gln Trp Ile Glu Lys Pro Gly Leu Ala
865                 870                 875                 880

Arg Asp Ser Ala Trp Thr Lys Lys Tyr Gln Asn Val Ile Asn Asp Ile
                885                 890                 895

Ser Asn Tyr Gln Trp Ala Lys Thr Lys Val Glu Leu Thr Gln Val Arg
            900                 905                 910

His Leu His Gln Leu Thr Ile Asp Leu Leu Ser Arg Leu Ala Gly Tyr
            915                 920                 925

Met Ser Ile Ala Asp Arg Asp Phe Gln Phe Ser Ser Asn Tyr Ile Leu
930                 935                 940

Glu Arg Glu Asn Ser Glu Tyr Arg Val Thr Ser Trp Ile Leu Leu Ser
945                 950                 955                 960

Glu Asn Lys Asn Lys Asn Lys Tyr Asn Asp Tyr Glu Leu Tyr Asn Leu
            965                 970                 975

Lys Asn Ala Ser Ile Lys Val Ser Ser Lys Asn Asp Pro Gln Leu Lys
            980                 985                 990

Val Asp Leu Lys Gln Leu Arg Leu Thr Leu Glu Tyr Leu Glu Leu Phe
            995                 1000                1005

Asp Asn Arg Leu Lys Glu Lys Arg Asn Asn Ile Ser His Phe Asn
    1010                1015                1020

Tyr Leu Asn Gly Gln Leu Gly Asn Ser Ile Leu Glu Leu Phe Asp
    1025                1030                1035

Asp Ala Arg Asp Val Leu Ser Tyr Asp Arg Lys Leu Lys Asn Ala
    1040                1045                1050

Val Ser Lys Ser Leu Lys Glu Ile Leu Ser Ser His Gly Met Glu
    1055                1060                1065

Val Thr Phe Lys Pro Leu Tyr Gln Thr Asn His His Leu Lys Ile
    1070                1075                1080

Asp Lys Leu Gln Pro Lys Lys Ile His His Leu Gly Glu Lys Ser
    1085                1090                1095

Thr Val Ser Ser Asn Gln Val Ser Asn Glu Tyr Cys Gln Leu Val
    1100                1105                1110

Arg Thr Leu Leu Thr Met Lys
    1115            1120

<210> SEQ ID NO 334
<211> LENGTH: 1051
<212> TYPE: PRT
<213> ORGANISM: Listeria newyorkensis

<400> SEQUENCE: 334

Met Lys Ile Thr Lys Met Arg Val Asp Gly Arg Thr Ile Val Met Glu
1               5                   10                  15

Arg Thr Ser Lys Glu Gly Gln Leu Gly Tyr Glu Gly Ile Asp Gly Asn
            20                  25                  30

Lys Thr Thr Glu Ile Ile Phe Asp Lys Lys Glu Ser Phe Tyr Lys
        35                  40                  45

Ser Ile Leu Asn Lys Thr Val Arg Lys Pro Asp Glu Lys Glu Lys Asn
    50                  55                  60

Arg Arg Lys Gln Ala Ile Asn Lys Ala Ile Asn Lys Glu Ile Thr Glu
65                  70                  75                  80

Leu Met Leu Ala Val Leu His Gln Glu Val Pro Ser Gln Lys Leu His
                85                  90                  95

Asn Leu Lys Ser Leu Asn Thr Glu Ser Leu Thr Lys Leu Phe Lys Pro
            100                 105                 110

Lys Phe Gln Asn Met Ile Ser Tyr Pro Pro Ser Lys Gly Ala Glu His
        115                 120                 125

Val Gln Phe Cys Leu Thr Asp Ile Ala Val Pro Ala Ile Arg Asp Leu
130                 135                 140

Asp Glu Ile Lys Pro Asp Trp Gly Ile Phe Glu Lys Leu Lys Pro
145                 150                 155                 160

Tyr Thr Asp Trp Ala Glu Ser Tyr Ile His Tyr Lys Gln Thr Thr Ile
                165                 170                 175

Gln Lys Ser Ile Glu Gln Asn Lys Ile Gln Ser Pro Asp Ser Pro Arg
            180                 185                 190

Lys Leu Val Leu Gln Lys Tyr Val Thr Ala Phe Leu Asn Gly Glu Pro
        195                 200                 205

Leu Gly Leu Asp Leu Val Ala Lys Lys Tyr Lys Leu Ala Asp Leu Ala
210                 215                 220

Glu Ser Phe Lys Leu Val Asp Leu Asn Glu Asp Lys Ser Ala Asn Tyr
225                 230                 235                 240

Lys Ile Lys Ala Cys Leu Gln Gln His Gln Arg Asn Ile Leu Asp Glu
                245                 250                 255

Leu Lys Glu Asp Pro Glu Leu Asn Gln Tyr Gly Ile Glu Val Lys Lys
            260                 265                 270

Tyr Ile Gln Arg Tyr Phe Pro Ile Lys Arg Ala Pro Asn Arg Ser Lys
        275                 280                 285

His Ala Arg Ala Asp Phe Leu Lys Lys Glu Leu Ile Glu Ser Thr Val
    290                 295                 300

Glu Gln Gln Phe Lys Asn Ala Val Tyr His Tyr Val Leu Glu Gln Gly
305                 310                 315                 320

Lys Met Glu Ala Tyr Glu Leu Thr Asp Pro Lys Thr Lys Asp Leu Gln
                325                 330                 335

Asp Ile Arg Ser Gly Glu Ala Phe Ser Phe Lys Phe Ile Asn Ala Cys
            340                 345                 350

```
Ala Phe Ala Ser Asn Asn Leu Lys Met Ile Leu Asn Pro Glu Cys Glu
            355                 360                 365

Lys Asp Ile Leu Gly Lys Gly Asn Phe Lys Lys Asn Leu Pro Asn Ser
    370                 375                 380

Thr Thr Arg Ser Asp Val Val Lys Lys Met Ile Pro Phe Phe Ser Asp
385                 390                 395                 400

Glu Leu Gln Asn Val Asn Phe Asp Glu Ala Ile Trp Ala Ile Arg Gly
                405                 410                 415

Ser Ile Gln Gln Ile Arg Asn Glu Val Tyr His Cys Lys Lys His Ser
            420                 425                 430

Trp Lys Ser Ile Leu Lys Ile Lys Gly Phe Glu Phe Glu Pro Asn Asn
            435                 440                 445

Met Lys Tyr Ala Asp Ser Asp Met Gln Lys Leu Met Asp Lys Asp Ile
            450                 455                 460

Ala Lys Ile Pro Glu Phe Ile Glu Glu Lys Leu Lys Ser Ser Gly Val
465                 470                 475                 480

Val Arg Phe Tyr Arg His Asp Glu Leu Gln Ser Ile Trp Glu Met Lys
                485                 490                 495

Gln Gly Phe Ser Leu Leu Thr Thr Asn Ala Pro Phe Val Pro Ser Phe
            500                 505                 510

Lys Arg Val Tyr Ala Lys Gly His Asp Tyr Gln Thr Ser Lys Asn Arg
            515                 520                 525

Tyr Tyr Asn Leu Asp Leu Thr Thr Phe Asp Ile Leu Glu Tyr Gly Glu
    530                 535                 540

Glu Asp Phe Arg Ala Arg Tyr Phe Leu Thr Lys Leu Val Tyr Tyr Gln
545                 550                 555                 560

Gln Phe Met Pro Trp Phe Thr Ala Asp Asn Asn Ala Phe Arg Asp Ala
                565                 570                 575

Ala Asn Phe Val Leu Arg Leu Asn Lys Asn Arg Gln Gln Asp Ala Lys
            580                 585                 590

Ala Phe Ile Asn Ile Arg Glu Val Glu Glu Gly Glu Met Pro Arg Asp
            595                 600                 605

Tyr Met Gly Tyr Val Gln Gly Gln Ile Ala Ile His Glu Asp Ser Ile
    610                 615                 620

Glu Asp Thr Pro Asn His Phe Glu Lys Phe Ile Ser Gln Val Phe Ile
625                 630                 635                 640

Lys Gly Phe Asp Arg His Met Arg Ser Ala Asn Leu Lys Phe Ile Lys
                645                 650                 655

Asn Pro Arg Asn Gln Gly Leu Glu Gln Ser Glu Ile Glu Glu Met Ser
            660                 665                 670

Phe Asp Ile Lys Val Glu Pro Ser Phe Leu Lys Asn Lys Asp Asp Tyr
            675                 680                 685

Ile Ala Phe Trp Ile Phe Cys Lys Met Leu Asp Ala Arg His Leu Ser
    690                 695                 700

Glu Leu Arg Asn Glu Met Ile Lys Tyr Asp Gly His Leu Thr Gly Glu
705                 710                 715                 720

Gln Glu Ile Ile Gly Leu Ala Leu Leu Gly Val Asp Ser Arg Glu Asn
                725                 730                 735

Asp Trp Lys Gln Phe Phe Ser Ser Glu Arg Glu Tyr Glu Lys Ile Met
            740                 745                 750

Lys Gly Tyr Val Val Glu Glu Leu Tyr Gln Arg Glu Pro Tyr Arg Gln
            755                 760                 765
```

```
Ser Asp Gly Lys Thr Pro Ile Leu Phe Arg Gly Val Glu Gln Ala Arg
770                 775                 780

Lys Tyr Gly Thr Glu Thr Val Ile Gln Arg Leu Phe Asp Ala Asn Pro
785                 790                 795                 800

Glu Phe Lys Val Ser Lys Cys Asn Leu Ala Glu Trp Glu Arg Gln Lys
                805                 810                 815

Glu Thr Ile Glu Glu Thr Ile Lys Arg Arg Lys Glu Leu His Asn Glu
                820                 825                 830

Trp Ala Lys Asn Pro Lys Lys Pro Gln Asn Asn Ala Phe Phe Lys Glu
                835                 840                 845

Tyr Lys Glu Cys Cys Asp Ala Ile Asp Ala Tyr Asn Trp His Lys Asn
850                 855                 860

Lys Thr Thr Leu Ala Tyr Val Asn Glu Leu His His Leu Leu Ile Glu
865                 870                 875                 880

Ile Leu Gly Arg Tyr Val Gly Tyr Val Ala Ile Ala Asp Arg Asp Phe
                885                 890                 895

Gln Cys Met Ala Asn Gln Tyr Phe Lys His Ser Gly Ile Thr Glu Arg
                900                 905                 910

Val Glu Tyr Trp Gly Asp Asn Arg Leu Lys Ser Ile Lys Lys Leu Asp
                915                 920                 925

Thr Phe Leu Lys Lys Glu Gly Leu Phe Val Ser Glu Lys Asn Ala Arg
930                 935                 940

Asn His Ile Ala His Leu Asn Tyr Leu Ser Leu Lys Ser Glu Cys Thr
945                 950                 955                 960

Leu Leu Tyr Leu Ser Glu Arg Leu Arg Glu Ile Phe Lys Tyr Asp Arg
                965                 970                 975

Lys Leu Lys Asn Ala Val Ser Lys Ser Leu Ile Asp Ile Leu Asp Arg
                980                 985                 990

His Gly Met Ser Val Val Phe Ala  Asn Leu Lys Glu Asn  Lys His Arg
                995                 1000                1005

Leu Val  Ile Lys Ser Leu Glu  Pro Lys Lys Leu Arg  His Leu Gly
    1010                1015                1020

Gly Lys  Lys Ile Asp Gly Gly  Tyr Ile Glu Thr Asn  Gln Val Ser
    1025                1030                1035

Glu Glu  Tyr Cys Gly Ile Val  Lys Arg Leu Leu Glu  Met
    1040                1045                1050

<210> SEQ ID NO 335
<211> LENGTH: 1182
<212> TYPE: PRT
<213> ORGANISM: Leptotrichia wadei

<400> SEQUENCE: 335

Met Tyr Met Lys Ile Thr Lys Ile Asp Gly Val Ser His Tyr Lys Lys
1               5                   10                  15

Gln Asp Lys Gly Ile Leu Lys Lys Trp Lys Asp Leu Asp Glu Arg
            20                  25                  30

Lys Gln Arg Glu Lys Ile Glu Ala Arg Tyr Asn Lys Gln Ile Glu Ser
            35                  40                  45

Lys Ile Tyr Lys Glu Phe Phe Arg Leu Lys Asn Lys Arg Ile Glu
            50                  55                  60

Lys Glu Glu Asp Gln Asn Ile Lys Ser Leu Tyr Phe Phe Ile Lys Glu
65                  70                  75                  80

Leu Tyr Leu Asn Glu Lys Asn Glu Glu Trp Glu Leu Lys Asn Ile Asn
                85                  90                  95
```

```
Leu Glu Ile Leu Asp Asp Lys Glu Arg Val Ile Lys Gly Tyr Lys Phe
            100                 105                 110

Lys Glu Asp Val Tyr Phe Phe Lys Glu Gly Tyr Lys Glu Tyr Tyr Leu
            115                 120                 125

Arg Ile Leu Phe Asn Asn Leu Ile Glu Lys Val Gln Asn Glu Asn Arg
            130                 135                 140

Glu Lys Val Arg Lys Asn Lys Glu Phe Leu Asp Leu Lys Glu Ile Phe
145                 150                 155                 160

Lys Lys Tyr Lys Asn Arg Lys Ile Asp Leu Leu Lys Ser Ile Asn
                165                 170                 175

Asn Asn Lys Ile Asn Leu Glu Tyr Lys Lys Glu Asn Val Asn Glu Glu
            180                 185                 190

Ile Tyr Gly Ile Asn Pro Thr Asn Asp Arg Glu Met Thr Phe Tyr Glu
            195                 200                 205

Leu Leu Lys Glu Ile Ile Glu Lys Lys Asp Glu Gln Lys Ser Ile Leu
            210                 215                 220

Glu Glu Lys Leu Asp Asn Phe Asp Ile Thr Asn Phe Leu Glu Asn Ile
225                 230                 235                 240

Glu Lys Ile Phe Asn Glu Glu Thr Glu Ile Asn Ile Lys Gly Lys
            245                 250                 255

Val Leu Asn Glu Leu Arg Glu Tyr Ile Lys Glu Lys Glu Asn Asn
            260                 265                 270

Ser Asp Asn Lys Leu Lys Gln Ile Tyr Asn Leu Glu Leu Lys Lys Tyr
            275                 280                 285

Ile Glu Asn Asn Phe Ser Tyr Lys Lys Gln Lys Ser Lys Ser Lys Asn
            290                 295                 300

Gly Lys Asn Asp Tyr Leu Tyr Leu Asn Phe Leu Lys Lys Ile Met Phe
305                 310                 315                 320

Ile Glu Glu Val Asp Glu Lys Lys Glu Ile Asn Lys Glu Lys Phe Lys
            325                 330                 335

Asn Lys Ile Asn Ser Asn Phe Lys Asn Leu Phe Val Gln His Ile Leu
            340                 345                 350

Asp Tyr Gly Lys Leu Leu Tyr Tyr Lys Glu Asn Asp Gly Tyr Ile Lys
            355                 360                 365

Asn Thr Gly Gln Leu Glu Thr Lys Asp Leu Glu Tyr Ile Lys Thr Lys
            370                 375                 380

Glu Thr Leu Ile Arg Lys Met Ala Val Leu Val Ser Phe Ala Ala Asn
385                 390                 395                 400

Ser Tyr Tyr Asn Leu Phe Gly Arg Val Ser Gly Asp Ile Leu Gly Thr
                405                 410                 415

Glu Val Val Lys Ser Ser Lys Thr Asn Val Ile Lys Val Gly Ser His
            420                 425                 430

Ile Phe Lys Glu Lys Met Leu Asn Tyr Phe Phe Asp Phe Glu Ile Phe
            435                 440                 445

Asp Ala Asn Lys Ile Val Glu Ile Leu Glu Ser Ile Ser Tyr Ser Ile
            450                 455                 460

Tyr Asn Val Arg Asn Gly Val Gly His Phe Asn Lys Leu Ile Leu Gly
465                 470                 475                 480

Lys Tyr Lys Lys Asp Ile Asn Thr Asn Lys Arg Ile Glu Glu Asp
                485                 490                 495

Leu Asn Asn Asn Glu Glu Ile Lys Gly Tyr Phe Ile Lys Lys Arg Gly
            500                 505                 510
```

-continued

Glu Ile Glu Arg Lys Val Lys Glu Lys Phe Leu Ser Asn Asn Leu Gln
            515                 520                 525

Tyr Tyr Tyr Ser Lys Glu Lys Ile Glu Asn Tyr Phe Glu Val Tyr Glu
        530                 535                 540

Phe Glu Ile Leu Lys Arg Lys Ile Pro Phe Ala Pro Asn Phe Lys Arg
545                 550                 555                 560

Ile Ile Lys Lys Gly Glu Asp Leu Phe Asn Asn Lys Asn Asn Lys Lys
                565                 570                 575

Tyr Glu Tyr Phe Lys Asn Phe Asp Lys Asn Ser Ala Glu Glu Lys Lys
            580                 585                 590

Glu Phe Leu Lys Thr Arg Asn Phe Leu Leu Lys Glu Leu Tyr Tyr Asn
        595                 600                 605

Asn Phe Tyr Lys Glu Phe Leu Ser Lys Glu Glu Phe Glu Lys Ile
    610                 615                 620

Val Leu Glu Val Lys Glu Glu Lys Lys Ser Arg Gly Asn Ile Asn Asn
625                 630                 635                 640

Lys Lys Ser Gly Val Ser Phe Gln Ser Ile Asp Asp Tyr Asp Thr Lys
                645                 650                 655

Ile Asn Ile Ser Asp Tyr Ile Ala Ser Ile His Lys Lys Glu Met Glu
            660                 665                 670

Arg Val Glu Lys Tyr Asn Glu Lys Gln Lys Asp Thr Ala Lys Tyr
        675                 680                 685

Ile Arg Asp Phe Val Glu Glu Ile Phe Leu Thr Gly Phe Ile Asn Tyr
    690                 695                 700

Leu Glu Lys Asp Lys Arg Leu His Phe Leu Lys Glu Glu Phe Ser Ile
705                 710                 715                 720

Leu Cys Asn Asn Asn Asn Val Val Asp Phe Asn Ile Asn Ile Asn
                725                 730                 735

Glu Glu Lys Ile Lys Glu Phe Leu Lys Glu Asn Asp Ser Lys Thr Leu
            740                 745                 750

Asn Leu Tyr Leu Phe Phe Asn Met Ile Asp Ser Lys Arg Ile Ser Glu
        755                 760                 765

Phe Arg Asn Glu Leu Val Lys Tyr Lys Gln Phe Thr Lys Lys Arg Leu
    770                 775                 780

Asp Glu Glu Lys Glu Phe Leu Gly Ile Lys Ile Glu Leu Tyr Glu Thr
785                 790                 795                 800

Leu Ile Glu Phe Val Ile Leu Thr Arg Glu Lys Leu Asp Thr Lys Lys
                805                 810                 815

Ser Glu Glu Ile Asp Ala Trp Leu Val Asp Lys Leu Tyr Val Lys Asp
            820                 825                 830

Ser Asn Glu Tyr Lys Glu Tyr Glu Glu Ile Lys Leu Phe Val Asp
        835                 840                 845

Glu Lys Ile Leu Ser Ser Lys Glu Ala Pro Tyr Tyr Ala Thr Asp Asn
    850                 855                 860

Lys Thr Pro Ile Leu Leu Ser Asn Phe Glu Lys Thr Arg Lys Tyr Gly
865                 870                 875                 880

Thr Gln Ser Phe Leu Ser Glu Ile Gln Ser Asn Tyr Tyr Ser Lys
                885                 890                 895

Val Glu Lys Glu Asn Ile Glu Asp Tyr Asn Lys Lys Glu Glu Ile Glu
            900                 905                 910

Gln Lys Lys Lys Ser Asn Ile Glu Lys Leu Gln Asp Leu Lys Val Glu
        915                 920                 925

```
Leu His Lys Lys Trp Glu Gln Asn Lys Ile Thr Glu Lys Glu Ile Glu
            930                 935                 940

Lys Tyr Asn Asn Thr Thr Arg Lys Ile Asn Glu Tyr Asn Tyr Leu Lys
945                 950                 955                 960

Asn Lys Glu Glu Leu Gln Asn Val Tyr Leu His Glu Met Leu Ser
                965                 970                 975

Asp Leu Leu Ala Arg Asn Val Ala Phe Phe Asn Lys Trp Glu Arg Asp
            980                 985                 990

Phe Lys Phe Ile Val Ile Ala Ile Lys Gln Phe Leu Arg Glu Asn Asp
        995                 1000                1005

Lys Glu Lys Val Asn Glu Phe Leu Asn Pro Pro Asp Asn Ser Lys
    1010                1015                1020

Gly Lys Lys Val Tyr Phe Ser Val Ser Lys Tyr Lys Asn Thr Val
    1025                1030                1035

Glu Asn Ile Asp Gly Ile His Lys Asn Phe Met Asn Leu Ile Phe
    1040                1045                1050

Leu Asn Asn Lys Phe Met Asn Arg Lys Ile Asp Lys Met Asn Cys
    1055                1060                1065

Ala Ile Trp Val Tyr Phe Arg Asn Tyr Ile Ala His Phe Leu His
    1070                1075                1080

Leu His Thr Lys Asn Glu Lys Ile Ser Leu Ile Ser Gln Met Asn
    1085                1090                1095

Leu Leu Ile Lys Leu Phe Ser Tyr Asp Lys Lys Val Gln Asn His
    1100                1105                1110

Ile Leu Lys Ser Thr Lys Thr Leu Leu Glu Lys Tyr Asn Ile Gln
    1115                1120                1125

Ile Asn Phe Glu Ile Ser Asn Asp Lys Asn Glu Val Phe Lys Tyr
    1130                1135                1140

Lys Ile Lys Asn Arg Leu Tyr Ser Lys Lys Gly Lys Met Leu Gly
    1145                1150                1155

Lys Asn Asn Lys Phe Glu Ile Leu Glu Asn Glu Phe Leu Glu Asn
    1160                1165                1170

Val Lys Ala Met Leu Glu Tyr Ser Glu
    1175                1180

<210> SEQ ID NO 336
<211> LENGTH: 1285
<212> TYPE: PRT
<213> ORGANISM: Rhodobacter capsulatus

<400> SEQUENCE: 336

Met Gln Ile Gly Lys Val Gln Gly Arg Thr Ile Ser Glu Phe Gly Asp
1               5                   10                  15

Pro Ala Gly Gly Leu Lys Arg Lys Ile Ser Thr Asp Gly Lys Asn Arg
            20                  25                  30

Lys Glu Leu Pro Ala His Leu Ser Ser Asp Pro Lys Ala Leu Ile Gly
        35                  40                  45

Gln Trp Ile Ser Gly Ile Asp Lys Ile Tyr Arg Lys Pro Asp Ser Arg
    50                  55                  60

Lys Ser Asp Gly Lys Ala Ile His Ser Pro Thr Pro Ser Lys Met Gln
65                  70                  75                  80

Phe Asp Ala Arg Asp Asp Leu Gly Glu Ala Phe Trp Lys Leu Val Ser
                85                  90                  95
```

```
Glu Ala Gly Leu Ala Gln Asp Ser Asp Tyr Asp Gln Phe Lys Arg Arg
            100                 105                 110

Leu His Pro Tyr Gly Asp Lys Phe Gln Pro Ala Asp Ser Gly Ala Lys
            115                 120                 125

Leu Lys Phe Glu Ala Asp Pro Pro Glu Pro Gln Ala Phe His Gly Arg
130                 135                 140

Trp Tyr Gly Ala Met Ser Lys Arg Gly Asn Asp Ala Lys Glu Leu Ala
145                 150                 155                 160

Ala Ala Leu Tyr Glu His Leu His Val Asp Glu Lys Arg Ile Asp Gly
            165                 170                 175

Gln Pro Lys Arg Asn Pro Lys Thr Asp Lys Phe Ala Pro Gly Leu Val
            180                 185                 190

Val Ala Arg Ala Leu Gly Ile Glu Ser Ser Val Leu Pro Arg Gly Met
            195                 200                 205

Ala Arg Leu Ala Arg Asn Trp Gly Glu Glu Ile Gln Thr Tyr Phe
            210                 215                 220

Val Val Asp Val Ala Ala Ser Val Lys Glu Val Ala Lys Ala Val
225                 230                 235                 240

Ser Ala Ala Gln Ala Phe Asp Pro Pro Arg Gln Val Ser Gly Arg Ser
            245                 250                 255

Leu Ser Pro Lys Val Gly Phe Ala Leu Ala Glu His Leu Glu Arg Val
            260                 265                 270

Thr Gly Ser Lys Arg Cys Ser Phe Asp Pro Ala Ala Gly Pro Ser Val
            275                 280                 285

Leu Ala Leu His Asp Glu Val Lys Lys Thr Tyr Lys Arg Leu Cys Ala
            290                 295                 300

Arg Gly Lys Asn Ala Ala Arg Ala Phe Pro Ala Asp Lys Thr Glu Leu
305                 310                 315                 320

Leu Ala Leu Met Arg His Thr His Glu Asn Arg Val Arg Asn Gln Met
            325                 330                 335

Val Arg Met Gly Arg Val Ser Glu Tyr Arg Gly Gln Gln Ala Gly Asp
            340                 345                 350

Leu Ala Gln Ser His Tyr Trp Thr Ser Ala Gly Gln Thr Glu Ile Lys
            355                 360                 365

Glu Ser Glu Ile Phe Val Arg Leu Trp Val Gly Ala Phe Ala Leu Ala
370                 375                 380

Gly Arg Ser Met Lys Ala Trp Ile Asp Pro Met Gly Lys Ile Val Asn
385                 390                 395                 400

Thr Glu Lys Asn Asp Arg Asp Leu Thr Ala Ala Val Asn Ile Arg Gln
            405                 410                 415

Val Ile Ser Asn Lys Glu Met Val Ala Glu Ala Met Ala Arg Arg Gly
            420                 425                 430

Ile Tyr Phe Gly Glu Thr Pro Glu Leu Asp Arg Leu Gly Ala Glu Gly
            435                 440                 445

Asn Glu Gly Phe Val Phe Ala Leu Leu Arg Tyr Leu Arg Gly Cys Arg
            450                 455                 460

Asn Gln Thr Phe His Leu Gly Ala Arg Ala Gly Phe Leu Lys Glu Ile
465                 470                 475                 480

Arg Lys Glu Leu Glu Lys Thr Arg Trp Gly Lys Ala Lys Glu Ala Glu
            485                 490                 495

His Val Val Leu Thr Asp Lys Val Ala Ala Ile Arg Ala Ile Ile
            500                 505                 510
```

```
Asp Asn Asp Ala Lys Ala Leu Gly Ala Arg Leu Leu Ala Asp Leu Ser
            515                 520                 525

Gly Ala Phe Val Ala His Tyr Ala Ser Lys Glu His Phe Ser Thr Leu
        530                 535                 540

Tyr Ser Glu Ile Val Lys Ala Val Lys Asp Ala Pro Glu Val Ser Ser
545                 550                 555                 560

Gly Leu Pro Arg Leu Lys Leu Leu Lys Arg Ala Asp Gly Val Arg
                565                 570                 575

Gly Tyr Val His Gly Leu Arg Asp Thr Arg Lys His Ala Phe Ala Thr
            580                 585                 590

Lys Leu Pro Pro Pro Ala Pro Arg Glu Leu Asp Asp Pro Ala Thr
            595                 600                 605

Lys Ala Arg Tyr Ile Ala Leu Leu Arg Leu Tyr Asp Gly Pro Phe Arg
            610                 615                 620

Ala Tyr Ala Ser Gly Ile Thr Gly Thr Ala Leu Ala Gly Pro Ala Ala
625                 630                 635                 640

Arg Ala Lys Glu Ala Ala Thr Ala Leu Ala Gln Ser Val Asn Val Thr
                645                 650                 655

Lys Ala Tyr Ser Asp Val Met Glu Gly Arg Ser Ser Arg Leu Arg Pro
                660                 665                 670

Pro Asn Asp Gly Glu Thr Leu Arg Glu Tyr Leu Ser Ala Leu Thr Gly
            675                 680                 685

Glu Thr Ala Thr Glu Phe Arg Val Gln Ile Gly Tyr Glu Ser Asp Ser
            690                 695                 700

Glu Asn Ala Arg Lys Gln Ala Glu Phe Ile Glu Asn Tyr Arg Arg Asp
705                 710                 715                 720

Met Leu Ala Phe Met Phe Glu Asp Tyr Ile Arg Ala Lys Gly Phe Asp
                725                 730                 735

Trp Ile Leu Lys Ile Glu Pro Gly Ala Thr Ala Met Thr Arg Ala Pro
                740                 745                 750

Val Leu Pro Glu Pro Ile Asp Thr Arg Gly Gln Tyr Glu His Trp Gln
            755                 760                 765

Ala Ala Leu Tyr Leu Val Met His Phe Val Pro Ala Ser Asp Val Ser
            770                 775                 780

Asn Leu Leu His Gln Leu Arg Lys Trp Glu Ala Leu Gln Gly Lys Tyr
785                 790                 795                 800

Glu Leu Val Gln Asp Gly Asp Ala Thr Asp Gln Ala Asp Ala Arg Arg
                805                 810                 815

Glu Ala Leu Asp Leu Val Lys Arg Phe Arg Asp Val Leu Val Leu Phe
                820                 825                 830

Leu Lys Thr Gly Glu Ala Arg Phe Glu Gly Arg Ala Ala Pro Phe Asp
            835                 840                 845

Leu Lys Pro Phe Arg Ala Leu Phe Ala Asn Pro Ala Thr Phe Asp Arg
            850                 855                 860

Leu Phe Met Ala Thr Pro Thr Thr Ala Arg Pro Ala Glu Asp Pro
865                 870                 875                 880

Glu Gly Asp Gly Ala Ser Glu Pro Glu Leu Arg Val Ala Arg Thr Leu
                885                 890                 895

Arg Gly Leu Arg Gln Ile Ala Arg Tyr Asn His Met Ala Val Leu Ser
            900                 905                 910

Asp Leu Phe Ala Lys His Lys Val Arg Asp Glu Glu Val Ala Arg Leu
            915                 920                 925
```

```
Ala Glu Ile Glu Asp Glu Thr Gln Glu Lys Ser Gln Ile Val Ala Ala
    930                 935                 940

Gln Glu Leu Arg Thr Asp Leu His Asp Lys Val Met Lys Cys His Pro
945                 950                 955                 960

Lys Thr Ile Ser Pro Glu Glu Arg Gln Ser Tyr Ala Ala Ala Ile Lys
                965                 970                 975

Thr Ile Glu Glu His Arg Phe Leu Val Gly Arg Val Tyr Leu Gly Asp
            980                 985                 990

His Leu Arg Leu His Arg Leu Met Met Asp Val Ile Gly Arg Leu Ile
        995                 1000                1005

Asp Tyr Ala Gly Ala Tyr Glu Arg Asp Thr Gly Thr Phe Leu Ile
    1010                1015                1020

Asn Ala Ser Lys Gln Leu Gly Ala Gly Ala Asp Trp Ala Val Thr
    1025                1030                1035

Ile Ala Gly Ala Ala Asn Thr Asp Ala Arg Thr Gln Thr Arg Lys
    1040                1045                1050

Asp Leu Ala His Phe Asn Val Leu Asp Arg Ala Asp Gly Thr Pro
    1055                1060                1065

Asp Leu Thr Ala Leu Val Asn Arg Ala Arg Glu Met Met Ala Tyr
    1070                1075                1080

Asp Arg Lys Arg Lys Asn Ala Val Pro Arg Ser Ile Leu Asp Met
    1085                1090                1095

Leu Ala Arg Leu Gly Leu Thr Leu Lys Trp Gln Met Lys Asp His
    1100                1105                1110

Leu Leu Gln Asp Ala Thr Ile Thr Gln Ala Ala Ile Lys His Leu
    1115                1120                1125

Asp Lys Val Arg Leu Thr Val Gly Gly Pro Ala Ala Val Thr Glu
    1130                1135                1140

Ala Arg Phe Ser Gln Asp Tyr Leu Gln Met Val Ala Ala Val Phe
    1145                1150                1155

Asn Gly Ser Val Gln Asn Pro Lys Pro Arg Arg Arg Asp Asp Gly
    1160                1165                1170

Asp Ala Trp His Lys Pro Pro Lys Pro Ala Thr Ala Gln Ser Gln
    1175                1180                1185

Pro Asp Gln Lys Pro Pro Asn Lys Ala Pro Ser Ala Gly Ser Arg
    1190                1195                1200

Leu Pro Pro Pro Gln Val Gly Glu Val Tyr Glu Gly Val Val Val
    1205                1210                1215

Lys Val Ile Asp Thr Gly Ser Leu Gly Phe Leu Ala Val Glu Gly
    1220                1225                1230

Val Ala Gly Asn Ile Gly Leu His Ile Ser Arg Leu Arg Arg Ile
    1235                1240                1245

Arg Glu Asp Ala Ile Ile Val Gly Arg Arg Tyr Arg Phe Arg Val
    1250                1255                1260

Glu Ile Tyr Val Pro Pro Lys Ser Asn Thr Ser Lys Leu Asn Ala
    1265                1270                1275

Ala Asp Leu Val Arg Ile Asp
    1280                1285

<210> SEQ ID NO 337
<211> LENGTH: 1159
<212> TYPE: PRT
<213> ORGANISM: Leptotrichia buccalis
```

<400> SEQUENCE: 337

```
Met Lys Val Thr Lys Val Gly Gly Ile Ser His Lys Lys Tyr Thr Ser
1               5                   10                  15

Glu Gly Arg Leu Val Lys Ser Glu Ser Glu Glu Asn Arg Thr Asp Glu
            20                  25                  30

Arg Leu Ser Ala Leu Leu Asn Met Arg Leu Asp Met Tyr Ile Lys Asn
        35                  40                  45

Pro Ser Ser Thr Glu Thr Lys Glu Asn Gln Lys Arg Ile Gly Lys Leu
    50                  55                  60

Lys Lys Phe Phe Ser Asn Lys Met Val Tyr Leu Lys Asp Asn Thr Leu
65                  70                  75                  80

Ser Leu Lys Asn Gly Lys Lys Glu Asn Ile Asp Arg Glu Tyr Ser Glu
                85                  90                  95

Thr Asp Ile Leu Glu Ser Asp Val Arg Asp Lys Lys Asn Phe Ala Val
            100                 105                 110

Leu Lys Lys Ile Tyr Leu Asn Glu Asn Val Asn Ser Glu Glu Leu Glu
        115                 120                 125

Val Phe Arg Asn Asp Ile Lys Lys Leu Asn Lys Ile Asn Ser Leu
    130                 135                 140

Lys Tyr Ser Phe Glu Lys Asn Lys Ala Asn Tyr Gln Lys Ile Asn Glu
145                 150                 155                 160

Asn Asn Ile Glu Lys Val Glu Gly Lys Ser Lys Arg Asn Ile Ile Tyr
                165                 170                 175

Asp Tyr Tyr Arg Glu Ser Ala Lys Arg Asp Ala Tyr Val Ser Asn Val
            180                 185                 190

Lys Glu Ala Phe Asp Lys Leu Tyr Lys Glu Glu Asp Ile Ala Lys Leu
        195                 200                 205

Val Leu Glu Ile Glu Asn Leu Thr Lys Leu Glu Lys Tyr Lys Ile Arg
    210                 215                 220

Glu Phe Tyr His Glu Ile Ile Gly Arg Lys Asn Asp Lys Glu Asn Phe
225                 230                 235                 240

Ala Lys Ile Ile Tyr Glu Glu Ile Gln Asn Val Asn Asn Met Lys Glu
                245                 250                 255

Leu Ile Glu Lys Val Pro Asp Met Ser Glu Leu Lys Lys Ser Gln Val
            260                 265                 270

Phe Tyr Lys Tyr Leu Asp Lys Glu Glu Leu Asn Asp Lys Asn Ile
        275                 280                 285

Lys Tyr Ala Phe Cys His Phe Val Glu Ile Glu Met Ser Gln Leu Leu
290                 295                 300

Lys Asn Tyr Val Tyr Lys Arg Leu Ser Asn Ile Ser Asn Asp Lys Ile
305                 310                 315                 320

Lys Arg Ile Phe Glu Tyr Gln Asn Leu Lys Lys Leu Ile Glu Asn Lys
            325                 330                 335

Leu Leu Asn Lys Leu Asp Thr Tyr Val Arg Asn Cys Gly Lys Tyr Asn
        340                 345                 350

Tyr Tyr Leu Gln Asp Gly Glu Ile Ala Thr Ser Asp Phe Ile Ala Arg
    355                 360                 365

Asn Arg Gln Asn Glu Ala Phe Leu Arg Asn Ile Ile Gly Val Ser Ser
370                 375                 380

Val Ala Tyr Phe Ser Leu Arg Asn Ile Leu Glu Thr Glu Asn Glu Asn
385                 390                 395                 400

Asp Ile Thr Gly Arg Met Arg Gly Lys Thr Val Lys Asn Asn Lys Gly
            405                 410                 415
```

```
Glu Glu Lys Tyr Val Ser Gly Glu Val Asp Lys Ile Tyr Asn Glu Asn
            420             425             430

Lys Lys Asn Glu Val Lys Glu Asn Leu Lys Met Phe Tyr Ser Tyr Asp
            435             440             445

Phe Asn Met Asp Asn Lys Asn Glu Ile Glu Asp Phe Phe Ala Asn Ile
450             455             460

Asp Glu Ala Ile Ser Ser Ile Arg His Gly Ile Val His Phe Asn Leu
465             470             475             480

Glu Leu Glu Gly Lys Asp Ile Phe Ala Phe Lys Asn Ile Ala Pro Ser
            485             490             495

Glu Ile Ser Lys Lys Met Phe Gln Asn Glu Ile Asn Glu Lys Lys Leu
            500             505             510

Lys Leu Lys Ile Phe Arg Gln Leu Asn Ser Ala Asn Val Phe Arg Tyr
            515             520             525

Leu Glu Lys Tyr Lys Ile Leu Asn Tyr Leu Lys Arg Thr Arg Phe Glu
            530             535             540

Phe Val Asn Lys Asn Ile Pro Phe Val Pro Ser Phe Thr Lys Leu Tyr
545             550             555             560

Ser Arg Ile Asp Asp Leu Lys Asn Ser Leu Gly Ile Tyr Trp Lys Thr
            565             570             575

Pro Lys Thr Asn Asp Asp Asn Lys Thr Lys Glu Ile Ile Asp Ala Gln
            580             585             590

Ile Tyr Leu Leu Lys Asn Ile Tyr Tyr Gly Glu Phe Leu Asn Tyr Phe
            595             600             605

Met Ser Asn Asn Gly Asn Phe Phe Glu Ile Ser Lys Glu Ile Ile Glu
            610             615             620

Leu Asn Lys Asn Asp Lys Arg Asn Leu Lys Thr Gly Phe Tyr Lys Leu
625             630             635             640

Gln Lys Phe Glu Asp Ile Gln Glu Lys Ile Pro Lys Glu Tyr Leu Ala
            645             650             655

Asn Ile Gln Ser Leu Tyr Met Ile Asn Ala Gly Asn Gln Asp Glu Glu
            660             665             670

Glu Lys Asp Thr Tyr Ile Asp Phe Ile Gln Lys Ile Phe Leu Lys Gly
            675             680             685

Phe Met Thr Tyr Leu Ala Asn Asn Gly Arg Leu Ser Leu Ile Tyr Ile
            690             695             700

Gly Ser Asp Glu Glu Thr Asn Thr Ser Leu Ala Glu Lys Lys Gln Glu
705             710             715             720

Phe Asp Lys Phe Leu Lys Lys Tyr Glu Gln Asn Asn Asn Ile Lys Ile
            725             730             735

Pro Tyr Glu Ile Asn Glu Phe Leu Arg Glu Ile Lys Leu Gly Asn Ile
            740             745             750

Leu Lys Tyr Thr Glu Arg Leu Asn Met Phe Tyr Leu Ile Leu Lys Leu
            755             760             765

Leu Asn His Lys Glu Leu Thr Asn Leu Lys Gly Ser Leu Glu Lys Tyr
            770             775             780

Gln Ser Ala Asn Lys Glu Glu Ala Phe Ser Asp Gln Leu Glu Leu Ile
785             790             795             800

Asn Leu Leu Asn Leu Asp Asn Asn Arg Val Thr Glu Asp Phe Glu Leu
            805             810             815

Glu Ala Asp Glu Ile Gly Lys Phe Leu Asp Phe Asn Gly Asn Lys Val
            820             825             830
```

Lys Asp Asn Lys Glu Leu Lys Lys Phe Asp Thr Asn Lys Ile Tyr Phe
            835                 840                 845

Asp Gly Glu Asn Ile Ile Lys His Arg Ala Phe Tyr Asn Ile Lys Lys
        850                 855                 860

Tyr Gly Met Leu Asn Leu Leu Glu Lys Ile Ala Asp Lys Ala Gly Tyr
865                 870                 875                 880

Lys Ile Ser Ile Glu Glu Leu Lys Lys Tyr Ser Asn Lys Lys Asn Glu
                885                 890                 895

Ile Glu Lys Asn His Lys Met Gln Glu Asn Leu His Arg Lys Tyr Ala
            900                 905                 910

Arg Pro Arg Lys Asp Glu Lys Phe Thr Asp Glu Asp Tyr Glu Ser Tyr
        915                 920                 925

Lys Gln Ala Ile Glu Asn Ile Glu Glu Tyr Thr His Leu Lys Asn Lys
        930                 935                 940

Val Glu Phe Asn Glu Leu Asn Leu Leu Gln Gly Leu Leu Leu Arg Ile
945                 950                 955                 960

Leu His Arg Leu Val Gly Tyr Thr Ser Ile Trp Glu Arg Asp Leu Arg
                965                 970                 975

Phe Arg Leu Lys Gly Glu Phe Pro Glu Asn Gln Tyr Ile Glu Glu Ile
            980                 985                 990

Phe Asn Phe Glu Asn Lys Lys Asn Val Lys Tyr Lys Gly Gly Gln Ile
        995                 1000                1005

Val Glu Lys Tyr Ile Lys Phe Tyr Lys Glu Leu His Gln Asn Asp
        1010                1015                1020

Glu Val Lys Ile Asn Lys Tyr Ser Ser Ala Asn Ile Lys Val Leu
        1025                1030                1035

Lys Gln Glu Lys Lys Asp Leu Tyr Ile Arg Asn Tyr Ile Ala His
        1040                1045                1050

Phe Asn Tyr Ile Pro His Ala Glu Ile Ser Leu Leu Glu Val Leu
        1055                1060                1065

Glu Asn Leu Arg Lys Leu Leu Ser Tyr Asp Arg Lys Leu Lys Asn
        1070                1075                1080

Ala Val Met Lys Ser Val Val Asp Ile Leu Lys Glu Tyr Gly Phe
        1085                1090                1095

Val Ala Thr Phe Lys Ile Gly Ala Asp Lys Lys Ile Gly Ile Gln
        1100                1105                1110

Thr Leu Glu Ser Glu Lys Ile Val His Leu Lys Asn Leu Lys Lys
        1115                1120                1125

Lys Lys Leu Met Thr Asp Arg Asn Ser Glu Glu Leu Cys Lys Leu
        1130                1135                1140

Val Lys Ile Met Phe Glu Tyr Lys Met Glu Glu Lys Lys Ser Glu
        1145                1150                1155

Asn

<210> SEQ ID NO 338
<211> LENGTH: 1389
<212> TYPE: PRT
<213> ORGANISM: Leptotrichia shahii

<400> SEQUENCE: 338

Met Gly Asn Leu Phe Gly His Lys Arg Trp Tyr Glu Val Arg Asp Lys
1               5                   10                  15

Lys Asp Phe Lys Ile Lys Arg Lys Val Lys Val Lys Arg Asn Tyr Asp
            20                  25                  30

```
Gly Asn Lys Tyr Ile Leu Asn Ile Asn Glu Asn Asn Asn Lys Glu Lys
             35                  40                  45

Ile Asp Asn Asn Lys Phe Ile Arg Lys Tyr Ile Asn Tyr Lys Lys Asn
 50                  55                  60

Asp Asn Ile Leu Lys Glu Phe Thr Arg Lys Phe His Ala Gly Asn Ile
 65                  70                  75                  80

Leu Phe Lys Leu Lys Gly Lys Glu Gly Ile Ile Arg Ile Glu Asn Asn
                 85                  90                  95

Asp Asp Phe Leu Glu Thr Glu Glu Val Val Leu Tyr Ile Glu Ala Tyr
                100                 105                 110

Gly Lys Ser Glu Lys Leu Lys Ala Leu Gly Ile Thr Lys Lys Lys Ile
                115                 120                 125

Ile Asp Glu Ala Ile Arg Gln Gly Ile Thr Lys Asp Lys Lys Ile
130                 135                 140

Glu Ile Lys Arg Gln Glu Asn Glu Glu Ile Glu Ile Asp Ile Arg
145                 150                 155                 160

Asp Glu Tyr Thr Asn Lys Thr Leu Asn Asp Cys Ser Ile Ile Leu Arg
                165                 170                 175

Ile Ile Glu Asn Asp Glu Leu Glu Thr Lys Lys Ser Ile Tyr Glu Ile
                180                 185                 190

Phe Lys Asn Ile Asn Met Ser Leu Tyr Lys Ile Ile Glu Lys Ile Ile
                195                 200                 205

Glu Asn Glu Thr Glu Lys Val Phe Glu Asn Arg Tyr Tyr Glu His
                210                 215                 220

Leu Arg Glu Lys Leu Leu Lys Asp Asp Lys Ile Asp Val Ile Leu Thr
225                 230                 235                 240

Asn Phe Met Glu Ile Arg Glu Lys Ile Lys Ser Asn Leu Glu Ile Leu
                245                 250                 255

Gly Phe Val Lys Phe Tyr Leu Asn Val Gly Gly Asp Lys Lys Lys Ser
                260                 265                 270

Lys Asn Lys Lys Met Leu Val Glu Lys Ile Leu Asn Ile Asn Val Asp
                275                 280                 285

Leu Thr Val Glu Asp Ile Ala Asp Phe Val Ile Lys Glu Leu Glu Phe
290                 295                 300

Trp Asn Ile Thr Lys Arg Ile Glu Lys Val Lys Lys Val Asn Asn Glu
305                 310                 315                 320

Phe Leu Glu Lys Arg Arg Asn Arg Thr Tyr Ile Lys Ser Tyr Val Leu
                325                 330                 335

Leu Asp Lys His Glu Lys Phe Lys Ile Glu Arg Glu Asn Lys Lys Asp
                340                 345                 350

Lys Ile Val Lys Phe Phe Val Glu Asn Ile Lys Asn Asn Ser Ile Lys
                355                 360                 365

Glu Lys Ile Glu Lys Ile Leu Ala Glu Phe Lys Ile Asp Glu Leu Ile
                370                 375                 380

Lys Lys Leu Glu Lys Glu Leu Lys Gly Asn Cys Asp Thr Glu Ile
385                 390                 395                 400

Phe Gly Ile Phe Lys Lys His Tyr Lys Val Asn Phe Asp Ser Lys Lys
                405                 410                 415

Phe Ser Lys Lys Ser Asp Glu Glu Lys Glu Leu Tyr Lys Ile Ile Tyr
                420                 425                 430

Arg Tyr Leu Lys Gly Arg Ile Glu Lys Ile Leu Val Asn Glu Gln Lys
                435                 440                 445
```

```
Val Arg Leu Lys Lys Met Glu Lys Ile Glu Ile Glu Lys Ile Leu Asn
    450                 455                 460

Glu Ser Ile Leu Ser Glu Lys Ile Leu Lys Arg Val Lys Gln Tyr Thr
465                 470                 475                 480

Leu Glu His Ile Met Tyr Leu Gly Lys Leu Arg His Asn Asp Ile Asp
                    485                 490                 495

Met Thr Thr Val Asn Thr Asp Asp Phe Ser Arg Leu His Ala Lys Glu
                500                 505                 510

Glu Leu Asp Leu Glu Leu Ile Thr Phe Phe Ala Ser Thr Asn Met Glu
            515                 520                 525

Leu Asn Lys Ile Phe Ser Arg Glu Asn Ile Asn Asn Asp Glu Asn Ile
530                 535                 540

Asp Phe Phe Gly Gly Asp Arg Glu Lys Asn Tyr Val Leu Asp Lys Lys
545                 550                 555                 560

Ile Leu Asn Ser Lys Ile Lys Ile Ile Arg Asp Leu Asp Phe Ile Asp
                565                 570                 575

Asn Lys Asn Asn Ile Thr Asn Asn Phe Ile Arg Lys Phe Thr Lys Ile
                580                 585                 590

Gly Thr Asn Glu Arg Asn Arg Ile Leu His Ala Ile Ser Lys Glu Arg
            595                 600                 605

Asp Leu Gln Gly Thr Gln Asp Asp Tyr Asn Lys Val Ile Asn Ile Ile
        610                 615                 620

Gln Asn Leu Lys Ile Ser Asp Glu Glu Val Ser Lys Ala Leu Asn Leu
625                 630                 635                 640

Asp Val Val Phe Lys Asp Lys Lys Asn Ile Ile Thr Lys Ile Asn Asp
                645                 650                 655

Ile Lys Ile Ser Glu Glu Asn Asn Asn Asp Ile Lys Tyr Leu Pro Ser
                660                 665                 670

Phe Ser Lys Val Leu Pro Glu Ile Leu Asn Leu Tyr Arg Asn Asn Pro
        675                 680                 685

Lys Asn Glu Pro Phe Asp Thr Ile Glu Thr Glu Lys Ile Val Leu Asn
690                 695                 700

Ala Leu Ile Tyr Val Asn Lys Glu Leu Tyr Lys Lys Leu Ile Leu Glu
705                 710                 715                 720

Asp Asp Leu Glu Glu Asn Glu Ser Lys Asn Ile Phe Leu Gln Glu Leu
                725                 730                 735

Lys Lys Thr Leu Gly Asn Ile Asp Glu Ile Asp Glu Asn Ile Ile Glu
            740                 745                 750

Asn Tyr Tyr Lys Asn Ala Gln Ile Ser Ala Ser Lys Gly Asn Asn Lys
        755                 760                 765

Ala Ile Lys Lys Tyr Gln Lys Lys Val Ile Glu Cys Tyr Ile Gly Tyr
770                 775                 780

Leu Arg Lys Asn Tyr Glu Glu Leu Phe Asp Phe Ser Asp Phe Lys Met
785                 790                 795                 800

Asn Ile Gln Glu Ile Lys Lys Gln Ile Lys Asp Ile Asn Asp Asn Lys
                805                 810                 815

Thr Tyr Glu Arg Ile Thr Val Lys Thr Ser Asp Lys Thr Ile Val Ile
            820                 825                 830

Asn Asp Asp Phe Glu Tyr Ile Ile Ser Ile Phe Ala Leu Leu Asn Ser
        835                 840                 845

Asn Ala Val Ile Asn Lys Ile Arg Asn Arg Phe Phe Ala Thr Ser Val
850                 855                 860
```

```
Trp Leu Asn Thr Ser Glu Tyr Gln Asn Ile Ile Asp Ile Leu Asp Glu
865                 870                 875                 880

Ile Met Gln Leu Asn Thr Leu Arg Asn Glu Cys Ile Thr Glu Asn Trp
            885                 890                 895

Asn Leu Asn Leu Glu Glu Phe Ile Gln Lys Met Lys Glu Ile Glu Lys
        900                 905                 910

Asp Phe Asp Asp Phe Lys Ile Gln Thr Lys Glu Ile Phe Asn Asn
    915                 920                 925

Tyr Tyr Glu Asp Ile Lys Asn Asn Ile Leu Thr Glu Phe Lys Asp Asp
930                 935                 940

Ile Asn Gly Cys Asp Val Leu Glu Lys Lys Leu Glu Lys Ile Val Ile
945                 950                 955                 960

Phe Asp Asp Glu Thr Lys Phe Glu Ile Asp Lys Lys Ser Asn Ile Leu
                965                 970                 975

Gln Asp Glu Gln Arg Lys Leu Ser Asn Ile Asn Lys Lys Asp Leu Lys
            980                 985                 990

Lys Lys Val Asp Gln Tyr Ile Lys Asp Lys Asp Gln Glu Ile Lys Ser
        995                 1000                1005

Lys Ile Leu Cys Arg Ile Ile Phe Asn Ser Asp Phe Leu Lys Lys
    1010                1015                1020

Tyr Lys Lys Glu Ile Asp Asn Leu Ile Glu Asp Met Glu Ser Glu
    1025                1030                1035

Asn Glu Asn Lys Phe Gln Glu Ile Tyr Tyr Pro Lys Glu Arg Lys
    1040                1045                1050

Asn Glu Leu Tyr Ile Tyr Lys Lys Asn Leu Phe Leu Asn Ile Gly
    1055                1060                1065

Asn Pro Asn Phe Asp Lys Ile Tyr Gly Leu Ile Ser Asn Asp Ile
    1070                1075                1080

Lys Met Ala Asp Ala Lys Phe Leu Phe Asn Ile Asp Gly Lys Asn
    1085                1090                1095

Ile Arg Lys Asn Lys Ile Ser Glu Ile Asp Ala Ile Leu Lys Asn
    1100                1105                1110

Leu Asn Asp Lys Leu Asn Gly Tyr Ser Lys Glu Tyr Lys Glu Lys
    1115                1120                1125

Tyr Ile Lys Lys Leu Lys Glu Asn Asp Asp Phe Phe Ala Lys Asn
    1130                1135                1140

Ile Gln Asn Lys Asn Tyr Lys Ser Phe Glu Lys Asp Tyr Asn Arg
    1145                1150                1155

Val Ser Glu Tyr Lys Lys Ile Arg Asp Leu Val Glu Phe Asn Tyr
    1160                1165                1170

Leu Asn Lys Ile Glu Ser Tyr Leu Ile Asp Ile Asn Trp Lys Leu
    1175                1180                1185

Ala Ile Gln Met Ala Arg Phe Glu Arg Asp Met His Tyr Ile Val
    1190                1195                1200

Asn Gly Leu Arg Glu Leu Gly Ile Ile Lys Leu Ser Gly Tyr Asn
    1205                1210                1215

Thr Gly Ile Ser Arg Ala Tyr Pro Lys Arg Asn Gly Ser Asp Gly
    1220                1225                1230

Phe Tyr Thr Thr Thr Ala Tyr Lys Phe Phe Asp Glu Glu Ser
    1235                1240                1245

Tyr Lys Lys Phe Glu Lys Ile Cys Tyr Gly Phe Gly Ile Asp Leu
    1250                1255                1260
```

```
Ser Glu Asn Ser Glu Ile Asn Lys Pro Glu Asn Glu Ser Ile Arg
    1265                1270                1275

Asn Tyr Ile Ser His Phe Tyr Ile Val Arg Asn Pro Phe Ala Asp
    1280                1285                1290

Tyr Ser Ile Ala Glu Gln Ile Asp Arg Val Ser Asn Leu Leu Ser
    1295                1300                1305

Tyr Ser Thr Arg Tyr Asn Asn Ser Thr Tyr Ala Ser Val Phe Glu
    1310                1315                1320

Val Phe Lys Lys Asp Val Asn Leu Asp Tyr Asp Glu Leu Lys Lys
    1325                1330                1335

Lys Phe Lys Leu Ile Gly Asn Asn Asp Ile Leu Glu Arg Leu Met
    1340                1345                1350

Lys Pro Lys Lys Val Ser Val Leu Glu Leu Glu Ser Tyr Asn Ser
    1355                1360                1365

Asp Tyr Ile Lys Asn Leu Ile Ile Glu Leu Leu Thr Lys Ile Glu
    1370                1375                1380

Asn Thr Asn Asp Thr Leu
    1385
```

<210> SEQ ID NO 339
<211> LENGTH: 17
<212> TYPE: RNA
<213> ORGANISM: Artificial
<220> FEATURE:
<223> OTHER INFORMATION: Nucleic acid encoding CRISPR guide RNA

<400> SEQUENCE: 339
acauuuuuag gcuugac                                                 17

<210> SEQ ID NO 340
<211> LENGTH: 17
<212> TYPE: RNA
<213> ORGANISM: Artificial
<220> FEATURE:
<223> OTHER INFORMATION: Nucleic acid encoding CRISPR guide RNA

<400> SEQUENCE: 340
uccugggagu cugucau                                                 17

<210> SEQ ID NO 341
<211> LENGTH: 17
<212> TYPE: RNA
<213> ORGANISM: Artificial
<220> FEATURE:
<223> OTHER INFORMATION: Nucleic acid encoding CRISPR guide RNA

<400> SEQUENCE: 341
augaugcuau aauacca                                                 17

<210> SEQ ID NO 342
<211> LENGTH: 17
<212> TYPE: RNA
<213> ORGANISM: Artificial
<220> FEATURE:
<223> OTHER INFORMATION: Nucleic acid encoding CRISPR guide RNA

<400> SEQUENCE: 342
gaaaguacau aggaccu                                                 17

<210> SEQ ID NO 343
<211> LENGTH: 17

```
<212> TYPE: RNA
<213> ORGANISM: Artificial
<220> FEATURE:
<223> OTHER INFORMATION: Nucleic acid encoding CRISPR guide RNA

<400> SEQUENCE: 343
uaucauaacu cuuacca                                              17
```

MULTI-ARMED POLYROTAXANE PLATFORM FOR PROTECTED NUCLEIC ACID DELIVERY

CROSS-REFERENCE TO RELATED APPLICATIONS

This application is a U.S. 371 National Phase of PCT International Application No. PCT/US2018/053221, filed on Sep. 27, 2018, which claims benefit of and priority to U.S. Ser. No. 62/566,100, filed on Sep. 29, 2017, and to U.S. Ser. No. 62/687,713, filed on Jun. 20, 2018, all of which are incorporated herein by reference in their entirety for all purposes.

STATEMENT OF GOVERNMENTAL SUPPORT

This invention was made with government support under Grant Number CA198846, awarded by the National Institutes of Health. The Government has certain rights in the invention.

INCORPORATION BY REFERENCE OF SEQUENCE LISTING PROVIDED AS A TEXT FILE

This application contains references to nucleic acid sequences that have been submitted concurrently herewith as the sequence listing text file "UCLA-P193US_ST25.txt", file size 370 kb, created on 08/07/2020, which is incorporated by reference in its entirety pursuant to 37 C.F.R. § 1.52(e)(5).

BACKGROUND

The ability to deliver DNA to target cells plays a key role in the development of new approaches, such as gene therapy and DNA vaccination, for treating and controlling diseases. DNA delivery systems have been classified as viral and non-viral vector systems. Although viral vectors are highly efficient at delivering DNA into cells, their routine uses in the clinic has been limited because of, inter alia, their high toxicity, restricted targeting of cells, limited DNA carrying capacity, production and packaging problems, recombination, and high cost.

Non-viral vectors, the majority of which are synthetic gene carrier systems, have advantages in terms of simplicity of use, ease of large-scale production, and lack of specific immune response.

The use of polymers carrying/complexing DNA is a non-viral delivery approach. Most polymers used for DNA delivery consist of or comprise cationic polymer segments that form a condensed complex with DNA to protect the DNA digestion by enzymes. The condensed polymer-DNA complex also packs into compact and small nanoparticles, that can be internalized by cells through endocytosis.

Cationic polymers of linear, branched, star and dendritic structures have been studied as DNA condensation agents in the context of non-viral gene delivery. Controlled chemical synthesis of cationic polymers ensures that the size and shape of the polymers are consistent and defined, thereby improving the reproducibility of DNA delivery. Polyethyleneimine (PEI) is one of the most frequently studied polycations for use in DNA delivery. The size and the structure of PEI has strongly influenced the efficiency of nucleic acid delivery with regard to transfection activity and cytotoxicity. Generally, low molecular weight branched PEI (e.g., $\leq$2000 Da) has proven to be nontoxic, but has often displayed very poor transfection activity. By contrast, high molecular weight branched PEI ($\geq$25 kDa) has showed high transgene expression, but also significant cytotoxicity. In the intermediate molecular weight range (2000 kDa-25 kDa), the PEI is of medium to low cytotoxicity and also medium transfection activity.

SUMMARY

In various embodiments polyrotaxane carriers are provided for the delivery of nucleic acids. The carriers self-assemble with nucleic acids to form complexes that are effective to deliver the nucleic acids to cells in vivo (e.g., in a mammal). The carriers described herein show reduced opsonization, improved serum half-life, improved cellular uptake and the like as compared to other polyrotaxane carriers.

Various embodiments contemplated herein may include, but need not be limited to, one or more of the following:

Embodiment 1

A polyrotaxane carrier for in vivo delivery of a nucleic acid, said carrier comprising:
- a multi-arm polyethylene glycol (PEG) backbone comprising at least three arms;
- at least one cyclic compound having a cavity, where an arm of said multi-arm PEG backbone is threaded into the cavity of said cyclic compound forming an inclusion complex;
- a bulky moiety capping the terminal of the arm(s) threaded into said cyclic compound where said moiety inhibits dethreading of the cyclodextrin from the arm(s) of said backbone;
- where at least one arm of said PEG backbone is free of cyclic compounds; and where said carrier has a net positive charge.

Embodiment 2

The carrier of embodiment 1, wherein said carrier complexes with a nucleic acid when contacted to said nucleic acid.

Embodiment 3

The carrier according to any one of embodiments 1-2, wherein said multi-arm polyethylene glycol backbone comprises a star polymer.

Embodiment 4

The carrier according to any one of embodiments 1-3, wherein said multi-arm PEG comprises at least 2 arms free of cyclic compounds.

Embodiment 5

The carrier according to any one of embodiments 1-4, wherein said multi-arm PEG comprises from 3 up to about 12, or up to about 10, or up to about 8 arms.

Embodiment 6

The carrier according to any one of embodiments 1-5, wherein said PEG comprises 4 arms, or 5 arms, or 6 arms, or seven arms, or 8 arms.

Embodiment 7

The carrier according to any one of embodiments 1-4, wherein said PEG comprises 4 arms.

Embodiment 8

The carrier according to any one of embodiments 1-4, wherein said PEG comprise 4 arms where two of said arms are free of cyclic compounds.

Embodiment 9

The carrier according to any one of embodiments 1-8, wherein said PEG backbone has a molecular weight ranging from about 1.0 to about 10 kDA per arm.

Embodiment 10

The carrier according to any one of embodiments 1-9, wherein said PEG backbone comprise about 22 to about 227 ethylene oxides per arm.

Embodiment 11

The carrier according to any one of embodiments 1-8, wherein said PEG backbone has a molecular weight of about 2.5 kDa per arm.

Embodiment 12

The carrier according to any one of embodiments 1-11, wherein the arm(s) threaded into said cyclic compound(s) each bear on average from about 5 to about 110 cyclic compounds.

Embodiment 13

The carrier according to any one of embodiments 1-11, wherein the arm(s) threaded into said cyclic compound(s) each bear, on average, about 20 cyclic compounds per arm.

Embodiment 14

The carrier according to any one of embodiments 1-13, wherein said cyclic compound comprise a compound selected from the group consisting of a cyclodextrin, a crown ether, a cucurbituril and a cyclofructan.

Embodiment 15

The carrier of embodiment 14, wherein said cyclic compound comprises a cyclodextrin.

Embodiment 16

The carrier of embodiment 15, wherein said cyclic compound comprises a cyclodextrin selected from the group consisting of an α-cyclodextrin, a β-cyclodextrin, a γ-cyclodextrin, a hydroxypropylated α-cyclodextrin, a hydroxypropylated β-cyclodextrin, a hydroxypoylated γ-cyclodextrin, a dimethylcyclodextrin, a chemically modified cyclodextrin (e.g., carboxyl modified cyclodextrin).

Embodiment 17

The carrier of embodiment 14, wherein said cyclic compound comprises a cucurbituril.

Embodiment 18

The carrier of embodiment 17, wherein said cyclic compound comprises a cucurbituril selected from the group consisting of cucurbit[5]uril, cucurbit[6]uril, cucurbit[7]uril, cucurbit[8]uril, cucurbit[9]uril, cucurbit[10]uril, and a chemically modified cucubituril.

Embodiment 19

The carrier of embodiment 18, wherein said cyclic compound comprises a cucurbit[6]uril (CB[6]).

Embodiment 20

The carrier according to any one of embodiments 1-19, wherein said cyclic compound(s) are substituted with one or more nucleophilic groups.

Embodiment 21

The carrier of embodiment 20, wherein said cyclic compound(s) are substituted with one or more amine groups or groups derived from an amine group.

Embodiment 22

The carrier of embodiment 21, wherein said cyclic compound(s) are substituted with one or more groups selected from the group consisting of a primary amine, a secondary amine, a tertiary amine, and an imine group.

Embodiment 23

The carrier of embodiment 22, wherein said cyclic compound(s) are substituted with one or more primary amines.

Embodiment 24

The carrier according to any one of embodiments 20-23, where the number of nucleophilic group substituted on the cyclic compound(s) ranges from 1 up to about 20 substitutions per cyclic compound.

Embodiment 25

The carrier according to any one of embodiments 20-24, wherein the cyclic compounds are substituted with nucleophilic groups to provide a positive zeta potential for said carrier ranging from about +1V or from about +5 mV up to about +50 mV, or up to about +25 mV.

Embodiment 26

The carrier according to any one of embodiments 1-25, wherein said carrier has a zeta potential of about +15 mV.

Embodiment 27

The carrier according to any one of embodiments 1-26, wherein the bulky moiety capping the terminal of the arm(s)

threaded into said cyclic compound(s) comprises a compound having a 3 dimensional size greater than the internal diameter of the cyclic compound(s).

Embodiment 28

The carrier of embodiment 27, wherein the bulky moiety capping the terminal of the arm(s) threaded into said cyclic compound(s) comprises a moiety selected from the group consisting of Z-tyrosine, phenylalanine, a group having at least one benzene ring, and a group having at least one tertiary butyl.

Embodiment 29

The carrier of embodiment 28, wherein the bulky moiety comprises a moiety selected from the group consisting of a Z-tyrosine, phenylaline, a benzyloxycarbonyl (Z) group, a 9-fluorenylmethyloxycarbonyl (Fmoc) group, a benzyl ester (OBz) group, a tertiary butylcarbonyl (Boc) group, and an amino acid-tertiary butyl ester (OBu) group.

Embodiment 30

The carrier of embodiment 28, wherein the bulky moiety comprises Z-tyrosine.

Embodiment 31

The carrier according to any one of embodiments 1-30, wherein at least one arm not threaded into said cyclic compound is terminated with a protecting group, and/or a fluorophore, and/or a targeting moiety.

Embodiment 32

The carrier of embodiment 31, wherein all the arms not threaded into said cyclic compound are terminated with a protecting group, and/or a fluorophore, and/or a targeting moiety.

Embodiment 33

The carrier according to any one of embodiments 31-32, wherein at least one arm not threaded into said cyclic compound are terminated with a protecting group selected from the group consisting of dansyl, acetyl, amide, and 3 to 20 carbon alkyl groups, Fmoc, Tboc, 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pme), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), Benzyloxymethyl (Bom), t-butoxycarbonyl (Boc), cyclohexyloxy (cHxO), t-butoxymethyl (Bum), t-butoxy (tBuO), t-Butyl (tBu), Acetyl (Ac), and Trifluoroacetyl (TFA).

Embodiment 34

The carrier of embodiment 31, wherein at least one arm not threaded into said cyclic compound is attached to a fluorophore.

Embodiment 35

The carrier of embodiment 34, wherein said fluorophore is selected from the group consisting of a rhodamine, a cyanine, an oxazine, a thiazine, a porphyrin, a phthalocyanine, and a fluorescent protein.

Embodiment 36

The carrier of embodiment 34, wherein said fluorophore is selected from the group consisting of fluorescein isothiocyanate (especially fluorescein-5-isothiocyanate), 5-FAM (5-carboxyfluorescein), 6-FAM (6-carboxyfluorescein), 5,6-FAM, 7-hydroxycoumarin-3-carboxamide, 6-chloro-7-hydroxycoumarin-3-carboxamide-, dichlorotriazinylaminofluorescein, tetramethylrhodamine-5 (and-6)-isothiocyanate, 1,3-bis-(2-dialkylamino-5-thienyl)-substituted squarines, succinimidyl esters of 5 (and 6) carboxyfluoroscein, 5 (and 6)-carboxytetramethylrhodamine, 7-amino-4-methylcoumarin-3-acetic acid, DyLight 350, DyLight 405, DyLight 488, DyLight 550, DyLight 594, DyLight 633, DyLight 650, DyLight 680, DyLight 755, DyLight 800, Alexa fluor 350, Alexa fluor 405, Alexa fluor 488, Alexa fluor 546, Alexa fluor 555, Alexa fluor 568, Alexa fluor 594, Alexa fluor 633, Alexa fluor 647, and Alexa fluor 750.

Embodiment 37

The carrier of embodiment 31, wherein at least one arm not threaded into said cyclic compound is attached to a targeting moiety that specifically or preferentially binds to a cell.

Embodiment 38

The carrier of embodiment 37, wherein said targeting moiety is selected from the group consisting of an antibody, a receptor ligand, a nucleic acid aptamer, a peptide aptamer, neural cell adhesion molecule (NCAM), a cell penetrating peptide (CPP), a peptide aptamer, and a lectin.

Embodiment 39

The carrier of embodiment 38, wherein said targeting moiety comprises an antibody.

Embodiment 40

The carrier of embodiment 38, wherein said targeting moiety comprises an antibody selected from the group consisting of full-length immunoglobulins, Fab, Fab', Fab'-SH, F(ab')$_2$, Fv, Fv', Fd, Fd', scFv, hsFv fragments, single-chain antibodies, cameloid antibodies.

Embodiment 41

The carrier according to any one of embodiments 38-40, wherein said targeting moiety binds to a stem cell.

Embodiment 42

The carrier according to any one of embodiments 38-40, wherein said targeting moiety binds to a hematopoietic cell.

Embodiment 43

The carrier according to any one of embodiments 38-40, wherein said targeting moiety binds to a T-cell.

Embodiment 44

The carrier according to any one of embodiments 38-40, wherein said targeting moiety binds to a muscle cell.

Embodiment 45

The carrier according to any one of embodiments 38-40, wherein said targeting moiety binds a target selected from the group consisting of CD45, CD3, erbB2, Her2, CD22, CD74, CD19, CD20, CD33, CD40, MUC1, IL-15R, HLA-DR, EGP-1, EGP-2, G250, prostate specific membrane antigen (PSMA), prostate specific antigen (PSA), prostatic acid phosphatase (PAP), and placental alkaline phosphatase.

Embodiment 46

The carrier according to any one of embodiments 38-40, wherein said targeting moiety binds to a cancer cell marker.

Embodiment 47

The carrier of embodiment 46, wherein said targeting moiety binds to a cancer cell marker selected from the group consisting of 5 alpha reductase, α-fetoprotein, AM-1, APC, APRIL, BAGE, β-catenin, Bc12, bcr-abl (b3a2), CA-125, CASP-8/FLICE, Cathepsins, CD19, CD20, CD21, CD23, CD22, CD38, CD33, CD35, CD44, CD45, CD46, CD5, CD52, CD55, CD59 (791Tgp72), CDC127, CDK4, CEA, c-myc, Cox-2, DCC, DcR3, E6/E7, EGFR, EMBP, Ena78, FGF8b and FGF8a, FLK-1/KDR, Folic Acid Receptor, G250, GAGE-Family, gastrin 17, Gastrin-releasing hormone (bombesin), GD2/GD3/GM2, GnRH, GnTV, gp100/Pmel17, gp-100-in4, gp15, gp75/TRP-1, hCG, Heparanase, Her2/neu, Her3, HMTV, Hsp70, hTERT, (telomerase), IGFR1, IL-13R, iNOS, Ki 67, KIAA0205, K-ras, H-ras, N-ras, KSA, (CO17-1A), LDLR-FUT, MAGE Family (MAGE1, MAGE3, etc.), Mammaglobin, MAP17, Melan-A/, MART-1, mesothelin, MIC A/B, MT-MMP's, such as MMP2, MMP3, MMP7, MMP9, Mox, Mucin, such as MUC-1, MUC-2, MUC-3, and MUC-4, MUM-1, NY-ESO-1, Osteonectin, p15, P170/MDR, p53, p97/melanotransferrin, PAI-1, PDGF, Plasminogen (uPA), PRAME, Probasin, Progenipoietin, PSA, PSM, RAGE-1, Rb, RCAS1, SART-1, SSX gene, family, STAT3, STn, (mucin assoc.), TAG-72, TGF-α, TGF-β, Thymosin β 15, TPA, TPI, TRP-2, Tyrosinase, VEGF, ZAG, p16INK4, and Glutathione S-transferase.

Embodiment 48

The carrier of embodiment 38, wherein said targeting moiety comprises a ligand that binds a receptor where said ligand is selected from the group consisting of transferrin, mannose, glucose, and folic acid.

Embodiment 49

The carrier of embodiment 38, wherein said targeting moiety comprises a ligand that binds a receptor where said ligand comprises transferrin.

Embodiment 50

The carrier according to any one of embodiments 1-49, wherein said bulky moiety is attached to an arm of said backbone by a cleavable linkage.

Embodiment 51

The carrier according to any one of embodiments 20-49, wherein said one or more nucleophilic groups are attached to said cyclic compounds by a cleavable linkage.

Embodiment 52

The carrier according to any one of embodiments 50-51, wherein said cleavable linkage is selected from the group consisting of a redox-responsive linker, a pH responsive linker, a photo-responsive linker, a thermal responsive linker and an enzymatically cleavable linker.

Embodiment 53

The carrier of embodiment 52, wherein said cleavable linkage comprises a redox-responsive disulfide linker.

Embodiment 54

The carrier of embodiment 52, wherein said cleavable linkage comprises a pH responsive hydrazine linker.

Embodiment 55

The carrier of embodiment 52, wherein said cleavable linkage comprises an enzymatically cleavable linker.

Embodiment 56

The carrier of embodiment 55, wherein said linkage comprises a linker cleavable by a protease.

Embodiment 57

The carrier of embodiment 56, wherein said linkage comprises a linker cleavable by a matrix metalloprotease or a cathepsin.

Embodiment 58

The carrier according to any one of embodiments 56-57, wherein said peptide linker comprises a linker comprises a moiety selected from the group consisting of dipeptide valine-citrulline (Val-Cit), dipeptide Phe-Lys, Mc-vc-PAB- MMAE, Mc-vc-PAB-MMAF, Mc-va-PBD dimer, Mc-vc-PAB-CM-seco-DUBA, Gly-Phe-Leu-Gly (GFLG), GPLGV, and GPLGVRG.

Embodiment 59

The carrier according to any one of embodiments 1-58, wherein said carrier is complexed with a nucleic acid.

Embodiment 60

The carrier of embodiment 59, wherein said carrier is complexed with an RNA.

Embodiment 61

The carrier according to any one of embodiments 59-60, wherein said carrier is complexed with a DNA.

Embodiment 62

The carrier of embodiment 61, wherein said carrier is complexed with a plasmid.

Embodiment 63

The carrier of embodiment 62, wherein said carrier is complexed with a plasmid that encodes a heterologous gene or cDNA.

Embodiment 64

The carrier of embodiment 62, wherein said carrier is complexed with a plasmid that encodes a class 2 CRISPR/Cas endonuclease and a guide RNA.

Embodiment 65

The carrier of embodiment 64, wherein said class 2 CRISPR/Cas endonuclease is a type II CRISPR/Cas endonuclease.

Embodiment 66

The carrier according to any one of embodiments 64-65, wherein the class 2 CRISPR/Cas endonuclease is a Cas9 polypeptide and the corresponding CRISPR/Cas guide RNA is a Cas9 guide RNA.

Embodiment 67

The carrier of embodiment 66, wherein said Cas9 protein is selected from the group consisting of a *Streptococcus pyogenes* Cas9 protein (spCas9) or a functional portion thereof, a *Staphylococcus aureus* Cas9 protein (saCas9) or a functional portion thereof, a *Streptococcus thermophilus* Cas9 protein (stCas9) or a functional portion thereof, a *Neisseria meningitides* Cas9 protein (nmCas9) or a functional portion thereof, and a *Treponema denticola* Cas9 protein (tdCas9) or a functional portion thereof.

Embodiment 68

The carrier of embodiment 67, wherein said Cas9 protein comprises a *Streptococcus pyogenes* Cas9 protein (spCas9).

Embodiment 69

The carrier of embodiment 67, wherein said Cas9 protein comprises a *Staphylococcus aureus* Cas9 protein (saCas9).

Embodiment 70

The carrier of embodiment 67, wherein said Cas9 protein comprises a *Streptococcus thermophilus* Cas9 protein.

Embodiment 71

The carrier of embodiment 67, wherein said Cas9 protein comprises a *Neisseria meningitides* Cas9 protein (nmCas9).

Embodiment 72

The carrier of embodiment 67, wherein said Cas9 protein comprises a *Treponema denticola* Cas9 protein (tdCas9).

Embodiment 73

The carrier of embodiment 64, wherein the class 2 CRISPR/Cas endonuclease is a type V or type VI CRISPR/Cas endonuclease.

Embodiment 74

The carrier of embodiment 73, wherein the class 2 CRISPR/Cas endonuclease is selected from the group consisting of a Cpf1 polypeptide or a functional portion thereof, a C2c1 polypeptide or a functional portion thereof, a C2c3 polypeptide or a functional portion thereof, and a C2c2 polypeptide or a functional portion thereof.

Embodiment 75

The carrier of embodiment 74, wherein the class 2 CRISPR/Cas endonuclease comprises a Cpf1 polypeptide.

Embodiment 76

The carrier according to any one of embodiments 59-75, wherein the N/P ratio of said carrier complexed to a nucleic acid ranges from about 0.01:1 up to about 100:1, or from about 2:1 up to about 50:1, or up to about 40:1, or up to about 30:1, or up to about 25:1, or ranges from about 2:1 up to about 25:1.

Embodiment 77

The carrier of embodiment 70, wherein the N/P ratio of said carrier complexed to a nucleic acid is about 10:1.

Embodiment 78

A pharmaceutical formulation comprising: a polyrotaxane carrier according to any one of embodiments 1-58; and a pharmaceutically acceptable carrier.

Embodiment 79

The formulation of embodiment 78, wherein said polyrotaxane carrier is complexed with a nucleic acid.

Embodiment 80

The formulation according to any one of embodiments 78-79, wherein said formulation is formulated for administration via a route selected from the group consisting of isophoretic delivery, transdermal delivery, aerosol administration, administration via inhalation, oral administration, intravenous administration, intraarterial administration, intramuscular administration, topical delivery to the eye, intraocular injection, vaginal administration, and rectal administration.

Embodiment 81

The formulation according to any one of embodiments 78-80, wherein said formulation is a unit dosage formulation.

Embodiment 82

A construct for the treatment of Duchenne Muscular Dystrophy, said construct comprising:
a polyrotaxane carrier according to any one of embodiments 1-58, wherein said carrier is complexed with a plasmid encoding a class 2 CRISPR/Cas endonuclease, and a guide RNA that hybridizes to a target sequence within intron 44 of a mutant dystrophin gene, and/or a second CRISPR/Cas guide RNA guide sequence that hybridizes to a target sequence within intron 55 of the mutant dystrophin gene.

Embodiment 83

The construct of embodiment 82, wherein: the first CRISPR/Cas guide RNA comprises a guide sequence having 100% complementarity over 17 or more contiguous nucleotides with a first target sequence corresponding to intron 44 of the human dystrophin gene, and/or the second CRISPR/Cas guide RNA comprises a guide sequence having 100% complementarity over 17 or more contiguous nucleotides with a second target sequence corresponding to intron 55 of the human dystrophin gene.

Embodiment 84

The construct of embodiment 82, wherein the class 2 CRISPR/Cas endonuclease is a type II CRISPR/Cas endonuclease.

Embodiment 85

The construct of embodiment 84, wherein the class 2 CRISPR/Cas endonuclease is a Cas9 protein and the corresponding CRISPR/Cas guide RNA is a Cas9 guide RNA.

Embodiment 86

The construct of embodiment 82, wherein the class 2 CRISPR/Cas endonuclease is a type V or type VI CRISPR/Cas endonuclease.

Embodiment 87

The construct of embodiment 86, wherein the class 2 CRISPR/Cas endonuclease is a Cpf1 protein, a C2c1 protein, a C2c3 protein, or a C2c2 protein.

Embodiment 88

The construct of any of embodiments 82-85, wherein the guide sequence of the first CRISPR/Cas guide RNA comprises a sequence selected from the group consisting of guguccuuug aauaaugc (SEQ ID NO:225), uuguccagga uauaauu (SEQ ID NO:226), gcaaccaaau uauaucc (SEQ ID NO:227), gaaauuaaac uacacac (SEQ ID NO:228), and uuuaccugca uauucaa (SEQ ID NO:229) (the 17 nucleotide sequence set forth in any of SEQ ID NOs: 1155-1159 of PCT/US2017/017255).

Embodiment 89

The construct of embodiment 88, wherein the guide sequence of the first CRISPR/Cas guide RNA comprises a sequence selected from the group consisting of gugguguccu uugaauaugc (SEQ ID NO:78), agauugucca ggauauaauu (SEQ ID NO:80), uuagcaacca aauuauaucc (SEQ ID NO:82), guugaaauua aacuacacac (SEQ ID NO:84), aucuuuaccu gcauauucaa (SEQ ID NO:86), cucugcauug uuuuggccuc (SEQ ID NO:88), uccuccaaag aguagaaugg (SEQ ID NO:90), gcccuaaacu uacacuguuc (SEQ ID NO:92), aaagauagau uagauugucc (SEQ ID NO:94), guugcuaaau uacauaguuu (SEQ ID NO:96), uguugcaaua gucaaucaag (SEQ ID NO:98), auacugauua agacagauga (SEQ ID NO:100), aauacugauu aagacagaug (SEQ ID NO:102), cucuauacaa augccaacgc (SEQ ID NO:104), acuugcaugc acaccagcgu (SEQ ID NO:106), uugggcuaau guagcauaau (SEQ ID NO:108), gcguuggcau uuguauagag (SEQ ID NO:110), ugggcuaagu agcauaaug (SEQ ID NO:112), uuugggcuaa uguagcauaa (SEQ ID NO:114), gcuuaacucc uuaauauuaa (SEQ ID NO:116), ucuucuauau uaaagcagau (SEQ ID NO:118), cuucuauauu aaagcagauu (SEQ ID NO:120), aauauauaac uaccuuggu (SEQ ID NO:122), accuccauuc uacucuuugg (SEQ ID NO:124), uuucaaugau auccaaccca (SEQ ID NO:126), aguaccucca uucuacucuu (SEQ ID NO:128), cuauccucca aagaguagaa (SEQ ID NO:130), uuuugcuaca uauuucaggc (SEQ ID NO:132), uuugcuacau auuucaggcu (SEQ ID NO:134), ggguuggaua ucauugaaaa (SEQ ID NO:136), auauuucagg cugguucu (SEQ ID NO:138), uugaaauaua uaacuaccuu (SEQ ID NO:140), auugaaauau auaacuaccu (SEQ ID NO:142), gugaguagug gggcacuuua (SEQ ID NO:144), uguauguaga agguuaacua (SEQ ID NO:146), gagccuaaua aauguacaau (SEQ ID NO:148), uuguauguag aagguuaacu (SEQ ID NO:150), caauuuguuu ugaguaacu (SEQ ID NO:152), ugccuucuga aauaguccag (SEQ ID NO:154), guuaauaggg aaacagcaua (SEQ ID NO:156), aacaaugcag aguuaauugu (SEQ ID NO:158), gaacauguug aguagacaca (SEQ ID NO:160), uuuaucaucu gugucuauuc (SEQ ID NO:162), ucuuuacuuu cuugacuaua (SEQ ID NO:164), aauauucuca aaccucguuc (SEQ ID NO:166), auuaacugug uuccagaacg (SEQ ID NO:168), uaacugcuuc uuuggaugac (SEQ ID NO:170), gaccagaaca guguaaguuu (SEQ ID NO:172), accagaacag uguaaguuua (SEQ ID NO:174), cuacuuuuuc cccacuacug (SEQ ID NO:176), uggaacacag uuaauucacu (SEQ ID NO:178), and guguuguuua acugcuucuu (SEQ ID NO:180), (the 20 nucleotide sequence set forth in any of SEQ ID NOs: 1150-1154 and SEQ ID NOs: 1223-1269 of PCT/US2017/017255).

Embodiment 90

The construct of any of embodiments 82-85, 88, or 89, wherein the guide sequence of the second CRISPR/Cas guide RNA comprises a sequence selected from the group consisting of acauuuuag gcuugac (SEQ ID NO:339), uccugggagu cugucau (SEQ ID NO:340), augaugcuau aauacca (SEQ ID NO:341), gaaaguacau aggaccu (SEQ ID NO:342), and uaucauaacu cuuacca (SEQ ID NO:343) (the 17 nucleotide sequence set forth in any of SEQ ID NOs: 1175-1179 of PCT/US2017/017255).

Embodiment 91

The construct of embodiment 82-85, 88, or 89, wherein the guide sequence of the second CRISPR/Cas guide RNA comprises a sequence selected from the group consisting of uacacauuuu uaggcuugac (SEQ ID NO:182), cauuccuggg agucugucau (SEQ ID NO:184), uguaugaugc uauaauacca (SEQ ID NO:186), guggaaagua cauaggaccu (SEQ ID NO:188), and ucuuaucaua acucuuacca (SEQ ID NO:190), aacugucagu ugcauauucc (SEQ ID NO:192), cagaaaggaa ugcugguacc (SEQ ID NO:194), ucugccuaca caaugaaugg (SEQ ID NO:196), cacagaucaa uccaauuguu (SEQ ID NO:198), uugacaggug gaaaguacau (SEQ ID NO:200), acauuuuuag gcuugacagg (SEQ ID NO:202), cucucccaug acagacuccc (SEQ ID NO:204), uugguaagag uuaugauaag (SEQ ID NO:206), aacacaaauu aaguucaccu (SEQ ID NO:208), aggaucagug cuguagugcc (SEQ ID NO:210), ggccguuuau uauuauugac (SEQ ID NO:212), ucucaggauu gcuaugcaac (SEQ ID NO:214), caggaagaca uaccauguaa (SEQ ID NO:216), agcagggcuc uuucaguuuc (SEQ ID NO:218), uaacauuuuc agcuugaacc (SEQ ID NO:230), ucaagcugaa aauguuacac (SEQ ID NO:223), guaacauuuu cagcuugaac (SEQ ID NO:224), cagaaugaau uuuggagcac (SEQ ID NO:226), uuuauuauua uugacuggug (SEQ ID NO:228), agaagaaucu gaccuuuaca (SEQ ID NO:230), gcagggcucu uucaguuucu (SEQ ID NO:232), cuaaacagua gecaggegug (SEQ ID NO:234), cgccuggcua cuguuuagug (SEQ ID NO:236), cuccgcacua aacaguagcc (SEQ ID NO:238), guagccagge guguggaugu (SEQ ID NO:240), cuuggcuuug acuauucugc (SEQ ID NO:242), aguagccagg cgugugaug (SEQ ID NO:244), uccucccaca uccacacgcc (SEQ ID NO:246), uuggcuuuga cuauucugcu (SEQ ID NO:248), auaaugucuc uggcuuguaa (SEQ ID NO:250), ugguacccgg cagcucucug (SEQ ID NO:252), gugggaggaa ccucaaagag (SEQ ID NO:254), ugacuauucu gcugggaaca (SEQ ID NO:256), cucucugagg aauguucccu (SEQ ID NO:258), aacauuccuc agagageuge (SEQ ID NO:260), auucugaagc uccaaacaau (SEQ ID NO:262), uaaauuacuc ugcuaaagua (SEQ ID NO:264), aguacaaacc agguuuguac (SEQ ID NO:266), auauccuucc aguacaaacc (SEQ ID NO:268), caaaccaggu uuguacugga (SEQ ID NO:270), ggcagcuaaa gcaucacuga (SEQ ID NO:272), aucucugagu aguacaaacc (SEQ ID NO:274), gugucccauu cucuuugacu (SEQ ID NO:276), ugugucccau ucucuuugac (SEQ ID NO:278), uucugaaugu ugaacaagua (SEQ ID NO:280), gucucccagu caaagagaau (SEQ ID NO:282), auucucuuug acugggacag (SEQ ID NO:284), and ucuuugacug ggagacaggc (SEQ ID NO:286), (the 20 nucleotide sequence set forth in any of SEQ ID NOs: 1170-1174 and SEQ ID NOs: 1318-1365 of PCT/US2017/017255).

Embodiment 92

The construct of any of embodiments 82-85, wherein the guide sequence of the first CRISPR/Cas guide RNA comprises the 17 nucleotide sequence GAAAUUAAACUA-CACAC (SEQ ID NO:305) (SEQ ID NO:1158 in PCT/US2017/017255), and the guide sequence of the second CRISPR/Cas guide RNA comprises the 17 nucleotide sequence AUGAUGCUAUAAUACCA (SEQ ID NO:306) (SEQ ID NO:1177 in PCT/US2017/017255).

Embodiment 93

The construct of any of embodiments 82-85, wherein the guide sequence of the first CRISPR/Cas guide RNA comprises the 20 nucleotide sequence GUUGAAAUUAAAC-UACACAC (SEQ ID NO:307) (SEQ ID NO:1153 in PCT/US2017/017255) and the guide sequence of the second CRISPR/Cas guide RNA comprises the 20 nucleotide sequence UGUAUGAUGCUAUAAUACCA (SEQ ID NO:308) (SEQ ID NO:1172 in PCT/US2017/017255).

Embodiment 94

The construct of any of embodiments 82-87, wherein the target sequence within intron 44 and the target sequence within intron 55 are separated from each other by 500 kb or more.

Embodiment 95

The construct of embodiment 94, wherein the target sequence within intron 44 and the target sequence within intron 55 are separated from each other by 700 kb or more.

Embodiment 96

A method of modifying a mutant dystrophin gene in a cell's genome of a mammal in vivo, said method comprising: administering to said mammal an effective amount of a construct according to any one of embodiments 82-95.

Embodiment 97

The method of embodiment 96, wherein said cell comprises a muscle cell or a pericyte.

Embodiment 98

The method of embodiment 97, wherein said cell comprises a skeletal muscle cell.

Embodiment 99

The method of embodiment 97, wherein said cell comprises a cardiomyocyte.

Embodiment 100

The method of embodiment 96, wherein said cell comprises a stem cell.

Embodiment 101

The method according to any one of embodiments 96-100, wherein said administering comprises administration via a route selected from the group consisting of epidural, intracerebral, intracerebroventricular, epicutaneous, intraarterial, intracardiac intracavernous injection, an injection into the base of the penis, intradermal, intralesional, intramuscular, intraocular administration, intraocular, intraosseous infusion, intraperitoneal, intrathecal, intrauterine, intravaginal administration, intravenous, intravesical infusion, intravitreal, subcutaneous, transdermal, perivascular administration, and transmucosal administration.

Embodiment 102

The method according to any one of embodiments 96-100, wherein said administering comprises systemic administration.

Embodiment 103

The method of embodiment 101, wherein said administration comprises nasal administration, intramuscular administration, or intravenous administration.

Embodiment 104

The method according to any one of embodiments 96-103, wherein said mammal is a human.

Embodiment 105

The method of embodiment 104, wherein said mammal is a human diagnosed with DMD or BMD.

Embodiment 106

The method of embodiment 105, wherein CRISPR acts to restore the shifted DMA reading frame and switch said DMD to the milder Becker's muscular dystrophy (BMD) phenotype.

Embodiment 107

The method according to any one of embodiments 96-103, wherein said mammal is a non-human mammal.

Embodiment 108

The method according to any one of embodiments 96-107, wherein said method is performed in combination with another treatment for DMD.

Embodiment 109

The method of embodiment 108, wherein said another treatment comprises administration of one or more drugs selected from the group consisting of Eteplirsen (Exondys 51), a steroid, and a blood pressure medication.

Embodiment 110

The method of embodiment 109, wherein said another treatment comprises administration of the oral corticosteroid deflazacort (Emflaza), and/or prednisone.

Embodiment 111

A method of delivering a nucleic acid to a cell in vivo in a mammal, said method comprising:
providing a carrier according to any one of embodiments 1-58 where said carrier forms a complex with the nucleic acid to be delivered, and
administering said complex to said mammal in an amount effective to deliver said nucleic acid to said cell.

Embodiment 112

The method of embodiment 111, wherein said cell comprises a muscle cell, a neural cell, a hematopoietic cell, a stem cell, or a T-cell.

Embodiment 113

The method of embodiment 112, wherein said cell comprises a cancer cell.

Embodiment 114

The method of embodiment 113, wherein said cancer cell comprises a cell selected from the group consisting of a solid tumor cell, a metastatic cell, and a cancer stem cell.

Embodiment 115

The method according to any one of embodiments 111-114, wherein said administering comprises systemic administration.

Embodiment 116

The method of embodiment 115, wherein said administration comprises nasal or intravenous administration.

Embodiment 117

The method according to any one of embodiments 111-116, wherein said mammal is a human.

Embodiment 118

The method according to any one of embodiments 111-116, wherein said mammal is a non-human mammal.

Embodiment 119

The method according to any one of embodiments 111-118, wherein said nucleic acid comprises RNA.

Embodiment 120

The method according to any one of embodiments 111-118, wherein said nucleic acid comprises DNA.

Embodiment 121

The method of embodiment 120, wherein said nucleic acid comprises a plasmid.

Embodiment 122

The method of embodiment 121, wherein said nucleic acid comprises a plasmid that encodes a heterologous gene or cDNA.

Embodiment 123

The method of embodiment 121, wherein said nucleic acid comprises a plasmid that encodes a class 2 CRISPR/Cas endonuclease and a guide RNA.

Embodiment 124

The method of embodiment 123, wherein said class 2 CRISPR/Cas endonuclease is a type II CRISPR/Cas endonuclease.

Embodiment 125

The method according to any one of embodiments 123-124, wherein the class 2 CRISPR/Cas endonuclease is a Cas9 polypeptide and the corresponding CRISPR/Cas guide RNA is a Cas9 guide RNA.

Embodiment 126

The method of embodiment 125, wherein said Cas9 protein is selected from the group consisting of a *Strepto-* coccus pyogenes Cas9 protein (spCas9) or a functional portion thereof, a *Staphylococcus aureus* Cas9 protein (saCas9) or a functional portion thereof, a *Streptococcus thermophilus* Cas9 protein (stCas9) or a functional portion thereof, a *Neisseria meningitides* Cas9 protein (nmCas9) or a functional portion thereof, and a *Treponema denticola* Cas9 protein (tdCas9) or a functional portion thereof.

Embodiment 127

The method of embodiment 126, wherein said Cas9 protein comprises a *Streptococcus pyogenes* Cas9 protein (spCas9).

Embodiment 128

The method of embodiment 126, wherein said Cas9 protein comprises a *Staphylococcus aureus* Cas9 protein (saCas9).

Embodiment 129

The method of embodiment 126, wherein said Cas9 protein comprises a *Streptococcus thermophilus* Cas9 protein.

Embodiment 130

The method of embodiment 126, wherein said Cas9 protein comprises a *Neisseria meningitides* Cas9 protein (nmCas9).

Embodiment 131

The method of embodiment 126, wherein said Cas9 protein comprises a *Treponema denticola* Cas9 protein (tdCas9).

Embodiment 132

The method of embodiment 123, wherein the class 2 CRISPR/Cas endonuclease is a type V or type VI CRISPR/Cas endonuclease.

Embodiment 133

The method of embodiment 132, wherein the class 2 CRISPR/Cas endonuclease is selected from the group consisting of a Cpf1 polypeptide or a functional portion thereof, a C2c1 polypeptide or a functional portion thereof, a C2c3 polypeptide or a functional portion thereof, and a C2c2 polypeptide or a functional portion thereof.

Embodiment 134

The method of embodiment 132, wherein the class 2 CRISPR/Cas endonuclease comprises a Cpf1 polypeptide.

Embodiment 135

The method according to any one of embodiments 111-134, wherein the N/P ratio of said carrier complexed to a nucleic acid ranges from about 0.01:1 up to about 100:1, or from about 2:1 up to about 25:1.

Embodiment 136

The method of embodiment 135, wherein the N/P ratio of said carrier complexed to a nucleic acid is about 10:1.

Embodiment 137

A method of making a polyrotaxane carrier for in vivo delivery of a nucleic acid, said method comprising:
providing a multi-arm PEG backbone comprising m arms where m ranges from 3 to 8;
coupling first protecting groups to x arms of said backbone where x ranges from 1 to m−1;
forming cyclic compound inclusion bodies on the arms of said PEG backbone that are not coupled to said first protecting groups; and
adding blocking groups to the arms of said PEG backbone that bear cyclic compound inclusion bodies.

Embodiment 138

The method of embodiment 137, wherein said cyclic compound comprise a compound selected from the group consisting of a cyclodextrin, a crown ether, a cucurbituril and a cyclofructan.

Embodiment 139

The method of embodiment 138, wherein said cyclic compound comprises a cyclodextrin.

Embodiment 140

The method of embodiment 139, wherein said cyclic compound comprises a cyclodextrin selected from the group consisting of an α-cyclodextrin, a β-cyclodextrin, a γ-cyclodextrin, a hydroxypropylated α-cyclodextrin, a hydroxypropylated β-cyclodextrin, a hydroxypropoylated γ-cyclodextrin, and a dimethylcyclodextrin.

Embodiment 141

The method of embodiment 138, wherein said cyclic compound comprises a cucurbituril.

Embodiment 142

The method of embodiment 141, wherein said cyclic compound comprises a cucurbituril selected from the group consisting of cucurbit[5]uril, cucurbit[6]uril, cucurbit[7]uril, cucurbit[8]uril, cucurbit[9]uril, and cucurbit[10]uril.

Embodiment 143

The method of embodiment 142, wherein said cyclic compound comprises a cucurbit[6]uril (CB[6]).

Embodiment 144

The method according to any one of embodiments 137-143, wherein said method comprises introducing one or more nucleophilic groups on cyclic compound(s).

Embodiment 145

The method of embodiment 144, wherein said cyclic compound(s) are substituted with one or more amine groups or groups derived from an amine group.

Embodiment 146

The method of embodiment 145, wherein said cyclic compound(s) are substituted with one or more groups selected from the group consisting of a primary amine, a secondary amine, a tertiary amine, and an imine group.

Embodiment 147

The method of embodiment 146, wherein said cyclic compound(s) are substituted with one or more primary amines.

Embodiment 148

The method according to any one of embodiments 144-147, where the number of nucleophilic group substituted on the cyclic compound(s) ranges from 1 up to about 20 substitutions per cyclic compound.

Embodiment 149

The method according to any one of embodiments 144-148, wherein the cyclic compounds are substituted with nucleophilic groups to provide a positive zeta potential for said carrier ranging from about +5 My up to about +50 mV.

Embodiment 150

The method according to any one of embodiments 144-149, wherein the cyclic compounds are substituted with nucleophilic groups to provide a zeta potential of about 15 mV.

Embodiment 151

The method according to any one of embodiments 137-150, wherein said multi-arm PEG comprises at least 2 arms free of cyclic compounds.

Embodiment 152

The method according to any one of embodiments 137-151, wherein said multi-arm PEG comprises from 3 up to about 12, or up to about 10, or up to about 8 arms.

Embodiment 153

The method according to any one of embodiments 137-152, wherein said PEG comprises 4 arms, or 5 arms, or 6 arms, or seven arms, or 8 arms.

Embodiment 154

The method according to any one of embodiments 137-151, wherein said PEG comprises 4 arms.

Embodiment 155

The method according to any one of embodiments 137-151, wherein said PEG comprise 4 arms where two of said arms are free of cyclic compounds.

Embodiment 156

The method according to any one of embodiments 137-155, wherein said PEG backbone has a molecular weight ranging from about 2.5 to about 10 kDA per arm.

Embodiment 157

The method according to any one of embodiments 137-156, wherein said PEG backbone comprise about 56 to about 227 ethylene oxides per arm.

Embodiment 158

The method according to any one of embodiments 137-155, wherein said PEG backbone has a molecular weight of about 1.0 kDa up to about 10 kDa per arm.

Embodiment 159

The method according to any one of embodiments 137-158, wherein the arm(s) threaded into said cyclic compound(s) each bear on average from about 5 up to about 110 cyclic compounds.

Embodiment 160

The method according to any one of embodiments 137-158, wherein the arm(s) threaded into said cyclic compound(s) each bear, on average, about 20 cyclic compounds per arm.

Embodiment 161

The method according to any one of embodiments 137-160, wherein the blocking group(s) comprise a moiety selected from the group consisting of Z-tyrosine, phenylalanine, a group having at least one benzene ring, and a group having at least one tertiary butyl.

Embodiment 162

The method of embodiment 161, wherein the blocking group(s) comprise a moiety selected from the group consisting of a Z-tyrosine, phenylaline, a benzyloxycarbonyl (Z) group, a 9-fluorenylmethyloxycarbonyl (Fmoc) group, a benzyl ester (OBz) group, a tertiary butylcarbonyl (Boc) group, and an amino acid-tertiary butyl ester (OBu) group.

Embodiment 163

The method of embodiment 161, wherein the blocking groups comprises Z-tyrosine.

Embodiment 164

The method according to any one of embodiments 137-163, wherein said first protecting group(s) comprise a protecting group, and/or a fluorophore, and/or a targeting moiety.

Embodiment 165

The method of embodiment 164, wherein said first protecting group(s) comprise a protecting group selected from the group consisting of dansyl, acetyl, amide, and 3 to 20 carbon alkyl groups, Fmoc, Tboc, 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), Benzyloxymethyl (Bom), t-butoxycarbonyl (Boc), cyclohexyloxy (cHxO), t-butoxymethyl (Bum), t-butoxy (tBuO), t-Butyl (tBu), Acetyl (Ac), and Trifluoroacetyl (TFA).

Embodiment 166

The method of embodiment 164, wherein said first protecting group(s) comprise a fluorophore.

Embodiment 167

The method of embodiment 166, wherein said fluorophore is selected from the group consisting of a rhodamine, a cyanine, an oxazine, a thiazine, a porphyrin, a phthalocyanine, a fluorescent protein, and a quantum dot.

Embodiment 168

The method of embodiment 166, wherein said fluorophore is selected from the group consisting of fluorescein isothiocyanate (especially fluorescein-5-isothiocyanate), 5-FAM (5-carboxyfluorescein), 6-FAM (6-carboxyfluorescein), 5,6-FAM, 7-hydroxycoumarin-3-carboxamide, 6-chloro-7-hydroxycoumarin-3-carboxamide-, dichlorotriazinylaminofluorescein, tetramethylrhodamine-5 (and-6)-isothiocyanate, 1,3-bis-(2-dialkylamino-5-thienyl)-substituted squarines, succinimidyl esters of 5 (and 6) carboxyfluoroscein, 5 (and 6)-carboxytetramethylrhodamine, 7-amino-4-methylcoumarin-3-acetic acid, DyLight 350, DyLight 405, DyLight 488, DyLight 550, DyLight 594, DyLight 633, DyLight 650, DyLight 680, DyLight 755, DyLight 800, Alexa fluor 350, Alexa fluor 405, Alexa fluor 488, Alexa fluor 546, Alexa fluor 555, Alexa fluor 568, Alexa fluor 594, Alexa fluor 633, Alexa fluor 647, and Alexa fluor 750.

Embodiment 169

The method of embodiment 164, wherein said first protecting group(s) comprise a targeting moiety that specifically or preferentially binds to a cell.

Embodiment 170

The method of embodiment 169, wherein said targeting moiety is selected from the group consisting of an antibody, a receptor ligand, neural cell adhesion molecule (NCAM), a cell penetrating peptide (CPP), a nucleic acid aptamer, a peptide aptamer, and a lectin.

Embodiment 171

The method of embodiment 170, wherein said targeting moiety comprises an antibody.

Embodiment 172

The method according to any one of embodiments 170-171, wherein said targeting moiety comprises a moiety that binds to a stem cell.

Embodiment 173

The method according to any one of embodiments 170-171, wherein said targeting moiety comprises a moiety that binds to a hematopoietic cell.

Embodiment 174

The method according to any one of embodiments 170-171, wherein said targeting moiety comprises a moiety that binds to a T-cell.

Embodiment 175

The method according to any one of embodiments 170-171, wherein said targeting moiety comprises a moiety that binds to a muscle cell.

Embodiment 176

The method according to any one of embodiments 170-171, wherein said targeting moiety binds a target selected from the group consisting of CD45, CD3, erbB2, Her2, CD22, CD74, CD19, CD20, CD33, CD40, MUC1, IL-15R, HLA-DR, EGP-1, EGP-2, G250, prostate specific membrane antigen (PSMA), prostate specific antigen (PSA), prostatic acid phosphatase (PAP), and placental alkaline phosphatase.

Embodiment 177

The method according to any one of embodiments 170-171, wherein said targeting moiety comprises a moiety that binds to a cancer cell marker.

Embodiment 178

The method of embodiment 177, wherein said targeting moiety comprises a moiety that binds to a cancer cell marker selected from the group consisting of 5 alpha reductase, α-fetoprotein, AM-1, APC, APRIL, BAGE, β-catenin, Bcl2, bcr-abl (b3a2), CA-125, CASP-8/FLICE, Cathepsins, CD19, CD20, CD21, CD23, CD22, CD38, CD33, CD35, CD44, CD45, CD46, CD5, CD52, CD55, CD59 (791Tgp72), CDC127, CDK4, CEA, c-myc, Cox-2, DCC, DcR3, E6/E7, EGFR, EMBP, Ena78, FGF8b and FGF8a, FLK-1/KDR, Folic Acid Receptor, G250, GAGE-Family, gastrin 17, Gastrin-releasing hormone (bombesin), GD2/GD3/GM2, GnRH, GnTV, gp100/Pmel17, gp-100-in4, gp15, gp75/TRP-1, hCG, Heparanase, Her2/neu, Her3, HMTV, Hsp70, hTERT, (telomerase), IGFR1, IL-13R, iNOS, Ki 67, KIAA0205, K-ras, H-ras, N-ras, KSA, (CO17-1A), LDLR-FUT, MAGE Family (MAGE1, MAGE3, etc.), Mammaglobin, MAP17, Melan-A/, MART-1, mesothelin, MIC A/B, MT-MMP's, such as MMP2, MMP3, MMP7, MMP9, Mox1, Mucin, such as MUC-1, MUC-2, MUC-3, and MUC-4, MUM-1, NY-ESO-1, Osteonectin, p15, P170/MDR1, p53, p97/melanotransferrin, PAI-1, PDGF, Plasminogen (uPA), PRAME, Probasin, Progenipoietin, PSA, PSM, RAGE-1, Rb, RCAS1, SART-1, SSX gene, family, STAT3, STn, (mucin assoc.), TAG-72, TGF-□, TGF-β, Thymosin β 15, IFN-□, TPA, TPI, TRP-2, Tyrosinase, VEGF, ZAG, p16INK4, and Glutathione S-transferase.

Embodiment 179

The method of embodiment 170, wherein said targeting moiety comprises a transferrin.

Embodiment 180

The method according to any one of embodiments 137-179, wherein said blocking group(s) are attached arm(s) of said backbone by a cleavable linkage.

Embodiment 181

The method according to any one of embodiments 144-179, wherein said a or more nucleophilic groups are attached to said cyclic compounds by a cleavable linkage.

Embodiment 182

The method according to any one of embodiments 180-181, wherein said cleavable linkage comprises a redox-responsive linker, a pH responsive linker, and an enzymatically cleavable linker.

Embodiment 183

The method of embodiment 182, wherein said cleavable linkage comprises a redox-responsive disulfide linker.

Embodiment 184

The method of embodiment 182, wherein said cleavable linkage comprises a pH responsive hydrazine linker.

Embodiment 185

The method of embodiment 182, wherein said cleavable linkage comprises an enzymatically cleavable linker.

Embodiment 186

The method of embodiment 185, wherein said linkage comprises a linker cleavable by a protease.

Embodiment 187

The method of embodiment 186, wherein said linkage comprises a linker cleavable by a matrix metalloprotease or a cathepsin.

Embodiment 188

The construct according to any one of embodiments 186-187, wherein said peptide linker comprises a linker comprises a moiety selected from the group consisting of dipeptide valine-citrulline (Val-Cit), dipeptide Phe-Lys, Mc-vc-PAB-MMAE, Mc-vc-PAB-MMAF, Mc-va-PBD dimer, Mc-vc-PAB-CM-seco-DUBA, Gly-Phe-Leu-Gly (GFLG), GPLGV, and GPLGVRG.

Embodiment 189

A kit for delivering a nucleic acid in vivo to a mammal, said kit comprising: a container containing a polyrotaxane carrier according to any one of embodiments 1-58.

Embodiment 190

The kit of embodiment 189, wherein said kit further comprises a container containing a nucleic acid that is to be delivered to said mammal.

Embodiment 191

The kit of embodiment 190, wherein said nucleic acid is in a container separate from the container containing said carrier.

Embodiment 192

The kit of embodiment 191, wherein said nucleic acid comprises a nucleic acid as recited in any one of embodiments 59-93.

Embodiment 193

The kit of embodiment 190, wherein said nucleic acid is provided as a complex with said carrier.

Embodiment 194

The kit of embodiment 193, wherein said carrier complexed with said nucleic acid comprises a complex according to any one of embodiments 59-77.

Embodiment 195

The kit of embodiment 193, wherein said carrier complexed with said nucleic acid comprises a construct according to any one of embodiments 82-95.

Embodiment 196

The kit according to any one of embodiments 189-195, wherein said kit comprise instructional materials teaching the use of said carrier to deliver a nucleic acid to a cell in vivo.

Embodiment 197

A construct for the treatment of a cancer, said construct comprising: a polyrotaxane carrier according to any one of embodiments 1-58, wherein said carrier is complexed with a plasmid encoding a cytokine.

Embodiment 198

The construct of embodiment 197, wherein said cytokine comprises one or more cytokines selected from the group consisting of interleukin 12 (IL-12), interferon alpha (IFN-α), interferon beta (IFN-β), interferon gamma (IFN-γ), interleukin 1 (IL-1), interleukin (IL-2), interleukin 4 (IL-4), interleukin 6 (IL-6), interleukin 7 (IL-7), interleukin 11 (IL-11), interleukin 15 (IL-15), and interleukin 18 (IL-18).

Embodiment 199

The construct of embodiment 197, wherein said cytokine comprises IL-12.

Embodiment 200

The construct of embodiment 199, wherein said cytokine comprises a combination of IL2 and IL-12.

Embodiment 201

The construct of embodiment 199, wherein said cytokine comprises a combination of IL-15 and IL-12.

Embodiment 202

The construct of embodiment 199, wherein said cytokine comprises a combination of IL-7 and IL-12.

Embodiment 203

The construct of embodiment 199, wherein said cytokine comprises a combination of IL-21 and IL-12.

Embodiment 204

The construct of embodiment 199, wherein said cytokine comprises a combination of IL-18 and IL-12.

Embodiment 205

The construct of embodiment 199, wherein said cytokine comprises a combination of GM-CSF and IL-12.

Embodiment 206

The construct of embodiment 199, wherein said cytokine comprises a combination of interferon alpha and IL-12.

Embodiment 207

The construct of embodiment 199, wherein said cytokine comprises a combination of a chemokine and/or an antiogenic cytokine and IL-12.

Embodiment 208

The construct of embodiment 197, wherein said cytokine comprises an interferon.

Embodiment 209

The construct of embodiment 208, wherein said cytokine comprises an interferon alpha.

Embodiment 210

The construct of embodiment 209, wherein said cytokine comprises an interferon beta.

Embodiment 211

The construct of embodiment 209, wherein said cytokine comprises an interferon gamma.

Embodiment 212

The construct according to any one of embodiments 197-211, wherein said plasmid comprises a nucleic acid encoding said cytokine under the control of a constitutive promoter.

Embodiment 213

The construct according to any one of embodiments 197-211, wherein said plasmid comprises a nucleic acid encoding said cytokine under the control of an inducible promoter.

Embodiment 214

The construct according to any one of embodiments 197-211, wherein said plasmid comprises a nucleic acid encoding said cytokine under the control of a tissue-specific promoter.

Embodiment 215

A pharmaceutical formulation comprising: a polyrotaxane construct according to any one of embodiments 197-214; and a pharmaceutically acceptable carrier.

Embodiment 216

The formulation of embodiment 215, wherein said polyrotaxane carrier is complexed with a nucleic acid.

Embodiment 217

The formulation according to any one of embodiments 215-216, wherein said formulation is formulated for administration via a route selected from the group consisting of isophoretic delivery, transdermal delivery, aerosol administration, administration via inhalation, oral administration, intravenous administration, intraarterial administration, intramuscular administration, topical delivery to the eye, intraocular injection, vaginal administration, and rectal administration.

Embodiment 218

The formulation according to any one of embodiments 215-217, wherein said formulation is a unit dosage formulation.

Embodiment 219

A method of treating a cancer in a mammal, said method comprising: administering to said mammal an effective amount of a construct according to any one of embodiments 197-214.

Embodiment 220

The method of embodiment 219, wherein said cancer comprises a colon cancer.

Embodiment 221

The method of embodiment 219, wherein said cancer comprises pancreatic ductal adenocarcinoma (PDAC).

Embodiment 222

The method of embodiment 219, wherein said cancer comprises a cancer selected from the group consisting of acute lymphoblastic leukemia (ALL), acute myeloid leukemia (AML), Adrenocortical carcinoma, AIDS-related cancers (e.g., Kaposi sarcoma, lymphoma), anal cancer, appendix cancer, astrocytomas, atypical teratoid/rhabdoid tumor, bile duct cancer, extrahepatic cancer, bladder cancer, bone cancer (e.g., Ewing sarcoma, osteosarcoma, malignant fibrous histiocytoma), brain stem glioma, brain tumors (e.g., astrocytomas, brain and spinal cord tumors, brain stem glioma, central nervous system atypical teratoid/rhabdoid tumor, central nervous system embryonal tumors, central nervous system germ cell tumors, craniopharyngioma, ependymoma, breast cancer, bronchial tumors, burkitt lymphoma, carcinoid tumors (e.g., childhood, gastrointestinal), cardiac tumors, cervical cancer, chordoma, chronic lymphocytic leukemia (CLL), chronic myelogenous leukemia (CML), chronic myeloproliferative disorders, colon cancer, colorectal cancer, craniopharyngioma, cutaneous t-cell lymphoma, duct cancers e.g. (bile, extrahepatic), ductal carcinoma in situ (DCIS), embryonal tumors, endometrial cancer, ependymoma, esophageal cancer, esthesioneuroblastoma, extracranial germ cell tumor, extragonadal germ cell tumor, extrahepatic bile duct cancer, eye cancer (e.g., intraocular melanoma, retinoblastoma), fibrous histiocytoma of bone, malignant, and osteosarcoma, gallbladder cancer, gastric (stomach) cancer, gastrointestinal carcinoid tumor, gastrointestinal stromal tumors (GIST), germ cell tumors (e.g., ovarian cancer, testicular cancer, extracranial cancers, extragonadal cancers, central nervous system), gestational trophoblastic tumor, brain stem cancer, hairy cell leukemia, head and neck cancer, heart cancer, hepatocellular (liver) cancer, histiocytosis, langerhans cell cancer, Hodgkin lymphoma, hypopharyngeal cancer, intraocular melanoma, islet cell tumors, pancreatic neuroendocrine tumors, kaposi sarcoma, kidney cancer (e.g., renal cell, Wilm's tumor, and other kidney tumors), langerhans cell histiocytosis, laryngeal cancer, leukemia, acute lymphoblastic (ALL), acute myeloid (AML), chronic lymphocytic (CLL), chronic myelogenous (CML), hairy cell, lip and oral cavity cancer, liver cancer (primary), lobular carcinoma in situ (LCIS), lung cancer (e.g., childhood, non-small cell, small cell), lymphoma (e.g., AIDS-related, Burkitt (e.g., non-Hodgkin lymphoma), cutaneous T-Cell (e.g., mycosis fungoides, Sezary syndrome), Hodgkin, non-Hodgkin, primary central nervous system (CNS)), macroglobulinemia, Waldenström, male breast cancer, malignant fibrous histiocytoma of bone and osteosarcoma, melanoma (e.g., childhood, intraocular (eye)), merkel cell carcinoma, mesothelioma, metastatic squamous neck cancer, midline tract carcinoma, mouth cancer, multiple endocrine neoplasia syndromes, multiple myeloma/plasma cell neoplasm, mycosis fungoides, myelodysplastic syndromes, Myelogenous Leukemia, Chronic (CML), multiple myeloma, nasal cavity and paranasal sinus cancer, nasopharyngeal cancer, neuroblastoma, oral cavity cancer, lip and oropharyngeal cancer, osteosarcoma, ovarian cancer, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm, pleuropulmonary blastoma, primary central nervous system (CNS) lymphoma, prostate cancer, rectal cancer, renal cell (kidney) cancer, renal pelvis and ureter, transitional cell cancer, rhabdomyosarcoma, salivary gland cancer, sarcoma (e.g., Ewing, Kaposi, osteosarcoma, rhadomyosarcoma, soft tissue, uterine), Sezary syndrome, skin cancer (e.g., melanoma, merkel cell carcinoma, basal cell carcinoma, nonmelanoma), small intestine cancer, squamous cell carcinoma, squamous neck cancer with occult primary, stomach (gastric) cancer, testicular cancer, throat cancer, thymoma and thymic carcinoma, thyroid cancer, trophoblastic tumor, ureter and renal pelvis cancer, urethral cancer, uterine cancer, endometrial cancer, uterine sarcoma, vaginal cancer, vulvar cancer, Waldenstrom macroglobulinemia, and Wilm's tumor.

Embodiment 223

The method according to any one of embodiments 219-222, wherein said method comprises a primary therapy in a chemotherapeutic regimen.

Embodiment 224

The method according to any one of embodiments 219-222, wherein said method comprises an adjunct therapy in a chemotherapeutic regimen.

Embodiment 225

The method according to any one of embodiments 219-224, wherein said polyrotaxane construct is a component in a multi-drug chemotherapeutic regimen.

Embodiment 226

The method according to any one of embodiments 219-225, wherein said administering comprises administration via a route selected from the group consisting of isophoretic delivery, transdermal delivery, aerosol administration, administration via inhalation, oral administration, intravenous administration, intraarterial administration, intramuscular administration, topical delivery to the eye, intraocular injection, vaginal administration, and rectal administration.

Embodiment 227

The method according to any one of embodiments 219-225, wherein said administering comprises systemic administration.

Embodiment 228

The method according to any one of embodiments 219-227, wherein said mammal is a human.

Embodiment 229

The method according to any one of embodiments 219-227, wherein said mammal is a non-human mammal.

Embodiment 230

The method according to any one of embodiments 219-229, wherein said polyrotaxane carrier comprises a targeting moiety that specifically or preferentially binds to a cell.

Embodiment 231

The method of embodiment 228, wherein said targeting moiety is selected from the group consisting of an antibody, a receptor ligand, neural cell adhesion molecule (NCAM), a cell penetrating peptide (CPP), a nucleic acid aptamer, a peptide aptamer, and a lectin.

Embodiment 232

The method of embodiment 228, wherein said targeting moiety comprises an antibody.

Embodiment 233

The method according to any one of embodiments 228-232, wherein said targeting moiety comprises a moiety that binds to cancer cell marker.

Embodiment 234

The method of embodiment 233, wherein said targeting moiety binds a target selected from the group consisting of 5 alpha reductase, α-fetoprotein, AM-1, APC, APRIL, BAGE, β-catenin, Bc12, bcr-abl (b3a2), CA-125, CASP-8/FLICE, Cathepsins, CD19, CD20, CD21, CD23, CD22, CD38, CD33, CD35, CD44, CD45, CD46, CD5, CD52, CD55, CD59 (791Tgp72), CDC127, CDK4, CEA, c-myc, Cox-2, DCC, DcR3, E6/E7, EGFR, EMBP, Ena78, FGF8b and FGF8a, FLK-1/KDR, Folic Acid Receptor, G250, GAGE-Family, gastrin 17, Gastrin-releasing hormone (bombesin), GD2/GD3/GM2, GnRH, GnTV, gp100/Pmel17, gp-100-in4, gp15, gp75/TRP-1, hCG, Heparanase, Her2/neu, Her3, HMTV, Hsp70, hTERT, (telomerase), IGFR1, IL-13R, iNOS, Ki 67, KIAA0205, K-ras, H-ras, N-ras, KSA, (CO17-1A), LDLR-FUT, MAGE Family (MAGE1, MAGE3, etc.), Mammaglobin, MAP17, Melan-A/, MART-1, mesothelin, MIC A/B, MT-MMP's, such as MMP2, MMP3, MMP7, MMP9, Mox, Mucin, such as MUC-1, MUC-2, MUC-3, and MUC-4, MUM-1, NY-ESO-1, Osteonectin, p15, P170/MDR1, p53, p97/melanotransferrin, PAI-1, PDGF, Plasminogen (uPA), PRAME, Probasin, Progenipoietin, PSA, PSM, RAGE-1, Rb, RCAS1, SART-1, SSX gene, family, STAT3, STn, (mucin assoc.), TAG-72, TGF-α, TGF-β, Thymosin β 15, TPA, TPI, TRP-2, Tyrosinase, VEGF, ZAG, p16INK4, and Glutathione S-transferase.

Embodiment 235

The method of embodiment 228, wherein said targeting moiety comprises a transferrin.

While the polyrotaxane nucleic acid delivery vehicles are described herein with respect to polyethylene glycol (PEG) backbones, in certain embodiments, other polymer backbones are contemplated. Accordingly, in certain embodiments, the polymer backbone comprise one or more polymers selected from the group consisting of polyethylene glycol, polypropylene glycol, polybutylene glycol, polypentylene glycol, polyhexylene glycol, polymethyl vinyl ether, polyethyl vinyl ether, polyisoprene, polyisobutylene, polybutadiene, and copolymers thereof. In one embodiment, the polymer is a poly(ethylene glycol), a derivative thereof, or a copolymer that reacts with the poly(ethylene glycol) segment. In certain embodiments, the polymer can also be poly(propylene glycol) or other poly(alkylene glycols). In certain embodiments, the copolymer may be any one of a variety of biodegradable and biocompatible copolymers that contain ethylene glycol units such as polyesters, polyurethanes, polyamides, polyethers, polysaccharides, poly(amino acids), polypeptides, or a protein. Modified poly(ethylene glycol) may be also be used, such as pegylated polysaccharides, pegylated polyaminoacids, and pegylated proteins. In certain embodiments, the poly(ethylene glycol) derivatives or copolymers may have poly(ethylene glyol) or polypropylene oxide) segment(s) at the end(s), in which the middle segment carries positive charge.

In various embodiments, the carriers described and/or claimed herein exclude backbones that are dendrimers.

Definitions

The terms "subject," "individual," and "patient" and "mammal" may be used interchangeably and refer to a mammal, preferably a human or a non-human primate, but also domesticated mammals (e.g., canine or feline), laboratory mammals (e.g., mouse, rat, rabbit, hamster, guinea pig), and agricultural mammals (e.g., equine, bovine, porcine, ovine). In various embodiments, the subject can be a human (e.g., adult male, adult female, adolescent male, adolescent female, male child, female child) under the care of a physician or other health worker in a hospital, psychiatric care facility, as an outpatient, or other clinical context. In certain embodiments, the subject may not be under the care or prescription of a physician or other health worker.

The terms "cyclic compound", "cyclic molecule" and grammatical variations thereof refer to a molecule that is cyclic in that it has a ring structure and also to a molecule which is of a substantial ring structure. That is, the term "substantial ring" means to include molecules in which the ring is not closed completely, as in the letter "C", and molecules having a helical structure in which as in the letter "C", one end and the other end are not connected and placed in a piled manner. Cyclic compounds include, but are not limited to, cyclodextrins, crown ethers, cucurbiturils cyclofructans, and the like.

Cucurbiturils are macrocyclic molecules made of glycoluril ($=C_4H_2N_4O_2=$) monomers linked by methylene bridges ($—CH_2—$). The oxygen atoms are located along the edges of the band and are tilted inwards, forming a partly enclosed cavity. The name is derived from the resemblance of this molecule with a pumpkin of the family of Cucurbitaceae.

An "inclusion compound" or "inclusion complex" is a complex in which one chemical compound forms a cavity in which molecules of a second "guest" compound are located.

The term "nucleophile-substituted cyclic compound" refers to a cyclic compound having at least one attached nucleophilic group.

The term "amine-substituted cyclic compound" refers to a cyclic compound having at least one attached amine group. Likewise, the term "amine-substituted cyclodextrins" refers to a cyclodextrin compound having at least one attached amine group.

The term "amine group" refers to primary, secondary and tertiary amine groups as well as groups derived from amine groups, such as imine groups.

The term "nucleic acid", and equivalent terms such as polynucleotide, refers to a polymeric form of nucleotides of any length, such as ribonucleotides, deoxyribonucleotides or peptide nucleic acids (PNAs), that comprise purine and pyrimidine bases, or other natural, chemically or biochemically modified, non-natural, or derivatized nucleotide bases. The nucleic acid may be double stranded or single stranded. References to single stranded nucleic acids include references to the sense or antisense strands. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The terms nucleoside, nucleotide, deoxynucleoside and deoxynucleotide generally include complements, fragments and variants of the nucleoside, nucleotide, deoxynucleoside and deoxynucleotide, or analogs thereof.

As used herein, the term recombinant refers to a compound or composition produced by human intervention.

As used herein, a "recombinant" nucleic acid or protein molecule is a molecule where the nucleic acid molecule which encodes the protein has been modified in vitro, so that its sequence is not naturally occurring, or corresponds to naturally occurring sequences that are not positioned as they would be positioned in a genome which has not been modified.

The term "target cell" is used herein to mean any cell into which an exogenous nucleic acid molecule is to be introduced.

The term "branched" polymer is meant to designate a polymer having side chains or branches that are bonded to the polymer (e.g., PEG) backbone. In certain embodiments side-chains all branch from the same or approximately the same location on the backbone. In certain embodiments, different side-chains attach to different locations along the backbone. In certain embodiments, the backbone comprises a star polymer. The term "star polymer" is used to describe polymer molecule structures that have multiple arms extending generally from a central core.

The term "bulky moieties" and grammatical variations thereof refers to any substituents group that has sufficient bulk to substantially inhibit dethreading of cyclic compounds from a chain (arm) chain of a polymer backbone.

The terms "cleavable linkage", "biocleavable linkage", "biocleavable linker" "biodegradable linker", "biodegradable linkages", "bio responsive linker or linkage", "on-demand released linker or linkage" and grammatical variations thereof are defined as types of specific chemical moieties or groups used within the polycation that couple and optionally cross-link a bulky moiety to the polymer backbone and which, in vivo, and preferably during or after transfection, cleave the bulky moieties from said polymer backbone.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

By "hybridizable" or "complementary" or "substantially complementary" it is meant that a nucleic acid (e.g. RNA, DNA) comprises a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. Standard Watson-Crick base-pairing includes: adenine (A) pairing with thymidine (T), adenine (A) pairing with uracil (U), and guanine (G) pairing with cytosine (C) [DNA, RNA]. In addition, for hybridization between two RNA molecules (e.g., dsRNA), and for hybridization of a DNA molecule with an RNA molecule (e.g., when a DNA target nucleic acid base pairs with a guide RNA, etc.): guanine (G) can also base pair with uracil (U). For example, G/U base-pairing is partially responsible for the degeneracy (i.e., redundancy) of the genetic code in the context of tRNA anti-codon base-pairing with codons in mRNA. Thus, in the context of this disclosure, a guanine (G) (e.g., of a guide RNA molecule; of a target nucleic acid base pairing with a guide RNA, etc.) is considered complementary to both a uracil (U) and to an adenine (A). For example, when a G/U base-pair can be made at a given nucleotide position of a protein• binding segment (e.g., dsRNA duplex) of a guide RNA molecule, the position is not considered to be non-complementary, but is instead considered to be complementary.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementarity, variables well known in the art. The greater the degree of complementarity between two nucleotide sequences, the greater the value of the melting temperature (Tm) for hybrids of nucleic acids having those sequences. For hybridizations between nucleic acids with short stretches of complementarity (e.g., complementarity over 35 or less, 30 or less, 25 or less, 22 or less, 20 or less, or 18 or less nucleotides) the position of mismatches can become important (see Sambrook et al., supra). Typically, the length for a hybridizable nucleic acid is 8 nucleotides or more (e.g., 10 nucleotides or more, 12 nucleotides or more, 15 nucleotides or more, 20 nucleotides or more, 22 nucleotides or more, 25 nucleotides or more, or 30 nucleotides or more). Temperature, wash solution salt concentration, and other conditions may be adjusted as necessary according to factors such as length of the region of complementation and the degree of complementation.

It is understood that the sequence of a polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a bulge, a loop structure or hairpin structure, etc.). A polynucleotide can comprise 60% or more, 65% or more, 70% or more, 75% or more, 80% or more, 85% or more, 90% or more, 95% or more, 98% or more, 99% or more, 99.5% or more, or 100% sequence complementarity to a target region within the target nucleic acid sequence to which it will hybridize. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined using any convenient method. Example methods include BLAST programs (basic local alignment search tools) and PowerBLAST programs (see, e.g., Altschul et al. (1990) *J. Mol. Biol.*, 215: 403-410; Zhang and Madden (1997) *Genome Res.*, 7: 649-656), the Gap program (Wisconsin Sequence Analysis Package, Version 8 for Unix, Genetics Computer Group, University Research Park, Madison Wis.), e.g., using default settings, which uses the algorithm of Smith and Waterman (1981) *Adv. Appl. Math.* 2: 482-489), and the like.

"Binding" as used herein (e.g. with reference to an RNA-binding domain of a polypeptide, binding to a target nucleic acid, and the like) refers to a non-covalent interaction between macromolecules (e.g., between a protein and a nucleic acid; between a Cas9 protein/guide RNA complex and a target nucleic acid; and the like). While in a state of non•covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant ($K_D$) of less than $10^{-6}$ M, less than $10^{-7}$ M, less than $10^{-8}$ M, less than $10^{-9}$ M, less than $10^{-10}$ M, less than $10^{-+}$ M, less than $10^{-12}$ M, less than $10^{-13}$ M, less than $10^{-4}$ M, or less than $10^{-1}$ M. "Affinity" refers to the strength of binding, increased binding affinity being correlated with a lower $K_D$.

A DNA sequence that "encodes" a particular RNA is a DNA nucleic acid sequence that is transcribed into RNA. A DNA polynucleotide may encode an RNA (mRNA) that is translated into protein (and therefore the DNA and the mRNA both encode the protein), or a DNA polynucleotide may encode an RNA that is not translated into protein (e.g. tRNA, rRNA, microRNA (miRNA), a "non-coding" RNA (ncRNA), a guide RNA, etc.).

A "protein coding sequence" or a sequence that encodes a particular protein or polypeptide, is a nucleic acid sequence that is transcribed into mRNA (in the case of DNA) and is translated (in the case of mRNA) into a polypeptide in vitro or in vivo when placed under the control of appropriate regulatory sequences. The boundaries of the coding sequence are determined by a start codon at the 5' terminus (N-terminus) and a translation stop nonsense codon at the 3' terminus (C-terminus). A coding sequence can include, but is not limited to, cDNA from prokaryotic or eukaryotic mRNA, genomic DNA sequences from prokaryotic or eukaryotic DNA, and synthetic nucleic acids. A transcription termination sequence will usually be located 3' to the coding sequence.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., guide RNA) or a coding sequence (e.g., a class 2 CRISPR/Cas endonuclease such as a Cas9 protein) and/or regulate translation of an encoded polypeptide.

As used herein, a "promoter sequence" is a DNA regulatory region capable of binding RNA polymerase and initiating transcription of a downstream (3' direction) coding or non-coding sequence. For purposes of the present disclosure, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present disclosure.

The term "naturally-occurring" or "unmodified" or "wild type" as used herein as applied to a nucleic acid, a polypeptide, a cell, or an organism, refers to a nucleic acid, polypeptide, cell, or organism that is found in nature. For example, a polypeptide or polynucleotide sequence that is present in an organism (including viruses) that can be isolated from a source in nature and which has not been intentionally modified by a human in the laboratory is wild type (and naturally occurring).

"Heterologous," as used herein, means a nucleotide or polypeptide sequence that is not found in the native nucleic acid or protein, respectively. For example, in a chimeric Cas9 protein, the RNA-binding domain of a naturally-occurring bacterial Cas9 polypeptide (or a variant thereof) may be fused to a heterologous polypeptide sequence (i.e. a polypeptide sequence from a protein other than Cas9 or a polypeptide sequence from another organism). The heterologous polypeptide sequence may exhibit an activity (e.g., enzymatic activity) that will also be exhibited by the chimeric Cas9 protein (e.g., methyltransferase activity, acetyltransferase activity, kinase activity, ubiquitinating activity, etc.). A heterologous nucleic acid sequence may be linked to a naturally-occurring nucleic acid sequence (or a variant thereof) (e.g., by genetic engineering) to generate a chimeric nucleotide sequence encoding a chimeric polypeptide. As another example, in a fusion variant Cas9 polypeptide, a variant Cas9 polypeptide may be fused to a heterologous polypeptide (i.e. a polypeptide other than Cas9), which exhibits an activity that will also be exhibited by the fusion variant Cas9 polypeptide. A heterologous nucleic acid sequence may be linked to a variant Cas9 polypeptide (e.g., by genetic engineering) to generate a nucleotide sequence encoding a fusion protein.

A "vector" or "expression vector" is a replicon, such as plasmid, or cosmid, to which another DNA segment, i.e. an "insert", may be attached so as to bring about the expression of the attached segment in a cell.

An "expression cassette" comprises a DNA coding sequence operably linked to a promoter. "Operably linked" refers to a juxtaposition wherein the components so described are in a relationship permitting them to function in their intended manner. For instance, a promoter is operably linked to a coding sequence (or the coding sequence can also be said to be operably linked to the promoter) if the promoter affects its transcription or expression.

The terms "recombinant expression vector," or "DNA construct" are used interchangeably herein to refer to a DNA molecule comprising a vector and one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

A "target nucleic acid" as used herein is a polynucleotide (e.g., DNA such as genomic DNA) that includes a site ("target site" or "target sequence") targeted by a construct, e.g., a genome editing endonuclease. When the genome editing endonuclease is a CRISPR/Cas endonuclease, the target sequence is the sequence to which the guide sequence of a subject CRISPR/Cas guide RNA (e.g., a Cas9 guide RNA) will hybridize. For example, the target site (or target sequence) 5'-GAGCAUATC-3' within a target nucleic acid is targeted by (or is bound by, or hybridizes with, or is complementary to) the sequence 5'-GAUAUGCUC-3'. Suitable hybridization conditions include physiological conditions normally present in a cell. For a double stranded target nucleic acid, the strand of the target nucleic acid that is complementary to and hybridizes with the guide RNA is referred to as the "complementary strand" or "target strand"; while the strand of the target nucleic acid that is complementary to the "target strand" (and is therefore not complementary to the guide RNA) is referred to as the "non-target strand" or "non• complementary strand".

By "cleavage" it is meant the breakage of the covalent backbone of a target molecule, e.g., a nucleic acid molecule (e.g., RNA, DNA). Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. In some embodiments, a complex comprising a CRISPR/Cas protein (e.g., a Cas9 protein) and a corresponding guide RNA is used for targeted cleavage of a double stranded DNA (dsDNA), e.g., induction of a double-stranded DNA break (DSB).

"Nuclease" and "endonuclease" are used interchangeably herein to mean an enzyme which possesses catalytic activity for nucleic acid cleavage (e.g., ribonuclease activity (ribonucleic acid cleavage), deoxyribonuclease activity (deoxyribonucleic acid cleavage), etc.). A "genome editing endonuclease" is an endonuclease that can be used for the editing of a cell's genome (e.g., by cleaving at a targeted location within the cell's genomic DNA). Examples of genome editing endonucleases include but are not limited to class 2 CRISPR/Cas endonucleases such as: (a) type II CRISPR/Cas proteins, e.g., a Cas9 protein; (b) type V CRISPR/Cas proteins, e.g., a Cpf1 protein, a C2c1 protein, a C2c3 protein, and the like; and (c) type VI CRISPR/Cas proteins, e.g., a C2c2 protein.

By "cleavage domain" or "active domain" or "nuclease domain" of a nuclease it is meant the polypeptide sequence or domain within the nuclease which possesses the catalytic activity for nucleic acid cleavage. A cleavage domain can be contained in a single polypeptide chain or cleavage activity can result from the association of two (or more) polypeptides. A single nuclease domain may consist of more than one isolated stretch of amino acids within a given polypeptide.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

In some instances, a component (e.g., a nucleic acid component (e.g., a CRISPR/Cas guide RNA); a protein component (e.g., genome editing endonuclease such as a Cas9 protein); and the like) includes a label moiety. The terms "label", "detectable label", or "label moiety" as used herein refer to any moiety that provides for signal detection and may vary widely depending on the particular nature of the assay. Label moieties of interest include both directly detectable labels (direct labels)(e.g., a fluorescent label) and indirectly detectable labels (indirect labels)(e.g., a binding pair member). A fluorescent label can be any fluorescent pair member). A fluorescent label can be any fluorescent label (e.g., a fluorescent dye (e.g., fluorescein, Texas red, rhodamine, ALEXAFLUOR® labels, and the like), a fluorescent protein (e.g., green fluorescent protein (GFP), enhanced GFP (EGFP), yellow fluorescent protein (YFP), red fluorescent protein (RFP), cyan fluorescent protein (CFP), cherry, tomato, tangerine, and any fluorescent derivative thereof), etc.). Suitable detectable (directly or indirectly) label moieties for use in the methods include any moiety that is detectable by spectroscopic, photochemical, biochemical, immunochemical, electrical, optical, chemical, or other means. For example, suitable indirect labels include biotin (a binding pair member), which can be bound by streptavidin (which can itself be directly or indirectly labeled). Labels can also include: a radiolabel (a direct label) (e.g., $^3$H, $^{125}$I, $^{35}$S $^{14}$C, $^{32}$P, and the like); an enzyme (an indirect label) (e.g., peroxidase, alkaline phosphatase, galactosidase, luciferase, glucose oxidase, and the like); a fluorescent protein (a direct label)(e.g., green fluorescent protein, red fluorescent protein, yellow fluorescent protein, and any convenient derivatives thereof); a metal label (a direct label); a colorimetric label; a binding pair member; and the like. By "partner of a binding pair" or "binding pair member" is meant one of a first and a second moiety, wherein the first and the second moiety have a specific binding affinity for each other. Suitable binding pairs include, but are not limited to: antigen/antibodies (for example, digoxigenin/anti-digoxigenin, dinitrophenyl (D NP)/anti-D NP, dansyl-X-anti-dansyl, fluorescein/anti-fluorescein, lucifer yellow/anti-lucifer yellow, and rhodamine anti-rhodamine), biotin/avidin (or biotin/streptavidin) and calmodulin binding protein (CBP)/calmodulin. Any binding pair member can be suitable for use as an indirectly detectable label moiety. Any given component, or combination of components can be unlabeled, or can be detectably labeled with a label moiety. In some cases, when two or more components are labeled, they can be labeled with label moieties that are distinguishable from one another.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to V$_H$-C$_H$1 by a disulfide bond. The F(ab)'$_2$ may be reduced under mild conditions to break the disulfide linkage in the hinge region thereby converting the (Fab')$_2$ dimer into a Fab' monomer. The Fab' monomer is essentially a Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Certain preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked V$_H$-V$_L$ heterodimer which may be expressed from a nucleic acid including V$_H$- and V$_L$-encoding sequences either joined directly or joined by a peptide-encoding linker. Huston, et al. (1988) *Proc. Nat. Acad. Sci. USA*, 85: 5879-5883. While the V$_H$ and V$_L$ are connected to each as a single polypeptide chain, the V$_H$ and V$_L$ domains associate non-covalently. The first functional antibody molecules to be expressed on the surface of filamentous phage were single-chain Fvs (scFv), however, alternative expression strategies have also been successful. For example, Fab molecules can be displayed on phage if one of the chains (heavy or light) is fused to g3 capsid protein and the complementary chain exported to the periplasm as a soluble molecule. The two chains can be encoded on the same or on different replicons. The important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three-dimensional structure substantially similar to the structure of an antigen-binding site are known to those of skill in the art (see e.g., U.S. Pat. Nos. 5,091,513, 5,132,405 and 4,956,778). In various embodiments antibodies include all that have been displayed on phage (e.g., scFv, Fv, Fab and disulfide linked Fv) (Reiter et al. (1995) *Protein Eng.* 8: 1323-1331). In certain embodiments antibodies include, but are not limited to antibodies or antibody fragments selected from the group consisting of Fab, Fab', Fab'-SH, F(ab')$_2$, Fv, Fv', Fd, Fd', scFv, hsFv fragments, single-chain antibodies, cameloid antibodies, diabodies, and other fragments.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (1. Lefkovits ed., Academic Press 1997); and Cell and Tissue Culture: Laboratory Procedures in Biotechnology (Doyle & Griffiths, John Wiley & Sons 1998).

BRIEF DESCRIPTION OF THE DRAWINGS

As shown in FIG. 3A, the G4 PRX combines the use of a multi-arm PEG backbone to improve biodistribution and bio-cleavable linkages to enhance intracellular plasmid release. R1 and R1' are independently selected bulky end groups (e.g., with aromatic rings and/or fused rings) (e.g., Z-tyrosine, phenylalanine). R2 and R2' are independently selected protecting groups and/or fluorophores, and/or targeting moieties (e.g., FITC, folic acid, targeting peptide, antibody, etc.). The cleavable linkers are cleavable in response to biological conditions at the target site (e.g., target cell). Such linkages include, but are not limited to redox-responsive disulfide linkers, pH-responsive hydrazine linkers, enzyme responsive linkers, etc.). and include. FIG. 3B illustrates a G4 PRX with cleavable linkages (e.g., a disulfide linkage) between the PEG backbone and bulky stopper (top), or between the cyclic compound (e.g., CD ring) and its conjugated cationic tertiary amine groups, which upon cleavage and removal of amines, can lead to the PRX and plasmid dissociation via a charge reduction mechanism.

FIG. 22, panels A and B, shows that multi-arm PRX nanocarrier improved the safety of pIL-12 immunogene therapy in the MC38 mouse model. In a separate experiment, C57BL/6 mice received IV injection of pIL-12 laden 4-arm PRX, following the same treatment regimen as the tumor inhibition study shown in FIG. 4. Saline and pC laden 4-arm PRX were used as controls. For comparison purpose, we also included IV administration of mouse rIL-12 as an additional control. The dose rIL-12 (100 µg/kg/injection) was designed based on literature (see, e.g., Brunda et al. (1993) *J. Exp. Med.* 178(4): 1223-1230). Panel A: Blood chemistry test and complete blood count test were performed on day 7 and day 21. The results are expressed as mean±SD. *p<0.05. Panel B: Representative lung and kidney histology obtained from C57BL/6 mice sacrificed on day 21. The arrows in the H&E staining of rIL-12 treated lung sections point to interstitial thickening and macrophage infiltrates, and the sites marked with asterisks denote pulmonary edema. The arrows in rIL-12 treated kidneys sections marked the zoomed-in morphology of glomerulus, where glomerular swelling and edema of Bowman's space were observed. Scale bar represents 200 µm.

FIG. 25, panel B, shows $^1$H-NMR characterization of 2-occupied 4-arm PEG backbone in deuterated water ($D_2O$).

FIG. 26, panel B: $^1$H-NMR spectra of $1/4^{CD}$, $2/4^{CD}$, and $3/4^{CD}$ 4-arm polypseudototaxane in DMSO-d6. FIG. 26, panel C: $^1$H-NMR spectra of $2/4^{CD}$ 4-arm polypseudototaxane with 5 kDa, 10 kDa or 20 kDa 4-arm PEG backbone in DMSO-d6. The calculation for cationic charge density and total CD per PRX were shown in FIG. 18, panel C, 19, panels C and E, respectively. Collectively, the comprehensive characterization confirms successful synthesis of 4-arm PRX analogues and manipulation over different design parameters.

FIG. 27, panel B: Heat map display of in vitro transfection by 4-arm PRX at various N/P ratios. The optimum N/P ratio was defined by the threshold N/P ratio that provided the most efficient reporter expression. FIG. 27, panel C: We also tested the tdTomato plasmid transfection efficiency in another cancer cell line. B16 melanoma cells incubated with tdTomato plasmid laden optimized 4-arm PRX (1 µg plasmid/mL) for 72 h and the representative fluorescence image of $Td^+$ cells were shown (scale bar represents 100 μm). This allowed us to demonstrate abundant Td+ cells (19% of total cell population) in tissue culture, similar to what we found in MC38 cells.

FIG. 29, panel B: Size and ζ-potential characterization of plasmid laden optimized 4-arm PRX or linear PRX at various N/P ratios. Values represent the mean±SD (n=3). While the optimized 4-arm PRX showed similar plasmid packaging capability, hydrodynamic size and ζ-potential (zeta potential) compared to the linear PRX, we found distinct features between these two PRX types in terms of PK and biodistribution in vivo (see FIG. 20).

FIG. 30, panel B: RT-qPCR detection of the fold change of IL-12 gene expression normalized to untreated control cells. Values represent the mean±SD (n=3). Statistical significance: *, $p<0.05$.

DETAILED DESCRIPTION

Figure 1A:
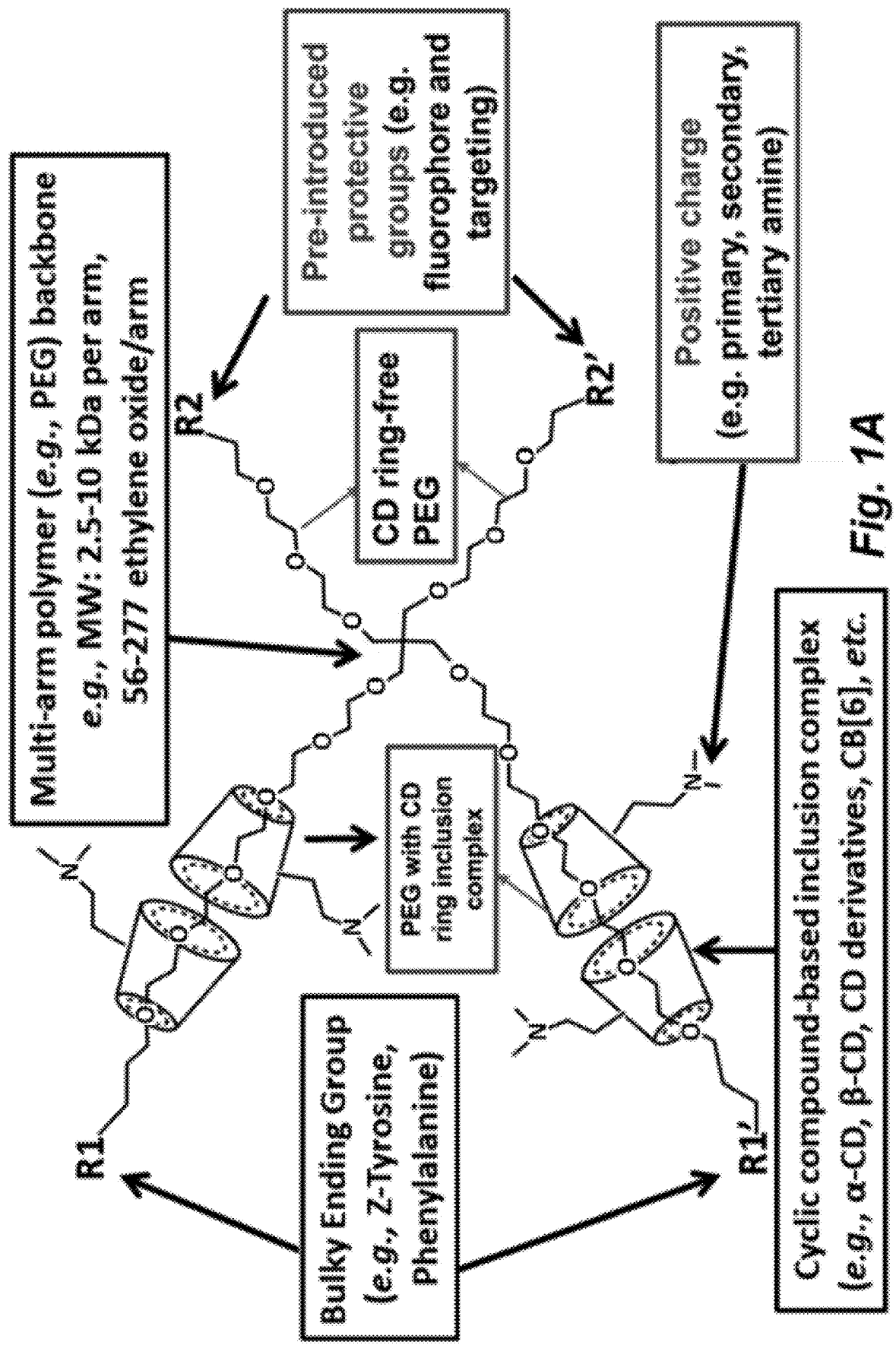
FIG. 1A schematically illustrates various design features of a multi-arm polyrotaxane (PRX) carrier. The illustrated embodiment shows a 4-arm PEG backbone. Various design features include, but are not limited to the formation of inclusion complexes using cyclic compounds (e.g., cyclodextrin) threaded on at least one arm, but not on all arms of the backbone. The inclusion complexes are retained on the arms by bulky groups R1 and R1' which can be the same or different. One or more of the inclusion-complex free arms can be attached to (e.g., terminated with) a protecting group, and/or a fluorophore and/or a targeting moiety (R2 and R2' which can be the same or different). The cyclic compound(s) can optionally be functionalized with a nucleophile (e.g., an amine) to regulate the charge of the carrier. In certain embodiments, the nucleophile and/or the bulky groups are attached to the backbone and/or to the cyclic compound by a cleavable linkage. The backbone need not be a 4-arm backbone.

In certain embodiments carriers are provided for the effective in vivo delivery of nucleic acids including small or large nucleic acids (such as plasmids). The nanocarriers described herein are polyrotaxane (PRX) structures comprised of a multi-arm polymer backbone with cyclic compounds threaded on the arms of the backbone thereby forming inclusion complexes. The complexes are designed to readily complex via self-assembly with nucleic acids to form a carrier/nucleic acid complex that can readily be administered to an organism.

Advantages of the multi-arm polyrotaxane carriers described herein include, but are not limited to, large packaging space, nucleic acid (e.g., plasmid) encapsulation via self-assembly, potential for modification to increase targeting, high stability, multi-functionality, bio-degradability and intrinsic safety.

One of the applications of the multi-arm polyrotaxane carriers described herein is the in vivo delivery nucleic acids to cell. In certain embodiments, the delivery can be systemic, while in other embodiments, the delivery can be targeted (e.g., to particular cell or tissue type) by the incorporation of targeting moieties. In either approach, however the carriers are well suited to systemic administration and show a long serum half-life and effective delivery of the nucleic acid to cells.

In certain embodiments the nucleic acids to be delivered include, but are not limited to antisense molecules, ribozymes, and plasmids encoding one or more heterologous gene(s), RNAs, and the like. In certain embodiments, the carriers described herein are particularly well suited for the delivery of clustered regularly interspaced short palindromic repeats (CRISPR)/Cas9 plasmid for various biological applications.

One example is the CRISPR/Cas9 based gene editing to reframe the mutated gene in Duchenne Muscular Dystrophy (DMD). Our data demonstrated that CRISPR/Cas9 plasmid delivery by PRX nanocarriers showed improved biodistribution at muscle sites over various controls in a stringent DMD mouse model. We have also achieved progress in plasmid delivery to cancer cells. In this regard, the polyrotaxane carriers have been used for comparison against commercial transfection reagents in a range of cancer cell types to provide proof-of-principle demonstration of the wider utility of this platform, including for example, treatment of melanoma, pancreatic cancer, colon cancer, and the like.

In various embodiments the carriers described herein are polyrotaxane (PRX) structures comprised of a multi-arm polymer (e.g., polyethylene glycol) backbone with cyclic compounds (e.g., cationic cyclodextrins (CDs)) threaded on the arms of the backbone thereby forming inclusion complexes. The cyclic molecules are retained on the backbones by the presence of bulky moieties capping the terminals of the arms bearing cyclic compounds. Notably at least one of the arms of the polymer, and in certain embodiments two or more of the arms of the polymer backbone do not bear any cyclic compounds. Thus, the polyrotaxane (PRX) carrier comprises cyclic molecules selectively threaded on the backbone (e.g., threaded on some arms, but not other arms, and not on all arms of the backbone). In certain embodiments, the bulky capping groups can be attached to the arms of the backbone (the arm(s) bearing cyclic compounds) with or without a cleavable linkage. The cleavable linkage, when present, can facilitate unloading of a complexed nucleic acid in response to local (e.g., intracellular) conditions such as low pH, redox-potential, the presence of various proteases, and the like.

In certain embodiments the arms of the backbone that are free of cyclic compounds can be attached to protecting groups, and/or to a fluorophore (or quantum dot), and/or to one or more targeting moieties.

In certain embodiments the charge of the polyrotaxane carrier can be controlled by the functionalization of the cyclic compounds with one or more nucleophiles (e.g., amines).

One of a number of key innovations in the design of the polyrotaxane carriers described herein is the use of a multi-arm PRX polymer that was constructed from a multi-arm polyethylene glycol (PEG) backbone for spatially selective inclusion complexation, leading to an appropriately tuned PEGylation density and positive charge density, that are suitable for in vivo applications including systemic nucleic acid delivery. Through an electrostatic mediated self-assembly progress, the mixing of PRX carrier and a nucleic acid (e.g., plasmid) leads to the spontaneous formation of nano-sized particles that are resistant to enzyme-mediated nucleic acid degradation. In a DMD mouse model (e.g. mdx mice) receiving intravenous injected (IV) plasmid laden PRXs, a long particle circulation half-life and abundant skeletal muscle distribution via passive targeting mechanism were demonstrated.

Without being bound to a particular theory, it is believed that the spatially selective complexation (inclusion of cyclic molecules on some, but not all polymer arms) in the polyrotaxane carriers described herein result in reduced particle opsonization and unwanted uptake by reticuloendothelial system.

Certain design features of this multi-arm PRX carrier platform are shown in FIG. 1A. As illustrated in this figure, the multi-arm part of the polymer backbone was blocked by bulky groups (R2 and R2' groups in FIG. 1A) before inclusion complexation. This was followed by introducing cyclic compounds (e.g., CD rings) to the unblocked PEG arms via inclusion complexation process. The polyseudorotaxane was blocked to prevent the cyclic molecules from falling off the arm(s) by the attachment of a bulky capping group (R1 and R1' group in FIG. 1A), such as an aromatic molecule. In certain embodiments R2 and R2' can be the same or different and can comprise a protecting group and/or an imaging probe (e.g. FITC or NIR dye), and/or a targeting moiety (e.g., an antibody or targeting peptide). Using similar strategy, it is possible to extrapolate the design principle to build additional multi-arm PRXs with spatially selective inclusion complexes.

Figure 1B:
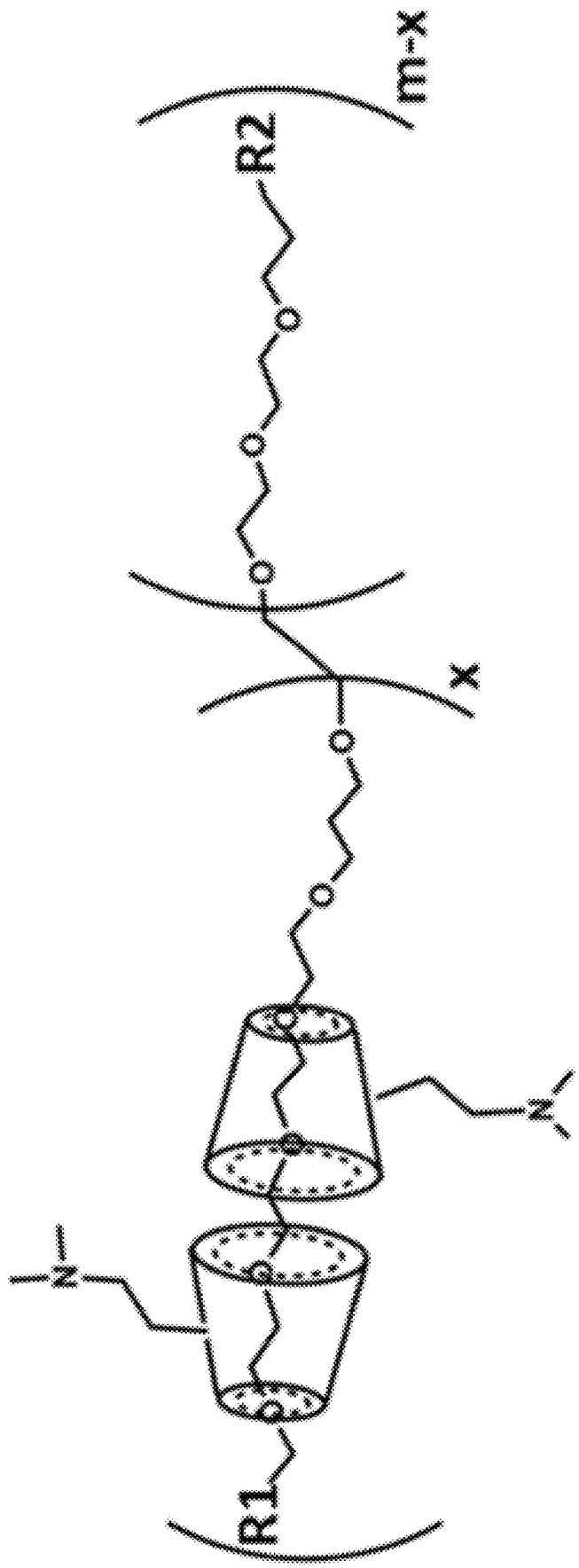
FIG. 1B illustrates a multi-arm polyrotaxane (PRX) with a total of m arms. In certain embodiments the number of arms in the multi-arm PEG backbone m ranges from 3 to 12, or from 3 to 10, or from 3 to 8. In certain embodiments, the number of cyclic molecule threaded PEG arms (x) ranges from 1 to m–1. In certain embodiments, the backbone comprises 3 arms, or 4 arms, or 5 arms, or 6 arms, or 7 arms, or 8 arms.

The general characteristics of these novel PRXs include the following chemical properties (see, e.g., FIG. 1B): (i) A multi-arm polymer (e.g., PEG) backbone that contains m arms (where $3 \leq m \leq 12$, or $3 \leq m \leq 10$, $3 \leq m \leq 8$); (ii) Where the backbone comprises PEG, the PEG MW ranges from about 2.5 kDa per arm up to about 10 kDa per arm, which means about 56-227 ethylene oxide repeat units per arm; (iii) Prior to the inclusion complex process, pre-introduction of bulky molecules (R2 group(s) in FIG. 1B), such as fluorophore (e.g. FITC and NIR dye) or targeting modalities (e.g., antibody, targeting peptide, folic acid, etc.) in at least 1 PEG arm, up to m−1 arms; (iv) Spatially selective formation of inclusion complex using cyclic compounds (e.g., alpha, beta cyclodextrin, or cyclodextrin derivatives (e.g. 2-Hydroxypropyl-α-cyclodextrin)) with appropriate ring number per PEG arm; (v) polyseudorotaxane is stabilized by ending group with appropriate steric hindrance molecules (e.g., aromatic rings and fused rings; R1 group(s) in FIG. 1B); (vi) Cationic cyclic molecules (e.g., cyclodextrin) can be achieved by positive functional group(s), such as primary, secondary and tertiary amine; (vii) bio-cleavable linker(s) can be introduced at pendant sides or chain ends if necessary (see, e.g., FIG. 3B). It is believed the resulting multi-arm PRXs with spatially selective inclusion complexes are a group of new chemical entities.

The availability of the free (inclusion complex-free) backbone arms helps prevent nanocomplex opsonization in blood circulation, which is important to facilitate long plasma half-life and high accumulation in targeted sites in vivo.

The polyrotaxane delivery vehicle (carrier) is believed to be particularly effective in the complexation/encapsulation and delivery of large nucleic acids such as plasmids and other therapeutic nucleic acids or a mixture of therapeutic nucleic acids. In certain embodiments, the nucleic acid can comprise a plasmid (e.g., a plasmid ranging in size up to 20 kb, or up to about 15 kb, or up to about 12 kb, or up to about 10 kb). In certain embodiments the nucleic acid comprises a linear nucleic acid (e.g., a linear nucleic acid up to about 15 kb, or up to about 12 kb, or up to about 10 kb). In certain embodiments, the complexed nucleic acid can comprise an RNA (e.g., an RNA up to about 10 kb, or up to about 8 kb, or up to about 6 kb, or up to about 5 kb, or multiple pieces of RNA). Accordingly, in various embodiments, the PRX carrier is an excellent supramolecular carrier for delivery of gene therapeutics, such as expression vectors for expressing heterologous genes and/or for delivering CRISPR enzymes and guide RNAs.

Compared to other carriers in the field, the unique advantages of polyrotaxane (PRX) carriers described herein for nucleic acid delivery involves the formation of a stable polyplex complex against a counter polyanion. The design also includes controllable intracellular release mechanisms via supramolecular dissociation in response to specific intracellular stimuli, i.e. lysosomal low pH and high intracellular GSH. The PRX features additionally include tunable particle sizes, controllable charge type and density, tailorable backbone rigidity, colloidal stability in biological medium, and the ability to functionalize the ends of the PEG chain and surface of the cyclic compounds (e.g., CDs) (for targeting and/or imaging). Moreover, these materials are highly biocompatible, due to the intrinsic safety of PEG and CD.

The presently described polyrotaxane carriers are the product of multiple iterations of rotaxane carrier development involving systematic tuning of physicochemical properties of the, such as PEG molecular weight and structure, type and density of amine group(s), CD ring number, the presence or absence of cleavable linkers, etc., in order to overcome a list of challenges for the delivery of large nucleic acids (e.g., plasmids) in vivo.

For example, therapeutic plasmids (e.g., CRISPR/Cas9 plasmids) are rapidly degraded macromolecules in the presence of DNases in vivo. In order to overcome this challenge, we synthesized a first generation (G1) of polyrotaxane nucleic acid carrier using a linear PEG backbone (see, e.g., FIG. 2, left illustration). Through an electrostatic mediated self-assembly progress, the plasmid was fully protected by the complexation with the rotaxane, leading to a ~100 nm nanoparticulate.

Based on the first generation polyrotaxane carrier a list of key characteristics (e.g. PEG molecular weight, number of CD rings, type and density of amines, etc.) was determined which served as the basis for the next iteration (generation 2 (G2)). Although the first generation PRX exhibited effective cellular uptake, we showed a slow rate of release of the plasmid inside the cells (e.g. cultured primary myotubes). This informed design of a second generation polyrotaxane carrier (G2 PRX), which contained a disulfide linker that responds to an intracellular reducing environment. Compared to G1, delivery of a plasmid containing the CRISPR platform (px333 with gRNAs 44C4 and 55C36) using G2 PRXs showed successful exon 45-55 deletion in myotube cells at an early time point. In order to utilize the polyrotaxane carrier in vivo, the multi-arm polyrotaxane carriers described herein (generation 3 (G3), see, e.g., FIG. 7A). The selective inclusion complex design of these carriers has been discussed above. The rest of characteristics, such as CD ring density and type of amines were determined. The multi-arm design is important for systemic delivery because, inter alia, of the introduction of free PEG chain and higher PEGylation that prevent opsonization and unwanted uptake by reticuloendothelial system in vivo.

Figure 2:
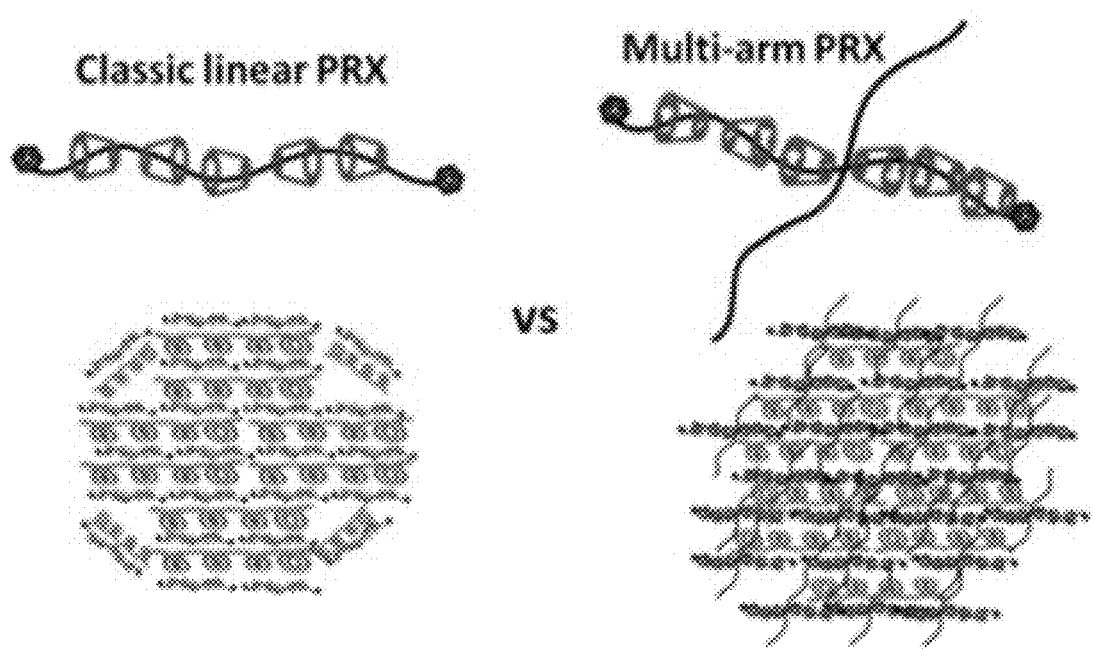
FIG. 2 shows a comparison of the multi-arm PRX compared to the linear PRX.

As illustrated in FIG. 2, the G3 (and G4) multi-arm PRX design where cyclic compounds (e.g., cyclodextrins) form inclusion complexes on a subset of the polymer arms offers numerous advantages over the classical linear (and certain other polyrotaxane deliver vehicles). As illustrated the linker PRX structures are not effectively pegylated. The particles can form a protein corona in vivo. Additionally, particle opsonization can occur and the particles have a short serum half-life. In contrast introduction of the cyclic molecules in a spatially selective fashion provides available (inclusion complex-free) polymer backbone arms that afford effective pegylation. Particle opsonization is prevented in vivo and the PRX/nucleic acid complex shows a long serum half-life.

Figure 4:
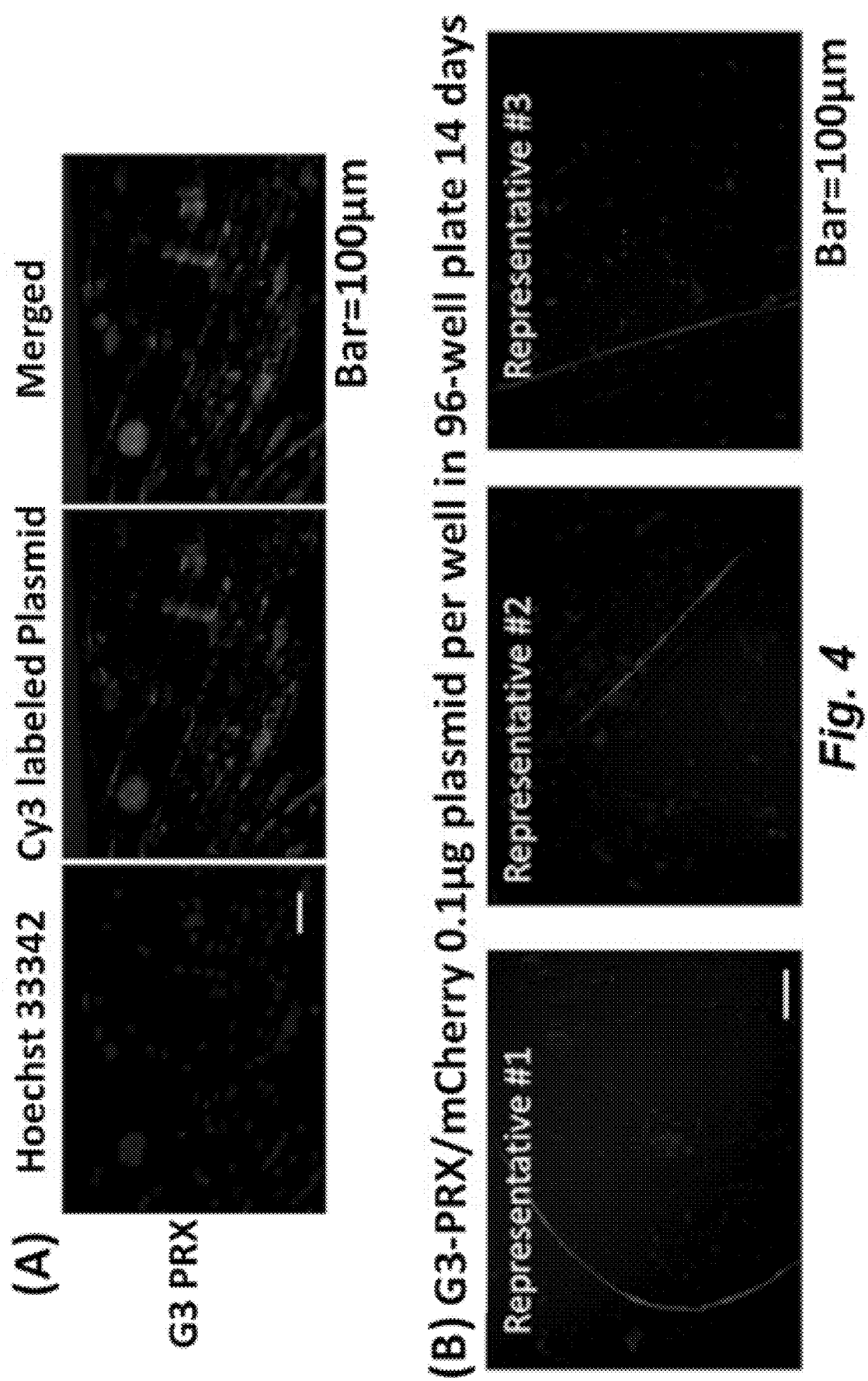
FIGS. 4, panels A and B, shows results of a study of intracellular uptake and in vitro transfection using G3 PRX as a carrier. Panel A) Cellular uptake of the plasmid loaded by G3 PRX. Myotube cells received Cy3 labeled plasmid loaded G3 PRX for 3 days. Panel B) Demonstration of in vitro transfection effectiveness of mCherry plasmid delivered by G3 PRX in myotube cells. The commercial transfection reagents, such as Lipofectamine, are very inefficient in myotube cells.

Experiments shows that the multi-arm carriers show improved biodistribution, post intravenous injection (IV) and are capable of CRISPR-mediated gene cutting. In particular, FIG. 4, panels A shows the results of a study of intracellular uptake and in vitro transfection using G3 PRX as a carrier. Myotube cells received Cy3 labeled plasmid loaded G3 PRX for 3 days and showed effective uptake. Panel B shows a demonstration of in vitro transfection effectiveness of mCherry plasmid delivered by G3 PRX in myotube cells. The commercial transfection reagents, such as Lipofectamine, are very inefficient in myotube cells.

Figure 5:
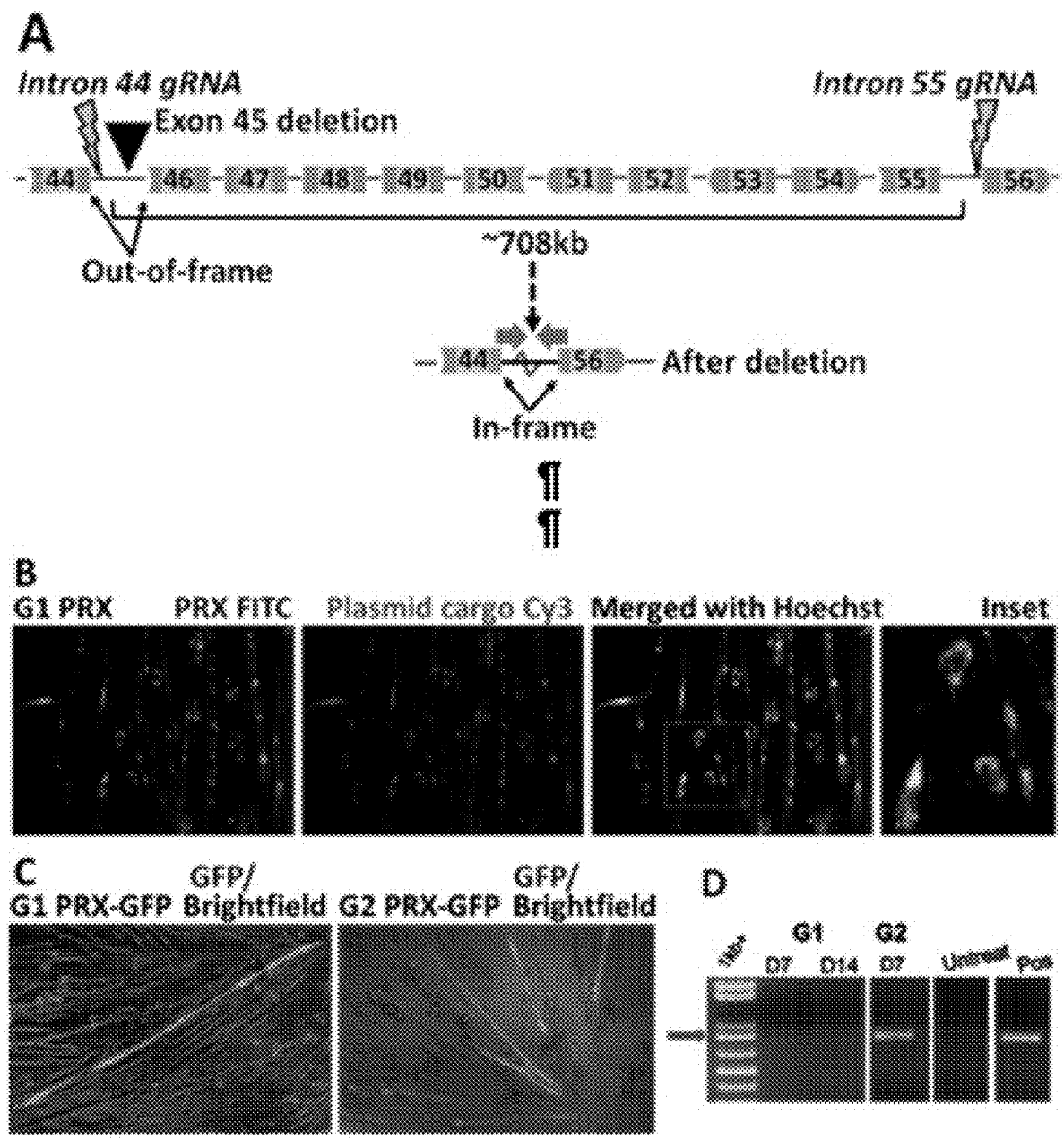
FIGS. 5, panels A-D, shows that PRXs demonstrate successful uptake and plasmid delivery to muscle cells in vitro. Panel A: Cartoon of the DMD gene targeted for CRISPR-mediated deletion of exons 45-55. Guide RNAs (lightening bolts) targeting introns 44 and 55 cause cutting and NHEJ of the region restoring the reading frame for out-of-frame mutations (black arrow head). Purple arrows represent deletion PCR primers. Panel B: Imaging of G1 PRX nanoparticles labeled with FITC (green) and plasmid cargo (labeled with Cy3, red) in hDMD myotubes at day 3 after administration. There is a high colocalization of the particle and cargo signal in the cells demonstrating a lack of plasmid release. Panel C: Imaging of G1 and G2 PRX particles carrying a GFP plasmid in hDMD myotubes at day 7 after administration. G2, which contains the disulfide linker, results in more GFP positive cells. Panel D: Genomic DNA PCR for an exon 45-55 deletion (using primers that flank the deletion, shown in panel A 7 or 14 days after administration of G1 or G2 carrying the CRISPR/Cas9 plasmid to hDMD myotubes. G2 PRX-CRISPR results in deletion at day 7. Untreated (untreat) negative and positive (pos) controls are shown.

FIG. 5 illustrates the delivery of plasmid by G1 and G2 PRX. Panel A schematically illustrates targeting of exons 44-55 of the DMD gene. Panel B demonstrates high colocalization of cargo and PRX in G1. Panel C demonstrates improved GFP reporter plasmid delivery in G2 compared to G1 PRX. Panel D demonstrates successful application of CRISPR and an exon 45-55 deletion in myotubes using G2 PRX 7 days post treatment compared to G1.

Figure 6:
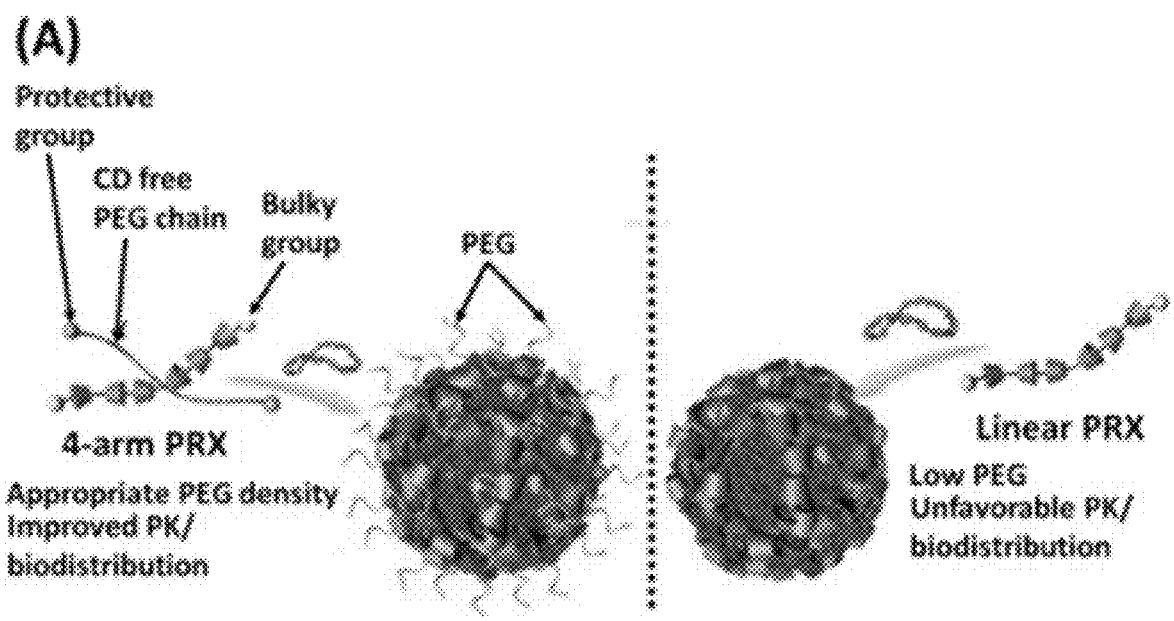
FIG. 6, panels A-C, shows a comparison between classic linear PRX vs 4-arm PRX. Panel A: The cartoon shows the two main designs of PRX. The linear structure has a PEG backbone (black line) and cationic CD rings (pink) that bind nucleic acid (blue) via an electrostatic mediated self-assembly process. Since 2 out of 4 arms were pre-protected by a bulky group (green ball in the left panel) in the 4-arm PRX design, this leads to CD ring-free PEG chains during the complex process. This design differs from the classic linear design in which the PEG backbone is already occupied during the introduction of positive CD, leading to a non- or low PEG nanoparticle. Panel B: Typical AFM pictures of free plasmid and self-assembled PRX/plasmid. Panel C) IVIS imaging of mdx muscles from mice injected with either the linear or the 4-arm PRX. More abundant plasmid was observed in muscles of mice injected with the 4-arm PRX. Plasmid was labeled by Cy3 for IVIS.
Figure 6:
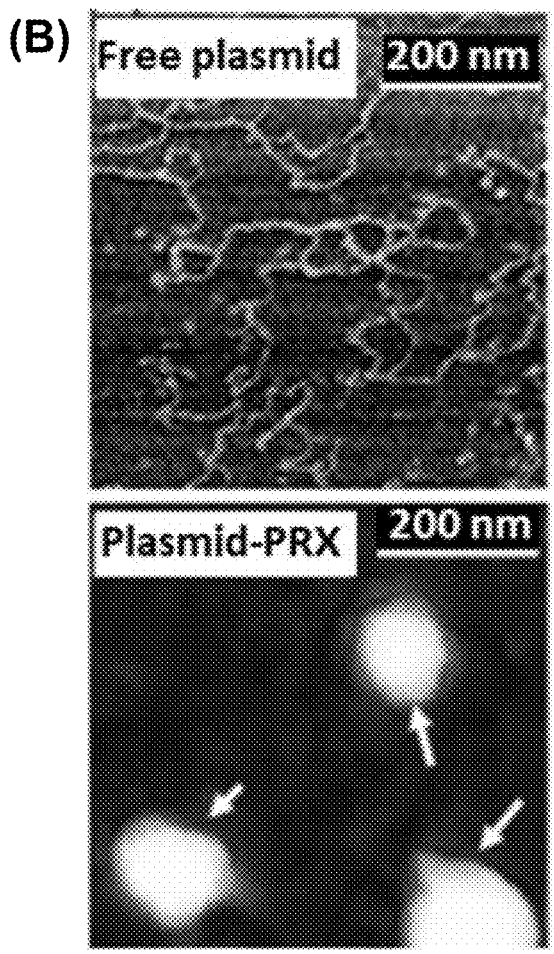

FIG. 6 shows the comparative biodistribution and PK profiles of linear vs multi-arm PRX in DMD mice. Panel A: The cartoon shows the two main designs of PRX. The linear structure has a PEG backbone (black line) and cationic CD rings (pink) that bind nucleic acid (blue) via an electrostatic mediated self-assembly process. Since 2 out of 4 arms were pre-protected by a bulky group (green ball in the left panel) in the 4-arm PRX design, this leads to CD ring-free PEG chains during the complex process. This design differs from the classic linear design in which the PEG backbone is already occupied during the introduction of positive CD, leading to a non- or low PEG nanoparticle. Panel B: Typical AFM pictures of free plasmid and self-assembled PRX/plasmid. Panel C) IVIS imaging of mdx muscles from mice injected with either the linear or the 4-arm PRX. More abundant plasmid was observed in muscles of mice injected with the 4-arm PRX. Plasmid was labeled by Cy3 for IVIS.

Figure 7:
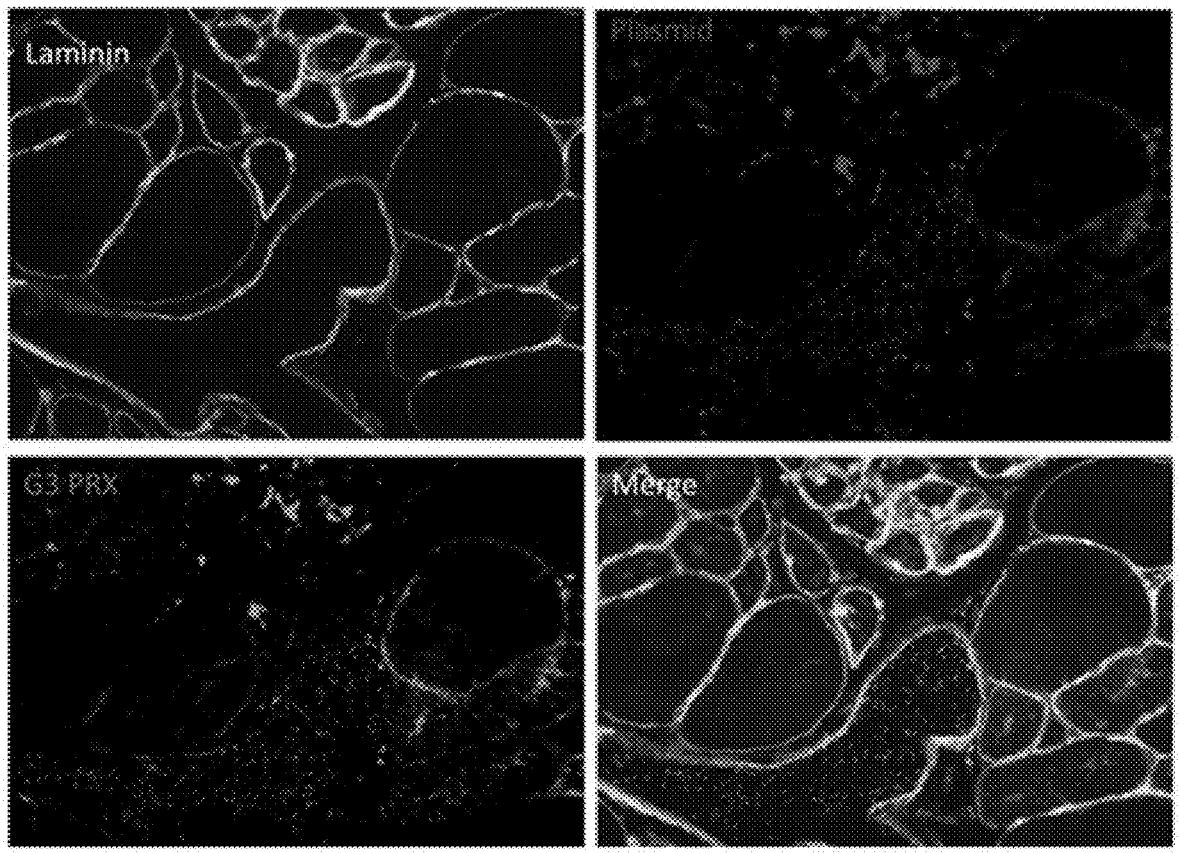
FIG. 7 shows sections of quadriceps muscle tissues were collected 24 hours post Cy3 plasmid laden G3 PRX injection and embedded in OCT for frozen section. Slides were visualized under a fluorescence microscope. The particle and plasmid biodistribution in the muscle section was visualized. Laminin was labelled using IHC (white).

FIG. 7 shows the carrier (G3 PRX loaded with Cy3 plasmid) particle and plasmid biodistribution in quadriceps muscle section.

Figure 3A:
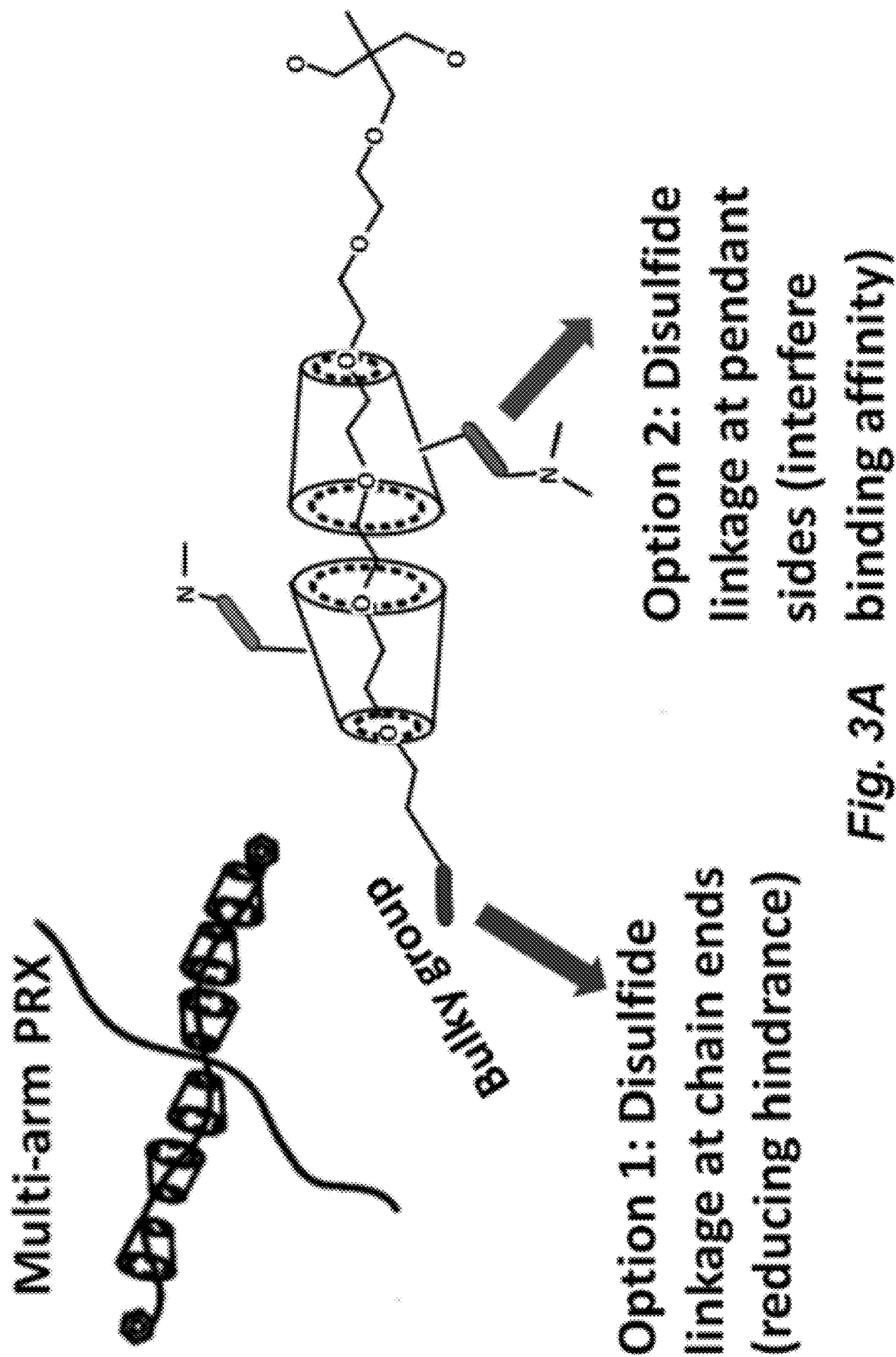
FIGS. 3A and 3B, illustrate various design features of a fourth generation (G4) polyrotaxane carrier (PRX).
Figure 3B:
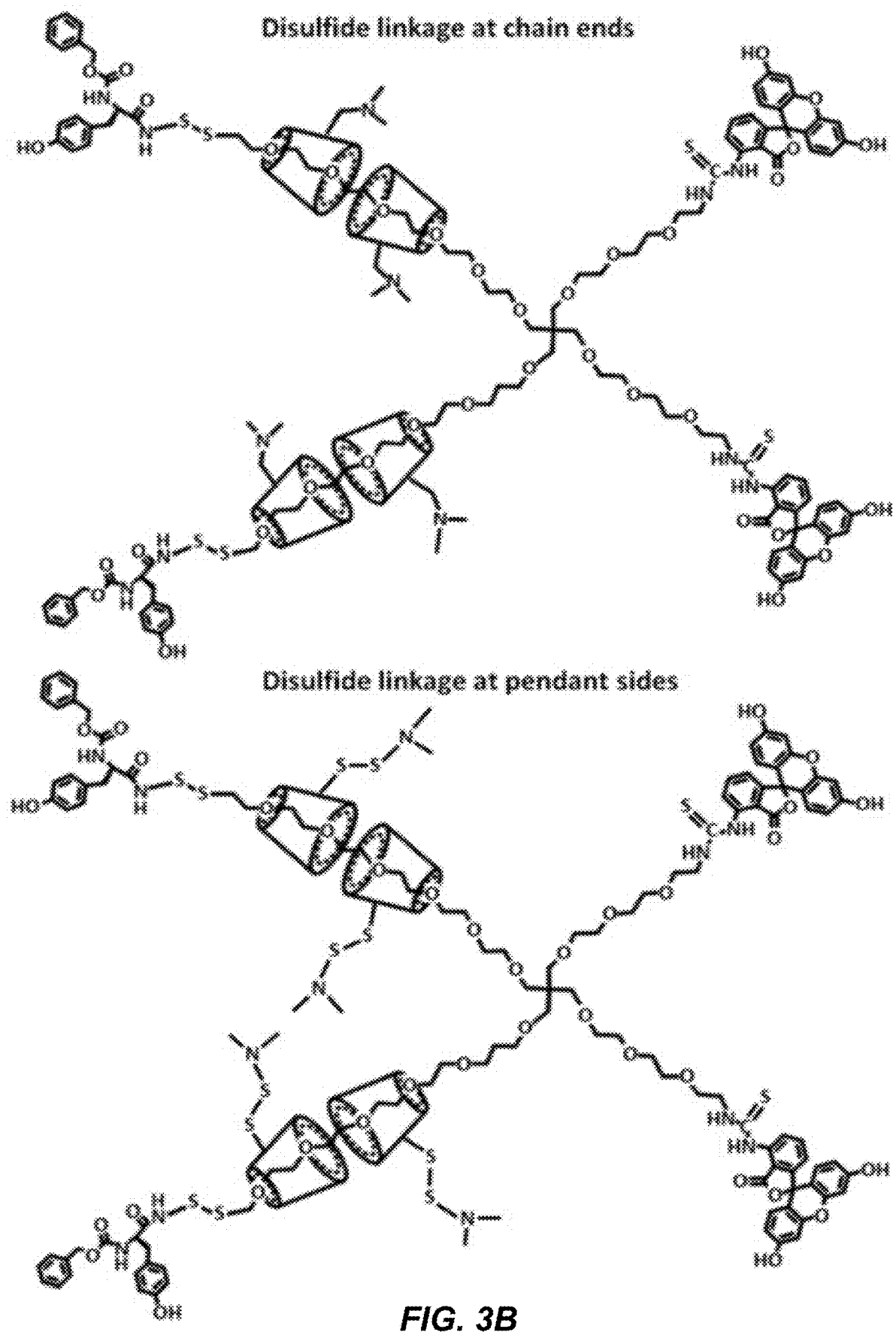

Based on the third generation multi-arm polyrotaxane carrier, fourth generation (G4) polyrotaxane carrier was developed that combined the use of a multi-arm PEG backbone (with selectively distributed inclusion complexes to provide at least one inclusion complex-free arm) to improve biodistribution and one or more cleavable linkages (e.g., bio-cleavable linkers) to enhance intracellular plasmid release (see, e.g., FIGS. 3A and 3B). Through medicinal chemistry, we have identified functional groups in the PRX where cleavable linkages can be placed to enhance intracellular release of a complexed nucleic acid (e.g., a plasmid). In one illustrated embodiment, the cleavable linkage is placed between the backbone (e.g., the PEG backbone) and one or more of the bulky moieties (bulky stopper(s) that prevent cyclic compounds from falling off the backbone arm(s). In another illustrative, but non-limiting embodiment, a cleavable linkage (e.g., a disulfide linker) is placed between the cyclic compound(s) (e.g., cyclodextrin) and their conjugated nucleophile(s) (e.g., conjugated cationic tertiary amine groups), which upon cleavage and removal of the nucleophile(s), can lead to the PRX and plasmid dissociation via a charge reduction mechanism. Two representative examples were shown to demonstrate the site of an illustrative disulfide linker in multi-arm PRX (see, e.g., FIG. 3B).

Figure 8:
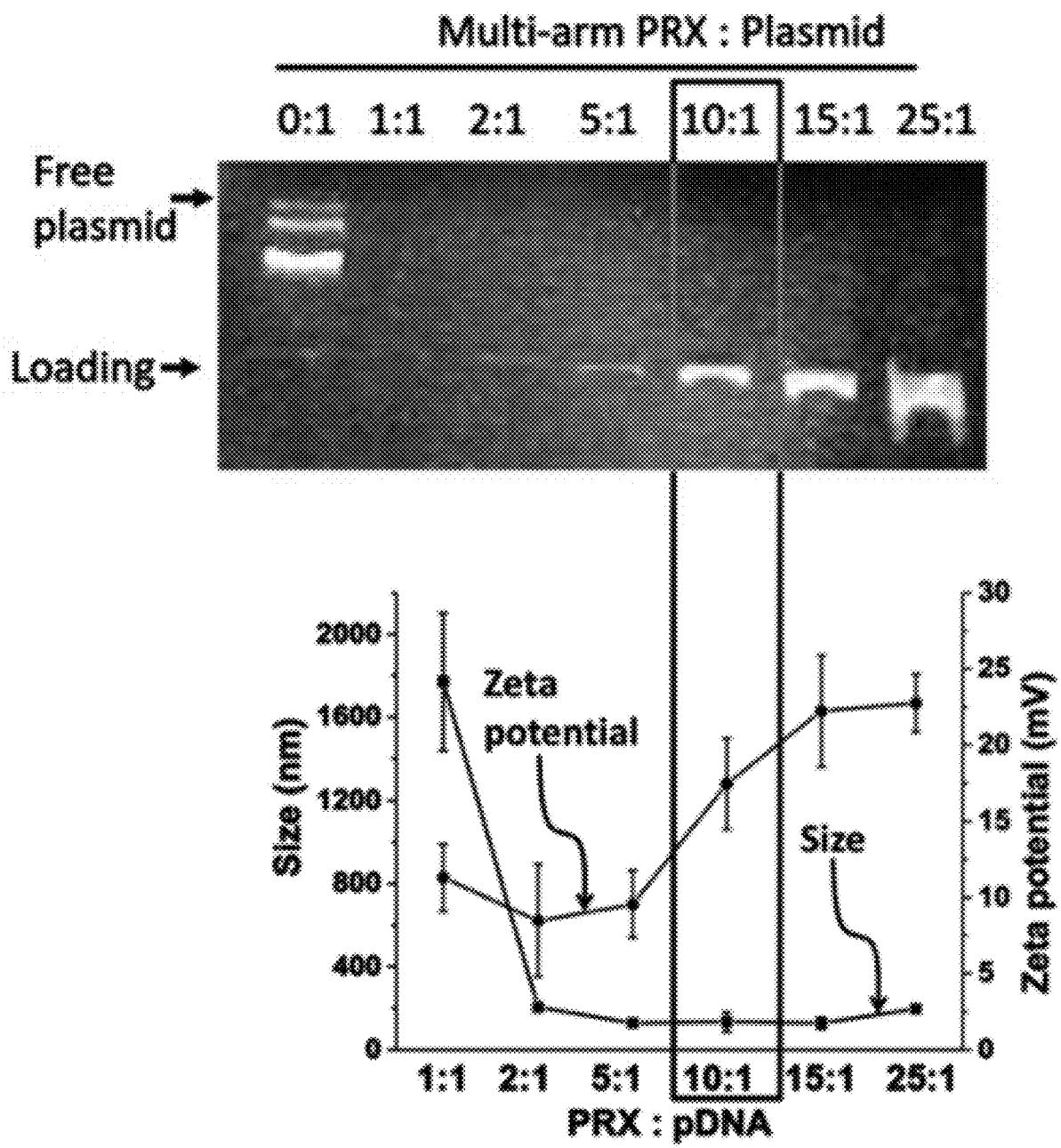
FIG. 8 illustrates determination of the N/P ratio of a multi-arm PRX.

FIG. 8 illustrates determination of the N/P ratio of a multi-arm (G3) PRX. As shown, in certain embodiments, an optimal N/P ratio is about 10:1. However, in various embodiments, the N:P ratio ranges from about 0.01:1 up to about 100:1, or from about 0.1:1 up to about 50:1, or from about 1:1 up to about 30:1, or up to about 20:1, or up to about 10:1.

FIG. 6, panel B, illustrates formation (self-assembly) of the G3 plasmid-PRX complex.

Figure 9:
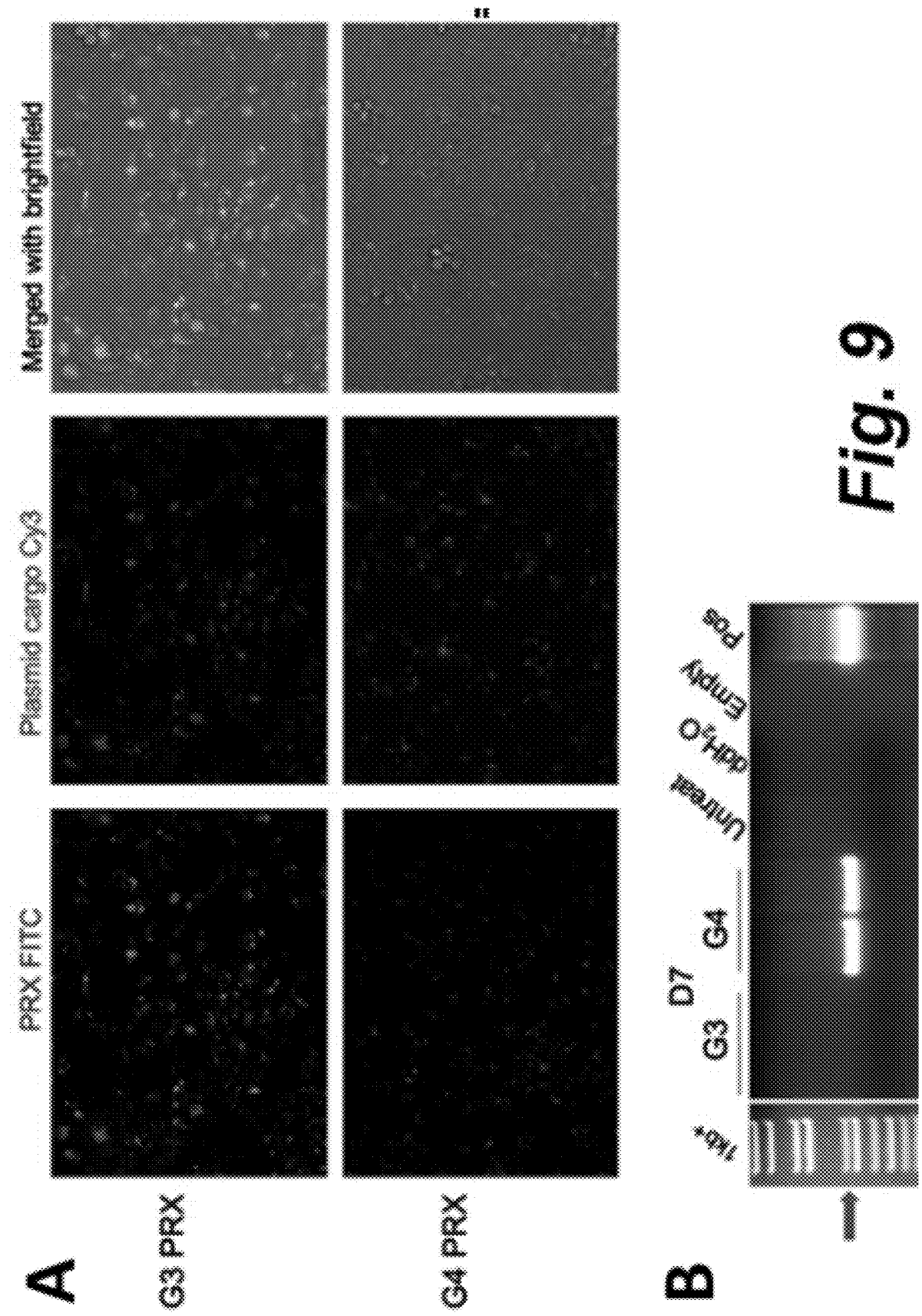
FIG. 9, panels A-B, shows that multi-arm PRXs demonstrate successful uptake and plasmid delivery to muscle cells in vitro. Panel A) Imaging of G3 and G4 PRX nanoparticles labeled with FITC (green) and labeled plasmid cargo (red) in hDMD del45 myoblasts 24 hrs after administration. There is less particle/plasmid colocalization in the cells seen with G4, which contains a disulfide linker. Panel B) Genomic DNA PCR for an exon 45-55 deletion at day 7 after administration of G3 or G4 carrying the CRISPR/Cas9 plasmid to hDMD del45 myoblasts. G4 PRX-CRISPR results in successful deletion. Untreated (untreat), water only (ddH$_2$O), and positive (pos) controls are shown.
Figure 10:
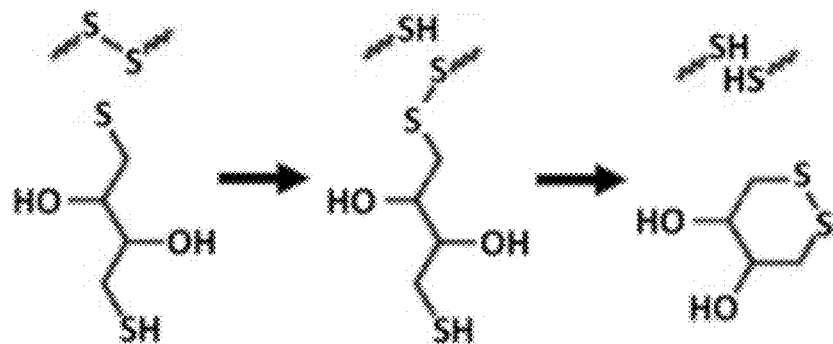
FIG. 10 illustrates DTT induced reductive cleavage of cationic charge on G4 PRX. The cleavage further resulted in size change of G4/plasmid complex.
Figure 10:
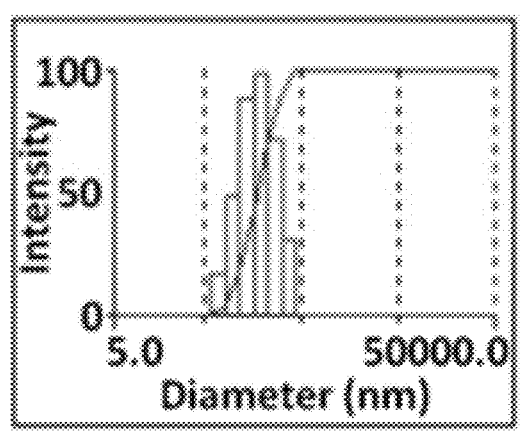
Figure 10:
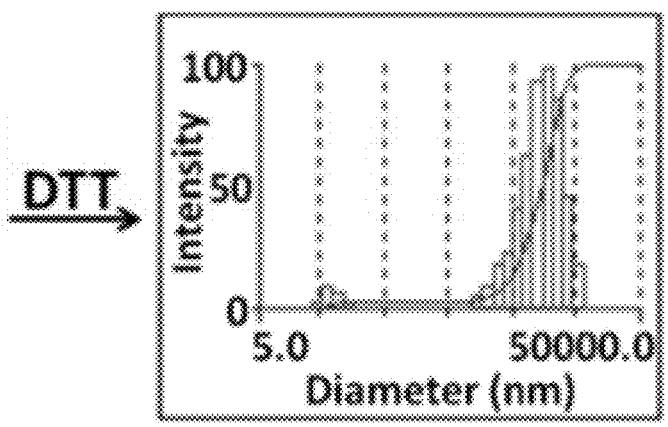

FIG. 9 demonstrates G3 and G4 PRX are taken up efficiently in vitro. This figure also shows that a CRISPR/Cas9 plasmid laden G4 multi-arm PRX exhibited CRISPR-mediated cutting effect at day 7 in cultured myotube cells. Without being bound by a particular theory, it is believed that the fourth generation (G4) multi-PRX carriers described herein incorporating cleavable linkages can increase intracellular release of a complexed nucleic acid (e.g., a plasmid). In this regard, FIG. 10 illustrates data obtained from a G4 multi-arm PRX using option 1 (reducing steric hindrance).

In view of the foregoing (and the Examples presented herein) it will be recognized that the polyrotaxane (PRX) nanocarriers described herein can deliver large nucleic acids (e.g., large plasmids, and other constructs) in vivo. While the use of cationic nanoparticles for nucleic acid delivery has been reported in the literature, the delivery of 1) This nanoparticle is designed to deliver large plasmids in vivo. While the use of cationic nanoparticle for gene product delivery is reported in the literature, the delivery of large constructs (e.g., an intact plasmid) has heretofore proven to be particularly challenging due to the large molecular weight, steric hindrance, loading capacity of the carrier, etc.

Moreover, the carries described herein offer a non-viral method of in vivo nucleic acid deliver which is advantageous over competing technologies such viral vectors (e.g., AAV-CRISPR). AAV is not able to efficiently target muscle stem cells in vivo, which is a requirement for a long term sustained effect, as the corrected myofibers may be lost over time during muscle degeneration/regeneration.

On the other hand, the PRX nanoparticle carriers described herein can be easily modified and targeted and can be adapted and optimized to target muscle stem cells or any other cell or tissue type of interest.

In addition, viral vectors can typically only be delivered a single time, due to the immune response that often develops against the viral serotype. So, unless the nucleic acid construct (e.g., CRISPR) works at very high efficiency, the potential to lose the corrected cells after treatment is high. Conversely, the nanoparticle PRX carriers described herein can be repeatedly administered. Also, importantly, with viral mediated delivery, the active agent (e.g., CRISPR/Cas9) can be present for an extended period of time, which increases the potential for off target effects and for development of an immune response. In contrast, the PRX carriers and complexes thereof are believed to be non-immunogenic and biodegradable to surpass these downfalls.

Multi-Arm Polyrotaxane (PRX) Nucleic Acid Carriers.

In view of the foregoing, in various embodiments, a polyrotaxane carrier for in vivo delivery of a nucleic acid is provided. In certain embodiments the carrier comprises a multi-arm polyethylene glycol (PEG) backbone comprising at least three arms; at least one cyclic compound having a cavity, where an arm of said multi-arm PEG backbone is threaded into the cavity of said cyclic compound forming an inclusion complex; a bulky moiety capping the terminal of the arm(s) threaded into said cyclic compound where said moiety inhibits dethreading of the cyclodextrin from the arm(s) of said backbone; and where at least one arm of said PEG backbone is free of cyclic compounds; and where said carrier has a net positive charge. Typically, the carrier complexes with (self-assembles with) a nucleic acid when contacted to the nucleic acid. In certain embodiments, the multi-arm polyethylene glycol backbone comprises a star polymer. In certain embodiments, the multi-arm backbone comprises multiple branches along a main chain. In certain embodiments, the multi-arm PEG comprises at least 2 arms free of cyclic compounds. In certain embodiments, the multi-arm PEG comprises from 3 up to about 12, or up to about 10, or up to about 8 arms. In certain embodiments, the PEG comprises 4 arms, or 5 arms, or 6 arms, or seven arms, or 8 arms. In certain embodiments, the PEG comprises 4 arms. In certain embodiments, the PEG comprise 4 arms where two of said arms are free of cyclic compounds.

In various embodiments, the PEG backbone has a molecular weight ranging from about 1.0 to about 10 kDa per arm. In certain embodiments, the PEG backbone comprises about 22 to about 227 ethylene oxides per arm. In certain embodiments, the PEG backbone has a molecular weight of about 2.5 kDa per arm. In certain embodiments, the arm(s) threaded into said cyclic compound(s) each bear on average from about 5, or from about 10, or from about 15 up to about 110, or up to about 80, or up to about 50, or up to about 40, or up to about 30 cyclic compounds. In certain embodiments, the arm(s) threaded into said cyclic compound(s) each bear, on average, about 10 to about 20 cyclic compounds per arm.

Any of a number of cyclic compounds are known to those of skill in the art. Illustrative cyclic molecules include, but are not limited to a cyclodextrin, a crown ether, a cucurbituril, or a cyclofructan. Other cyclic compounds that may be used include, but are not limited to various heterocyclic compounds, inorganic cyclic compounds, carbocycles, and chelating macrocyclic compounds. Typically, all of the cyclic molecules in a PRX carrier are the same type of cyclic molecule. However, in certain embodiments, the PRX can comprise multiple species of cyclic compound. In certain embodiments the cyclic compound comprises a cyclodextrin. Illustrative, but non-limiting, cyclodextrins include a cyclodextrin selected from the group consisting of α-cyclodextrins, β-cyclodextrins, and γ-cyclodextrins. In certain embodiments, the cyclodextrin comprises about 5 to about 8, or about 6 to about 7, aminated D-glucose units. In certain embodiments, the α-cyclodextrins may comprise from 1 to 6 aminated D-glucose units. In certain embodiments the β-cyclodextrins may comprise from 1 to 7 aminated D-glucose units. In certain embodiments the γ-cyclodextrins may comprise from 1 to 8 aminated D-glucose units. In certain embodiments the aminated D-glucose units may be represented by the general Formula:

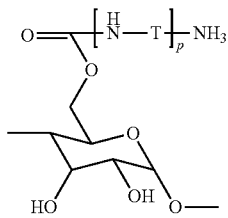

Where p is an integer from 0 to about 8, or 0 to 1 to 4, and where T is optional, and when present is an alkyl selected from the group consisting of methyl (—CH$_3$), ethyl (—CH$_2$CH$_3$) and propyl (—CH$_2$CH$_2$CH$_3$). In one illustrative embodiment, p=5. In one illustrative embodiment, T is ethyl.

In certain embodiments the cyclic compound comprises a cyclodextrin selected from the group consisting of an α-cyclodextrin, a β-cyclodextrin, a γ-cyclodextrin, a hydroxypropylated α-cyclodextrin, a hydroxypropylated β-cyclodextrin, a hydroxypropylated γ-cyclodextrin, and a dimethylcyclodextrin. In certain embodiments, the cyclic compound comprises a cucurbituril (e.g., cucurbit[5]uril, cucurbit[6]uril, cucurbit[7]uril, cucurbit[8]uril, cucurbit[9]uril, and cucurbit[10]uril, etc.). In certain embodiments, the cyclic compound comprises a cucurbit[6]uril (CB[6]).

In certain embodiments, the cyclic compound(s) are substituted with one or more nucleophilic groups. In certain embodiments, the cyclic compound(s) are substituted with one or more amine groups or groups derived from an amine group. In certain embodiments, the cyclic compound(s) are substituted with one or more groups selected from the group consisting of a primary amine, a secondary amine, a tertiary amine, and an imine group. In certain embodiments, the cyclic compound(s) are substituted with one or more primary amines. In certain embodiments, the number of nucleophilic group substituted on the cyclic compound(s) ranges from 1 up to about 20 substitutions per cyclic compound. In certain embodiments, the cyclic compounds are substituted with nucleophilic groups to provide a positive zeta potential for said carrier ranging from about 5 mV up to about 50 mV, or from about 5 mV, or from about 10 mV up to about 40 mV, or up to about 30 mV, or up to about 20 mV. In certain embodiments, the carrier has a zeta potential of about 15 mV.

In certain embodiments, the moiety capping the terminal of the arm(s) threaded into said cyclic compound(s) comprises a moiety selected from the group consisting of Z-tyrosine, phenylalanine, a group having at least one benzene ring, and a group having at least one tertiary butyl. In certain embodiments, the bulky moiety comprises moiety selected from the group consisting of a Z-tyrosine, phenylaline, a benzyloxycarbonyl (Z) group, a 9-fluorenylmethyloxycarbonyl (Fmoc) group, a benzyl ester (OBz) group, a tertiary butylcarbonyl (Boc) group, and an amino acid-tertiary butyl ester (OBu) group. In certain embodiments, the bulky moiety comprises Z-tyrosine.

In various embodiments, at least one arms not threaded into the cyclic compound is terminated with a protecting group, and/or a fluorophore, and/or a targeting moiety. In certain embodiments, all the arms not threaded into the cyclic compound are terminated with a protecting group, and/or a fluorophore, and/or a targeting moiety. In certain embodiments, least one arm not threaded into said cyclic compound is terminated with a protecting group selected from the group consisting of dansyl, acetyl, amide, and 3 to 20 carbon alkyl groups, Fmoc, Tboc, 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pme), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), Benzyloxymethyl (Bom), t-butoxycarbonyl (Boc), cyclohexyloxy (cHxO), t-butoxymethyl (Bum), t-butoxy (tBuO), t-Butyl (tBu), Acetyl (Ac), and Trifluoroacetyl (TFA).

In certain embodiments, at least one arm not threaded into said cyclic compound is attached to a fluorophore (e.g., a rhodamine, a cyanine, an oxazine, a thiazine, a porphyrin, a phthalocyanine, a fluorescent protein, a quantum dot, etc.). In certain embodiments, the fluorophore is selected from the group consisting of fluorescein isothiocyanate (especially fluorescein-5-isothiocyanate), 5-FAM (5-carboxyfluorescein), 6-FAM (6-carboxyfluorescein), 5,6-FAM, 7-hydroxycoumarin-3-carboxamide, 6-chloro-7-hydroxycoumarin-3-carboxamide-, dichlorotriazinylaminofluorescein, tetramethylrhodamine-5 (and-6)-isothiocyanate, 1,3-bis-(2-dialkylamino-5-thienyl)-substituted squarines, succinimidyl esters of 5 (and 6) carboxyfluoroscein, 5 (and 6)-carboxytetramethylrhodamine, and 7-amino-4-methylcoumarin-3-acetic acid, DyLight 350, DyLight 405, DyLight 488, DyLight 550, DyLight 594, DyLight 633, DyLight 650, DyLight 680, DyLight 755, DyLight 800. Alexa fluor 350, Alexa fluor 405, Alexa fluor 488, Alexa fluor 546, Alexa fluor 555, Alexa fluor 568, Alexa fluor 594, Alexa fluor 633, Alexa fluor 647, Alexa fluor 750.

In certain embodiments, at least one backbone arm not threaded into said cyclic compound is attached to a targeting moiety that specifically or preferentially binds to a cell. In certain embodiments, the targeting moiety is selected from the group consisting of an antibody, a receptor ligand, a nucleic acid aptamer, a peptide aptamer, and a lectin. In certain embodiments targeting moiety comprises an antibody (e.g., a full-length antibody, an scFV, an affibody, an antibody fragment, etc.). In certain embodiments, the targeting moiety binds to a stem cell. In certain embodiments, the targeting moiety binds to a hematopoietic cell. In certain embodiments, the targeting moiety binds to a T-cell. In certain embodiments, the targeting moiety binds a target selected from the group consisting of CD45, CD3, erbB2, Her2, CD22, CD74, CD19, CD20, CD33, CD40, MUC1, IL-15R, HLA-DR, EGP-1, EGP-2, G250, prostate specific membrane antigen (PSMA), prostate specific antigen (PSA), prostatic acid phosphatase (PAP), and placental alkaline phosphatase. In certain embodiments, the targeting moiety binds to a cancer cell marker. In certain embodiments, the targeting moiety binds to a cancer cell marker selected from the group consisting of 5 alpha reductase, α-fetoprotein, AM-1, APC, APRIL, BAGE, 0-catenin, Bc12, bcr-abl (b3a2), CA-125, CASP-8/FLICE, Cathepsins, CD19, CD20, CD21, CD23, CD22, CD38, CD33, CD35, CD44, CD45, CD46, CD5, CD52, CD55, CD59 (791Tgp72), CDC127, CDK4, CEA, c-myc, Cox-2, DCC, DcR3, E6/E7, EGFR, EMBP, Ena78, FGF8b and FGF8a, FLK-1/KDR, Folic Acid Receptor, G250, GAGE-Family, gastrin 17, Gastrin-releasing hormone (bombesin), GD2/GD3/GM2, GnRH, GnTV, gp100/Pmel17, gp-100-in4, gp15, gp75/TRP-1, hCG, Heparanase, Her2/neu, Her3, HMTV, Hsp70, hTERT, (telomerase), IGFR1, IL-13R, iNOS, Ki 67, KIAA0205, K-ras, H-ras, N-ras, KSA, (CO17-1A), LDLR-FUT, MAGE Family (MAGE1, MAGE3, etc.), Mammaglobin, MAP17, Melan-A/, MART-1, mesothelin, MIC A/B, MT-MMP's, such as MMP2, MMP3, MMP7, MMP9, Mox, Mucin, such as MUC-1, MUC-2, MUC-3, and MUC-4, MUM-1, NY-ESO-1, Osteonectin, p15, P170/MDR1, p53, p97/melanotransferrin, PAI-1, PDGF, Plasminogen (uPA), PRAME, Probasin, Progenipoietin, PSA, PSM, RAGE-1, Rb, RCAS1, SART-1, SSX gene, family, STAT3, STn, (mucin assoc.), TAG-72, TGF-α, TGF-β, Thymosin β 15, IFN-α, TPA, TPI, TRP-2, Tyrosinase, VEGF, ZAG, p16INK4, and Glutathione S-transferase.

Any of the foregoing markers can be used as targets for the targeting moieties comprising the multi-arm PRX carriers described herein. In certain embodiments the target markers include, but are not limited to members of the epidermal growth factor family (e.g., HER2, HER3, EGF, HER4), CD1, CD2, CD3, CD5, CD7, CD13, CD14, CD15, CD19, CD20, CD21, CD23, CD25, CD33, CD34, CD38, 5E10, CEA, HLA-DR, HM 1.24, HMB 45, 1a, Leu-M1, MUC1, PMSA, TAG-72, phosphatidyl serine antigen, and the like.

In certain embodiments the one or more targeting moieties on the PRX carrier can comprise a cell penetrating peptide (CPP). Cell Penetrating Peptides (CPPs, also known as Cell Permeable Peptides or as Protein Transduction Domains, PTDs), are carriers with small peptide domains (generally less than 40 amino acids) that can easily cross cell membranes. Multiple cell permeable peptides have been identified that facilitate cellular uptake of various molecular cargo, ranging from nanosize particles to small chemical molecules.

The most commonly used CPP is the HIV-TAT sequence. There are multiple other cell penetrating sequences, a small selection of which is shown below in Table 1. For a comprehensive review of currently available CPPs see, e.g., Reissman (2014) *J. Pept. Sci.* 20: 760-784).

TABLE 1

Illustrative, but non-limiting list of cell penetrating peptides.

| Name | Sequence | SEQ ID NO. |
|---|---|---|
| HIV-TAT | GRKKRRQRRRPQ | 3 |
| Oligo-Arginine | RRRRRRRR | 4 |
| MPG | Ac-GALFLGFLGAAGSTMG AWSQPKKKRKV-cya | 5 |
| PEP-1 | Ac-KETWWETWWTEWSQPK KKRKC-cya | 6 |
| EB1 | LIKLWSHLIHIWFQNRRLK WKKK | 7 |
| Transportan | GWTLNSAGYLLGKINLKAL AALAKKIL | 8 |
| p-Antp | RQIKIWFQNRRMKWKK | 9 |
| hCT(18-32) | KFHTFPQTAIGVGAP-NH2 | 10 |
| KLAseq | KLALKLALKALKAALKLA | 11 |

In certain embodiments, the targeting moiety comprises a moiety that binds surface markers of skeletal muscle cells. Illustrative muscle cell markers include, but are not limited to N-CAM (see, e.g., Walsh (1990) N-CAM is a Target Cell Surface Antigen for the Purification of Muscle Cells for Myoblast Transfer Therapy. In: Griggs R. C., Karpati G. (eds) Myoblast Transfer Therapy. Advances in Experimental Medicine and Biology, vol 280. Springer, Boston, Mass.), and 16.3A5 (see, e.g., Woodroofe et al. (1984) Som. Cell Mol. Genet. 10(5): 535-540).

The foregoing markers (targets) are intended to be illustrative and not limiting. Other tumor associated antigens will be known to those of skill in the art.

Where the tumor marker is a cell surface receptor, ligand to that receptor can function as targeting moieties. Similarly, mimetics of such ligands can also be used as targeting moieties.

In certain embodiments, the targeting moiety comprises a folic acid or a transferrin.

In certain embodiments the multi-arm polyrotaxane carrier is a fourth generation carrier (G4-PRX). Accordingly, in certain embodiments the bulky moiety is attached to an arm of the backbone by a cleavable linkage and/or the one or more nucleophilic groups are attached to the cyclic compounds by a cleavable linkage. A linkage or linking agent as used herein, refers to a molecule or functional group that is used to join two or more molecules. In certain embodiments, the linker is typically capable of forming covalent bonds to both molecule(s). Suitable linkages/linkers are well known to those of skill in the art and include, but are not limited to, straight or branched-chain carbon linkers, heterocyclic carbon linkers, or peptide linkers.

In certain embodiments, the cleavable linkage comprises a redox-responsive linker, a pH responsive linker, an enzymatically cleavable linker, a photo-responsive linker, or a thermal-responsive linker. In certain embodiments, the cleavable linkage comprises a redox-responsive disulfide linker. In certain embodiments, the cleavable linkage comprises a pH responsive hydrazine linker. In certain embodiments, the cleavable linkage comprises an enzymatically cleavable linker. In certain embodiments, the linkage comprises a linker cleavable by a protease. In certain embodiments, the linkage comprises a linker cleavable by a matrix metalloprotease or a cathepsin. In certain embodiments, the peptide linker comprises a dipeptide valine-citrulline (Val-Cit), or Phe-Lys. Additional linker can include, but are not limited to, Mc-vc-PAB-MMAE, Mc-vc-PAB-MMAF, Mc-va-PBD dimer, Mc-vc-PAB-CM-seco-DUBA, and the like.

As noted above, the multi-polyrotaxane carries can be complexed with the nucleic acid simply by combining the two moieties where they self-assemble to form a deliverable nanocarrier.

In various embodiments the multi-arm polyrotaxane carriers are made by:
  providing a multi-arm PEG backbone comprising m arms where m ranges from 3 to 8;
  coupling first protecting groups to x arms of said backbone where x ranges from 1 to m−1;
  forming cyclic compound inclusion bodies on the arms of said PEG backbone that are not coupled to said first protecting groups; and
  adding blocking groups to the arms of said PEG backbone that bear cyclic compound inclusion bodies.

Figure 11:
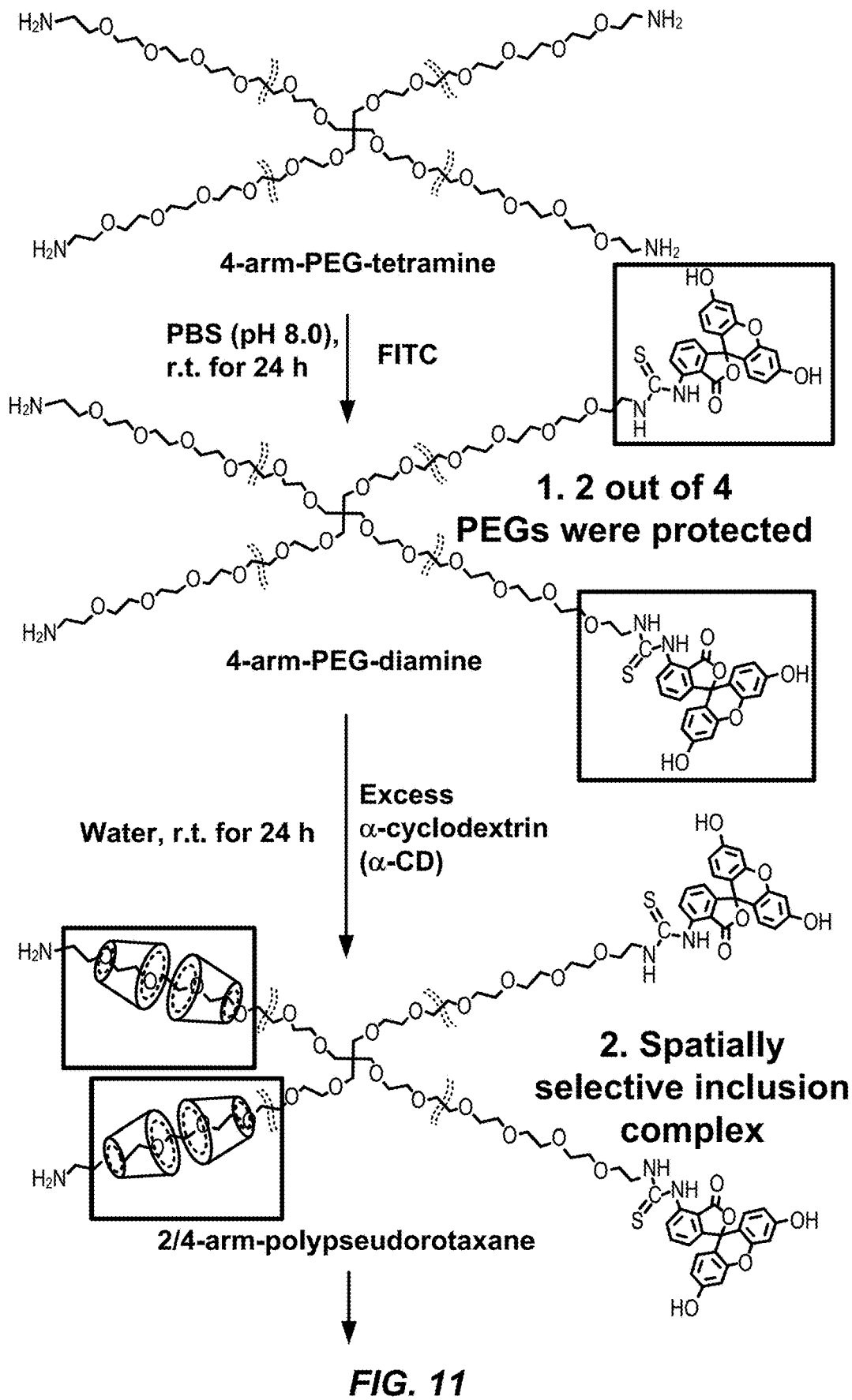
FIG. 11 shows the general synthesis steps of multiarm PRX.
Figure 12:
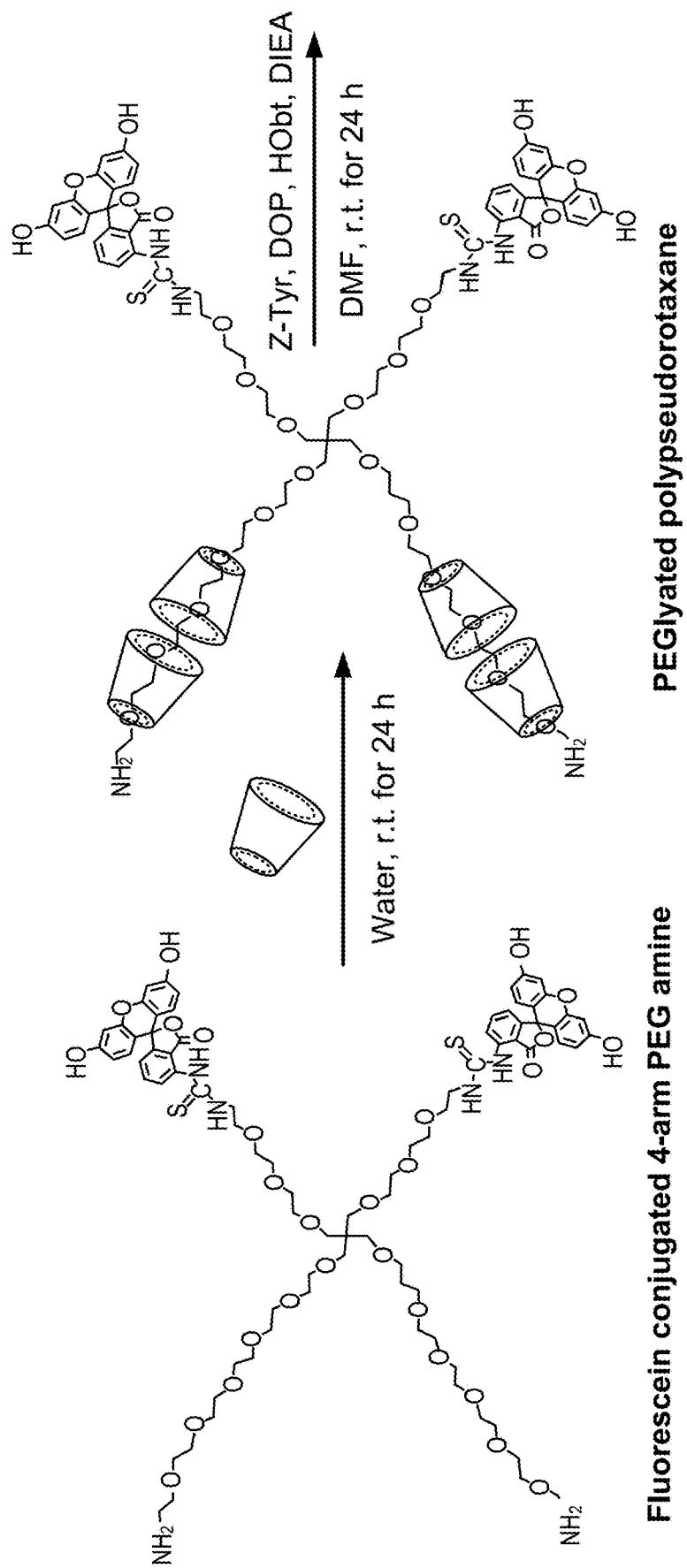
FIG. 12 shows illustrative synthesis steps of a representative G4 PRX.
Figure 13:
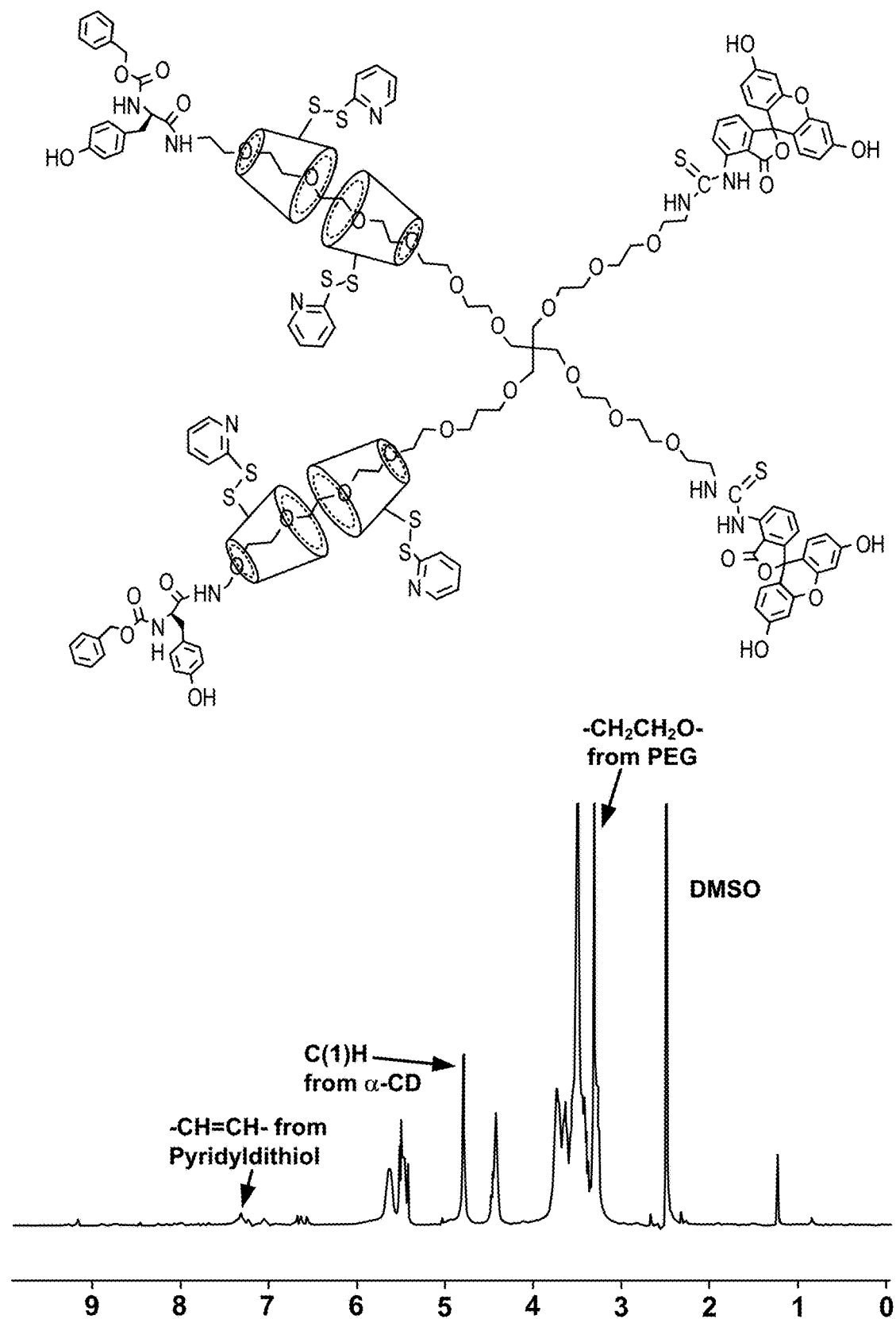
FIG. 13 shows NMR data of the intermediary product for G4 PRX, namely, pyridyldithiol-polyrotaxane.

A synthesis scheme for making a third generation (G3) multi-arm polyrotaxane carrier described herein is shown in FIG. 11, and protocols are also provided in the Examples. An illustrative synthesis scheme for making a fourth generation (G4) multi-arm polyrotaxane carrier incorporating cleavable linkages described herein is shown in FIG. 12, and NMR data of the intermediary product (pyridyldithiol-polyrotaxane) for this G4 PRX is shown in FIG. 13 and described in the Examples. These synthesis schemes are illustrative and non-limiting. Using the teachings provided herein, numerous variants of the multi-arm polyrotaxanes shown herein will be available to one of skill in the art and readily synthesized.

Uses.

One of skill in the art will recognize that the PRX carriers described herein can be used to deliver any of a number of nucleic acid constructs to cells and/or tissues in vivo. Moreover, particularly when the nanocarriers bear one or more targeting moieties, specific cell and tissue types can be directly targeted while reducing systemwide exposure to the nanocarrier.

The nanocarriers described herein find a number of uses. As proof of principle, the a nanocarrier targeted to skeletal muscle that delivers a CRISPR/Cas9 platform for the correction of the dystrophin gene and treatment of Duchenne's Muscular Dystrophy by restoration on of the DMD reading frame.

The nanocarriers, however are not limited to the use of a CRISPR/Cas9 platform for this purpose. For example, in certain embodiments, the polyrotaxane carriers (e.g., G3 or G4 carriers) complexed with a plasmid that encodes a CRISPR/Cas9 construct that targets (e.g., knocks out) particular genes (e.g., genes that are mutated in various cancers) can be used in the treatment of a number of cancers or other diseases. Illustrative, but non-limiting, list of conditions and associated targets is shown in Table 2.

TABLE 2

Illustrative diseases that can be targeted/treated using CRISPR/Cas9 constructs delivered using the polyrotaxane constructs described herein.

| Disease | Target |
| --- | --- |
| Breast cancer | Her2/Neu, BRCA |
| Lung cancer | EGFR |
| Pancreatic cancer | KRAS |
| Colon cancer | KRAS |

TABLE 2-continued

Illustrative diseases that can be targeted/treated using CRISPR/Cas9 constructs delivered using the polyrotaxane constructs described herein.

| Disease | Target |
| --- | --- |
| Melanoma | BRAF |
| Thyroid cancer | TERT promoter |
| Lymphoma | cMyc, TRP53 |
| Multiple cancers | PD-1, PD-L1 |
| Alzheimer's disease | Presenilin 1 |
| Beta-thalassemia | HBB |
| Huntington | RNF216 |

As indicated in Table 2, in certain embodiments, the constructs delivered by the multi-arm polyrotaxane carriers can encode a gene or cDNA encoding a protein that shows efficacy against various cancers. In certain embodiments the protein comprises a cytokine. A number of cytokines have been used for the treatment of cancer. These include, but are not hinted to interferon alpha (IFN-α), interferon beta (IFN-β), interferon gamma (IFN-γ), interleukin 1 (IL-1), interleukin (IL-2), and interleukin 12 (IL-12). These cytokines demonstrate their efficacy by inducing apoptosis and other anticancer functions in tumor microenvironment. For example, IFN-α exerts its anticancer efficacy by inducing NK cells and DCs against tumor cells by inhibiting cell proliferation and killing cancer cells, thus showing anticancer effects in, inter alia, melanoma and Kaposi sarcoma (see, e.g., Sutlu & Alici (2009) *J. Intern. Med.* 266: 154-181; Joshi et al. (2009) *Proc. Natl. Acad. Sci. USA*, 106: 12097-12102; Jonasch & Haluska (2001) *Oncologist*, 6: 34-55). IL-1α shows cytotoxic-cytostatic activity against refractory malignancies and solid tumor cells (see, e.g., Rosenthal et al. 91998) *J. Immunother.* 21: 371-378; Furman et al. (1997) *Med. Pediatr. Oncol.* 28: 444-450).

Th1 cytokine IL-2 shows anticancer efficacy against several types of cancer including hematologic malignancies in in vitro, in vivo, and clinical studies (see, e.g., Sznol & Parkinson (1994) *Blood*, 83: 2020-2022). Cytokine IL-2 exerts it anticancer efficacy by enhancing anticancer immunity that is evident by the use of recombinant antibody-IL-2 fusion protein (huKS1/4-IL-2) in colorectal carcinoma (see, e.g., Xiang et al. (1998) *Cancer Res.* 58: 3918-3925). IL-4 has been reported to facilitate its anticancer efficacy by inhibiting growth of human lung tumor cells (see, e.g., Topp et al. (1993) *Blood*, 82: 2837-2844). In MCF-7 breast cancer cells, IL-4 showed growth inhibition and induction of apoptosis via insulin receptor substrates and STAT-6 phosphorylation (see, e.g., Gooch et al. (2002) *Neoplasia*, 4: 324-331).

While IL-6 expression has often been viewed as undesirable in regulation/treatment of cancers, a lesser known role for IL-6 signaling has emerged in which it plays a beneficial role that opposes tumor growth by mobilizing anti-tumor T cell immune responses to attain tumor control. Accumulating evidence establishes IL-6 as a key player in the activation, proliferation and survival of lymphocytes during active immune responses. IL-6 signaling can also resculpt the T cell immune response, shifting it from a suppressive to a responsive state that can effectively act against tumors. Additionally IL-6 plays a role in boosting T cell trafficking to lymph nodes and to tumor sites, where they have the opportunity to become activated and execute their cytotoxic effector functions, respectively (see, e.g., Fisher et al. (2014) *Semin. Immunol.*, 26(1): 38-47).

IL-7 in combination with human T cells has been shown to exert significant anticancer activity in human colon carcinoma (see, e.g., Murphy et al. (1993) *J. Clin. Invest.* 92:

1918-1924). It is believed the protective function of IL-7 is mediated via activation of the PI3K/AKT pathway (see, e.g., Zhang et al. (2011) *Clin. Cancer Res.* 17: 4975-4986). IL-11 is used in myelosuppressive chemotherapy to minimize the chance of thrombocytopenia in patients with malignancies (see, e.g., Bhatia et al. (2007) *Leuk. Lymphoma*, 48: 9-15).

Being a key player in cellular immunity against tumor, IL-12 has been an attractive option for immunotherapy, but prior to the development of the polyrotaxane delivery system described herein (see, e.g., Example 3) the presence of severe toxicity has minimized its use in cancer therapy.

IL-15 plays important role in the induction of NK cells, T-cells, and B cells that demonstrate therapeutic potential of this key cytokine in malignancy (see, e.g., Mishra et al. (2014) *Clin. Cancer Res.* 20: 2044-2050).

Accordingly, in certain embodiments the constructs delivered by the multi-arm polyrotaxane carriers described herein comprise plasmids that encode and express a cytokine. In certain embodiments the plasmids encode a cytokine selected from the group consisting of interleukin 12 (IL-12), interferon alpha (IFN-α), interferon beta (IFN-β), interferon gamma (IFN-γ), interleukin 1 (IL-1), interleukin (IL-2), interleukin 4 (IL-4), interleukin 6 (IL-6), interleukin 7 (IL-7), interleukin 11 (IL-11), interleukin 15 (IL-15), interleukin 18 (IL-18), and the like.

In certain embodiments the constructs delivered by the multi-arm polyrotaxane carriers described herein comprise a plasmid that encodes multiple cytokines and/or multiple plasmids where each plasmid encodes a different cytokines. Accordingly the the multi-arm polyrotaxane carriers described herein can effectively used to deliver any of a number of combinations of cytokines. Illustrative combinations of cytokines include, but are not limited to IL-2/IL-12, IL-15/IL-12, IL-7/IL-12, IL-21/IL-12, IL-18/IL-12, GM-CSF/IL-12, IFN alpha/IL-12, chemokines and anti-angiogenic cytokines plus IL-12 and the like. These various combinations of cytokines have found utility in the treatment of various cancers (see, e.g., Weiss et al. (2007) *Exp. Opin. Biol. Ther.* 7(11):1705-1721).

Plasmids expressing any of these cytokines are readily created by one of skill in the art and a number are commercially available. The creation of a plasmid expressing IL-12 and incorporating that plasmid in a polyrotaxane carrier is illustrated in Example 3. Using the teachings provided there polyrotaxane carriers incorporating plasmids encoding any of the above-described cytokines or any other cytokine or other protein can readilby be produced by one of skill in the art.

The constructs delivered by the multi-arm polyrotaxane carriers described herein are not limited to plasmids encoding CRISPR/Cas9 components or cytokines. For example, in certain embodiments, the complexed plasmid can encode a heterologous gene whose expression corrects a genetic deficiency or improves the health of a subject. In certain embodiments, the complexed plasmid can encode one or a pluralityh of inhibitory nucleic acids (e.g., antisense nucleic acids, ribozymes, and the like) that inhibit or downregulate the expression of particular genes.

By way of illustration, angiotensin-converting enzyme (ACE) inhibitors are used in medicine to treat hypertension and life extension by ACE inhibition has been shown in nematode worms. Similarly, knockout of Adenylyl Cyclase Type 5 (AC5) extends life in mice, with the most plausible mechanism being increased resilience of the cardiovascular system. Accordingly, in certain embodiments, the plasmid complexed with the multi-arm polyrotaxane carriers described herein can encode a CRISPR/Cas9 construct, or other construct, that inhibits (or knocks out) ACE or AC5.

A recent study suggests that a rare variant in the Angiopoietin-like 4 (ANGPTL4) gene, present in less than 1% of the European population, reduces the risk of heart attack by half. In certain embodiments, the polyrotaxane constructs described herein can deliver a complexed plasmid that encodes this genetic variant.

Other gene therapies that can be delivered using the multi-polyrotaxane carriers described herein include, but are not limited to: Lowering angiotensin II receptor type 1 (Agtr1a) which protects mitochondrial function and has been observed to modestly extends life in mice. Increasing Apolipoprotein A-1, can alter cholesterol metabolism in a beneficial way, slowing progression of atherosclerosis by transporting away some of the damaged lipids where they are build up in blood vessel walls. APOE is one of the only human genes with variants that are robustly associated with greater longevity. Gene knockout of ARID1A has been observed to produce regenerative capacity in mice, particularly in the liver. Increased levels of Activating transcription factor 4 (ATF4) in the liver are found in many of the methods of slowing aging in laboratory species. Increased amounts of atoh1 have been used to spur growth of hair cells in guinea pigs, making it one of a number of possible approaches to address the proximate cause of forms of age-related deafness that result from loss of these cells, rather than from other causes. The azot gene in fruit flies is a part of a mechanism by which cells collaborate to identify damaged or dysfunctional neighbors, flagging them for destruction and replacement. Adding an extra copy of the azot gene to increase levels of the azot protein results in more effective destruction of less fit cells, and an increase in life span—in fruit flies at least. The gene and associated mechanism of quality control appears to be conserved in mammals. Inhibition of bcat-1 is shown to extend life in nematode worms, possibly via a form of hormesis or calorie restriction effect by blocking the processing of some dietary molecules. β2 microglobulin (B2M) levels rise with age, and in mice and reducing the amount of B2M in older individuals restores some of the loss of cognitive decline that occurs in aging. Mice engineered to express higher levels of BubR1 have lower levels of cancer, greater exercise capacity, and live modestly longer. The cancer effect makes sense in the context of what is known of BubR1, that it is involved in an important checkpoint mechanism of cellular replication. Researchers have shown that lowered levels of c-myc can modestly slow aging and extend life in mice, with some evidence that this is due to effects on insulin metabolism. The C1Q gene plays a role in the immune system. Removing it from mice spurs greater regeneration via Wnt signaling. C1Q levels rise in the brain with aging, and again, removing it improves the state of cognitive function in later life in mice. Gene therapy to increase levels of the antioxidant catalase in the mitochondria in mice have produced mixed results, but some studies show improved health and extended life. Other approaches to mitochondrially targeted antioxidants have produced similar benefits. The prevailing theory is that this reduces damage to mitochondria occurring as a result of the reactive oxygen species generated within these organelles, with localized antioxidants soaking up reactive molecules before they can cause harm. Reduced CLK1 activity can extend life in mice due to altered mitochondrial function and consequently lowered generation of reactive oxygen species. A reduced amount of CRTC1 can extend life in nematode worms, and is probably involved in the calorie restriction response. This protein is closely related to AMPK, and manipulations of both CRTC1 and AMPK are likely achieving much the same alterations in the operation of metabolism. Increased levels of cyclin A2 have been shown to increase the regenerative capacity of heart tissue, one of an array of proteins that might for the basis for regenerative gene therapies for heart disease, and thus also might be beneficial to undergo far in advance of old age so as to slow or postpone degeneration of the heart. Overexpression of FGF21 occurs in the calorie restriction response, and when induced artificially using gene therapy it can extend life in mice. Gene therapy to boost levels of FKBP1b to youthful levels can reverse age-related dysfunction of calcium metabolism in the brains of rats. Cognitive function improved as a result, as assessed with tests of spatial memory. Increased follistatin produces increased muscle growth, a potentially useful compensation for the loss of muscle mass and strength that occurs with aging. It is the flip-side of myostatin, as increased follistatin blocks the activity of myostatin: either increased follistatin or reduced myostatin produce similar outcomes in animal studies, with treated individuals demonstrating increased muscle mass. A variant of FOXO3 is associated with a modest reduction in cardiovascular disease and mortality in human data. Higher levels of GDF11 have been shown to improve numerous measures of aging in mice, such as heart function, exercise capacity, and sense of smell. This is most likely occurring due to increased stem cell activity, though there continues to be some debate as to what exactly the researchers are observing in these studies. The level of GHK in blood and tissues declines with aging, and is implicated in some of the detrimental changes in wound healing that occur in later life. Since delivering GHK on its own appears to be beneficial, using gene therapy to reset GHK levels may restore some of this loss of regenerative capacity. In flies, higher levels of Glycine N-methyltransferase (Gnmt) act to inhibit the use of methionine in protein synthesis, which mimics some of the efforts of calorie restriction on health and longevity. Reaction to lower methionine levels—or the appearance of lower methionine levels—is a key trigger for the calorie restriction response. The longest lived genetically altered mice are those without a functional growth hormone receptor gene (growth hormone/growth hormone receptor/insulin-like growth factor/insulin receptor). They are small and vulnerable to cold, but otherwise healthy. Many similar approaches to disrupting the well-studied operations of growth hormone and insulin metabolism also extend life in mice to various degrees, some of which are whole-body, while others are tissue-specific. Mice engineered to have low levels of—or entirely absent histone deacetylase 2 (HDAC2) have improved memory function and neural plasticity. Heat shock proteins are molecular chaperones involved in cellular housekeeping processes that clear out damaged or misfolded proteins. Their activity increases in response to heat, toxins, and various other forms of cellular stress, and dialing up the activity of heat shock proteins is involved in a number of methods demonstrated to slow aging in laboratory animals. Many of these invoke altering the level of other proteins that interact with or regulate heat shock proteins. A range of hepatic transcription factors are associated with development and regeneration in the liver. Researchers have demonstrated that some of these can be upregulated to reduce liver fibrosis by steering cell lineages away from the production of scar tissue and towards the production of useful liver cells. Hepatocyte growth factor (HGF) is a potential compensatory therapy to spur remodeling and regrowth of blood vessels in ischemic disease. The INDY gene, I'm Not Dead Yet, was one of the first longevity-associated genes discovered in flies. Reduced levels of the INDY protein extend life, with the evidence pointing to increased intestinal stem cell function as the cause. Delivering higher levels of IL-21 has been demonstrated to improve the state of the immune system by increasing the pace at which new immune cells are generated. Loss of immune function with age is an important component of age-related frailty, and even partially compensating for this decline might be very beneficial. Selectively lowering levels of klf4 in smooth muscle cells in blood vessel walls causes beneficial changes in the behavior of these cells. Their overreaction to damaged lipids arriving in the bloodstream is muted, which slows the progression of damage and reaction to that damage that leads towards atherosclerosis. Overexpression of klotho has been shown to increase life span in mice, possibly through some of the same mechanisms as calorie restriction. There are three lamin isoforms, A, B, and C. The cause of progeria, a rare condition with the appearance of accelerated aging, is a mutation in Lamin A. Much smaller amounts of malformed lamin A are found in old tissues, though it is uncertain as to whether or not this contributes in any meaningful way to the progression of aging. Intriguingly, mice engineered to produce only lamin C live modestly longer. The A variant of lysosome-associated membrane protein 2 (LAMP2a) is a receptor involved in the cellular maintenance processes of autophagy, but levels decrease with age, and in at least some species this appears to be one of the factors involved in the age-related decline of autophagy. Nearly a decade ago now, researchers demonstrated restoration of more youthful levels of liver function in old mice by adding a duplicate gene to increase amounts of this protein. Increased efficiency of autophagy shows up as a feature of many of the interventions shown to slow aging in animals, but this is one of the few examples in which some rejuvenation of function in old animals was observed. Altered Leukemia inhibitory factor (LIF) levels have been used to spur neural cells into greater activity that can better restore lost myelin sheathing on nerves. Since we all lose some of this sheathing with age, this is of general interest, applicable to more than just conditions such as multiple sclerosis in which a great deal of myelin is lost. Increased Lin28a expression enhances regenerative capacity in mice. This is another gene that has been used in reprogramming ordinary cells to become stem cells. LOS1 may be involved in a variety of fundamental cellular processes, ranging from protein synthesis to DNA repair. The effects of LOS1 knockout on longevity have only been explored in yeas. The microRNA miR-195 interacts with telomerase, and inhibiting it has much the same beneficial effect on stem activity as increasing levels of telomerase. More stem cell activity means more regeneration, though possibly also a higher risk of cancer in later life. Since stem cell activity declines with age, there are many research groups working on potential ways to restore that activity to youthful levels. Partial disruption of the function of mitochondrial complex I has been shown to modestly extend life in a number of species, with the dominant theory being that this is a hormetic effect—an increase in the creation of reactive oxygen species prompts cells to react with greater repair and maintenance efforts. Alterations to the Mechanistic target of rapamycin (mTOR) gene and levels of protein produced have been shown to modestly extend life span in several species. There are also a few synergistic genetic alterations involving mTOR and other genes discovered in lower animals that produce much larger effects. The mTOR protein is involved in many fundamental cellular processes, like many of the longevity-associated genes in laboratory species, and produces fairly sweeping alterations in cellular metabolism. Reduced myostatin produces increased muscle growth, which may be a useful compensation for the loss of muscle mass and strength that occurs with aging. As a result of a number of natural animal lineages with this mutation, myostatin knockout is by far the most examined and tested of all potential gene therapies. There have been human trials of myostatin blockade via antibodies, for example, and there are even a few well-muscled natural human myostatin loss of function mutants. Higher levels of NAD-dependent methylenetetrahydrofolate dehydrogenase-methenyltetrahydrofolate cyclohydrolase (NMDMC) have been shown to modestly slow aging in flies, most likely through improved mitochondrial function. Inhibition of NF-κB extends life modestly in a number of lower species, though given its involvement in immunity, inflammation, apoptosis, and other fundamental processes. Increased levels of NRF2 in mice or its homolog SKN-1 in nematodes results in slower aging and modestly extended life spans—normally NRF2 levels decline with age. This can be achieved by manipulation of the levels of other, interacting proteins such as glutathione transferase (gGsta4). The mechanism of action here is thought to involve resistance to oxidative damage and increased quality control of damaged proteins. Interestingly, long-lived naked mole rats exhibit high levels of NRF2. One of the target genes used in reprogramming cells into induced pluripotent stem cells is Oct4. It was recently found that Oct4 can act to stabilize plaques in atherosclerosis to make the disease less deadly. P16 is perhaps best known as an indicator of cellular senescence, a part of the mechanisms that cause damaged cells or those at the Hayflick limit to become senescent or self-destruct. There are signs that targeted reductions in p16 levels can in some cases produce a net benefit, such as when used to make stem cell populations more active in old age. Both MRL mice and P21 knockout mice can regenerate small injuries with no scarring, something that most other mammals cannot achieve, and reduced levels of the p21 protein seems to be the common factor in these engineered mouse lineages. The protein p53 plays the role of tumor suppressor, but creating a general increase in p53 levels will, in addition to reducing cancer incidence, also accelerate aging by reducing tissue maintenance through the creation of new cells. There are, however, a number of ways in which p53 levels can be increased only when needed. One involves reduced levels of mdm2, a p53 inhibitor. Another involves an additional copy of the p53 gene, inserted without disrupting the existing regulatory process that manages p53 levels. In the latter case, engineered mice live modestly longer thanks to a lower rate of cancer. An increased level of parkin is one of the ways in which greater cell maintenance via autophagy can be induced, resulting in improved health and modestly extended life spans. There is a lot of support in the literature for more autophagy as an unalloyed good when it comes to health and aging. Many methods of extending life in laboratory species are associated with increased autophagy, and in some cases—such as calorie restriction—that autophagy has been shown to be necessary for life extension. Loss of function mutations in PCSK9 reduce the risk of cardiovascular disease, most likely through lowered blood cholesterol levels. Proof of principle studies have been carried out in mice. Deletion of the PER2 gene in mice, associated with the mechanisms of circadian rhythm, appears to improve DNA repair in stem cell populations relevant to the immune system, resulting in a healthier immune cell population, better immune function in old age, and a modestly extended life span. Increased levels of PGC-1 in the intestinal tissues of flies extend life, possibly due to improved mitochondrial and stem cell function. Intestinal function is especially important as a determinant of fly aging and mortality, and many exploratory interventions target this organ. In mice, introducing a variant of PGC-1 produces enhanced muscle growth, most likely via its interaction with myostatin. The protein PHD1 serves as an oxygen sensor. Mice lacking this protein are protected from ischemic injury in stroke, suffering less cell death and recovering to a greater degree afterwards. Increased levels of PEPCK achieved through genetic engineering produces mice that are much more energetic, eat more, but are also modestly longer lived than their unmodified counterparts. Overexpression of PIM1 in the heart produces mice that live longer by improving the ability of heart tissue to repair and maintain itself. Reducing levels of plasminogen activator inhibitor-1 appears to modestly slow aging, possibly by removing one aspect of the harmful impact of senescent cells. Knockout of pregnancy-associated plasma protein-A (PAPP-A) gene interferes with insulin metabolism, and produces a similar extension of health and life in mice when compared with other methods of achieving this end. Adding an extra copy of the tumor suppressor gene PTEN to mice produces lower rates of cancer, much as expected, but also increased life span. Levels of RbAp48 fall with age in the hippocampus. Researchers have demonstrated that targeted restoration of youthful levels of this protein in old mice reversed a large fraction of age-related decline in memory function. Lowered levels of RTN4R can increase plasticity in the adult brain in mice, improving recovery from brain injury and increasing the ability to learn new tasks. This appears to be a part of the mechanism by which plasticity is dialed down after childhood. A reduction in Rpd3 level produces improved cardiac function and modestly increased longevity in flies, though the mechanism of action remains to be explored in more detail. Increased levels of either SERCA2a/SUMO-1 can produce greater beneficial remodeling of blood vessels and heart tissue than would normally take place, and is thus a potential compensatory therapy that might slow the progression of many cardiovascular and circulatory diseases. Increased levels of telomerase have been shown to extend life in mice, as well as reducing cancer incidence in that species. TGF-β1 expression rises with age, and is implicated in loss of stem cell function. Interfering in this pathway via any of the related proteins so as to reduce TGF-β1 levels may be a viable way to increase stem cell activity in later life. Increased activation of Transcription factor EB (TFEB) spurs greater autophagy and so helps to ensure better maintenance of cells. Higher levels of autophagy seem to be an unalloyed good in near all situations, and appear as a feature of many of the ways of modestly slowing aging in laboratory species. Researchers have shown that delivering a modified version of the calcium receptor troponin C into the mammalian heart can improve heart function and the performance of the cardiovascular system. Gene knockout of the pain receptor TRPV1 is one of a number of methods of slowing aging and extending life in mice that appears to work through altered insulin signaling. Another potential mechanism is that this gene knockout blocks the interaction between pain receptors and chronic inflammation, a process that is thought to cause harm in old tissues and organs. Uncoupling proteins manipulate mitochondrial function in order to regulate body heat. As is the case for many proteins that interact with mitochondrial function, altered levels or genetic variants can improve health and longevity. The UMUPA mouse lineage has the addition of a urokinase gene and has a longer life span as a result. The uPA gene is related to PAI-1, also in this list, and is argued to achieve life extension in mice through behavioral change—these mice eat less, and thus the calorie restriction response comes into play. A number of research and development efforts have focused on delivery of VEGF to spur regeneration in the cardiovascular system, and particularly in the heart, an organ with only limited regenerative capacity in mammals. One of the more effective of these attempts in rodents used a mix of VEGF, Gata4, Mef 2c, and Tbx5 to encourage scar tissue in the heart to change itself into healthy tissue.

The foregoing therapeutic modalities are illustrative and non-limiting. These interventions and numerous others can be facilitated by using the multi-arm polyrotaxane carriers described herein for the delivery of the relevant nucleic acid construct(s).

The CRISPR/Cas System—Class 2 CRISPR/Cas Endonucleases

As noted above, the polyrotaxane (PRX) carriers described herein are particularly well suited for the in vivo delivery of large nucleic acid including, but not limited to plasmids. In certain embodiments the plasmid can encode a heterologous gene, or other nucleic acid construct (e.g., an antisense molecule, a ribozyme, etc.).

In certain embodiments, the plasmid or RNA can encode components of a CRISPR/Cas system (e.g., Class 2 CRISPR/Cas endonuclease and one or more guide RNAs) as illustrated in the proofs of principle shown herein. The plasmid(s) encoding the CRISPR/Cas system, when delivered to a cell in vivo using the polyrotaxane carriers described herein can be designed/exploited to introduce extremely specific alterations to the genomic DNA of the target cell(s).

Compelling evidence has recently emerged for the existence of an RNA-mediated genome defense pathway in archaea and many bacteria that has been hypothesized to parallel the eukaryotic RNAi pathway (for reviews, see Godde and Bickerton (2006) *J. Mol. Evol.* 62: 718-729; Lillestol et al. (2006) Archaea 2: 59-72; Makarova et al. (2006) *Biol. Direct* 1: 7.; Sorek et al. (2008) *Nat. Rev. Microbiol.* 6: 181-186). Known as the CRISPR-Cas system or prokaryotic RNAi (pRNAi), the pathway is believed to arise from two evolutionarily and often physically linked gene loci: the CRISPR (clustered regularly interspaced short palindromic repeats) locus, that encodes RNA components of the system, and the cas (CRISPR-associated) locus, that encodes proteins (see, e.g., Jansen et al. (2002) *Mol. Microbiol.* 43: 1565-1575; Makarova et al., (2002) *Nucl. Acids Res.* 30: 482-496; Makarova et al. (2006) *Biol. Direct* 1: 7; Haft et al. (2005) *PLoS Comput. Biol.* 1: e60). CRISPR loci in microbial hosts contain a combination of CRISPR-associated (Cas) genes as well as non-coding RNA elements capable of programming the specificity of the CRISPR-mediated nucleic acid cleavage. The individual Cas proteins do not share significant sequence similarity with protein components of the eukaryotic RNAi machinery, but have analogous predicted functions (e.g., RNA binding, nuclease, helicase, etc.) (see, e.g., Makarova et al. (2006) *Biol. Direct* 1: 7). The CRISPR-associated (cas) genes are often associated with CRISPR repeat-spacer arrays. More than forty different Cas protein families have been described. Of these protein families, Cas1 appears to be ubiquitous among different CRISPR/Cas systems. Particular combinations of cas genes and repeat structures have been used to define 8 CRISPR subtypes (Ecoli, Ypest, Nmeni, Dvulg, Tneap, Hmari, Apern, and Mtube), some of which are associated with an additional gene module encoding repeat-associated mysterious proteins (RAMPs). More than one CRISPR subtype may occur in a single genome. The sporadic distribution of the CRISPR/Cas subtypes suggests that the system is subject to horizontal gene transfer during microbial evolution.

In class 2 CRISPR systems, the functions of the effector complex (e.g., the cleavage of target DNA) can be carried out by a single endonuclease (see, e.g., Zetsche et al. (2015) *Cell,* 163(3): 759-771; Makarova et al. (2015) *Nat. Rev. Microbiol.* 13(11): 722-736; Shmakov et al. (2015) *Mol. Cell.* 60(3): 385-397; and the like). As such, the term "class 2 CRISPR/Cas protein" is used herein to encompass the endonuclease (the target nucleic acid cleaving protein) from class 2 CRISPR systems. Thus, the term "class 2 CRISPR/Cas endonuclease" as used herein encompasses type II CRISPR/Cas proteins (e.g., Cas9), type V CRISPR/Cas proteins (e.g., Cpf1, C2c1, C2C3), and type VI CRISPR/Cas proteins (e.g., C2c2). To date, class 2 CRISPR/Cas proteins encompass type II, type V, and type VI CRISPR/Cas proteins, but the term is also meant to encompass any class 2 CRISPR/Cas protein suitable for binding to a corresponding guide RNA and forming an RNP complex (e.g., and cleaving target DNA).

Type II CRISPR/Cas Endonucleases (e.g., Cas 9)

In natural Type II CRISPR/Cas systems, Cas9 functions as an RNA-guided endonuclease that uses a dual-guide RNA having a crRNA and trans-activating crRNA (tracrRNA) for target recognition and cleavage by a mechanism involving two nuclease active sites in Cas9 that together generate double-stranded DNA breaks (DSBs), or can individually generate single-stranded DNA breaks (SSBs). The Type II CRISPR endonuclease Cas9 and engineered dual-(dgRNA) or single guide RNA (sgRNA) form a ribonucleoprotein (RNP) complex that can be targeted to a desired DNA sequence. Guided by a dual-RNA complex or a chimeric single-guide RNA, Cas9 generates site-specific DSBs or SSBs within double-stranded DNA (dsDNA) target nucleic acids, that are repaired either by non-homologous end joining (NHEJ) or homology-directed recombination (HDR).

In some cases, the plasmid or other therapeutic nucleic acid including RNA, mRNA, etc. complexed with and delivered by the polyrotaxane (PRX) carriers described herein encodes a Cas9 protein. A Cas9 protein forms a complex with a Cas9 guide RNA. The guide RNA provides target specificity to a Cas9-guide RNA complex by having a nucleotide sequence (a guide sequence) that is complementary to a sequence (the target site) of a target nucleic acid (as described elsewhere herein). The Cas9 protein of the complex provides the site-specific activity. In other words, the Cas9 protein is guided to a target site (e.g., stabilized at a target site) within a target nucleic acid sequence (e.g. genomic DNA) by virtue of its association with the protein-binding segment of the Cas9 guide RNA.

In some cases, the CRISPR/Cas endonuclease (e.g., Cas9 protein) is a naturally-occurring protein (e.g., naturally occurs in bacterial and/or archaeal cells). In other cases, the CRISPR/Cas endonuclease (e.g., Cas9 protein) is not a naturally-occurring polypeptide (e.g., the CRISPR/Cas endonuclease is a variant CRISPR/Cas endonuclease, a chimeric protein, and the like, e.g., in some cases the CRISPR/Cas endonuclease includes one or more NLSs).

Examples of suitable Cas9 proteins include, but are not limited to, those set forth in SEQ ID NOs: 5-816 of PCT Application No: PCT/US2017/017255 (WO 2017/139505), which are incorporated herein by reference for the sequences described therein. Naturally occurring Cas9 proteins bind a Cas9 guide RNA, are thereby directed to a specific sequence within a target nucleic acid (a target site), and cleave the target nucleic acid (e.g., cleave dsDNA to generate a double strand break). A chimeric Cas9 protein is a fusion protein comprising a Cas9 polypeptide that is fused to a heterologous protein (referred to as a fusion partner), where the heterologous protein provides an activity (e.g., one that is not provided by the Cas9 protein). The fusion partner can provide an activity, e.g., enzymatic activity (e.g., nuclease activity, activity for DNA and/or RNA methylation, activity for DNA and/or RNA cleavage, activity for histone acetylation, activity for histone methylation, activity for RNA modification, activity for RNA-binding, activity for RNA splicing etc.). In some cases, a portion of the Cas9 protein (e.g., the RuvC domain and/or the HNH domain) exhibits reduced nuclease activity relative to the corresponding portion of a wild type Cas9 protein (e.g., in some cases the Cas9 protein is a nickase). In some cases, the Cas9 protein is enzymatically inactive, or has reduced enzymatic activity relative to a wild-type Cas9 protein (e.g., relative to *Streptococcus pyogenes* Cas9). In some cases, the Cas9 protein is enzymatically enhanced, e.g., or has enhanced enzymatic activity and/or specificity relative to a wild-type Cas9 protein (e.g., relative to *Streptococcus pyogenes* Cas9).

Assays to determine whether given protein interacts with a Cas9 guide RNA can be any convenient binding assay that tests for binding between a protein and a nucleic acid. Suitable binding assays (e.g., gel shift assays) will be known to one of ordinary skill in the art (e.g., assays that include adding a Cas9 guide RNA and a protein to a target nucleic acid).

Assays to determine whether a protein has an activity (e.g., to determine if the protein has nuclease activity that cleaves a target nucleic acid and/or some heterologous activity) can be any convenient assay (e.g., any convenient nucleic acid cleavage assay that tests for nucleic acid cleavage). Suitable assays (e.g., cleavage assays) will be known to one of ordinary skill in the art and can include adding a Cas9 guide RNA and a protein to a target nucleic acid.

In some cases, a chimeric Cas9 protein includes a heterologous polypeptide that has enzymatic activity that modifies a target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In some cases, a chimeric Cas9 protein includes a heterologous polypeptide that has enzymatic activity that modifies a polypeptide (e.g., a histone) associated with target nucleic acid (e.g., methyltransferase activity, demethylase activity, acetyltransferase activity, deacetylase activity, kinase activity, phosphatase activity, u biquitin ligase activity, deu biquitinating activity, adenylation activity, deadenylation activity, SUMOylating activity, deSUMOylating activity, ribosylation activity, deribosylation activity, myristoylation activity or demyristoylation activity).

In some cases, a CRISPR/Cas endonuclease (e.g., a Cas9 protein) includes a heterologous polypeptide that provides for localization within the cell. For example, in some cases, a subject CRISPR/Cas endonuclease (e.g., a Cas9 protein) includes one or more (e.g., 2 or more, 3 or more, 4 or more, 5 or more, etc.) nuclear localization sequences (NLSs). The one or more (e.g., 2 or more, 3 or more, 4 or more, 5 or more, etc.) NLSs can be at any convenient position within the CRISPR/Cas endonuclease (e.g., a Cas9 protein), e.g., N-terminus, C-terminus, internal, etc. In some cases, a CRISPR/Cas endonuclease (e.g., a Cas9 protein) includes one or more (e.g., 2 or more, 3 or more, 4 or more, 5 or more, etc.) NLSs at the N-terminus and one or more (e.g., 2 or more, 3 or more, 4 or more, 5 or more, etc.) NLSs at the C-terminus.

Many Cas9 orthologs from a wide variety of species have been identified and in some cases the proteins share only a few identical amino acids. Identified Cas9 orthologs have similar domain architecture with a central HNH endonuclease domain and a split RuvC/RNaseH domain (e.g., RuvCI, RuvCII, and RuvCIII) (e.g., see Table 3). For example, a Cas9 protein can have 3 different regions (sometimes referred to as RuvC-I, RuvC-11, and RucC-III), that are not contiguous with respect to the primary amino acid sequence of the Cas9 protein, but fold together to form a RuvC domain once the protein is produced and folds. Thus, Cas9 proteins can be said to share at least 4 key motifs with a conserved architecture. Motifs 1, 2, and 4 are RuvC like motifs while motif 3 is an HNH-motif. The motifs set forth in Table 3 may not represent the entire RuvC-like and/or HNH domains as accepted in the art, but Table 3 does present motifs that can be used to help determine whether a given protein is a Cas9 protein.

TABLE 3

Four 4 motifs that are present in Cas9 sequences from various species. The amino acids listed in Table 1 are from the Cas9 from S. pyogenes (SEQ ID NO: 309, see also SEQ ID NO: 5 in PCT/US2017/017255).

| Motif # | Motif | Amino acids (residue #s) | Highly conserved |
|---|---|---|---|
| 1 | RuvC-like I | IGLDIGTNSVGWAVI (7-21) (SEQ ID NO: 12) | D10, G12, G17 |
| 2 | RuvC-like II | IVIEMARE (757-766) (SEQ ID NO: 13) | E762 |
| 3 | HNH-motif | DVDHIVPQSFLKDDSIDN KVLTRSDKN (887-863) (SEQ ID NO: 14) | H840, N854, N863 |
| 4 | RuvC-like III | HHAHDAYL (982-989) (SEQ ID NO: 15) | H982, H983, A984, D986, A987 |

In some cases, a suitable Cas9 protein comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 as set forth in SEQ ID NOs: 12-15, respectively (e.g., see Table 3), or to the corresponding portions in any of the amino acid sequences set forth in SEQ ID NOs: 5-816 in PCT/US2017/017255).

In other words, in some cases, a suitable Cas9 polypeptide comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence set forth in SEQ ID NO:309 (see also SEQ ID NO:5 in PCT/US2017/017255) (e.g., the sequences set forth in SEQ ID NOs: 12-15, e.g., see Table 3), or to the corresponding portions in any of the amino acid sequences set forth in SEQ ID NOs 6-816 in PCT/US2017/017255.

In some cases, a suitable Cas9 protein comprises an amino acid sequence having 4 motifs, each of motifs 1-4 having 60% or more amino acid sequence identity to motifs 1-4 of the Cas9 amino acid sequence set forth as SEQ ID NO:309 (the motifs are in Table 3, and are set forth as SEQ ID NOs: 12-15, respectively), or to the corresponding portions in any of the amino acid sequences set forth in SEQ ID NOs: 6-816 in PCT/US2017/017255. In some cases, a suitable Cas9 protein comprises an amino acid sequence having 4 motifs, each of motifs 1-4 having 70% or more amino acid sequence identity to motifs 1-4 of the Cas9 amino acid sequence set forth as SEQ ID NO:309 (the motifs are in Table 3, and are set forth as SEQ ID NOs: 12-15, respectively), or to the corresponding portions in any of the amino acid sequences set forth in SEQ ID NOs: 6-816 in PCT/US2017/017255. In some cases, a suitable Cas9 protein comprises an amino acid sequence having 4 motifs, each of motifs 1-4 having 75% or more amino acid sequence identity to motifs 1-4 of the Cas9 amino acid sequence set forth as SEQ ID NO:309 (the motifs are in Table 3, and are set forth as SEQ ID NOs: 12-15, respectively), or to the corresponding portions in any of the amino acid sequences set forth in SEQ ID NOs: 6-816 in PCT/US2017/017255. In some cases, a suitable Cas9 protein comprises an amino acid sequence having 4 motifs, each of motifs 1-4 having 80% or more amino acid sequence identity to motifs 1-4 of the Cas9 amino acid sequence set forth as SEQ ID NO:309 (the motifs are in Table 3, and are set forth as SEQ ID NOs: 12-15, respectively), or to the corresponding portions in any of the amino acid sequences set forth in SEQ ID NOs: 6-816 in PCT/US2017/017255. In some cases, a suitable Cas9 protein comprises an amino acid sequence having 4 motifs, each of motifs 1-4 having 85% or more amino acid sequence identity to motifs 1-4 of the Cas9 amino acid sequence set forth as SEQ ID NO:309 (the motifs are in Table 3, and are set forth as SEQ ID NOs: 12-15, respectively), or to the corresponding portions in any of the amino acid sequences set forth in SEQ ID NOs: 6-816 in PCT/US2017/017255. In some cases, a suitable Cas9 protein comprises an amino acid sequence having 4 motifs, each of motifs 1-4 having 90% or more amino acid sequence identity to motifs 1-4 of the Cas9 amino acid sequence set forth as SEQ ID NO:309 (the motifs are in Table 3, and are set forth as SEQ ID NOs: 12-15, respectively), or to the corresponding portions in any of the amino acid sequences set forth in SEQ ID NOs: 6-816 in PCT/US2017/017255. In some cases, a suitable Cas9 protein comprises an amino acid sequence having 4 motifs, each of motifs 1-4 having 95% or more amino acid sequence identity to motifs 1-4 of the Cas9 amino acid sequence set forth as SEQ ID NO:309 (the motifs are in Table 3, and are set forth as SEQ ID NOs: 12-15, respectively), or to the corresponding portions in any of the amino acid sequences set forth in SEQ ID NOs: 6-816 in PCT/US2017/017255. In some cases, a suitable Cas9 protein comprises an amino acid sequence having 4 motifs, each of motifs 1-4 having 99% or more amino acid sequence identity to motifs 1-4 of the Cas9 amino acid sequence set forth as SEQ ID NO:309 (the motifs are in Table 3, and are set forth as SEQ ID NOs: 12-15, respectively), or to the corresponding portions in any of the amino acid sequences set forth in SEQ ID NOs: 6-816 in PCT/US2017/017255. In some cases, a suitable Cas9 protein comprises an amino acid sequence having 4 motifs, each of motifs 1-4 having 100% amino acid sequence identity to motifs 1-4 of the Cas9 amino acid sequence set forth as SEQ ID NO:309 (the motifs are in Table 3, and are set forth as SEQ ID NOs: 12-15, respectively), or to the corresponding portions in any of the amino acid sequences set forth in SEQ ID NOs: 6-816 in PCT/US2017/017255. Any Cas9 protein as defined above can be used as a Cas9 polypeptide, as part of a chimeric Cas9 polypeptide (e.g., a Cas9 fusion protein), any of which can be used in an RNP of the present disclosure.

In some cases, a suitable Cas9 protein comprises an amino acid sequence having 60% or more, 70% or more, 75% or more, 80% or more, 85% or more, 90% or more, 95% or more, 99% or more or 100% amino acid sequence identity to amino acids 7-166 or 731-1003 of the Cas9 amino acid sequence set forth in SEQ ID NO:309, or to the corresponding portions in any of the amino acid sequences set forth as SEQ ID NOs: 6-816 in PCT/US2017/017255.

In some cases, a suitable Cas9 protein comprises an amino acid sequence having 60% or more amino acid sequence identity to amino acids 7-166 or 731-1003 of the Cas9 amino acid sequence set forth in SEQ ID NO:309, or to the corresponding portions in any of the amino acid sequences set forth as SEQ ID NOs: 6-816 in PCT/US2017/017255. In some cases, a suitable Cas9 protein comprises an amino acid sequence having 70% or more amino acid sequence identity to amino acids 7-166 or 731-1003 of the Cas9 amino acid sequence set forth in SEQ ID NO:309, or to the corresponding portions in any of the amino acid sequences set forth as SEQ ID NOs: 6-816 in PCT/US2017/017255. In some cases, a suitable Cas9 protein comprises an amino acid sequence having 75% or more amino acid sequence identity to amino acids 7-166 or 731-1003 of the Cas9 amino acid sequence set forth in SEQ ID NO:309, or to the corresponding portions in any of the amino acid sequences set forth as SEQ ID NOs: 6-816. In some cases, a suitable Cas9 protein comprises an amino acid sequence having 80% or more amino acid sequence identity to amino acids 7-166 or 731-1003 of the Cas9 amino acid sequence set forth in SEQ ID NO:309, or to the corresponding portions in any of the amino acid sequences set forth as SEQ ID NOs: 6-816 in PCT/US2017/017255. In some cases, a suitable Cas9 protein comprises an amino acid sequence having 85% or more amino acid sequence identity to amino acids 7-166 or 731-1003 of the Cas9 amino acid sequence set forth in SEQ ID NO:309, or to the corresponding portions in any of the amino acid sequences set forth as SEQ ID NOs: 6-816 in PCT/US2017/017255. In some cases, a suitable Cas9 protein comprises an amino acid sequence having 90% or more amino acid sequence identity to amino acids 7-166 or 731-1003 of the Cas9 amino acid sequence set forth in SEQ ID NO:309, or to the corresponding portions in any of the amino acid sequences set forth as SEQ ID NOs: 6-816 in PCT/US2017/017255. In some cases, a suitable Cas9 protein comprises an amino acid sequence having 95% or more amino acid sequence identity to amino acids 7-166 or 731-1003 of the Cas9 amino acid sequence set forth in SEQ ID NO:309, or to the corresponding portions in any of the amino acid sequences set forth as SEQ ID NOs: 6-816. In some cases, a suitable Cas9 protein comprises an amino acid sequence having 99% or more amino acid sequence identity to amino acids 7-166 or 731-1003 of the Cas9 amino acid sequence set forth in SEQ ID NO:309, or to the corresponding portions in any of the amino acid sequences set forth as SEQ ID NOs: 6-816. In some cases, a suitable Cas9 protein comprises an amino acid sequence having 100% amino acid sequence identity to amino acids 7-166 or 731-1003 of the Cas9 amino acid sequence set forth in SEQ ID NO:309, or to the corresponding portions in any of the amino acid sequences set forth as SEQ ID NOs: 6-816 in PCT/US2017/017255. Any Cas9 protein as defined above can be used as a Cas9 polypeptide, as part of a chimeric Cas9 polypeptide (e.g., a Cas9 fusion protein), any of which can be used in an RNP of the present disclosure.

In some cases, a suitable Cas9 protein comprises an amino acid sequence having 60% or more, 70% or more, 75% or more, 80% or more, 85% or more, 90% or more, 95% or more, 99% or more or 100% amino acid sequence identity to the Cas9 amino acid sequence set forth in SEQ ID NO:309, or to any of the amino acid sequences set forth as SEQ ID NOs: 6-816 in PCT/US2017/017255.

In some cases, a suitable Cas9 protein comprises an amino acid sequence having 60% or more amino acid sequence identity to the Cas9 amino acid sequence set forth in SEQ ID NO:309, or to any of the amino acid sequences set forth as SEQ ID NOs: 6-816 in PCT/US2017/017255. In some cases, a suitable Cas9 protein comprises an amino acid sequence having 70% or more amino acid sequence identity to the Cas9 amino acid sequence set forth in SEQ ID NO:309, or to any of the amino acid sequences set forth as SEQ ID NOs: 6-816. In some cases, a suitable Cas9 protein comprises an amino acid sequence having 75% or more amino acid sequence identity to the Cas9 amino acid sequence set forth in SEQ ID NO:309, or to any of the amino acid sequences set forth as SEQ ID NOs: 6-816. In some cases, a suitable Cas9 protein comprises an amino acid sequence having 80% or more amino acid sequence identity to the Cas9 amino acid sequence set forth in SEQ ID NO:309, or to any of the amino acid sequences set forth as SEQ ID NOs: 6-816. In some cases, a suitable Cas9 protein comprises an amino acid sequence having 85% or more amino acid sequence identity to the Cas9 amino acid sequence set forth in SEQ ID NO:309, or to any of the amino acid sequences set forth as SEQ ID NOs: 6-816 in PCT/US2017/017255. In some cases, a suitable Cas9 protein comprises an amino acid sequence having 90% or more amino acid sequence identity to the Cas9 amino acid sequence set forth in SEQ ID NO:309, or to any of the amino acid sequences set forth as SEQ ID NOs: 6-816. In some cases, a suitable Cas9 protein comprises an amino acid sequence having 95% or more amino acid sequence identity to the Cas9 amino acid sequence set forth in SEQ ID NO:309, or to any of the amino acid sequences set forth as SEQ ID NOs: 6-816 in PCT/US2017/017255. In some cases, a suitable Cas9 protein comprises an amino acid sequence having 99% or more amino acid sequence identity to the Cas9 amino acid sequence set forth in SEQ ID NO:309, or to any of the amino acid sequences set forth as SEQ ID NOs: 6-816 in PCT/US2017/017255. In some cases, a suitable Cas9 protein comprises an amino acid sequence having 100% amino acid sequence identity to the Cas9 amino acid sequence set forth in SEQ ID NO:309, or to any of the amino acid sequences set forth as SEQ ID NOs: 6-816 in PCT/US2017/017255. Any Cas9 protein as defined above can be used as a Cas9 polypeptide, as part of a chimeric Cas9 polypeptide (e.g., a Cas9 fusion protein), any of which can be used in an RNP of the present disclosure.

In some cases, a Cas9 protein comprises 4 motifs (as listed in Table 1), at least one with (or each with) amino acid sequences having 75% or more, 80% or more, 85% or more, 90% or more, 95% or more, 99% or more or 100% amino acid sequence identity to each of the 4 motifs listed in Table 1 (SEQ ID NOs: 12-15), or to the corresponding portions in any of the amino acid sequences set forth as SEQ ID NOs: 6-816 in PCT/US2017/017255.

In some cases, a Cas9 protein is a high fidelity Cas9 protein (see, e.g., Kleinstiver et al. (2016) *Nature*, 529 (7587): 490-495).

In some cases, a suitable Cas9 protein is a Cas9 protein as described in Slaymaker et al. (2016) *Science* 351: 84. For example, a suitable Cas9 protein can include a *Streptococcus pyogenes* Cas9 with substitutions of one or more of K810, K848, K855, K1003, and R1060 (where the amino acid numbering is based on the numbering set out in SEQ ID NO:309 (SEQ ID No:5 in PCT/US2017/017255)). For example, a suitable Cas9 protein includes a *Streptococcus pyogenes* Cas9 with K810A, K1003A, and R1060A substitutions (where the amino acid numbering is based on the numbering set out in SEQ ID NO:309 (SEQ ID No:5 in PCT/US2017/017255)). As another example, a suitable Cas9 protein includes a *Streptococcus pyogenes* Cas9 with K848A, K1003A, and R060A substitutions (where the amino acid numbering is based on the numbering set out in SEQ ID N0:5). As another example, a suitable Cas9 protein includes a *Streptococcus pyogenes* Cas9 with a K855A substitution (where the amino acid numbering is based on the numbering set out in SEQ ID NO:309 (SEQ ID No:5 in PCT/US2017/017255).

Type V and Type VI CRISPR/Cas Endonucleases

In certain embodiments the plasmid(s) complexed with the PRX carriers described herein encode a type V or type VI CRISPR/Cas endonuclease (e.g., Cpf1, C2c1, C2c2, C2c3) and associated guide RNA(s). Type V and type VI CRISPR/Cas endonucleases are a type of class 2 CRISPR/Cas endonuclease. Examples of type V CRISPR/Cas endonucleases include, but are not limited to, Cpf1, C2c1, and C2c3. An example of a type VI CRISPR/Cas endonuclease is C2c2. In some cases, the plasmid encodes a type V CRISPR/Cas endonuclease (e.g., Cpf1, C2c1, C2c3). In some cases, a Type V CRISPR/Cas endonuclease is a Cpf1 protein. In some cases, the plasmid encodes a type VI CRISPR/Cas endonuclease (e.g., C2c2).

Like type II CRISPR/Cas endonucleases, type V and VI CRISPR/Cas endonucleases form a complex with a corresponding guide RNA. The guide RNA provides target specificity to an endonuclease-guide RNA RNP complex by having a nucleotide sequence (a guide sequence) that is complementary to a sequence (the target site) of a target nucleic acid (as described elsewhere herein). The endonuclease of the complex provides the site-specific activity. In other words, the endonuclease is guided to a target site (e.g., stabilized at a target site) within a target nucleic acid sequence (e.g. genomic DNA) by virtue of its association with the protein-binding segment of the guide RNA.

Examples and guidance related to type V and type VI CRISPR/Cas proteins (e.g., cpf1, C2c1, C2c2, and C2c3 guide RNAs) can be found in the art (see, e.g., Zetsche et al. (2015) *Cell*, 163(3):759-771; Makarova et al. (2015) *Nat. Rev. Microbiol.* 13(11): 722-736; Shmakov et al. (2015) *Mol. Cell*, 60(3): 385-397; and the like).

In some cases, the Type V or type VI CRISPR/Cas endonuclease (e.g., Cpf1, C2c1, C2c2, C2c3) is enzymatically active, e.g., the Type V or type VI CRISPR/Cas polypeptide, when bound to a guide RNA, cleaves a target nucleic acid. In some cases, the Type V or type VI CRISPR/Cas endonuclease (e.g., Cpf1, C2c1, C2c2, C2c3) exhibits reduced enzymatic activity relative to a corresponding wild-type a Type V or type VI CRISPR/Cas endonuclease (e.g., Cpf1, C2c1, C2c2, C2c3), and retains DNA binding activity (e.g., in some cases the endonuclease is a nickase).

In some cases a type V CRISPR/Cas endonuclease is a Cpf1 protein. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 310-314 (SEQ ID NOs: 1088-1092 in PCT/US2017/017255). In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the Cpf1 amino acid sequence set forth in any of SEQ ID NOs: 310-314.

In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvC1 domain of the Cpf1 amino acid sequence set forth in any of SEQ ID NOs: 310-314. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the Cpf1 amino acid sequence set forth in any of SEQ ID NOs: 310-314. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the Cpf1 amino acid sequence set forth in any of SEQ ID NOs: 310-314. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the Cpf1 amino acid sequence set forth in any of SEQ ID NOs: 310-314.

In some cases, the Cpf1 protein exhibits reduced enzymatic activity relative to a wild-type Cpf1 protein (e.g., relative to a Cpf1 protein comprising the amino acid sequence set forth in any of SEQ ID NOs: 310-314), and retains DNA binding activity. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 310-314; and comprises an amino acid substitution (e.g., a D→A substitution) at an amino acid residue corresponding to amino acid 917 of the Cpf1 amino acid sequence set forth in SEQ ID NO:310. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 310-314; and comprises an amino acid substitution (e.g., an E→A substitution) at an amino acid residue corresponding to amino acid 1006 of the Cpf1 amino acid sequence set forth in SEQ ID NO:310. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 310-314; and comprises an amino acid substitution (e.g., a D→A substitution) at an amino acid residue corresponding to amino acid 1255 of the Cpf1 amino acid sequence set forth in SEQ ID NO:310.

In some cases, a suitable Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 310-314.

In some cases a type V CRISPR/Cas endonuclease is a C2c1 protein (examples include those set forth as SEQ ID NOs: 315-322 (SEQ ID NOs: 1112-1119 in PCT/US2017/017255). In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c1 amino acid sequence set forth in any of SEQ ID NOs: 315-322. In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the C2c1 amino acid sequence set forth in any of SEQ ID NOs: 315-322.

In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the C2c1 amino acid sequences set forth in any of SEQ ID NOs: 315-322). In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the C2c1 amino acid sequence set forth in any of SEQ ID NOs: 315-322. In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the C2c1 amino acid sequence set forth in any of SEQ ID NOs: 315-322. In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the C2c1 amino acid sequence set forth in any of SEQ ID NOs: 315-322.

In some cases, the C2c1 protein exhibits reduced enzymatic activity relative to a wild-type C2c1 protein (e.g., relative to a C2c1 protein comprising the amino acid sequence set forth in any of SEQ ID NOs: 315-322), and retains DNA binding activity. In some cases, a suitable C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c1 amino acid sequence set forth in any of SEQ ID NOs: 315-322.

In some cases a type V CRISPR/Cas endonuclease is a C2c3 protein (examples include those set forth as SEQ ID NOs: 323-326 (SEQ ID NOs: 1120-1123 in pCT/US2017/017255). In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c3 amino acid sequence set forth in any of SEQ ID NOs: 323-326. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the C2c3 amino acid sequence set forth in any of SEQ ID NOs: 323-326.

In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the C2c3 amino acid sequence set forth in any of SEQ ID NOs: 323-326. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the C2c3 amino acid sequence set forth in any of SEQ ID NOs: 323-326. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the C2c3 amino acid sequence set forth in any of SEQ ID NOs: 323-326. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the C2c3 amino acid sequence set forth in any of SEQ ID NOs: 323-326.

In some cases, the C2c3 protein exhibits reduced enzymatic activity relative to a wild-type C2c3 protein (e.g., relative to a C2c3 protein comprising the amino acid sequence set forth in any of SEQ ID NOs: 323-326), and retains DNA binding activity. In some cases, a suitable C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c3 amino acid sequence set forth in any of SEQ ID NOs: 323-326.

In some cases a type VI CRISPR/Cas endonuclease is a C2c2 protein (examples include those set forth as SEQ ID NOs: 327-338 (SEQ ID NOs: 1124-1135 in PCT/US2017/017255). In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c2 amino acid sequence set forth in any of SEQ ID NOs: 327-338. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the C2c2 amino acid sequence set forth in any of SEQ ID NOs: 327-338.

In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the C2c2 amino acid sequence set forth in any of SEQ ID NOs: 327-338. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the C2c2 amino acid sequence set forth in any of SEQ ID NOs: 327-338. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the C2c2 amino acid sequence set forth in any of SEQ ID NOs: 1124-1135. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the C2c2 amino acid sequence set forth in any of SEQ ID NOs: 327-338.

In some cases, the C2c2 protein exhibits reduced enzymatic activity relative to a wild-type C2c2 protein (e.g., relative to a C2c2 protein comprising the amino acid sequence set forth in any of SEQ ID NOs: 327-338), and retains DNA binding activity. In some cases, a suitable C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c2 amino acid sequence set forth in any of SEQ ID NOs: 327-338.

PAM Sequence

A wild type class 2 CRISPR/Cas endonuclease (e.g., Cas9 protein) normally has nuclease activity that cleaves a target nucleic acid (e.g., a double stranded DNA (dsDNA)) at a target site defined by complementarity between the guide sequence of the CRISPR/Cas guide RNA and the target nucleic acid. In some cases, site-specific cleavage of the target nucleic acid occurs at locations determined by both (i) base-pairing complementarity between the CRISPR/Cas guide RNA and the target nucleic acid; and (ii) a short motif referred to as the protospacer adjacent motif (PAM) in the target nucleic acid. For example, when the class 2 CRISPR/Cas endonuclease is a wild type Cas9 protein, the PAM sequence that is recognized (e.g., bound) by the Cas9 protein is present on the non-complementary strand (the strand that does not hybridize with the guide sequence of the Cas9 guide RNA) of the target DNA and is adjacent to the target site.

In some cases, (e.g., in some cases where the class 2 CRISPR/Cas endonuclease is an *S. pyogenes* Cas9 protein) the PAM sequence of the non-complementary strand is 5'-XGG-3', where X is any DNA nucleotide and X is immediately 3' of the target sequence of the non-complementary strand of the target DNA. As such, the sequence of the complementary strand that hybridizes with the PAM sequence is 5'-CCY-3', where Y is any DNA nucleotide and Y is immediately 5' of the target sequence of the complementary strand of the target DNA. In some such embodiments, X and Y can be complementary and the X-Y base pair can be any base pair (e.g., X=C and Y=G; X=G and Y=C; X=A and Y=T, X=T and Y=A).

In some cases, it may be advantageous to use plasmids encoding different class 2 CRISPR/Cas endonucleases (e.g., Cas9 proteins from various species, type V or type VI CRISPR/Cas endonucleases, and the like) for the subject methods in order to capitalize on various characteristics (e.g., enzymatic characteristics) of the different endonucleases (e.g., for different PAM sequence preferences; for increased or decreased enzymatic activity; for an increased or decreased level of cellular toxicity; to change the balance between NHEJ, homology-directed repair, single strand breaks, double strand breaks, etc.).

Class 2 CRISPR/Cas endonucleases (e.g., Cas9 proteins) from various species can require different PAM sequences in the target DNA, and different types of Class 2 CRISPR/Cas endonucleases (e.g., type II proteins, e.g., Cas9 proteins; type V proteins; type VI proteins; and the like) can have different requirements (e.g., 5', 3', complementary strand, non-complementary strand, distance from target sequence, and the like) for the location of the PAM sequence relative to the targeted sequence of the target DNA. Thus, for a particular Class 2 CRISPR/Cas endonuclease of choice, the PAM sequence requirement may be different than the 5'-XGG-3' sequence described above for the *S. pyogenes* Cas9 protein.

In some embodiments (e.g., when the Cas9 protein is derived from *S. pyogenes* or a closely related Cas9 is used), a PAM sequence can be can be 5'-NGG-3', where N is any nucleotide (see, e.g., Chylinski et al. (2013) *RNA Biol.* 10(5): 726-737; Jinek et al. (2012) *Science,* 337(6096): 816-821; and the like). In some embodiments (e.g., when a Cas9 protein is derived from the Cas9 protein of *Neisseria meningitidis* or a closely related Cas9 is used), the PAM sequence can be 5'-NNNNGANN-3', 5'-NNNNGTTN-3', 5'-NNNNGNNT-3', 5'-NNNNGTNN-3', 5'-NNNGNTN-3', or 5'-NNNNGATT-3', where N is any nucleotide. In some embodiments (e.g., when a Cas9 protein is derived from *Streptococcus thermophilus* #1 or a closely related Cas9 is used), the PAM sequence can be 5'-NNAGAA-3', 5'-NNAGGA-3', 5'-NNGGAA-3', 5'-NNANAA-3', or 5'-NNGGGA-3' where N is any nucleotide. In some embodiments (e.g., when a Cas9 protein is derived from *Treponema denticola* (TD) or a closely related Cas9 is used), the PAM sequence can be 5'-NAAAAN-3', 5'-NAAAAC-3', 5'-NAAANC-3', 5'-NANAAC-3', or 5'-NNAAAC-3', where N is any nucleotide.

The PAM requirements for any given Class 2 CRISPR/Cas endonuclease can be determined using standard, routine, conventional methods, which can include experimental methods and/or in silica analysis of naturally existing sequences from species of interest. For example, as would be known by one of ordinary skill in the art, additional PAM sequences for other Class 2 CRISPR/Cas endonucleases (e.g., Cas9 proteins of different species; type IV CRISPR/Cas endonucleases, type V CRISPR/Cas endonucleases, and the like) can readily be determined using bioinformatic analysis (e.g., analysis of genomic sequencing data) (see, e.g., Mojica et al. (2009) *Microbiology,* 155(Pt 3): 733-740; Esvelt et al. (2013) *Nat. Meth.* 10(11): 1116-11121; and the like).

In addition, as known in the art, the PAM-interacting domain of a Class 2 CRISPR/Cas endonuclease (e.g., a Cas9 protein) can be derived from an endonuclease (e.g., Cas9 protein) from a first species, and the PAM sequence can correspond to that domain. Thus, in some cases, a Class 2 CRISPR/Cas endonuclease has a PAM-interacting domain that is derived from (e.g., that is from) a Class 2 CRISPR/Cas endonuclease (e.g., Cas9 protein) of a first species, and other portions of the Class 2 CRISPR/Cas endonuclease (e.g., Cas9 protein) can be derived from (e.g., can be from) a second species.

Guide RNA (for CRISPR/Cas Endonucleases)

A nucleic acid molecule that binds to a class 2 CRISPR/Cas endonuclease (e.g., a Cas9 protein; a type V or type VI CRISPR/Cas protein; a Cpf1 protein; etc.) and targets the complex to a specific location within a target nucleic acid is referred to as a "guide RNA" or "CRISPR/Cas guide nucleic acid" or "CRISPR/Cas guide RNA."

A guide RNA provides target specificity to the complex (the RNP complex) by including a targeting segment, which includes a guide sequence (also referred to herein as a targeting sequence), which is a nucleotide sequence that is complementary to a sequence of a target nucleic acid.

A guide RNA can be referred to by the protein to which it corresponds. For example, when the class 2 CRISPR/Cas endonuclease is a Cas9 protein, the corresponding guide RNA can be referred to as a "Cas9 guide RNA." Likewise, as another example, when the class 2 CRISPR/Cas endonuclease is a Cpf1 protein, the corresponding guide RNA can be referred to as a "Cpf1 guide RNA."

In some embodiments, a guide RNA includes two separate nucleic acid molecules: an "activator" and a "targeter" and is referred to as a "dual guide RNA", a "double-molecule guide RNA", a "two-molecule guide RNA", or a "dgRNA." In some embodiments, the guide RNA is one molecule (e.g., for some class 2 CRISPR/Cas proteins, the corresponding guide RNA is a single molecule; and in some cases, an activator and targeter are covalently linked to one another, e.g., via intervening nucleotides), and the guide RNA is referred to as a "single guide RNA", a "single-molecule guide RNA," a "one-molecule guide RNA", or simply "sgRNA."

Cas9 Guide RNA

A nucleic acid molecule that binds to a Cas9 protein and targets the complex to a specific location within a target nucleic acid is referred to herein as a "Cas9 guide RNA." A Cas9 guide RNA (can be said to include two segments, a first segment (referred to herein as a "targeting segment"); and a second segment (referred to herein as a "protein-binding segment"). By "segment" it is meant a segment/section/region of a molecule, e.g., a contiguous stretch of nucleotides in a nucleic acid molecule. A segment can also mean a region/section of a complex such that a segment may comprise regions of more than one molecule.

The first segment (targeting segment) of a Cas9 guide RNA includes a nucleotide sequence (a guide sequence) that is complementary to (and therefore hybridizes with) a specific sequence (a target site) within a target nucleic acid (e.g., a target genomic DNA). The protein-binding segment (or "protein-binding sequence") interacts with (binds to) a Cas9 polypeptide. The protein-binding segment of a subject Cas9 guide RNA includes two complementary stretches of nucleotides that hybridize to one another to form a double stranded RNA duplex (dsRNA duplex). Site-specific binding and/or cleavage of a target nucleic acid (e.g., genomic DNA) can occur at locations (e.g., target sequence of a target locus, e.g., introns 44 and 55 of the human dystrophin gene) determined by base-pairing complementarity between the Cas9 guide RNA (the guide sequence of the Cas9 guide RNA) and the target nucleic acid.

A Cas9 guide RNA and a Cas9 protein form a complex (e.g., bind via non-covalent interactions). The Cas9 guide RNA provides target specificity to the complex by including a targeting segment, which includes a guide sequence (a nucleotide sequence that is complementary to a sequence of a target nucleic acid). The Cas9 protein of the complex provides the site-specific activity (e.g., cleavage activity). In other words, the Cas9 protein is guided to a target nucleic acid sequence (e.g. genomic DNA) by virtue of its association with the Cas9 guide RNA.

The "guide sequence" also referred to as the "targeting sequence" of a Cas9 guide RNA can be modified so that the Cas9 guide RNA can target a Cas9 protein to any desired sequence of any desired target nucleic acid, with the exception that the protospacer adjacent motif (PAM) sequence can be taken into account. Thus, for example, a Cas9 guide RNA can have a targeting segment with a sequence (a guide sequence) that has complementarity with (e.g., can hybridize to) a sequence in a nucleic acid in a eukaryotic cell (e.g., genomic DNA).

In some embodiments, a Cas9 guide RNA includes two separate nucleic acid molecules: an "activator" and a "targeter" and is referred to herein as a "dual Cas9 guide RNA", a "double-molecule Cas9 guide RNA", or a "two-molecule Cas9 guide RNA" a "dual guide RNA", or a "dgRNA." In some embodiments, the activator and targeter are covalently linked to one another (e.g., via intervening nucleotides) and the guide RNA is referred to as a "single guide RNA", a "Cas9 single guide RNA", a "single-molecule Cas9 guide RNA," or a "one-molecule Cas9 guide RNA", or simply "sgRNA."

A Cas9 guide RNA comprises a crRNA-like ("CRISPR RNA" I "targeter"/"crRNA"/"crRNA repeat") molecule and a corresponding tracrRNA-like ("trans-acting CRISPR RNA"/"activator" I "tracrRNA") molecule. A crRNA-like molecule (targeter) comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator/tracrRNA) comprises a stretch of nucleotides (duplex-forming segment) that forms the other half of the dsRNA duplex of the protein-binding segment of the guide nucleic acid. In other words, a stretch of nucleotides of a crRNA-like molecule are complementary to and hybridize with a stretch of nucleotides of a tracrRNA-like molecule to form the dsRNA duplex of the protein-binding domain of the Cas9 guide RNA. As such, each targeter molecule can be said to have a corresponding activator molecule (which has a region that hybridizes with the targeter). The targeter molecule additionally provides the targeting segment. Thus, a targeter and an activator molecule (as a corresponding pair) hybridize to form a Cas9 guide RNA. The exact sequence of a given crRNA or tracrRNA molecule is characteristic of the species in which the RNA molecules are found. A subject dual Cas9 guide RNA can include any corresponding activator and targeter pair.

The term "activator" or "activator RNA" is used herein to mean a tracrRNA-like molecule (tracrRNA: "trans-acting CRISPR RNA") of a Cas9 dual guide RNA (and therefore of a Cas9 single guide RNA when the "activator" and the "targeter" are linked together by, e.g., intervening nucleotides). Thus, for example, a Cas9 guide RNA (dgRNA or sgRNA) comprises an activator sequence (e.g., a tracrRNA sequence). A tracr molecule (a tracrRNA) is a naturally existing molecule that hybridizes with a CRISPR RNA molecule (a crRNA) to form a Cas9 dual guide RNA. The term "activator" is used herein to encompass naturally existing tracrRNAs, but also to encompass tracrRNAs with modifications (e.g., truncations, sequence variations, base modifications, backbone modifications, linkage modifications, etc.) where the activator retains at least one function of a tracrRNA (e.g., contributes to the dsRNA duplex to which Cas9 protein binds). In some cases the activator provides one or more stem loops that can interact with Cas9 protein. An activator can be referred to as having a tracr sequence (tracrRNA sequence) and in some cases is a tracrRNA, but the term "activator" is not limited to naturally existing tracrRNAs.

The term "targeter" or "targeter RNA" is used herein to refer to a crRNA-like molecule (crRNA: "CRISPR RNA") of a Cas9 dual guide RNA (and therefore of a Cas9 single guide RNA when the "activator" and the "targeter" are linked together, e.g., by intervening nucleotides). Thus, for example, a Cas9 guide RNA (dgRNA or sgRNA) comprises a targeting segment (which includes nucleotides that hybridize with (are complementary to) a target nucleic acid, and a duplex-forming segment (e.g., a duplex forming segment of a crRNA, which can also be referred to as a crRNA repeat). Because the sequence of a targeting segment (the segment that hybridizes with a target sequence of a target nucleic acid) of a targeter is modified by a user to hybridize with a desired target nucleic acid, the sequence of a targeter will often be a non-naturally occurring sequence. However, the duplex-forming segment of a targeter (described in more detail below), which hybridizes with the duplex-forming segment of an activator, can include a naturally existing sequence (e.g., can include the sequence of a duplex-forming segment of a naturally existing crRNA, which can also be referred to as a crRNA repeat). Thus, the term targeter is used herein to distinguish from naturally occurring crRNAs, despite the fact that part of a targeter (e.g., the duplex-forming segment) often includes a naturally occurring sequence from a crRNA. However, the term "targeter" encompasses naturally occurring crRNAs.

A Cas9 guide RNA can also be said to include 3 parts: (i) a targeting sequence (a nucleotide sequence that hybridizes with a sequence of the target nucleic acid); (ii) an activator sequence (as described above)(in some cases, referred to as a tracr sequence); and (iii) a sequence that hybridizes to at least a portion of the activator sequence to form a double stranded duplex. A targeter has (i) and (iii); while an activator has (ii).

A Cas9 guide RNA (e.g. a dual guide RNA or a single guide RNA) can be comprised of any corresponding activator and targeter pair. In some cases, the duplex forming segments can be swapped between the activator and the targeter. In other words, in some cases, the targeter includes a sequence of nucleotides from a duplex forming segment of a tracrRNA (which sequence would normally be part of an activator) while the activator includes a sequence of nucleotides from a duplex forming segment of a crRNA (which sequence would normally be part of a targeter).

As noted above, a targeter comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator) comprises a stretch of nucleotides (a duplex-forming segment) that forms the other half of the dsRNA duplex of the protein-binding segment of the Cas9 guide RNA. In other words, a stretch of nucleotides of the targeter is complementary to and hybridizes with a stretch of nucleotides of the activator to form the dsRNA duplex of the protein-binding segment of a Cas9 guide RNA. As such, each targeter can be said to have a corresponding activator (which has a region that hybridizes with the targeter). The targeter molecule additionally provides the targeting segment. Thus, a targeter and an activator (as a corresponding pair) hybridize to form a Cas9 guide RNA. The particular sequence of a given naturally existing crRNA or tracrRNA molecule is characteristic of the species in which the RNA molecules are found. Examples of suitable activator and targeter are well known in the art.

A Cas9 guide RNA (e.g. a dual guide RNA or a single guide RNA) can be comprised of any corresponding activator and targeter pair. Non-limiting examples of nucleotide sequences that can be included in a Cas9 guide RNA (dgRNA or sgRNA) include sequences set forth in SEQ ID NOs: 827-1075 in PCT/US2017/017255, or complements thereof. For example, in some cases, sequences from SEQ ID NOs: 827-957 in PCT/US2017/017255 (which are from tracrRNAs) or complements thereof, can pair with sequences from SEQ ID NOs: 964-1075 in PCT/US2017/017255 (which are from crRNAs), or complements thereof, to form a dsRNA duplex of a protein binding segment. In some cases, the duplex-forming portion of a guide RNA suitable for use herein comprises the sequence: gtttagagctaGAAAtagcaagttaaaataagg ctagtccgttatcaactt gaaaaagtggcac cgagtcggtgcTTTTTT (SEQ ID NO:16) (SEQ ID NO:1366 in PCT/US2017/017255), or guuuuagagcua-GAAAuagcaaguuaa aauaaggcuaguccguuaucaacuugaaa aaguggcaccgagucggug cUU UUUUU (SEQ ID NO:17) (SEQ ID NO:1367 in PCT/US2017/017255).

Targeting Segment of a Cas9 Guide RNA

A subject guide RNA includes a guide sequence (i.e., a targeting sequence) (a nucleotide sequence that is complementary to a sequence (a target site) in a target nucleic acid). In other words, the targeting segment of a subject guide nucleic acid can interact with a target nucleic acid (e.g., double stranded DNA (dsDNA)) in a sequence-specific manner via hybridization (i.e., base pairing). As such, the nucleotide sequence of the targeting segment may vary (depending on the target) and can determine the location within the target nucleic acid that the Cas9 guide RNA and the target nucleic acid will interact. The targeting segment of a Cas9 guide RNA can be modified (e.g., by genetic engineering)/designed to hybridize to any desired sequence (target site) within a target nucleic acid (e.g., a eukaryotic target nucleic acid such as genomic DNA).

In various embodiments, the targeting segment can have a length of 7 or more nucleotides (nt) (e.g., 8 or more, 9 or more, 10 or more, 12 or more, 15 or more, 20 or more, or more, 30 or more, or 40 or more nucleotides). In some cases, the targeting segment can have a length of from 7 to 100 nucleotides (nt) (e.g., from 7 to 80 nt, from 7 to 60 nt, from 7 to 40 nt, from 7 to 30 nt, from 7 to 25 nt, from 7 to 22 nt, from 7 to 20 nt, from 7 to 18 nt, from 8 to 80 nt, from 8 to 60 nt, from 8 to 40 nt, from 8 to 30 nt, from 8 to 25 nt, from 8 to 22 nt, from 8 to 20 nt, from 8 to 18 nt, from 10 to 100 nt, from 10 to 80 nt, from 10 to 60 nt, from 10 to 40 nt, from 10 to 30 nt, from 10 to 25 nt, from 10 to 22 nt, from 10 to 20 nt, from 10 to 18 nt, from 12 to 100 nt, from 12 to 80 nt, from 12 to 60 nt, from 12 to 40 nt, from 12 to 30 nt, from 12 to 25 nt, from 12 to 22 nt, from 12 to 20 nt, from 12 to 18 nt, from 14 to 100 nt, from 14 to 80 nt, from 14 to 60 nt, from 14 to 40 nt, from 14 to 30 nt, from 14 to 25 nt, from 14 to 22 nt, from 14 to 20 nt, from 14 to 18 nt, from 16 to 100 nt, from 16 to 80 nt, from 16 to 60 nt, from 16 to 40 nt, from 16 to 30 nt, from 16 to 25 nt, from 16 to 22 nt, from 16 to 20 nt, from 16 to 18 nt, from 18 to 100 nt, from 18 to 80 nt, from 18 to 60 nt, from 18 to 40 nt, from 18 to 30 nt, from 18 to 25 nt, from 18 to 22 nt, or from 18 to 20 nt).

In various embodiments, the nucleotide sequence (the targeting sequence, the guide sequence) of the targeting segment that is complementary to a nucleotide sequence (target site) of the target nucleic acid can have a length of 10 nt or more. For example, the targeting sequence of the targeting segment that is complementary to a target site of the target nucleic acid can have a length of 12 nt or more, 15 nt or more, 17 nt or more, 18 nt or more, 19 nt or more, or 20 nt or more. In some cases, the nucleotide sequence (the targeting sequence) of the targeting segment that is complementary to a nucleotide sequence (target site) of the target nucleic acid has a length of 12 nt or more. In some cases, the nucleotide sequence (the targeting sequence) of the targeting segment that is complementary to a nucleotide sequence (target site) of the target nucleic acid has a length of 17 nt or more. In some cases, the nucleotide sequence (the targeting sequence) of the targeting segment that is complementary to a nucleotide sequence (target site) of the target nucleic acid has a length of 18 nt or more.

For example, in certain embodiments, the targeting sequence (guide sequence) of the targeting segment that is complementary to a target sequence of the target nucleic acid can have a length of from 10 to 100 nucleotides (nt) (e.g., from 10 to 90 nt, from 10 to 75 nt, from 10 to 60 nt, from 10 to 50 nt, from 10 to 35 nt, from 10 to 30 nt, from 10 to 25 nt, from 10 to 22 nt, from 10 to 20 nt, from 12 to 100 nt, from 12 to 90 nt, from 12 to 75 nt, from 12 to 60 nt, from 12 to 50 nt, from 12 to 35 nt, from 12 to 30 nt, from 12 to 25 nt, from 12 to 22 nt, from 12 to 20 nt, from 15 to 100 nt, from 15 to 90 nt, from 15 to 75 nt, from 15 to 60 nt, from 15 to 50 nt, from 15 to 35 nt, from 15 to 30 nt, from 15 to 25 nt, from 15 to 22 nt, from 15 to 20 nt, from 17 to 100 nt, from 17 to 90 nt, from 17 to 75 nt, from 17 to 60 nt, from 17 to 50 nt, from 17 to 35 nt, from 17 to 30 nt, from 17 to 25 nt, from 17 to 22 nt, from 17 to 20 nt, from 18 to 100 nt, from 18 to 90 nt, from 18 to 7 5 nt, from 18 to 60 nt, from 18 to 50 nt, from 18 to 35 nt, from 18 to 30 nt, from 18 to 25 nt, from 18 to 22 nt, or from 18 to 20 nt). In some cases, the targeting sequence of the targeting segment that is complementary to a target sequence of the target nucleic acid has a length of from 15 nt to 30 nt. In some cases, the targeting sequence of the targeting segment that is complementary to a target sequence of the target nucleic acid has a length of from 15 nt to 25 nt. In some cases, the targeting sequence of the targeting segment that is complementary to a target sequence of the target nucleic acid has a length of from 17 nt to 30 nt. In some cases, the targeting sequence of the targeting segment that is complementary to a target sequence of the target nucleic acid has a length of from 17 nt to 25 nt. In some cases, the targeting sequence of the targeting segment that is complementary to a target sequence of the target nucleic acid has a length of from 17 nt to 22 nt. In some cases, the targeting sequence of the targeting segment that is complementary to a target sequence of the target nucleic acid has a length of from 18 nt to 30 nt. In some cases, the targeting sequence of the targeting segment that is complementary to a target sequence of the target nucleic acid has a length of from 18 nt to 25 nt. In some cases, the targeting sequence of the targeting segment that is complementary to a target sequence of the target nucleic acid has a length of from 18 nt to 22 nt. In some cases, the targeting sequence of the targeting segment that is complementary to a target site of the target nucleic acid is 20 nucleotides in length. In some cases, the targeting sequence of the targeting segment that is complementary to a target site of the target nucleic acid is 19 nucleotides in length. In some cases, the targeting sequence of the targeting segment that is complementary to a target site of the target nucleic acid is 18 nucleotides in length. In some cases, the targeting sequence of the targeting segment that is complementary to a target site of the target nucleic acid is 17 nucleotides in length.

In various embodiments, the percent complementarity between the targeting sequence (guide sequence) of the targeting segment and the target site of the target nucleic acid can be 60% or more (e.g., 65% or more, 70% or more, 75% or more, 80% or more, 85% or more, 90% or more, 95% or more, 97% or more, 98% or more, 99% or more, or 100%). In some cases, the percent complementarity between the targeting sequence of the targeting segment and the target site of the target nucleic acid is 100% over the seven contiguous 5'-most nucleotides of the target site of the target nucleic acid. In some cases, the percent complementarity between the targeting sequence of the targeting segment and the target site of the target nucleic acid is 60% or more over about 20 contiguous nucleotides. In some cases, the percent complementarity between the targeting sequence of the targeting segment and the target site of the target nucleic acid is 100% over the fourteen contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the seven contiguous 5'-most nucleotides of the target site of the target nucleic acid and as low as 0% or more over the remainder.

In some cases, the percent complementarity between the targeting sequence of the targeting segment and the target site of the target nucleic acid is 100% over the 7 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 8 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 9 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 10 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 17 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 18 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 60% or more (e.g., e.g., 65% or more, 70% or more, 75% or more, 80% or more, 85% or more, 90% or more, 95% or more, 97% or more, 98% or more, 99% or more, or 100%) over 20 contiguous nucleotides. In some cases, the percent complementarity between the targeting sequence of the targeting segment and the target site of the target nucleic acid is 60% or more (e.g., e.g., 65% or more, 70% or more, 75% or more, 80% or more, 85% or more, 90% or more, 95% or more, 97% or more, 98% or more, 99% or more, or 100%) over 17 contiguous nucleotides.

In some cases, the percent complementarity between the targeting sequence of the targeting segment and the target site of the target nucleic acid is 100% over the 7 contiguous 5'-most nucleotides of the target site of the target nucleic acid and as low as 0% or more over the remainder. In such a case, the targeting sequence can be considered to be 7 nucleotides in length. In some cases, the percent complementarity between the targeting sequence of the targeting segment and the target site of the target nucleic acid is 100% over the 8 contiguous 5'-most nucleotides of the target site of the target nucleic acid and as low as 0% or more over the remainder. In such a case, the targeting sequence can be considered to be 8 nucleotides in length. In some cases, the percent complementarity between the targeting sequence of the targeting segment and the target site of the target nucleic acid is 100% over the 9 contiguous 5'-most nucleotides of the target site of the target nucleic acid and as low as 0% or more over the remainder. In such a case, the targeting sequence can be considered to be 9 nucleotides in length. In some cases, the percent complementarity between the targeting sequence of the targeting segment and the target site of the target nucleic acid is 100% over the 10 contiguous 5'-most nucleotides of the target site of the target nucleic acid and as low as 0% or more over the remainder. In such a case, the targeting sequence can be considered to be 10 nucleotides in length. In some cases, the percent complementarity between the targeting sequence of the targeting segment and the target site of the target nucleic acid is 100% over the 11 contiguous 5'-most nucleotides of the target site of the target nucleic acid and as low as 0% or more over the remainder. In such a case, the targeting sequence can be considered to be 11 nucleotides in length. In some cases, the percent complementarity between the targeting sequence of the targeting segment and the target site of the target nucleic acid is 100% over the 12 contiguous 5'-most nucleotides of the target site of the target nucleic acid and as low as 0% or more over the remainder. In such a case, the targeting sequence can be considered to be 12 nucleotides in length. In some cases, the percent complementarity between the targeting sequence of the targeting segment and the target site of the target nucleic acid is 100% over the 13 contiguous 5'-most nucleotides of the target site of the target nucleic acid and as low as 0% or more over the remainder. In such a case, the targeting sequence can be considered to be 13 nucleotides in length. In some cases, the percent complementarity between the targeting sequence of the targeting segment and the target site of the target nucleic acid is 100% over the 14 contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the 17 contiguous 5'-most nucleotides of the target site of the target nucleic acid and as low as 0% or more over the remainder. In such a case, the targeting sequence can be considered to be 17 nucleotides in length. In some cases, the percent complementarity between the targeting sequence of the targeting segment and the target site of the target nucleic acid is 100% over the 18 contiguous 5'-most nucleotides of the target site of the target nucleic acid and as low as 0% or more over the remainder. In such a case, the targeting sequence can be considered to be 18 nucleotides in length.

Examples of various Cas9 proteins and Cas9 guide RNAs (as well as information regarding requirements related to protospacer adjacent motif (PAM) sequences present in targeted nucleic acids) can be found in the art (see, e.g., Jinek et al., (2012) *Science,* 337(6096):816-821; Chylinski et al. (2013) *RNA Biol.* 10(5): 726-737; Ma et al., (2013) *Biomed Res Int.* 2013:270805; Hou et al. (2013) *Proc. Natl. Acad. Sci. USA,* 110(39): 15644-15649; Jinek et al. (2013) *Elife,* 2: e00471; Pattanayak et al. (2013) *Nat. Biotechnol.* 31(9): 839-843; Qi et al. (2013) *Cell,* 152(5): 1173-1183; Wang et al. (2013) *Cell,* 153(4): 910-918; Chen et al. (2013) *Nucleic Acids Res.* 41(20): e19; Cheng et al. (2013) *Cell Res.* 23(10): 1163-1171; Cho et al. (2013) *Genetics,* 195(3): 1177-1180; DiCarlo et al. (2013) *Nucleic Acids Res.* 41(7): 4336-4343; Dickinson et al. (2013) *Nat. Meth.* 10(10): 1028-1034; Ebina et al. (2013) *Sci Rep.* 3: 2510; Fujii et. al. (2013) *Nucleic Acids Res.* 41(20): e187; Hu et al. (2013) *Cell Res.* 23(11): 1322-1325; Jiang et al. (2013) *Nucleic Acids Res.* 41(20): e188; Larson et al. (2013) *Nat. Protoc.* 8(11): 2180-2196; Mali et al. (2013) *Nat. Meth.* 10(10): 957-963; Nakayama et al. (2013) *Genesis,* 51(12): 835-843; Ran et al. (2013) *Nat. Protoc.* 8(11): 2281-308; Ran et al. (2013) *Cell,* 154(6): 1380-1389; Upadhyay et al. (2013) G3 (Bethesda) 3(12): 2233-2238; Walsh et al. (2013) *Proc. Natl. Acad. Sci. USA,* 110(39): 15514-15515; Yang et al. (2013) *Cell,* 154(6): 1370-1379; Briner et al. (2014)*Mol. Cell,* 56(2): 333-339; and U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

Guide RNAs Corresponding to Type V and Type VI CRISPR/Cas Endonucleases (e.g., Cpf1 Guide RNA)

A guide RNA that binds to a type V or type VI CRISPR/Cas protein (e.g., Cpf1, C2c1, C2c2, C2c3), and targets the complex to a specific location within a target nucleic acid is referred to herein generally as a "type V or type VI CRISPR/Cas guide RNA". An example of a more specific term is a "Cpf1 guide RNA."

A type V or type VI CRISPR/Cas guide RNA (e.g., cpf1 guide RNA) can have a total length of from 30 nucleotides (nt) to 200 nt, e.g., from 30 nt to 180 nt, from 30 nt to 160 nt, from 30 nt to 150 nt, from 30 nt to 125 nt, from 30 nt to 100 nt, from 30 nt to 90 nt, from 30 nt to 80 nt, from 30 nt to 70 nt, from 30 nt to 60 nt, from 30 nt to 50 nt, from 50 nt to 200 nt, from 50 nt to 180 nt, from 50 nt to 160 nt, from 50 nt to 150 nt, from 50 nt to 125 nt, from 50 nt to 100 nt, from 50 nt to 90 nt, from 50 nt to 80 nt, from 50 nt to 70 nt, from 50 nt to 60 nt, from 70 nt to 200 nt, from 70 nt to 180 nt, from 70 nt to 160 nt, from 70 nt to 150 nt, from 70 nt to 125 nt, from 70 nt to 100 nt, from 70 nt to 90 nt, or from 70 nt to 80 nt). In some cases, a type V or type VI CRISPR/Cas guide RNA (e.g., cpf1 guide RNA) has a total length of at least 30 nt (e.g., at least 40 nt, at least 50 nt, at least 60 nt, at least 70 nt, at least 80 nt, at least 90 nt, at least 100 nt, or at least 120 nt).

In some cases, a Cpf1 guide RNA has a total length of 35 nt, 36 nt, 37 nt, 38 nt, 39 nt, 40 nt, 41 nt, 42 nt, 43 nt, 44 nt, 45 nt, 46 nt, 47 nt, 48 nt, 49 nt, or 50 nt.

Like a Cas9 guide RNA, a type V or type VI CRISPR/Cas guide RNA (e.g., cpf1 guide RNA) can include a target nucleic acid-binding segment and a duplex-forming region (e.g., in some cases formed from two duplex-forming segments, i.e., two stretches of nucleotides that hybridize to one another to form a duplex).

The target nucleic acid-binding segment of a type V or type VI CRISPR/Cas guide RNA (e.g., cpf1 guide RNA) can have a length of from 15 nt to 30 nt, e.g., 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, or 30 nt. In some cases, the target nucleic acid-binding segment has a length of 23 nt. In some cases, the target nucleic acid-binding segment has a length of 24 nt. In some cases, the target nucleic acid-binding segment has a length of 25 nt.

The guide sequence of a type V or type VI CRISPR/Cas guide RNA (e.g., cpf1 guide RNA) can have a length of from 15 nt to 30 nt (e.g., 15 to 25 nt, 15 to 24 nt, 15 to 23 nt, 15 to 22 nt, 15 to 21 nt, 15 to 20 nt, 15 to 19 nt, 15 to 18 nt, 17 to 30 nt, 17 to 25 nt, 17 to 24 nt, 17 to 23 nt, 17 to 22 nt, 17 to 21 nt, 17 to 20 nt, 17 to 19 nt, 17 to 18 nt, 18 to 30 nt, 18 to 25 nt, 18 to 24 nt, 18 to 23 nt, 18 to 22 nt, 18 to 21 nt, 18 to 20 nt, 18 to 19 nt, 19 to 30 nt, 19 to 25 nt, 19 to 24 nt, 19 to 23 nt, 19 to 22 nt, 19 to 21 nt, 19 to 20 nt, 20 to 30 nt, 20 to 25 nt, 20 to 24 nt, 20 to 23 nt, 20 to 22 nt, 20 to 21 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, or 30 nt). In some cases, the guide sequence has a length of 17 nt. In some cases, the guide sequence has a length of 18 nt. In some cases, the guide sequence has a length of 19 nt. In some cases, the guide sequence has a length of 20 nt. In some cases, the guide sequence has a length of 21 nt. In some cases, the guide sequence has a length of 22 nt. In some cases, the guide sequence has a length of 23 nt. In some cases, the guide sequence has a length of 24 nt.

The guide sequence of a type V or type VI CRISPR/Cas guide RNA (e.g., cpf1 guide RNA) can have 100% complementarity with a corresponding length of target nucleic acid sequence. The guide sequence can have less than 100% complementarity with a corresponding length of target nucleic acid sequence. For example, the guide sequence of a type V or type VI CRISPR/Cas guide RNA (e.g., cpf1 guide RNA) can have 1, 2, 3, 4, or 5 nucleotides that are not complementary to the target nucleic acid sequence. For example, in some cases, where a guide sequence has a length of 25 nucleotides, and the target nucleic acid sequence has a length of 25 nucleotides, in some cases, the target nucleic acid-binding segment has 100% complementarity to the target nucleic acid sequence. As another example, in some cases, where a guide sequence has a length of 25 nucleotides, and the target nucleic acid sequence has a length of 25 nucleotides, in some cases, the target nucleic acid-binding segment has 1 non-complementary nucleotide and 24 complementary nucleotides with the target nucleic acid sequence. As another example, in some cases, where a guide sequence has a length of 25 nucleotides, and the target nucleic acid sequence has a length of 25 nucleotides, in some cases, the target nucleic acid-binding segment has 2 non-complementary nucleotides and 23 complementary nucleotides with the target nucleic acid sequence.

The duplex-forming segment of a type V or type VI CRISPR/Cas guide RNA (e.g., cpf1 guide RNA) (e.g., of a targeter RNA or an activator RNA) can, in some cases, have a length of from 15 nt to 25 nt (e.g., 15 nt, 16 nt, 17 nt, 18 nt, 19 nt, 20 nt, 21 nt, 22 nt, 23 nt, 24 nt, or 25 nt).

In some cases, the RNA duplex of a type V or type VI CRISPR/Cas guide RNA (e.g., cpf1 guide RNA) can have a length of from 5 base pairs (bp) to 40 bp (e.g., from 5 to 35 bp, 5 to 30 bp, 5 to 25 bp, 5 to 20 bp, 5 to 15 bp, 5-12 bp, 5-10 bp, 5-8 bp, 6 to 40 bp, 6 to 35 bp, 6 to 30 bp, 6 to 25 bp, 6 to 20 bp, 6 to 15 bp, 6 to 12 bp, 6 to 10 bp, 6 to 8 bp, 7 to 40 bp, 7 to 35 bp, 7 to 30 bp, 7 to 25 bp, 7 to 20 bp, 7 to 15 bp, 7 to 12 bp, 7 to 10 bp, 8 to 40 bp, 8 to 35 bp, 8 to 30 bp, 8 to 25 bp, 8 to 20 bp, 8 to 15 bp, 8 to 12 bp, 8 to 10 bp, 9 to 40 bp, 9 to 35 bp, 9 to 30 bp, 9 to 25 bp, 9 to 20 bp, 9 to 15 bp, 9 to 12 bp, 9 to 10 bp, 10 to 40 bp, 10 to 35 bp, 10 to 30 bp, 10 to 25 bp, 10 to 20 bp, 10 to 15 bp, or 10 to 12 bp).

As an example, a duplex-forming segment of a Cpf1 guide RNA can comprise a nucleotide sequence selected from (5' to 3'): AAUUUCUACUGUUGUAGAU (SEQ ID NO:18), AAUUUCUGCUGUUGCAGAU (SEQ ID NO:19), AAUUUCCACUGUUGUGGAU (SEQ ID NO:20), AAUUCCUACUGUUGUAGGU (SEQ ID NO:21), AAUUUCUACUAUUGUAGAU (SEQ ID NO:22), AAUUUCUACUGCUGUAGAU (SEQ ID NO:23), AAUUUCUACUUUGUAGAU (SEQ ID NO:24), and AAUUUCUACUUGUAGAU (SEQ ID NO:25). The guide sequence can then follow (5' to 3') the duplex forming segment.

A non-limiting example of an activator RNA (e.g. tracrRNA) of a C2c1 guide RNA (dual guide or single guide) is an RNA that includes the nucleotide sequence GAAUUUUUCAACGGGUGUGCCAAUGGCCAC-UUUCCAGGUGGCAAAGCCCGUUG A GCUUCU-CAAAAAG (SEQ ID NO:26). In some cases, a C2c guide RNA (dual guide or single guide) is an RNA that includes the nucleotide sequence In some cases, a C2c guide RNA (dual guide or single guide) is an RNA that includes the nucleotide sequence GUCUAGAGGACAGAAUUUUU-CAACGGGUGUGCCAAUGGCCACUUUCCAGGUG GC AAAGCCCGUUGAGCUUCUCAAAAAG (SEQ ID NO:27). In some cases, a C2c1 guide RNA (dual guide or single guide) is an RNA that includes the nucleotide sequence UCUAGAGGACAGAAUUUUUCAACGGGU-GUGCCAAUGGCCACUUUCCAGGUGGC A AAGCCCGUUGAGCUUCUCAAAAAAG (SEQ ID NO:28). A non-limiting example of an activator RNA (e.g. tracrRNA) of a C2c1 guide RNA (dual guide or single guide) is an RNA that includes the nucleotide sequence ACUUUCCAGGCAAAGCCCGU UGAGCUUCU-CAAAAAG (SEQ ID NO:29). In some cases, a duplex forming segment of a C2c1 guide RNA (dual guide or single guide) of an activator RNA (e.g. tracrRNA) includes the nucleotide sequence AGCUUCUCA (SEQ ID NO:30) or the nucleotide sequence GCUUCUCA (SEQ ID NO:31) (the duplex forming segment from a naturally existing tracrRNA.

A non-limiting example of a targeter RNA (e.g. crRNA) of a C2c1 guide RNA (dual guide or single guide) is an RNA with the nucleotide sequence CUGAGAAGUGG-CACNNNNNNNNNNNNNNNNNNNN (SEQ ID NO:32), where the Ns represent the guide sequence, that will vary depending on the target sequence, and although 20 Ns are depicted a range of different lengths are acceptable. In some cases, a duplex forming segment of a C2c1 guide RNA (dual guide or single guide) of a targeter RNA (e.g. crRNA) includes the nucleotide sequence CUGAGAAGUGGCAC (SEQ ID NO:33) or includes the nucleotide sequence CUGAGAAGU (SEQ ID NO:34) or includes the nucleotide sequence UGAGAAGUGGCAC (SEQ ID NO:35) or includes the nucleotide sequence UGAGAAGU (SEQ ID NO:36).

Examples and guidance related to type V or type VI CRISPR/Cas endonucleases and guide RNAs (as well as information regarding requirements related to protospacer adjacent motif (PAM) sequences present in targeted nucleic acids) can be found in the art (see, e.g., Zetsche et al. (2015) *Cell*, 163(3): 759-771; Makarova et al. (2015)*Nat. Rev. Microbiol.* 13(11): 722-736; Shmakov et al. (2015) *Mol. Cell.* 60(3): 385-397, and the like).

Target Cells

Because the polyrotaxane (PRX) carriers described herein are effective to deliver complexed nucleic acids in vivo, the target nucleic acid (e.g., target genomic DNA) can be located within a eukaryotic cell in vivo.

In some cases a target cell (a cell into which a class 2 CRISPR/Cas endonuclease and a pair of corresponding CRISPR/Cas guide RNAs can be introduced) is a cell of a vertebrate animal (e.g., fish, amphibian, reptile, bird, mammal); a cell of a mammal (e.g., a cell of a rodent such as a mouse or rat, a cell of a non-human primate, a cell of a human, etc.); and the like. In some cases, a target cell (a cell into which a class 2 CRISPR/Cas endonuclease and a pair of corresponding CRISPR/Cas guide RNAs can be introduced) is a mammalian cell (e.g., a human cell or a non-human mammalian cell).

The cell(s) targeted in vivo, can be any type of cell of interest (e.g., a stem cell, e.g. an embryonic stem (ES) cell, a hematopoietic stem cell, a germ cell (e.g., an oocyte, a sperm, an oogonia, a spermatogonia, etc.), a somatic cell, a muscle cell, an in in vivo embryonic cell of an embryo at any stage, e.g., a 1-cell, 2-cell, 4-cell, 8-cell, etc. stage zebrafish embryo; etc.).

In some cases, the cell is a pericyte. A pericyte is a multipotent stem cell that is located within the blood vessels of skeletal muscle.

Thus, in some cases, a target cell (a cell into which a class 2 CRISPR/Cas endonuclease and a pair of corresponding CRISPR/Cas guide RNAs can be introduced) is a pericyte (e.g., see Dellavalle et al. (2007) Nat. Cell Biol. 9(3): 255-267). In some cases, the cell is a type 2 pericyte (e.g., which can form myotubes and can be characterized by positive expression for nestin (PDGFRB+ CD146+ NG2+)). In some cases, is a muscle stem cell. In some cases, the cell is a myogenic precursor cell.

The foregoing cells and/or tissues are illustrative and non-limiting. Using the teachings provided herein, nucleic acid constructs can be delivered in vivo to essentially any desired cell.

Illustrative Modification of Mutant Dystrophin.

Duchenne Muscular Dystrophy (DMD) is a muscle genetic disorder in boys, resulting in loss of ambulation and premature death due to frame-shifting mutations in the DMD gene resulting in the loss of dystrophin protein in muscle. Currently, no cure has been found. Dystrophin stabilizes the dystrophin-glycoprotein complex (DGC) and loss of functional dystrophin leads to the degradation of DGC components, muscle membrane damage, and dysfunctional muscle stem cells. DMD can lead to wheelchair dependence, life threatening infection, cardiomyopathy, and the like.

One approach to the treatment of DMD described in PCT Pub. No: WO 2017/139505 (PCT/US2017/017255, which is incorporated herein by reference for the constructs and sequences described therein) involves the use of CRISPR to restore the reading frame for DMD. By restoring the reading frame, DMD can be switched to a milder phenotype, Becker's muscular dystrophy (BMD).

Accordingly, in certain embodiments the CRISPR components encoded by the plasmid that is complexed with the polyrotaxane carrier(s) described herein are designed to modify a mutant dystrophin gene in the genome of a cell (e.g., a human cell), e.g., as described in PCT/US2017/017255. In various embodiments, the PRX carrier introduced into the cell carries: (a) a nucleic acid comprising a nucleotide sequence encoding the class 2 CRISPR/Cas endonuclease; and (b) one or more nucleic acids comprising nucleotide sequences encoding the first and/or second CRISPR/Cas guide RNAs. In certain embodiments, the first CRISPR/Cas guide RNA comprises a guide sequence that hybridizes to a target sequence within intron 44 of the mutant dystrophin gene, and the second CRISPR/Cas guide RNA comprises a guide sequence that hybridizes to a target sequence within intron 55 of the mutant dystrophin gene (see, e.g., FIG. 5). In this illustrative, but non-limiting embodiment, introduction of these components into the cell by the PRX carrier/plasmid complex results in deletion of a greater than 330 kilobase region of the mutant dystrophin gene comprising exons 45-55 (e.g., in some cases due to non-homologous end-joining (NHEJ)).

Thus, in some cases, the subject methods result in cleavage of the cell's genome in introns 44 and 55 of the mutant dystrophin gene and deletion of a greater than 330-kilobase region of the mutant dystrophin gene comprising exons 45-55. The subject methods thus result in deletion of a greater than 330-kilobase region of the mutant dystrophin gene, where the deleted region comprises exons 45-55 (e.g., such that the remaining sequence encode a dystrophin mRNA missing exons 45-55, e.g., remaining sequence of intron 44 and remaining sequence of intron 55 become a single intron, and exon 44 is therefore spliced directly to exon 56). Thus, in some cases, the deleted region includes intron sequence and the remaining sequence also includes intron sequence.

In some cases, the subject methods result in a genomic deletion of greater than 330 kilobases (kb). In some cases, the subject methods result in a genomic deletion of 400 kilobases (kb) or more (e.g., 450 kb or more, 500 kb or more, 550 kb or more, 600 kb or more, 650 kb or more, 700 kb or more, etc.). For example, in some cases, the target sequence within intron 44 and the target sequence within intron 55 are separated from each other by greater than 330 kilobases (kb). In some cases, the target sequence within intron 44 and the target sequence within intron 55 are separated from each other by 400 kb or more (e.g., 450 kb or more, 500 kb or more, 550 kb or more, 600 kb or more, 650 kb or more, 700 kb or more, etc.). In some cases, the target sequence within intron 44 and the target sequence within intron 55 are separated from each other by 700 kb or more.

Figure 23:
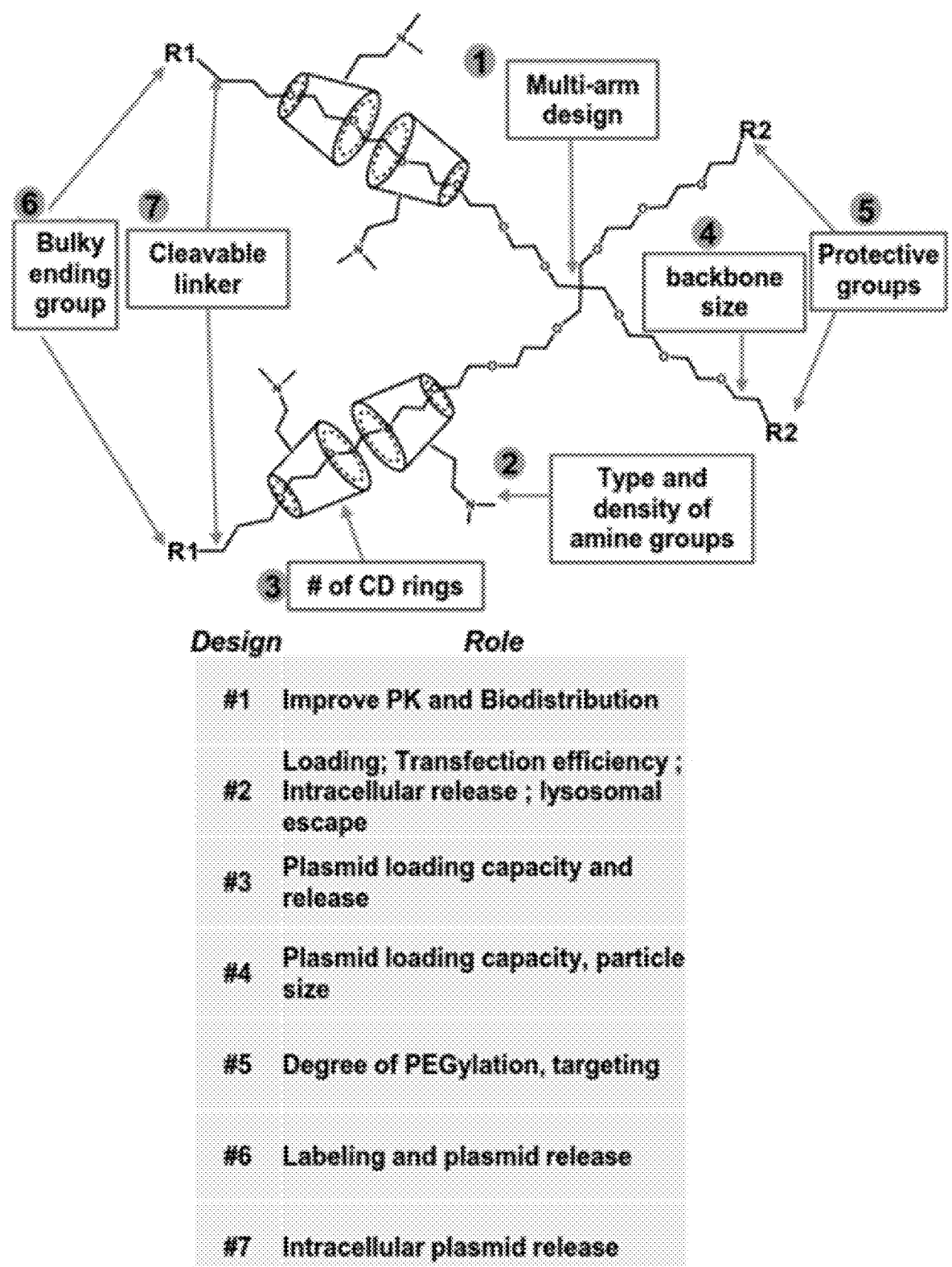
FIG. 23 shows Scheme 1 illustrating various polyrotaxane structural design features and their possible impacts.
Figure 24:
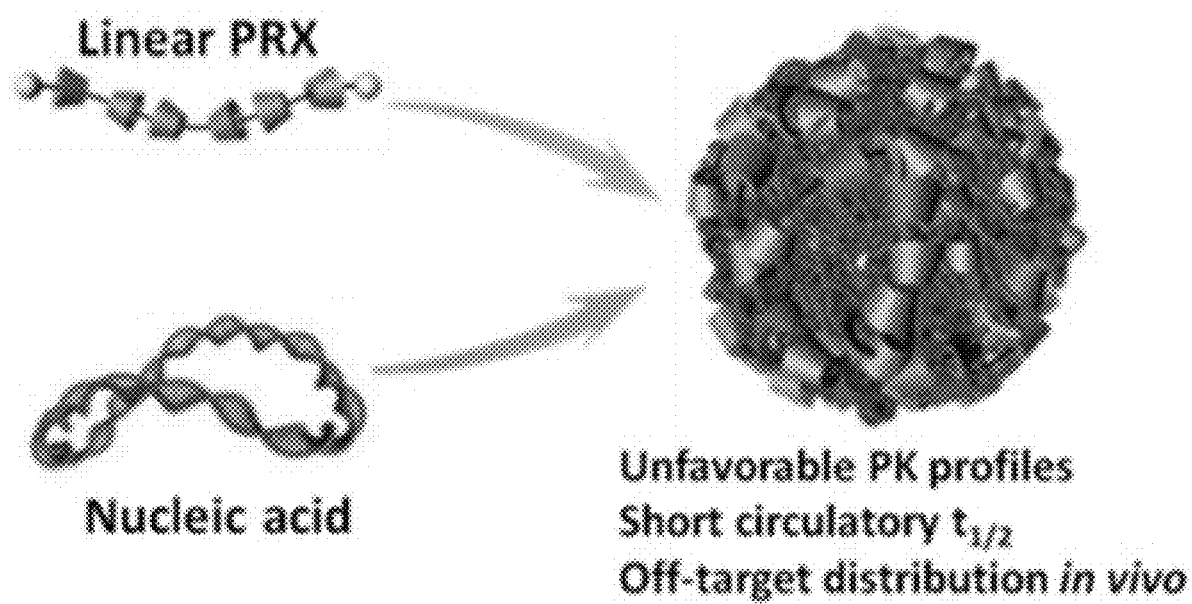
FIG. 24 shows a schematic of the structure of linear PRX, with CD rings distributed non-selectively along the linear PEG backbone. Self-assembled nanoparticles were formed from linear PRX and plasmid DNA. This leads to cationic nanoparticles with low or no PEG modification, which is unfavorable for in vivo application because of poor PK, short circulatory $t_{1/2}$, non-specific binding and off-target distribution.

Thus, in some cases, the guide sequence of the first CRISPR/Cas guide RNA (e.g., a Cas9 guide RNA) has 100% complementarity over 20 contiguous nucleotides with a target sequence corresponding to intron 44 of the human dystrophin gene (e.g., a target sequence within intron 44 of the human dystrophin gene, a target sequence within a mouse dystrophin gene, etc.), and the guide sequence of the second CRISPR/Cas guide RNA (e.g., a Cas9 guide RNA) has 100% complementarity over 20 contiguous nucleotides with a target sequence corresponding to intron 55 of the human dystrophin gene (e.g., a target sequence within intron 55 of the human dystrophin gene, a target sequence within a mouse dystrophin gene, etc.). In some such cases, the target sequence corresponding to intron 44 and the target sequence corresponding to intron 55 are separated from each other by greater than 330 kilobases (kb). In some cases, the target sequence corresponding to intron 44 and the target sequence corresponding to intron 55 are separated from each other by 400 kilobases (kb) or more (e.g., 450 kb or more, 500 kb or more, 550 kb or more, 600 kb or more, 650 kb or more, 700 kb or more, etc.). In some cases, the target sequence within intron 44 and the target sequence within intron 55 are separated from each other by 700 kb or more. Examples guide RNAs (e.g., guide sequences of guide RNAs) and target sequences that can be used to accomplish such genomic deletions in human cells are provided in Tables 4 and 5 (see also FIGS. 23 and 24 in PCT/US2017/017255).

TABLE 4

Illustrative, but non-limiting examples, of guide sequences of guide RNAs and non-complementary strands of target sequences that can be used to accomplish genomic deletion of a mutant dystrophin gene in human cells. Note PCT/US2017/017255 SEQ ID shown in parenthiticals)

| Intron | Site | | Length | Sequence | Followed by PAM | SEQ ID NO |
|---|---|---|---|---|---|---|
| 44 | 1 (44C1) | Non-complementary strand of target sequence | 20 nt<br>17 nt | GTGGTGTCCTTTGAATATGCAGG<br>GTGTCCTTTGAATATGC | <br>AGG | 37(1140)<br>38(1145) |
| | | Guide Sequence of Guide RNA | 20 nt<br>17 nt | GUGGUGUCCUUUGAAUAUGC<br>GUGUCCUUUGAAUAUGC | | 39(1150)<br>40(1155) |
| | 2 (44C2) | Non-complementary strand of target sequence | 20 nt<br>17 nt | AGATTGTCCAGGATATAATTTGG<br>TTGTCCAGGATATAATT | <br>TGG | 41(1141)<br>42(1146) |
| | | Guide Sequence of Guide RNA | 20 nt<br>17 nt | AGAUUGUCCAGGAUAUAAUU<br>UUGUCCAGGAUAUAAUU | | 43(1151)<br>44(1156) |
| | 3 (44C3) | Non-complementary strand of target sequence | 20 nt<br>17 nt | TTAGCAACCAAATTATATCCTGG<br>GCAACCAAATTATATCC | <br>TGG | 45(1142)<br>46(1147) |
| | | Guide Sequence of Guide RNA | 20 nt<br>17 nt | UUAGCAACCAAAUUAUAUCC<br>GCAACCAAAUUAUAUCC | | 47(1152)<br>48(1157) |
| | 4 (44C4) | Non-complementary strand of target sequence | 20 nt<br>17 nt | GTTGAAATTAAACTACACACTGG<br>GAAATTAAACTACACAC | <br>TGG | 49(1143)<br>50(1148) |
| | | Guide Sequence of Guide RNA | 20 nt<br>17 nt | GUUGAAAUUAAACUACACAC<br>GAAAUUAAACUACACAC | | 51(1153)<br>52(1158) |
| | 5 (44C5) | Non-complementary strand of target sequence | 20 nt<br>17 nt | ATCTTTACCTGCATATTCAAAGG<br>TTTACCTGCATATTCAA | <br>AGG | 53(1144)<br>54(1149) |
| | | Guide Sequence of Guide RNA | 20 nt<br>17 nt | AUCUUUACCUGCAUAUUCAA<br>UUUACCUGCAUAUUCAA | | 55(1154)<br>56(1159) |
| 55 | 1 (55C1) | Non-complementary strand of target sequence | 20 nt<br>17 nt | TACACATTTTTAGGCTTGACAGG<br>ACATTTTTAGGCTTGAC | <br>AGG | 57(1160)<br>58(1165) |
| | | Guide Sequence of Guide RNA | 20 nt<br>17 nt | UACACAUUUUUAGGCUUGAC<br>ACAUUUUUAGGCUUGAC | | 59(1170)<br>60(1175) |
| | 2 (55C2) | Non-complementary strand of target sequence | 20 nt<br>17 nt | CATTCCTGGGAGTCTGTCATGGG<br>TCCTGGGAGTCTGTCAT | <br>GGG | 61(1161)<br>62(1166) |
| | | Guide Sequence of Guide RNA | 20 nt<br>17 nt | CAUUCCUGGGAGUCUGUCAU<br>UCCUGGGAGUCUGUCAU | | 63(1171)<br>64(1176) |
| | 3 (55C3) | Non-complementary strand of target sequence | 20 nt<br>17 nt | TGTATGATGCTATAATACCAAGG<br>ATGATGCTATAATACCA | <br>AGG | 65(1162)<br>66(1167) |
| | | Guide Sequence of Guide RNA | 20 nt<br>17 nt | UGUAUGAUGCUAUAAUACCA<br>AUGAUGCUAUAAUACCA | | 67(1172)<br>68(1177) |

TABLE 4-continued

Illustrative, but non-limiting examples, of guide sequences of guide RNAs and non-complementary strands of target sequences that can be used to accomplish genomic deletion of a mutant dystrophin gene in human cells. Note PCT/US2017/017255 SEQ ID shown in parenthiticals)

| Intron | Site | | Length | Sequence | Followed by PAM | SEQ ID NO |
|---|---|---|---|---|---|---|
| 4 | (55C4) | Non-complementary strand of target sequence | 20 nt | GTGGAAAGTACATAGGACCTTGG | | 69(1163) |
| | | | 17 nt | GAAAGTACATAGGACCT | TGG | 70(1168) |
| | | Guide Sequence of Guide RNA | 20 nt | GUGGAAAGUACAUAGGACCU | | 71(1173) |
| | | | 17 nt | GAAAGUACAUAGGACCU | | 72(1178) |
| 5 | (55C5) | Non-complementary strand of target sequence | 20 nt | TCTTATCATAACTCTTACCAAGG | | 73(1164) |
| | | | 17 nt | TATCATAACTCTTACCA | AGG | 74(1169) |
| | | Guide Sequence of Guide RNA | 20 nt | UCUUAUCAUAACUCUUACCA | | 75(1174) |
| | | | 17 nt | UAUCAUAACUCUUACCA | | 76(1179) |

Table 5 shows example guide sequences of guide RNAs and non-complementary strands of target sequences that can be used to accomplish genomic deletions of a mutant dystrophin gene in human cells.

| Name | Target seq; gRNA seq (w/out PAM) | SEQ ID NO | PCT/US2017/017255 SEQ ID NO |
|---|---|---|---|
| 44C1 | gtggtgtcct ttgaatatgc | 77 | 1140 |
| | gugguguccu uugaauaugc | 78 | 1150 |
| 44C1 | agattgtcca ggatataatt | 79 | 1141 |
| | agauugucca ggauauaauu | 80 | 1151 |
| 44C1 | ttagcaacca aattatatcc | 81 | 1142 |
| | uuagcaacca aauuauaucc | 82 | 1152 |
| 44C1 | gttgaaatta aactacacac | 83 | 1143 |
| | guugaaauua aacuacacac | 84 | 1153 |
| 44C1 | atctttacct gcatattcaa | 85 | 1144 |
| | aucuuuaccu gcauauucaa | 86 | 1154 |
| 44C6md | ctctgcattg ttttggcctc | 87 | 1136 |
| | cucugcauug uuuuggccuc | 88 | 1223 |
| 44C7m | tcctccaaag agtagaatgg | 89 | 1137 |
| | uccuccaaag aguagaaugg | 90 | 1224 |
| 44C8m | gccctaaact tacactgttc | 91 | 1138 |
| | gcccuaaacu uacacuguuc | 92 | 1225 |
| 44r1-3 | aaagatagat tagattgtcc | 93 | 1139 |
| | aaagauagau uagauugucc | 94 | 1226 |
| 44r1-7 | gttgctaaat tacatagttt | 95 | 1180 |
| | guugcuaaau uacauaguuu | 96 | 1227 |
| 44r1-1 | tgttgcaata gtcaatcaag | 97 | 1181 |
| | uguugcaaua gucaaucaag | 98 | 1228 |
| 44r2-2 | atactgatta agacagatga | 99 | 1182 |
| | auacugauua agacagauga | 100 | 1229 |
| 44r2-3 | aatactgatt aagacagatg | 101 | 1183 |
| | aauacugauu aagacagaug | 102 | 1230 |
| 44r3-1 | ctctatacaa atgccaacgc | 103 | 1184 |
| | cucuauacaa augccaacgc | 104 | 1231 |
| 44r3-2 | acttgcatgc acaccagcgt | 105 | 1185 |
| | acuugcaugc acaccagcgu | 106 | 1232 |
| 44r3-3 | ttgggctaat gtagcataat | 107 | 1186 |
| | uugggcuaau guagcauaau | 108 | 1233 |
| 44r3-4 | gcgttggcat ttgtatagag | 109 | 1187 |
| | gcguuggcau uuguauagag | 110 | 1234 |
| 44r3-5 | tgggctaatg tagcataatg | 111 | 1188 |
| | ugggcuaaug uagcauaaug | 112 | 1235 |
| 44r3-6 | tttgggctaa tgtagcataa | 113 | 1189 |
| | uuugggcuaa uguagcauaa | 114 | 1236 |
| 44r3-7 | gcttaactcc ttaatattaa | 115 | 1190 |
| | gcuuaacucc uuaauauuaa | 116 | 1237 |

| Name | Target seq; gRNA seq (w/out PAM) | SEQ ID NO | PCT/US2017/ 017255 SEQ ID NO |
|---|---|---|---|
| 44r3-8 | tcttctatat taaagcagat | 117 | 1191 |
| | ucuucuauau uaaagcagau | 118 | 1238 |
| 44r3-9 | cttctatatt aaagcagatt | 119 | 1192 |
| | cuucuauauu aaagcagauu | 120 | 1239 |
| 44r4-1 | aatatataac taccttgggt | 121 | 1193 |
| | aauauauaac uaccuggguu | 122 | 1240 |
| 44r4-2 | acctccattc tactctttgg | 123 | 1194 |
| | accuccauuc uacucuuugg | 124 | 1241 |
| 44r4-3 | tttcaatgat atccaaccca | 125 | 1195 |
| | uuucaaugau auccaaccca | 126 | 1242 |
| 44r4-5 | agtacctcca ttctactctt | 127 | 1196 |
| | aguaccucca uucuacucuu | 128 | 1243 |
| 44r4-6 | ctatcctcca agagtagaa | 129 | 1197 |
| | cuauccucca aagaguagaa | 130 | 1244 |
| 44r4-7 | ttttgctaca tatttcaggc | 131 | 1198 |
| | uuuugcuaca uauuucaggc | 132 | 1245 |
| 44r4-8 | tttgctacat atttcagct | 133 | 1199 |
| | uuugcuacau auuucaggcu | 134 | 1246 |
| 44r4-9 | gggttggata tcattgaaaa | 135 | 1200 |
| | ggguuggaua ucauugaaaa | 136 | 1247 |
| 44r4-10 | atatttcagg ctgggtttct | 137 | 1201 |
| | auauuucagg cuggguucu | 138 | 1248 |
| 44r4-11 | ttgaaatata taactaccct | 139 | 1202 |
| | uugaaauaua uaacuaccuu | 140 | 1249 |
| 44r4-12 | attgaaatat ataactacct | 141 | 1203 |
| | auugaaauau auaacuaccu | 142 | 1250 |
| 44r5-1 | gtgagtagtg gggcacttta | 143 | 1204 |
| | gugaguagug gggcacuuua | 144 | 1251 |
| 44r5-2 | tgtatgtaga aggttaacta | 145 | 1205 |
| | uguauguaga agguuaacua | 146 | 1252 |
| 44r5-3 | gagcctaata aatgtacaat | 147 | 1206 |
| | gagccuaaua aauguacaau | 148 | 1253 |
| 44r5-4 | ttgtatgtag aaggttaact | 149 | 1207 |
| | uuguauguag agguuaacu | 150 | 1254 |
| 44r5-5 | caatttgttt tgatgtaact | 151 | 1208 |
| | caauuuguuu ugauguaacu | 152 | 1255 |
| 44r6-1 | tgccttctga aatagtccag | 153 | 1209 |
| | ugccuucuga aauaguccag | 154 | 1256 |
| 44r6-3 | gttaataggg aaacagcata | 155 | 1210 |
| | guuaauaggg aaacagcaua | 156 | 1257 |
| 44r6-4 | aacaatgcag agttaattgt | 157 | 1211 |
| | aacaaugcag aguuaauugu | 158 | 1258 |
| 44r7-1 | gaacatgttg agtagacaca | 159 | 1212 |
| | gaacauguug aguagacaca | 160 | 1259 |
| 44r7-2 | tttatcatct gtgtctattc | 161 | 1213 |
| | uuuaucaucu gugucuauuc | 162 | 1260 |
| 44r7-3 | tctttacttt cttgactata | 163 | 1214 |
| | ucuuuacuuu cuugacuaua | 164 | 1261 |
| 44r8-1 | aatattctca aacctcgttc | 165 | 1215 |
| | aauauucuca aaccucguuc | 166 | 1262 |
| 44r8-3 | attaactgtg ttccagaacg | 167 | 1216 |
| | auuaacugug uuccagaacg | 168 | 1263 |
| 44r8-4 | taactgcttc tttggatgac | 169 | 1217 |
| | uaacugcuuc uuuggaugac | 170 | 1264 |
| 44r8-5 | gaccagaaca gtgtaagttt | 171 | 1218 |
| | gaccagaaca guguaaguuu | 172 | 1265 |
| 44r8-6 | accagaacag tgtaagttta | 173 | 1219 |
| | accagaacag uguaaguuua | 174 | 1266 |
| 44r8-7 | ctacttttc cccactactg | 175 | 1220 |
| | cuacuuuuc cccacuacug | 176 | 1267 |
| 44r8-8 | tggaacacag ttaattcact | 177 | 1221 |
| | uggaacacag uuaauucacu | 178 | 1268 |
| 44r8-9 | gtgttgttta actgcttctt | 179 | 1222 |
| | guguuguuua acugcuucuu | 180 | 1269 |
| 55C1 | tacacatttt taggcttgac | 181 | 1160 |
| | uacacauuuu uaggcuugac | 182 | 1170 |
| 55C2 | cattcctggg agtctgtcat | 183 | 1161 |
| | cauuccuggg agucugucau | 184 | 1171 |
| 55C3 | tgtatgatgc tataatacca | 185 | 1162 |
| | uguaugaugc uauaauacca | 186 | 1172 |
| 55C4 | gtggaaagta cataggacct | 187 | 1163 |
| | guggaaagua cauaggaccu | 188 | 1173 |
| 55C5 | tcttatcata actcttacca | 189 | 1164 |
| | ucuuaucaua acucuuacca | 190 | 1174 |

| Name | Target seq; gRNA seq (w/out PAM) | SEQ ID NO | PCT/US2017/ 017255 SEQ ID NO |
|---|---|---|---|
| 55C6d | aactgtcagt tgcatattcc | 191 | 1270 |
| | aacugucagu ugcauauucc | 192 | 1318 |
| 55C7d | cagaaaggaa tgctggtacc | 193 | 1271 |
| | cagaaaggaa ugcugguacc | 194 | 1319 |
| 55C8d | tctgcctaca caatgaatgg | 195 | 1272 |
| | ucugccuaca caaugaaugg | 196 | 1320 |
| 55C9d | cacagatcaa tccaattgtt | 197 | 1273 |
| | cacagaucaa uccaauuguu | 198 | 1321 |
| 55r1-5 | ttgacaggtg gaaagtacat | 199 | 1274 |
| | uugacaggug gaaaguacau | 200 | 1322 |
| 55r1-6 | acatttttag gcttgacagg | 201 | 1275 |
| | acauuuuuag gcuugacagg | 202 | 1323 |
| 55r1-8 | ctctcccatg acagactccc | 203 | 1276 |
| | cucucccaug acagacuccc | 204 | 1324 |
| 55r1-9 | ttggtaagag ttatgataag | 205 | 1277 |
| | uugguaagag uuaugauaag | 206 | 1325 |
| 55r1-10 | aacacaaatt aagttcacct | 207 | 1278 |
| | aacacaaauu aaguucaccu | 208 | 1326 |
| 55r2-1 | aggatcagtg ctgtagtgcc | 209 | 1279 |
| | aggaucagug cuguagugcc | 210 | 1327 |
| 55r2-2 | ggccgtttat tattattgac | 211 | 1280 |
| | ggccguuuau uauuauugac | 212 | 1328 |
| 55r2-3 | tctcaggatt gctatgcaac | 213 | 1281 |
| | ucucaggauu gcuaugcaac | 214 | 1329 |
| 55r2-4 | caggaagaca taccatgtaa | 215 | 1282 |
| | caggaagaca uaccauguaa | 216 | 1330 |
| 55r2-5 | agcagggctc tttcagtttc | 217 | 1283 |
| | agcagggcuc uuucaguuuc | 218 | 1331 |
| 55r2-6 | taacattttc agcttgaacc | 219 | 1284 |
| | uaacauuuuc agcuugaacc | 220 | 1332 |
| 55r2-7 | tcaagctgaa aatgttacac | 221 | 1285 |
| | ucaagcugaa aauguuacac | 222 | 1333 |
| 55r2-8 | gtaacatttt cagcttgaac | 223 | 1286 |
| | guaacauuuu cagcuugaac | 224 | 1334 |
| 55r2-9 | cagaatgaat tttggagcac | 225 | 1287 |
| | cagaaugaau uuuggagcac | 226 | 1335 |
| 55r2-10 | tttattatta ttgactggtg | 227 | 1288 |
| | uuuauuauua uugacuggug | 228 | 1336 |
| 55r2-11 | agaagaatct gacctttaca | 229 | 1289 |
| | agaagaaucu gaccuuuaca | 230 | 1337 |
| 55r2-12 | gcagggtctc ttcagtttct | 231 | 1290 |
| | gcagggcucu uucaguuucu | 232 | 1338 |
| 55r3-1 | ctaaacagta gccaggcgtg | 233 | 1291 |
| | cuaaacagua gccaggcgug | 234 | 1339 |
| 55r3-2 | cgcctggcta ctgtttagtg | 235 | 1292 |
| | cgccuggcua cuguuuagug | 236 | 1340 |
| 55r3-3 | ctccgcacta aacagtagcc | 237 | 1293 |
| | cuccgcacua aacaguagcc | 238 | 1341 |
| 55r3-4 | gtagccaggc gtgtggatgt | 239 | 1294 |
| | guagccaggc gugugaaugu | 240 | 1342 |
| 55r3-6 | cttggctttg actattctgc | 241 | 1295 |
| | cuuggcuuug acuauucugc | 242 | 1343 |
| 55r3-7 | agtagccagg cgtgtggatg | 243 | 1296 |
| | aguagccagg cgugugaaug | 244 | 1344 |
| 55r3-8 | tcctcccaca tccacacgcc | 245 | 1297 |
| | uccucccaca uccacacgcc | 246 | 1345 |
| 55r3-10 | ttggctttga ctattctgct | 247 | 1298 |
| | uuggcuuuga cuauucugcu | 248 | 1346 |
| 55r3-11 | ataatgtctc tggcttgtaa | 249 | 1299 |
| | auaaugucuc uggcuuguaa | 250 | 1347 |
| 55r3-12 | tggtacccgg cagctctctg | 251 | 1300 |
| | ugguacccgg cagcucucug | 252 | 1348 |
| 55r3-13 | gtgggaggaa cctcaaagag | 253 | 1301 |
| | gugggaggaa ccucaaagag | 254 | 1349 |
| 55r3-14 | tgactattct gctgggaaca | 255 | 1302 |
| | ugacuauucu gcugggaaca | 256 | 1350 |
| 55r3-15 | ctctctgagg aatgttccct | 257 | 1303 |
| | cucucugagg aauguucccu | 258 | 1351 |
| 55r3-16 | aacattcctc agagagctgc | 259 | 1304 |
| | aacauuccuc agagagcugc | 260 | 1352 |
| 55r4-2 | attctgaagc tccaaacaat | 261 | 1305 |
| | auucugaagc uccaaacaau | 262 | 1353 |
| 55r4-3 | taaattactc tgctaaagta | 263 | 1306 |
| | uaaauuacuc ugcuaaagua | 264 | 1354 |

| Name | Target seq; gRNA seq (w/out PAM) | SEQ ID NO | PCT/US2017/017255 SEQ ID NO |
|---|---|---|---|
| 55r5-1 | agtacaaacc aggtttgtac | 265 | 1307 |
| | aguacaaacc agguuuguac | 266 | 1355 |
| 55r5-2 | atatccttcc agtacaaacc | 267 | 1308 |
| | auauccuucc aguacaaacc | 268 | 1356 |
| 55r5-3 | caaaccaggt ttgtactgga | 269 | 1309 |
| | caaaccaggu uuguacugga | 270 | 1357 |
| 55r5-4 | ggcagctaaa gcatcactga | 271 | 1310 |
| | ggcagcuaaa gcaucacuga | 272 | 1358 |
| 55r5-5 | atctctgagt agtacaaacc | 273 | 1311 |
| | aucucugagu aguacaaacc | 274 | 1359 |
| 55r5-6 | gtgtcccatt ctctttgact | 275 | 1312 |
| | gugucccauu cucuuugacu | 276 | 1360 |
| 55r5-7 | tgtgtcccat tctctttgac | 277 | 1313 |
| | ugugucccau ucucuuugac | 278 | 1361 |
| 55r5-8 | ttctgaatgt tgaacaagta | 279 | 1314 |
| | uucugaaugu ugaacaagua | 280 | 1362 |
| 55r5-9 | gtctcccagt caaagagaat | 281 | 1315 |
| | gucucccagu caaagagaau | 282 | 1363 |
| 55r5-10 | attctctttg actgggagac | 283 | 1316 |
| | auucucuuug acugggagac | 284 | 1364 |
| 55r5-11 | tctttgactg ggagacaggc | 285 | 1317 |
| | ucuuugacug ggagacaggc | 286 | 1365 |

The full sequence of the gRNA is the above sequence in the Table plus the rest of the scaffold sequence: gttttagagctaGAAAtagcaagttaaaataaggctagtccgttatcaacttgaaaaagtggcaccgagtcggtgcTTTTTT (SEQ ID NO :287)

In various embodiments, the CRISPR components (e.g., (a) a class 2 CRISPR/Cas endonuclease, e.g., Cas9, Cpf1, etc.; and/or (b) first and second corresponding guide RNAs, e.g., Cas9 guide RNAs, a Cpf1 guide RNAs, etc.) can be delivered to a cell using the polyrotaxane carriers described herein as DNA, or RNA. Thus, for example, a class 2 CRISPR/Cas endonuclease (e.g., Cas9) can be introduced into a cell as a DNA and/or RNA encoding the endonuclease and guide RNA(s). The CRISPR/Cas guide RNA can be introduced into a cell as RNA, or as DNA encoding the guide RNA.

In some cases, the encoded class 2 CRISPR/Cas endonuclease (e.g., a Cas9 protein) is encoded as a fusion protein that is fused to a heterologous polypeptide (also referred to as a "fusion partner"). In some cases, a class 2 CRISPR/Cas endonuclease is fused to an amino acid sequence (a fusion partner) that provides for subcellular localization, e.g., the fusion partner is a subcellular localization sequence (e.g., one or more nuclear localization signals (NLSs) for targeting to the nucleus, two or more NLSs, three or more NLSs, etc.). In some embodiments, a class 2 CRISPR/Cas endonuclease is fused to an amino acid sequence (a fusion partner) that provides a tag (e.g., the fusion partner is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like). In some embodiments, the fusion partner can provide for increased or decreased stability (i.e., the fusion partner can be a stability control peptide, e.g., a degron, which in some cases is controllable (e.g., a temperature sensitive or drug controllable degron sequence).

In some cases the class 2 CRISPR/Cas endonuclease encoded by the plasmid includes a "Protein Transduction Domain" or PTD (also known as a CPP—cell penetrating peptide), which refers to a polypeptide that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane and can facilitate translocation of the CRISPR/Cas endojnuclease into the cell nucleus. In some embodiments, the PTD, when present, is covalently linked to the amino terminus or to the carboxyl terminus of the class 2 CRISPR/Cas endonuclease (e.g., a Cas9 protein). In some cases, the PTD is inserted internally in the class 2 CRISPR/Cas endonuclease (e.g., Cas9 protein) (i.e., is not at the N- or C-terminus of the class 2 CRISPR/Cas endonuclease). In some cases, a subject class 2 CRISPR/Cas endonuclease (e.g., Cas9 protein) includes (is conjugated to, is fused to) one or more PTDs (e.g., two or more, three or more, four or more PTDs). In some cases a PTD includes a nuclear localization signal (NLS) (e.g, in some cases 2 or more, 3 or more, 4 or more, or 5 or more NLSs).

In some cases, the nucleic acid encoding the class 2 CRISPR/Cas endonuclease (e.g., Cas9 protein) also encodes one or more NLSs (e.g., 2 or more, 3 or more, 4 or more, or 5 or more NLSs). In some embodiments, a PTD is covalently linked to the construct. Examples of PTDs include but are not limited to a minimal undecapeptide protein transduction domain (corresponding to residues 47-57 of HIV-1 TAT comprising YGRKKRRQRRR (SEQ ID NO:288); a polyarginine sequence comprising a number of arginines sufficient to direct entry into a cell (e.g., 3, 4, 5, 6, 7, 8, 9, 10, or $10^{-50}$ arginines); a VP22 domain (Zender et al. (2002) *Cancer Gene Ther.* 9(6): 489-496); a *Drosophila* Antennapedia protein transduction domain (Noguchi et al. (2003) *Diabetes* 52(7): 1732-1737); a truncated human calcitonin peptide (Trehin et al. (2004) *Pharm. Res.* 21:1248-1256); polylysine (Wender et al. (2000) *Proc. Nal. Acad. Sci. USA*, 97:13003-13008); RRQRRTSKLMKR (SEQ ID NO:289); Transportan GWTLNSAGYLLGKINLKALAALAKKIL (SEQ ID NO:290); KALAWEAKLAKALAKA-LAKHLAKALAKALKCEA (SEQ ID N0:291); and RQIKIWFQNRRMKWKK (SEQ ID NO:292). Exemplary PTDs include but are not limited to, YGRKKRRQRRR (SEQ ID NO:293), RKKRRQRRR (SEQ ID NO:294); an arginine homopolymer of from 3 arginine residues to 50 arginine residues. Exemplary PTD domain amino acid sequences include, but are not limited to, any of the following: YGRKKRRQRRR (SEQ ID NO:295); RKKRRQRR (SEQ ID NO:296); YARAAARQARA (SEQ ID NO:297); THRLPRRRRRR (SEQ ID NO:298); and GGRRARRRRRR (SEQ ID NO:299). In some embodiments, the PTD is an activatable CPP (ACPP) (Aguilera et al. (2009) *Integr Biol* (*Camb*) 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

A class 2 CRISPR/Cas endonuclease (e.g., Cas9 protein) can have multiple (1 or more, 2 or more, 3 or more, etc.) fusion partners in any combination of the above. As an illustrative example, a class 2 CRISPR/Cas endonuclease (e.g., Cas9 protein) can have a fusion partner that provides for tagging (e.g., GFP), and can also have a subcellular localization sequence (e.g., one or more NLSs). In some cases, such a fusion protein might also have a tag for ease of tracking and/or purification (e.g., a histidine tag, e.g., a 6×His tag; a hemagglutinin (HA) tag; a FLAG tag; a Myc tag; and the like). As another illustrative example, class 2 CRISPR/Cas endonuclease (e.g., Cas9 protein) can have one or more NLSs (e.g., two or more, three or more, four or more, five or more, 1, 2, 3, 4, or 5 NLSs). In some cases a fusion partner (or multiple fusion partners, e.g., 1, 2, 3, 4, or 5 NLSs) (e.g., an NLS, a tag, a fusion partner providing an activity, etc.) is located at or near the C-terminus of the class 2 CRISPR/Cas endonuclease (e.g., Cas9 protein). In some cases a fusion partner (or multiple fusion partners, e.g., 1, 2, 3, 4, or 5 NLSs) (e.g., an NLS, a tag, a fusion partner providing an activity, etc.) is located at the N-terminus of the class 2 CRISPR/Cas endonuclease (e.g., Cas9 protein). In some cases the class 2 CRISPR/Cas endonuclease (e.g., Cas9 protein) has a fusion partner (or multiple fusion partners, e.g., 1, 2, 3, 4, or 5 NLSs) (e.g., an NLS, a tag, a fusion partner providing an activity, etc.) at both the N-terminus and C-terminus.

Guide RNAs for Modification of Dystrophin.

In some embodiments a subject CRISPR/Cas guide RNA (e.g., a Cas9 guide RNA) targets a target sequence depicted in Table 4 (also provided in FIG. 23 of PCT/US2017/017255) (e.g., also see Table 3 of PCT/US2017/017255). In some embodiments, a subject CRISPR/Cas guide RNA (e.g., a Cas9 guide RNA) targets a target sequence depicted in Table 5 (also provided in FIG. 24 in PCT/US2017/017255).

Table 5 provides examples of (i) target sequences (non-complementary strand) of target DNA, and (ii) guide sequences of CRISPR/Cas guide RNAs (e.g., for CRISPR/Cas proteins such as S. pyogenes Cas9 that have a PAM requirement of NGG in the non-complementary strand), where the first targeted sequence is within intron 44 of the human dystrophin gene and the second targeted sequence is within intron 55 of the human dystrophin gene. A guide sequence that is targeted to a target sequence within intron 44 of the human dystrophin gene is referred to as a "44" series guide sequence; and a guide sequence that is targeted to a target sequence within intron 55 of the human dystrophin gene is referred to as a "55" series guide sequence.

For example, in some cases, the non-complementary strand of target sequence that is targeted by a first CRISPR/Cas guide RNA (e.g., a Cas9 guide RNA) includes a sequence selected from SEQ ID NOs: 1140-1144 (PCT/US2017/017255 numbering in Table 5) (which sequences are 20 nucleotides long and are within intron 44 of the human dystrophin gene). In some cases, the non-complementary strand of target sequence that is targeted by a first CRISPR/Cas guide RNA (e.g., a Cas9 guide RNA) includes a sequence selected from SEQ ID NOs: 1145-1149 (PCT/US2017/017255 numbering in Table 4, supra.) (which sequences are 17 nucleotides long and are within intron 44 of the human dystrophin gene). In some cases, a first CRISPR/Cas guide RNA (e.g., a Cas9 guide RNA) includes a guide sequence that includes a sequence selected from SEQ ID NOs: 1150-1154 (PCT/US2017/017255 numbering in Table 4, supra.) (which sequences are 20 nucleotides long and hybridize to a target sequence within intron 44 of the human dystrophin gene). In some cases, a first CRISPR/Cas guide RNA (e.g., a Cas9 guide RNA) includes a guide sequence that includes a sequence selected from SEQ ID NOs: 1155-1159 (PCT/US2017/017255 numbering in Table 4, supra.) (which sequences are 17 nucleotides long and hybridize to a target sequence within intron 44 of the human dystrophin gene). In some cases, the non-complementary strand of target sequence that is targeted by a first CRISPR/Cas guide RNA (e.g., a Cas9 guide RNA) includes a sequence selected from SEQ ID NOs: 1136-1139 (PCT/US2017/017255 numbering in Table 5, supra.) and SEQ ID NOs: 1180-1222 (PCT/US2017/017255 numbering in Table 5, supra.) (which sequences are within intron 44 of the human dystrophin gene). In some cases, a first CRISPR/Cas guide RNA (e.g., a Cas9 guide RNA) includes a guide sequence that includes a sequence selected from SEQ ID NOs: 1223-1269 (PCT/US2017/017255 numbering in Table 5, supra.) (which sequences hybridize to a target sequence within intron 44 of the human dystrophin gene).

In some embodiments, the non-complementary strand of target sequence that is targeted by a second CRISPR/Cas guide RNA (e.g., a Cas9 guide RNA) includes a sequence selected from SEQ ID NOs: 1160-1164 (PCT/US2017/017255 numbering in Table 4, supra.) (which sequences are 20 nucleotides long and are within intron 55 of the human dystrophin gene). In some cases, the non-complementary strand of target sequence that is targeted by a second CRISPR/Cas guide RNA (e.g., a Cas9 guide RNA) includes a sequence selected from SEQ ID NOs: 1165-1169 (PCT/US2017/017255 numbering in Table 4, supra.) (which sequences are 17 nucleotides long and are within intron 55 of the human dystrophin gene). In some cases, a second CRISPR/Cas guide RNA (e.g., a Cas9 guide RNA) includes a guide sequence that includes a sequence selected from SEQ ID NOs: 1170-1174 (PCT/US2017/017255 numbering in Table 4, supra.) (which sequences are 20 nucleotides long and hybridize to a target sequence within intron 55 of the human dystrophin gene). In some cases, a second CRISPR/Cas guide RNA (e.g., a Cas9 guide RNA) includes a guide sequence that includes a sequence selected from SEQ ID NOs: 1175-1179 (PCT/US2017/017255 numbering in Table 5, supra.) (which sequences are 17 nucleotides long and hybridize to a target sequence within intron 55 of the human dystrophin gene). In some cases, the non-complementary strand of target sequence that is targeted by a second CRISPR/Cas guide RNA (e.g., a Cas9 guide RNA) includes a sequence selected from SEQ ID NOs: 1270-1317 (PCT/US2017/017255 numbering in Table 5, supra.) (which sequences are within intron 55 of the human dystrophin gene). In some cases, a second CRISPR/Cas guide RNA (e.g., a Cas9 guide RNA) includes a guide sequence that includes a sequence selected from SEQ ID NOs: 1318-1365 (PCT/US2017/017255 numbering in Table 5, supra.) (which sequences hybridize to a target sequence within intron 55 of the human dystrophin gene).

In some cases, the non-complementary strand of target sequence that is targeted by a first CRISPR/Cas guide RNA (e.g., a Cas9 guide RNA) includes a sequence selected from SEQ ID NOs: 1140-1144 (PCT/US2017/017255 numbering in Table 5, supra.) (which sequences are 20 nucleotides long and are within intron 44 of the human dystrophin gene), and the non-complementary strand of target sequence that is targeted by a second CRISPR/Cas guide RNA (e.g., a Cas9 guide RNA) includes a sequence selected from SEQ ID NOs: 1160-1164 (PCT/US2017/017255 numbering in Table 4, supra.) (which sequences are 20 nucleotides long and are within intron 55 of the human dystrophin gene).

In some cases, the non-complementary strand of target sequence that is targeted by a first CRISPR/Cas guide RNA (e.g., a Cas9 guide RNA) includes a sequence selected from SEQ ID NOs: 1136-1139 and SEQ ID NOs: 1180-1222 (PCT/US2017/017255 numbering in Tables 4 and/or Table 5, supra.) (which sequences are within intron 44 of the human dystrophin gene), and the non-complementary strand of target sequence that is targeted by a second CRISPR/Cas guide RNA (e.g., a Cas9 guide RNA) includes a sequence selected from SEQ ID NOs: 1270-1317 (PCT/US2017/017255 numbering in Tables 4 and/or Table 5, supra.) (which sequences are 20 nucleotides long and are within intron 55 of the human dystrophin gene).

In some cases, the non-complementary strand of target sequence that is targeted by a first CRISPR/Cas guide RNA (e.g., a Cas9 guide RNA) includes a sequence selected from SEQ ID NOs: 1145-1149 (PCT/US2017/017255 numbering in Tables 4 and/or Table 5, supra.) (which sequences are 17 nucleotides long and are within intron 44 of the human dystrophin gene), and the non-complementary strand of target sequence that is targeted by a second CRISPR/Cas guide RNA (e.g., a Cas9 guide RNA) includes a sequence selected from SEQ ID NOs: 1165-1169 (PCT/US2017/017255 numbering in Tables 4 and/or Table 5, supra.) (which sequences are 17 nucleotides long and are within intron 55 of the human dystrophin gene).

In some cases, a first CRISPR/Cas guide RNA (e.g., a Cas9 guide RNA) includes a guide sequence that includes a sequence selected from SEQ ID NOs: 1150-1154 (PCT/US2017/017255 numbering in Tables 4 and/or Table 5, supra.) (which sequences are 20 nucleotides long and hybridize to a target sequence within intron 44 of the human dystrophin gene), and a second CRISPR/Cas guide RNA (e.g., a Cas9 guide RNA) includes a guide sequence that includes a sequence selected from SEQ ID NOs: 1170-1174 (PCT/US2017/017255 numbering in Tables 4 and/or Table 5, supra.) (which sequences are 20 nucleotides long and hybridize to a target sequence within intron 55 of the human dystrophin gene).

In some cases, a first CRISPR/Cas guide RNA (e.g., a Cas9 guide RNA) includes a guide sequence that includes a sequence selected from SEQ ID NOs: 1150-1154 (PCT/US2017/017255 numbering in Tables 4 and/or Table 5, supra.) (which sequences are 20 nucleotides long and hybridize to a target sequence within intron 44 of the human dystrophin gene), and a second CRISPR/Cas guide RNA (e.g., a Cas9 guide RNA) includes a guide sequence that includes a sequence selected from SEQ ID NOs: 1170-1174 (PCT/US2017/017255 numbering in Tables 4 and/or Table 5, supra.) (which sequences are 20 nucleotides long and hybridize to a target sequence within intron 55 of the human dystrophin gene).

In some cases, a first CRISPR/Cas guide RNA (e.g., a Cas9 guide RNA) includes a guide sequence that includes a sequence selected from SEQ ID NOs: 1223-1269 (PCT/US2017/017255 numbering in Tables 4 and/or Table 5, supra.) (which sequences hybridize to a target sequence within intron 44 of the human dystrophin gene), and a second CRISPR/Cas guide RNA (e.g., a Cas9 guide RNA) includes a guide sequence that includes a sequence selected from SEQ ID NOs: 1318-1365 (PCT/US2017/017255 numbering in Tables 4 and/or Table 5, supra.) (which sequences hybridize to a target sequence within intron 55 of the human dystrophin gene).

In some cases, the duplex-forming portion of a guide RNA suitable for use herein comprises the sequence: gtttagagctaGAAAtagcaagttaaaataaggctagtccgttatca acttgaaaaagtggcaccgagtcggtgcTTTTTT (SEQ ID NO:16 (SEQ ID NO:1366 in PCT/US2017/017255)), or guuuuagagcuaGAAAuagcaaguuaaaauaaggcuaguccguua ucaacuugaaaaaguggcaccgagucggugcUU UUUU (SEQ ID NO:300, SEQ ID NO:1367 in PCT/US2017/017255)).

In some cases, a first CRISPR/Cas guide RNA (e.g., a Cas9 guide RNA) includes a guide sequence comprising the nucleotide sequence set forth in SEQ ID NO:1223; and a second CRISPR/Cas guide RNA (e.g., a Cas9 guide RNA) includes a guide sequence comprising the nucleotide sequence set forth in SEQ ID NO:1320. In some cases, the duplex-forming portion of a guide RNA suitable for use herein comprises the sequence: gttttagagctaGAAAtagcaagttaaaataaggctagtccgttatcaacttgaaaaagtggcaccgagtcggtgcTTTTTT (SEQ ID NO:16), or guuuuagagcuaGAAAuagcaaguuaaaauaaggcuaguccguua ucaacuugaaaaaguggcaccgagucggugcUU UUUU (SEQ ID NO:300).

In some cases, a first CRISPR/Cas guide RNA (e.g., a Cas9 guide RNA) includes a guide sequence comprising the nucleotide sequence set forth in SEQ ID NO:1224 (PCT/US2017/017255 numbering in Tables 4 and/or Table 5, supra.); and a second CRISPR/Cas guide RNA (e.g., a Cas9 guide RNA) includes a guide sequence comprising the nucleotide sequence set forth in SEQ ID N0:1320 (PCT/US2017/017255 numbering in Tables 4 and/or Table 5, supra.). In some cases, the duplex-forming portion of a guide RNA suitable for use herein comprises the sequence: gttttagagctaGAAAtagcaagtta aaataaggctagtccgttatcaacttgaaaaagtggcaccgagtcggtgcTTTTTT (SEQ ID NO: 16), or guuuuagagcuaGAAAuagcaaguuaaaauaaggcuaguccguuaucaacuugaaaaaguggcaccgagucggugc UU UUUU (SEQ ID NO:300).

In some cases, a first CRISPR/Cas guide RNA (e.g., a Cas9 guide RNA) includes a guide sequence comprising the nucleotide sequence set forth in SEQ ID NO:1225 (PCT/US2017/017255 numbering in Tables 4 and/or Table 5, supra.); and a second CRISPR/Cas guide RNA (e.g., a Cas9 guide RNA) includes a guide sequence comprising the nucleotide sequence set forth in SEQ ID NO:1320 (PCT/US2017/017255 numbering in Tables 4 and/or Table 5, supra.). In some cases, the duplex-forming portion of a guide RNA suitable for use herein comprises the sequence: gttttagagctaGAAAtagcaagttaaaata aggctagtccgttatcaacttgaaaaagtggcaccgagtcggtgcTTTTTT (SEQ ID NO: 16), or guuuuagagcuaGAAAuagcaaguuaaaauaaggcuaguccguuaucaacuugaaaaaguggcaccgagucggugc UU UUUU (SEQ ID NO:300).

In some cases, a first CRISPR/Cas guide RNA (e.g., a Cas9 guide RNA) includes a guide sequence comprising the nucleotide sequence set forth in SEQ ID NO:1153 (PCT/US2017/017255 numbering in Tables 4 and/or Table 5, supra.); and a second CRISPR/Cas guide RNA (e.g., a Cas9 guide RNA) includes a guide sequence comprising the nucleotide sequence set forth in SEQ ID NO:1172 (PCT/US2017/017255 numbering in Tables 4 and/or Table 5, supra.). In some cases, the duplex-forming portion of a guide RNA suitable for use herein comprises the sequence: gtttagagctaGAAAtagcaagttaaaataagg ctagtccgttatcaacttgaaaaagtggcaccgagtcggtgcTTTTTT (SEQ ID NO: 16), or guuuuagagcuaGAAAuagcaaguuaaaauaaggcuaguccguuau-caacuugaaaaaguggcaccgagucggugc UU UUUU (SEQ ID NO:300).

In some cases, a first CRISPR/Cas guide RNA (e.g., a Cas9 guide RNA) includes a guide sequence comprising the nucleotide sequence set forth in SEQ ID NO:1153 (PCT/US2017/017255 numbering in Tables 4 and/or Table 5, supra.); and a second CRISPR/Cas guide RNA (e.g., a Cas9 guide RNA) includes a guide sequence comprising the nucleotide sequence set forth in SEQ ID NO:1171 (PCT/US2017/017255 numbering in Tables 4 and/or Table 5, supra.). In some cases, the duplex-forming portion of a guide RNA suitable for use herein comprises the sequence: gttt-tagagctaGAAAtagcaagttaaaat aaggctagtccgttatcaactt-gaaaaagtggcaccgagtcggtgcTTTTTT (SEQ ID NO: 16), or guuuuagagcuaGAAAuagcaaguuaaaauaaggcuaguccguuau-caacuugaaaaaguggcaccgagucggugc UU UUUU (SEQ ID NO:300).

In some cases, a first CRISPR/Cas guide RNA (e.g., a Cas9 guide RNA) includes a guide sequence comprising the nucleotide sequence set forth in SEQ ID NO:1152 (PCT/US2017/017255 numbering in Tables 4 and/or Table 5, supra.); and a second CRISPR/Cas guide RNA (e.g., a Cas9 guide RNA) includes a guide sequence comprising the nucleotide sequence set forth in SEQ ID NO:1172 (PCT/US2017/017255 numbering in Tables 4 and/or Table 5, supra.). In some cases, the duplex-forming portion of a guide RNA suitable for use herein comprises the sequence: gttt-tagagctaGAAAtagcaagttaaaataag gctagtccgttatcaactt-gaaaaagtggcaccgagtcggtgcTTTTTT (SEQ ID NO: 16), or guuuuagagcuaGAAAuagcaaguuaaaauaag gcuaguccguuau-caacuugaa aaaguggcaccg agucggugcUU UUUU (SEQ ID NO:300).

In some cases, a first CRISPR/Cas guide RNA (e.g., a Cas9 guide RNA) includes a guide sequence comprising the nucleotide sequence set forth in SEQ ID NO:1152 (PCT/US2017/017255 numbering in Tables 4 and/or Table 5, supra.); and a second CRISPR/Cas guide RNA (e.g., a Cas9 guide RNA) includes a guide sequence comprising the nucleotide sequence set forth in SEQ ID NO:1171 (PCT/US2017/017255 numbering in Tables 4 and/or Table 5, supra.). In some cases, the duplex-forming portion of a guide RNA suitable for use herein comprises the sequence: gttt-tagagctaGAAAtagcaagttaaaataag gctagtccgttatcaactt-gaaaaagtggcaccgagtcggtgcTTTTTT (SEQ ID NO: 16), or guuuuagagcuaGAAAuagcaaguuaaaauaa ggcuaguccguuau-caac uugaaaaaguggc accgagucggugcUU UUUU (SEQ ID NO:300).

In some cases, a first CRISPR/Cas guide RNA (e.g., a Cas9 guide RNA) includes a guide sequence comprising the nucleotide sequence set forth in SEQ ID NO:1150 (PCT/US2017/017255 numbering in Tables 4 and/or Table 5, supra.); and a second CRISPR/Cas guide RNA (e.g., a Cas9 guide RNA) includes a guide sequence comprising the nucleotide sequence set forth in SEQ ID NO:1172 (PCT/US2017/017255 numbering in Tables 4 and/or Table 5, supra.). In some cases, the duplex-forming portion of a guide RNA suitable for use herein comprises the sequence: gttt-tagagctaGAAAtagcaagttaaaataag gctagtccgttatcaactt-gaaaaagtggcaccgagtcggtgcTTTTTT (SEQ ID NO: 16), or guuuuagagcuaGAAAuagcaaguuaaaauaaggcuaguccguuau-caacuugaaaaaguggcaccgagucggugc UU UUUU (SEQ ID NO:300).

In some cases, a first CRISPR/Cas guide RNA (e.g., a Cas9 guide RNA) includes a guide sequence comprising the nucleotide sequence set forth in SEQ ID NO:1150 (PCT/US2017/017255 numbering in Tables 4 and/or Table 5, supra.); and a second CRISPR/Cas guide RNA (e.g., a Cas9 guide RNA) includes a guide sequence comprising the nucleotide sequence set forth in SEQ ID NO:1171 (PCT/US2017/017255 numbering in Tables 4 and/or Table 5, supra.). In some cases, the duplex-forming portion of a guide RNA suitable for use herein comprises the sequence: gttt-tagagctaGAAAtagcaagttaaaata aggctagtccgtta tcaactt-gaaaaagtggcaccgagtcggtgcTTTTTT (SEQ ID NO: 16), or guuuuagagcuaGAAAuagcaaguuaaaauaaggcuaguccguuau-caacuugaaaaaguggcaccgagucggugc UU UUUU (SEQ ID NO:300).

In some cases, a first CRISPR/Cas guide RNA (e.g., a Cas9 guide RNA) includes a guide sequence comprising the nucleotide sequence set forth in SEQ ID NO:1150 (PCT/US2017/017255 numbering in Tables 4 and/or Table 5, supra.); and a second CRISPR/Cas guide RNA (e.g., a Cas9 guide RNA) includes a guide sequence comprising the nucleotide sequence set forth in SEQ ID NO:1174 (PCT/US2017/017255 numbering in Tables 4 and/or Table 5, supra.). In some cases, the duplex-forming portion of a guide RNA suitable for use herein comprises the sequence: gttt-tagagctaGAAAtagcaagttaaaata aggctagtccgttatcaactt-gaaaaagtggcaccgagtcggtgcTTTTTT (SEQ ID NO: 16), or guuuuagagcuaGAAAuagcaaguuaaaauaaggcuaguccguuau-caacuugaaaaaguggcaccgagucggugc UU UUUU (SEQ ID NO:300).

In some cases, a first CRISPR/Cas guide RNA (e.g., a Cas9 guide RNA) includes a guide sequence comprising the nucleotide sequence set forth in SEQ ID NO:1152 (PCT/US2017/017255 numbering in Tables 4 and/or Table 5, supra.); and a second CRISPR/Cas guide RNA (e.g., a Cas9 guide RNA) includes a guide sequence comprising the nucleotide sequence set forth in SEQ ID NO:1174 (PCT/US2017/017255 numbering in Tables 4 and/or Table 5, supra.). In some cases, the duplex-forming portion of a guide RNA suitable for use herein comprises the sequence: gtt-tagagctaGAAAtagcaagtta aaataaggctag tccgttatcaactt-gaaaaagtggcaccgagtcggtgcTTTTTT (SEQ ID NO: 16), or guuuuagagcuaGAAAuagcaaguuaaaauaaggcuaguccguuau-caacuugaaaaaguggcaccgagucggugc UU UUUU (SEQ ID NO:300).

In some cases, a first CRISPR/Cas guide RNA (e.g., a Cas9 guide RNA) includes a guide sequence that includes a sequence selected from SEQ ID NOs: 1155-1159 (PCT/US2017/017255 numbering in Tables 4 and/or Table 5, supra.) (which sequences are 17 nucleotides long and hybridize to a target sequence within intron 44 of the human dystrophin gene), and a second CRISPR/Cas guide RNA (e.g., a Cas9 guide RNA) includes a guide sequence that includes a sequence selected from SEQ ID NOs: 1175-1179 (PCT/US2017/017255 numbering in Tables 4 and/or Table 5, supra.) (which sequences are 17 nucleotides long and hybridize to a target sequence within intron 55 of the human dystrophin gene).

In some cases, the non-complementary strand of target sequence that is targeted by a first CRISPR/Cas guide RNA (e.g., a Cas9 guide RNA) includes the sequence set forth in SEQ ID NO:1143 (PCT/US2017/017255 numbering in Tables 4 and/or Table 5, supra.) (within intron 44), and the non-complementary strand of target sequence that is targeted by a second CRISPR/Cas guide RNA (e.g., a Cas9 guide RNA) includes the sequence set forth in SEQ ID NO:1162 (PCT/US2017/017255 numbering in Tables 4 and/or Table 5, supra.) (within intron 55). In some cases, the non-complementary strand of target sequence that is targeted by a first CRISPR/Cas guide RNA (e.g., a Cas9 guide RNA) includes the sequence set forth in SEQ ID NO:1148

(PCT/US2017/017255 numbering in Tables 4 and/or Table 5, supra.) (within intron 44), and the non-complementary strand of target sequence that is targeted by a second CRISPR/Cas guide RNA (e.g., a Cas9 guide RNA) includes the sequence set forth in SEQ ID NO:1167 (PCT/US2017/017255 numbering in Tables 4 and/or Table 5, supra.) (within intron 55).

In some cases, a first CRISPR/Cas guide RNA (e.g., a Cas9 guide RNA) includes a guide sequence that includes the sequence set forth in SEQ ID NO:1153 (PCT/US2017/017255 numbering in Tables 4 and/or Table 5, supra.) (targets intron 44), and a second CRISPR/Cas guide RNA (e.g., a Cas9 guide RNA) includes a guide sequence that includes the sequence set forth in SEQ ID NO:1172 (PCT/US2017/017255 numbering in Tables 4 and/or Table 5, supra.) (targets intron 55). In some cases, a first CRISPR/Cas guide RNA (e.g., a Cas9 guide RNA) includes a guide sequence that includes the sequence set forth in SEQ ID NO:1158 (PCT/US2017/017255 numbering in Tables 4 and/or Table 5, supra.) (targets intron 44), and a second CRISPR/Cas guide RNA (e.g., a Cas9 guide RNA) includes a guide sequence that includes the sequence set forth in SEQ ID NO:1177 (PCT/US2017/017255 numbering in Tables 4 and/or Table 5, supra.) (targets intron 55).

Nucleic Acids to be Complexed with PRX Carriers

As noted above, the polyrotaxane carriers described herein are effective to delivery large nucleic acids in vivo to cells. Thus, in various embodiments, the nucleic acids carriers by the multi-arm PRX include nucleic acids (RNA or DNA) encoding one or more of: (i) a class 2 CRISPR/Cas endonuclease (e.g., a Cas9 protein), (ii) a first CRISPR/Cas guide RNA (that hybridizes to intron 44, e.g., as described elsewhere herein), and (iii) a second CRISPR/Cas guide RNA (e.g., that hybridizes to intron 55, e.g., as described elsewhere herein). In some cases, one nucleic acid (e.g., an expression vector) encodes the first and second CRISPR/Cas guide RNAs. In some cases, the same nucleic acid (e.g., expression vector) also encodes the class 2 CRISPR/Cas endonuclease.

Many vectors, e.g. plasmids, cosmids, minicircles, are available and can be delivered using the carriers described herein. The vectors comprising the nucleic acid(s) may be maintained episomally, e.g. as plasmids, minicircle DNAs, or they may be integrated into the target cell genome, through homologous recombination or random integration.

In various embodiments the polyrotaxane carriers described herein are effective to deliver vectors directly to the subject cells. In other words, cells can be contacted with the carriers described herein, e.g., via local injection of the carrier, by nasal administration, by systemic administration, and the like.

In certain embodiments the vectors (e.g., plasmids) complexed with the carriers can include suitable promoters for driving expression, that is, transcriptional activation, of the nucleic acid of interest. In other words, the nucleic acid of interest (e.g., a heterologous nucleic acid, a nucleotide sequence encoding the first CRISPR/Cas guide RNA, a nucleotide sequence encoding the second CRISPR/Cas guide RNA, a nucleotide sequence encoding a class 2 CRISPR/Cas endonuclease, etc.) can be operably linked to a promoter (e.g., a promoter operable in the target cell). This may include ubiquitously acting promoters, for example, the CMV-R-actin promoter, the EF-1 alpha promoter, and the like, or inducible promoters, such as promoters that are active in particular cell populations or that respond to the presence of drugs such as tetracycline. By transcriptional activation, it is intended that transcription will be increased above basal levels in the target cell by at least about 10-fold, by at least about 100-fold, more usually by at least about 1000-fold. Expression vectors may include nucleic acid sequences that encode for selectable markers in the target cells, so as to identify cells that have taken up the introduced nucleic acid.

As noted above, a promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Tissue-specific promoters are known in the art. Non-limiting examples of tissue-specific promoters are muscle cell-specific promoters. Suitable muscle-specific promoters include, e.g., a desmin promoter; an α-myosin heavy chain promoter; a myosin light chain-2 promoter; a cardiac troponin C promoter; a muscle creatine kinase promoter; an a-actinin promoter; a cardiac troponin I promoter; and the like (see, e.g., Pacak et al. (2008) Genet. Vaccines Ther. 6:13).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Illustrative promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (see, e.g., Miyagishi et al. (2002), Nat. Biotechnol. 20: 497-500), an enhanced U6 promoter (e.g., Xia et al., (2003) Nucleic Acids Res. 31(17)), a human HI promoter (HI), and the like.

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; RNA polymerase, e.g., T7 RNA polymerase; an estrogen receptor; an estrogen receptor fusion; etc.

As noted above, in certain embodiments the nucleic acid (e.g., a nucleic acid encoding a class 2 CRISPR/Cas endonuclease, and/or a CRISPR/Cas guide RNA may be introduced into cells by the multi-arm polyrotaxane carriers described herein as RNA.

Kits

In certain embodiments kits are provided for practice of the methods described herein. In certain embodiments, the kits comprise a container containing a polyrotaxane carrier as described herein. In certain embodiments, the kit further comprises a container containing a nucleic acid that is to be delivered to said mammal. In certain embodiments, the nucleic acid is in a container separate from the container containing said carrier. In certain embodiments, the nucleic acid comprises a nucleic acid as described and/or claimed herein. In certain embodiments, the nucleic acid comprises a plasmid encoding a CRISPR/Cas9 and one or more guide RNAs as described herein. In certain embodiments, the nucleic acid is provided as a complex with the carrier, e.g., as described and/or claimed herein.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are offered to illustrate, but not to limit the claimed invention.

Example 1

Development of Multi-Arm Polyrotaxane (PRX) Nucleic Acid Delivery Vehicles

Methods and Reagents During the Nano DMD Study

Mice

All animal work was conducted under protocols approved by the UCLA Animal Research Committee in the Office of Animal Research Oversight. hDMD (Tg(DMD)72Thoen/J, 018900), C57BL/10 mdx (001801), and mdxD2 (D1.B10-Dmdmdx/J, 013141) mice were obtained from Jackson Laboratories. hDMD del45 mdx and hDMD del45 mdxD2 mice were generated as described (Young et al. 2017).

Cell Culture

Primary hDMD or hDMD del45 mdx myoblasts were obtained from 11-13 day old pups by dissociation of muscle tissue using dispase and collagenase II. Fibroblasts were removed by repeated pre-plating. Myoblasts were maintained in F-10 HAM with 20% FBS, 5 ng/ml bFGF and 1% penicillin/streptomycin (P/S). Myoblasts were differentiated to form myotubes (at >85% confluence) in DMEM with 2% horse serum, 1% insulin-transferrin-selenium (ITS) and 1% P/S.

CRISPR Plasmid gRNAs for the exon 45-55 deletion (44C4, 55C3) from Young et al. 2016 were cloned into px333 (Addgene 64073, Andrea Ventura) in tandem using BbsI and BsaI.

PRX Synthesis

Synthesis of G1 PRX Prototype.

Briefly, the procedures could be divided into three steps, namely, (i) Preparation of an inclusion complex between PEG and α-CDs to form polyseudorotaxane. (ii) Synthesis of polyrotaxane by ending the α-CD complexed PEG chain with big blocking group benzyloxycarbonyl tyrosine; (iii) Modification of α-CDs in the polyrotaxane with positively charged amine groups by reaction with N,N-dimethylethylenediamine (DMAE). Briefly, PEG-diamine (Mw 3000, Polysciences) powder (160 mg) was added to a saturated solution of a-CDs (5 g in 35 ml $H_2O$). After stirring at rt. for 24 h, then white precipitate was collected by centrifugation and dried in vacuum at 60° C. to obtain an inclusion complex. The product was confirmed by $^1$H-NMR in DMSO-d6. The number of a-CDs per PEG chain is calculated by comparing the value for the area of the resonance peak due to C(1)H of a-CD with that of the resonance peak due to the methylene protons of PEG. Next, the polyseudorotaxane inclusion complex (1.9 g) was added in the mixture of Z-L-Tyr (0.82 g), BOP reagent (1.15 g), HOBt (0.35 g) and DIEA (0.45 ml) which dissolved in 10 ml DMF. The mixture suspension was stirred at rt. for 24 h. Then, the Pour the suspension was precipitated into 100 ml diethyl ether and the precipitate was collected by centrifugation. The precipitate was further washed by stirring three times in succession in abundant acetone, methanol and water. The precipitate was dried in vacuum at 60° C. to obtain a Z-L-Tyr-capped polyrotaxane (PRX). The product was confirmed by $^1$H-NMR in DMSO-d6. The number of a-CDs per PEG chain is calculated by comparing the value for the area of the resonance peak due to C(1)H of a-CD with that of the resonance peak due to the methylene protons of PEG. PRX (0.8 g) was dissolved in 15 ml dry DMSO and CDI (2.3 g) was add to the solution later. The mixture was stirred for 3 h under nitrogen atmosphere, and then DMEDA (5.6 ml) was slowly added to the solution. After stirring overnight at rt., the reaction mixture was precipitated into 500 ml diethyl ether and the precipitate was collected by centrifugation. The precipitate was further washed by stirring in succession in abundant ether and acetone. In order to completely remove the unreacted CDI and DMEDA, the product was dialyzed against water (2-3 d) using dialysis membrane (Mw cutoff. 3,400). Finally the solution was lyophilized to obtain solid DMAE modified PRX (G1-PRX). The product was confirmed by $^1$H-NMR in DMSO-d6. The numbers of a-CDs and DMAE groups per PEG chain are calculated by comparing, respectively, values for the areas of the resonance peaks due to C(1)H of α-CD, and to $CH_3$ of DMAE, with the area of the resonance peak due to the methylene protons of PEG.

Synthesis of G2 PRX Prototype.

Briefly, the procedures could be divided into four steps, namely, (i) Preparation of a diamino-PEG with disulfide linkages at both terminals; (ii) Preparation of an inclusion complex between SS-PEG-diamine and α-CDs to form SS-polyseudorotaxane. (iii) Synthesis of polyrotaxane by ending the α-CD complexed PEG chain with big blocking group benzyloxycarbonyl tyrosine; (iv) Modification of α-CDs in the polyrotaxane with positively charged amine groups by reaction with N,N-dimethylethylenediamine (DMAE). PEG di(OPSS) (Mw 3000, Polysciences) powder (400 mg) was dissolved in 20 mL 0.1 M PBS (pH=8.0) and the solution was degassed by bubbling nitrogen gas for 15 min. 2-aminoethanethiol (0.54 g was added to the solution and stirred for 10 min under nitrogen atmosphere. The reaction mixture was dialyzed (2-3 d) against 3% NaCl aq and then water, sequentially, using Spectra/Por dialysis membrane (Mw cutoff. 1,000). The solution was finally lyophilized to obtain PEG-SS-diamine as a white powder. The product was confirmed by $^1$H-NMR in DMSO-d6. Then PEG-SS-diamine powder (50 mg) was added to a saturated solution of a-CDs (1.6 g in 12 ml $H_2O$). After stirring at rt.

for 24 h, then white precipitate was collected by centrifugation and dried in vacuum at 60° C. to obtain an inclusion complex (SS-polyseudorotaxane). The product was confirmed by $^1$H-NMR in DMSO-d6. The number of a-CDs per PEG chain is calculated by comparing the value for the area of the resonance peak due to C(1)H of a-CD with that of the resonance peak due to the methylene protons of PEG. Next, the SS-polyseudorotaxane inclusion complex (0.36 g) was added in the mixture of Z-L-Tyr (0.64 g), BOP reagent (0.23 g), HOBt (0.07 g) and DIEA (0.09 ml) which dissolved in 2 ml DMF. The mixture suspension was stirred at rt. for 24 h. Then, the Pour the suspension was precipitated into 50 ml diethyl ether and the precipitate was collected by centrifugation. The precipitate was further washed by stirring three times in succession in abundant acetone, methanol and water. The precipitate was dried in vacuum at 60° C. to obtain a Z-L-Tyr-capped SS-polyrotaxane (SS-PRX). The product was confirmed by $^1$H-NMR in DMSO-d6. The number of a-CDs per PEG chain is calculated by comparing the value for the area of the resonance peak due to C(1)H of a-CD with that of the resonance peak due to the methylene protons of PEG. Finally, SS-PRX (0.1 g) was dissolved in 2 ml dry DMSO and CDI (0.25 g) was add to the solution later. The mixture was stirred for 3 h under nitrogen atmosphere, and then DMEDA (0.66 ml) was slowly added to the solution. After stirring overnight at rt., the reaction mixture was precipitated into 500 ml diethyl ether and the precipitate was collected by centrifugation. The precipitate was further washed by stirring in succession in abundant ether and acetone. In order to completely remove the unreacted CDI and DMEDA, the product was dialyzed against water (2-3 d) using dialysis membrane (Mw cutoff: 3,400). Finally, the solution was lyophilized to obtain solid DMAE modified SS-PRX (G2-PRX). The product was confirmed by $^1$H-NMR in DMSO-d6. The numbers of α-CDs and DMAE groups per PEG chain are calculated by comparing, respectively, values for the areas of the resonance peaks due to C(1)H of α-CD, and to CH3 of DMAE, with the area of the resonance peak due to the methylene protons of PEG.

Synthesis of G3 PRX Prototype.

Briefly, the procedures could be divided into four steps, namely, (i) Block two arms of 4-arm-PEG-tetramine by bulk group, e.g. FITC; (ii) Preparation of an inclusion complex between the partly blocked 4-arm-PEG and α-CDs to form 2/4-arm-polyseudorotaxane. (iii) Synthesis of 2/4-arm-polyrotaxane by ending the α-CD complexed PEG chain with big blocking group benzyloxycarbonyl tyrosine; (iv) Modification of α-CDs in the 2/4-arm-polyrotaxane with positively charged amine groups by reaction with N,N-dimethylethylenediamine (DMAE). 4-arm-PEG-tetramine (Mw 10, 000, JenKem Technology USA) powder (100 mg) was dissolved in 2 mL 0.1 M PBS (pH=8.0) and then 7.8 mg FITC in 0.1 mL DMF was added to the solution. The mixture was stirred at rt. for overnight. The reaction mixture was purified by centrifugal filter (cutoff, 3 K). Finally the solution was lyophilized to obtain 4-arm-PEG with two arms blocked by FITC (2/4-arm-PEG-diamine). Then the 2/4-arm-PEG-diamine powder (65 mg) was added to a saturated solution of a-CDs (0.625 g in 4 ml H$_2$O). After stirring at rt. for 24 h, then white precipitate was collected by centrifugation and dried in vacuum at 60° C. to obtain an inclusion complex (2/4-arm-polyseudorotaxane). The product was confirmed by $^1$H-NMR in DMSO-d6. The number of a-CDs per PEG chain is calculated by comparing the value for the area of the resonance peak due to C(1)H of a-CD with that of the resonance peak due to the methylene protons of PEG. Next, the 2/4-arm-polyseudorotaxane inclusion complex (240 mg) was added in the mixture of Z-L-Tyr (0.082 g), BOP reagent (0.115 g), HOBt (0.035 g) and DIEA (0.045 ml) which dissolved in 1 ml DMF. The mixture suspension was stirred at rt. for 24 h. Then, the Pour the suspension was precipitated into 50 ml diethyl ether and the precipitate was collected by centrifugation. The precipitate was further washed by stirring three times in succession in abundant acetone, methanol and water. The precipitate was dried in vacuum at 60° C. to obtain a Z-L-Tyr-capped 2/4-arm-polyrotaxane (2/4-arm-PRX). The product was confirmed by $^1$H-NMR in DMSO-d6. The number of a-CDs per PEG chain is calculated by comparing the value for the area of the resonance peak due to C(1)H of a-CD with that of the resonance peak due to the methylene protons of PEG. 2/4-arm-PRX PRX (0.1 g) was dissolved in 2 ml dry DMSO and CDI (0.364 g) was add to the solution later. The mixture was stirred for 3 h under nitrogen atmosphere, and then DMEDA (1 ml) was slowly added to the solution. After stirring overnight at rt., the reaction mixture was precipitated into 50 ml diethyl ether and the precipitate was collected by centrifugation. The precipitate was further washed by stirring in succession in abundant ether and acetone. In order to completely remove the unreacted CDI and DMEDA, the product was dialyzed against water (2-3 d) using dialysis membrane (Mw cutoff: 3,400). Finally, the solution was lyophilized to obtain solid DMAE modified 2/4-arm-PRX (G3-PRX). The product was confirmed by $^1$H-NMR in DMSO-d6. The numbers of a-CDs and DMAE groups per PEG chain are calculated by comparing, respectively, values for the areas of the resonance peaks due to C(1)H of a-CD, and to CH3 of DMAE, with the area of the resonance peak due to the methylene protons of PEG.

Synthesis of G4 PRX Prototype.

Briefly, the procedures could be divided into five steps, namely, (i) Block two arms of 4-arm-PEG-tetramine by bulk group, e.g. FITC; (ii) Preparation of an inclusion complex between the partly blocked 4-arm-PEG and α-CDs to form 2/4-arm-polyseudorotaxane. (iii) Synthesis of 2/4-arm-polyrotaxane by ending the α-CD complexed PEG chain with big blocking group benzyloxycarbonyl tyrosine; (iv) Modification of α-CDs in the 2/4-arm-polyrotaxane with pyridyl-dithiol groups (v) introduce cleavable cationic charge by reaction with N,N-dimethylethylenediamine (DMAE). Briefly, 4-arm-PEG-tetramine (Mw 10, 000, JenKem Technology USA) powder (100 mg) was dissolved in 2 mL 0.1 M PBS (pH=8.0) and then 7.8 mg FITC in 0.1 mL DMF was added to the solution. The mixture was stirred at rt. for overnight. The reaction mixture was purified by centrifugal filter (cutoff, 3 K). Finally, the solution was lyophilized to obtain 4-arm-PEG with two arms blocked by FITC (2/4-arm-PEG-diamine). Then the 2/4-arm-PEG-diamine powder (65 mg) was added to a saturated solution of a-CDs (0.625 g in 4 ml H2O). After stirring at rt. for 24 h, then white precipitate was collected by centrifugation and dried in vacuum at 60° C. to obtain an inclusion complex (2/4-arm-polyseudorotaxane). The product was confirmed by $^1$H-NMR in DMSO-d6. The number of a-CDs per PEG chain is calculated by comparing the value for the area of the resonance peak due to C(1)H of a-CD with that of the resonance peak due to the methylene protons of PEG. Next, the 2/4-arm-polyseudorotaxane inclusion complex (240 mg) was added in the mixture of Z-L-Tyr (0.082 g), BOP reagent (0.115 g), HOBt (0.035 g) and DIEA (0.045 ml) which dissolved in 1 ml DMF. The mixture suspension was stirred at rt. for 24 h. Then, the Pour the suspension was precipitated into 50 ml diethyl ether and the precipitate was collected by centrifugation. The precipitate was further washed by stirring three times in succession in abundant acetone, methanol and water. The precipitate was dried in vacuum at 60° C. to obtain a Z-L-Tyr-capped 2/4-arm-polyrotaxane (2/4-arm-PRX). The product was confirmed by $^1$H-NMR in DMSO-d6. The number of a-CDs per PEG chain is calculated by comparing the value for the area of the resonance peak due to C(1)H of a-CD with that of the resonance peak due to the methylene protons of PEG. 2/4-arm-PRX PRX (0.1 g) was dissolved in 2 ml dry DMSO and CDI (0.364 g) was add to the solution later. The mixture was stirred for 3 h under nitrogen atmosphere, and then pyridyldithiol-cysteamine (0.1 g) was slowly added to the solution. After stirring overnight at rt., the reaction mixture was precipitated into 50 ml diethyl ether and the precipitate was collected by centrifugation. The precipitate was further washed by stirring in succession in abundant ether and acetone. In order to completely remove the unreacted CDI and pyridyldithiol-cysteamine, the product was repeated concentrated by centrifugal filter unit (Mw cutoff. 3,000). The solution was lyophilized and the product was confirmed by $^1$H-NMR in DMSO-d6.

PRX Delivery in Muscle Cells In Vitro

Myoblasts were seeded at $1.2 \times 10^5$ cells/cm$^2$ for growth conditions or $1.7 \times 10^5$ cells/cm$^2$ for differentiation where the media was changed to differentiation media the following day. PRX complexed with pmax GFP (Lonza), an mCherry/luciferase plasmid or px333 44C4+55C3 was added to the cells (plasmid 1 ug/mL, PRX 10 ug/ml). For trafficking studies, the particles were labeled with FITC and the plasmid labeled with Cy3 using Label IT® Tracker™ kit (Mirus Bio) Media was changed every 2-3 days. Imaging for GFP or mCherry was done at timepoints between 24 hrs-21 days. For CRISPR delivery, cells were harvested at day 7, 14 or 21 and pelleted for genomic DNA extraction using the Quick gDNA mini prep kit (Zymo Research) and analyzed with the deletion PCR described below. 4 µL Lipofectamine (Life Technologies) per 1 µg plasmid DNA and 3 ul ViaFect (Promega) per 1 ug plasmid DNA were used as controls for plasmid transfection.

PRX Delivery In Vivo 50 or 100 ug px333 44C4+55C3 plasmid complexed with PRX was injected systemically into the tail vein of mdx or hDMD del45 mdxD2 mice. For biodistribution studies, the plasmid was labeled with Cy3 using Label IT® Tracker™ kit (Mirus Bio) and mice were sacrificed 24 hrs later. Muscles and organs were imaged with IVIS imaging. Muscles were flash frozen in isopentane and cryosectioned at 10 µm for staining and imaging. For short term efficacy studies, mice were dosed 2x/wk for 3 wks. For short term systemic efficacy studies, 50 or 100 µg px333 44C4+55C3 plasmid complexed with PRX was injected into the tail vein of hDMD del45 mdxD2 mice (2$^{nd}$ backcross) at 11 wks of age. Mice were dosed 4 times over 2.5 wks. Muscles were harvested and flash frozen in isopentane after ~5 wks (34 days).

CRISPR Exon 45-55 Deletion PCR

For determining if the exon 45-55 deletion occurred, individual PCR reactions containing primers flanking the deletion (del) or internal to the deletion (undel) was performed with AccuPrime Taq High Fidelity (Life Technologies) or Herculase II Fusion Polymerase (Agilent Genomics). PCR products were run on a 2% agarose gel and visualized with ethidium bromide staining.

Immunostaining Muscle Sections

Cryosections were stained as described in Young et al. 2016. Anti-laminin (1:200, rabbit, Sigma) primary antibody was used with an Alexa Fluor 647 secondary. For dystrophin staining, sections were fixed in cold acetone for 1-2 mins, then TrueBlack (Biotium, 20-fold diluted in 70% ethanol) was added for 30 s–1 min, then blocking buffer (PBS with 5% horse serum and 10% goat serum) was added for at least 1 hr, followed by the M.O.M. kit (Vector Labs) according to the manufacturer's protocol. Primary antibodies MANDYS106 (1:60) MANEX55/56B (1:100), laminin (1:200) were added overnight. The following day secondary antibodies at 1:250 were added for 1.5 hrs.

Example 2

Use of PRX Nanocarrier to Deliver Various Plasmids in Cancer Cells

Figure 14:
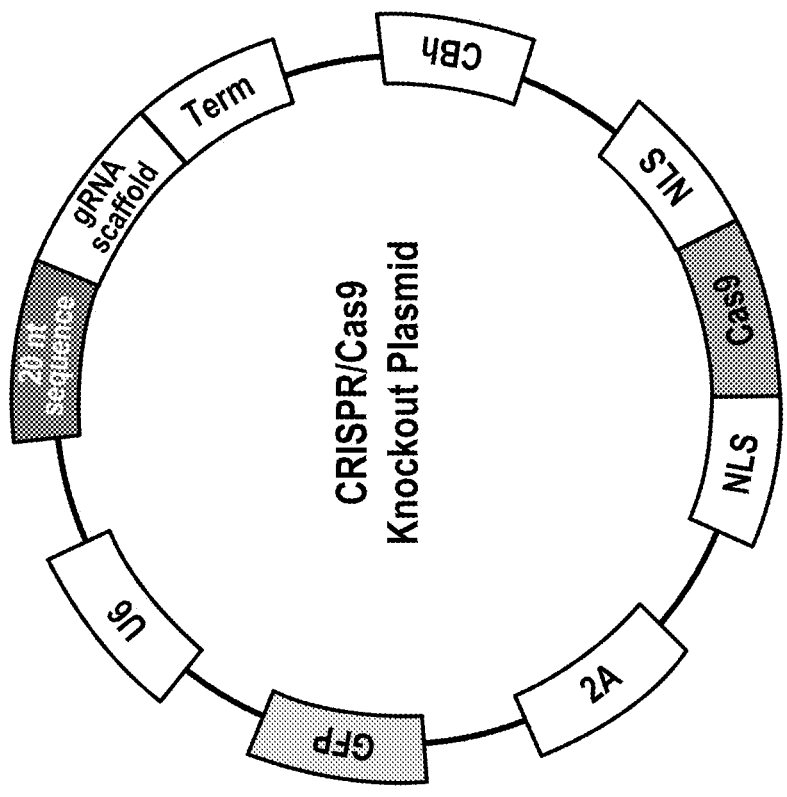
FIG. 14. In cancer cells, GFP (M.W.=3.4 kpb, 2,210 kD) and CRISPR/Cas9 knockout plasmid (M.W.=9.3 kpb, 6,045 kD) were encapsulated by G3 PRX. The pmaxGFP plasmid is constructed with CMV promoter to facilitate the expression of GFP, the plasmid is also with kanamycin resistance for amplification. CRISPR/Cas9 knockout plasmid is constructed with U6 promoter to facilitate the expression of gRNA (sequence: CTGAATTAGCTGTATCGTCA (SEQ ID NO:1) and GAATATAAACTTGTGGTAGT (SEQ ID NO:2)) to target KRAS gene, as well as Cas9 protein functionalized with nuclear-localization sequence (NLS).
Figure 14:
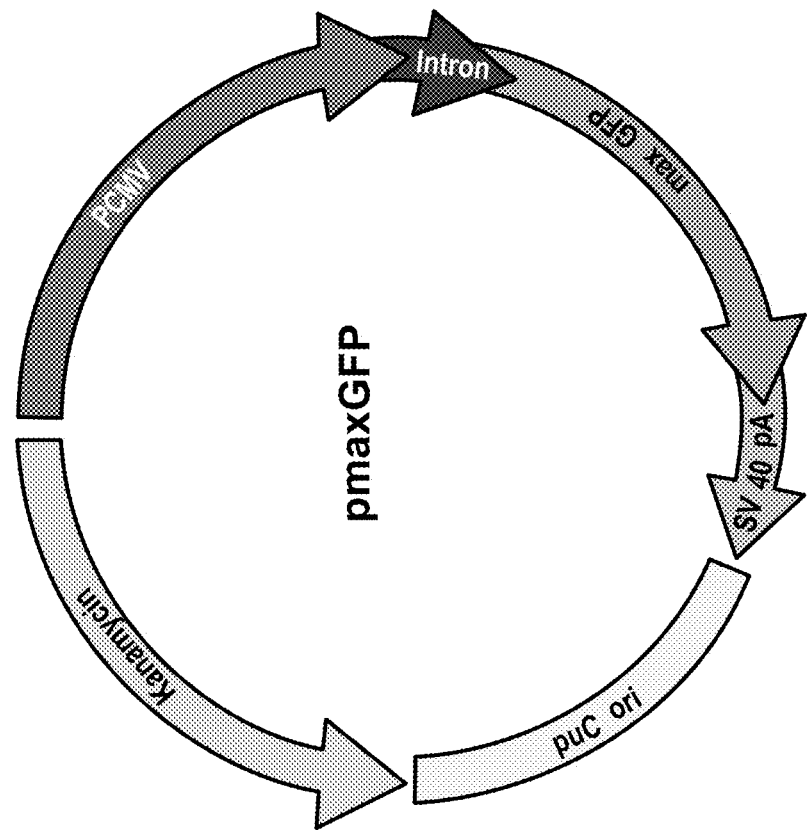
Figure 15:
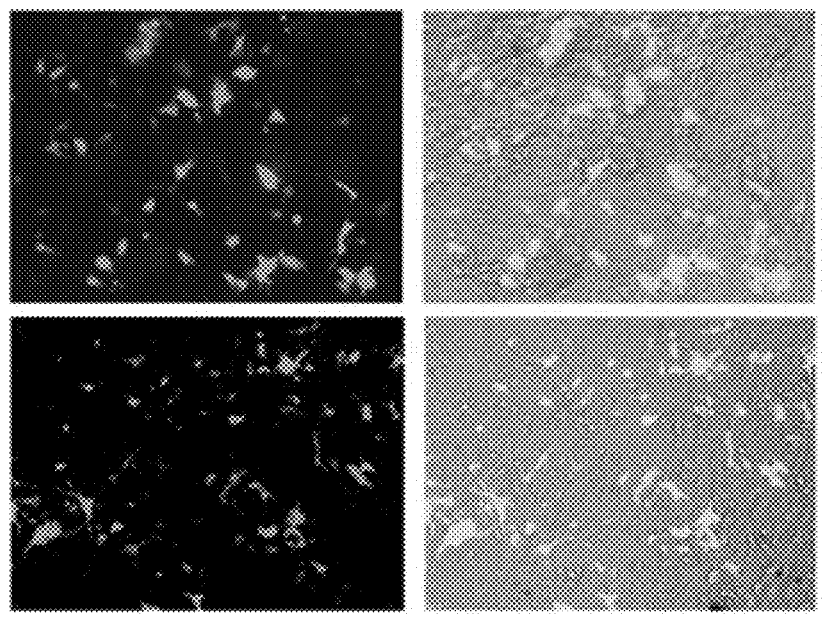
FIG. 15 shows a comparative analysis of GFP plasmid delivered by G3 PRX versus Lipofectamine 2000 in B16 melanoma cells. B16 cells were seeded into 12-well plate and received plasmid laden G3 PRX at a plasmid dose of 1 µg plasmid per well. The cells were used for imaging by a fluorescent microscope. The images were taken at day 4.
Figure 16:
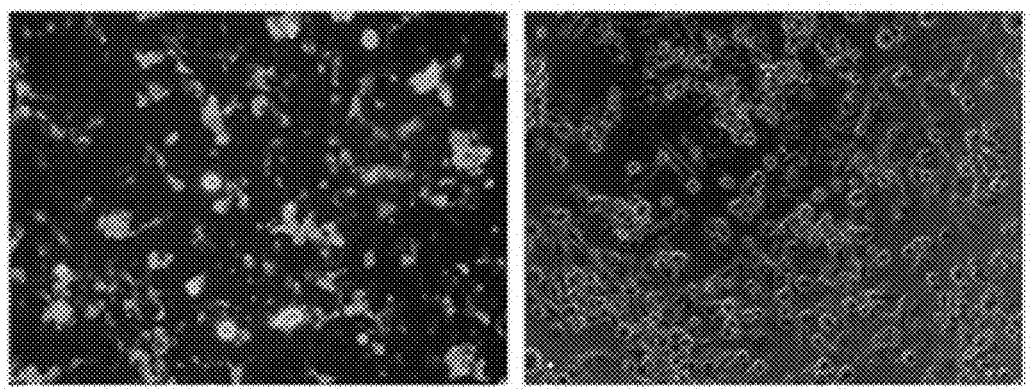
FIG. 16 shows CRISPR/Cas9 knockout plasmid delivered by G3 PRX in Kras-mutated human pancreatic and colon cells. Panc-1 and HCT116 cells were seeded into 12-well plate and received plasmid laden G3 PRX at a plasmid dose of 1 µg plasmid per well. The cells were used for imaging by a fluorescent microscope. The images were taken at day 4. The commercial transfection reagent, i.e. lipofectamine 2000, exhibited inefficient transfection effect (not shown).
Figure 16:
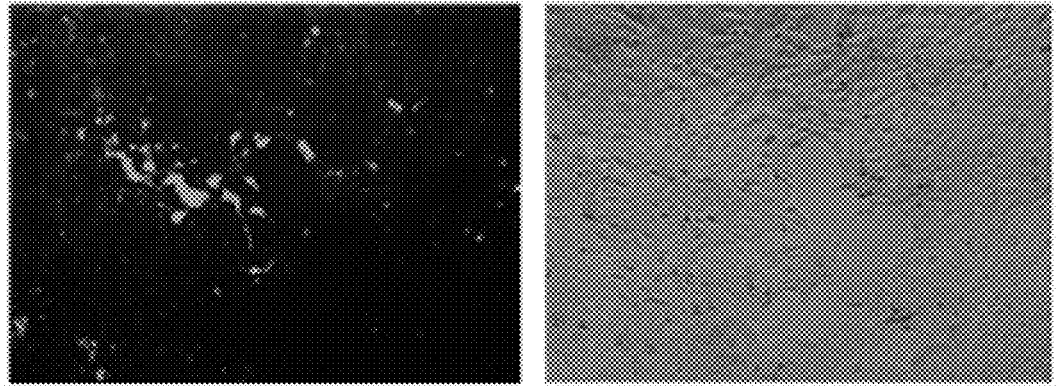

In addition to DMD, we have achieved some progresses for large plasmid delivery in non-muscle cells, such as cancer cells. In this regard, we have used our PRX carriers for comparison against commercial transfection reagent in a range of cancer cell types to provide proof-of-principle demonstration of the wider utility of our platform, including for melanoma, pancreatic cancer and colon cancer, etc. The PRX delivery systems described herein find use in numerous other fields, such as infectious disease, organ transplantation, liver disease, cardiovascular disease and other non-DMD rare diseases (e.g. Huntington's Disease) etc. To illustrate these possibilities, two plasmids were tested as payloads, namely a pmaxGFP plasmid and CRISPR/Cas9 knockout plasmid (FIG. 14). The latter is a commercial K-Ras CRISPR/Cas9 KO Plasmid (h) that is designed to disrupt gene expression by causing a double-strand break in a 5' constitutive exon within the human KRAS gene. The K-Ras CRISPR/Cas9 KO Plasmid (h) consists of a pool of 3 plasmids, each encoding the Cas9 nuclease and a target-specific 20 nt guide RNA designed for maximum knockout efficiency. Since there is a GFP sequence in the K-Ras CRISPR/Cas9 KO Plasmid, the expression of GFP protein in an indicative of the success of gene editing. The effect of GFP plasmid laden G3 PRX was tested in murine B16 melanoma cells (FIG. 15). The effect of K-Ras CRISPR/Cas9 KO Plasmid loaded G3 PRX was tested in Kras-mutated human pancreatic cancer (Panc-1) and colon cancer (HCT116) cells (FIG. 16). This suggests that G3 PRX allows a sufficient CRISPR/Cas9 KO plasmid delivery in Panc-1 cells as compared to HCT116 cells in which transfection efficient is relatively low.

Figure 17:
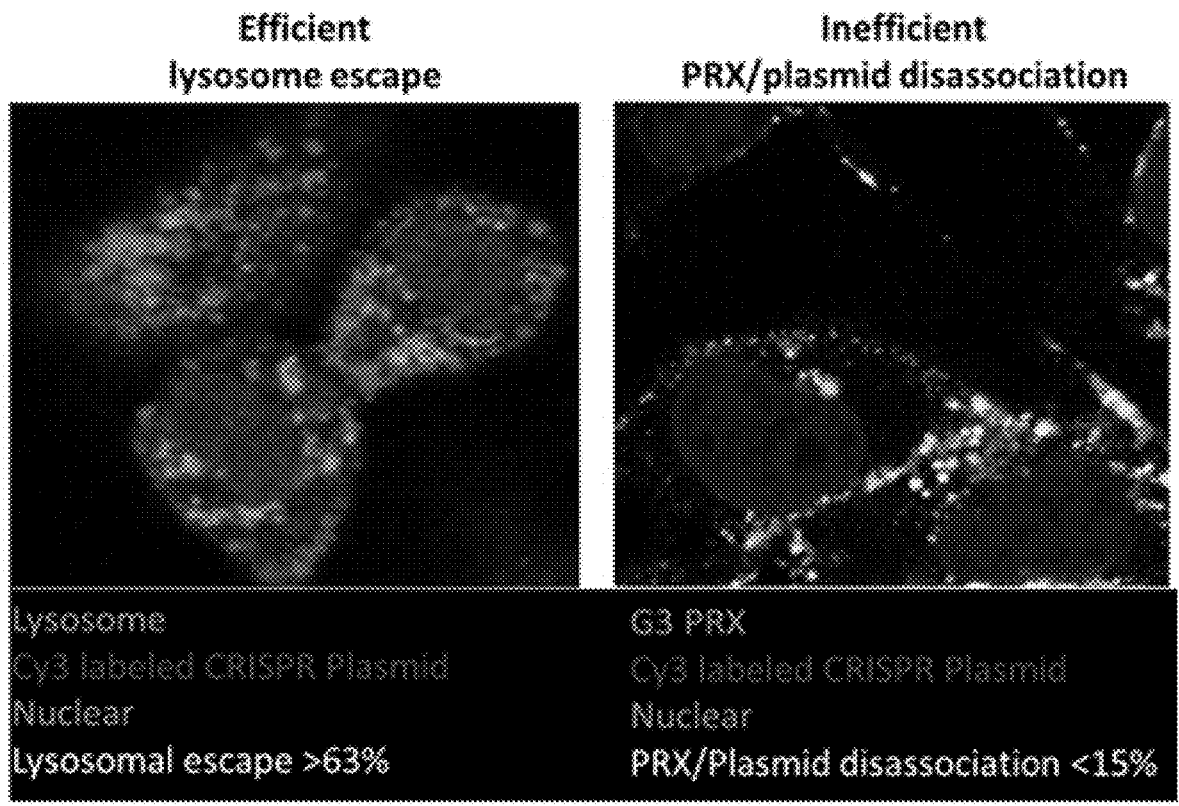
FIG. 17. Use of confocal microscope to study the lysosomal escape and G3 PRX/CRISPR plasmid disassociation in cells.

We also studied the intracellular localization of red-labeled PRX in relation to lysosomal co-staining by green fluorescent labeled anti-LAMP-1 antibody. Confocal microscopy confirmed high percentage co-localization of the red-labeled PRX particles with the green-labeled lysosomes at early time point (not shown). At 24 hrs post incubation, we continued to demonstrate >63% G3 PRX has escaped from the acidic lysosomal compartment, presumably due to the proton sponge effect (FIG. 17, left panel). In a subsequent confocal study we demonstrated that less than 15% CRISPR plasmid can be released from G3 PRX particles after entrance into the lysosome, which inspired us to further improve the plasmid intracellular release in cancer cells (FIG. 17, right panel). One solution is to use the G4 PRX.

An important consideration in the use of positively charged nanocarrier is its potential cytotoxicity. Although no cytotoxicity was seen with the PRX nanocarriers, commercially available transfection reagent such as Lipofectamine 2000 is relatively toxic to the cells.

REFERENCES (1) Yamashita, A.; Yui, N.; Ooya, T.; Kano, A.; Maruyama, A.; Akita, H.; Kogure, K.; Harashima, H.: Synthesis of a biocleavable polyrotaxane-plasmid DNA (pDNA) polyplex and its use for the rapid nonviral delivery of pDNA to cell nuclei. *Nat. Protocols* 2007, 1: 2861-2869.
(2) Ooya, T.; Choi, H. S.; Yamashita, A.; Yui, N.; Sugaya, Y.; Kano, A.; Maruyama, A.; Akita, H.; Ito, R.; Kogure, K.; Harashima, H.: Biocleavable Polyrotaxane-Plasmid DNA Polyplex for Enhanced Gene Delivery. *Journal of the American Chemical Society* 2006, 128: 3852-3853.
(3) Kulkarni, A.; DeFrees, K.; Schuldt, R. A.; Vlahu, A.; VerHeul, R.; Hyun, S.-H.; Deng, W.; Thompson, D. H.: Multi-armed cationic cyclodextrin:poly(ethylene glycol) polyrotaxanes as efficient gene silencing vectors( ). *Integrative biology: quantitative biosciences from nano to macro* 2013, 5: 10.1039/c2ib20107k.
(4) Ermolova, N. V.; Martinez, L.; Vetrone, S. A.; Jordan, M. C.; Roos, K. P.; Sweeney, H. L.; Spencer, M. J.: Long-term administration of the TNF blocking drug Remicade (cV1q) to mdx mice reduces skeletal and cardiac muscle fibrosis, but negatively impacts cardiac function. *Neuromuscular Disorders* 2014, 24: 583-595.
(5) Vetrone, S. A.; Montecino-Rodriguez, E.; Kudryashova, E.; Kramerova, I.; Hoffman, E. P.; Liu, S. D.; Miceli, M. C.; Spencer, M. J.: Osteopontin promotes fibrosis in dystrophic mouse muscle by modulating immune cell subsets and intramuscular TGF-β. *The Journal of Clinical Investigation* 2009, 119: 1583-1594.
(6) Young, C. S.; Hicks, M. R.; Ermolova, N. V.; Nakano, H.; Jan, M.; Younesi, S.; Karumbayaram, S.; Kumagai-Cresse, C.; Wang, D.; Zack, J. A.; Kohn, D. B.; Nakano, A.; Nelson, S. F.; Miceli, M. C.; Spencer, M. J.; Pyle, A. D.: Therapeutically relevant CRISPR/Cas9 platform applicable to majority of DMD patients restores dystrophin function in hiPSC-derived muscle cells. *Cell Stem Cell* 2016, 18: 533-540.
(7) Malerba, A.; Thorogood, F. C.; Dickson, G.; Graham, I. R.: Dosing Regimen Has a Significant Impact on the Efficiency of Morpholino Oligomer-Induced Exon Skipping in mdx Mice. *Human Gene Therapy* 2009, 20: 955-965.
(8) Ferlini, A.; Sabatelli, P.; Fabris, M.; Bassi, E.; Falzarano, S.; Vattemi, G.; Perrone, D.; Gualandi, F.; Maraldi, N. M.; Merlini, L.; Sparnacci, K.; Laus, M.; Caputo, A.; Bonaldo, P.; Braghetta, P.; Rimessi, P.: Dystrophin restoration in skeletal, heart and skin arrector pili smooth muscle of mdx mice by ZM2 NP-AON complexes. *Gene Ther* 2010, 17: 432-438.
(9) Bassi, E.; Falzarano, S.; Fabris, M.; Gualandi, F.; Merlini, L.; Vattemi, G.; Perrone, D.; Marchesi, E.; Sabatelli, P.; Sparnacci, K.; Laus, M.; Bonaldo, P.; Rimessi, P.; Braghetta, P.; Ferlini, A.: Persistent Dystrophin Protein Restoration 90 Days after a Course of Intraperitoneally Administered Naked 2'OMePS AON and ZM2 NP-AON Complexes in mdx Mice. *Journal of Biomedicine and Biotechnology* 2012, 2012: Article ID 897076.
(10) Bibee, K. P.; Cheng, Y.-J.; Ching, J. K.; Marsh, J. N.; Li, A. J.; Keeling, R. M.; Connolly, A. M.; Golumbek, P. T.; Myerson, J. W.; Hu, G.; Chen, J.; Shannon, W. D.; Lanza, G. M.; Weihl, C. C.; Wickline, S. A.: Rapamycin nanoparticles target defective autophagy in muscular dystrophy to enhance both strength and cardiac function. *The FASEB Journal* 2014, 28: 2047-2061.
(11) Nance, M. E.; Hakim, C. H.; Yang, N. N.; Duan, D.: Nanotherapy for Duchenne muscular dystrophy. *Wiley Interdisciplinary Reviews: Nanomedicine and Nanobiotechnology* 2017, e1472-n/a.
(12) Long, C.; Amoasii, L.; Mireault, A. A.; McAnally, J. R.; Li, H.; Sanchez-Ortiz, E.; Bhattacharyya, S.; Shelton, J. M.; Bassel-Duby, R.; Olson, E. N.: Postnatal genome editing partially restores dystrophin expression in a mouse model of muscular dystrophy. *Science* 2016, 351: 400-403.
(13) Nelson, C. E.; Hakim, C. H.; Ousterout, D. G.; Thakore, P. I.; Moreb, E. A.; Rivera, R. M. C.; Madhavan, S.; Pan, X.; Ran, F. A.; Yan, W. X.; Asokan, A.; Zhang, F.; Duan, D.; Gersbach, C. A.: In vivo genome editing improves muscle function in a mouse model of Duchenne muscular dystrophy. *Science* 2016, 351: 403-407.
(14) Tabebordbar, M.; Zhu, K.; Cheng, J. K. W.; Chew, W. L.; Widrick, J. J.; Yan, W. X.; Maesner, C.; Wu, E. Y.; Xiao, R.; Ran, F. A.; Cong, L.; Zhang, F.; Vandenberghe, L. H.; Church, G. M.; Wagers, A. J.: In vivo gene editing in dystrophic mouse muscle and muscle stem cells. *Science* 2016, 351: 407-411.
(15) Sun, W.; Ji, W.; Hall, J.; Hu, Q.; Wang, C.; Beisel, C.; Gu, Z.: Self-Assembled DNA Nanoclews for the Efficient Delivery of CRISPR-Cas9 for Genome Editing. *Angew Chem Int Ed Engl.* 2015 54: 12029-12033.

Example 3

Development of Self-Assembled Multi-Arm Polyrotaxanes Nanocarriers for Systemic Plasmid Delivery In Vivo Polyrotaxane (PRX) has been extensively studied for gene delivery. Classic PRX exhibits a linear structure in which the amine-functionalized α-cyclodextrin (CD) is threaded along the entire polyethylene glycol (PEG) backbone. While the classic PRX is promising in vitro, the in vivo implementation is limited due to unfavorable pharmacokinetics (PK), which can be partially explained by the formation of unprotected cationic surface and lack of functional PEG after CD threading. Herein, we developed a multi-arm PRX platform, which has been designed for protective loading and improved PK, allowing intravenous (IV) delivery of nucleic acid. A key design is to introduce cationic CDs onto a multi-arm backbone in a spatially selective fashion. This was achieved by the controlled protection of PEG arms using protective group with steric hindrance. The optimal carrier was obtained through iterative rounds of experimentation to determine the appropriate features, such as charge density, the degree of PEGlyation and polymer backbone size, etc. Post IV injection, the multi-arm design significantly enhanced the biodistribution and circulatory half-life. We also used our PRX to formulate an IL-12 plasmid for cancer immunogene therapy in a solid tumor (colon cancer) model, leading to efficacious and safe anti-tumor effect in vivo.

Introduction

Polyrotaxanes (PRX) are supramolecular inclusion complex assembled from the threading of macrocycles onto a polymer backbone. PRXs are excellent carriers for the delivery of nucleic acids due to their advantageous properties (Mellet et al. (2011) *Chem. Soc. Rev.* 40: 1586), such as effective and spontaneous nucleic acid (e.g., plasmid) and polymer self-assembly, protective nucleic acids encapsulation, tunability of condensation/decondensation by choosing various types/densities of amine groups, functionalizability of PRX through the introduction of cleavable linkers for controlling intracellular gene delivery, etc. (Ooya et al. (2006) *J. Am. Chem. Soc.* 128: 3852). Moreover, these materials are very biocompatible due to the intrinsic safety of polyethylene glycol (PEG) and cyclodextrin sugar rings (Li & Loh (2008) *Adv. Drug Deliv. Rev.* 60: 1000). The general structure of the classic PRX carrier (Yamashita et al. (2006) *Nat. Protocol.* 1: 2861; Badwaik et al. (2016) *Biomaterials,* 84: 86; Tamura & Yui (2013) *Biomaterials,* 34: 2480; Kayashima et al. (2010) *J. Immunol.* 185: 698; Morille et al. (2008) *Biomaterials,* 29: 3477) involves the threading of cationically-rendered cyclodextrin (α-CD) along the linear PEG polymer backbone, capable of condensing DNA to sub-200 nm polyplex (Scheme S1 shown in FIG. 24). The reported in vitro transfection efficiency by linear PRXs was competent with polyethylene imine (PEI) but with no apparent cytotoxicity (Li & Loh (2008)*Adv. Drug Deliv. Rev.* 60: 1000). The in vitro effectiveness was achieved by systemic tuning of the cationic charge and molecular weight of these linear PRXs.[7] While the classic PRXs are promising in vitro (Yamashita et al. (2006)*Nat. Protocol.* 1: 2861; Badwaik et al. (2016) *Biomaterials,* 84: 86; Tamura & Yui (2013) *Biomaterials,* 34: 2480; Kayashima et al. (2010) *J. Immunol.* 185: 698; Morille et al. (2008) *Biomaterials,* 29: 3477), they are rarely tested in vivo. The utilization of the linear PRXs is limited at intact organism level, partially because the inclusion complex largely reduces the availability of PEG on the nano surface (see, e.g., Scheme 1 in FIG. 23). As a result, these PRX nano particulates lead to rapid formation of protein corona and can be effectively removed by the phagocytic cells in the reticuloendothelial system (RES) organs. Moreover, there is a possibility that the colloidal instability of these low- or non-PEG protected PRX nanocarriers could lead to agglomeration in the circulation and therefore excluded the plasmid payload from the intended "target site" (Suk et al. (2016) *Adv. Drug Deliv. Rev.,* 99: 28).

Figure 18:
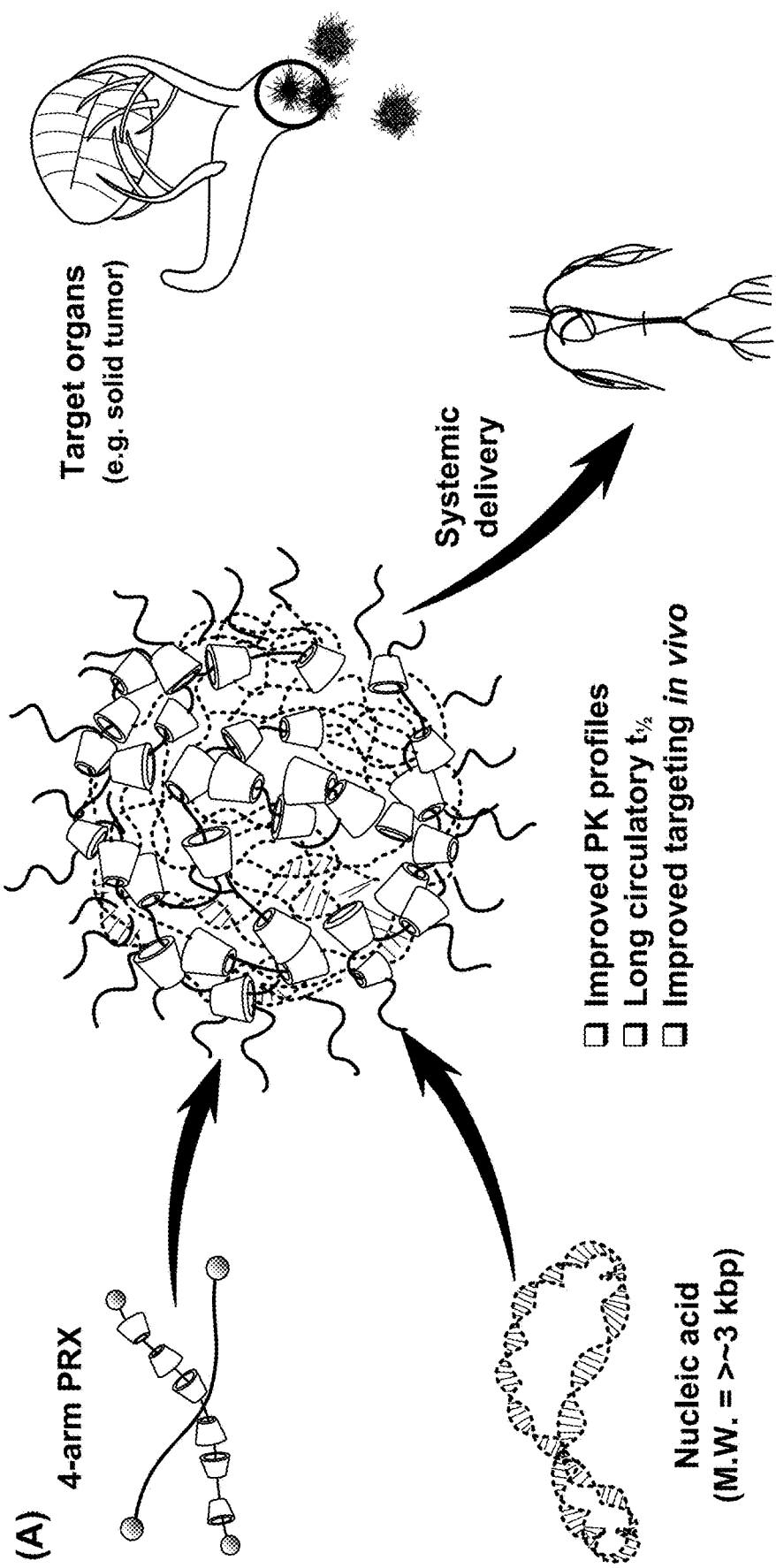
FIG. 18. Panel A: Schematic of 4-arm PRX delivery platform for systemic plasmid delivery. Cationic α-CDs were threaded onto 4-arm PEG backbone in a spatially selective fashion, resulting in available PEG moieties for enhanced delivery performances in vivo. Panel B: The detailed synthesis routes of 4-arm PRX. Detailed synthetic procedures were described in the result and method sections in Example 3. Panel C: The number of amines per α-CDs can be calculated via the $^1$H-NMR spectra in deuterated water (D$_2$O), which demonstrated the tuning of charge density on 4-arm PRX. Panel D) In vitro transfection of tdTomato reporter plasmid by 4-arm PRX with different cationic charge densities. 4-arm PRXs with ~1, ~3 or ~6 amines per α-CD were complexed with tdTomato plasmid at multiple N/P ratios and incubated with MC38 colon cancer cells for 72 h (1 µg plasmid/mL). The percentages of tdTomato$^+$ MC38 cells were quantitatively displayed at various N/P ratios in the heat map. In vitro transfection efficiency at the optimum N/P ratio was compared between 4-arm PRX with different charge densities (n=6). Representative fluorescence image of tdTomato$^+$ MC38 cells (red) confirmed that 4-arm PRX with 6 amines per α-CD resulted in the most efficient reporter transfection in vitro. Nuclei were counterstained with DAPI. The results are expressed as mean±SD. *p<0.05.

As described in this example, our aim was to develop an in vivo effective PRX platform, that can address the above challenges. A major innovation is the creative use of multi-arm PEG backbone with spatially selective threading of α-CD, resulting in available PEG arms after inclusion complexation, which serves as a safeguard for in vivo administration, including intravenous (IV) injection (FIG. 18, panel A). Inspired by the previous studies in which CD-based polymer was optimized across multiple structural parameters (Popielarski et al. (2003) *Bioconjug. Chem.* 14: 672; Reineke & Davis (2003) *Bioconjug. Chem.,* 14: 247), we generated a series of multi-arm PRX analogues through tuning the key design features. This allowed us to establish nano quantitative structure-activity relationship (QSAR) and multi-variants design features to iteratively improve biodistribution, pharmacokinetics (PK), transfection efficiency and safety of PRX nanocarriers. In order to determine the best PRX phenotype, we have systemically dissected the role of cationic charge density, level of available free PEG moieties, size of PEG backbones via cellular test of reporter plasmid transfection. We also test the optimal multi-arm PRX delivery system using a reporter plasmid and a therapeutic plasmid in normal and disease mouse models.

To demonstrate the therapeutic impact of our PRX, we constructed an interleukin-12 (IL-12) encoding IV formulation to solid tumor (e.g., colon cancer). Although IL-12 is an important anti-tumor cytokine, the direct administration of recombinant IL-12 (rIL-12) was pharmacologically abandoned due to serious side effects including patient deaths, attributed to its unfavorable PK profile (Tugues et al. (2015) *Cell Death & Diff* 22: 237 Tugues et al. (2015) *Cell Death & Diff* 22: 237). Researchers have developed various advanced delivery mechanisms (e.g., adenovirus (Sangro et al. (2004) *J. Clin. Oncol.* 22: 1389), gene gun (Rakhmilevich et al. (1996) *Proc. Natl. Acad. Sci. USA,* 93: 6291), electroporation (Daud et al. (2008) *J. Clin. Oncol.* 26: 5896), and nanoparticles (Dass et al. (2010) *J. Pharm. & Pharm. Sci.* 13: 472)) to improve the PK and safety of IL-12 immunotherapy. Some of them include nano formulations for IL-12 plasmid (pIL-12) delivery, administrated intratumorally (IT) or intraperitoneally (IP), which have resulted in early stage clinical trials in skin cancer (Daud et al. (2008) *J. Clin. Oncol.* 26: 5896) and ovarian cancer (that is usually confined in peritoneal cavity) (Edwards, ClinicalTrials.gov Identifier: NCT00003439 2004). However, for a deep seated solid tumor that metastasizes hematogenously and lymphatically to distant organs (e.g., colon cancer), there is a need to implement IL-12 therapy through systemic administration with additional consideration of toxicity reduction and tumor targeting. We have demonstrated that IV injected multi-arm PRX significantly improved the PK and biodistribution at a colon cancer site in mice, leading to efficacious and safe anti-tumor effect in vivo. Our data suggests that the presence of PRX/pIL-12 nano complex in colon cancer becomes a sustained source of continuous replenishment of IL-12 without major toxicity.

Results and Discussion

Development and Optimization of Multi-Arm (i.e. 4-Arm) PRX Gene Delivery Platform Classic linear PRX gene carriers were established based on the supramolecular assembly of CD rings threading along the entire linear PEG backbone, followed by introducing bulky end-caps and further functionalization of CD molecules by various amine groups (Ooya et al. (2006) *J. Am. Chem. Soc.* 128: 3852). When combining negatively charged nucleic acid with linear PRX, the self-assembly process is instantaneous and mediated by the electrostatic interaction between nucleic acid and cationic CDs, which distribute non-selectively along —(O—CH$_2$—CH$_2$)— repeating units in the PEG backbone (see Scheme S1 in FIG. 24) (Id.). While an ideal scenario would be to use such a linear PRX for gene delivery in vivo, the linear PRX is unlikely to make therapeutic delivery possible, especially for IV treatment. From a nanomaterial property perspective, the net outcome using linear PRX is the formation of none or low PEGylated but cationic nano particulates, which are generally inefficient for systemic application because of non-specific binding, short $t_{1/2}$ and unwanted macrophage uptake (Ogris et al. (1999) *Gene Ther.,* 6: 595). It is also found that IV-injected cationic nanoparticles typically ended up in the lung (Morille et al. (2008) *Biomaterials,* 29: 3477). In this example, we describe an IV-injectable multi-arm PRX platform with a group of optimal design features, allowing for the introduction of cationic CDs onto multi-arm PEG backbone in a spatially selective fashion (see, FIG. 18, panel A). Our hypothesis is that spatially selective CD threading into multi-arm PRX maintains the availability of functional PEG, which is the safeguard for improved PK profile, and therefore suitable for systemic gene delivery in vivo.

For proof-of-principle, we used commercially available 4-arm PEG as a precursor to make representative multi-arm PRXs. Generally speaking, the synthesis of the 4-arm PRX consists of the following 4 steps (FIG. 18, panel B and Table 6). 4-arm PEG-amine was selectively end-capped with bulky groups (i.e., fluorescein group) by controlling the feed ratio between 4-arm PEG-tetra-amine and fluorescein-NHS ("I" in FIG. 18, panel B). Subsequently, the modified 4-arm PEG was added to a saturated aqueous solution of α-CD. α-CD selectively threaded onto the PEG arms ended with free amine and formed inclusion complex. The steric hindrance of bulky end-caps would prevent α-CD from threading onto the occupied arms and resulted in CD-free PEG arms ("II" in FIG. 18, panel B). This was followed by an amide coupling reaction to introduce Z-L-tyrosine to the amine terminals, which prevented the de-threading of α-CD ("III" in FIG. 18, panel B). Finally, amine functionalization was achieved by introducing N,N-dimethylethylenediamine (DMEA) to α-CD via carbonyldiimidazole (CDI) activation to generate cationic 4-arm polyrotaxane (4-arm PRX) ("IV", FIG. 18, panel B). Detailed synthesis procedures were described in the method section.

TABLE 6

Detailed steps and intermediate products in the synthesis of 4-arm PRX, as shown in FIG. 18, panel B.

| | Starting Materials | Catalytic materials/ Reaction solution | Product | Yield % |
|---|---|---|---|---|
| Step 1 | 4-arm PEG tetra-amine | NHS-Fluorescein | NHS-Fluorescein PEG | >90% |
| Step 2 | Occupied 4-arm PEG | A-CD | Water | 4-arm polypseudo-rotaxane | 95% |
| Step 3 | 2/4 CD 4-arm pseudorotaxane | Z-Tyr | BOP, HOBt, DIEA, DMF | 4-arm polyrotaxane | 70% |
| Step 4 | 4-arm polyrotaxane | DMEA | CDI, DMSO | 4-arm polyrotaxane-DMEA | 56% |

Since multiple design features are involved in the synthesis of 4-arm PRX, we decide to perform iterative optimization to obtain the appropriate design features to make the therapeutic PRX carrier (Reineke & Davis (2003) *Bioconjug. Chem.* 14: 255). Since charge density on the nonviral carriers is one the most important variants that governs self-assembly and the delivery performances of polyplex (Pack et al. (2005) *Nat. Rev. Drug Discov.* 4: 581), our first attempt was to explore the effect of charge density per α-CD in 4-arm PRX while keep other structural parameters the same. For ease of experimentation, the abiotic characterization and in vitro transfection efficiency were first determined by a tdTomato reporter plasmid (Addgene plasmid 30530, MW=5.5 kbp). We prepared a library of 4-arm PRXs with different amine density per α-CD by adjusting the molar feed ratio of CDI to α-CD ranging from 5:1 to 30:1. The molecular weight (i.e., 10 kDa) and the number of protective groups (i.e., 2 out of 4 arms are protected) in 4-arm PEG precursors were not changed at this stage. The charge density was determined by $^1$H-NMR spectra (FIG. 18, panel C and FIG. 26A). The integration of —CH$_3$ peak (2.35 ppm) from DMAE divided by C1(H) peak (5.15 ppm) from α-CD gave the number of tertiary amines per α-CD. This allowed us to obtain a list of PRXs with amine density values of ~1, ~3 and ~6 per α-CD sugar ring (FIG. 18, panel C).

To compare the effectiveness of in vitro transfection, MC38 colon adenocarcinoma cells were used as a cellular model that allowed us to visualize tdTomato expression using various PRX carriers. Four-arm PRXs with 3 different charge densities were complexed with tdTomato plasmid at various N/P ratios ranging from 0.5:1 to 20:1. MC38 cells were treated with various polyplexes for 72 h, before the tdTomato$^+$ cells were identified by fluorescence microscopy. The heat map in FIG. 18, panel D provided a semi-quantitative display of the impact of charge density and N/P ratio on the transfection efficiency in vitro. Compared to PRX with lower charge density, the best reporter expression was obtained with 4-arm PRX at 6 amines per α-CD. The optimum N/P ratio to achieve sufficient reporter expression was 3:1 for the PRX with 6 amines per α-CD, and shifted to higher values with decreasing charge density. Comparing the transfection results at their optimum N/P, 4-arm PRX with 6 amines per α-CD revealed significant increase over 3 amines per α-CD, while the 4-arm PRX with 1 amine per α-CD barely transfected MC38 cells. Since decreasing the charge density negatively affected the transfection efficiency, the following experimentation was performed at the fixed charge density, i.e., 6 amines per α-CD.

Figure 19:
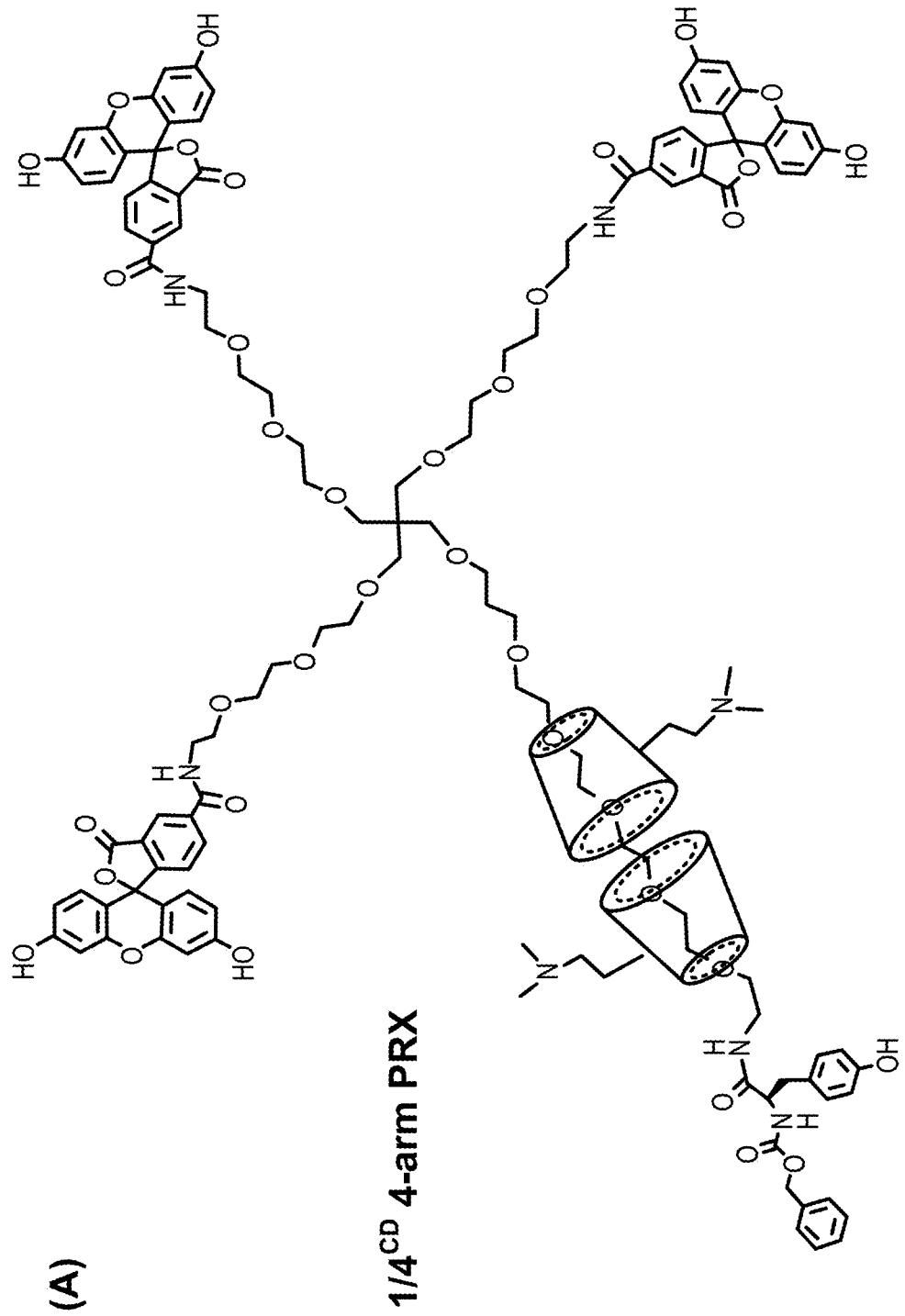
FIG. 19, panels A-E, illustrates use of abiotic and in vitro assays to determine the optimal multi-arm design and polymer backbone size. Panel A: The chemical structure of 4-arm PRX with different level of available PEG moieties. Panel B: The structural scheme of 4-arm PEG precursors occupied with different number of end-caps, which provided the steric hindrance for the selective threading of α-CD. MALDI-TOF molecular weight detection demonstrated the synthesis success of the 4-arm PEG precursors. Panel C: The number of total α-CDs per PRX was calculated via the $^1$H-NMR spectra of $1/4^{CD}$, $2/4^{CD}$, and $3/4^{CD}$ 4-arm polypseudototaxane in DMSO-d6, which demonstrated the tuning of the level of available PEG moieties. Panel D: In vitro reporter gene transfection by $1/4^{CD}$, $2/4^{CD}$, and $3/4^{CD}$ 4-arm PRX analogues was performed on MC38 cells for 72 h (1 µg plasmid/mL). The tdTomato expression at various N/P ratios was quantitatively expressed in the heat map. The reporter gene transfection efficiency at the optimum N/P ratio was compared between 4-arm PRX with different level of available PEG moieties (n=6). The results are expressed as mean±SD. *p<0.05. (E) The tuning of the molecular weight of the backbone was demonstrated by $^1$H-NMR spectra of $2/4^{CD}$ 4-arm polypseudototaxane with 5 kDa, 10 kDa or 20 kDa 4-arm PEG backbone size in DMSO-d6.
Figure 25:
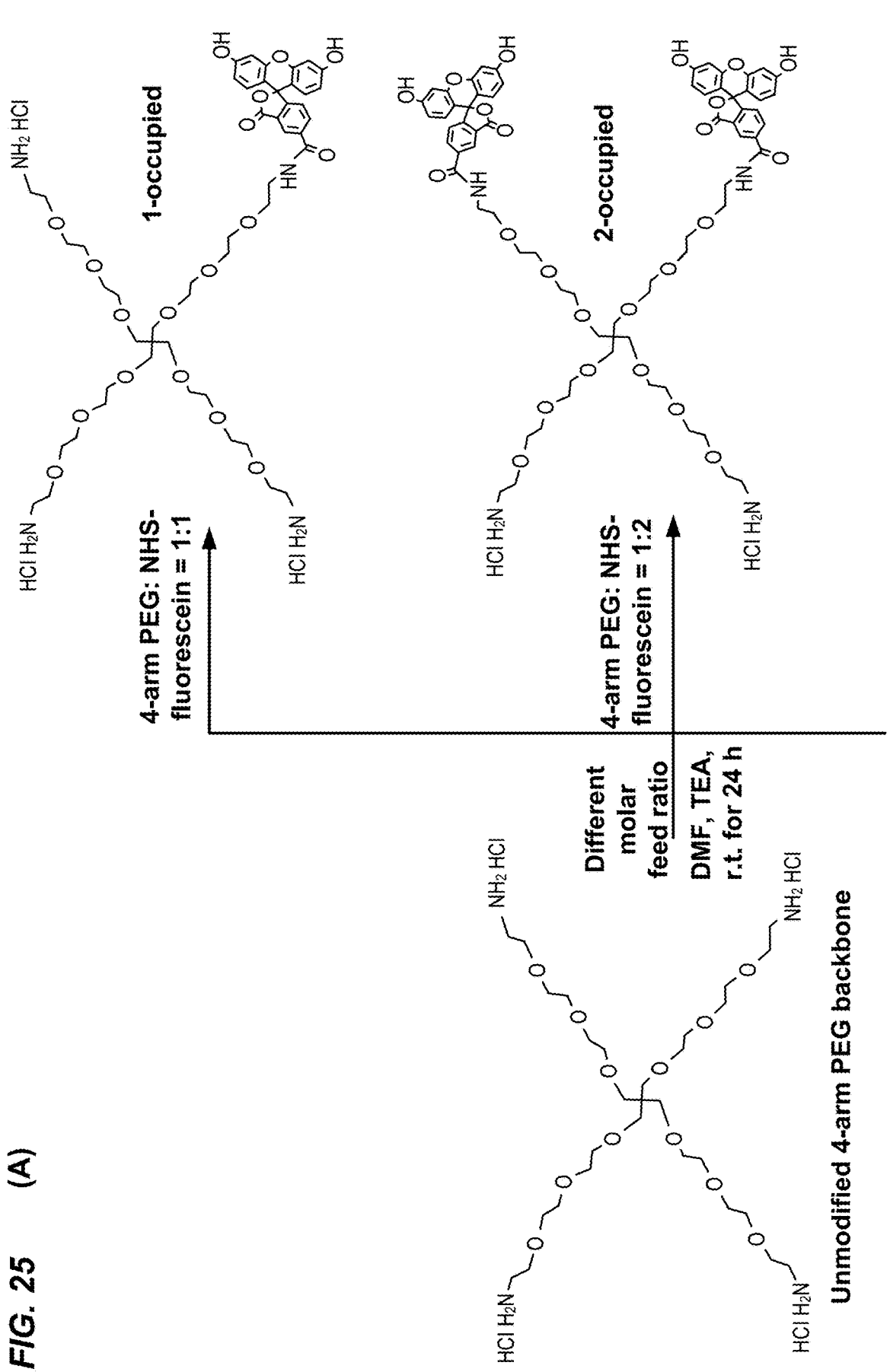
FIG. 25, panel A shows a scheme for the synthesis of modified 4-arm PEG backbone selectively end-capped with bulky groups (fluorescein). The number of bulky end-caps was manipulated via different feed ratio between 4-arm PEG-tetra-amine and NHS-fluorescein.

The second design feature to optimize was the level of free PEG moieties. By manipulation of the number of bulky end-caps on 4-arm PEG backbone, we constructed 3 different PRXs with α-CD threading onto 1 out of 4 arms (1/4 CD), 2 out of 4 arms (2/4 D) or 3 out 4 arms ($3/4^{CD}$), respectively (FIG. 19, panel A). To start with, 4-arm PEG tetra-amines were selectively functionalized with NHS-fluorescein, as illustrated in FIG. 25, panel A. Synthesis success was confirmed by MALDI-TOF-MS (FIG. 26, panel B) and $^1$H-NMR spectroscopy (FIG. 25, panel B). As demonstrated, the increase of average molecular weight in 4-arm PEG was associated with increasing degree of end-capping. For example, the experimental molecular weight of $2/4^{CD}$ 4-arm PRX (10680 Da) was in close accordance with the theoretical molecular weight (10629 Da) (FIG. 19, panel B). As the inclusion complex was formed in a saturated aqueous solution of α-CD, the number of α-CD on 4-arm PRX was directly related to the availability of free PEG arms. From $^1$H-NMR spectra, the integration of C1(H) peak (5.15 ppm) from α-CD and —CH$_2$CH$_2$O— peak from PEG was used to calculate the total number of α-CD per PRX polymer. As demonstrated in FIG. 19, panel C and FIG. 26, panel B, an average of 37α-CDs per polymer was resulted for $3/4^{CD}$ PRX, while the total number of α-CDs decreased to 26 per $2/4^{CD}$ PRX and 13 per $1/4^{CD}$ PRX, due to the increased level of free PEG moieties (FIG. 19, panel C). While the degree of free PEG moieties on PRX/plasmid nano particulates requires additional PK and biodistribution assessment in vivo, it suffices to perform tdTomato plasmid in vitro screening at this stage to exclude inefficient candidate in vitro (FIG. 19, panel D). We did not pursue $1/4^{CD}$ PRX because it exhibited the lowest transfection efficiency in MC38 cells. The result was in line with previous study, which suggested the excessive level of free PEG moieties could impede the access of polycation to plasmid DNA and reduce gene expression (Mishra et al. (2004) *Eur. J Cell Biol.* 83: 97). Furthermore, $3/4^{CD}$ PRX and $2/4^{CD}$ PRX resulted in comparable tdTomato gene expression, and no significant difference was observed in terms of optimum N/P ratio. Since the additional PEG arm on $2/4^{CD}$ PRX did not compromise transfection efficiency, we focused on $2/4^{CD}$ PRX in order to achieve sufficient level of free PEG moieties, which is a favorable feature for IV administration.

Figure 26:
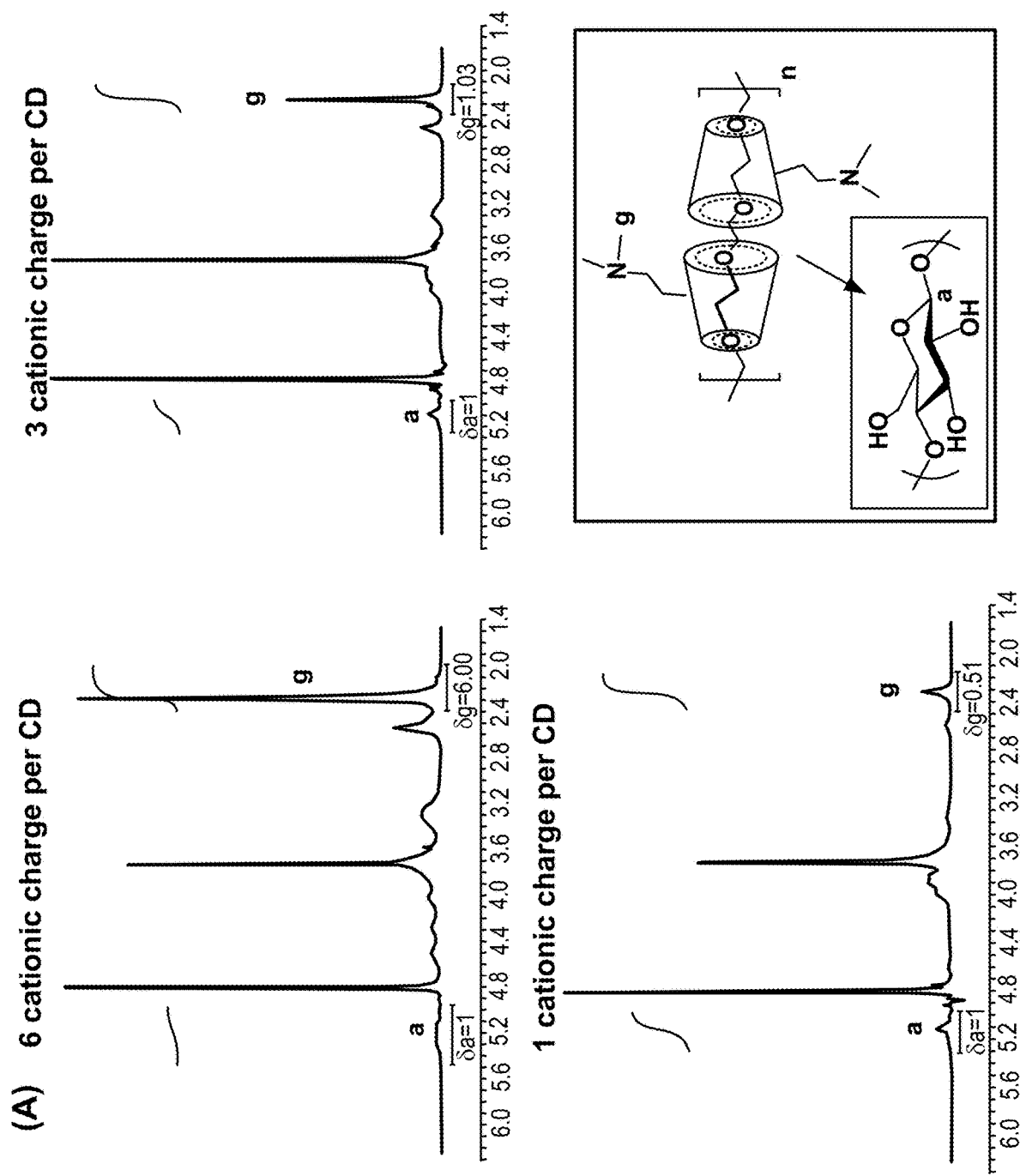
FIG. 26, panel A: $^1$H-NMR characterization of $2/4^{CD}$ 4-arm PEG backbone with different cationic charge densities in deuterated water ($D_2O$).
Figure 27:
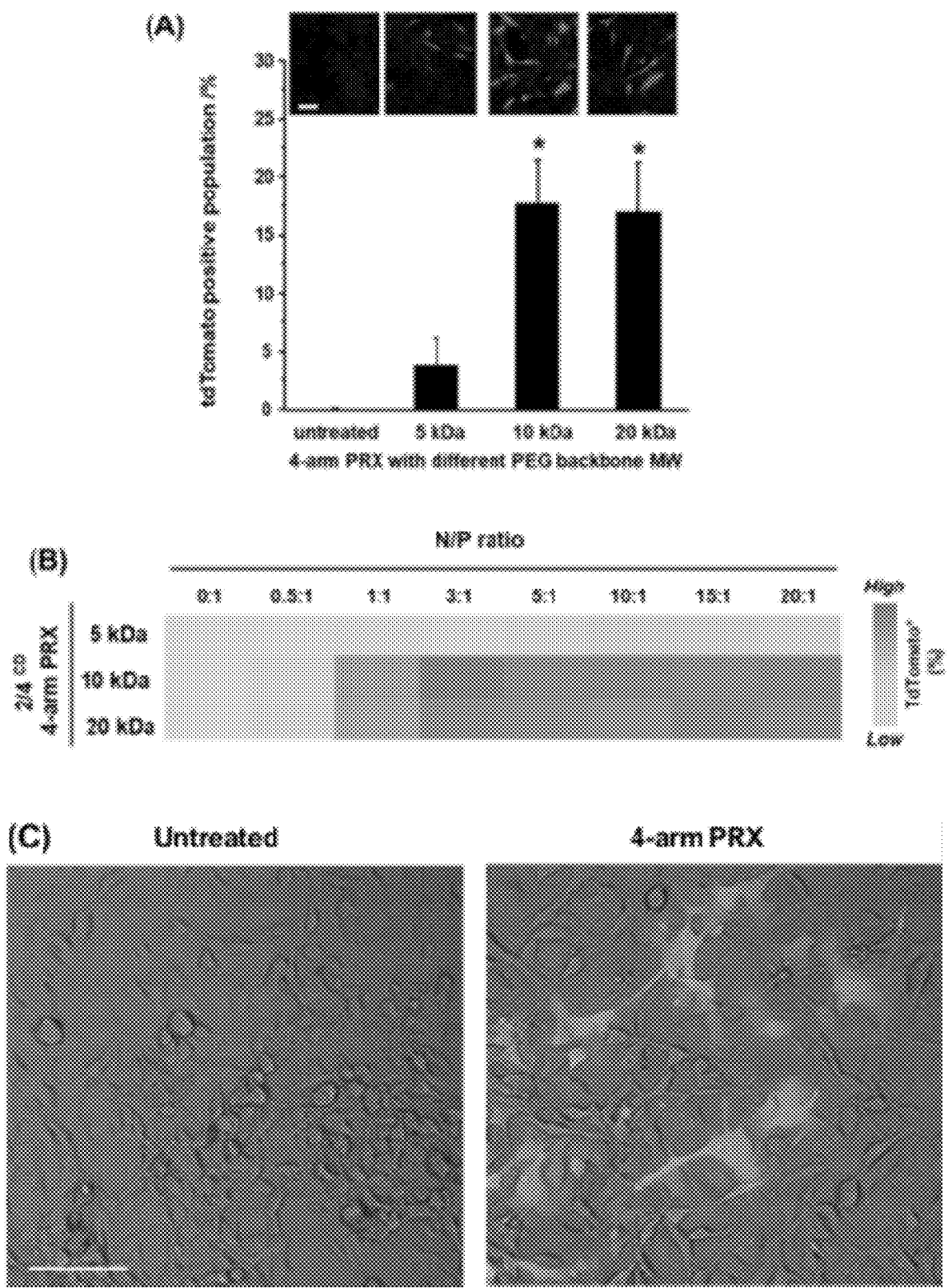
FIG. 27, panel A: In vitro transfection of MC38 cells by tdTomato plasmid. The reporter gene was delivered by 4-arm PRX analogues with different molecular weights (MW) of the PEG backbone and incubated with MC38 cells for 72 h (1 µg plasmid/mL). Percentage of red positive MC38 cells treated by reporter gene laden 4-arm PRX with 5 kDa, 10 kDa or 20 kDa backbone at the optimum N/P ratio, and representative fluorescence images of reporter gene expression by each treatment (scale bar represents 50 µm). Values represent the mean±SD (n=3).
Figure 28:
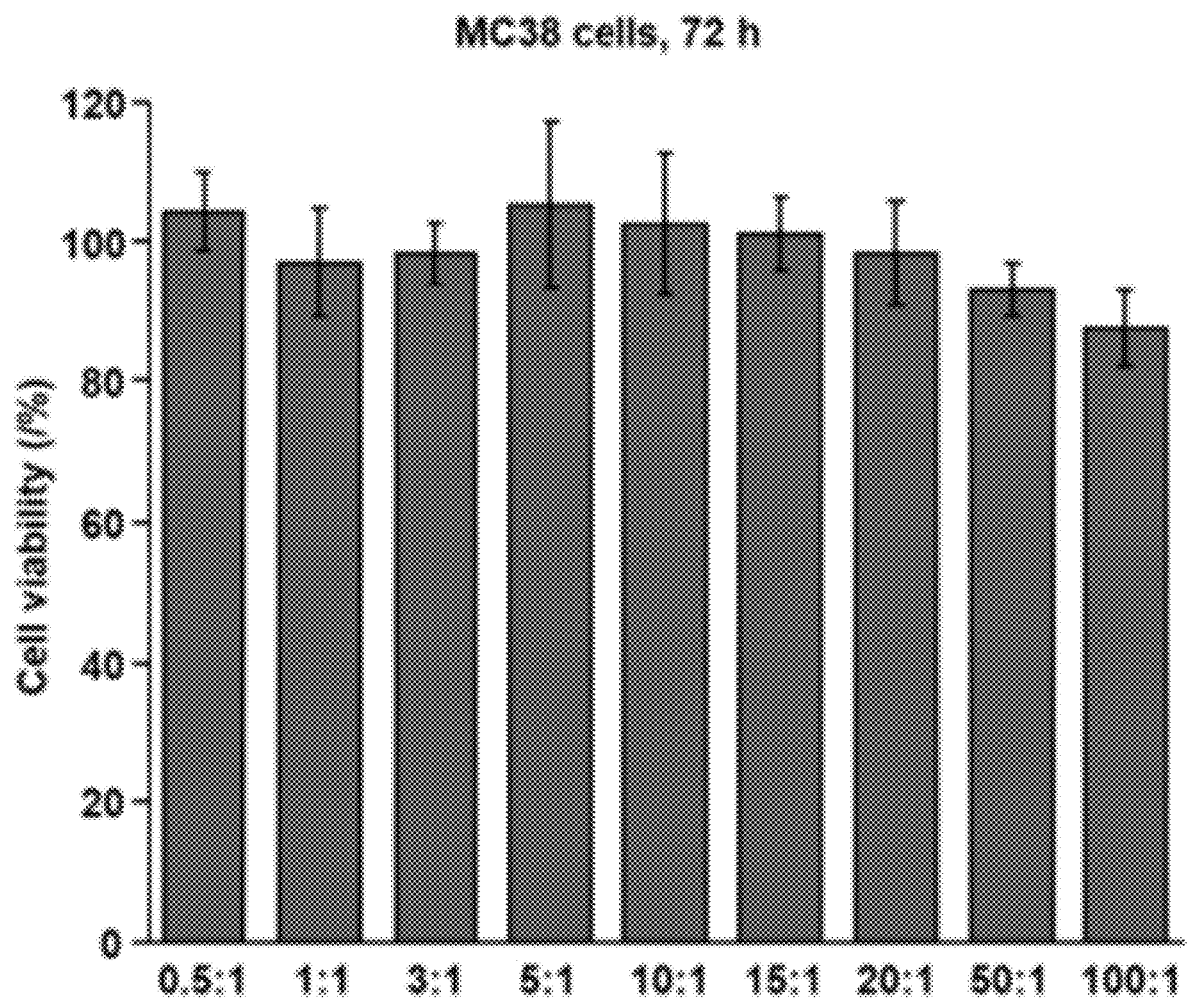
FIG. 28 shows the viability of MC38 cells after 72 h incubation with tdTomato plasmid laden 4-arm at various N/P ratios, the concentration of plasmid was fixed at 1 μg/mL. Values represent the mean±SD (n=6).

Moreover, we also optimized the molecular weight of the 4-arm PEG backbone in PRXs. In this case, 3 PRXs were constructed from 5 kDa, 10 kDa and 20 kDa 4-arm PEG backbone structures, and characterized by $^1$H-NMR spectroscopy (FIG. 19, panel E and FIG. 26, panel C). The number of α-CDs per PRX polymer was positively correlated with the size of the 4-arm PEG backbone. 5 kDa 4-arm PRX required higher N/P ratio for tdTomato transfection compared to PRXs with 10 kDa or 20 kDa PEG backbone (FIG. 27), with >4-fold reduction in transfection efficiency at optimum N/P ratio. The results suggested that the in vitro delivery performance of 4-arm PRX was molecular weight-dependent, which can be explained by the reduced level of plasmid condensation by low-molecular weight polycations. The molecular-weight dependent transfection efficiency was also reported with other polycations including poly(lysine) (Ward et al. (2001) Blood, 97: 2221), polyethyleneimine (Fischer et al. 91999) Pharmaceut. Res. 16: 1273), etc. In addition to MC38 cells, we also demonstrated abundant tdTomato expression in B16 melanoma cells (FIG. 27, panel C) and normal cells (not shown) treated by tdTomato plasmid laden 4-arm PRX. The results suggested that the 4-arm PRX platform could accommodate multiple cell types. A separate MTS cytotoxicity assay demonstrated that 4-arm PRX was devoid of toxicity in MC38 cells up N/P ratio of 100:1 for 72 h (FIG. 28).

In general, the direct in vitro transfection study of 4-arm PRX analogues provided further insights into the role of multiple design features along the polymer structure. Our optimized PRXs exhibit the following characteristics, i.e., 4-arm PEG backbone with a molecular weight of 10 kDa, 2 out 4 arms protected, ~26 CD rings per PRX molecule, and ~6 amines per CD ring. We are aware of other design features yet to be optimized, including the type of cyclodextrin derivatives, the type of cationic functional groups, bulky end-caps with additional functionalities, etc. However, we decided to generate in vivo data at this point because the decision making of these parameters may require in vivo data input, including disease-specific considerations. The features of optimized 4-arm PRX were summarized in FIG. 20, panel A, and the self-assembly of PRX/plasmid was confirmed by AFM topographs. The polyplex nanoparticles formed by optimized 4-arm PRX and plasmid had a hydrodynamic size of 172±8.7 nm (PDI=0.18), with an average zeta potential of 15.3±3.2 mV.

Figure 20:
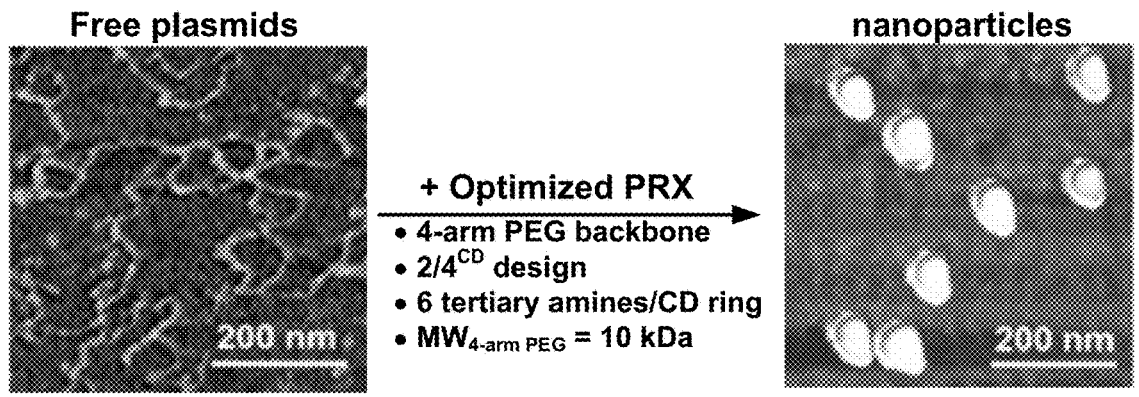
FIG. 20, panels A-D, show that optimized 4-arm PRX enhanced the PK and tumor biodistribution of Cy3-labeled plasmid after IV injection in mice. Panel A: The summary of physicochemical properties of the optimized 4-arm PRX. Representative AFM images of free plasmid (upper left) and plasmid after complexation with optimized 4-arm PRX (upper right). Scale bar represents 200 nm. Panel B: Evaluating the PK profile of Cy3-plasmid in C57BL/6 mice (n=3). Normal mice received single IV injection of Cy3-plasmid laden 4-arm PRX or linear PRX (5 mg plasmid/kg). Plasma was collected after 0.083, 1, 2, 4, 8 and 24 h, the Cy3-plasmid content were quantified by fluorescence spectroscopy and expressed as % total injected dose (% ID) per mL. The PK parameters were calculated by PKSolver software. Panel C: In a separate study, MC38 subcutaneous tumor bearing mice received single IV injection of Cy3-plasmid laden optimized 4-arm PRX or linear PRX (5 mg plasmid/kg). 24 h post IV injection, tumors and organs were collected for ex vivo IVIS imaging. The fluorescence intensity of Cy3-plasmid in different organs were quantitatively expressed by normalizing to saline-treated control (n=3). Panel D: In the same experiment, confocal microscopy confirmed higher intratumoral abundance of Cy-3 plasmid (red) delivered by 4-arm PRX, compared to linear PRX. The blood vessels (green) and nuclei (blue) at the tumor site were stained with CD31 and DAPI, respectively. Scale bar represents 100 µm. The results are expressed as mean±SD. *p<0.05.
Figure 20:
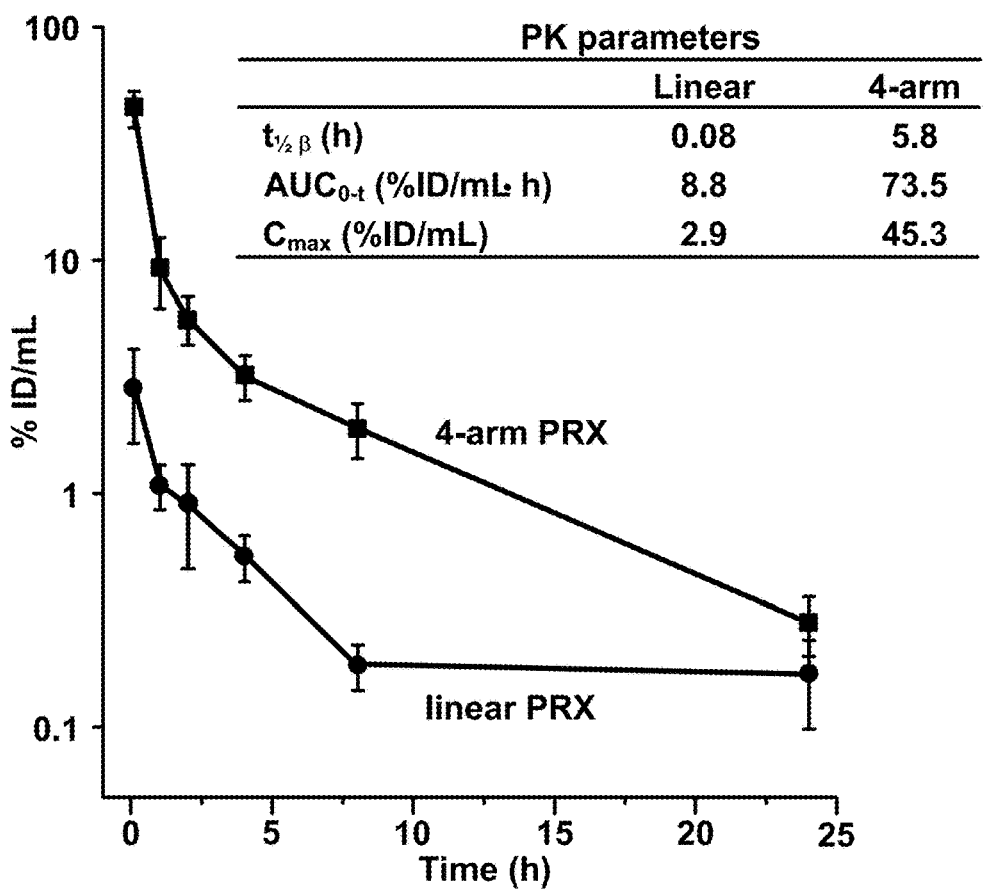
Figure 29:
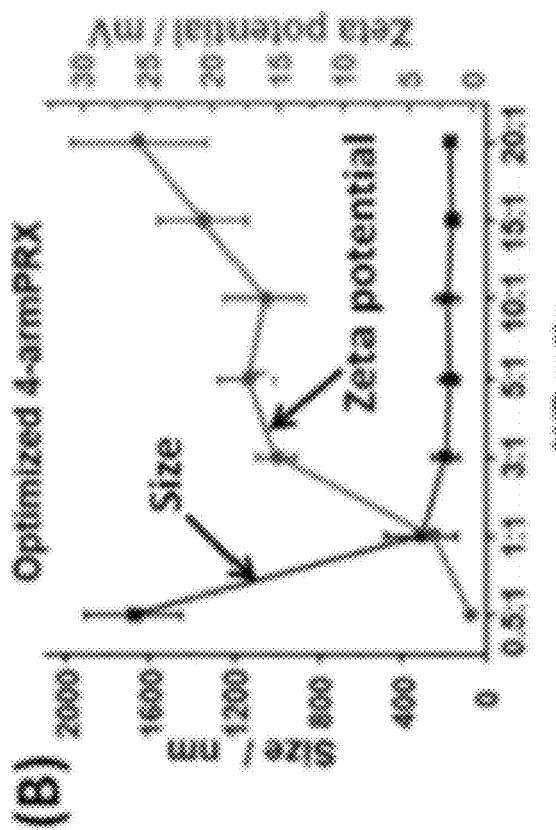
FIG. 29, panel A: DNA gel retardation assay of optimized 4-arm PRX ($2/4^{CD}$ 4-arm PRX with 10 kDa backbone, 6 cationic charge per CD) at various N/P ratios. Classic linear PRX was included for comparison.
Figure 29:
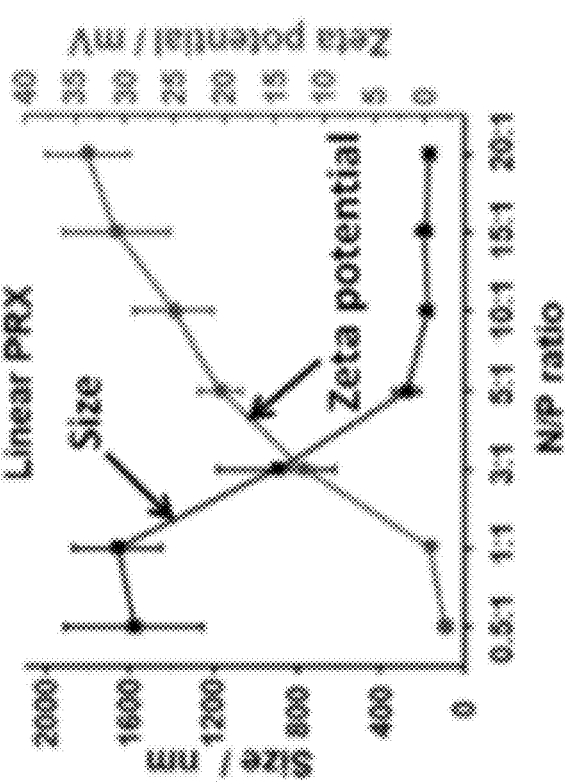
Figure 29:
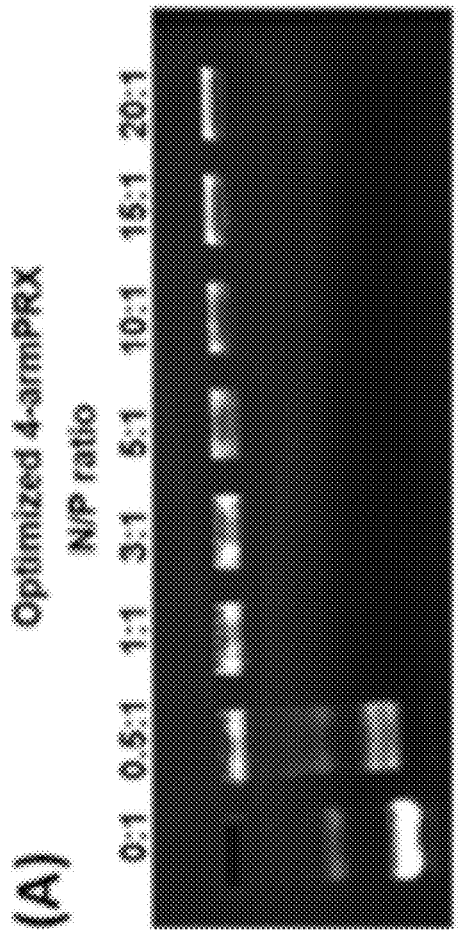
Figure 29:
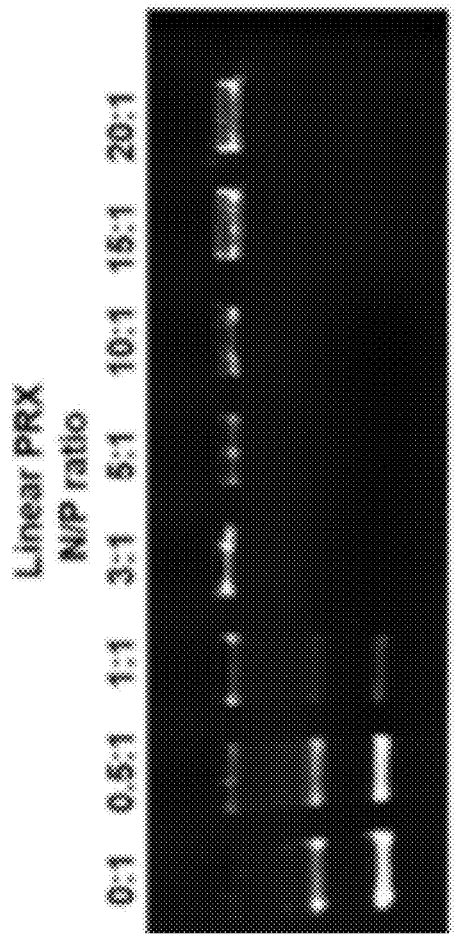
Figure 30:
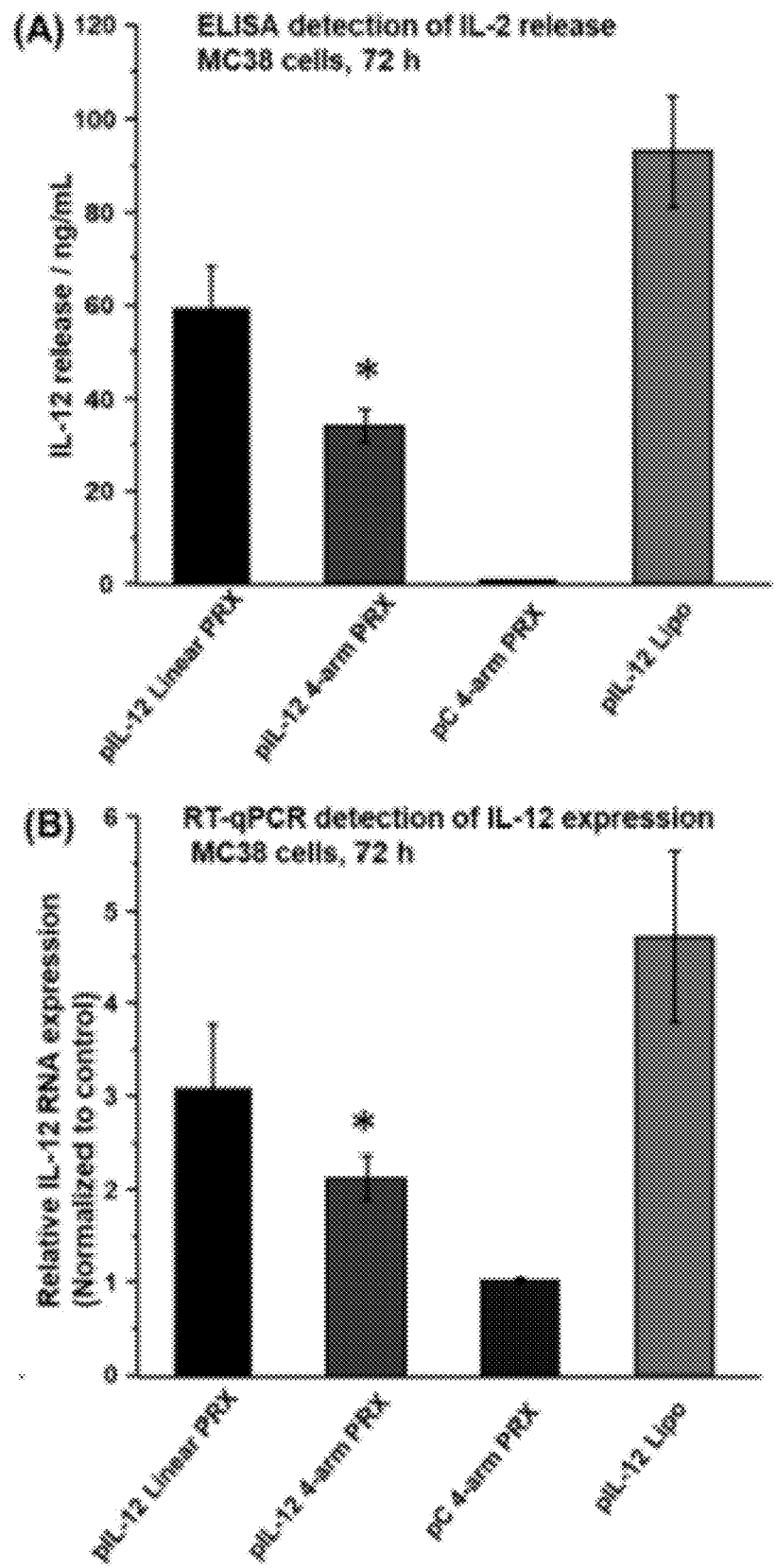
FIG. 30, panel A: MC 38 cells were incubated with pIL-12 laden optimized 4-arm PRX or linear PRX (1 μg plasmid/mL) for 72 h. pIL-12 complexed with Lipofectamine 2000 reagents were tested as positive control, and tdTomato plasmid (control plasmid, pC) laden 4-arm PRX was tested as non-functional negative control. Panel A: ELISA detection of IL-12 protein release in the cell culture supernatant.
Figure 31:
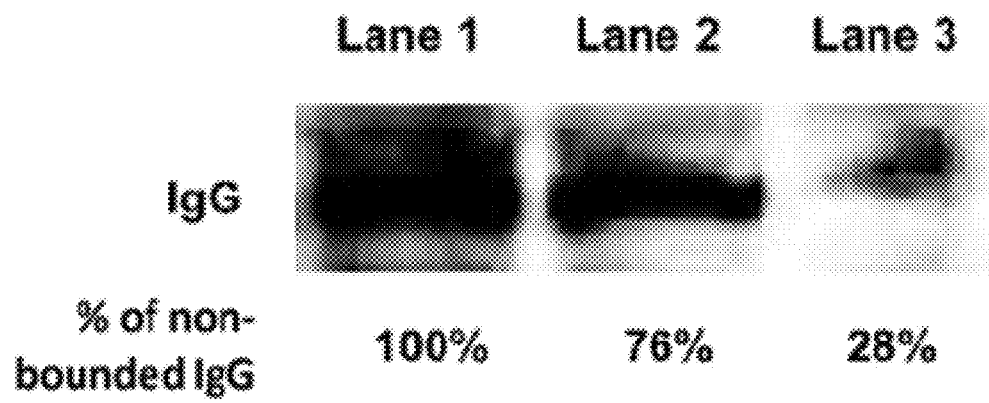
FIG. 31. Use of native gel electrophoresis to demonstrate 4-arm design is capable of interfering with nanoparticle opsonization. Mouse IgG (10 μg/μL) was incubated with pIL-12 laden 4-arm PRX or linear PRX for 30 min at 37° C., the concentration of plasmid was 1 μg/μL. After incubation, the samples were loaded into the gel at 40 μg IgG per lane. The electrophoresis condition was 150 V for 30 min. Only the non-bound IgG can migrate and be detected by silver staining in the gel. Image J was used to semi-quantify the free IgG in each group. While 76% free IgG was found in 4-arm PRX group, only 28% free IgG was detected in linear PRX. This suggested a prevention of nanoparticle opsonization due to the availability of PEG in the multi-arm PRX. Lane 1: Free IgG without nanoparticle; Lane 2: IgG incubated with 4-arm PRX (that led to 24% IgG binding and 76% free non-bound IgG); and Lane 3: IgG incubated with linear PRX (that led to 72% IgG attachment and 28% non-bound IgG).

Improved Pharmacokinetics (PK) and Biodistribution in Plasmid Delivery by 4-Arm PRX Compared to Linear PRX Nanocarrier In order to determine whether the 4-arm design improved the biodistribution and PK profile post IV injection, comparative analysis on PK parameters was performed in C57BL/6 mice. To quantify plasmid concentration in the blood, plasmid was covalently labeled by Cy3 fluorescent probe. Animals were IV injected with Cy3-plasmid laden 4-arm PRX at dose of 5 mg plasmid/kg (PRX dose: 15 mg/kg). The control is the nano assembly formed by linear PRX complexed with the same amount of plasmid, which exhibited similar level of gene packaging capabilities (FIG. 29) and in vitro transfection efficiency (FIG. 30). Plasma was collected at the indicated time points (0.083, 1, 2, 4, 8 and 24 h). The plasmid concentration in each sample was calculated based on the fluorescence intensity using plasmid standard curve, and expressed as total ID/mL (total injection dose per mL) (FIG. 20, panel B). The $1^{st}$ measurement at 0.083 h represents $C_{max}$. The PK parameters of each formulation were assessed using PKSolver software (Zhang et al. (2010) Comp. Meth. Prog. Biomed. 99: 306). When delivered by linear PRX, >90% ID/mL declined 5 min post injection, which can be reflected by AUC and $C_{max}$ results. This clearly contrasted with 4-arm PRX, which maintained an AUC of 73.5% ID/mL·h (compared to 8.8% ID/mL·h in the case of linear PRX). Four-arm PRX significantly prolonged the circulatory t/2 of plasmid from <0.083 h to 5.8 h in mice. To further corroborate this phenomena, we incubated plasmid laden 4-arm PRX or linear PRX with a representative opsonin protein (mouse immunoglobulin IgG) abiotically. Compared to linear PRX, native gel electrophoresis demonstrated significantly reduced IgG binding to 4-arm PRX nanoparticles (FIG. 31). However, we found the retardation of IgG by linear PRX, which suggested significant opsonization in biological solutions such as serum (Owens & Peppas (2006) Int. J. Pharmaceut. 307: 93). Presumably, the reduced interaction between 4-arm PRX particle and opsonin protein contributed to its prolonged circulatory t/2 and enhanced PK profile in vivo.

Figure 32:
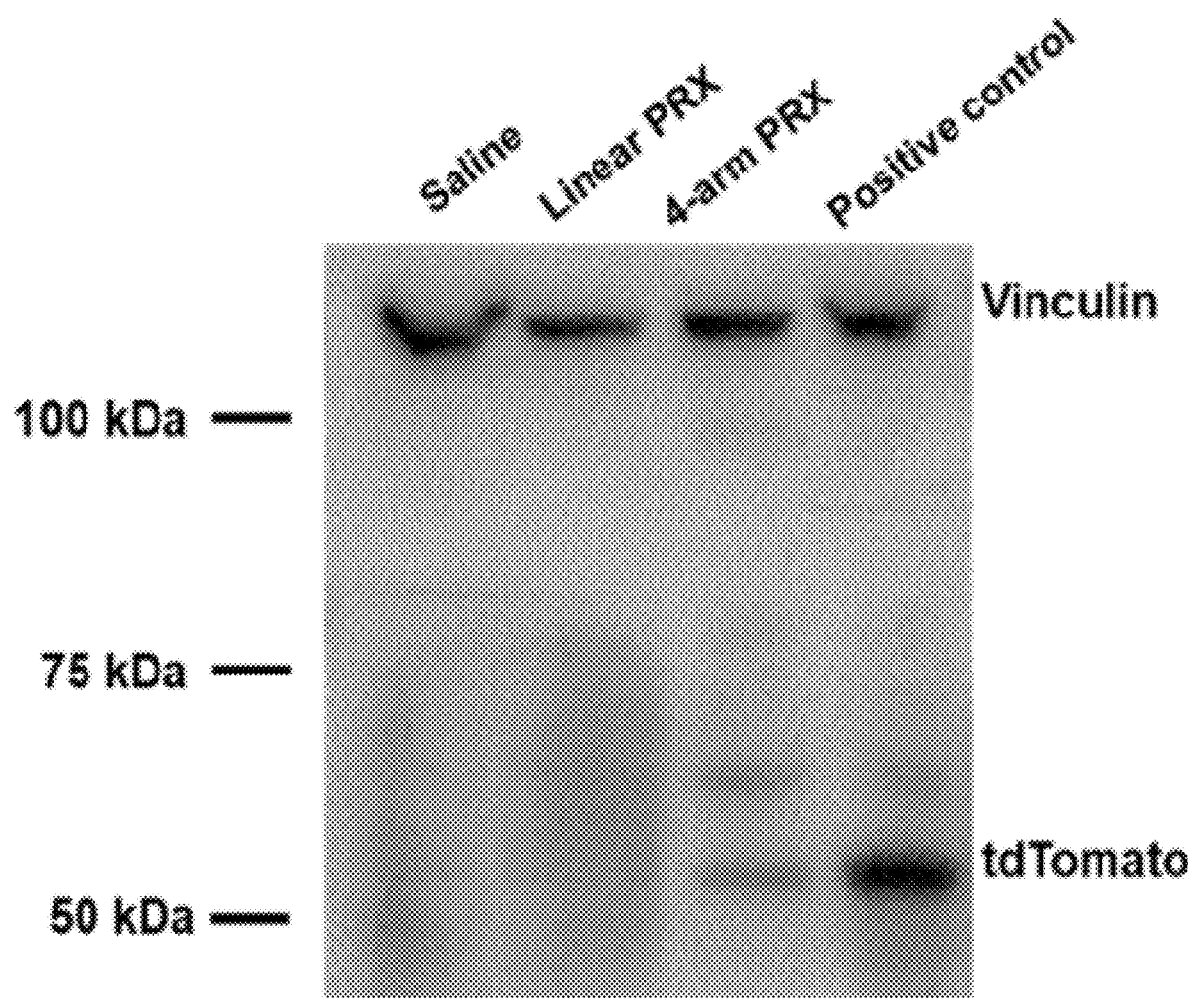
FIG. 32. Mice bearing MC38 subcutaneous tumors received single IV injection of tdTomato plasmid laden 4-arm PRX or linear PRX (5 mg plasmid/kg). 7 day post IV injection, the tumors were harvested for the detection of tdTomato reporter protein. Western blot detection of tdTomato protein from tumor tissue extracts treated by tdTomato plasmid laden 4-arm PRX or linear PRX. Saline treated tumor extract was tested as negative control. Lysate from MC38 cells transfected with tdTomato plasmid 4-arm PRX in vitro was tested as positive control. tdTomato plasmid delivered by 4-arm PRX IV, but not the linear PRX, led to tdTomato expression at tumor site.

The improved PK and prolonged $t_{1/2}$ prompted us to consider the use of such carrier for targeted gene delivery at solid tumor site, which is colon cancer in this case. It is generally believed that IV-injected nanoparticles tend to accumulate in solid tumor partially due to the abnormal tumor vasculature and enlarged tumor fenestration, a.k.a. enhanced permeability and retention (EPR) effect (Maeda et al. (2000) J. Control. Release, 65: 271). In order to determine whether the redesigned PRX carrier improves plasmid delivery and tumor targeting, imaging studies were performed in C57BL/6 mice model bearing subcutaneous MC38 tumor. To determine the biodistribution, ex vivo imaging of the tumors and major organs was performed 24 h post IV injection of Cy3-labeled plasmid PRX (FIG. 20, panel C). The radiance efficiency of labeled plasmid in tumors and other organs was quantified by IVIS software and normalized to control. The majority of plasmid delivered by linear PRX was entrapped in lung, the most typical off-target organ for cationic gene carrier (Morille et al. (2008) Biomaterials, 29: 3477), but barely distributed in tumor presumably due to non-specific binding and rapid clearance of opsonin-attached linear PRX particles (FIG. 20, panel B). However, when delivered by 4-arm PRX, minimized distribution in lung was observed (similar to control mice), and abundant plasmid uptake was shifted to the tumor site (FIG. 20, panel C). The liver was still a major site of plasmid distribution, a phenomena commonly observed for IV injected nanoparticles subjected to sequestration by Kupffer cells (Moghimi et al. (2001) Pharmacol. Rev. 53: 283). Hardly any plasmid was detected in the heart, spleen or kidney. The Cy-3 labelling of plasmid allowed the visualization of the abundance of plasmid at tumor site. To facilitate the interpretation on intratumoral particle distribution, the tumor blood vessels were stained with CD31 immunofluorescence (FIG. 20, panel D). We demonstrated higher plasmid abundance at the tumor site for 4-arm PRX. The CD31 staining suggested the plasmid laden 4-arm-PRX traveled from blood vessels and accessed the tumor tissue. In addition, perinuclear distribution of plasmid was confirmed. Furthermore, we performed an in vivo reporter transfection study with IV injected tdTomato plasmid laden 4-arm PRX and linear PRX in MC38 tumor bearing mice. Western blot identification of protein expression from tumor extracts was performed 7 days post injection (FIG. 32). As expected, hardly any tdTomato expression was detected in MC38 tumors receiving linear PRX. However, tdTomato signals were identified in 4-arm PRX treated tumor, which demonstrated the feasibility of systemic delivery of plasmid by 4-arm PRX that leads to successful protein expression at tumor site. Collectively, careful tuning of the free PEG moieties on 4-arm PRX effectively enhanced the PK profile and distribution, and did not significantly compromise gene packaging properties or transfection efficiency. Given this background, we continued to use this optimized 4-arm PRX for therapeutic IL-12 plasmid delivery in the same syngeneic MC38 colon cancer model.

Figure 21:
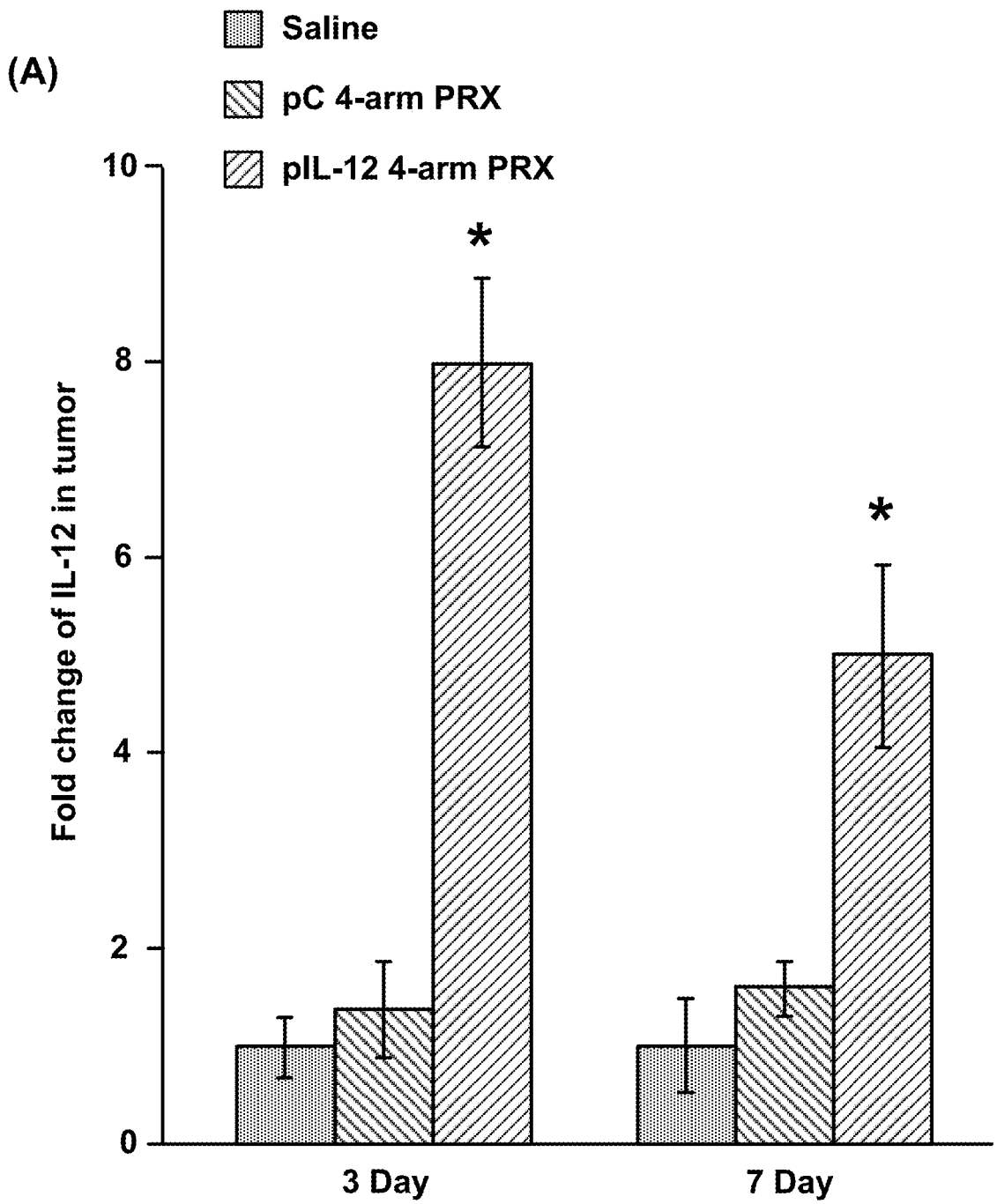
FIG. 21, panels A-E, shows that systemic delivery of a placmid encoding interleukin (pIL-12) by 4-arm PRX nanocarrier induced effective anti-colon cancer immunity in the MC38 tumor model. Panel A: MC38 tumor bearing mice received single IV injection of pIL-12 laden 4-arm PRX (5 mg plasmid/kg). ELISA detection of IL-12 protein in tumor extracts were performed 3 and 7 day post IV injection. Mice injected with pC laden 4-arm PRX (as non-functional control) were also tested as non-functional control (n=3). Panel B) MC38-luc bearing mice received repetitive IV injection of pIL-12 laden 4-arm PRX (5 mg plasmid/kg/injection). Interval IVIS imaging was used for monitoring tumor growth, which was quantitatively expressed according to the tumor signal at the operator-defined ROI (n=4). Representative bioluminescence images demonstrated the anti-tumor efficacy of pIL-12 laden 4-arm PRX. Panel C: The scheme for IL-12 mediated anti-tumor immunity, by activation of NK cells, CD8 T cells and anti-angiogenesis machinery in the tumor microenvironment. Panel D: MC38-luc bearing mice from the same experiment in panel B were sacrificed at day 21. The tumor cells were analyzed by multi-parameter flow cytometry to identify $CD45^+NK1.1^+$ and $CD45^+CD3^+CD8^+$ tumor infiltrating lymphocytes TILs. IFN-γ secreting TIL population ($IFN-γ^+CD45^+NK1.1^+$ and $IFN-γ^+CD45^+CD8^+$) were also determined (n=4). Representative IHC staining of IL-12, NK1.1, CD8 and IFN-γ in tumor section further demonstrated the concurrent innate and adaptive immuno-activation effect of pIL-12 4-arm PRX at the tumor site. Panel E: Immunofluorescence staining of CD31 (red) and quantitative display of $CD31^+$ blood vessel in tumor section confirmed the anti-angiogenesis effect of pIL-12 4-arm PRX. Scale bar represents 100 µm. The results are expressed as mean±SD. *p<0.05.
Figure 33:
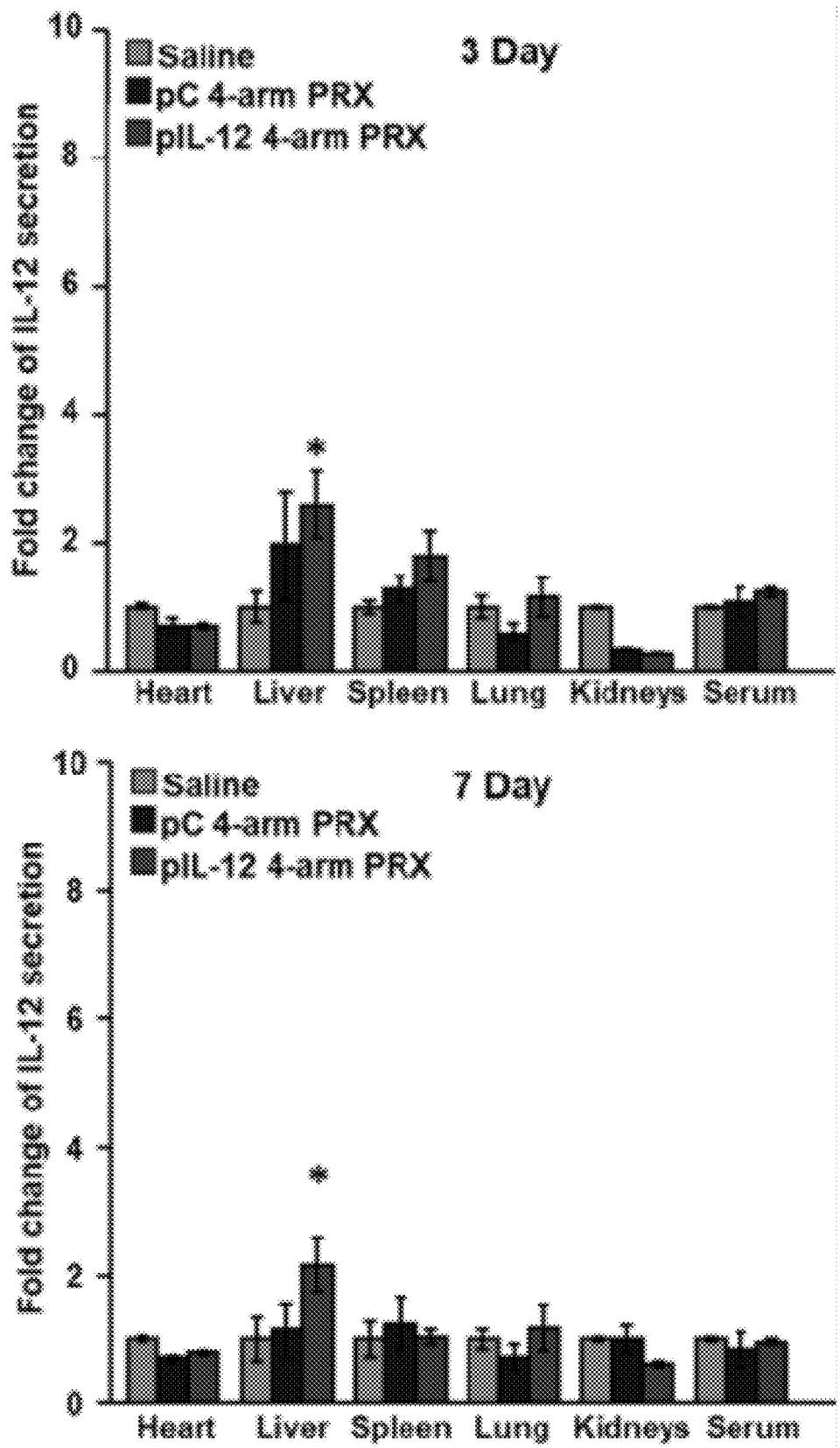
FIG. 33. Mice bearing MC38 subcutaneous tumors received single IV injection of pIL-12 laden 4-arm PRX or tdTomato plasmid (pC) laden 4-arm PRX (5 mg plasmid/kg). 3 or 7 day post IV injection, the tumors and major organs were harvested for the ELISA detection of IL-12 protein. The fold increase values of IL-12 protein in different organs were obtained by normalizing to saline treated control. Values represent the mean SD (n=3). Multiple injections of therapeutic dose of pIL-12 PRX led to minimal increase of IL-12 levels in serum as well as most organs. Interestingly, while a slight increase of IL-12 was found in the liver at day 7, we did not found abnormality in the liver panel of our blood chemistry analysis (FIG. 22, panel A). We surmise that the relatively low rate of IL-12 production in the liver may explain why low liver toxicity was seen in animals injected with pIL-12 laden PRX. This contrasts with the use of rIL12 protein in which the rapid buildup of the cytokine may overwhelm the hepatic metabolism capacity.

Systemic Delivery of Interleukinin-12 Plasmid by 4-Arm PRX Leads to Efficacious Anti-Tumor Effect Through Concurrent Activation of Innate and Adaptive Immunity To demonstrate the therapeutic impact of our PRX, we used the optimized carrier to deliver an IL-12 plasmid (pIL-12), which encodes a potent cytokine that bridges the innate and adaptive immunity in solid tumor, including colon cancer (Tugues et al. (2015) Cell Death & Diff 22: 237). IL-12 targets natural killer (NK) cells and T lymphocytes, effectively stimulating their activity and the secretion of IFN-γ (a cytokine coordinating anticancer defense) (Lasek et al. (2014) Cancer Immunol. Immunotherap. 63: 419). Moreover, IL-12 has proven to be very effective in various solid tumor models for both immunogenic (e.g., CT26 colon cancer (Melero et al. (1999) Gene Therap. 6: 1779), RENCA renal cancer (Brunda et al. (1993) J. Exp. Med. 178: 1223)) and poorly immunogenic tumor models (e.g., LLC lung cancer (Cui et al. (1997) Science, 278: 1623), B16 melanoma (Tahara et al. (1994) Canc. Res. 54: 182)) in mice. While there is high level of awareness and interest in using IL-12 for solid tumor treatment, practical use of IL-12 as a cancer therapy requires novel delivery mechanism because recombinant IL-12 (rIL-12) protein did not meet the successful criteria in patients because of serious side effects. The adverse effects in human and preclinical models include fatal pulmonary, hepatic, intestinal and hematopoietic toxicities (Car et al. (1999) Toxicol. Path., 27: 58). This seems to be true for both IP (Lenzi, ClinicalTrials.gov Identifier: NCT00003046, 2004) and IV (Carson, ClinicalTrials.gov Identifier: NCT01468896, 2011) administration of rIL-12 in solid tumor patients. An important lesson from rIL-12's failures is that IL-12 protein appears to elicit more potent antitumor responses when existing directly in the tumor whereabouts, rather than systemically (Lasek et al. (2014) Cancer Immunol. Immunotherap. 63: 419). To address the challenges in IL-12 immunotherapy, we investigated the IV-injectable 4-arm PRX as a delivery carrier for plasmid encoding IL-12 (pIL-12, MW=4.8 kbp, InvivoGen). The $1^{st}$ set of animal experiment is a short-term study, in which pIL-12 (MW=4.8 kbp, InvivoGen) laden 4-arm PRX was IV injected once (5 mg plasmid/kg) into mice bearing subcutaneous MC38 tumor. 3 or 7 days post single IV injection, tumors and major organs were harvested for ELISA detection of IL-12 (p70). At both time points, significantly enhanced IL-12 production was observed in PRX group compared to saline control at tumor site (FIG. 21, panel A). In most normal organs, such as spleen, lung, kidney and heart where rIL-12 leads to toxicity (Ryffel (1997) Clin. Immunol. Immunopath. 83: 18) no significantly elevated IL-12 was detected (FIG. 33). Importantly, IV pIL-12 PRX did not generate detectable IL-12 level in serum, which is crucial in reducing systemic off-target toxicity (Car et al. (1999) Toxicol. Path., 27: 58). With a view to elucidate any nonspecific IL-12 stimulation (presumably related to the general immunogenicity of bacteria-derived plasmid) (Dow et al. (1999) J. Immunol. 163: 1552), tumor mice receiving tdTomato plasmid laden 4-arm PRX (pC 4-arm PRX) were used as an additional control. Our data demonstrated that no significant secretion of IL-12 was found in tumors receiving IV pC laden PRX. This finding is in agreement with literature (Lohr et al. (2001) Canc. Res. 61: 3281). Moreover, the time-dependency of IL-12 expression at the tumor site provides the rationale for planning the injection regimen in the following proof-of-principle efficacy study.

Figure 34:
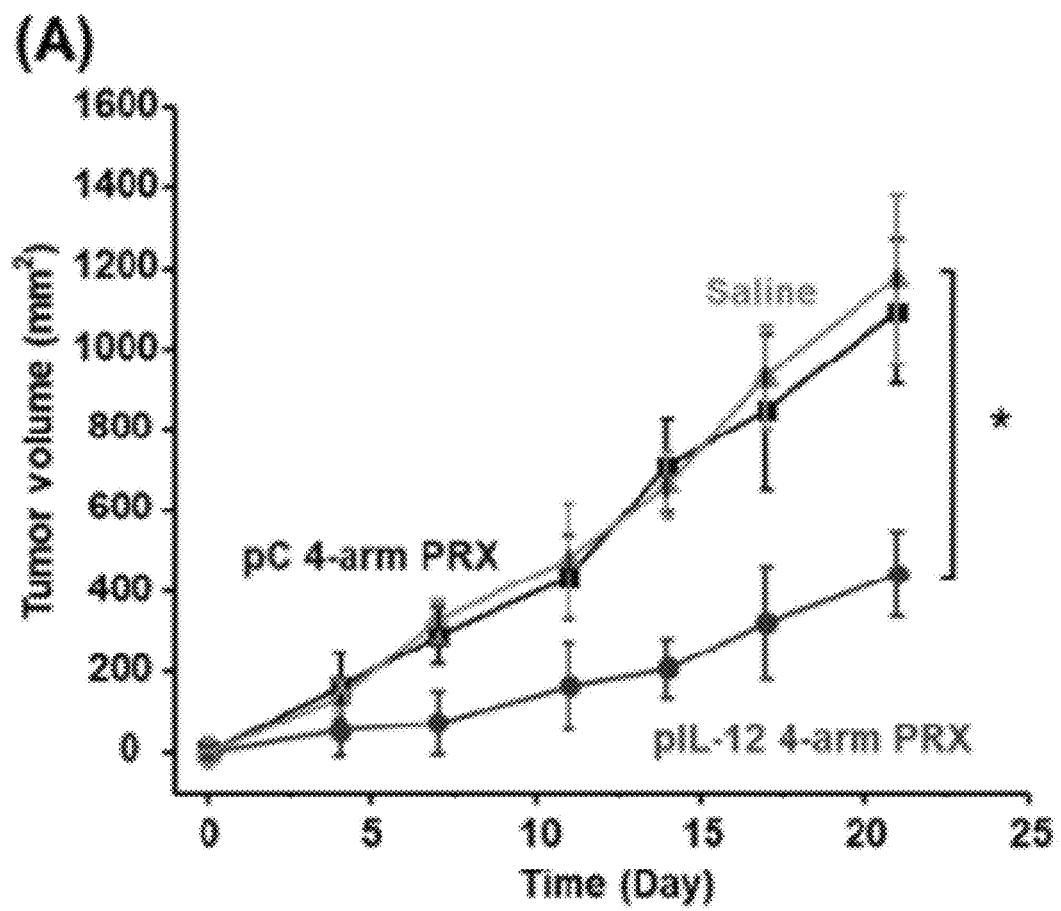
FIG. 34, panels A and B: Mice bearing MC38-luc subcutaneous tumors were IV injected with pIL-12 laden 4-arm PRX, as shown in FIG. 21, panel B. Panel A: After first injection, the tumor size were determined by caliper and plotted vs. time. Values represent the mean±SD (n=4). Panel B: Image of tumor tissues harvested on day 21.
Figure 34:
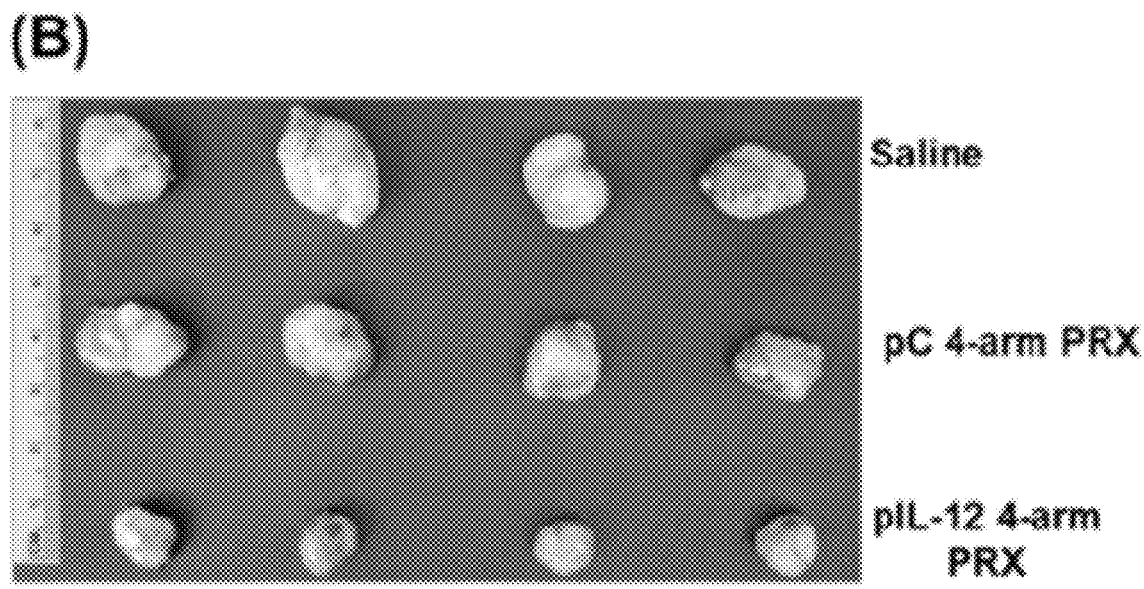

For the anti-tumor efficacy study, we subcutaneously implanted luciferase-expressing MC38-luc cells to C57BL/6 mice. Following tumor growth to 5-8 mm in size, the mice received IV injections of 5 mg plasmid/kg twice per week, 5 injections in total (FIG. 21, panel B). Control mice received IV injection with saline or pC laden 4-arm PRX. Tumor growth was monitored in situ by IVIS bioluminescence imaging (FIG. 21, panel B), followed by euthanization of animals on day 21. Quantitative expression of tumor growth by IVIS (the intensity of tumor signals normalized to day 1), demonstrated significantly slower tumor growth when treated by pIL-12 laden 4-arm PRX, compared to saline or pC controls. Representative tumor images after euthanizing the animal on day 21 (FIG. 34) further revealed the anti-tumor effect.

Figure 35:
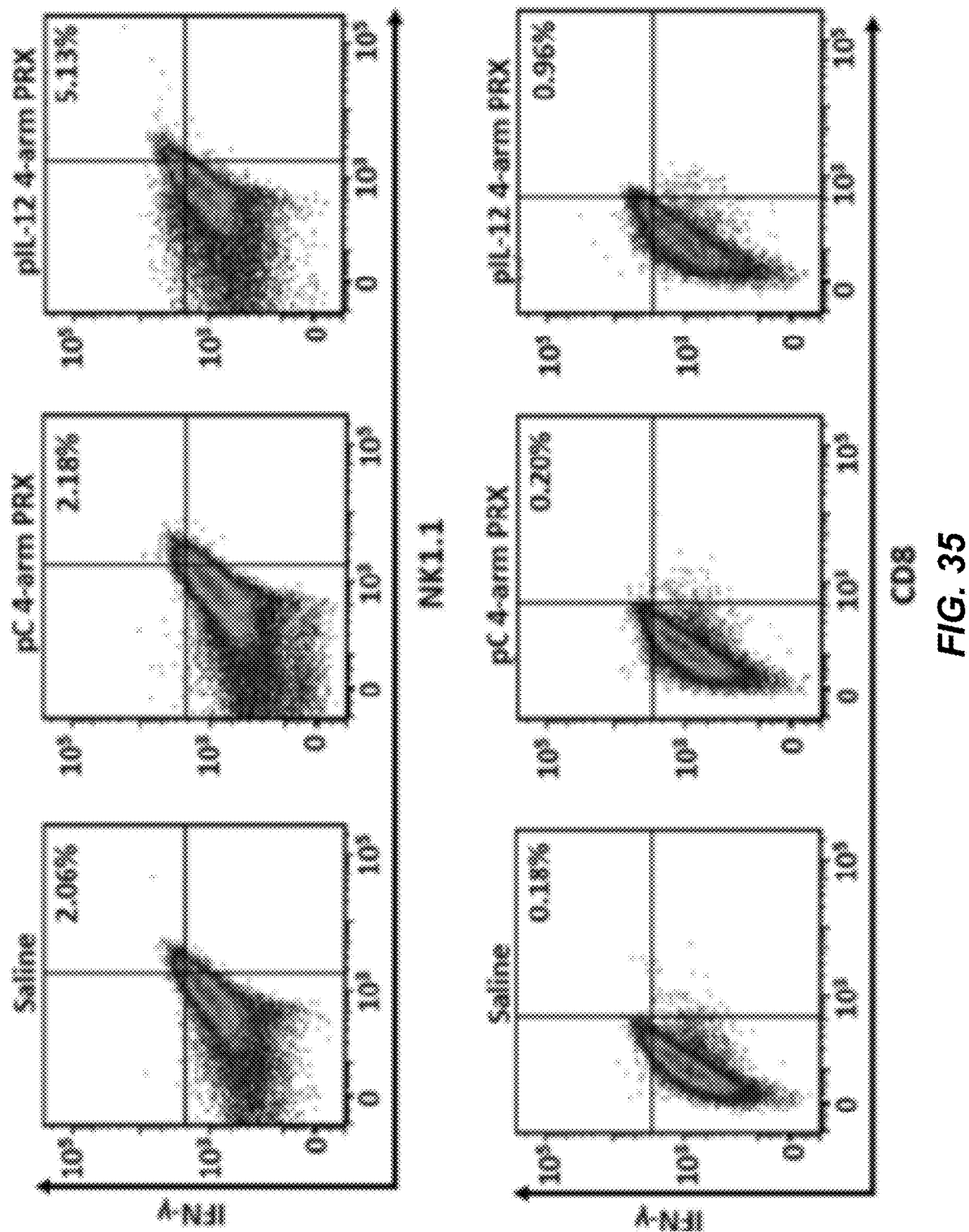
FIG. 35 shows representative raw flow cytometry data of single cell suspensions prepared from MC38 tumors on day 21 in the study of anti-tumor efficacy, as shown in FIG. 21, panel D. Representative images from cell populations were gated with: IFN-γ+CD45+NK1.1+, IFN-γ+CD45+CD8+, CD45+NK1.1+, and CD45+CD3+CD8+.
Figure 36:
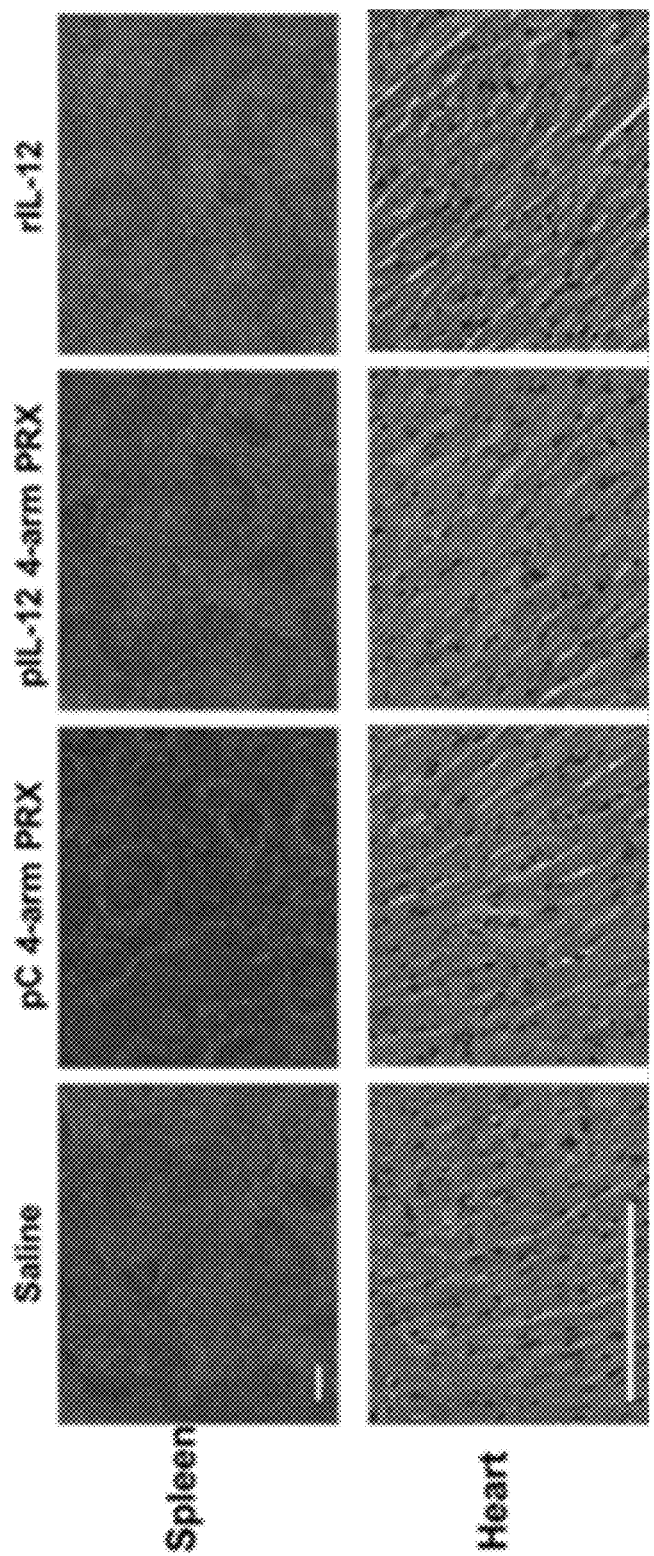
FIG. 36 shows representative H&E staining of heart and spleen tissue harvested from C57BL/6 mice on day 21. The mice received IV injection of pIL-12 or pC laden 4-arm PRX, 5 mg plasmid/kg/injection, 5 injections in total, as shown in FIG. 22, panel B. Organs from mice receiving IV injection of recombinant IL-12 (rIL-12) (100 μg/kg/injection, the same injection frequency as 4-arm PRX) were also studied as control. Scale bar represents 200 μm.
Figure 37:
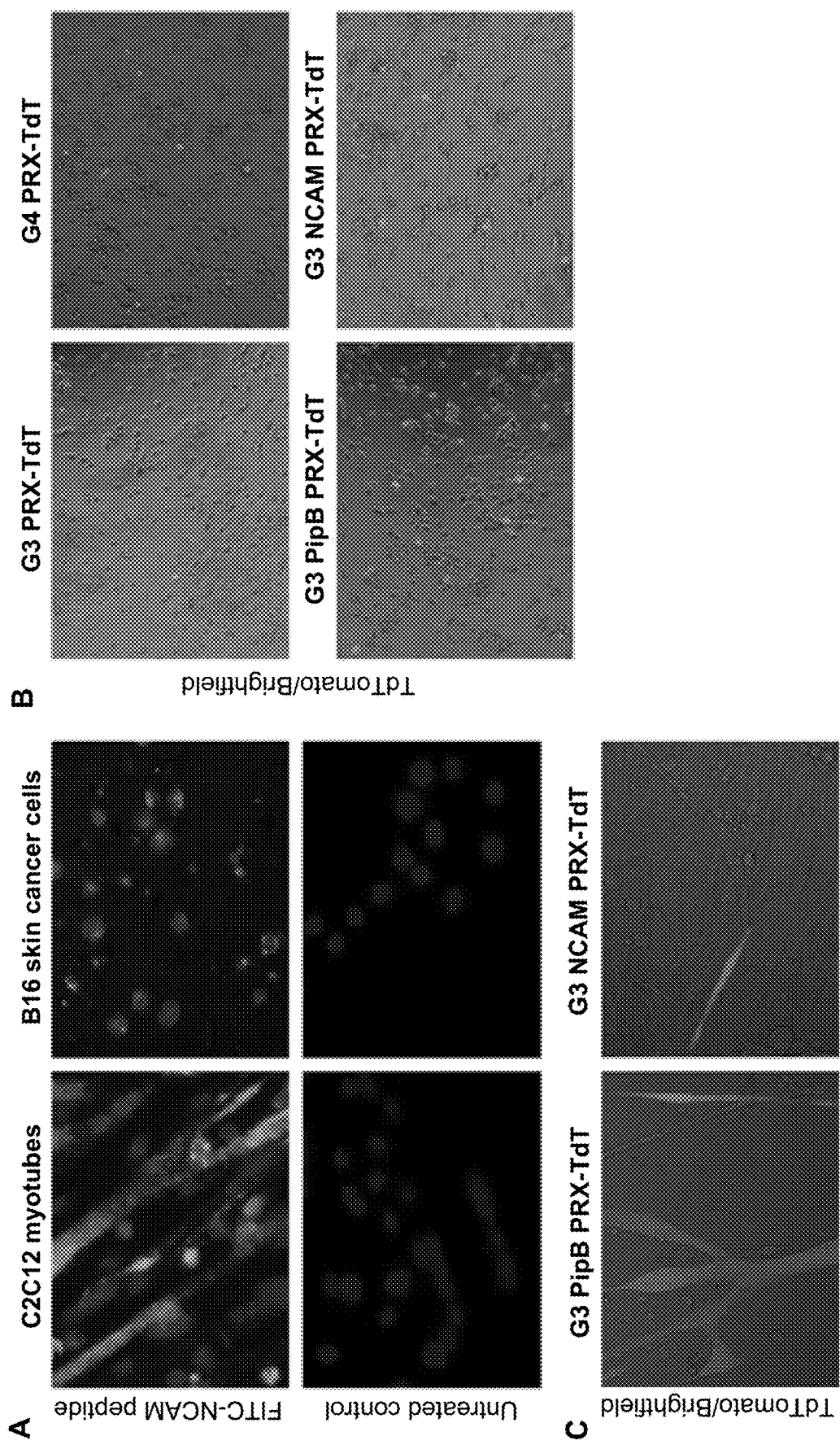
FIG. 37, panels A-C, shows that peptide conjugated PRXs demonstrate improved delivery of a reporter plasmid in muscle cells in vitro. Panel A: Imaging of an NCAM peptide labeled with FITC added to C2C12 myotubes or B16 skin cancer cells for 6 hrs. There is increased binding of the peptide on the C2C12 cells compared to the controls, demonstrating successful peptide binding to NCAM. Panel B: Imaging of G3, G4 and peptide conjugated G3 PRXs carrying a TdTomato (TdT, red) reporter plasmid in hDMD del45 myoblasts 48 hrs after administration. Both peptide conjugated versions demonstrate a higher percentage of TdTomato+ cells (~70 fold higher than unconjugated). Panel C: Imaging of peptide conjugated G3 PRXs carrying a TdTomato reporter plasmid in hDMD del45 myotubes 24 hrs after administration, demonstrating successful delivery.
Figure 38:
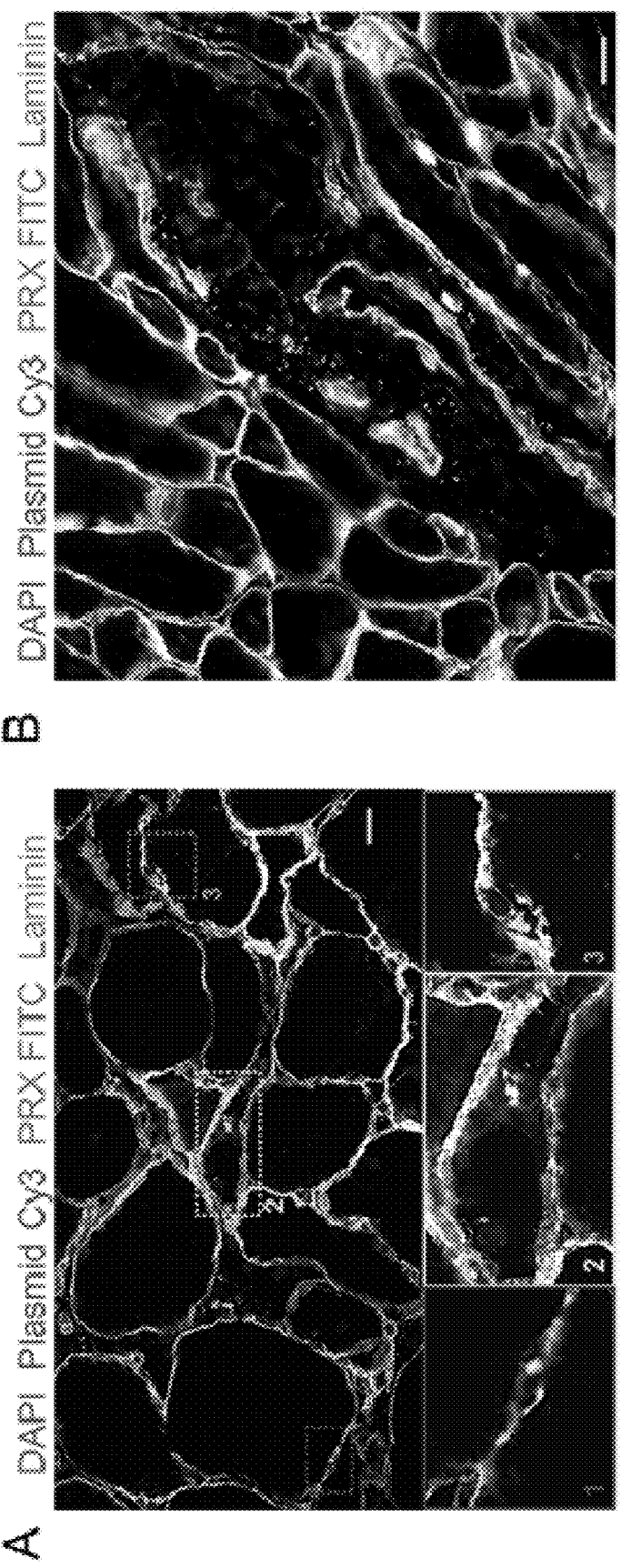
FIG. 38, panels A and B, show that PRX nanoparticles appear trapped in the basal lamina or ECM after in vivo delivery. Panel A: Imaging of quadriceps muscle 24 hrs after i.v. administration of G4 PRX where the nanoparticle is labeled with FITC (green), the cargo with Cy3 (red) and the fibers stained with laminin (grey). No particles are found within fibers and many appear to be trapped in the basement membrane marked by laminin near nuclei, that could be myonuclei, satellite cells or other interstitial cells (insets 1 and 3). Inset 2 highlights PRXs found within a blood vessel. Scale bar 20 μm. Panel B: Imaging of interosseous muscle 24 hrs after footpad injection of G3 PRX where the nanoparticle is labeled with FITC (green), the cargo with Cy3 (red) and the fibers stained with laminin (grey). No particles are found within fibers and they appear to be trapped in the interstitial space. Scale bar 20 μm.
Figure 39:
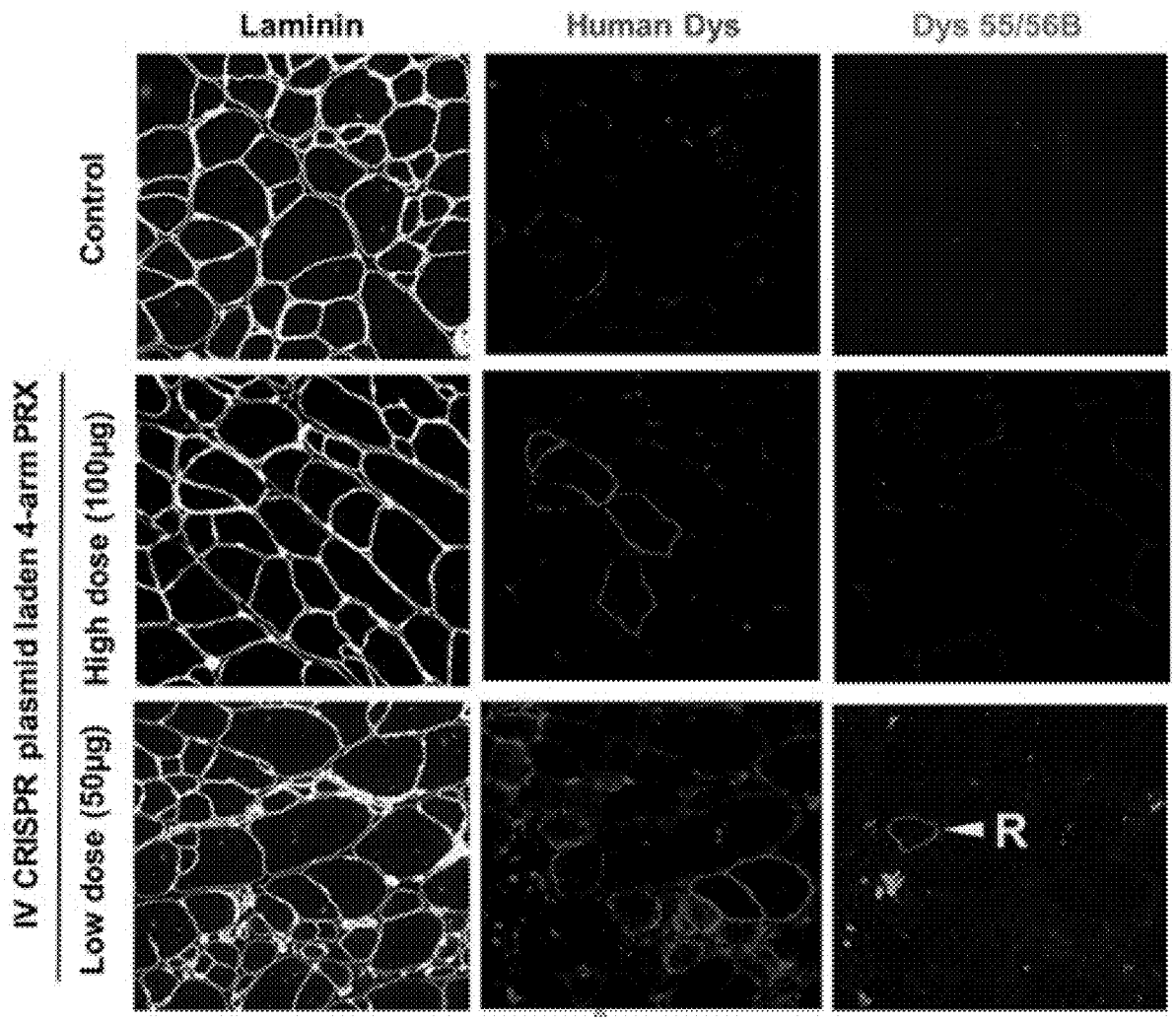
FIG. 39, illustrates detection of dystrophin positive fibers after systemic administration of nano-CRISPR. Shown are micrographs taken of hDMD del45 mdx quadriceps muscle cross sections stained with laminin (white), human dystrophin (red) or mouse/human dystrophin targeting exons 55/56. The latter antibody is used to identify revertant fibers ("R"). Animals were treated with 4 injections of G3-PRX carrying the pX333 CRISPR platform targeting exons 45-55 and harvested 5 weeks later.

Shown in the schematic FIG. 21, panel C, as a potent inducer of anti-tumor immunity, IL-12 directly augments the proliferation and cytolytic potential of NK cells and promotes the development of $CD8^+$ T cells in tumor microenvironment, including colon cancer (Caruso et al. (1996) Proc. Natl. Acad. Sci. USA, 93: 11302). In addition, the anti-angiogenesis function by IL-12 contributes pivotally to the tumoricidal efficacy (Colombo & Trinchieri (2002) Cytokine & Growth Factor Rev. 13: 155). To dissect the immunomodulatory effect elicited by IL-12 expression, the tumor tissues (day 21) were used for IHC and multi-parameter flow cytometry analysis (Lu et al. (2017) Nat. Comm. 8: 1811). IHC staining for CD8, NK1.1 and IFN-$\gamma^+$ showed that pIL-12 laden 4-arm PRX resulted in significantly enhanced recruitment of $CD8^+$ T cells along with NK cells (FIG. 21, panel D). These findings were corroborated by flow cytometry (FIG. 21, panel D and FIG. 35), suggesting that pIL-12 4-arm PRX enhanced the $CD45^+CD3^+CD8^+$ TILs populations (by 1.8-fold) and $CD45^+NK1.1$ populations (by 4-fold) compared to saline or pC treated groups. As a central effector in IL-12-mediated anti-tumor immunity, significantly increased IFN-γ release was revealed by IHC staining of pIL-12 4-arm PRX treated tumor section (FIG. 21, panel D). Phenotypic identification of $CD45^+CD8^+IFN-\gamma^+$ and $CD45^+NK1.1^+IFN-\gamma^+$ population suggested the recruited NK cells and $CD8^+$ T cells were the sources for IFN-$\gamma^+$ production. Furthermore, immunofluorescence staining of $CD31^+$ blood vessels (FIG. 21, panel E), demonstrated distinct anti-angiogenesis effect in tumor sections treated by pIL-12 laden 4-arm PRX.

pIL-12 Laden 4-Arm PRX Improves Toxicity Profiles in Mice Compared to rIL-12

The major reason for the rIL12 failure is its safety issue, which is a key concern for IL-12 immunotherapy. Rapid buildup of rIL12 systemically leads to significant toxicity, including a severe impact on hepatic serum enzymes, leukopenia, pulmonary edema and interstitial macrophage infiltrates in lung tissues, etc (Car et al. (1999) Toxicol. Path., 27: 58). The possibility of reducing IL-12 toxicity by encapsulated plasmid delivery is one of the major objectives of this study. In order to address IL-12 toxicity through IV plasmid delivery, in a separate experiment, we performed IV injections following exactly the same treatment regimen as the tumor inhibition study in normal C57BL/6 mice. We preferred normal mice in this case because the late stage tumor burden may introduce a large standard deviation within the same group, leading to complexity for data interpretation. The pIL-12 laden PRX did not elicit adverse effects after repetitive IV injections in the most parameters in the blood biochemistry measurement, such as liver function enzymes (e.g., AST, ALT, ALP), kidney panel (BUN and creatinine) at both 7 days and 21 (FIG. 22, panel A). Transit and moderate decrease of white blood cells, lymphocytes and neutrophils were observed in mice receiving pIL-12 4-arm PRX on day 7; however, these abnormalities were reversible at day 21 without medication. For comparison, we also included IV injection of rIL-12 at a rodent therapeutic dose (100 µg/kg) in the literature (Brunda et al. (1993) *J. Exp. Med.* 178: 1223). This allowed for the demonstration of severe and extensive abnormalities in multiple organs in animals treated with rIL-12, similar to the side effects in the human (Leonard et al. (1997) *Blood,* 90: 2541). Different from pIL-12 PRX, rIL-12 induced adverse changes were persistent, up to 21 days post treatment. Moreover, major organs, such as the lung, kidneys, heart and spleen were collected from the same safety animal experiment. Animals receiving treatment with rIL-12 showed sign of pulmonary toxicities, such as pulmonary edema and interstitial thickening in H&E staining of lung section (FIG. 22, panel B). In contrast, no damage was seen in the lungs of animals treated with saline and pIL-12 laden PRX. In rIL-12 group, histological assessment of kidney tissues showed glomerular swelling and edema of Bowman's space in the glomeruli of the kidneys (FIG. 22, panel B). However, this histological alteration was not found in other groups or accompanied by urea and electrolyte disturbances.

For IL-12, there is continuous interest and critical need to improve PK and safety, with a hope to practically implement safe and efficacious cancer immunotherapy. Other strategies have immerged including developing tumor-targeting IL-12 derivatives (NHS-IL-12) (Fallon et al. (2014) *Oncotarget,* 5: 1869) and IL-12 gene therapeutics (Hemandez-Alcoceba et al. (2016) *Immunother.* 8: 179). GEN-1 (Thaker et al. (2017) *Gynecologic Oncol.* 147: 283) formulated with IL-12 plasmid and PEG-PEI-cholesterol lipopolymer, is designed for IP administration in ovarian cancer. Unlike ovarian cancer that primarily disseminates within the peritoneal cavity with massive ascites (Lengyel (2010) *Am. J Pathol.* 177: 1053), colon cancer is a deep-seated solid tumor that metastasizes to lung and liver (Sadahiro et al. (2014) *J. Clin. Oncol.* 43: 444; Leake (2014) *Nat. rev. Gastroentrol.* & *Amp Hepatology,* 11: 270). While local injection of IL-12 might lead to systemic anti-cancer immunity, safe and effective IV-injectable formulation is still the preferred route for pIL-12 delivery from tumor targeting perspective (Hallaj-Nezhadi & Lotfipour (2010) *J. Pharm. Pharm. Sci.* 13: 472). Further studies are needed to investigate the capability of metastasis management.

While our current formulation (that relies on passive targeting principle to biodistribute at colon cancer site) has led to promising data, we can also include tumor targeting ligand such as iRGD peptide (Liu et al. (2017) *J. Clin. Invest.* 127: 2007). However, we also consider the design complexity and the cost increase of each component in terms of clinical application. Moreover, preclinical and clinical data have suggested the benefit of IL-12 combination because repeated IL-12 dosing may activate various immunosuppressive mechanisms (Lasek & Zagozdzon, in *Interleukin 12: Antitumor Activity and Immunotherapeutic Potential in Oncology,* Springer, 2016, 43). Thus, it is also interesting to look at the effect of pIL-12 PRX monotherapy or combined with treatments such as other cytokines (e.g., IL-2) (Addison et al. (1998) *Gene therapy,* 5: 1400), neoadjuvant chemotherapeutic agents (e.g., oxaliplatin, doxorubicin and paclitaxel) (Kayashima et al. (2010) *J. Immunol.* 185: 698) and checkpoint inhibitors (e.g., anti-PD-1, anti-PD-L1, anti-CTL4 and IDO inhibitors) (Fallon et al. (2017) *Oncotarget,* 8: 20558).

The multifunctional properties of multi-arm PRX can be further tuned to accommodate different clinical needs. In Scheme 1 (see FIG. 23), we included the list of structural design features and their possible impacts. Fine-tuning of cationic entities and their spatial arrangement, as well as other components along PRX structure, can make this delivery platform available for multiple APIs, including large plasmid (e.g., CRISPR/Cas9 plasmid for gene editing). However, while the use of multi-arm PRX platform is practical for these purposes, it is necessary to consider the disease-specific complexity that may require extra optimization and re-design of the carrier.

To conclude, we have established a multi-functional multi-arm PRX platform that is suitable for systemic nucleic acid delivery in vivo. Our comprehensive biodistribution and PK analyses demonstrated the spatially selective design of inclusion complexation of CD rings in multi-arm PRX polymer maintains appropriate degree of PEGylation, which play a key role for the improved t/2 and bioavailability. When delivering a pIL-12 plasmid to a colon tumor site, we also demonstrated a protective and effective plasmid self-assembly, which led to efficacious and safe immunogene therapy at intact animal level.

Materials and Experimental Methods

Materials

α-Cyclodextrin, triethylamine (TEA), Z-L-tyrosine, Benzotriazol-1-yl-oxy-tris(dimethylamino) phosphonium hexafluorophosphate (BOP), 1-hydroxybenzotriazole (HOBt,) N,N-diisopropylethylamine (DIEA), 1,1'-carbonyldiimidazole (CDI), N,N-dimethylethylenediamine (DMAE), dimethylformamide (DMF), dimethyl sulfoxide (DMSO) were purchased from Sigma Aldrich. Four-arm PEG tetra-amine hydrochloride salt with different molecular weight (5 kDa, 10 kDa or 20 kDa) and linear PEG-diamine hydrochloride salt (3.5 kDa) were purchased from Jen Kem Technology. NHS-fluorescein and Snakeskin dialysis tubing (MWCO=3.5 kDa or 10 kDa) were purchased from Thermo Fisher. Plasmid pUNO1-mIL12 (p40p35) (designated as pIL-12) encoding mouse IL-12 p70, was provided by InvivoGen. Plasmid encoding tdTomato reporter protein was provided by Addgene (Addgene plasmid 30530). Matrigel™ matrix basement membrane was purchased from BD Bioscience, USA. Centrifugal filter units (MWCO=3 kDa, 10 kDa, 100 kDa) were purchased from EMD Millipore.

Synthesis of 4-Arm PRX Analogues

4-Arm-PEG Backbone with End-Caps.

4-arm PEG tetra-amine hydrochloride salt 10 kDa (103 mg) was dissolved in DMF (5 mL) with TEA (6 mg) before NHS-fluorescein was added and stirred at room temperature for 24 h. The amount of NHS-fluorecein was manipulated to achieve different number of fluorescein end-caps, i.e., 4.7 mg NHS-fluorecein for 1-occupied 4-arm PEG amine (4-arm PEG:NHS-fluorescein=1:1 molar ratio), 9.5 mg NHS-fluorecein for 2-occupied 4-arm PEG amine (4-arm PEG:NHS-fluorescein=1:2 molar ratio) and 14.2 mg NHS-fluorecein for 3-occupied 4-arm PEG amine (4-arm PEG:NHS-fluorescein=1:3 molar ratio), respectively. The resulting solution was precipitated in cold diethyl ether, dissolved in DI water and purified by repeated washing with DI water in centrifugal filter units (MWCO=3 kDa), and lyophilized (Labconco FreeZone). To detect the average molecular weight after modification, 4-arm PEG amine compounds with different number of fluorescein end-caps were dissolved in THF/H$_2$O (1:1, v/v) at a concentration of 10 mg/mL for MALDI-TOF (Bruker Ultraflex). Fluorescein occupied 4-arm PEG amine compounds were dissolved in deuterated water for $^1$H-NMR spectroscopy.

4-Arm Polypseudorotaxane.

Fluorescein occupied 4-arm PEG amine (100 mg) was added to a saturated solution of α-CDs (1.01 g in 7 mL of DI water) and stirred at room temperature for 24 h, resulting in supramolecular polypseudorotaxane formed from α-CDs threading onto 4-arm PEG backbone. The precipitate was collected via centrifugation at 3,000 rcf for 10 min and lyophilized to obtain 4-arm polypseudorotaxane as yellow powder.

4-Arm Polyrotaxane.

To prevent the de-threading of α-CDs, bulky end caps (Z-tyrosine) were further introduced to 4-arm polypseudorotaxane. An example was given here for $2/4^{CD}$ 4-arm polypseudorotaxane preparation. Z-L-tyrosine-OH (126 mg), HOBt (54 mg), BOP (177 mg) and DIEA (69 µL) were dissolved in 2.5 mL anhydrous DMF. 370 mg polypseudorotaxane was then added and the reaction was stirred at room temperature for 24 h. The mixture was precipitated in 50 mL diethyl ether, and sequentially washed by acetone (50 mL), methanol (50 mL) and DI water (15 mL). Each washing steps were 2 h at room temperature under constant stirring and the precipitate was collected via centrifugation at 3,000 rcf for 10 min. After the last washing step, the 4-arm polyrotaxane was lyophilized. $^1$H-NMR was performed in DMSO-$d_6$ to characterize the product.

4-Arm Polyrotaxane-DMAE.

An example was given here for the synthesis of $2/4^{CD}$ 4-arm PRX with 6 amines per CD. Z-L-Tyrosine capped $2/4^{CD}$ 4-arm polyrotaxane (100 mg) was dissolved in dry DMSO (2 mL). CDI (364 mg, 30 molar excessive to α-CDs) was added and the reaction was stirred for 3 h under nitrogen atmosphere. DMAE (1 mL) was then added dropwise to the solution, and the reaction was further stirred overnight at room temperature. The resulting mixture was precipitated in diethyl ether, and washed sequentially by acetone (50 mL) and methanol (50 mL). Each washing steps were 2 h at room temperature under constant stirring and the precipitate was collected via centrifugation at 3,000 rcf for 10 min. The precipitate was redissolved in DI water and dialyzed against DI water for 72 h (MWCO=3 kDa). The final product of 4-arm PRX was lyophilized as yellow powder. The density of amine functionalization on α-CD was manipulated via tuning the feed ratio between CDI and α-CDs in 4-arm polyrotaxane. CDI at 5 molar excessive to α-CDs resulted in 4-arm PRX with 1 amine group per CD, and CDI at 20 molar excessive to α-CDs resulted in 3 amine groups per CD, respectively. The purified 4-arm PRX was lyophilized and $^1$H-NMR characterization was performed in deuterated water to characterize the product. In addition, $2/4^{CD}$ 4-arm polyrotaxane-DMAE with 5 kDa or 20 kDa 4-arm PEG backbone were synthesized, following the same procedures and molar ratio between reactants for $2/4^{CD}$ 4-arm polyrotaxane-DMAE (6 amines per α-CD) with 10 kDa backbone.

Synthesis of Linear PRX

The synthesis of linear PRX was performed as previously reported (Yamashita et al. (2006) *Nat. Protocol.* 1: 2861). 100 mg of linear PEG-diamine hydrochloride salt (3.5 kDa) was dissolved in a saturated solution of α-CDs (1.01 g in 7 mL of DI water) and stirred for 24 h at room temperature to give linear polypseudorotaxane as white precipitate. The precipitate was collected via centrifugation at 3,000 rcf for 10 min and lyophilized. The lyophilized white powder (190 mg) was then dissolved in a mixture solution of Z-L-tyrosine-OH (82 mg), HOBt (35 mg), BOP (115 mg) and DIEA (45 µL) in 0.5 mL anhydrous DMF. The reaction was stirred at room temperature for 24 h. The mixture was precipitated in 50 mL diethyl ether, and sequentially washed by acetone (50 mL), methanol (50 mL) and DI water (50 mL). The dried precipitate (108 mg) was dissolved in 2 mL dry DMSO and CDI (300 mg) was added. The reaction was stirred for 3 h under nitrogen atmosphere. DMAE (1 mL) was then added dropwise to the solution, and the reaction was further stirred overnight at room temperature. The resulting mixture was precipitated in diethyl ether and washed in succession in acetone (50 mL), methanol (50 mL). The precipitate was redissolved in DI water, dialyzed against DI water for 72 h (MWCO=3 kDa) and lyophilized to result in linear PRX.

Physicochemical Characterization of Plasmid Laden 4-Arm PRX

The size and ζ-potential of plasmid laden 4-arm PRX were measured by a ZETAPALS instrument (Brookhaven Instruments Corporation), with an equivalent plasmid concentration of 1 µg/mL. The morphology of plasmid laden 4-arm PRX was visualized by atomic force microscope (AFM). Plasmid laden 4-arm PRX was directly added to mica substrate (1 cm×1 cm), and free plasmid was premixed with 5 mM $MgCl_2$-HEPES buffer before addition to mica substrate. The equivalent concentration of plasmid was 0.2 µg/mL. The samples were dried with nitrogen gas and imaged on Bruker Dimension FastScan AFM. DNA gel retardation assay was performed with Precast agarose gel (Sigma Aldrich). Plasmid DNA was complexed with 4-arm PRX analogues in multiple N/P ratio, with a constant plasmid concentration of 50 µg/mL. Samples were loaded in gel loading buffer (Sigma Aldrich), running in TBE buffer at 50 V for 30 min, followed by visualization on gel imaging system (MultiImage II AlphaImager HP, Alpha Innotech).

In Vitro Cell Culture and Transfection

To facilitate bioluminescence imaging of tumor growth, MC38 colon adenocarcinoma cells were permanently transfected with a luciferase-lentiviral vector in the UCLA vector core facility, as previously described (Meng et al. (2015) *ACS Nano*, 9: 3540). Limiting dilution was performed to generate monoclonal MC38 cells. MC38 cells were cultured in DMEM, supplemented with 10% FBS, 100 U/mL penicillin, 100 µg/mL streptomycin, and 2 mM L-glutamine. 24 h prior to transfection, MC38 cells were seeded at $1 \times 10^4$ cells/well on 96-well plates. Plasmid encoding tdTomato reporter protein was complexed with 4-arm PRX analogues in multiple N/P ratios and incubated with MC38 cells (1 µg plasmid/mL) in medium containing 10% FBS. MC38 cells were further incubated for 72 h and the expression of tdTomato was examined on a fluorescence microscope (Observer D1, Zeiss). For pIL-12 transfection, optimized 4-arm PRX or linear PRX were complexed with pIL-12 and incubated with MC38 cells (1 µg plasmid/mL) for 72 h. The supernatant of cell culture media were collected and subjected to ELISA detection of IL-12 p70 protein with DuoSet ELISA kit (R&D Systems). Untreated MC 38-luc cells or MC38 cells treated with control plasmid (pC) laden 4-arm PRX were also detected as control. For real-time qPCR detection, total RNA was isolated from MC38 cells with RNeasy Mini Kit (Qiagen), and then reverse-transcribed with iTaq University SYBR Green Supermix (Biorad). The following primers were used: IL12: forward, 5'-AAC CTC ACC TGT ACA CGC C-3' (SEQ ID NO:301), reverse, 5'-CAA GTC CAT GTT TCT TTG CAC G-3' (SEQ ID NO:302); β-actin, forward, 5'-AGA GCT ACG AGC TGC CTG AC-3' (SEQ ID NO:303), reverse, 5'-AGC ACT GTG TTG GCG TAC AG-3' (SEQ ID NO:304). The ΔCT for IL-12 mRNA was divided by that of β-actin to give the fold increase of gene expression, and then normalized to untreated control to obtain the relative IL-12 expression.

Native Gel Electrophoresis

Mouse immunoglobulin (IgG) was prepared as 10 µg/µL aqueous solution and incubated with pIL-12 laden optimized 4-arm PRX or linear PRX (plasmid concentration 1 µg/µL) for 30 min at 37° C. The treated IgG solutions were directly loaded in 4-16% NativePAGE gel system (10 µg IgG per lane) for 100 min at 150 V. The protein bands were visualized by Coomassie blue stainingN. The intensity of IgG band was semi-quantified by Image J software.

In Vivo Biodistribution and PK Study

Female C57BL/6 mice (~8 weeks) were purchased from The Jackson Laboratory and maintained under pathogen-free conditions. All animal experiments were performed with protocols approved by the UCLA Animal Research Committee. To study the PK profile, Cy3-labeled plasmid was prepared with Label IT® Tracker™ kit (Mirus Bio) according to manufacturer's instruction. Normal C57BL/6 mice received single IV injection of Cy3-plasmid laden 4-arm PRX or linear PRX (5 mg plasmid/kg). This is equivalent to PRX dose of 15 mg/kg. Plasma was collected at the indicated time points (0.083, 1, 2, 4, 8 and 24 h). The fluorescence intensity of plasma samples were detected on microplate reader (M5e, Molecular Device), with Ex/Em of 544 nm/590 nm. The plasmid concentration in the sample was calculated based on the fluorescence intensity using the standard curve of plasmid. The PK profiles of Cy3-labeled plasmid were assessed using PKsolver software (Zhang et al. (2010) Computer methods and programs in biomedicine, 99: 306). We continued to perform biodistribution study in a subcutaneous tumor bearing mice model. Female C57BL/6 mice were subcutaneously inoculated in the right flank with MC38 cells ($1\times10^6$ cells/mouse). The animals were maintained under pathogen-free conditions and all animal experiments were approved by the UCLA Animal Research Committee. Following tumor growth to 8-10 mm in size, mice were IV injected with Cy3-labeled plamid laden 4-arm PRX, or linear PRX (5 mg plasmid/kg). 24 h post IV injection, the mice were sacrificed to collect tumors and the major organs (heart, liver, spleen, lung and kidney). Ex-vivo imaging was performed on IVIS system (Xenogen) with Ex/Em of 535 nm/575-650 nm. Tumor tissues were then embedded in OCT reagents and cryo-sectioned. CD31 immuno-fluorescence staining was performed to locate the blood vessels as we shown before (Meng et al. (2011) ACS Nano, 5: 4131). The intratumoral distribution of Cy3-labeled plasmid was visualized by confocal microscopy (SP8-SMD, Leica).

ELISA and Western Blot Analysis for Short-Term In Vivo Efficacy Study

To study the short-term efficacy, C57/BL6 mice bearing subcutaneous MC38 tumors were IV injected with pIL-12 laden 4-arm PRX (5 mg plasmid/kg), tdTomato plasmid laden 4-arm PRX (as non-functional control) or saline. To validate the in vivo transfection efficacy, western blot detection of tdTomato reporter protein was performed in MC38 tumors 7 days post IV injection. The snap-freezed MC38 tumors were weighed and homogenized in RIPA buffer (Cell Signaling Technology) supplemented with protease inhibitor cocktail (Roche Diagnostics), followed by centrifugation at 10,000 rcf for 20 min. Western blot was performed according to published procedures (Lu et al. (2017) Nat. Comm. 8: 1811). Briefly, electrophoresis was performed on 4-12% SDS-PAGE gel (Invitrogen), and the proteins were subsequently transferred to a PVDF membrane. After blocking in 5% BSA, the membrane was overlaid with primary antibodies including anti-mCherry (ab167453, Abcam) to detect tdTomato and anti-vinculin XP® mAb (Cell Signaling Technology) as loading control. Staining with HRP-conjugated secondary antibodies was sequentially performed and the blots were developed by the addition of the ECL solution.

To detect the IL-12 expression in vivo, 3 and 7 days post IV injection, the mice were sacrificed, and tumors, major organs (heart, liver, spleen, lung and kidney) were collected and snap-freezed in liquid nitrogen. Serum was also collected for IL-12 detection. For ELISA detection of IL-12, the snap-freezed MC38 tumors and major organs were weighed, cut into pieces and suspended in tissue extraction reagent I (Invitrogen) supplemented with protease inhibitor cocktail (Roche Diagnostics). Tissue samples were then homogenized on ice and centrifuged at 10,000 rcf for 20 min. Serum samples were centrifuged at 3,000 rpm for 10 min before testing. The above procedures were all performed at 4° C. The IL-12 p70 protein level in tissue extracts and plasma was determined by Quantikine ELISA Kit (R&D Systems).

In Vivo Antitumor Efficacy Study

Female C57BL/6 mice were subcutaneously inoculated in the right flank with MC38-luc cells ($1\times10^6$ cells/mouse). Following tumor growth to 5-8 mm in size, C57BL/6 mice were randomly assigned to 3 groups (n=4), and received IV injection of pIL-12 laden 4-arm PRX, pC laden 4-arm PRX as non-functional control, or saline twice per week (5 mg plasmid/kg/injection, 5 injections in total). To monitor the tumor burden weekly, mice received intraperitoneal injection of 75 mg/kg D-Luciferin for 8 min, before IVIS detection of bioluminescent signal from tumor site. Quantitative expression of tumor growth was obtained by normalizing the bioluminescent radiance of tumor to day 1. The size of the tumor were also measured by caliper and plotted vs. time. The size of tumor was calculated as $\pi/6\times length\times width^2$, in which a represented width of the rumor and b represented the length of the tumor. The animals were sacrificed on day 21, and the tumor tissues were collected for further analysis.

Flow Cytometry Analysis

Right after tissue collection on day 21, the treated MC38 tumors were cut into smaller pieces digested in DMEM with 0.5 mg/mL collagenase type I (Worthington Biochemical Corporation) at 37° C. for 1 h. The digested tissues were gently meshed though a 70 µm cell strainer and treated by ACK lysing buffer (Gibco) as per manufacturer's instructions. The harvested cells were washed twice and resuspended in stain buffer (BD Pharmigen), and incubated with FcBlock (TruStain fcX™ anti-mouse CD16/32, clone 93, BioLegend) to avoid nonspecific binding. Staining was then performed with primary antibodies for 30 min at 4° C. The following anti-mouse antibodies were purchased from eBiosciences: CD45-eFluor 450 (clone 30-F11), CD8α-Alexa Flour 488 (clone 53-6.7), NK1.1-PerCP-Cyanine 5.5 (clone PK136), CD3e-APC-eFlour780 (clone 17A2). For the staining of intracellular Interferon-γ, the cell were treated with intracellular fixation and permeabilization kit (eBioscience) as per manufacturer's instruction, and stained with anti-Interferon-γ-APC (clone XMG1.2, eBioscience). After washing, cells were analyzed on a flow cytometer (LSRII, BD Biosciences). The data were processed by FlowJo software (Tree Star). Dead cells and doublets were excluded based on forward and side scatter.

Immunohistochemistry (IHC) Analysis

MC38 Tumor tissues harvested on day 21 were fixed in 10% formalin solution. Tissue sectioning and IHC staining were performed by the UCLA Jonsson Comprehensive Cancer Center Translational Pathology Core Laboratory. Briefly, the slides were deparaffinized, incubated in 3% methanol-hydrogen peroxide, followed by incubation with 10 mM EDTA at 95° C. using the Decloaking NxGen Chamber (Biocare Medical, DC2012). The slides were incubated with individual primary antibodies for 1 h including anti-CD8 (eBioscience, 4SM15, 1/100), anti-NK1.1 (Bioss, bs4682R, 1/100), anti-IFN-γ (Abcam, ab9657, 1/200) or anti-IL-12p70 (Novus Biologics, NBP1-85564, 1/100). After washing, the slides were further incubated with HRP-conjugated secondary antibodies at room temperature for 30 min. After rinsing with PBST, the slides were incubated with 3,3'-diaminobenzidine and counterstained with hematoxylin. The slides were scanned by an Aperio AT Turbo Digital Pathology Scanner (Leica Biosystems).

Immunofluorescence Staining

To determine the density of CD31-positive blood vessels and evaluate the anti-angiogenesis effect, the treated MC38 tumor tissues harvested on day 21 were embedded with OCT reagent and cyro-sectioned. The sections were stained with anti-CD31 monoclonal antibody (Clone 390, BD Pharmingen) at 4° C. overnight. After removal of the primary antibody and washing in PBS 3 times, the Alexa Fluor® 647 secondary antibody was added and incubated for 1 h at room temperature, and counter-stained with DAPI. The stained slides were examined with a confocal microscope (SP8-SMD, Leica).

Safety Profile of pIL-12 Laden 4-Arm PRX

IV injection of pIL-12 laden 4-arm PRX, pC laden 4-arm PRX as non-functional control or saline was performed in non-tumor bearing C57BL/6 mice. The dose and injection scheme was the same as the antitumor efficacy study. For comparison, we also included IV mouse rIL-12 at a therapeutic dose (100 μg/kg). Mice were sacrificed on day 7 and day 21, blood and major organs (heart, liver, spleen, and lung) were collected. Major organs were fixed in 10% formalin, followed by paraffin embedding. Tissue sections were stained by Haemotoxylin and Eosin (H&E) for histological analysis. Blood chemistry test were also performed by Pathology & Laboratory Medicine Services from UCLA Division of Laboratory Animal Medicine (DLAM).

Statistical Analysis

Comparative analysis of the differences between groups was performed using the two-sided Student's t-test (Excel software, Microsoft). A statistically significant difference was determined at $p<0.05$. Values were expressed as mean±SD of multiple determinations, as stated in the figure legends.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A polyrotaxane carrier for in vivo delivery of a nucleic acid, said carrier comprising:
- a multi-arm polyethylene glycol (PEG) backbone comprising 4 arms;
- at least one cyclic compound having a cavity, where an arm of said multi-arm PEG backbone is threaded into the cavity of said cyclic compound forming an inclusion complex;
- a bulky moiety capping the terminal of the arm(s) threaded into said cyclic compound where said moiety inhibits dethreading of the cyclodextrin from the arm(s) of said backbone;
- where two arms of said PEG backbone are free of cyclic compounds; and
- where said carrier has a net positive charge.

2. The carrier of claim 1, wherein:
- said PEG backbone has a molecular weight ranging from about 1.0 to about 10 kDA per arm; and/or
- said PEG backbone comprise about 22 to about 227 ethylene oxides per arm; and/or
- said PEG backbone has a molecular weight of about 2.5 kDa per arm.

3. The carrier of claim 1, wherein:
- the arm(s) threaded into said cyclic compound(s) each bear on average from about 5 to about 110 cyclic compounds; and/or
- the arm(s) threaded into said cyclic compound(s) each bear, on average, about 20 cyclic compounds per arm.

4. The carrier of claim 1, wherein:
- said cyclic compound comprise a compound selected from the group consisting of a cyclodextrin, a crown ether, a cucurbituril and a cyclofructan; and/or
- said cyclic compound comprises a cyclodextrin; and/or
- said cyclic compound comprises a cyclodextrin selected from the group consisting of an α-cyclodextrin, a ß-cyclodextrin, a γ-cyclodextrin, a hydroxypropylated α-cyclodextrin, a hydroxypropylated ß-cyclodextrin, a hydroxypropoylated γ-cyclodextrin, a dimethylcyclodextrin, a chemically modified cyclodextrin (e.g., carboxyl modified cyclodextrin); and/or
- said cyclic compound comprises a cucurbituril; and/or
- said cyclic compound comprises a cucurbituril selected from the group consisting of cucurbit[5]uril, cucurbit[6]uril, cucurbit[7]uril, cucurbit[8]uril, cucurbit[9]uril, cucurbit[10]uril, and a chemically modified cucubituril; and/or
- said cyclic compound comprises a cucurbit[6]uril (CB[6]).

5. The carrier of claim 1, wherein:
- said cyclic compound(s) are substituted with one or more nucleophilic groups; and/or
- said cyclic compound(s) are substituted with one or more amine groups or groups derived from an amine group; and/or
- said cyclic compound(s) are substituted with one or more groups selected from the group consisting of a primary amine, a secondary amine, a tertiary amine, and an imine group; and/or
- said cyclic compound(s) are substituted with one or more primary amines; and/or
- the number of nucleophilic group substituted on the cyclic compound(s) ranges from 1 up to about 20 substitutions per cyclic compound; and/or
- the cyclic compounds are substituted with nucleophilic groups to provide a positive zeta potential for said carrier ranging from about +1V or from about +5 mV up to about +50 m V, or up to about +25 mV.

6. The carrier of claim 1, wherein:
- the bulky moiety capping the terminal of the arm(s) threaded into said cyclic compound(s) comprises a compound having a 3 dimensional size greater than the internal diameter of the cyclic compound(s); and/or
- the bulky moiety capping the terminal of the arm(s) threaded into said cyclic the bulky moiety capping the terminal of the arm(s) threaded into said cyclic compound(s) comprises a moiety selected from the group consisting of Z-tyrosine, phenylalanine, a group having at least one benzene ring, and a group having at least one tertiary butyl; and/or
- the bulky moiety capping the terminal of the arm(s) threaded into said cyclic the bulky moiety capping the terminal of the arm(s) threaded into said cyclic compound(s) comprises a moiety selected from the group consisting of a Z-tyrosine, phenylaline, a benzyloxycarbonyl (Z) group, a 9-fluorenylmethyloxycarbonyl (Fmoc) group, a benzyl ester (OBz) group, a tertiary butylcarbonyl (Boc) group, and an amino acid-tertiary butyl ester (OBu) group; and/or
- the bulky moiety capping the terminal of the arm(s) threaded into said cyclic compound(s) comprises a Z-tyrosine.

7. A polyrotaxane carrier for in vivo delivery of a nucleic acid, said carrier comprising:
- a multi-arm polyethylene glycol (PEG) backbone comprising at least three arms;
- at least one cyclic compound having a cavity, where an arm of said multi-arm PEG backbone is threaded into the cavity of said cyclic compound forming an inclusion complex;
- a bulky moiety capping the terminal of the arm(s) threaded into said cyclic compound where said moiety inhibits dethreading of the cyclodextrin from the arm(s) of said backbone;
- where at least one arm of said PEG backbone is free of cyclic compounds;
- where said carrier has a net positive charge;
- where:
  - at least one arm not threaded into said cyclic compound is terminated with a protecting group, and/or a fluorophore, and/or a targeting moiety; and/or at least one arm not threaded into said cyclic compound are terminated with a protecting group selected from the group consisting of dansyl, acetyl, amide, and 3 to 20 carbon alkyl groups, Fmoc, Tboc, 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh),Tosyl (Tos), 2,2,5,7,8-pentamethyl chroman-6-sulphonyl (Pmc), 4-methylbenzyl (Me-Bzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), t-butoxycarbonyl (Boc), cyclohexyloxy (cHxO),t-butoxymethyl (Bum), t-butoxy (tBuO), t-Butyl (tBu), Acetyl (Ac), and Trifluoroacetyl (TFA); and/or at least one arm not threaded into said cyclic compound is attached to a fluorophore; and/or at least one arm not threaded into said cyclic compound is attached to a targeting moiety that specifically or preferentially binds to a cell; and/or at least one arm not threaded into said cyclic compound is attached to a at least one arm not threaded into said cyclic compound is attached to a targeting moiety selected from the group consisting of an antibody, a receptor ligand, a nucleic acid aptamer, a peptide aptamer, neural cell adhesion molecule (NCAM), a cell penetrating peptide (CPP), a peptide aptamer, and a lectin; and/or at least one arm not threaded into said cyclic compound is attached to a at least one arm not threaded into said cyclic compound is attached to a targeting moiety comprising a ligand that binds a receptor where said ligand is selected from the group consisting of transferrin, mannose, glucose, and folic acid; and/or at least one arm not threaded into said cyclic compound is attached to a targeting moiety comprising transferrin.

8. The carrier of claim 1, wherein:
said bulky moiety is attached to an arm of said backbone by a cleavable linkage; and/or
said one or more nucleophilic groups are attached to said cyclic compounds by a cleavable linkage.

9. The carrier of claim 1, wherein:
said carrier is complexed with a nucleic acid; and/or
said carrier is complexed with an RNA; and/or
said carrier is complexed with a DNA; and/or
said carrier is complexed with a plasmid; and/or
said carrier is complexed with a plasmid that encodes a heterologous gene or cDNA; and/or
said carrier is complexed with a plasmid that encodes a class 2 CRISPR/Cas endonuclease and a guide RNA; and/or
the N/P ratio of said carrier complexed to a nucleic acid ranges from about 0.01:1 up to about 100:1, or from about 2:1 up to about 50:1, or up to about 40:1, or up to about 30:1, or up to about 25:1, or ranges from about 2:1 up to about 25:1; and/or
the N/P ratio of said carrier complexed to a nucleic acid is about 10:1.

10. A pharmaceutical formulation comprising:
a polyrotaxane carrier of claim 7; and
a pharmaceutically acceptable carrier.

11. A construct for the treatment of Duchenne Muscular Dystrophy, said construct comprising:
a polyrotaxane carrier comprising:
a multi-arm polyethylene glycol (PEG) backbone comprising at least three arms;
at least one cyclic compound having a cavity, where an arm of said multi-arm PEG backbone is threaded into the cavity of said cyclic compound forming an inclusion complex;
a bulky moiety capping the terminal of the arm(s) threaded into said cyclic compound where said moiety inhibits dethreading of the cyclodextrin from the arm(s) of said backbone;
where at least one arm of said PEG backbone is free of cyclic compounds; and
where said carrier has a net positive charge; and
where said carrier is complexed with a plasmid encoding a class 2 CRISPR/Cas endonuclease, and a guide RNA that hybridizes to a target sequence within intron 44 of a mutant dystrophin gene, and/or a second CRISPR/Cas guide RNA guide sequence that hybridizes to a target sequence within intron 55 of the mutant dystrophin gene.

12. The construct of claim 11, wherein:
the first CRISPR/Cas guide RNA comprises a guide sequence having 100% complementarity over 17 or more contiguous nucleotides with a first target sequence corresponding to intron 44 of the human dystrophin gene, and/or
the second CRISPR/Cas guide RNA comprises a guide sequence having 100% complementarity over 17 or more contiguous nucleotides with a second target sequence corresponding to intron 55 of the human dystrophin gene.

13. The construct of claim 11, wherein:
the class 2 CRISPR/Cas endonuclease is a type II CRISPR/Cas endonuclease; and/or
the class 2 CRISPR/Cas endonuclease is a type II CRISPR/Cas endonuclease wherein the class 2 CRISPR/Cas endonuclease is a Cas9 protein and the corresponding CRISPR/Cas guide RNA is a Cas9 guide RNA; and/or
the guide sequence of the first CRISPR/Cas guide RNA comprises the 17 nucleotide sequence GAAAUUAAACUACACAC (SEQ ID NO:304) (SEQ ID NO:1158 in PCT/US2017/017255), and the guide sequence of the second CRISPR/Cas guide RNA comprises the 17 nucleotide sequence AUGAUGCUAUAAUACCA (SEQ ID NO:305) (SEQ ID NO:1177 in PCT/US2017/017255); and/or
the guide sequence of the first CRISPR/Cas guide RNA comprises the 20 nucleotide sequence GUUGAAAUUAAACUACACAC (SEQ ID NO:306) (SEQ ID NO:1153 in PCT/US2017/017255) and the guide sequence of the second CRISPR/Cas guide RNA comprises the 20 nucleotide sequence UGUAUGAUGCUAUAAUACCA (SEQ ID NO:307) (SEQ ID NO:1172 in PCT/US2017/017255).

14. A pharmaceutical formulation comprising:
a polyrotaxane construct of claim 11; and
a pharmaceutically acceptable carrier.

15. The carrier of claim 7, wherein said carrier is complexed with a nucleic acid.

16. The carrier of claim 15, wherein said carrier is complexed with a plasmid.

17. The carrier of claim 15, wherein the N/P ratio of said carrier complexed to a nucleic acid ranges from about 0.01:1 up to about 100:1, or from about 2:1 up to about 50:1, or up to about 40:1, or up to about 30:1, or up to about 25:1, or ranges from about 2:1 up to about 25:1.

18. The carrier of claim 17, wherein the N/P ratio of said carrier complexed to a nucleic acid is about 10:1.

19. The carrier of claim 1, wherein:
   said PEG backbone has a molecular weight ranging from about 1.0 to about 10 kDA per arm; and/or
   said PEG backbone comprise about 22 to about 227 ethylene oxides per arm; and/or
   said PEG backbone has a molecular weight of about 2.5 kDa per arm.

20. The carrier of claim 1, wherein:
   the arm(s) threaded into said cyclic compound(s) each bear on average from about 5 to about 110 cyclic compounds; and/or
   the arm(s) threaded into said cyclic compound(s) each bear, on average, about 20 cyclic compounds per arm.

21. A pharmaceutical formulation comprising:
   a polyrotaxane carrier of claim 1; and
   a pharmaceutically acceptable carrier.

* * * * *